US011225509B2

(12) United States Patent
Poma et al.

(10) Patent No.: US 11,225,509 B2
(45) Date of Patent: Jan. 18, 2022

(54) HER2-TARGETING MOLECULES COMPRISING DE-IMMUNIZED, SHIGA TOXIN A SUBUNIT SCAFFOLDS

(71) Applicant: Molecular Templates, Inc., Austin, TX (US)

(72) Inventors: Eric Poma, New York, NY (US); Erin Willert, Round Rock, TX (US); Jack Higgins, Georgetown, TX (US)

(73) Assignee: Molecular Templates, Inc., Austin, TX (US)

( * ) Notice: Subject to any disclaimer, the term of this patent is extended or adjusted under 35 U.S.C. 154(b) by 0 days.

(21) Appl. No.: 17/072,562

(22) Filed: Oct. 16, 2020

(65) Prior Publication Data

US 2021/0040160 A1 Feb. 11, 2021

Related U.S. Application Data

(63) Continuation of application No. PCT/US2019/027627, filed on Apr. 16, 2019.

(60) Provisional application No. 62/659,116, filed on Apr. 17, 2018.

(51) Int. Cl.

| | |
|---|---|
| *A61K 39/00* | (2006.01) |
| *A61K 39/02* | (2006.01) |
| *A61K 39/38* | (2006.01) |
| *C07K 14/25* | (2006.01) |
| *A61P 35/00* | (2006.01) |
| *A61K 47/02* | (2006.01) |
| *A61K 47/26* | (2006.01) |
| *C07K 16/32* | (2006.01) |
| *A61K 38/00* | (2006.01) |
| *A61K 45/06* | (2006.01) |

(52) U.S. Cl.
CPC .............. *C07K 14/25* (2013.01); *A61K 47/02* (2013.01); *A61K 47/26* (2013.01); *A61P 35/00* (2018.01); *C07K 16/32* (2013.01); *A61K 38/00* (2013.01); *A61K 45/06* (2013.01)

(58) Field of Classification Search
CPC ......... A61K 39/00; A61K 39/02; A61K 39/38
USPC ......... 424/130.1, 138.1, 184.1, 185.1, 234.1, 424/236.1
See application file for complete search history.

(56) References Cited

U.S. PATENT DOCUMENTS

| | | |
|---|---|---|
| 5,080,898 A | 1/1992 | Murphy |
| 5,135,736 A | 8/1992 | Anderson et al. |
| 5,635,384 A | 6/1997 | Walsh et al. |
| 5,668,255 A | 9/1997 | Murphy |
| 5,858,682 A | 1/1999 | Gruenwald et al. |
| 6,022,950 A | 2/2000 | Murphy |
| 6,080,400 A | 6/2000 | Williams |
| 6,492,498 B1 | 12/2002 | Vallera et al. |
| 6,652,857 B2 | 11/2003 | Williams |
| 6,770,456 B1 | 8/2004 | Coulie et al. |
| 7,144,991 B2 | 12/2006 | Goshom et al. |
| 7,267,973 B2 | 9/2007 | Backer et al. |
| 7,527,787 B2 | 5/2009 | Chang et al. |
| 7,700,557 B2 | 4/2010 | Backer et al. |
| 7,713,915 B1 | 5/2010 | Gariepy et al. |
| 7,799,900 B2 | 9/2010 | Adams |
| 7,834,258 B2 | 11/2010 | Choe et al. |
| 7,887,801 B2 | 2/2011 | Wels et al. |
| 8,048,985 B2 | 11/2011 | Harrison et al. |
| 8,147,832 B2 | 4/2012 | Carr et al. |
| 8,337,844 B2 | 12/2012 | Carr et al. |
| 8,470,314 B2 | 6/2013 | Davis |
| 8,530,637 B2 | 9/2013 | Wels et al. |
| 8,865,866 B2 | 10/2014 | Harrison et al. |
| 8,895,006 B2 | 11/2014 | Tumer et al. |
| 8,969,529 B2 | 3/2015 | O'Brien et al. |
| 9,175,059 B2 | 11/2015 | Pieczykolan et al. |
| 9,364,557 B2 | 6/2016 | Neville et al. |
| 10,815,469 B2 | 10/2020 | Poma et al. |
| 2002/0012658 A1 | 1/2002 | Williams et al. |
| 2002/0168370 A1 | 11/2002 | McDonald et al. |
| 2003/0166196 A1 | 9/2003 | Better et al. |

(Continued)

FOREIGN PATENT DOCUMENTS

| | | |
|---|---|---|
| AU | 750367 B1 | 2/1999 |
| CN | 1272882 A | 11/2000 |

(Continued)

OTHER PUBLICATIONS

Palumbo et al., "Daratumumab, bortezomib, and dexamethasone for multiple myeloma." New England Journal of Medicine 375.8 (2016): 754-766.

(Continued)

*Primary Examiner* — Rodney P Swartz

(74) *Attorney, Agent, or Firm* — Cooley LLP

(57) ABSTRACT

Provided herein are HER2-targeting molecules comprising Shiga toxin A Subunit derived polypeptides having 1) de-immunization and 2) reduced, protease-cleavage sensitivity while retaining Shiga toxin function(s), such as, e.g., potent cytotoxicity via ribosome inhibition. Certain HER2-targeting molecules of the present invention exhibit reduced immunogenic potential in mammals and are well-tolerated by mammals while retaining aforementioned features. The HER2-targeting molecules of the present invention have uses for selectively killing specific cells (e.g., HER positive tumor cells); for selectively delivering cargos to specific cells (e.g., HER positive tumor cells), and as therapeutic and/or diagnostic molecules for treating and diagnosing a variety of conditions, including cancers and tumors involving the expression or over-expression of cell-surface HER2.

6 Claims, 22 Drawing Sheets

Specification includes a Sequence Listing.

(56) References Cited

U.S. PATENT DOCUMENTS

| | | |
|---|---|---|
| 2004/0141982 A1 | 7/2004 | Lust et al. |
| 2004/0166565 A1 | 8/2004 | Backer et al. |
| 2005/0054835 A1 | 3/2005 | Better et al. |
| 2005/0069545 A1 | 3/2005 | Carr et al. |
| 2009/0023649 A1 | 1/2009 | Backer et al. |
| 2009/0092578 A1 | 4/2009 | Su et al. |
| 2009/0156417 A1 | 6/2009 | Gariepy et al. |
| 2009/0156502 A1 | 6/2009 | Harrison et al. |
| 2010/0093563 A1 | 4/2010 | Williamson et al. |
| 2011/0189209 A1 | 8/2011 | Neville et al. |
| 2011/0280913 A1 | 11/2011 | Byrd et al. |
| 2012/0039908 A1 | 2/2012 | Combs et al. |
| 2012/0149650 A1 | 6/2012 | Harrison et al. |
| 2012/0251542 A1 | 10/2012 | Tumer et al. |
| 2013/0071325 A1 | 3/2013 | Sahin et al. |
| 2013/0189271 A1 | 7/2013 | De Goeij et al. |
| 2013/0196928 A1 | 8/2013 | Gariepy et al. |
| 2015/0044210 A1 | 2/2015 | Mechaly et al. |
| 2015/0259428 A1 | 9/2015 | Poma et al. |
| 2016/0017047 A1 | 1/2016 | Poma et al. |
| 2016/0068577 A1 | 3/2016 | Poma et al. |
| 2016/0177284 A1 | 6/2016 | Poma et al. |
| 2016/0340394 A1 | 11/2016 | Poma et al. |
| 2016/0347798 A1 | 12/2016 | Poma et al. |
| 2016/0355803 A1 | 12/2016 | Poma et al. |
| 2016/0376328 A1 | 12/2016 | Poma et al. |
| 2017/0002016 A1 | 1/2017 | Shishido et al. |
| 2017/0002046 A1 | 1/2017 | Poma et al. |
| 2017/0101636 A1 | 4/2017 | Poma et al. |
| 2017/0143814 A1 | 5/2017 | Poma et al. |
| 2017/0275382 A1 | 9/2017 | Poma et al. |
| 2018/0057544 A1 | 3/2018 | Poma et al. |
| 2018/0243432 A1 | 8/2018 | Poma et al. |
| 2018/0258143 A1 | 9/2018 | Poma et al. |
| 2018/0258144 A1 | 9/2018 | Poma et al. |
| 2018/0291359 A1 | 10/2018 | Poma et al. |
| 2019/0083644 A1 | 3/2019 | Yoo et al. |
| 2019/0100597 A1 | 4/2019 | Keyt et al. |
| 2019/0153044 A1 | 5/2019 | Poma et al. |
| 2019/0153471 A1 | 5/2019 | Paul et al. |
| 2019/0249145 A1 | 8/2019 | Jang et al. |
| 2020/0024312 A1 | 1/2020 | Poma et al. |

FOREIGN PATENT DOCUMENTS

| | | |
|---|---|---|
| CN | 101289511 A | 10/2008 |
| CN | 105713087 A | 1/2016 |
| EP | 1654287 A2 | 5/2006 |
| EP | 3265575 A2 | 1/2018 |
| EP | 3448874 A1 | 3/2019 |
| JP | 199308502880 A | 3/1996 |
| JP | 2011507389 A1 | 6/1999 |
| JP | 2001500730 A | 1/2001 |
| JP | 2002521019 A | 7/2002 |
| JP | 2002544173 A | 12/2002 |
| JP | 2003531588 A | 10/2003 |
| JP | 2007536905 A | 12/2007 |
| JP | 2008533977 A | 8/2008 |
| JP | 2009502936 A | 1/2009 |
| JP | 2011050388 A | 3/2011 |
| JP | 2012044997 A | 3/2012 |
| JP | 2012070737 A | 4/2012 |
| JP | 2012515551 A | 7/2012 |
| JP | 2014515921 A | 7/2014 |
| KR | 20110033233 A | 3/2011 |
| KR | 20110119725 A | 11/2011 |
| WO | 19991009871 A1 | 7/1991 |
| WO | 1994026910 A1 | 11/1994 |
| WO | 1996030043 A1 | 10/1996 |
| WO | 1996040200 A1 | 12/1996 |
| WO | 1998011229 A3 | 3/1998 |
| WO | 1999040185 A1 | 8/1999 |
| WO | 2000004926 A2 | 2/2000 |
| WO | 2000067795 A1 | 11/2000 |
| WO | 2001070945 A1 | 9/2001 |
| WO | 2001077342 A1 | 10/2001 |
| WO | 2003066854 A1 | 8/2003 |
| WO | 2004056312 A2 | 7/2004 |
| WO | 2004058158 A2 | 7/2004 |
| WO | 2005000902 A1 | 1/2005 |
| WO | 2005016969 A2 | 2/2005 |
| WO | 2005017148 A1 | 2/2005 |
| WO | 2005052006 A2 | 6/2005 |
| WO | 2005052129 A2 | 6/2005 |
| WO | 2005092917 A1 | 10/2005 |
| WO | 2006099875 A1 | 9/2006 |
| WO | 2007005874 A2 | 1/2007 |
| WO | 2007014238 A2 | 2/2007 |
| WO | 2007033497 A1 | 3/2007 |
| WO | 2007071061 A1 | 6/2007 |
| WO | 2008080218 A1 | 7/2008 |
| WO | 2009017823 A2 | 2/2009 |
| WO | 2009032954 A1 | 3/2009 |
| WO | 2007098201 A2 | 4/2009 |
| WO | 2009014835 A3 | 5/2009 |
| WO | 2009064815 A1 | 5/2009 |
| WO | 2009088403 A2 | 7/2009 |
| WO | 2009110944 A1 | 9/2009 |
| WO | 2010011697 A1 | 1/2010 |
| WO | 2010085539 A1 | 7/2010 |
| WO | 2011009624 A1 | 1/2011 |
| WO | 2012022985 A1 | 2/2012 |
| WO | 2012093158 A1 | 7/2012 |
| WO | 2012101235 A1 | 8/2012 |
| WO | 2012104344 A1 | 8/2012 |
| WO | 2012154530 A1 | 11/2012 |
| WO | 2013080147 A2 | 6/2013 |
| WO | 2014164680 A1 | 10/2014 |
| WO | 2014164693 A1 | 10/2014 |
| WO | 2015063187 A1 | 10/2014 |
| WO | 2015113005 A1 | 7/2015 |
| WO | 2015113007 A1 | 7/2015 |
| WO | 2015120058 A9 | 8/2015 |
| WO | 2015138435 A9 | 9/2015 |
| WO | 2015138452 A1 | 9/2015 |
| WO | 2015191764 A1 | 12/2015 |
| WO | 2015193411 A1 | 12/2015 |
| WO | 2016126950 A1 | 8/2016 |
| WO | 2016196344 A1 | 12/2016 |
| WO | 2017019623 A1 | 2/2017 |
| WO | 2018080812 A1 | 5/2018 |
| WO | 2018106895 A1 | 6/2018 |
| WO | 2018136553 A1 | 7/2018 |
| WO | 2018140427 A1 | 8/2018 |
| WO | 2018159615 A1 | 9/2018 |
| WO | 2018162749 A1 | 9/2018 |
| WO | WO 2018/183182 A1 | 10/2018 |
| WO | WO 2019/059400 A1 | 3/2019 |
| WO | 2019183093 A1 | 9/2019 |
| WO | WO 2019/204272 A1 | 10/2019 |
| WO | WO 2020/081493 A1 | 4/2020 |
| WO | WO 2020/154475 A1 | 7/2020 |

OTHER PUBLICATIONS

Parakh et al., "Evolution of anti-HER2 therapies for cancer treatment." Cancer Treatment Reviews 59 (2017): 1-21.

Ramos, HJ, et al., "In vivo efficacy of a PD-L1 targeted, antigen seeding engineered toxin body", Proceedings: American Association for Cancer Research (AACR) Annual Meeting 2020, Abstract #3366, (Jun. 22, 2020).

Reddy, S, et al., "Evaluation of the anti-HER2 C6.5 Diabody as a PET Radiotracer to Monitor HER2 status and Predict Response to Trastuzumab Treatment", Clinical Cancer Research, 17(6), (2011), Mar. 15, 1509-1520.

Rosato et al., "Virus-specific memory T cells populate tumors and can be repurposed for tumor immunotherapy." Nature Communications 10.1 (2019): 1-9.

Samstein et al., "Tumor mutational load predicts survival after immunotherapy across multiple cancer types." Nature Genetics 51.2 (2019): 202-206.

Schubert, B, Kohlbacher, O, "Designing string-of-beads vaccines with optimal spacers", Genome Medicine, 8(1), (2016), Jan. 26, 9.

(56) References Cited

OTHER PUBLICATIONS

Simonetti et al., "Novel Humanized Monoclonal Antibodies to PD-L1", Abeome Corporation, (2017).
Subudhi et al., "Clonal expansion of CD8 T cells in the systemic circulation precedes development of ipilimumab-induced toxicities." Proceedings of the National Academy of Sciences 113.42 (2016): 11919-11924.
Swain et al., "Pertuzumab, trastuzumab, and docetaxel in HER2-positive metastatic breast cancer." New England Journal of Medicine 372.8 (2015): 724-734.
Tang et al., "Tumor cells versus host immune cells: whose PD-L1 contributes to PD-1/PD-L1 blockade mediated cancer immunotherapy?." Cell & Bioscience 8.1 (2018): 34.
Tine, BA Van, et al., "A Phase 1 Open-Label Study to Investigate Safety and Tolerability, Efficacy, Pharmacokinetics, Pharmacodynamics, and Immunogenicity of MT-5111 in Subjects With HER2-Positive Tumors", Presented at: Gastrointestinal Cancers Symposium, Jan. 23-25, 2020, The American Society of Clinical Oncology, San Francisco, California, Abstract L9.
Van De Donk et al., "CD38 antibodies in multiple myeloma: back to the future." Blood 131.1 (2018): 13-29.
Van De Donk et al., "CD38 antibodies in multiple myeloma: mechanisms of action and modes of resistance." Frontiers in Immunology 9 (2018): 2134.
Vernet et al., "Affinity-based entrapment of the HER2 receptor in the endoplasmic reticulum using an affibody molecule." Journal of Immunological Methods 338.1-2 (2008): 1-6.
Wang et al., "Ontak-like human IL-2 fusion toxin." Journal of Immunological Methods 448 (2017): 51-58.
"Wang et al., ""Targeted therapeutic options and future perspectivesfor HER2-positive breast cancer"" Target Therapy 4 (2019): 34".
Wolff et al., "Human epidermal growth factor receptor 2 testing in breast cancer: American Society of Clinical Oncology/College of American Pathologists clinical practice guideline focused update." Archives of Pathology & Laboratory medicine 142.11 (2018): 1364-1382.
Yan et al., "HER2 expression status in diverse cancers: review of results from 37,992 patients." Cancer and Metastasis Reviews 34.1 (2015): 157-164.
Zonder et al., "A phase 1, multicenter, open-label, dose escalation study of elotuzumab in patients with advanced multiple myeloma." Blood, The Journal of the American Society of Hematology 120.3 (2012): 552-559.
Lev et al., "Tumor-specific Ab-mediated targeting of MHC-peptide complexes induces regression of human tumor xenografts in vivo." Proceedings of the National Academy of Sciences 101.24 (2004): 9051-9056.
International Application Serial No. PCT/US2019/027627, Preliminary Report on Patentability, dated Aug. 18, 2020, 28 pgs.
Von Minckwitz et al., "Phase I clinical study of the recombinant antibody toxin scFv(FRP5)-ETA specific for the ErB2/HER2 receptor in patients with advanced solid malignomas" Breast Cancer Research, 7(5):R617-R626 (2005).
Sieber et al., "Selective internalization of monoclonal antibodies by B-cell chronic lymphocytic leukemia cells", 121(3): 458-461 (2003).
Simsova, M, et al., "The adenylate cyclase toxin from Bordetella pertussis—a novel promising vehicle for antigen delivery to dendritic cells", International Journal of Medical Microbiology, 239, (2004), 571-576.
Sivam, G, et al., "Immunotoxin to a Human Melanoma-associated Antigen: Comparison of Gelonin with Ricin and Other A Chain Conjugates", Cancer Research, 47(12), (1987), 3169-3173.
Skinner et al., "Inhibition of prokaryotic translation by the Shiga toxin enzymatic subunit", Microbial Pathogenesis 24(2) 117-122 (1998).
Skinner et al., "Investigation of ribosome binding by the Shiga Toxin A1 subunit, using competition and site-directed mutagenesis", Journal of Bacteriology 179(4): 1368-1374 (1997).
Smith, DC, et al., "Exogenous Peptides Delivered by Ricin Require Processing by Signal Peptidase for Transporter Associated with Antigen Processing-Independent MHC Class I-Restricted Presentation", The Journal of Immunology, 169(1), (2002), 99-107.
Stenmark, H, et al., "Peptides fused to the amino-terminal end of Diphtheria toxin are translocated to the cytosol", The Journal of Cell Biology, 113(5), (1991), 1025-1032.
Su et al., "Clinical grade production and characterization of a fusion protein comprised of the chemokine CCL2-ligand genetically fused to a mutated and truncated form of the Shiga A1 subunit" Protein Expression and Purification 66(2) 149-157 (2009).
Suh, JK., et al., "Shiga Toxin Attacks Bacterial Ribosomes As Effectively as Eucaryotic Ribosomes", Biochemistry, 37(26), (1998), 9394-9398.
Suhan et al., "Disruption of an Internal Membrane-Spanning Region in Shiga Toxin I Reduces Cytotoxicity", Infection and Immunity 66(11): 5252-5259 (1998).
Tacken, PJ, et al., "Effective induction of naive and recall T-cell responses by targeting antigen to human dendritic cells via a humanized anti-DC-SIGN antibody", Blood, 106(4), (2005), 1278-85.
Tesh et al., "Comparison of the Relative Toxicities of Shiga-Like Toxins Type I and Type II for Mice", Infection and Immunity, 61(8): 3392-3402 (1993).
Thompson et al., "Improved binding of a bivalent single-chain immunotoxin results in increased efficacy for in vivo T-cell depletion", Protein Engineering 14(12): 1035-1041 (2001).
Thorpe, PE, et al., "Cytotoxicity Acquired by Conjugation of an Anti-Thy1.1 Monoclonal Antibody and the Ribosome-Inactivating Protein, Gelonin", European Journal of Biochemistry, 116(3), (1981), 447-454.
Torgersen, ML, et al., "The A-subunit of surface-bound Shiga toxin stimulates clathrin-dependent uptake of the toxin", The FEBS Journal, 272(16), (2005), 4103-4013.
Tosatto et al. "Large-Scale Prediction of Protein Structure and Function from Sequence", Current Pharmaceutical Design, 12(17): 2067-2086 (2006).
Vallera et al., "Bioengineering a unique deimmunized bispecific targeted toxin that simultaneously recognizes human CD22 and CD19 Receptors in a mouse model of B-Cell metastases" Molecular Cancer Therapeutics 9(6) 1872-1883 (2010).
Varner et al., "Recent Advances in Engineering Polyvalent Biological Interactions", Biomacromolecules 16(1): 43-55 (2014).
Vervoordeldonk et al., "Preclinical studies with radiolabeled monoclonal antibodies for treatment of patients with B-cell malignancies" Cancer 73(3) 1006-1011 (1994).
Vingert, B, et al., "The Shiga toxin B-subunit targets antigen in vivo to dendritic cells and elicits anti-tumor immunity", European Journal of Immunology 36(5), (2006) 1124-1135.
Voskoglou-Nomikos, T, et al., "Clinical Predictive Value of the In Vitro Cell Line, Human Xenograft, and Mouse Allograft Preclinical Cancer Models", Clinical Cancer Research 9(11), (2003), 4227-4239.
Wales, R, et al., "Addition of an endoplasmic reticulum retrieval sequence to ricin A chain significantly increases its cytotoxicity to mammalian cells", Journal of Biological Chemistry, 268(32), (1993), 23986-23990.
Wang, E, et al., "T-cell-directed cancer vaccines: the melanoma model", Expert Opinion on Biological Therapy 1(2), (2001), 277-290.
Wargalla et al., "Rate of internalization of an immunotoxin correlates with cytotoxic activity against human tumor cells", Proceedings of the National Academy of Sciences of the USA 86:13 5146-5150 (1989).
Willert et al., "TAK-169, an exceptionally potent CD38 targeted engineered toxin body, as a novel direct cell kill approach for the treatment of multiple myeloma", Proceedings: American Association for Cancer Research (AACR) Annual Meeting 2019, Poster #2384, (Apr. 1, 2019).
Willert, EK, et al., "Engineered toxin bodies: A next-generation immunotoxin scaffold with novel immuno-oncology functionality", Proceedings: American Association for Cancer Research (AACR) Annual Meeting 2015, Poster, Abstract #2477 (Apr. 18, 2015).

(56) References Cited

OTHER PUBLICATIONS

Willert, EK, et al., "Engineered toxin bodies: A next-generation immunotoxin scaffold with novel immuno-oncology functionality", The Journal of Cancer Research, 75(15 Suppl): Abstract # 2477, (Aug. 1, 2015).
Windschiegl, B, et al., "Lipid Reorganization Induced by Shiga Toxin Clustering on Planar Membranes", PLoS One, 4(7), (2009), e6238.
Wirth, R, et al., "Engineered Toxin Body demonstrating CD20-specific binding and cell kill in B-Cell Non-Hodgkin lymphoma cells", [abstract]. In: Proceedings of the 104th Annual Meeting of the American Association for Cancer Research, Cancer Research, Apr. 15, 2013, 73(8 Suppl), Abstract nr 5477.
Wirth, R, et al., "Engineered Toxin Body demonstrating CD20-specific binding and cell kill in B-Cell Non-Hodgkin lymphoma cells", Proceedings: American Association for Cancer Research (AACR) 104th Annual Meeting 2013, Poster, Abstract #5477, (Apr. 6-10, 2013).
Wu et al., "Humanization of a murine monoclonal antibody by simultaneous optimization of framework and CDR residues", J. Mol. Biol. 294: 151-162 (1999).
Wu et al., "Multimerization of a chimeric anti-CD20 single chain Fv-Fc fusion protein is mediated through variable domain exchange", Protein Engineering 14(12):1025-1033 (2001).
Yamasaki et al., "Importance of arginine at position 170 of the A subunit of Vero toxin 1 produced by enterohemorrahagic *Escherichia coli* for toxin activity" Microbial Pathogenesis 11(1) (1991).
Yu et al., "Interaction between Bevacizumab and Murine VEGF-A: A Reassessment", Investigative Ophthamology & Visual Science 49(2) 522-527 (2008).
Zacny et al., "Novel toxin library for the discovery of oncology therapeutics", Cancer Research, (Apr. 2010), 70(8 Suppl), Abstract #5506.
Zapata, G, et al., "Engineering linear F(ab')2 fragments for efficient production in *Escherichia coli* and enhanced antiproliferative activity", Protein Engineering, 8(10), (1995), 1057-1062.
Stepanov et al., "Design of Targeted B Cell Killing Agents", PloS One 6(6) e20991 (2011).
U.S. Appl. No. 14/643,619, Office Action of Jun. 27, 2018, 48 pgs.
U.S. Appl. No. 14/774,130, Office Action of Feb. 27, 2017, 19 pgs.
U.S. Appl. No. 14/774,130, Office Action of Aug. 24, 2017, 20 pgs.
U.S. Appl. No. 14/774,130, Office Action of Oct. 25, 2016, 5 pgs.
U.S. Appl. No. 14/965,882, Office Action of Mar. 22, 2018, 12 pgs.
U.S. Appl. No. 14/965,882, Office Action of Jun. 6, 2017, 19 pgs.
U.S. Appl. No. 15/114,474, Office Action of Jun. 18, 2018, 20 pgs.
U.S. Appl. No. 15/114,474, Office Action of Aug. 24, 2017, 11 pgs.
U.S. Appl. No. 15/114,474, Office Action of Oct. 26, 2017, 24 pgs.
U.S. Appl. No. 15/125,126 Office Action of Dec. 5, 2018, 20 pgs.
U.S. Appl. No. 15/290,266, Office Action of Jun. 27, 2018, 32 pgs.
U.S. Appl. No. 15/317,892, Office Action of Mar. 5, 2018, 22 pgs.
U.S. Appl. No. 15/421,758, Office Action of Apr. 17, 2017, 22 pgs.
Aatsinki et al. "An alternative use of basic pGEX vectors for producing both N- and C-terminal fusion proteins for production and affinity purification of antibodies," Protein Expression and Purification, 40(2), (2005), 287-291.
Ackerman et al., "SLT-VEGF Reduces Lung Metastases, Decreases Tumor Recurrence, and Improves Survival in an Orthotopic Melanoma Model", Toxins 2(9) 224-257 (2010).
Adotevi et al., "B Subunit of Shiga Toxin-Based Vaccines Synergize with α-Galactosylceramide to Break Tolerance against Self Antigen and Elicit Antiviral Immunity", The Journal of Immunology, 179(5), (2007), 3371-3379.
Al-Jaufy et al., "Cytotoxicity of a Shiga Toxin A Subunit-CD4 Fusion Protein to Human Immunodeficiency Virus-Infected Cells", Infection and Immunity, 62(3), (1994), 956-960.
Al-Jaufy et al., "Purification and Characterization of a Shiga Toxin A Subunit-CD4 Fusion Protein Cytotoxic to Human Immunodeficiency Virus-Infected Cells", Infection and Immunity, 63(8), (1995), 3073-3078.

Antignani "Immunotoxins: The Role of the Toxin", Toxins, 5(8), (2013), 1486-1502.
Apostolpoulos et al., "MUC1 peptide epitopes associated with five different H-2 class I molecules", European Journal of Immunology, 27(10), (1997), 2579-2587.
Baker, MP, et al., "Immunogenicity of Protein Therapeutics: the Key Causes, Consequences and Challenges, Self/Nonself", 1(4), (2010), 314-322.
Backer et al., "Shiga-like toxin-VEGF fusion proteins are selectively cytotoxic to endothelial cells overexpressing VEGFR-2", Journal of Controlled Release 74(1-3), 349-355 (2001).
Backer et al., "Targeting Endothelial Cells Overexpressing VEGFR-2: Selective Toxicity of Shiga-like Toxin-VEGF Fusion Proteins", Bioconjugate Chemistry 12(6) 1066-1073 (2001).
Ballard, JD, et al., "Anthrax Toxin as a Molecular Tool for Stimulation of Cytotoxic T Lymphocytes: Disulfide-Linked Epitopes, Multiple Injections, and Role of CD4+ Cells", Infection and Immunity, 66(10), (1998), 4696-4699.
Ballard, JD, et al., "Anthrax Toxin-Mediated Delivery In Vivo and In Vitro of a Cytotoxic T-Lymphocyte Epitope from Ovalbumin", Infection and Immunity, 66(2), (1998), 615-619.
Barnd, DL, et al., "Specific, Major Histocompatibility Complex-Unrestricted Recognition of Tumor-Associated Mucins by Human Cytotoxic T cells", Proceedings of the National Academy of Sciences U.S.A., 86(18), 7159-7163, (1989).
Barratt-Boyes, SM, et al., "Immunization of Chimpanzees with Tumor Antigen MUC1 Mucin Tandem Repeat Peptide Elicits Both Helper and Cytotoxic T-cell Responses", Clinical Cancer Research 5(7), (1999), 1918-1924.
Beers et al., "Antigenic modulation limits the efficacy of anti-CD20 antibodies: implications for antibody selection", Blood 1115(25): 5191-5201 (2010).
Beers et al., "CD20 as a Target for Therapeutic Type I and II Monoclonal Antibodies", Seminars in Hematology 47(2): 107-114(2010).
Beers et al., "Type II (tositumomab) anti-CD20 monoclonal antibody outperforms type I (rituximab-like) reagents in B-cell depletion regardless of complement activation", Blood 112, 4170-4177 (2008).
Bera et al., "A Bivalent Disulfide-stabilized Fv with Improved Antigen Binding to erbB2", Journal of Molecular Biology, 281(3) 475-483 (1998).
Bera et al., "Pharmacokinetics and Antitumor Activity of a Bivalent Disfulside-stabilized Fv Immunotoxin with improved Antigen Binding to erbB2", Cancer Research 59(16): 4018-4022 (1999).
Beum et al., Loss of CD20 and Bound CD20 Antibody from Opsonized B Cells Occurs More Rapidly Because of Trogocytosis Meditated by Fc Receptor-Expressing Effector Cells Than Direct Internalization by the B Cells, Journal of Immunology, 187(6) 3438-3447 (2011).
Beum et al., "The Shaving Reaction: Rituximab/CD20 Complexes Are Removed from Mantle cell Lymphoma and Chronic Lymphocytic Leukemia Cells by THP-1 Monocytes", Journal of Immunology, 176(4) 2600-2609 (2006).
Bevan et al. "Real-time 96-well antibody internalization assays using IncuCyte FabFlour Red Antibody Labeling Reagent, Application Note, Sartorious", Essen BioScience (2017).
Bibby "Orthotopic models of cancer for preclinical drug evaluation: advantages and disadvantages", European Journal of Cancer 40(6), (2004), 852-857.
Bolognesi, A, et al., "A comparison of anti-lymphocyte immunotoxins containing different ribosome-inactivating proteins and antibodies", Clinical & Experimental Immunology, 89(3), (1992), 341-346.
Bonifaz et al., "Efficient Targeting of Protein Antigen to the Dendritic Cell Receptor DEC-205 in the Steady State Leads to Antigen Presentation on Major Histocompatibility Complex Class I Products and Peripheral CD8+ T Cell Tolerance", Journal of Experimental Medicine, 196(12), (2002), 1627-1638.
Boross et al., "Both Activating and inhibitory Fc gamma receptors mediate rituximab-induced trogocytosis of CD20 in mice", Immunology Letters 143(1) 44-52 (2012).
Boross et al., "Mechanisms of action of CD20 antibodies", American Journal of Cancer Research 2(6) 676-690 (2012).

(56) References Cited

OTHER PUBLICATIONS

Braslawsky et al., "Adriamycin(hydrazone)-antibody conjugates require internalization and intracellular acid hydrolysis for antitumor activity", Cancer Immunology 33: 367-374 (1991).
Bray et al., "Probing the surface of eukaryotic cells using combinatorial toxin libraries", Current Biology 11(9) 697-701 (2001).
Brieschke, B, et al., "Antigen Seeding Technology by Engineered Toxin Bodies Provides a Targeted Immuno-Oncology Approach for Treatment of Cancers", Proceedings: American Association for Cancer Research (AACR) Annual Meeting 2018, Poster 2777, Abstract #4912, (2018).
Brieschke, B, et al., "Targeted Engineered Toxin Bodies provide a novel mechanism of action against HER2 positive cancers", Cancer Research, 78 (13 Suppl), (Jul. 2018), Abstract 5769.
Brieschke, B, et al., "Targeted Engineered Toxin Bodies provide a novel mechanism of action against HER2 positive cancers", Proceedings: American Association for Cancer Research (AACR) Annual Meeting 2018, Poster #5769, (Apr. 18, 2018).
Brieschke, B, et al., "Identification and Functional Profiling of PD-L1 Targeted Engineered Toxin Bodies for Antigen Seeding Technology (AST) and Redirection of T cell Response to Tumors", 33rd Annual Meeting of the Society for Immunotherapy of Cancer (SITC), Washington, D.C., Poster # 11078, (Nov. 7-11, 2018).
Brieschke, B, et al., "Identification and functional profiling of PD-L1 targeted engineered toxin bodies for antigen seeding technology and redirection of T cell response to tumors", Journal of ImmunoTherapy of Cancer, 6(Suppl 1): 114, (Nov. 6, 2018), Abstract P9.
Güssow, D, Seemann, G, "Humanization of Monoclonal Antibodies", Methods in Enzymology, 203, (1991), 99-121.
Haddad et al., "Minimum Domain of the Shiga Toxin A subunit Required for Enzymatic Activity", Journal of Bacteriology 175(16) 4970-4978 (1993).
Haicheur, N, et al., "The B Subunit of Shiga Toxin Fused to a Tumor Antigen Elicits CTLand Targets Dendritic Cells to Allow MHC Class I-Restricted Presentation of Peptides Derived from Exogenous Antigens", The Journal of Immunology, 165(6), (2000), 3301-3308.
Haisma et al., "Construction and Characterization of a Fusion Protein Single-Chain Anti-CD20 Antibody and Human beta-glucuronidase for Antibody-Directed Enzyme Prodrug Therapy", Blood 92:1 184-190 (1998).
Hamlin et al., "Safety and Efficacy of Anti-CD20 Immunotoxin MT-3724 in Relapsed/refractory B-cell Non-Hodgkin Lymphoma (NHL) in a Phase 1 study", American Society of Clinical Oncology Annual Meeting—ABSTRACT 7580 (2018).
Harris "Exploiting antibody-based technologies to manage environmental pollution", Trends in Biotechnology, DIAGRAM figure taken from 17(7): 290-296 (1999).
Head et al., Preparation of VT 1 and VT2 Hybrid Toxins from Their Purified Dissociated Subunits. Evidence for B Subunit Modulation of a Subunit Function, Journal of Biological Chemistry, 266(6): 3617-3621 (1991).
Hexham et al., "Influence of relative binding affinity on efficacy in a panel of anti-CD3 scFv immunotoxins", Molecular Immunology 38(5) 397-408 (2001).
Higgins, JP, et al., "Engineered toxin bodies with specific cell kill activity against mesenchymal cells", Cancer Research, 71(8 Suppl), (Apr. 2011), Abstract #1751.
Hiraga et al., "Down-regulation of CD20 expression in B-cell lymphoma cells after treatment with rituximab-containing combination chemotherapies: its prevalence and clinical significance", Blood 113 (20): 4885-4893 (2009).
Holubova, J, et al., "Delivery of Large Heterologous Polypeptides across the Cytoplasmic Membrane of Antigen-Presenting Cells by the Bordetella RTX Hemolysin Moiety Lacking the Adenylyl Cyclase Domain", Infection and Immunity, 80(3), (2012), 1181-1192.
Hooijberg et al., "Characterization of a series of isotype switch variants of new CD20 monoclonal antibody", Hybridoma 15(1) 23-31 (1996).
Hotz et al., "Specific Targeting of Tumor Endothelial Cells by a Shiga-like Toxin-Vascular Endothelial Growth Factor Fusion Protein as a Novel Treatment Strategy for Pancreatic Cancer" Neoplasia 12(10) 797-806 (2010).
Hovde et al., "Evidence that glutamic acid 167 is an active-site residue of Shiga-like toxin-I," Proceedings of the National Academy of Sciences of the United States of America, 85(8) 2568-2572 (1988).
Huang, S, et al., "The CD20-specific engineered toxin antibody MT-3724 exhibits lethal effects against mantle cell lymphoma", Blood Cancer Journal, 8(3), (2018), 33.
Huang et al. "Abstract 3651: Preclinical examination of the effects of MT-3724, an engineered toxin body targeting CD20, in mantle cell lymphoma" AACR Annual Meeting Abstract (2017).
Huang et al. "AACR 2017 | Poster 3651/24—Preclinical examination of the effects of a CD20-specific engineered toxin body, MT-3724, in Mantle Cell Lymphoma" AACR Annual Meeting, Poster 3651/24 (2017).
Iberg, A, et al., "Design and Characterization of Bispecific Engineered Toxin Bodies for Targeted Cancer Therapy", Proceedings: American Association for Cancer Research (AACR) Annual Meeting 2019, Poster #2984, (2019).
International Application Serial No. PCT/US2014/023198, International Search Report dated Sep. 18, 2014 and published Oct. 9, 2014, 5 pgs.
International Application Serial No. PCT/US2014/023198, Written Opinion dated Feb. 12, 2015, 7 pgs.
International Application Serial No. PCT/US2014/023198, Preliminary Report on Patentability dated Jan. 9, 2015 and dated Jul. 15, 2015, 8 pgs.
International Application Serial No. PCT/US2014/023231, International Search Report dated Oct. 24, 2014 and published Dec. 4, 2014, 4 pgs.
International Application Serial No. PCT/US2014/023231, Written Opinion dated Oct. 24, 2014, 6 pgs.
International Application Serial No. PCT/US2014/023231, Preliminary Report on Patentability, dated Sep. 15, 2015, 7 pgs.
International Application Serial No. PCT/US2015/012968, International Search Report dated Jul. 13, 2015 and published Jul. 30, 2015, 8 pgs.
International Application Serial No. PCT/US2015/012968, Written Opinion dated Jan. 11, 2016, 15 pgs.
International Application Serial No. PCT/US2015/012968, Preliminary Report on Patentability, dated Apr. 20, 2016 10 pgs.
International Application Serial No. PCT/US2015/012970, International Search Report dated Jun. 26, 2015 and published Jul. 30, 2015, 5 pgs.
International Application Serial No. PCT/US2015/012970, Written Opinion dated Jun. 26, 2015, 7 pgs.
International Application Serial No. PCT/US2015/012970, Preliminary Report on Patentability, dated Nov. 24, 2015 and dated Apr. 20, 2016, 10 pgs.
International Application Serial No. PCT/US2015/019684, International Search Report dated Jun. 29, 2015 and published Jul. 30, 2015, 6 pgs.
International Application Serial No. PCT/US2015/019684, Written Opinion dated Jun. 29, 2015, 8 pgs.
International Application Serial No. PCT/US2015/019708, International Search Report dated Jun. 29, 2015 and published Sep. 17, 2015, 5 pgs.
International Application Serial No. PCT/US2015/019708, Written Opinion, dated Jan. 2015, 8 pgs.
International Application Serial No. PCT/US2015/019708, Preliminary Report on Patentability, dated Sep. 13, 2016, 9 pgs.
International Application Serial No. PCT/US2015/035179, International Search Report dated Sep. 9, 2015 and published Dec. 17, 2015, 5 pgs.
International Application Serial No. PCT/US2015/035179, Written Opinion dated Sep. 9, 2015, 10 pgs.
International Application Serial No. PCT/US2015/035179, Written Opinion dated May 18, 2016, 9 pgs.
International Application Serial No. PCT/US2015/035179, Preliminary Report on Patentability dated Aug. 12, 2016, 8 pgs.

(56) References Cited

OTHER PUBLICATIONS

International Application Serial No. PCT/US2016/016580, International Search Report dated Apr. 22, 2016 and published Aug. 11, 2016, 4 pgs.
International Application Serial No. PCT/US2016/016580, Written Opinion, dated Apr. 22, 2016 dated Mar. 28, 2016, 5 pgs.
International Application Serial No. PCT/US2016/043902, International Search Report dated Jan. 30, 2017 and published Mar. 9, 2017, 6 pgs.
International Application Serial No. PCT/US2016/043902, Written Opinion dated Jan. 30, 2017, 9 pgs.
International Application Serial No. PCT/US2016/043902, Preliminary Report on Patentability dated Oct. 10, 2017, 7 pgs.
Ishikawa et al., Protection against Shiga Toxin I Challenge by Immunization of Mice with Purified Mutant Shiga Toxin 1., Infection and Immunity 71(6) 3235-3239 (2003).
Jackson et al., "Mutational analysis of the Shiga Toxin and Shiga-like toxin II enzymatic subunits", Journal of Bacteriology 172(6) 3346-3350 (1990).
Jackson, ME, et al., "The KDEL retrieval system is exploited by Pseudomonas exotoxin A, but not by Shiga-like toxin-1, during retrograde transport from the Golgi complex to the endoplasmic reticulum", Journal of Cell Science, 112 (4), (1999), 467-475.
Jain, RK, "Barriers to Drug Delivery in Solid Tumors", Scientific American 271(1), (1994), 58-65.
Jilani et al., "Anti-Idiotype versus anti-mouse Ig for detecting ritumixab", Blood 103(10): 3990 (2004).
Jilani et al., "Transient down-modulation of CD20 by rituximab in patients with chronic lymphocytic leukemia", Blood 102(10) 3514-3520 (2003).
Chatterjee, S. et al., "Noninvasive Imaging of Immune Checkpoint Ligand PD-L1 in Tumors and Metastases for Guiding Immunotherapy," Molecular Imaging, 16:1-5 (2017).
Gielis, S. et al., "Detection of Enriched T Cell Epitope Specificity in Full T Cell Receptor Sequence Repertoires," Frontiers in Immunology, vol. 10, Article 2820, pp. 1-2.
Grotzke, J. E. et al., "The ongoing saga of the mechanism(s) of MHC class I-restricted cross-presentation," Current Opinion in Immunology, 46:89-96 (2017).
Hegde, N. R. et al., "The use of databases, data mining and immunoinformatics in vaccinology: where are we?" Expert Opinion on Drug Discovery, 13(2): 117-130 (2018).
Kar, P. et al., "Current methods for the prediction of T-cell epitopes," Peptide Science, 110:e24046 (2018); https://doi.org/10.1002/pep2.24046, 17 pages.
Li, Y. et al., "Correction to: Discovery and preclinical characterization of the antagonist anti-PD-L1 monoclonal antibody LY3300054," Journal for ImmunoTherapy of Cancer, vol. 6, No. 1, Jun. 2018, p. 1.
Meeting Abstracts, "33rd Annual Meeting & Pre-Conference Programs of the Society for Immunotherapy of Cancer (SITC 2018)," Washington, D.C., USA, Nov. 7-11, 2018, Journal for ImmunoTherapy of Cancer, vol. 6, Supplement No. 1, Nov. 2018, pp. 1-205.
Meeting Abstracts, "34th Annual Meeting & Pre-Conference Programs of the Society for Immunotherapy of Cancer (SITC 2019): Part 2: National Harbor, MD, USA, Nov. 10, 2019," Journal for ImmunoTherapy of Cancer, vol. 7, Supplement No. 1, Nov. 2019, pp. 1-237, Abstract P804.
Moise, L. et al., "T cell epitope engineering: an avian H7N9 influenza vaccine strategy for pandemic preparedness and response," Human Vaccines & Immunotherapeutics, 14(9):2203-2207 (2018).
Molecular Templates Inc.: R&D Day, Conference Call Transcript (Nov. 15, 2019) Fair Disclosure Wire, pp. 1-17; retrieved on Jan. 15, 2021 from https://dialog.proquest.com/professional/docview/2320577373, 17 pages.
Ogishi, M. & Yotsuyanagi, H., "Quantitative Prediction of the Landscape of T Cell Epitope Immunogenicity in Sequence Space," Frontiers in Immunology, vol. 10, Article 827, pp. 1-20.
Rosenthal, A. et al., "A phase 2 study of lenalidomide, rituximab, cyclophosphamide, and dexamethasone (LR-CD) for untreated low-grade non-Hodgkin lymphoma requiring therapy," Am J Hematol., 92(5):467-472 (2017).
Schumacher, F.-R. et al., "Building proteomic tool boxes to monitor MHC class I and class II peptides," Proteomics, 17(1-2):1600061, 16 pages; doi:10.1002/pmic.201600061.
Strop, P. et al., "Location Matters: Site of Conjugation Modulates Stability and Pharmacokinetics of Antibody Drug Conjugates," Chemistry & Biology, 20:161-167 (2013).
Johannes et al., "Shiga toxins—from cell biology to biomedical applications" Nature Reviews Microbiology 8(2) 105-116 (2010).
Johannes, L, Decaudin, D, "Protein toxins: intracellular trafficking for targeted therapy" Gene Therapy, 12(18), (2005), 1360-1368.
Johannes, L, et al., "Retrograde Transport of KDEL-bearing B-fragment of Shiga Toxin", Journal of Biological Chemistry, 272(31), (1997), 19554-19561.
Johnson, N, et al., "Construction of an epitope vector utilizing the diphtheria toxin B-subunit", FEMS Microbiology Letters, 146(1), (1997), 91-96.
Jones "Critically Assessing the State-of-the-art in Protein Structure Prediction", The Pharmacogenomics Journal, 1(2): 126-134 (2001).
Jubala et al., "CD20 Expression in Normal Canine B cells and in Canine non-Hodgkin Lymphoma", Veterinary Pathology 42:4 468-476 (2005).
Karanikas et al., "Antibody and T Cell Responses of Patients with Adenocarcinoma Immunized with Mannan-MUC1 Fusion Protein", Journal of Clinical Investigation, 100(11): 2783-2792 (1997).
Kelland, LR, "'Of mice and men': values and liabilities of the athymic nude mouse model in anticancer drug development", European Journal of Cancer 40(6), (2004), 827-836.
Kim et al., "A fold-back single chain diabody format enhances the bioactivity of an anti-monkey CD3 recombinant diphtheria toxin-based immunotoxin", Protein Engineering 20(9) 425-432 (2007).
Kotera et al., "Humoral Immunity against a Tandem Repeat Epitope of Human Mucin MUC-1 in Sera from Breast, Pancreatic, and Colon Cancer Patients", Cancer Research 54(11): 2856-2860 (1994).
Kurmanova et al., "Structural requirements for furin-induced cleavage and activation of Shiga toxin", Biochemical and Biophysical Research Communications 357(1) 144-149 (2007).
Kyu, E, "Characterization of the A subunit mutants of Stx1 and Stx2 in *Saccharomyces cerevisiae*", thesis, Rutgers, The State University of New Jersey, New Brunswick, retrieved from http://dx.doi.org/doi:10.7282/T34F1QWJ (2009).
Lambert et al., "Purified Immunotoxins that are reactive with Human Lymphoid Cells: Monoclonal antibodies conjugated to the ribosome-inactivating proteins gelonin and the pokeweed antiviral proteins", Journal of Biological Chemistry 260(22) 12035-12041 (1985).
Lapointe et al., "A Role for the Protease-sensitive Loop Region of Shiga-like Toxin 1 in the Retrotranslocation of its A Domain from the Endoplasmic Reticulum Lumen", Journal of Biological Chemistry 280(24): 23310-23318 (2005).
Laske et al., "Intraventricular Immunotoxin Therapy for Leptomeningeal Neoplasia", Neurosurgery, 41(5): 1039-1051 (1997).
Law et al., "Efficient Elimination of B-Lineage Lymphomas by Anti-CD20-Auristatin Conjugates", Clinical Cancer Research 10(23) 7842-7851 (2004).
Lazar et al., "Transforming Growth Factor alpha: Mutation of Aspartic Acid 47 and Leucine 48 Results in Different Biological Activities", Molecular and Cellular Biology, 8(3): 1247-1252 (1988).
Lea et al., "Proteolytic cleavage of the A subunit is essential for maximal cytotoxicity of *Escherichia coli* O157:h7 Shiga-like toxin-1", Microbiology 145(5): 999-1004 (1999).
Lee, RS, et al., "Major histocompatibility complex class I presentation of exogenous soluble tumor antigen fused to the B-fragment of Shiga toxin", European Journal of Immunology, 28, (1998), 2726-2737.
Lehmann, CHK, et al., "Direct Delivery of Antigens to Dendritic Cells via Antibodies Specific for Endocytotic Receptors as a Promising Strategy for Future Therapies", Vaccines, 4(2):1-32 (2016).

(56) References Cited

OTHER PUBLICATIONS

Li et al., "Development of Novel Tetravalent Anti-CD20 Antibodies with Potent Antitumor Activity", Cancer Research 68(7) 2400-2408 (2008).
Li et al., "The CD20 Calcium Channel is Localized to Microvilli and Constitutively Associated with Membrane Rafts: Antibody binding increases the affinity of the association through an epitope-dependent cross-linking-independent mechanism", Journal of Biological Chemistry 279(19): 19893-19901 (2004).
Lim et al., "Fc gamma receptor IIb on target B cells promotes rituximab internalization and reduces clinical efficacy", Blood 118(9): 2530-2540 (2011).
Ling et al., "Structure of the Shiga-like Toxin I B-Pentamer Complexed with an Analogue of Its Receptor Gb3", Biochemistry, 37(7): 1777-1788 (1998).
Giansanti et al., "Strategies to Improve the Clinical Utility of Saporin-Based Targeted Toxins" Toxins 10(82): 1-32 (2018).
Harwerth et al., Monoclonal Antibodies against the Extracellular Domain of the erbB-2 Receptor Function as Partial Ligand Agonists, Journal of Biol. Chem 267(21):15160-15167 (1992).
Li et al., "Clinical targeting recombinant immunotoxins for cancer therapy", Onco Targets and Therapy 10:3645-3665 (2017).
Luqman et al., "The antileukemia activity of a human antiCD40 antagonist antibody, HCD122, on human chronic lymphocytic leukemia cells", Blood 112(3) 711-720 (2008).
Lyu et al., "Cell-targeting fusion constructs containing recombinant gelonin", Methods in Enzymology vol. 502 167-214 (2012).
Maak, M, et al., "Tumor-Specific Targeting of Pancreatic Cancer with Shiga Toxin B-Subunit", Molecular Cancer Therapeutics, 10(10), (2011), 1918-1928.
Mallard, F, et al., "Direct Pathway from Early/Recycling Endosomes to the Golgi Apparatus Revealed through the Study of Shiga Toxin B-fragment Transport", The Journal of Cell Biology, 143(4), (1998), 973-990.
Mascarell, L, et al., "Induction of Neutralizing Antibodies and Th1-Polarized and CD4-Independent CD8+ T-Cell Responses following Delivery of Human Immunodeficiency Virus Type 1 Tat Protein by Recombinant Adenylate Cyclase of Bordetella pertussis", Journal of Virology, 79(15), (2005), 9872-9884.
Mazor et al., "chFRP5-ZZ-PE38, a large IgG-toxin immunoconjugate outperforms the corresponding smaller FRP5 (Fv)-ETA immunotoxin in eradicating ErbB2-expressing tumor xenografts", Cancer Letters, 257(1) 124-135: (2007).
Mazor, R, et al., "Identification and elimination of an immunodominant T-cell epitope in recombinant immunotoxins based on Pseudomonas exotoxin A", Proceedings of the National Academy of Sciences U.S.A., 109(51), (2012), E3597-E3603.
McCluskey et al., "Charged and hydrophobic Surfaces on the A chain of Shiga-like Toxin 1 recognize the C-terminal Domain of Ribosomal Stalk Proteins," PLoS One 7(2): (2012).
McCluskey et al., "Shiga-like Toxin 1: Molecular Mechanism of Toxicity and Discovery of Inhibitors", thesis University of Toronto (2010).
McCluskey, AJ, et al., "The Catalytic Subunit of Shiga-like Toxin 1 Interacts with Ribosomal Stalk Proteins and is Inhibited by Their Conserved C-Terminal Domain", Journal of Molecular Biology, 378(2), (2008), 375-386.
McKenzie, J, et al., "Passage through the Golgi is necessary for Shiga toxin B subunit to reach the endoplasmic reticulum", The FEBS Journal, 276(6), (2009), 1581-1595.
Michel et al., "Intracellular Accumulation of the Anti-CD20 Antibody 1F5 in B-Lymphoma Cells", Clinical Cancer Research 8(8) 2701-2713 (2002).
Miller et al., "Design, Construction, and In-Vitro analyses of Multivalent Antibodies", Journal of Immunology 170(9) 4854-4861 (2003).
Minckwitz et al., "Phase I clinical study of the recombinant antibody toxin scFv(FRP5)-ETA specific for the ErbB2/HER2 receptor in patients with advanced solid malignomas" Breast Cancer Research 7(5): 617-626 (2005).

Newland et al., "Cloning of Genes for Production of *Escherichia coli* Shiga-Like Toxin Type II", Infection and Immunity, 55(11): 2675-2680 (1987).
Ninkovic, T, et al., "Identification of O-glycosylated decapeptides within the MUC1 repeat domain as potential MHC class I (A2) binding epitopes", Molecular Immunology 47(1), (2009), 131-140.
Noakes et al., "Exploiting retrograde transport of Shiga-like Toxin 1 for the delivery of exogenous antigens into the MHC class I presentation pathway" FEBS Letters 453(1-2) 95-99 (1999).
Ohmura et al., "Characterization of non-toxic mutant toxins of Vero toxin I that were constructed by replacing amino acids in the A subunit", Microbial Pathogenesis 15(3): 169-176 (1993).
Olafsen et al., "ImmunoPET imaging of B-cell lymphoma using anti-CD20 scFv dimers (diabodies)", Protein Engineering, Design & Selection 23(4): 243-249 (2010).
Olafsen et al., "Recombinant Anti-CD20 Antibody fragments for Small-Animal PET Imaging of B-Cell Lymphomas", Journal of Nuclear Medicine 50(9): 1500-1508 (2009).
Oloomi et al., "In vivo characterization of Fusion Protein Comprising of A1 Subunit of Shiga Toxin and Human GM-CSF: Assessment of Its immunogenicity and Toxicity", Iranian Biomedical Journal, 14(4) 136-141 (2010).
Onda, M, et al., "An immunotoxin with greatly reduced immunogenicity by identification and removal of B cell epitopes", Proceedings of the National Academy of Sciences U.S.A., 105(32), (2008), 11311-11316.
Osicka, R, et al., "Delivery of CD8+ T-cell epitopes into major histocompatibility complex class I antigen presentation", Infection and Immunity, 68(1), (2000), 247-256.
Brigotti, M, et al., "Damage to Nuclear DNA Induced by Shiga Toxin 1 and Ricin in Human Endothelial Cells", The FASEB Journal, 16(3), (2002), 365-372.
Brigotti et al., Change in Conformation with Reduction of alpha-Helix Content Causes Loss of Neutrophil Binding Activity in Fully Cytotoxic Shiga Toxin 1, The Journal of Biological Chemistry 286(40) 34514-34521 (2011).
Bujny et al., "The retromer component sorting nexin-1 is required for efficient retrograde transport of Shiga toxin from early endosome to the trans Golgi network", Journal of Cell Science, 120(Pt 12), (2007), 2010-2021.
Burgess et al., "Proteolytic cleavage at arginine residues within the hydrophillic disulphide loop of the *Escherichia coli* Shiga-like toxin I A subunit is not essential for cytotoxicity", Molecular Microbiology 10(1) 171-179 (1993).
Cao et al., "Construction of mutant genes for a non-toxic verotoxin 2 variant (VT2vp1) of *Escherichia coli* and characterization of purified mutant toxins", Microbiology and Immunology, 38(6) 441-447 (1994).
Cao et al., "Design optimization and characterization of Her2/neu-targeted immunotoxins: comparative in vitro and in vivo efficacy studies" Oncogene 33(4):1-11 (2013).
Carbonetti, NH, "Pertussis toxin and adenylate cyclase toxin: key virulence factors of Bordetella pertussis and cell biology tools", Future Microbiology 5, (2010), 455-469.
Carbonetti, NH, et al., "Intracellular Delivery of a Cytolytic T-Lymphocyte Epitope Peptide by Pertussis Toxin to Major Histocompatibility Complex Class I without Involvement of the Cytosolic Class I Antigen Processing Pathway", Infection and Immunity, 67(2), (1999), 602-607.
Carbonetti, NH, et al., "Stimulation of HIV gp120-specific cytolytic T lymphocyte responses in vitro and in vivo using a detoxified pertussis toxin vector", AIDS Research and Human Retroviruses, 17(9), (2001), 819-827.
Casalini et al., "Use of combination of Monoclonal Antibodies Directed Against three distinct epitopes of a Tumor-Associated Antigen: Analysis of Cell-Binding and Internalization", International Journal of Cancer, 48:2 284-290 (1991).
Cheung et al., "An evolved ribo-inactivating protein targets and kills human melanoma cells in vitro and in vivo", Molecular Cancer 9(28):1-14 (2010).
Cheung et al., "A Ribosome-inactivating Protein Toxin as a Template for Cancer Drug Discovery", thesis, University of Toronto, (2012), retrieved from http://hdl.handle.net/1807/33952.

(56) References Cited

OTHER PUBLICATIONS

Cizeau, J, et al., "Fusogenics: A Recombinant Immunotoxin-Based Screening Platform to Select Internalizing Tumor-Specific Antibody Fragments", Journal of Biomolecular Screening 16(1), (2011), 90-100.

Cizeau, JPA, et al., "DeBouganin: A de-immunized toxin payload and its applications in oncology", 8th Fabisch-Symposium, 3rd Targeted Tumor Therapies, Berlin 2012, Mar. 21, 2012.

Cleton-Jansen et al., "A Single Amino Acid Substitution Changes the Substrate Specificity of Quinoprotein Glucose Dehydrogenase in Gluconobacter oxydans", Molecular and General Genetics, 229(2): 206-212 (1991).

Cragg et al., "Apparent modulation of CD20 by rituximab: an alternative explanation", Blood 103(10) 3889-3990 (2004).

Cuesta et al., "Mutivalent antibodies: when design surpasses evolution", Trends in Biotechnology, 28(7): 355-362 (2010).

Dadaglio, G, et al., "Induction of a Polarized Th1 Response by Insertion of Multiple Copies of a Viral T-Cell Epitope into Adenylate Cyclase of Bordetella pertussis", Infection and Immunity, 68(7), (2000), 3867-3872.

Dadaglio, G, et al., "Recombinant adenylate cyclase toxin of Bordetella pertussis induces cytotoxic T lymphocyte responses against HLA*0201-restricted melanoma epitopes", International Immunology, 15(12), (2003), 1423-1430.

Dekker et al., "Engineered Toxin Bodies delivering immunogenic MHC class 1 peptides to tumor cells summon polyfunctional and relevant CTL responses against cancers", Presented at: IMMUNOLOGY 2019™, Annual Meeting of the American Association of Immunologists, May 10, 2019, The American Association of Immunologists, Inc., San Diego, Abstract 1791.

Deresiewicz et al., "Identification of amino acids critical for the cytotoxicity of Shiga Toxin I A-chain", Biochemistry 31(12) 3272-3280 (1992).

Dermer, GB, "Another Anniversary for the War on Cancer", Bio/Technology 12, (1994), 320.

Di et al., "Identification of amino acids critical for the cytotoxicity of Shiga toxin 1 and 2 in *Saccharomyces cerevisiae*", Toxicon 57(4) 525-539 (2011).

Doling, AM, et al., "Cytotoxic T-Lymphocyte Epitopes Fused to Anthrax Toxin Induce Protective Antiviral Immunity", Infection and Immunity, 67(7), (1999), 3290-3296.

Donnelly, JJ, et al., "Targeted delivery of peptide epitopes to class I major histocompatibility molecules by a modified Pseudomonas exotoxin", Proceedings of the National Academy of Sciences U.S.A., 90, (1993), 3530-3534.

Engedal, N, et al., "Shiga toxin and its use in targeted cancer therapy and imaging", Microbial Biotechnology, 4(1), (2011), 32-46.

EP 14720298.0, Office Action dated Oct. 21, 2016, 6 pgs.

EP 14720298.0, Office Action dated Jun. 23, 2017, 6 pgs.

Eriksson, K, et al., "Coupling of antigen to cholera toxin for dendritic cell vaccination promotes the induction of MHC class I-restricted cytotoxic T cells and the rejection of a cognate antigen-expressing model tumor", European Journal of Immunology, 34(5), (2004), 1272-1281.

Ewers et al., "Lipid-Mediated Endocytosis", Cold Spring Harbor Perspectives in Biology 3(8) 1-14 (2011).

Fanale, MA, et al., "Phase I/Ib study of the novel CD20-targeted immunotoxin MT-3724 in relapsed/refractory non-Hodgkin's B-cell lymphoma", Proceedings of the 107th Annual Meeting of the American Association for Cancer Research (AACR), Poster, Abstract #CT049, (Apr. 16-20, 2016).

Fanale, MA, et al., "Phase I/Ib study of the novel CD20-targeted immunotoxin MT-3724 in relapsed/refractory non-Hodgkin's B-cell lymphoma", Cancer Research, 76(14 Suppl), (Jul. 2016), Abstract nr CT049.

Fayolle, C, et al., "Delivery of Multiple Epitopes by Recombinant Detoxified Adenylate Cyclase of Bordetella pertussis Induces Protective Antiviral Immunity", Journal of Virology, 75(16), (2001), 7330-7338.

Fayolle, C, et al., "Therapy of Murine Tumors with Recombinant Bordetella pertussis Adenylate Cyclase Carrying a Cytotoxic T Cell Epitope", The Journal of Immunology, 162(7), (1999), 4157-4162.

Filpula, D, "Releasable PEGylation of Mesothelin Targeted Immunotoxin SSIP Achieves Single Dosage Complete Regression of a Human Carcinoma in Mice", Bioconjugate Chemistry, 18(3): 773-784 (2007).

Freshney, RI, "Culture of Animal Cells: A Manual of Basic Technique", Alan R. Liss, Inc., 1983, New York, pp. 3-4.

Gannon et al., "Molecular cloning and nucleotide sequence of another variant of the *Escherichia coli* Shiga-like toxin II family", Journal of General Microbiology 136(6): 1125-1135 (1990).

Garred et al., "Furin-induced cleavage and activation of Shiga toxin", Journal of Biological Chemistry, 270(18), (1995), 10817-10821.

Garred et al., "Role of processing and intracellular transport for optimal toxicity of Shiga toxin and toxin mutants", Experimental Cell Research 218(1) 39-49 (1995).

Gavrilov et al., "Effects of Glycosylation on Antigenicity and Immunogenicity of Classical Swine Fever Virus Envelope Proteins", Virology, 420(2):135-145 (2011).

Gendler et al., "A Highly Immunogenic Region of a Human Polymorphic Epithelial Mucin Expressed by Carcinomas Is Made Up of Tandem Repeats", Journal of Biological Chemistry, 263(26): 12820-12823 (1988).

Ghetie et al., "Homodimers but not monomers of Rituxan (chimeric anti-CD20) induce apoptosis in human B-lymphoma cells and synergize with a chemotherapeutic agent and an immunotoxin", Blood 97(5) 1392-1398 (2001).

Gilliland, DG, et al., "Antibody-directed cytotoxic agents: use of monoclonal antibody to direct the action of toxin A chains to colorectal carcinoma cells", Proceedings of the National Academy of Sciences of the United States of America, 77(8), (1980), 4539-43.

Glennie et al., "Mechanisms of killing by anti-CD20 monoclonal antibodies", Molecular Immunology 44(16) 3823-3837 (2007).

Gong, J, et al., "Selection and characterization of MUC1-specific CD8+ T cells from MUC1 transgenic mice immunized with dendritic-carcinoma fusion cells", Immunology, 101(3), (2000), 316-324.

Gordon et al., "An enzymatic Mutant of Shiga-like Toxin II Variant is a vaccine Candidate for Edema Disease of Swine", Infection and Immunity 60(2): 485-490 (1992).

Goulet et al. ,"Conjugation of Blocked Ricin to an Anti-CD19 Monoclonal Antibody Increases Antibody-Induced cell Calcium Mobilization and CD19 Internalization", Blood 90(6) 2364-2375 (1995).

Grant, K, et al., "Abstract 1380: Engineered toxin bodies with specific activity against EGFR and HER2 expressing cells" Proceedings of the 102nd Annual Meeting of the American Association for Cancer Research (AACR); Apr. 2-6, 2011; The Journal of Cancer Research, 71 (8 Suppl): Abstract #1380, (Apr. 2011).

Guermonprez, P, et al., "Les Toxines Bacteriennes Recombinantes: De Nouveaux Vecteurs Pour La Vaccination?", M/S Medecine Sciences, Societe Des Periodiques Flammarion, 16(5), (2000), 653-662 (English abstract only).

Guermonprez, P, et al., "The Adenylate Cyclase Toxin of Bordetella pertussis Binds to Target Cells via the αMβ2 Integrin (CD11b/CD18)", Journal of Experimental Medicine, 193(9), (2001), 1035-1044.

Pai-Scherf, LH, et al., "Hepatotoxicity in Cancer Patients Receiving erb-38, a Recombinant Immunotoxin that targets the erbB2 Receptor", Clinical Cancer Research, 5(9), (1999), 2311-2315.

Pastan et al., "Immunotoxin Treatment of Cancer" Annual Review of Medicine 58 221-237 (2007).

Paul "Fundamental Immunology" 3rd Edition Raven Press 292-295 (1993).

Peng, KW, et al., "Oncolytic measles viruses displaying a single-chain antibody against CD38, a myeloma cell marker", Blood, 101(7), (2003), 2557-2562.

Perampalam, S et al., "Designing combinatorial protein libraries based on a protein toxin template", Molecular and Cellular Proteomics, 2(9), (2003), 825-915.

Perampalam, S et al., "Designing combinatorial protein libraries based on a protein toxin template", HUPO 2nd Annual & IUBMB

(56) References Cited

OTHER PUBLICATIONS

IXI World Congress, Oct. 8-11, Montreal, Poster Session 28 Proteomics & Biotechnology, 80.16 (Oct. 2003).

Perampalam et al., "Cell-targeted Ribsosome-Inactivating Proteins derived from Protein Combinatorial Libraries", Thesis—University of Toronto (2008).

Peterson, JK, et al., "Integrating pharmacology and in vivo cancer models in preclinical and clinical drug development", European Journal of Cancer 40(6), (2004), 837-844.

Pirie et al., "Convergent Potency of Internalized Gelonin Immunotoxins across Varied Cell Lines, Antigens, and Targeting Moieties", Journal of Biological Chemistry 286(6): 4165-4172 (2011).

Pisarev, VM, et al., "T cells recognize PD(N/T)R motif common in a variable number of tandem repeat and degenerate repeat sequences of MUC1", International Immunopharmacology 5(2), (2005), 315-330.

Polito et al., "Saporin-S6: A Useful Tool in Cancer Therapy", Toxins 5: 1698-1722 (2013).

Polito et al., "The Conjugate Rituximab/saporin-S6 completely inhibits clonogenic growth of CD20-expressing cells and produces a synergistic toxic effect with Fludarabine", Leukemia 18(7): 1215-1222 (2004).

Polson et al., "Antibody-Drug Conjugates for the Treatment of Non-Hodgkin's Lymphoma: Target and Linker-Drug Selection," Cancer Research 69(6) 2358-2364 (2009).

Press et al., "Endocytosis and degradation of Monoclonal Antibodies Targeting Human B-Cell Malignancies", Cancer Research 49(17): 4906-4912 (1989).

Promega, Technical Reference, Amino Acids (2018).

Press et al., "Retention of B-Cell Specific Monoclonal Antibodies by Human Lymphoma Cells", Blood 83(5) 1390-1397 (1994).

Preville, X, et al., "Eradication of Established Tumors by Vaccination With Recombinant Bordetella pertussis Adenylate Cyclase Carrying the Human Papillomavirus 16 E7 Oncoprotein", Cancer Research, 65(2), (2005), 641-649.

Protein ID ABM97743, European Molecular Biology Laboratory (EMBL), Oloomi, M, et al., "synthetic construct partial A1-GMCSF chimeric protein", Sep. 10, 2007.

Ramos et al., "The safety and efficacy profile of a PD-L1 directed Engineered Toxin Body, as a novel targeted direct-cell kill approach for the treatment of PD-L1 expressing cancers" Proceedings: American Association for Cancer Research (AACR) Annual Meeting 2019, Poster#3900, (2019).

Rajagopalan et al.,"CD-20 Specific Engineered Toxin Body Demonstrates Direct Cell Kill of Multiple B-Cell Non-Hodgkin's Lymphoma Types" Blood 122(21) 5152 (2013).

Rajagopalan, S, et al., "A novel targeted engineered toxin body for treatment of HER2 positive breast cancer", Proceedings: Thirty-Seventh Annual CTRC-AACR San Antonio Breast Cancer Symposium, Poster, #P4-15-17, (Dec. 9-13, 2014).

Rajagopalan, S, et al., "CD20-specific Engineered Toxin Body demonstrates direct cell kill of multiple B-cell Non-Hodgkin's lymphoma types", The Journal of Cancer Research, 74(19 Suppl): Abstract # 647, (Oct. 1, 2014); Proceedings: AACR Annual Meeting 2014; Apr. 5-9, 2014.

Rajagopalan, S, et al., "CD38-specific engineered toxin body: Therapeutic potential for multiple myeloma", The Journal of Cancer Research, 74(19 Suppl): Abstract #671, (Oct. 1, 2014) from American Association for Cancer Research (AACR) Annual Meeting 2014, (Apr. 5-9, 2014).

Rajagopalan, S, et al., "HER2-targeted engineered toxin body demonstrates selective binding and cell kill of HER2-overexpressing breast cancer", Proceedings: American Association for Cancer Research (AACR) Annual Meeting 2013, Poster, (Apr. 6-10, 2013).

Rajagopalan, S, et al., "HER2-targeted engineered toxin body demonstrates selective binding and cell kill of HER2-overexpressing breast cancer", The Journal of Cancer Research, 73(8 Suppl): Abstract #868, (Apr. 15, 2013).

Rajagopalan, S, et al., "Next-generation engineered toxin bodies: CD38, PD-L1 and HER2 targeted ETBs", The Journal of Cancer Research, 76(14 Suppl), (Jul. 15, 2016), Abstract #595 from American Association for Cancer Research (AACR) Annual Meeting 2016, (Apr. 16-20, 2016).

Ramakrishnan, S, and Houston, L, "Comparison of the Selective Cytotoxic Effects of Immunotoxins Containing Ricin A Chain or Pokeweed Antiviral Protein and Anti-Thy 1.1. Monoclonal Antibodies", Cancer Research, 44(1), (1984), 201-208.

Robinson, GL, et al., "In vivo efficacy of a CD38-specific engineered toxin body", Clinical Cancer Research, 21(17 Suppl), (Sep. 1, 2015), Abstract A15.

Robinson, GL, et al., "In vivo efficacy of a CD38-specific engineered toxin body", Proceedings: American Association for Cancer Research (AACR) Special Conference on Hematologic Malignancies: Translating Discoveries to Novel Therapies, Poster A15 (Sep. 21, 2015).

Robinson, GL, et al., "MT-3724, an engineered toxin body targeting CD20 for non-Hodgkin's lymphoma", Proceedings of the 107th Annual Meeting of the American Association for Cancer Research, Cancer Research, Jul. 15, 2016, 76(14 Suppl), Abstract 1483.

Robinson, GL, et al., "MT-4019: a de-immunized engineered toxin body targeting CD38 for multiple myeloma", Proceedings: American Association for Cancer Research (AACR) Annual Meeting 2017, Poster, Abstract 2659 (Apr. 1-5, 2017).

Romaniuk, SI, et al., "Recombinant Diphtheria toxin derivatives: Perspectives of application", Russian Journal of Bioorganic Chemistry, 38(6), (2012), 565-577.

Rossi et al., "Novel Designs of Multivalent Anti-CD20 Humanized Antibodies as Improved Lymphoma Therapeutics", Cancer Research 68(20) 8384-8392 (2008).

Roudkenar et al., "Selective cytotoxicity of recombinant STXA1-GM-CSF protein in hematopoietic cancer cells", Cell Biology and Toxicology 22(3) 213-219 (2006).

Rudikoff et al., "Single amino acid substitution altering antigen-binding specificity", Proceedings of the National Academy of Sciences of the USA 79:6 1979-1983 (1982).

Saijo, N, "What are the reasons for negative phase III trials of molecular-target-based drugs?", Cancer Science 95(10), (2004), 772-776.

Sandvig et al., "Entry of Shiga Toxin into Cells", Zentralblatt fur Bakteriologie 278(2-3): 296-305 (1993).

Sandvig, K, et al., "Protein toxins: mode of action and cell entry," Biochemical Society Transactions, 20(4), (1992), 724-727.

Saron, MF, et al., "Anti-viral protection conferred by recombinant adenylate cyclase toxins from Bordetella pertussis carrying a CD8+ T cell epitope from lymphocytic choriomeningitis virus", Proceedings of the National Academy of Sciences U.S.A., 94(7), (1997), 3314-3319.

Schindler et al., "A Phase I Study of a Combination of anti-CD19 and anti-CD22 Immunotoxins (Combotox) in Adult Patients with Refractory B-Lineage Acute Lymphoblastic Leukaemia", British Journal of Haematology, 154(4): 1-11 (2011).

Schlecht, G, et al., "Antigen Targeting to CD11b Allows Efficient Presentation of CD4+ and CD8+ T Cell Epitopes and In Vivo Th1-Polarized T Cell Priming", The Journal of Immunology, 173(10), (2004), 6089-6097.

Schuh, JC, "Trials, Tribulations, and Trends in Tumor Modeling in Mice", Toxicologic Pathology 32 (Suppl. 1), (2004), 53-66.

Schultz et al., "A Tetravalent Single-chain Antibody-Streptavidin Fusion Protein for Pretargeted Lymphoma Therapy", Cancer Research 60(23): 6663-6669 (2000).

Sebo, P, et al., "Cell-Invasive Activity of Epitope-Tagged Adenylate Cyclase of Bordetella pertussis allows In Vitro Presentation of a Foreign Epitope to CD8+ Cytotoxic T Cells", Infection and Immunity, 63(10), (1995), 3851-3857.

Sebo, P, et al., "In vivo induction of CTL responses by recombinant adenylate cyclase of Bordetella pertussis carrying multiple copies of a viral CD8+ T-cell epitope", FEMS Immunology & Medical Microbiology, 26(2), (1999), 167-173.

Shan et al., "Characterization of scFV-Ig Constructs Generated from the Anti-CD20 mAb 1F5 Using Linker Peptides of Varying Lengths", Journal of Immunology 162(11): 6589-6595 (1999).

(56) References Cited

OTHER PUBLICATIONS

Shaw, CA, et al., "Stimulation of CD8+ T Cells following Diphtheria Toxin-Mediated Antigen Delivery into Dendritic Cells", Infection and Immunity, 74(2), (2006), 1001-1008.

Shen et al., "Evaluation of four CD22 Antibodies as Ricin A Chain-Containing Immunotoxins for the In Vivo Therapy of Human B-Cell Leukemias and Lymphomas", International Journal of Cancer 42(5): 792-797 (1988).

Shete, V, "Generation and Characterization of Random Site-Directed Mutants of Shiga-Like Toxin 1A by *Escherichia coli* O157:H7 in *Saccharomyces cerevisiae*", thesis, Rutgers, The State University of New Jersey, New Brunswick, (2009), retrieved from http://dx.doi.org/doi:10.7282/T300029Z.

Shiba, Y, et al., "AGAP2 regulates retrograde transport between early endosomes and the TGN", Journal of Cell Science, 123(Pt 14), (2010), 2381-2390.

UniProtKB/Swiss-Prot P09385 (STXA_BP933), Shiga-like toxin 2 subunit A, retrieved from https://www.ncbi.nlm.nih.gov/protein/P09385.2 on Jan. 10, 2018.

Weinstein et al., "In Vivo Formation of Hybrid Toxins Comprising Shiga Toxin and the Shiga-Like Toxins and Role of the B Subunit in Localization and Cytotoxic Activity", Infection and Immunity, 57(12): 3743-3750 (1989).

Weldon et al. "A guide to Taming a Toxin: Recombinant Immunotoxins Constructed from Pseudomonas Exotoxin A for the Treatment of Cancer", The FEBS Journal, 278(23): 4683-4700 (2011).

EP Application No. 182078113.1 Extended European Search Report dated Jun. 17, 2019, 10 pgs.

IL Application No. 240433 Office Action Translation dated May 30, 2019, 2 pgs.

IL Application No. 246701 Office Action Translation dated May 16, 2019, 5 pgs.

IL Application No. 247298 Office Action Translation dated May 21, 2019, 4 pgs.

IL Application No. 246632 Office Action Translation dated May 16, 2019, 5 pgs.

Boes et al., "Affinity Purification of a Framework 1 Engineered Mouse/Human Chimeric IgA2 Antibody From Tobacco", Biotechnology Bioengineering, 108(12): 2804-2814 (2011).

Lakhrif et al., "A method to confer protein L binding ability to any antibody fragment" MAbs, 8(2): 379-388 (2016).

Zahid et al., "Design and reshaping of an scFv directed against human platelet glycoprotein VI with diagnostic potential", Analytical Biochemistry, 417(2): 274-282 (2011).

Lee et al., "Molecular mechanism of PD-1/PD-L1 blockade via anti-PD-L1 antibodies atezolizumab and durvalumab", Scientific Reports 7(1):5532 (2017).

Rudikoff et al. "Single amino acid substitution altering antigen-binding specificity." Proceedings of the National Academy of Sciences 79(6): 1979-1983 (1982).

Pascalis et al., "Grafting of "abbreviated" complementarity-determining regions containing specificity-determining residues essential for ligand contact to engineers a less immunogenic humanized monoclonal antibody." The Journal of Immunology 169(6): 3076-3084 (2002).

Casset et al., "A peptide mimetic of an anti-CD4 monoclonal antibody by rational design." Biochemical and Biophysical Research Communications 307(1): 198-205 (2003).

Lee et al.,"Phylogenetic analysis of Shiga toxin 1 and Shiga toxin 2 genes associated with disease outbreaks." BMC Microbiology 7(1): 109 (2007).

Cao et al. "Construction and characterization of novel, recombinant immunotoxins targeting the Her2/neu oncogene product: in vitro and in vivo studies." Cancer Research 69(23): 8987-8995 (2009).

Alkharabsheh et al., "Clinical activity and tolerability of SL-401 (tagraxofusp): recombinant diphtheria toxin and interleukin-3 in hematologic malignancies." Biomedicines 7.1 (2019): 6.

Balandin, TG, et al., "Antitumor activity and toxicity of anti-HER immunoRNase scFv 4D5-dibarnase in mice bearing human breast cancer xenografts", Investigational New Drugs 29(1), (2011), Feb, 22-32.

Bang et al., "Trastuzumab in combination with chemotherapy versus chemotherapy alone for treatment of HER2-positive advanced gastric or gastro-oesophageal junction cancer (ToGA): a phase 3, open-label, randomised controlled trial." The Lancet 376.9742 (2010): 687-697.

Bartley et al., "Template for reporting results of HER2 (ERBB2) biomarker testing of specimens from patients with adenocarcinoma of the stomach or esophagogastric junction." Archives of Pathology and Laboratory Medicine 139.5 (2015): 618-620.

Boldicke "Blocking translocation of cell surface molecules from the ER to the cell surface by intracellular antibodies targeted to the ER." Journal of Cellular and Molecular Medicine 11.1 (2007): 54-70.

Brieschke, B, et al., "In vivo efficacy of a PD-L1 targeted Engineered Toxin Body (ETB) comprised of direct cytotoxicity and T-cell mediated tumor targeting", Abstract P804, SITC, (Nov. 9, 2019).

Brieschke, B, et al., "P840 In vivo efficacy of a PD-L1 targeted Engineered Toxin Body (ETB) comprised of direct cytotoxicity and T-cell mediated tumor targeting", 34th Annual Meeting & Pre-Conference Programs of the Society for Immunotherapy of Cancer (SITC 2019): part 2, Journal for ImmunoTherapy of Cancer, 7(Suppl 1) 283: P840, (Nov. 6, 2019).

Brieschke, B, et al., "P9 Identification and functional profiling of PD-L1 targeted engineered toxin bodies for antigen seeding technology and redirection of T cell response to tumors", Journal for ImmunoTherapy of Cancer 2018.

Brieschke, B, et al., "PD-L1 targeted engineered toxin body provides direct cytotoxicity and T-cell mediated tumor targeting", Presented at the 2020 ASCO-SITC Clinical Immuno-Oncology Symposium, Abstract No. 12, (Feb. 6, 2020).

Campbell et al., "Mechanisms of NK cell activation and clinical activity of the therapeutic SLAMF7 antibody, elotuzumab in multiple myeloma." Frontiers in Immunology 9 (2018): 2551.

Curea et al., "Current targeted therapies in HER2-positive gastric adenocarcinoma." Cancer Biotherapy & Radiopharmaceuticals 32.10 (2017): 351-363.

Das et al., "Immune-related adverse events and anti-tumor efficacy of immune checkpoint inhibitors." Journal for Immunotherapy of Cancer 7.1 (2019): 1-11.

Dhillon "Moxetumomab pasudotox: first global approval." Drugs 78.16 (2018): 1763-1767.

Dimopoulos et al., "Daratumumab, lenalidomide, and dexamethasone for multiple myeloma." New England Journal of Medicine 375.14 (2016): 1319-1331.

Dokter et al., "Preclinical profile of the HER2-targeting ADC SYD983/SYD985: introduction of a new duocarmycin-based linker-drug platform." Molecular Cancer Therapeutics 13.11 (2014): 2618-2629.

Du et al., "A reappraisal of CTLA-4 checkpoint blockade in cancer immunotherapy." Cell Research 28.4 (2018): 416-432.

Galon et al., "Approaches to treat immune hot, altered and cold tumours with combination immunotherapies." Nature Reviews Drug Discovery 18.3 (2019): 197-218.

Ghaffari-Nazari, H, et al., "Improving Multi-Epitope Long Peptide Vaccine Potency by Using a Strategy that Enhances CD4+ T Help in BALB/c Mice", PLoS One 10(11): e0142563, Nov. 10, 2015.

Ha et al., "Differential control of human Treg and effector T cells in tumor immunity by Fc-engineered anti-CTLA-4 antibody." Proceedings of the National Academy of Sciences 116.2 (2019): 609-618.

Higgins, JP, et al., "MT-5111: A Novel HER2 Targeting Engineered Toxin Body in Clinical Development", Presented at: Gastrointestinal Cancers Symposium, Jan. 23-25, 2020, The American Society of Clinical Oncology, San Francisco, California, Abstract G22.

Higgins, JP, et al., "MT-5111: A Novel HER2-Targeting Engineered Toxin Body Under Clinical Development to Overcome Mechanisms of Resistance to Existing HER2-Targeted Therapies", Proceedings of the 2019 San Antonio Breast Cancer Symposium; Dec. 10-14, 2019; San Antonio, TX, Abstract P1-18-35.

(56) References Cited

OTHER PUBLICATIONS

Ishii et al., "Pertuzumab in the treatment of HER2-positive breast cancer: an evidence-based review of its safety, efficacy, and place in therapy." Core Evidence 14 (2019): 51.
Ivanova, JL, et al., Application of fusion protein 4D5 scFv-dibarnase:barstar-gold complex for studying P185HER2 receptor distribution in human cancer cells, Biochimie, 94(8), Aug. 2012, 1833-1836.
Ji et al., "Myocarditis in cynomolgus monkeys following treatment with immune checkpoint inhibitors." Clinical Cancer Research 25.15 (2019): 4735-4748.
Kowanetz et al., "Differential regulation of PD-L1 expression by immune and tumor cells in NSCLC and the response to treatment with atezolizumab (anti—PD-L1)." Proceedings of the National Academy of Sciences 115.43 (2018): E10119-E10126.
Kumar et al., "International Myeloma Working Group consensus criteria for response and minimal residual disease assessment in multiple myeloma." The Lancet Oncology 17.8 (2016): e328-e346.
Mahmud, H, et al., "Induction of programmed cell death in Erb2/HER2-expressing cancer cells by targeted delivery of apoptosis-inducing factor", Molecular Cancer Therapeutics, 8(6), Jun. 2009, 1525-1535.
Menderes et al., "SYD985, a novel duocarmycin-based HER2-targeting antibody-drug conjugate, shows antitumor activity in uterine and ovarian carcinosarcoma with HER2/Neu expression." Clinical Cancer Research 23.19 (2017): 5836-5845.
Muzard, J, et al., "Grafting of protein L-binding activity onto recombinant antibody fragments", Analytical Biochemistry 388(2), May 15, 2009, 331-338.
Nakamura "Biomarkers for immune checkpoint inhibitor-mediated tumor response and adverse events." Frontiers in Medicine 6 (2019): 119.
Nilson, BHK, et al., "Protein L from Peptostreptococcus magnus Binds to the κ Light Chain Variable Domain", The Journal of Biological Chemistry, 267(4), Feb. 5, 1992, 2234-2239.
Nilson, BHK, et al., "Purification of antibodies using protein L-binding framework structures in the light chain variable domain", Journal of Immunological Methods, 164(1), Aug. 26, 1993, 33-40.
Nooka et al. "Daratumumab in multiple myeloma." Cancer 125.14 (2019): 2364-2382.
Boltezar, L. et al., "Comparison of the algorithms classifying the ABC and GCB subtypes in diffuse large B-cell lymphoma," Oncology Letters, 15:6903-6912 (2018).
clinical trials.gov [online], Identifier: NCT04029922, "MT-5111: A Novel HER2 Targeting Engineered Toxin Body in Clinical Development," Sponsor: Molecular Templates, Inc., Nov. 20, 2019; Retrieved from the Internet: https://clinicaltrials.gov/ct2/show/NCT04029922?term=Mt-5111&draw=2&rank=1>, 10 pages.
Coiffier, B. et al., "Diffuse large B-cell lymphoma: R-CHOP failure—what to do?," Hematology Am Soc Hematol Educ Program, 2016(1):366-378 (2016).
Crump, M. et al., "Outcomes in refractory diffuse large B-cell lymphoma: results from the international SCHOLAR-1 study," Blood, 130(16):1800-1808 (2017).
Czuczman, M. S. et al., "A Phase 2/3 Multicenter, Randomized, Open-Label Study to Compare the Efficacy and Safety of Lenalidomide Versus Investigator's Choice in Patients with Relapsed or Refractory Diffuse Large B-Cell Lymphoma," Clin Cancer Res, 23(15):4127-4137 (2017).
Delfau-Larue, M.-H. et al., "Lenalidomide/rituximab induces high molecular response in untreated follicular lymphoma: LYSA ancillary RELEVANCE study," Blood Advances, 4(14): 3217-3223 (2020).
Déret, S. et al., "SUBIM: a program for analysing the Kabat database and determining the variability subgroup of a new immunoglobulin sequence," CABIOS, 11(4):435-439 (1995).
Friedberg, J. W., "Relapsed/Refractory Diffuse Large B-Cell Lymphoma," Hematology Am Soc Hematol Educ Program, 2011(1):498-505 (2011).

Gnaoui, T. E. et al., "Rituximab, gemcitabine and oxaliplatin: an effective salvage regimen for patients with relapsed or refractory B-cell lymphoma not candidates for high-dose therapy," Annals of Oncology, 18:1363-1368 (2007).
Goy, A. et al., "Ibrutinib plus lenalidomide and rituximab has promising activity in relapsed/refractory non-germinal center B-cell DLBCL," Blood, 134(13):1024-1036 (2019).
Kondo, E., "Autologous Hematopoietic Stem Cell Transplantation for Diffuse Large B-Cell Lymphoma," J Clin Exp Hematol., 56(2):100-108 (2016).
Ma, L.-Y. & Su, L., "Application of Lenalidomide on Diffused Large B-cell Lymphoma: Salvage, Maintenance, and Induction Treatment," Chinese Medical Journal, 131(20):2510-2513 (2018).
Makita, S. et al., "Chimeric antigen receptor T-cell therapy for B-cell non-Hodgkin lymphoma: opportunities and challenges," Drugs in Context, 8:212567 (2019), 14 pages; doi:10.7573/dic.212567.
Molecular Templates, "New Data on Molecular Templates' Engineered Toxin Bodies to be Presented at the American Association of Cancer Research (AACR) Annual Meeting 2019," Feb. 27, 2019, 2 pages.
Molecular Templates, "Molecular Templates Announces FDA Acceptance of IND Application for MT-5111, An Engineered Toxin Body Targeting HER2," Apr. 22, 2019, 2 pages.
Molecular Templates Corporate Presentation, Nov. 2019, 26 pages.
National Comprehensive Cancer Network, NCCN Clinical Practice Guidelines in Oncology (NCCN Guidelines), "B-Cell Lymphomas," Version 4.2020—Aug. 13, 2020, 297 pages.
Mounier, N. et al., "Rituximab plus gemcitabine and oxaliplatin in patients with refractory/relapsed diffuse large B-cell lymphoma who are not candidates for high-dose therapy. A phase II Lymphoma Study Association trial," Haematologica, 98(11):1726-1731 (2013).
Nowakowski, G. et al., "ROBUST: Lenalidomide-R-CHOP versus placebo-R-CHOP in previously untreated ABC-type diffuse large B-cell lymphoma," Future Oncol., 12(13):1553-1563 (2016).
Philip, T. et al., "Autologous bone marrow transplantation as compared with salvage chemotherapy in relapses of chemotherapy-sensitive non-Hodgkin's lymphoma," The New England Journal of Medicine, 333(23):1540-1545 (1995), with Correction, "Autologous Bone Marrow Transplantation in Relapsed Non-Hodgkin's Lymphoma," The New England Journal of Medicine, 334:990 (1996).
Press Release Molecular Templates Presents Preclinical Data on De-Immunized Engineered Toxin Bodies (ETB) with Novel Immuno-Oncology Capabilities (AACR) Annual Meeting, Apr. 16, 2015, 1 page.
Rajagopalan, S. et al., "Next-generation engineered toxin bodies: CD38, PD-L1 and HER2 targeted ETBs," The Journal of Cancer Research, 76(14 Suppl) (Jul. 15, 2016), Abstract nr 595, Poster.
Van Imhoff, G. W. et al., "Ofatumumab Versus Rituximab Salvage Chemoimmunotherapy in Relapsed or Refractory Diffuse Large B-Cell Lymphoma: The ORCHARRD Study," Journal of Clinical Oncology, 35(5):544-551 (2017).
Van Tine, B. A. et al., "A Phase 1 Open-Label Study to Investigate Safety and Tolerability, Efficacy, Pharmacokinetics, Pharmacodynamics, and Immunogenicity of MT-5111 in Subjects With HER2-Positive Tumors," Presented at the American Society of Clinical Oncology Gastrointestinal Cancers Symposium, Jan. 23-25, 2020, San Francisco, California, USA, Molecular Templates, L9, 1 page.
Wainberg, Z. A. et al., "A phase 1 study of the novel immunotoxin, MT-5111, in subjects (subj) with HER-2 positive tumors: interim results," 2020 ASCO Annual Meeting, May 29-Jun. 2, 2020, 6 pages.
Wels, W. et al., "Selective Inhibition of Tumor Cell Growth by a Recombinant Single-Chain Antibody-Toxin Specific for the erbB-2 Receptor," Cancer Research, 52:6310-6317 (1992).
Westin, J. et al., Abstract 7508, "Smart start: Final results of rituximab, lenalidomide, and ibrutinib lead in prior to combination with chemotherapy for patients with newly diagnosed diffuse large B-cell lymphoma," May 2019, Journal of Clinical Oncology 37(15):7508, 2 pages.

SEQUENCE LISTING

<160> NUMBER OF SEQ ID NOS: 181

<210> SEQ ID NO 1
<211> LENGTH: 293
<212> TYPE: PRT
<213> ORGANISM: Escherichia coli

<400> SEQUENCE: 1

Lys Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
            20                  25                  30

Ser Gly Gly Thr Ser Leu Leu Met Ile Asp Ser Gly Ser Gly Asp Asn
        35                  40                  45

Leu Phe Ala Val Asp Val Arg Gly Ile Asp Pro Glu Glu Gly Arg Phe
    50                  55                  60

Asn Asn Leu Arg Leu Ile Val Glu Arg Asn Asn Leu Tyr Val Thr Gly
65                  70                  75                  80

Phe Val Asn Arg Thr Asn Asn Val Phe Tyr Arg Phe Ala Asp Phe Ser
                85                  90                  95

His Val Thr Phe Pro Gly Thr Thr Ala Val Thr Leu Ser Gly Asp Ser
                100                 105                 110

Ser Tyr Thr Thr Leu Gln Arg Val Ala Gly Ile Ser Arg Thr Gly Met
            115                 120                 125

Gln Ile Asn Arg His Ser Leu Thr Thr Ser Tyr Leu Asp Leu Met Ser
    130                 135                 140

His Ser Gly Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Arg Thr Thr Leu Asp Asp Leu Ser Gly Arg Ser Tyr Val Met

```
                180                 185                 190
Thr Ala Glu Asp Val Asp Leu Thr Leu Asn Trp Gly Arg Leu Ser Ser
            195                 200                 205
Val Leu Pro Asp Tyr His Gly Gln Asp Ser Val Arg Val Gly Arg Ile
            210                 215                 220
Ser Phe Gly Ser Ile Asn Ala Ile Leu Gly Ser Val Ala Leu Ile Leu
225                 230                 235                 240
Asn Cys His His His Ala Ser Arg Val Ala Arg Met Ala Ser Asp Glu
                245                 250                 255
Phe Pro Ser Met Cys Pro Ala Asp Gly Arg Val Arg Gly Ile Thr His
            260                 265                 270
Asn Lys Ile Leu Trp Asp Ser Ser Thr Leu Gly Ala Ile Leu Met Arg
            275                 280                 285

Arg Thr Ile Ser Ser
        290

<210> SEQ ID NO 2
<211> LENGTH: 293
<212> TYPE: PRT
<213> ORGANISM: Shigella dysenteriae

<400> SEQUENCE: 2

Lys Glu Phe Thr Leu Asp Phe Ser Thr Ala Lys Thr Tyr Val Asp Ser
1               5                   10                  15
Leu Asn Val Ile Arg Ser Ala Ile Gly Thr Pro Leu Gln Thr Ile Ser
            20                  25                  30
Ser Gly Gly Thr Ser Leu Leu Met Ile Asp Ser Gly Thr Gly Asp Asn
            35                  40                  45
Leu Phe Ala Val Asp Val Arg Gly Ile Asp Pro Glu Glu Gly Arg Phe
        50                  55                  60
Asn Asn Leu Arg Leu Ile Val Glu Arg Asn Asn Leu Tyr Val Thr Gly
65                  70                  75                  80
Phe Val Asn Arg Thr Asn Asn Val Phe Tyr Arg Phe Ala Asp Phe Ser
                85                  90                  95
His Val Thr Phe Pro Gly Thr Thr Ala Val Thr Leu Ser Gly Asp Ser
            100                 105                 110
Ser Tyr Thr Thr Leu Gln Arg Val Ala Gly Ile Ser Arg Thr Gly Met
            115                 120                 125
Gln Ile Asn Arg His Ser Leu Thr Thr Ser Tyr Leu Asp Leu Met Ser
        130                 135                 140
His Ser Gly Thr Ser Leu Thr Gln Ser Val Ala Arg Ala Met Leu Arg
145                 150                 155                 160
Phe Val Thr Val Thr Ala Glu Ala Leu Arg Phe Arg Gln Ile Gln Arg
                165                 170                 175
Gly Phe Arg Thr Thr Leu Asp Asp Leu Ser Gly Arg Ser Tyr Val Met
            180                 185                 190
Thr Ala Glu Asp Val Asp Leu Thr Leu Asn Trp Gly Arg Leu Ser Ser
            195                 200                 205
Val Leu Pro Asp Tyr His Gly Gln Asp Ser Val Arg Val Gly Arg Ile
            210                 215                 220
Ser Phe Gly Ser Ile Asn Ala Ile Leu Gly Ser Val Ala Leu Ile Leu
225                 230                 235                 240
Asn Cys His His His Ala Ser Arg Val Ala Arg Met Ala Ser Asp Glu
                245                 250                 255
```

```
Phe Pro Ser Met Cys Pro Ala Asp Gly Arg Val Arg Gly Ile Thr His
            260                 265                 270

Asn Lys Ile Leu Trp Asp Ser Thr Leu Gly Ala Ile Leu Met Arg
        275                 280                 285

Arg Thr Ile Ser Ser
    290
```

```
<210> SEQ ID NO 3
<211> LENGTH: 297
<212> TYPE: PRT
<213> ORGANISM: Escherichia coli

<400> SEQUENCE: 3

Asp Glu Phe Thr Val Asp Phe Ser Ser Gln Lys Ser Tyr Val Asp Ser
1               5                   10                  15

Leu Asn Ser Ile Arg Ser Ala Ile Ser Thr Pro Leu Gly Asn Ile Ser
            20                  25                  30

Gln Gly Gly Val Ser Val Ser Val Ile Asn His Val Leu Gly Gly Asn
        35                  40                  45

Tyr Ile Ser Leu Asn Val Arg Gly Leu Asp Pro Tyr Ser Glu Arg Phe
    50                  55                  60

Asn His Leu Arg Leu Ile Met Glu Arg Asn Asn Leu Tyr Val Ala Gly
65                  70                  75                  80

Phe Ile Asn Thr Glu Thr Asn Ile Phe Tyr Arg Phe Ser Asp Phe Ser
                85                  90                  95

His Ile Ser Val Pro Asp Val Ile Thr Val Ser Met Thr Thr Asp Ser
            100                 105                 110

Ser Tyr Ser Ser Leu Gln Arg Ile Ala Asp Leu Glu Arg Thr Gly Met
        115                 120                 125

Gln Ile Gly Arg His Ser Leu Val Gly Ser Tyr Leu Asp Leu Met Glu
    130                 135                 140

Phe Arg Gly Arg Ser Met Thr Arg Ala Ser Ser Arg Ala Met Leu Arg
145                 150                 155                 160

Phe Val Thr Val Ile Ala Glu Ala Leu Arg Phe Arg Gln Ile Gln Arg
                165                 170                 175

Gly Phe Arg Pro Ala Leu Ser Glu Ala Ser Pro Leu Tyr Thr Met Thr
            180                 185                 190

Ala Gln Asp Val Asp Leu Thr Leu Asn Trp Gly Arg Ile Ser Asn Val
        195                 200                 205

Leu Pro Glu Tyr Arg Gly Glu Glu Gly Val Arg Ile Gly Arg Ile Ser
    210                 215                 220

Phe Asn Ser Leu Ser Ala Ile Leu Gly Ser Val Ala Val Ile Leu Asn
225                 230                 235                 240

Cys His Ser Thr Gly Ser Tyr Ser Val Arg Ser Val Ser Gln Lys Gln
                245                 250                 255

Lys Thr Glu Cys Gln Ile Val Gly Asp Arg Ala Ala Ile Lys Val Asn
            260                 265                 270

Asn Val Leu Trp Glu Ala Asn Thr Ile Ala Ala Leu Leu Asn Arg Lys
        275                 280                 285

Pro Gln Asp Leu Thr Glu Pro Asn Gln
    290                 295
```

```
<210> SEQ ID NO 4
<211> LENGTH: 251
<212> TYPE: PRT
<213> ORGANISM: Escherichia coli
```

```
<400> SEQUENCE: 4

Lys Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
            20                  25                  30

Ser Gly Gly Thr Ser Leu Leu Met Ile Asp Ser Gly Thr Gly Asp Asn
        35                  40                  45

Leu Phe Ala Val Asp Val Arg Gly Ile Asp Pro Glu Glu Gly Arg Phe
    50                  55                  60

Asn Asn Leu Arg Leu Ile Val Glu Arg Asn Asn Leu Tyr Val Thr Gly
65                  70                  75                  80

Phe Val Asn Arg Thr Asn Asn Val Phe Tyr Arg Phe Ala Asp Phe Ser
                85                  90                  95

His Val Thr Phe Pro Gly Thr Thr Ala Val Thr Leu Ser Gly Asp Ser
                100                 105                 110

Ser Tyr Thr Thr Leu Gln Arg Val Ala Gly Ile Ser Arg Thr Gly Met
                115                 120                 125

Gln Ile Asn Arg His Ser Leu Thr Thr Ser Tyr Leu Asp Leu Met Ser
130                 135                 140

His Ser Gly Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Arg Thr Thr Leu Asp Asp Leu Ser Gly Arg Ser Tyr Val Met
                180                 185                 190

Thr Ala Glu Asp Val Asp Leu Thr Leu Asn Trp Gly Arg Leu Ser Ser
                195                 200                 205

Val Leu Pro Asp Tyr His Gly Gln Asp Ser Val Arg Val Gly Arg Ile
            210                 215                 220

Ser Phe Gly Ser Val Asn Ala Ile Leu Gly Ser Val Ala Leu Ile Leu
225                 230                 235                 240

Asn Cys His His His Ala Ser Arg Val Ala Arg
                245                 250

<210> SEQ ID NO 5
<211> LENGTH: 251
<212> TYPE: PRT
<213> ORGANISM: Escherichia coli

<400> SEQUENCE: 5

Lys Glu Phe Thr Leu Asp Phe Ser Thr Ala Lys Lys Tyr Val Asp Ser
1               5                   10                  15

Leu Asn Val Ile Arg Ser Ala Ile Gly Thr Pro Leu Gln Thr Ile Ser
            20                  25                  30

Ser Gly Gly Thr Ser Leu Leu Met Ile Asp Ser Gly Thr Gly Asp Asn
        35                  40                  45

Leu Phe Ala Val Asp Ile Met Gly Leu Glu Pro Glu Glu Glu Arg Phe
    50                  55                  60

Asn Asn Leu Arg Leu Ile Val Glu Arg Asn Asn Leu Tyr Val Thr Gly
65                  70                  75                  80

Phe Val Asn Arg Thr Asn Asn Val Phe Tyr Arg Phe Ala Asp Phe Ser
                85                  90                  95

His Val Thr Phe Pro Gly Thr Arg Ala Val Thr Leu Ser Gly Asp Ser
                100                 105                 110
```

Ser Tyr Thr Thr Leu Gln Arg Val Ala Gly Ile Ser Arg Thr Gly Met
        115                 120                 125

Gln Ile Asn Arg His Ser Leu Thr Thr Ser Tyr Leu Asp Leu Met Ser
130                 135                 140

Tyr Ser Gly Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Arg Thr Thr Leu Asp Asp Leu Ser Gly Arg Ser Tyr Val Met
            180                 185                 190

Thr Ala Glu Asp Val Asp Leu Thr Leu Asn Trp Gly Arg Leu Ser Ser
        195                 200                 205

Ile Leu Pro Asp Tyr His Gly Gln Asp Ser Val Arg Val Gly Arg Ile
    210                 215                 220

Ser Phe Gly Ser Ile Asn Ala Ile Leu Gly Ser Val Ala Leu Ile Leu
225                 230                 235                 240

Asn Cys His His His Ala Ser Arg Val Ala Arg
                245                 250

<210> SEQ ID NO 6
<211> LENGTH: 251
<212> TYPE: PRT
<213> ORGANISM: Escherichia coli

<400> SEQUENCE: 6

Gln Asp Phe Thr Val Asp Phe Ser Thr Ala Lys Lys Tyr Val Asp Ser
1               5                   10                  15

Leu Asn Ala Ile Arg Ser Ala Ile Gly Thr Pro Leu His Ser Ile Ser
                20                  25                  30

Ser Gly Gly Thr Ser Leu Leu Met Ile Asp Asn Gly Thr Gly Asp Asn
            35                  40                  45

Leu Phe Ala Val Asp Ile Arg Gly Leu Asp Pro Glu Glu Glu Arg Phe
    50                  55                  60

Asp Asn Leu Arg Leu Ile Ile Glu Arg Asn Asn Leu Tyr Val Thr Gly
65                  70                  75                  80

Phe Val Asn Arg Thr Ser Asn Ile Phe Tyr Arg Phe Ala Asp Phe Ser
                85                  90                  95

His Val Thr Phe Pro Gly Thr Arg Ala Val Thr Leu Ser Gly Asp Ser
            100                 105                 110

Ser Tyr Thr Thr Leu Gln Arg Val Ala Gly Ile Gly Arg Thr Gly Met
        115                 120                 125

Gln Ile Asn Arg His Ser Leu Thr Thr Ser Tyr Leu Asp Leu Met Ser
130                 135                 140

Tyr Ser Gly Ser Ser Leu Thr Gln Pro Val Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Arg Thr Thr Leu Asp Asp Val Ser Gly His Ser Tyr Thr Met
            180                 185                 190

Thr Val Glu Asp Val Asp Leu Thr Leu Asn Trp Gly Arg Leu Ser Ser
        195                 200                 205

Val Leu Pro Asp Tyr His Gly Gln Asp Ser Val Arg Val Gly Arg Ile
    210                 215                 220

Ser Phe Gly Gly Val Asn Ala Ile Leu Gly Ser Val Ala Leu Ile Leu

```
                225                 230                 235                 240
Asn Cys His His His Thr Ser Arg Val Ser Arg
                245                 250

<210> SEQ ID NO 7
<211> LENGTH: 250
<212> TYPE: PRT
<213> ORGANISM: Escherichia coli

<400> SEQUENCE: 7

Arg Glu Phe Thr Ile Asp Phe Ser Thr Gln Gln Ser Tyr Val Ser Ser
1               5                   10                  15

Leu Asn Ser Ile Arg Thr Glu Ile Ser Thr Pro Leu Glu His Ile Ser
                20                  25                  30

Gln Gly Thr Thr Ser Val Ser Val Ile Asn His Thr Pro Pro Gly Ser
            35                  40                  45

Tyr Phe Ala Val Asp Ile Arg Gly Leu Asp Val Tyr Gln Ala Arg Phe
        50                  55                  60

Asp His Leu Arg Leu Ile Ile Glu Gln Asn Asn Leu Tyr Val Ala Gly
65                  70                  75                  80

Phe Val Asn Thr Ala Thr Asn Thr Phe Tyr Arg Phe Ser Asp Phe Thr
                85                  90                  95

His Ile Ser Val Pro Gly Val Thr Thr Val Ser Met Thr Thr Asp Ser
            100                 105                 110

Ser Tyr Thr Thr Leu Gln Arg Val Ala Ala Leu Glu Arg Ser Gly Met
        115                 120                 125

Gln Ile Ser Arg His Ser Leu Val Ser Ser Tyr Leu Ala Leu Met Glu
130                 135                 140

Phe Ser Gly Asn Thr Met Thr Arg Asp Ala Ser Arg Ala Val Leu Arg
145                 150                 155                 160

Phe Val Thr Val Thr Ala Glu Ala Leu Arg Phe Arg Gln Ile Gln Arg
                165                 170                 175

Glu Phe Arg Gln Ala Leu Ser Glu Thr Ala Pro Val Tyr Thr Met Thr
            180                 185                 190

Pro Gly Asp Val Asp Leu Thr Leu Asn Trp Gly Arg Ile Ser Asn Val
        195                 200                 205

Leu Pro Glu Tyr Arg Gly Glu Asp Gly Val Arg Val Gly Arg Ile Ser
    210                 215                 220

Phe Asn Asn Ile Ser Ala Ile Leu Gly Thr Val Ala Val Ile Leu Asn
225                 230                 235                 240

Cys His His Gln Gly Ala Arg Ser Val Arg
                245                 250

<210> SEQ ID NO 8
<211> LENGTH: 250
<212> TYPE: PRT
<213> ORGANISM: Escherichia coli

<400> SEQUENCE: 8

Arg Glu Phe Thr Ile Asp Phe Ser Thr Gln Gln Ser Tyr Val Ser Ser
1               5                   10                  15

Leu Asn Ser Ile Arg Thr Glu Ile Ser Thr Pro Leu Glu His Ile Ser
                20                  25                  30

Gln Gly Thr Thr Ser Val Ser Val Ile Asn His Thr Pro Pro Gly Ser
            35                  40                  45

Tyr Phe Ala Val Asp Ile Arg Gly Leu Asp Val Tyr Gln Ala Arg Phe
```

```
        50                  55                  60
Asp His Leu Arg Leu Ile Ile Glu Gln Asn Asn Leu Tyr Val Ala Gly
 65                  70                  75                  80

Phe Val Asn Thr Ala Thr Asn Thr Phe Tyr Arg Phe Ser Asp Phe Ala
                 85                  90                  95

His Ile Ser Val Pro Gly Val Thr Thr Val Ser Met Thr Thr Asp Ser
                100                 105                 110

Ser Tyr Thr Thr Leu Gln Arg Val Ala Ala Leu Glu Arg Ser Gly Met
            115                 120                 125

Gln Ile Ser Arg His Ser Leu Val Ser Ser Tyr Leu Ala Leu Met Glu
        130                 135                 140

Phe Ser Gly Asn Thr Met Thr Arg Asp Ala Ser Arg Ala Val Leu Arg
145                 150                 155                 160

Phe Val Thr Val Thr Ala Glu Ala Leu Arg Phe Arg Gln Ile Gln Arg
                165                 170                 175

Glu Phe Arg Gln Ala Leu Ser Glu Thr Ala Pro Val Tyr Thr Met Thr
            180                 185                 190

Pro Gly Asp Val Asp Leu Thr Leu Asn Trp Gly Arg Ile Ser Asn Val
        195                 200                 205

Leu Pro Glu Tyr Arg Gly Glu Asp Gly Val Arg Val Gly Arg Ile Ser
    210                 215                 220

Phe Asn Asn Ile Ser Ala Ile Leu Gly Thr Val Ala Val Ile Leu Asn
225                 230                 235                 240

Cys His His Gln Gly Ala Arg Ser Val Arg
                245                 250

<210> SEQ ID NO 9
<211> LENGTH: 250
<212> TYPE: PRT
<213> ORGANISM: Escherichia coli

<400> SEQUENCE: 9

Arg Glu Phe Thr Ile Asp Phe Ser Thr Gln Gln Ser Tyr Val Ser Ser
  1               5                  10                  15

Leu Asn Ser Ile Arg Thr Glu Ile Ser Thr Pro Leu Glu His Ile Ser
             20                  25                  30

Gln Gly Thr Thr Ser Val Ser Val Ile Asn His Thr Pro Pro Gly Ser
         35                  40                  45

Tyr Phe Ala Val Asp Ile Arg Gly Leu Asp Ile Tyr Gln Ala Arg Phe
     50                  55                  60

Asp His Leu Arg Leu Ile Ile Glu Gln Asn Asn Leu Tyr Val Ala Gly
 65                  70                  75                  80

Phe Val Asn Thr Ala Thr Asn Thr Phe Tyr Arg Phe Ser Asp Phe Thr
                 85                  90                  95

His Ile Ser Val Pro Gly Val Thr Thr Val Ser Met Thr Thr Asp Ser
                100                 105                 110

Ser Tyr Thr Thr Leu Gln Arg Val Ala Ala Leu Glu Arg Ser Gly Met
            115                 120                 125

Gln Ile Ser Arg His Ser Leu Val Ser Ser Tyr Leu Ala Leu Met Glu
        130                 135                 140

Phe Ser Gly Asn Thr Met Thr Arg Asp Ala Ser Arg Ala Val Leu Arg
145                 150                 155                 160

Phe Val Thr Val Thr Ala Glu Ala Leu Arg Phe Arg Gln Ile Gln Arg
                165                 170                 175
```

```
Glu Phe Arg Gln Ala Leu Ser Glu Thr Ala Pro Val Tyr Thr Met Thr
                180                 185                 190

Pro Gly Asp Val Asp Leu Thr Leu Asn Trp Gly Arg Ile Ser Asn Val
            195                 200                 205

Leu Pro Glu Tyr Arg Gly Glu Asp Gly Val Arg Val Gly Arg Ile Ser
            210                 215                 220

Phe Asn Asn Ile Ser Ala Ile Leu Gly Thr Val Ala Val Ile Leu Asn
225                 230                 235                 240

Cys His His Gln Gly Ala Arg Ser Val Arg
                245                 250

<210> SEQ ID NO 10
<211> LENGTH: 250
<212> TYPE: PRT
<213> ORGANISM: Escherichia coli

<400> SEQUENCE: 10

Arg Glu Phe Thr Ile Asp Phe Ser Thr Gln Gln Ser Tyr Val Ser Ser
1               5                   10                  15

Leu Asn Ser Ile Arg Thr Glu Ile Ser Thr Pro Leu Glu His Ile Ser
            20                  25                  30

Gln Gly Thr Thr Ser Val Ser Val Ile Asn His Thr Pro Pro Gly Ser
        35                  40                  45

Tyr Phe Ala Val Asp Ile Arg Gly Leu Asp Val Tyr Gln Ala Arg Phe
    50                  55                  60

Asp His Leu Arg Leu Ile Ile Glu Gln Asn Asn Leu Tyr Val Ala Gly
65                  70                  75                  80

Phe Val Asn Thr Ala Thr Asn Thr Phe Tyr Arg Phe Ser Asp Phe Thr
                85                  90                  95

His Ile Ser Val Pro Ser Val Thr Val Ser Met Thr Thr Asp Ser
                100                 105                 110

Ser Tyr Thr Thr Leu Gln Arg Val Ala Ala Leu Glu Arg Ser Gly Met
            115                 120                 125

Gln Ile Ser Arg His Ser Leu Val Ser Ser Tyr Leu Ala Leu Met Glu
        130                 135                 140

Phe Ser Gly Asn Thr Met Thr Arg Asp Ala Ser Arg Ala Val Leu Arg
145                 150                 155                 160

Phe Val Thr Val Thr Ala Glu Ala Leu Arg Phe Arg Gln Ile Gln Arg
                165                 170                 175

Glu Phe Arg Gln Ala Leu Ser Glu Thr Ala Pro Val Tyr Thr Met Thr
                180                 185                 190

Pro Gly Asp Val Asp Leu Thr Leu Asn Trp Gly Arg Ile Ser Asn Val
            195                 200                 205

Leu Pro Glu Tyr Arg Gly Glu Asp Gly Val Arg Val Gly Arg Ile Ser
            210                 215                 220

Phe Asn Asn Ile Ser Ala Ile Leu Gly Thr Val Ala Val Ile Leu Asn
225                 230                 235                 240

Cys His His Gln Gly Ala Arg Ser Val Arg
                245                 250

<210> SEQ ID NO 11
<211> LENGTH: 250
<212> TYPE: PRT
<213> ORGANISM: Escherichia coli

<400> SEQUENCE: 11
```

```
Arg Glu Phe Thr Ile Asp Phe Ser Thr Gln Gln Ser Tyr Val Ser Ser
  1               5                  10                  15

Leu Asn Ser Ile Arg Thr Glu Ile Ser Thr Pro Leu Glu His Ile Ser
             20                  25                  30

Gln Gly Thr Thr Ser Val Ser Val Ile Asn His Thr Pro Pro Gly Ser
         35                  40                  45

Tyr Phe Ala Val Asp Ile Arg Gly Leu Asp Val Tyr Gln Ala Arg Phe
     50                  55                  60

Asp His Leu Arg Leu Ile Ile Glu Gln Asn Asn Leu Tyr Met Ala Gly
 65                  70                  75                  80

Phe Val Asn Thr Ala Thr Asn Thr Phe Tyr Arg Phe Ser Asp Phe Thr
                 85                  90                  95

His Ile Ser Val Pro Ser Val Thr Thr Val Ser Met Thr Thr Asp Ser
                100                 105                 110

Ser Tyr Thr Thr Leu Gln Arg Val Ala Ala Leu Glu Arg Ser Gly Met
            115                 120                 125

Gln Ile Ser Arg His Ser Leu Val Ser Ser Tyr Leu Ala Leu Met Glu
        130                 135                 140

Phe Ser Gly Asn Thr Met Thr Arg Asp Ala Ser Arg Ala Val Leu Arg
145                 150                 155                 160

Phe Val Thr Val Thr Ala Glu Ala Leu Arg Phe Arg Gln Ile Gln Arg
                165                 170                 175

Glu Phe Arg Gln Ala Leu Ser Glu Thr Ala Pro Val Tyr Thr Met Thr
            180                 185                 190

Pro Gly Asp Val Asp Leu Thr Leu Asn Trp Gly Arg Ile Ser Asn Val
        195                 200                 205

Leu Pro Glu Tyr Arg Gly Glu Asp Gly Val Arg Val Gly Arg Ile Ser
    210                 215                 220

Phe Asn Asn Ile Ser Ala Ile Leu Gly Thr Val Ala Val Ile Leu Asn
225                 230                 235                 240

Cys His His Gln Gly Ala Arg Ser Val Arg
                245                 250

<210> SEQ ID NO 12
<211> LENGTH: 250
<212> TYPE: PRT
<213> ORGANISM: Escherichia coli

<400> SEQUENCE: 12

Arg Glu Phe Thr Ile Asp Phe Ser Thr Gln Gln Ser Tyr Val Ser Ser
  1               5                  10                  15

Leu Asn Ser Ile Arg Thr Glu Ile Ser Thr Pro Leu Glu His Ile Ser
             20                  25                  30

Gln Gly Thr Thr Ser Val Ser Val Ile Asn His Thr Pro Pro Gly Ser
         35                  40                  45

Tyr Phe Ala Val Asp Ile Arg Gly Leu Asp Val Tyr Gln Ala Arg Phe
     50                  55                  60

Asp His Leu Arg Leu Ile Ile Glu Gln Asn Asn Leu Tyr Val Ala Gly
 65                  70                  75                  80

Phe Val Asn Thr Ala Thr Asn Thr Phe Tyr Arg Phe Ser Asp Phe Thr
                 85                  90                  95

His Ile Ser Val Pro Gly Val Thr Thr Val Ser Met Thr Thr Asp Ser
                100                 105                 110

Ser Tyr Thr Thr Leu Gln Arg Val Ala Ala Leu Glu Arg Ser Gly Met
            115                 120                 125
```

```
Gln Ile Ser Arg His Ser Leu Val Ser Ser Tyr Leu Ala Leu Met Glu
    130                 135                 140

Phe Ser Gly Asn Thr Met Thr Arg Asp Ala Ser Arg Ala Val Leu Arg
145                 150                 155                 160

Phe Val Thr Val Thr Ala Glu Ala Leu Arg Phe Arg Gln Ile Gln Arg
                165                 170                 175

Glu Phe Arg Gln Val Leu Ser Glu Thr Ala Pro Val Tyr Thr Met Thr
            180                 185                 190

Pro Gly Asp Val Asp Leu Thr Leu Asn Trp Gly Arg Ile Ser Asn Val
        195                 200                 205

Leu Pro Glu Tyr Arg Gly Glu Asp Gly Val Arg Val Gly Arg Ile Ser
    210                 215                 220

Phe Asn Asn Ile Ser Ala Ile Leu Ser Thr Val Ala Val Ile Leu Asn
225                 230                 235                 240

Cys His His Gln Gly Ala Arg Ser Val Arg
                245                 250

<210> SEQ ID NO 13
<211> LENGTH: 250
<212> TYPE: PRT
<213> ORGANISM: Escherichia coli

<400> SEQUENCE: 13

Arg Glu Phe Thr Ile Asp Phe Ser Thr Gln Gln Ser Tyr Val Ser Ser
1               5                   10                  15

Leu Asn Ser Ile Arg Thr Glu Ile Ser Thr Pro Leu Glu His Ile Ser
            20                  25                  30

Gln Gly Thr Thr Ser Val Ser Val Ile Asn His Thr Pro Pro Gly Ser
        35                  40                  45

Tyr Phe Ala Val Asp Ile Arg Gly Leu Asp Val Tyr Gln Ala Arg Phe
    50                  55                  60

Asp His Leu Arg Leu Ile Ile Glu Gln Asn Asn Leu Tyr Val Ala Gly
65              70                  75                  80

Phe Val Asn Thr Ala Thr Asn Thr Phe Tyr Arg Phe Ser Asp Phe Ala
                85                  90                  95

His Ile Ser Val Pro Gly Val Thr Thr Val Ser Met Thr Thr Asp Ser
            100                 105                 110

Ser Tyr Thr Thr Leu Gln Arg Val Ala Ala Leu Glu Arg Ser Gly Met
        115                 120                 125

Gln Ile Ser Arg His Ser Leu Val Ser Ser Tyr Leu Ala Leu Met Glu
    130                 135                 140

Phe Ser Gly Asn Thr Met Thr Arg Asp Ala Ser Arg Ala Val Leu Arg
145                 150                 155                 160

Phe Val Thr Val Thr Ala Glu Ala Leu Arg Phe Arg Gln Ile Gln Arg
                165                 170                 175

Glu Phe Arg Gln Ala Leu Ser Glu Thr Ala Pro Val Tyr Thr Met Thr
            180                 185                 190

Pro Gly Asp Val Asp Leu Thr Leu Asn Trp Gly Arg Ile Ser Asn Val
        195                 200                 205

Ile Pro Glu Tyr Arg Gly Glu Asp Gly Val Arg Val Gly Arg Ile Ser
    210                 215                 220

Phe Asn Asn Ile Ser Ala Ile Leu Gly Thr Val Ala Val Ile Leu Asn
225                 230                 235                 240

Cys His His Gln Gly Ala Arg Ser Val Arg
```

<210> SEQ ID NO 14
<211> LENGTH: 250
<212> TYPE: PRT
<213> ORGANISM: Escherichia coli

<400> SEQUENCE: 14

Arg Glu Phe Met Ile Asp Phe Ser Thr Gln Gln Ser Tyr Val Ser Ser
1               5                   10                  15

Leu Asn Ser Ile Arg Thr Glu Ile Ser Thr Pro Leu Glu His Ile Ser
            20                  25                  30

Gln Gly Thr Thr Ser Val Ser Val Ile Asn His Thr Pro Pro Gly Ser
        35                  40                  45

Tyr Phe Ala Val Asp Ile Arg Gly Leu Asp Val Tyr Gln Ala Arg Phe
    50                  55                  60

Asp His Leu Arg Leu Ile Ile Glu Gln Asn Asn Leu Tyr Val Ala Gly
65                  70                  75                  80

Phe Val Asn Thr Ala Thr Asn Thr Phe Tyr Arg Phe Ser Asp Phe Thr
                85                  90                  95

His Ile Ser Val Pro Gly Val Thr Val Ser Met Thr Thr Asp Ser
            100                 105                 110

Ser Tyr Thr Thr Leu Gln Arg Val Ala Ala Leu Glu Arg Ser Gly Met
            115                 120                 125

Gln Ile Ser Arg His Ser Leu Val Ser Ser Tyr Leu Ala Leu Met Glu
    130                 135                 140

Phe Ser Gly Asn Thr Met Thr Arg Asp Ala Ser Arg Ala Val Leu Arg
145                 150                 155                 160

Phe Val Thr Val Thr Ala Glu Ala Leu Arg Phe Arg Gln Ile Gln Arg
                165                 170                 175

Glu Phe Arg Gln Ala Leu Ser Glu Thr Ala Pro Val Tyr Thr Met Thr
            180                 185                 190

Pro Glu Glu Val Asp Leu Thr Leu Asn Trp Gly Arg Ile Ser Asn Val
        195                 200                 205

Leu Pro Glu Phe Arg Gly Glu Gly Gly Val Arg Val Gly Arg Ile Ser
    210                 215                 220

Phe Asn Asn Ile Ser Ala Ile Leu Gly Thr Val Ala Val Ile Leu Asn
225                 230                 235                 240

Cys His His Gln Gly Ala Arg Ser Val Arg
            245                 250

<210> SEQ ID NO 15
<211> LENGTH: 250
<212> TYPE: PRT
<213> ORGANISM: Escherichia coli

<400> SEQUENCE: 15

Arg Glu Phe Thr Ile Asp Phe Ser Thr Gln Gln Ser Tyr Val Ser Ser
1               5                   10                  15

Leu Asn Ser Ile Arg Thr Glu Ile Ser Thr Pro Leu Glu His Ile Ser
            20                  25                  30

Gln Gly Thr Thr Ser Val Ser Val Ile Asn His Thr Pro Pro Gly Ser
        35                  40                  45

Tyr Phe Ala Val Asp Ile Arg Gly Leu Asp Val Tyr Gln Ala Arg Phe
    50                  55                  60

Asp His Leu Arg Leu Ile Ile Glu Gln Asn Asn Leu Tyr Val Ala Gly

```
                65                  70                  75                  80
Phe Val Asn Thr Ala Thr Asn Thr Phe Tyr Arg Phe Ser Asp Phe Thr
                    85                  90                  95

His Ile Ser Val Pro Gly Val Thr Val Ser Met Thr Thr Asp Ser
            100                 105                 110

Ser Tyr Thr Thr Leu Gln Arg Val Ala Ala Leu Glu Arg Ser Gly Met
                115                 120                 125

Gln Ile Ser Arg His Ser Leu Val Ser Ser Tyr Leu Ala Leu Met Glu
            130                 135                 140

Phe Ser Gly Asn Thr Met Thr Arg Asp Ala Ser Arg Ala Val Leu Arg
145                 150                 155                 160

Phe Val Thr Val Thr Ala Glu Ala Leu Arg Phe Arg Gln Ile Gln Arg
                    165                 170                 175

Glu Phe Arg Gln Ala Leu Ser Glu Thr Ala Pro Val Tyr Thr Met Thr
                180                 185                 190

Pro Gly Asp Val Asp Leu Thr Leu Asn Trp Gly Arg Ile Ser Asn Val
                195                 200                 205

Ile Pro Glu Tyr Arg Gly Glu Asp Gly Val Arg Val Gly Arg Ile Ser
    210                 215                 220

Phe Asn Asn Ile Ser Ala Ile Leu Ser Thr Val Ala Val Ile Leu Asn
225                 230                 235                 240

Cys His His Gln Gly Ala Arg Ser Val Arg
                245                 250

<210> SEQ ID NO 16
<211> LENGTH: 250
<212> TYPE: PRT
<213> ORGANISM: Escherichia coli

<400> SEQUENCE: 16

Gln Glu Phe Thr Ile Asp Phe Ser Thr Gln Gln Ser Tyr Val Ser Ser
1               5                   10                  15

Leu Asn Ser Ile Arg Thr Ala Ile Ser Thr Pro Leu Glu His Ile Ser
                20                  25                  30

Gln Gly Ala Thr Ser Val Ser Val Ile Asn His Thr Pro Pro Gly Ser
            35                  40                  45

Tyr Ile Ser Val Gly Ile Arg Gly Leu Asp Val Tyr Gln Glu Arg Phe
    50                  55                  60

Asp His Leu Arg Leu Ile Ile Glu Arg Asn Asn Leu Tyr Val Ala Gly
65                  70                  75                  80

Phe Val Asn Thr Thr Thr Asn Thr Phe Tyr Arg Phe Ser Asp Phe Ala
                    85                  90                  95

His Ile Ser Leu Pro Gly Val Thr Thr Ile Ser Met Thr Thr Asp Ser
            100                 105                 110

Ser Tyr Thr Thr Leu Gln Arg Val Ala Ala Leu Glu Arg Ser Gly Met
                115                 120                 125

Gln Ile Ser Arg His Ser Leu Val Ser Ser Tyr Leu Ala Leu Met Glu
            130                 135                 140

Phe Ser Gly Asn Thr Met Thr Arg Asp Ala Ser Arg Ala Val Leu Arg
145                 150                 155                 160

Phe Val Thr Val Thr Ala Glu Ala Leu Arg Phe Arg Gln Ile Gln Arg
                    165                 170                 175

Glu Phe Arg Leu Ala Leu Ser Glu Thr Ala Pro Val Tyr Thr Met Thr
                180                 185                 190
```

```
Pro Glu Asp Val Asp Leu Thr Leu Asn Trp Gly Arg Ile Ser Asn Val
            195                 200                 205

Leu Pro Glu Tyr Arg Gly Glu Ala Gly Val Arg Val Gly Arg Ile Ser
        210                 215                 220

Phe Asn Asn Ile Ser Ala Ile Leu Gly Thr Val Ala Val Ile Leu Asn
225                 230                 235                 240

Cys His His Gln Gly Ala Arg Ser Val Arg
                245                 250

<210> SEQ ID NO 17
<211> LENGTH: 250
<212> TYPE: PRT
<213> ORGANISM: Escherichia coli

<400> SEQUENCE: 17

Gln Glu Phe Thr Ile Asp Phe Ser Thr Gln Ser Tyr Val Ser Ser
1               5                   10                  15

Leu Asn Ser Ile Arg Thr Ala Ile Ser Thr Pro Leu Glu His Ile Ser
            20                  25                  30

Gln Gly Ala Thr Ser Val Ser Val Ile Asn His Thr Pro Pro Gly Ser
        35                  40                  45

Tyr Ile Ser Val Gly Ile Arg Gly Leu Asp Val Tyr Gln Ala His Phe
    50                  55                  60

Asp His Leu Arg Leu Ile Ile Glu Gln Asn Asn Leu Tyr Val Ala Gly
65                  70                  75                  80

Phe Val Asn Thr Ala Thr Asn Thr Phe Tyr Arg Phe Ser Asp Phe Ala
                85                  90                  95

His Ile Ser Leu Pro Gly Val Thr Thr Ile Ser Met Thr Thr Asp Ser
            100                 105                 110

Ser Tyr Thr Thr Leu Gln Arg Val Ala Ala Leu Glu Arg Ser Gly Met
        115                 120                 125

Gln Ile Ser Arg His Ser Leu Val Ser Ser Tyr Leu Ala Leu Met Glu
    130                 135                 140

Phe Ser Gly Asn Thr Met Thr Arg Glu Ala Ser Arg Ala Val Leu Arg
145                 150                 155                 160

Phe Val Thr Val Thr Ala Glu Ala Leu Arg Phe Arg Gln Ile Gln Arg
                165                 170                 175

Glu Phe Arg Gln Ala Leu Ser Glu Thr Ala Pro Val Tyr Thr Met Thr
            180                 185                 190

Pro Glu Asp Val Asp Leu Thr Leu Asn Trp Gly Arg Ile Ser Asn Val
        195                 200                 205

Leu Pro Glu Tyr Arg Gly Glu Asp Gly Val Arg Val Gly Arg Ile Ser
    210                 215                 220

Phe Asn Asn Ile Ser Ala Ile Leu Gly Thr Val Ala Val Ile Leu Asn
225                 230                 235                 240

Cys His His Gln Gly Ala Arg Ser Val Arg
                245                 250

<210> SEQ ID NO 18
<211> LENGTH: 250
<212> TYPE: PRT
<213> ORGANISM: Escherichia coli

<400> SEQUENCE: 18

Asp Glu Phe Thr Val Asp Phe Ser Gln Lys Ser Tyr Val Asp Ser
1               5                   10                  15
```

```
Leu Asn Ser Ile Arg Ser Ala Ile Ser Thr Pro Leu Gly Asn Ile Ser
             20                  25                  30

Gln Gly Gly Val Ser Val Ser Val Ile Asn His Val Pro Gly Gly Asn
         35                  40                  45

Tyr Ile Ser Leu Asn Val Arg Gly Leu Asp Pro Tyr Ser Glu Arg Phe
 50                  55                  60

Asn His Leu Arg Leu Ile Met Glu Arg Asn Asn Leu Tyr Val Ala Gly
 65                  70                  75                  80

Phe Ile Asn Thr Glu Thr Asn Thr Phe Tyr Arg Phe Ser Asp Phe Ser
                 85                  90                  95

His Ile Ser Val Pro Asp Val Ile Thr Val Ser Met Thr Thr Asp Ser
             100                 105                 110

Ser Tyr Ser Ser Leu Gln Arg Ile Ala Asp Leu Glu Arg Thr Gly Met
         115                 120                 125

Gln Ile Gly Arg His Ser Leu Val Gly Ser Tyr Leu Asp Leu Met Glu
130                 135                 140

Phe Arg Gly Arg Ser Met Thr Arg Ala Ser Ser Arg Ala Met Leu Arg
145                 150                 155                 160

Phe Val Thr Val Ile Ala Glu Ala Leu Arg Phe Arg Gln Ile Gln Arg
                 165                 170                 175

Gly Phe Arg Pro Ala Leu Ser Glu Ala Ser Pro Leu Tyr Thr Met Thr
             180                 185                 190

Ala Gln Asp Val Asp Leu Thr Leu Asn Trp Gly Arg Ile Ser Asn Val
         195                 200                 205

Leu Pro Glu Tyr Arg Gly Glu Glu Gly Val Arg Ile Gly Arg Ile Ser
210                 215                 220

Phe Asn Ser Leu Ser Ala Ile Leu Gly Ser Val Ala Val Ile Leu Asn
225                 230                 235                 240

Cys His Ser Thr Gly Ser Tyr Ser Val Arg
                 245                 250

<210> SEQ ID NO 19
<211> LENGTH: 251
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 19

Ala Glu Phe Thr Leu Asp Phe Ser Thr Ala Lys Thr Tyr Val Asp Ser
 1               5                  10                  15

Leu Asn Val Ile Arg Ser Ala Ile Gly Thr Pro Leu Gln Thr Ile Ser
             20                  25                  30

Ser Gly Gly Thr Ser Leu Leu Met Ile Asp Ser Gly Ile Gly Asp Asn
         35                  40                  45

Leu Phe Ala Val Asp Ile Leu Gly Phe Asp Phe Thr Leu Gly Arg Phe
 50                  55                  60

Asn Asn Leu Arg Leu Ile Val Glu Arg Asn Asn Leu Tyr Val Thr Gly
 65                  70                  75                  80

Phe Val Asn Arg Thr Asn Asn Val Phe Tyr Arg Phe Ala Asp Phe Ser
                 85                  90                  95

His Val Thr Phe Pro Gly Thr Thr Ala Val Thr Leu Ser Ala Asp Ser
             100                 105                 110

Ser Tyr Thr Thr Leu Gln Arg Val Ala Gly Ile Ser Arg Thr Gly Met
```

```
                115                 120                 125
Gln Ile Asn Arg His Ser Leu Thr Thr Ser Tyr Leu Asp Leu Met Ser
130                 135                 140

His Ser Ala Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Arg Thr Thr Leu Asp Asp Leu Ser Gly Arg Ser Tyr Val Met
                180                 185                 190

Thr Ala Glu Asp Val Asp Leu Thr Leu Asn Trp Gly Arg Leu Ser Ser
                195                 200                 205

Val Leu Pro Asp Tyr His Gly Gln Asp Ser Val Arg Val Gly Arg Ile
                210                 215                 220

Ser Phe Gly Ser Ile Asn Ala Ile Leu Gly Ser Val Ala Leu Ile Leu
225                 230                 235                 240

Asn Ser His His His Ala Ser Ala Val Ala Ala
                245                 250

<210> SEQ ID NO 20
<211> LENGTH: 251
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 20

Lys Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
                20                  25                  30

Ser Gly Gly Thr Ser Leu Leu Met Ile Asp Ser Gly Ile Gly Asp Asn
            35                  40                  45

Leu Phe Ala Val Asp Ile Leu Gly Phe Asp Phe Thr Leu Gly Arg Phe
50                  55                  60

Asn Asn Leu Arg Leu Ile Val Glu Arg Asn Asn Leu Tyr Val Thr Gly
65                  70                  75                  80

Phe Val Asn Arg Thr Asn Asn Val Phe Tyr Arg Phe Ala Asp Phe Ser
                85                  90                  95

His Val Thr Phe Pro Gly Thr Thr Ala Val Thr Leu Ser Ala Asp Ser
                100                 105                 110

Ser Tyr Thr Thr Leu Gln Arg Val Ala Gly Ile Ser Arg Thr Gly Met
            115                 120                 125

Gln Ile Asn Arg His Ser Leu Thr Thr Ser Tyr Leu Asp Leu Met Ser
130                 135                 140

His Ser Gly Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Arg Thr Thr Leu Asp Asp Leu Ser Gly Ala Ser Tyr Val Met
                180                 185                 190

Thr Ala Glu Asp Val Asp Leu Thr Leu Asn Trp Gly Arg Leu Ser Ser
                195                 200                 205

Val Leu Pro Asp Tyr His Gly Gln Asp Ser Val Arg Val Gly Arg Ile
                210                 215                 220
```

```
Ser Phe Gly Ser Ile Asn Ala Ile Leu Gly Ser Val Ala Leu Ile Leu
225                 230                 235                 240

Asn Ser His His His Ala Ser Ala Val Ala Ala
                245                 250
```

<210> SEQ ID NO 21
<211> LENGTH: 251
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 21

```
Arg Glu Phe Thr Leu Asp Phe Ser Thr Ala Arg Thr Tyr Val Asp Ser
1               5                   10                  15

Leu Asn Val Ile Arg Ser Ala Ile Gly Thr Pro Leu Gln Thr Ile Ser
                20                  25                  30

Ser Gly Gly Thr Ser Leu Leu Met Ile Asp Ser Gly Ile Gly Asp Asn
            35                  40                  45

Leu Phe Ala Val Asp Ile Leu Gly Phe Asp Phe Thr Leu Gly Arg Phe
    50                  55                  60

Asn Asn Leu Arg Leu Ile Val Glu Arg Asn Asn Leu Tyr Val Thr Gly
65                  70                  75                  80

Phe Val Asn Arg Thr Asn Asn Val Phe Tyr Arg Phe Ala Asp Phe Ser
                85                  90                  95

His Val Thr Phe Pro Gly Thr Thr Ala Val Thr Leu Ser Ala Asp Ser
                100                 105                 110

Ser Tyr Thr Thr Leu Gln Arg Val Ala Gly Ile Ser Arg Thr Gly Met
            115                 120                 125

Gln Ile Asn Arg His Ser Leu Thr Thr Ser Tyr Leu Ala Leu Met Ser
    130                 135                 140

His Ser Gly Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Arg Thr Thr Leu Asp Asp Leu Ser Gly Ala Ser Tyr Val Met
            180                 185                 190

Thr Ala Glu Asp Val Asp Leu Thr Leu Asn Trp Gly Arg Leu Ser Ser
    195                 200                 205

Val Leu Pro Asp Tyr His Gly Gln Asp Ser Val Arg Val Gly Arg Ile
    210                 215                 220

Ser Phe Gly Ser Ile Asn Ala Ile Leu Gly Ser Val Ala Leu Ile Leu
225                 230                 235                 240

Asn Ser His His His Ala Ser Ala Val Ala Ala
                245                 250
```

<210> SEQ ID NO 22
<211> LENGTH: 501
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 22

```
Met Lys Glu Phe Thr Leu Asp Phe Ser Thr Ala Lys Thr Tyr Val Asp
1               5                   10                  15
Ser Leu Asn Val Ile Arg Ser Ala Ile Gly Thr Pro Leu Gln Thr Ile
            20                  25                  30
Ser Ser Gly Gly Thr Ser Leu Leu Met Ile Asp Ser Gly Ser Gly Asp
            35                  40                  45
Asn Leu Phe Ala Val Asp Val Arg Gly Ile Asp Pro Glu Glu Gly Arg
50                  55                  60
Phe Asn Asn Leu Arg Leu Ile Val Glu Arg Asn Asn Leu Tyr Val Thr
65                  70                  75                  80
Gly Phe Val Asn Arg Thr Asn Asn Val Phe Tyr Arg Phe Ala Asp Phe
                85                  90                  95
Ser His Val Thr Phe Pro Gly Thr Thr Ala Val Thr Leu Ser Gly Asp
                100                 105                 110
Ser Tyr Thr Thr Leu Gln Arg Val Ala Gly Ile Ser Arg Thr Gly
            115                 120                 125
Met Gln Ile Asn Arg His Ser Leu Thr Thr Ser Tyr Leu Asp Leu Met
            130                 135                 140
Ser His Ser Gly Thr Ser Leu Thr Gln Ser Val Ala Arg Ala Met Leu
145                 150                 155                 160
Arg Phe Val Thr Val Thr Ala Glu Ala Leu Arg Phe Arg Gln Ile Gln
                165                 170                 175
Arg Gly Phe Arg Thr Thr Leu Asp Asp Leu Ser Gly Arg Ser Tyr Val
                180                 185                 190
Met Thr Ala Glu Asp Val Asp Leu Thr Leu Asn Trp Gly Arg Leu Ser
            195                 200                 205
Ser Val Leu Pro Asp Tyr His Gly Gln Asp Ser Val Arg Val Gly Arg
            210                 215                 220
Ile Ser Phe Gly Ser Ile Asn Ala Ile Leu Gly Ser Val Ala Leu Ile
225                 230                 235                 240
Leu Asn Cys His His Ala Ser Ala Val Ala Ala Glu Phe Pro Lys
                245                 250                 255
Pro Ser Thr Pro Pro Gly Ser Ser Gly Gly Ala Pro Asp Ile Gln Met
                260                 265                 270
Thr Gln Ser Pro Ser Ser Leu Ser Ala Ser Val Gly Asp Arg Val Thr
            275                 280                 285
Ile Thr Cys Arg Ala Ser Gln Asp Val Asn Thr Ala Val Ala Trp Tyr
            290                 295                 300
Gln Gln Lys Pro Gly Lys Ala Pro Lys Leu Leu Ile Tyr Ser Ala Ser
305                 310                 315                 320
Phe Leu Tyr Ser Gly Val Pro Ser Arg Phe Ser Gly Ser Arg Ser Gly
                325                 330                 335
Thr Asp Phe Thr Leu Thr Ile Ser Ser Leu Gln Pro Glu Asp Phe Ala
                340                 345                 350
Thr Tyr Tyr Cys Gln Gln His Tyr Thr Thr Pro Pro Thr Phe Gly Gln
                355                 360                 365
Gly Thr Lys Val Glu Ile Lys Gly Gly Gly Ser Glu Val Gln Leu
    370                 375                 380
Val Glu Ser Gly Gly Gly Leu Val Gln Pro Gly Gly Ser Leu Arg Leu
385                 390                 395                 400
Ser Cys Ala Ala Ser Gly Phe Asn Ile Lys Asp Thr Tyr Ile His Trp
                405                 410                 415
Val Arg Gln Ala Pro Gly Lys Gly Leu Glu Trp Val Ala Arg Ile Tyr
```

```
                    420                 425                 430
Pro Thr Asn Gly Tyr Thr Arg Tyr Ala Asp Ser Val Lys Gly Arg Phe
                435                 440                 445

Thr Ile Ser Ala Asp Thr Ser Lys Asn Thr Ala Tyr Leu Gln Met Asn
            450                 455                 460

Ser Leu Arg Ala Glu Asp Thr Ala Val Tyr Tyr Cys Ser Arg Trp Gly
465                 470                 475                 480

Gly Asp Gly Phe Tyr Ala Met Asp Tyr Trp Gly Gln Gly Thr Leu Val
                485                 490                 495

Thr Val Ser Ser Ala
            500

<210> SEQ ID NO 23
<211> LENGTH: 519
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 23

Met Lys Glu Phe Thr Leu Asp Phe Ser Thr Ala Lys Thr Tyr Val Asp
1               5                   10                  15

Ser Leu Asn Val Ile Arg Ser Ala Ile Gly Thr Pro Leu Gln Thr Ile
            20                  25                  30

Ser Ser Gly Gly Thr Ser Leu Leu Met Ile Asp Ser Gly Ser Gly Asp
        35                  40                  45

Asn Leu Phe Ala Val Asp Val Arg Gly Ile Asp Pro Glu Glu Gly Arg
    50                  55                  60

Phe Asn Asn Leu Arg Leu Ile Val Glu Arg Asn Asn Leu Tyr Val Thr
65                  70                  75                  80

Gly Phe Val Asn Arg Thr Asn Asn Val Phe Tyr Arg Phe Ala Asp Phe
                85                  90                  95

Ser His Val Thr Phe Pro Gly Thr Thr Ala Val Thr Leu Ser Gly Asp
            100                 105                 110

Ser Ser Tyr Thr Thr Leu Gln Arg Val Ala Gly Ile Ser Arg Thr Gly
        115                 120                 125

Met Gln Ile Asn Arg His Ser Leu Thr Thr Ser Tyr Leu Asp Leu Met
    130                 135                 140

Ser His Ser Gly Thr Ser Leu Thr Gln Ser Val Ala Arg Ala Met Leu
145                 150                 155                 160

Arg Phe Val Thr Val Thr Ala Glu Ala Leu Arg Phe Arg Gln Ile Gln
                165                 170                 175

Arg Gly Phe Arg Thr Thr Leu Asp Asp Leu Ser Gly Arg Ser Tyr Val
            180                 185                 190

Met Thr Ala Glu Asp Val Asp Leu Thr Leu Asn Trp Gly Arg Leu Ser
        195                 200                 205

Ser Val Leu Pro Asp Tyr His Gly Gln Asp Ser Val Arg Val Gly Arg
    210                 215                 220

Ile Ser Phe Gly Ser Ile Asn Ala Ile Leu Gly Ser Val Ala Leu Ile
225                 230                 235                 240

Leu Asn Cys His His His Ala Ser Ala Val Ala Ala Glu Phe Pro Lys
                245                 250                 255

Pro Ser Thr Pro Pro Gly Ser Ser Gly Gly Ala Pro Gln Val Gln Leu
            260                 265                 270
```

Gln Gln Ser Gly Pro Glu Leu Lys Lys Pro Gly Glu Thr Val Lys Ile
            275                 280                 285

Ser Cys Lys Ala Ser Gly Tyr Pro Phe Thr Asn Tyr Gly Met Asn Trp
    290                 295                 300

Val Lys Gln Ala Pro Gly Gln Gly Leu Lys Trp Met Gly Trp Ile Asn
305                 310                 315                 320

Thr Ser Thr Gly Glu Ser Thr Phe Ala Asp Asp Phe Lys Gly Arg Phe
                325                 330                 335

Asp Phe Ser Leu Glu Thr Ser Ala Asn Thr Ala Tyr Leu Gln Ile Asn
            340                 345                 350

Asn Leu Lys Ser Glu Asp Ser Ala Thr Tyr Phe Cys Ala Arg Trp Glu
        355                 360                 365

Val Tyr His Gly Tyr Val Pro Tyr Trp Gly Gln Gly Thr Thr Val Thr
    370                 375                 380

Val Ser Ser Gly Gly Gly Gly Ser Gly Gly Gly Gly Ser Gly Gly Gly
385                 390                 395                 400

Gly Ser Gly Gly Gly Gly Ser Gly Gly Gly Gly Ser Asp Ile Gln Met
                405                 410                 415

Thr Gln Ser Pro Ser Ser Leu Ser Ala Ser Val Gly Asp Arg Val Thr
            420                 425                 430

Ile Thr Cys Lys Ala Ser Gln Asp Val Tyr Asn Ala Val Ala Trp Tyr
        435                 440                 445

Gln Gln Lys Pro Gly Gln Ser Pro Lys Leu Leu Ile Tyr Ser Ala Ser
    450                 455                 460

Ser Arg Tyr Thr Gly Val Pro Ser Arg Phe Thr Gly Ser Gly Ser Gly
465                 470                 475                 480

Pro Asp Phe Thr Phe Thr Ile Ser Ser Val Gln Ala Glu Asp Leu Ala
                485                 490                 495

Val Tyr Phe Cys Gln Gln His Phe Arg Thr Pro Phe Thr Phe Gly Ser
            500                 505                 510

Gly Thr Lys Leu Glu Ile Lys
        515

<210> SEQ ID NO 24
<211> LENGTH: 501
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 24

Met Ala Glu Phe Thr Leu Asp Phe Ser Thr Ala Lys Thr Tyr Val Asp
1               5                   10                  15

Ser Leu Asn Val Ile Arg Ser Ala Ile Gly Thr Pro Leu Gln Thr Ile
            20                  25                  30

Ser Ser Gly Gly Thr Ser Leu Leu Met Ile Asp Ser Gly Ile Gly Asp
        35                  40                  45

Asn Leu Phe Ala Val Asp Ile Leu Gly Phe Asp Phe Thr Leu Gly Arg
    50                  55                  60

Phe Asn Asn Leu Arg Leu Ile Val Glu Arg Asn Asn Leu Tyr Val Thr
65                  70                  75                  80

Gly Phe Val Asn Arg Thr Asn Asn Val Phe Tyr Arg Phe Ala Asp Phe
                85                  90                  95

```
Ser His Val Thr Phe Pro Gly Thr Thr Ala Val Thr Leu Ser Ala Asp
            100                 105                 110

Ser Ser Tyr Thr Thr Leu Gln Arg Val Ala Gly Ile Ser Arg Thr Gly
        115                 120                 125

Met Gln Ile Asn Arg His Ser Leu Thr Thr Ser Tyr Leu Asp Leu Met
    130                 135                 140

Ser His Ser Ala Thr Ser Leu Thr Gln Ser Val Ala Arg Ala Met Leu
145                 150                 155                 160

Arg Phe Val Thr Val Thr Ala Glu Ala Leu Arg Phe Arg Gln Ile Gln
                165                 170                 175

Arg Gly Phe Arg Thr Thr Leu Asp Asp Leu Ser Gly Arg Ser Tyr Val
            180                 185                 190

Met Thr Ala Glu Asp Val Asp Leu Thr Leu Asn Trp Gly Arg Leu Ser
        195                 200                 205

Ser Val Leu Pro Asp Tyr His Gly Gln Asp Ser Val Arg Val Gly Arg
    210                 215                 220

Ile Ser Phe Gly Ser Ile Asn Ala Ile Leu Gly Ser Val Ala Leu Ile
225                 230                 235                 240

Leu Asn Ser His His His Ala Ser Ala Val Ala Ala Glu Phe Pro Lys
                245                 250                 255

Pro Ser Thr Pro Pro Gly Ser Ser Gly Gly Ala Pro Asp Ile Gln Met
            260                 265                 270

Thr Gln Ser Pro Ser Ser Leu Ser Ala Ser Val Gly Asp Arg Val Thr
        275                 280                 285

Ile Thr Cys Arg Ala Ser Gln Asp Val Asn Thr Ala Val Ala Trp Tyr
    290                 295                 300

Gln Gln Lys Pro Gly Lys Ala Pro Lys Leu Leu Ile Tyr Ser Ala Ser
305                 310                 315                 320

Phe Leu Tyr Ser Gly Val Pro Ser Arg Phe Ser Gly Ser Arg Ser Gly
                325                 330                 335

Thr Asp Phe Thr Leu Thr Ile Ser Ser Leu Gln Pro Glu Asp Phe Ala
            340                 345                 350

Thr Tyr Tyr Cys Gln Gln His Tyr Thr Thr Pro Pro Thr Phe Gly Gln
        355                 360                 365

Gly Thr Lys Val Glu Ile Lys Gly Gly Gly Ser Glu Val Gln Leu
    370                 375                 380

Val Glu Ser Gly Gly Gly Leu Val Gln Pro Gly Gly Ser Leu Arg Leu
385                 390                 395                 400

Ser Cys Ala Ala Ser Gly Phe Asn Ile Lys Asp Thr Tyr Ile His Trp
                405                 410                 415

Val Arg Gln Ala Pro Gly Lys Gly Leu Glu Trp Val Ala Arg Ile Tyr
            420                 425                 430

Pro Thr Asn Gly Tyr Thr Arg Tyr Ala Asp Ser Val Lys Gly Arg Phe
        435                 440                 445

Thr Ile Ser Ala Asp Thr Ser Lys Asn Thr Ala Tyr Leu Gln Met Asn
    450                 455                 460

Ser Leu Arg Ala Glu Asp Thr Ala Val Tyr Tyr Cys Ser Arg Trp Gly
465                 470                 475                 480

Gly Asp Gly Phe Tyr Ala Met Asp Tyr Trp Gly Gln Gly Thr Leu Val
                485                 490                 495

Thr Val Ser Ser Ala
            500
```

<210> SEQ ID NO 25
<211> LENGTH: 513
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 25

```
Met Ala Glu Phe Thr Leu Asp Phe Ser Thr Ala Lys Thr Tyr Val Asp
1               5                   10                  15

Ser Leu Asn Val Ile Arg Ser Ala Ile Gly Thr Pro Leu Gln Thr Ile
            20                  25                  30

Ser Ser Gly Gly Thr Ser Leu Leu Met Ile Asp Ser Gly Ile Gly Asp
        35                  40                  45

Asn Leu Phe Ala Val Asp Ile Leu Gly Phe Asp Phe Thr Leu Gly Arg
    50                  55                  60

Phe Asn Asn Leu Arg Leu Ile Val Glu Arg Asn Asn Leu Tyr Val Thr
65                  70                  75                  80

Gly Phe Val Asn Arg Thr Asn Asn Val Phe Tyr Arg Phe Ala Asp Phe
                85                  90                  95

Ser His Val Thr Phe Pro Gly Thr Thr Ala Val Thr Leu Ser Ala Asp
            100                 105                 110

Ser Ser Tyr Thr Thr Leu Gln Arg Val Ala Gly Ile Ser Arg Thr Gly
        115                 120                 125

Met Gln Ile Asn Arg His Ser Leu Thr Thr Ser Tyr Leu Asp Leu Met
    130                 135                 140

Ser His Ser Ala Thr Ser Leu Thr Gln Ser Val Ala Arg Ala Met Leu
145                 150                 155                 160

Arg Phe Val Thr Val Thr Ala Glu Ala Leu Arg Phe Arg Gln Ile Gln
                165                 170                 175

Arg Gly Phe Arg Thr Thr Leu Asp Asp Leu Ser Gly Arg Ser Tyr Val
            180                 185                 190

Met Thr Ala Glu Asp Val Asp Leu Thr Leu Asn Trp Gly Arg Leu Ser
        195                 200                 205

Ser Val Leu Pro Asp Tyr His Gly Gln Asp Ser Val Arg Val Gly Arg
    210                 215                 220

Ile Ser Phe Gly Ser Ile Asn Ala Ile Leu Gly Ser Val Ala Leu Ile
225                 230                 235                 240

Leu Asn Ser His His His Ala Ser Ala Val Ala Ala Glu Phe Pro Lys
                245                 250                 255

Pro Ser Thr Pro Pro Gly Ser Ser Gly Gly Ala Pro Gln Val Gln Leu
            260                 265                 270

Leu Gln Ser Gly Ala Glu Leu Lys Lys Pro Gly Glu Ser Leu Lys Ile
        275                 280                 285

Ser Cys Lys Gly Ser Gly Tyr Ser Phe Thr Ser Tyr Trp Ile Ala Trp
    290                 295                 300

Val Arg Gln Met Pro Gly Lys Gly Leu Glu Tyr Met Gly Leu Ile Tyr
305                 310                 315                 320

Pro Gly Asp Ser Asp Thr Lys Tyr Ser Pro Ser Phe Gln Gly Gln Val
                325                 330                 335

Thr Ile Ser Val Asp Lys Ser Val Ser Thr Ala Tyr Leu Gln Trp Ser
            340                 345                 350

Ser Leu Lys Pro Ser Asp Ser Ala Val Tyr Phe Cys Ala Arg His Asp
        355                 360                 365
```

```
Val Gly Tyr Cys Ser Ser Asn Cys Ala Lys Trp Pro Glu Tyr Phe
        370                 375                 380

Gln His Trp Gly Gln Gly Thr Leu Val Thr Val Ser Ser Gly Gly Gly
385                 390                 395                 400

Gly Ser Gln Ser Val Leu Thr Gln Pro Pro Ser Val Ser Ala Ala Pro
                405                 410                 415

Gly Gln Lys Val Thr Ile Ser Cys Ser Gly Ser Ser Asn Ile Gly
                420                 425                 430

Asn Asn Tyr Val Ser Trp Tyr Gln Gln Leu Pro Gly Thr Ala Pro Lys
            435                 440                 445

Leu Leu Ile Tyr Gly His Thr Asn Arg Pro Ala Gly Val Pro Asp Arg
    450                 455                 460

Phe Ser Gly Ser Lys Ser Gly Thr Ser Ala Ser Leu Ala Ile Ser Gly
465                 470                 475                 480

Phe Arg Ser Glu Asp Glu Ala Asp Tyr Tyr Cys Ala Ala Trp Asp Asp
                485                 490                 495

Ser Leu Ser Gly Trp Val Phe Gly Gly Gly Thr Lys Leu Thr Val Leu
            500                 505                 510

Ala

<210> SEQ ID NO 26
<211> LENGTH: 499
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 26

Met Ala Glu Phe Thr Leu Asp Phe Ser Thr Ala Lys Thr Tyr Val Asp
1               5                   10                  15

Ser Leu Asn Val Ile Arg Ser Ala Ile Gly Thr Pro Leu Gln Thr Ile
                20                  25                  30

Ser Ser Gly Gly Thr Ser Leu Leu Met Ile Asp Ser Gly Ile Gly Asp
            35                  40                  45

Asn Leu Phe Ala Val Asp Ile Leu Gly Phe Asp Phe Thr Leu Gly Arg
50                  55                  60

Phe Asn Asn Leu Arg Leu Ile Val Glu Arg Asn Asn Leu Tyr Val Thr
65                  70                  75                  80

Gly Phe Val Asn Arg Thr Asn Asn Val Phe Tyr Arg Phe Ala Asp Phe
                85                  90                  95

Ser His Val Thr Phe Pro Gly Thr Thr Ala Val Thr Leu Ser Ala Asp
                100                 105                 110

Ser Ser Tyr Thr Thr Leu Gln Arg Val Ala Gly Ile Ser Arg Thr Gly
            115                 120                 125

Met Gln Ile Asn Arg His Ser Leu Thr Thr Ser Tyr Leu Asp Leu Met
    130                 135                 140

Ser His Ser Ala Thr Ser Leu Thr Gln Ser Val Ala Arg Ala Met Leu
145                 150                 155                 160

Arg Phe Val Thr Val Thr Ala Glu Ala Leu Arg Phe Arg Gln Ile Gln
                165                 170                 175

Arg Gly Phe Arg Thr Thr Leu Asp Asp Leu Ser Gly Arg Ser Tyr Val
                180                 185                 190

Met Thr Ala Glu Asp Val Asp Leu Thr Leu Asn Trp Gly Arg Leu Ser
```

```
              195                 200                 205

Ser Val Leu Pro Asp Tyr His Gly Gln Asp Ser Val Arg Val Gly Arg
210                 215                 220

Ile Ser Phe Gly Ser Ile Asn Ala Ile Leu Gly Ser Val Ala Leu Ile
225                 230                 235                 240

Leu Asn Ser His His His Ala Ser Ala Ala Glu Phe Pro Lys
                    245                 250                 255

Pro Ser Thr Pro Pro Gly Ser Ser Gly Gly Ala Pro Gln Val Gln Leu
            260                 265                 270

Gln Gln Ser Gly Pro Glu Leu Lys Lys Pro Gly Glu Thr Val Lys Ile
                275                 280                 285

Ser Cys Lys Ala Ser Gly Tyr Pro Phe Thr Asn Tyr Gly Met Asn Trp
        290                 295                 300

Val Lys Gln Ala Pro Gly Gln Gly Leu Lys Trp Met Gly Trp Ile Asn
305                 310                 315                 320

Thr Ser Thr Gly Glu Ser Thr Phe Ala Asp Asp Phe Lys Gly Arg Phe
                    325                 330                 335

Asp Phe Ser Leu Glu Thr Ser Ala Asn Thr Ala Tyr Leu Gln Ile Asn
                340                 345                 350

Asn Leu Lys Ser Glu Asp Ser Ala Thr Tyr Phe Cys Ala Arg Trp Glu
            355                 360                 365

Val Tyr His Gly Tyr Val Pro Tyr Trp Gly Gln Gly Thr Thr Val Thr
370                 375                 380

Val Ser Ser Gly Gly Gly Gly Ser Asp Ile Gln Leu Thr Gln Ser His
385                 390                 395                 400

Lys Phe Leu Ser Thr Ser Val Gly Asp Arg Val Ser Ile Thr Cys Lys
                    405                 410                 415

Ala Ser Gln Asp Val Tyr Asn Ala Val Ala Trp Tyr Gln Lys Pro
                420                 425                 430

Gly Gln Ser Pro Lys Leu Leu Ile Tyr Ser Ala Ser Ser Arg Tyr Thr
            435                 440                 445

Gly Val Pro Ser Arg Phe Thr Gly Ser Gly Ser Gly Pro Asp Phe Thr
        450                 455                 460

Phe Thr Ile Ser Ser Val Gln Ala Glu Asp Leu Ala Val Tyr Phe Cys
465                 470                 475                 480

Gln Gln His Phe Arg Thr Pro Phe Thr Phe Gly Ser Gly Thr Lys Leu
                    485                 490                 495

Glu Ile Lys

<210> SEQ ID NO 27
<211> LENGTH: 500
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 27

Met Ala Glu Phe Thr Leu Asp Phe Ser Thr Ala Lys Thr Tyr Val Asp
1               5                   10                  15

Ser Leu Asn Val Ile Arg Ser Ala Ile Gly Thr Pro Leu Gln Thr Ile
                20                  25                  30

Ser Ser Gly Gly Thr Ser Leu Leu Met Ile Asp Ser Gly Ile Gly Asp
            35                  40                  45
```

```
Asn Leu Phe Ala Val Asp Ile Leu Gly Phe Asp Phe Thr Leu Gly Arg
 50                  55                  60

Phe Asn Asn Leu Arg Leu Ile Val Glu Arg Asn Asn Leu Tyr Val Thr
 65                  70                  75                  80

Gly Phe Val Asn Arg Thr Asn Asn Val Phe Tyr Arg Phe Ala Asp Phe
                 85                  90                  95

Ser His Val Thr Phe Pro Gly Thr Thr Ala Val Thr Leu Ser Ala Asp
                100                 105                 110

Ser Ser Tyr Thr Thr Leu Gln Arg Val Ala Gly Ile Ser Arg Thr Gly
                115                 120                 125

Met Gln Ile Asn Arg His Ser Leu Thr Thr Ser Tyr Leu Asp Leu Met
130                 135                 140

Ser His Ser Ala Thr Ser Leu Thr Gln Ser Val Ala Arg Ala Met Leu
145                 150                 155                 160

Arg Phe Val Thr Val Thr Ala Glu Ala Leu Arg Phe Arg Gln Ile Gln
                165                 170                 175

Arg Gly Phe Arg Thr Thr Leu Asp Asp Leu Ser Gly Arg Ser Tyr Val
                180                 185                 190

Met Thr Ala Glu Asp Val Asp Leu Thr Leu Asn Trp Gly Arg Leu Ser
                195                 200                 205

Ser Val Leu Pro Asp Tyr His Gly Gln Asp Ser Val Arg Val Gly Arg
210                 215                 220

Ile Ser Phe Gly Ser Ile Asn Ala Ile Leu Gly Ser Val Ala Leu Ile
225                 230                 235                 240

Leu Asn Ser His His His Ala Ser Ala Val Ala Ala Glu Phe Pro Lys
                245                 250                 255

Pro Ser Thr Pro Pro Gly Ser Ser Gly Gly Ala Pro Asp Ile Gln Met
                260                 265                 270

Thr Gln Ser Pro Ser Ser Leu Ser Ala Ser Val Gly Asp Arg Val Thr
                275                 280                 285

Ile Thr Cys Lys Ala Ser Gln Asp Val Ser Ile Gly Val Ala Trp Tyr
                290                 295                 300

Gln Gln Lys Pro Gly Lys Ala Pro Lys Leu Leu Ile Tyr Ser Ala Ser
305                 310                 315                 320

Tyr Arg Tyr Thr Gly Val Pro Ser Arg Phe Ser Gly Ser Gly Ser Gly
                325                 330                 335

Thr Asp Phe Thr Leu Thr Ile Ser Ser Leu Gln Pro Glu Asp Phe Ala
                340                 345                 350

Thr Tyr Tyr Cys Gln Gln Tyr Tyr Ile Tyr Pro Tyr Thr Phe Gly Gln
                355                 360                 365

Gly Thr Lys Val Glu Ile Lys Gly Gly Gly Ser Glu Val Gln Leu
                370                 375                 380

Val Glu Ser Gly Gly Gly Leu Val Gln Pro Gly Gly Ser Leu Arg Leu
385                 390                 395                 400

Ser Cys Ala Ala Ser Gly Phe Thr Phe Thr Asp Tyr Thr Met Asp Trp
                405                 410                 415

Val Arg Gln Ala Pro Gly Lys Gly Leu Glu Trp Val Ala Asp Val Asn
                420                 425                 430

Pro Asn Ser Gly Gly Ser Ile Tyr Asn Gln Arg Phe Lys Gly Arg Phe
                435                 440                 445

Thr Leu Ser Val Asp Arg Ser Lys Asn Thr Leu Tyr Leu Gln Met Asn
450                 455                 460

Ser Leu Arg Ala Glu Asp Thr Ala Val Tyr Tyr Cys Ala Arg Asn Leu
```

```
              465                 470                 475                 480

Gly Pro Ser Phe Tyr Phe Asp Tyr Trp Gly Gln Gly Thr Leu Val Thr
                    485                 490                 495

Val Ser Ser Ala
            500

<210> SEQ ID NO 28
<211> LENGTH: 520
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 28

Met Lys Glu Phe Thr Leu Asp Phe Ser Thr Ala Lys Thr Tyr Val Asp
1               5                   10                  15

Ser Leu Asn Val Ile Arg Ser Ala Ile Gly Thr Pro Leu Gln Thr Ile
                20                  25                  30

Ser Ser Gly Gly Thr Ser Leu Leu Met Ile Asp Ser Gly Ile Gly Asp
            35                  40                  45

Asn Leu Phe Ala Val Asp Ile Leu Gly Phe Asp Phe Thr Leu Gly Arg
        50                  55                  60

Phe Asn Asn Leu Arg Leu Ile Val Glu Arg Asn Asn Leu Tyr Val Thr
65                  70                  75                  80

Gly Phe Val Asn Arg Thr Asn Asn Val Phe Tyr Arg Phe Ala Asp Phe
                85                  90                  95

Ser His Val Thr Phe Pro Gly Thr Thr Ala Val Thr Leu Ser Ala Asp
            100                 105                 110

Ser Ser Tyr Thr Thr Leu Gln Arg Val Ala Gly Ile Ser Arg Thr Gly
        115                 120                 125

Met Gln Ile Asn Arg His Ser Leu Thr Thr Ser Tyr Leu Asp Leu Met
130                 135                 140

Ser His Ser Gly Thr Ser Leu Thr Gln Ser Val Ala Arg Ala Met Leu
145                 150                 155                 160

Arg Phe Val Thr Val Thr Ala Glu Ala Leu Arg Phe Arg Gln Ile Gln
                165                 170                 175

Arg Gly Phe Arg Thr Thr Leu Asp Asp Leu Ser Gly Ala Ser Tyr Val
            180                 185                 190

Met Thr Ala Glu Asp Val Asp Leu Thr Leu Asn Trp Gly Arg Leu Ser
        195                 200                 205

Ser Val Leu Pro Asp Tyr His Gly Gln Asp Ser Val Arg Val Gly Arg
210                 215                 220

Ile Ser Phe Gly Ser Ile Asn Ala Ile Leu Gly Ser Val Ala Leu Ile
225                 230                 235                 240

Leu Asn Ser His His His Ala Ser Ala Val Ala Ala Glu Phe Pro Lys
                245                 250                 255

Pro Ser Thr Pro Pro Gly Ser Ser Gly Gly Ala Pro Asp Ile Gln Met
            260                 265                 270

Thr Gln Ser Pro Ser Ser Leu Ser Ala Ser Val Gly Asp Arg Val Thr
        275                 280                 285

Ile Thr Cys Arg Ala Ser Gln Asp Val Asn Thr Ala Val Ala Trp Tyr
290                 295                 300

Gln Gln Lys Pro Gly Lys Ala Pro Lys Leu Leu Ile Tyr Ser Ala Ser
305                 310                 315                 320
```

```
Phe Leu Tyr Ser Gly Val Pro Ser Arg Phe Gly Ser Arg Ser Gly
                325                 330                 335

Thr Asp Phe Thr Leu Thr Ile Ser Ser Leu Gln Pro Glu Asp Phe Ala
            340                 345                 350

Thr Tyr Tyr Cys Gln Gln His Tyr Thr Thr Pro Pro Thr Phe Gly Gln
        355                 360                 365

Gly Thr Lys Val Glu Ile Lys Gly Gly Gly Ser Gly Gly Gly Gly
    370                 375                 380

Ser Gly Gly Gly Gly Ser Gly Gly Gly Ser Gly Gly Gly Gly Ser
385                 390                 395                 400

Glu Val Gln Leu Val Glu Ser Gly Gly Gly Leu Val Gln Pro Gly Gly
                405                 410                 415

Ser Leu Arg Leu Ser Cys Ala Ala Ser Gly Phe Asn Ile Lys Asp Thr
            420                 425                 430

Tyr Ile His Trp Val Arg Gln Ala Pro Gly Lys Gly Leu Glu Trp Val
        435                 440                 445

Ala Arg Ile Tyr Pro Thr Asn Gly Tyr Thr Arg Tyr Ala Asp Ser Val
    450                 455                 460

Lys Gly Arg Phe Thr Ile Ser Ala Asp Thr Ser Lys Asn Thr Ala Tyr
465                 470                 475                 480

Leu Gln Met Asn Ser Leu Arg Ala Glu Asp Thr Ala Val Tyr Tyr Cys
                485                 490                 495

Ser Arg Trp Gly Gly Asp Gly Phe Tyr Ala Met Asp Tyr Trp Gly Gln
            500                 505                 510

Gly Thr Leu Val Thr Val Ser Ser
        515                 520

<210> SEQ ID NO 29
<211> LENGTH: 519
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 29

Met Lys Glu Phe Thr Leu Asp Phe Ser Thr Ala Lys Thr Tyr Val Asp
1               5                   10                  15

Ser Leu Asn Val Ile Arg Ser Ala Ile Gly Thr Pro Leu Gln Thr Ile
            20                  25                  30

Ser Ser Gly Gly Thr Ser Leu Leu Met Ile Asp Ser Gly Ile Gly Asp
        35                  40                  45

Asn Leu Phe Ala Val Asp Ile Leu Gly Phe Asp Phe Thr Leu Gly Arg
    50                  55                  60

Phe Asn Asn Leu Arg Leu Ile Val Glu Arg Asn Asn Leu Tyr Val Thr
65                  70                  75                  80

Gly Phe Val Asn Arg Thr Asn Asn Val Phe Tyr Arg Phe Ala Asp Phe
                85                  90                  95

Ser His Val Thr Phe Pro Gly Thr Thr Ala Val Thr Leu Ser Ala Asp
            100                 105                 110

Ser Ser Tyr Thr Thr Leu Gln Arg Val Ala Gly Ile Ser Arg Thr Gly
        115                 120                 125

Met Gln Ile Asn Arg His Ser Leu Thr Thr Ser Tyr Leu Asp Leu Met
    130                 135                 140
```

Ser His Ser Gly Thr Ser Leu Thr Gln Ser Val Ala Arg Ala Met Leu
145                 150                 155                 160

Arg Phe Val Thr Val Thr Ala Glu Ala Leu Arg Phe Arg Gln Ile Gln
                165                 170                 175

Arg Gly Phe Arg Thr Thr Leu Asp Asp Leu Ser Gly Ala Ser Tyr Val
            180                 185                 190

Met Thr Ala Glu Asp Val Asp Leu Thr Leu Asn Trp Gly Arg Leu Ser
        195                 200                 205

Ser Val Leu Pro Asp Tyr His Gly Gln Asp Ser Val Arg Val Gly Arg
    210                 215                 220

Ile Ser Phe Gly Ser Ile Asn Ala Ile Leu Gly Ser Val Ala Leu Ile
225                 230                 235                 240

Leu Asn Ser His His His Ala Ser Ala Val Ala Ala Glu Phe Pro Lys
                245                 250                 255

Pro Ser Thr Pro Pro Gly Ser Ser Gly Ala Pro Gln Val Gln Leu
            260                 265                 270

Gln Gln Ser Gly Pro Glu Leu Lys Lys Pro Gly Glu Thr Val Lys Ile
        275                 280                 285

Ser Cys Lys Ala Ser Gly Tyr Pro Phe Thr Asn Tyr Gly Met Asn Trp
    290                 295                 300

Val Lys Gln Ala Pro Gly Gln Gly Leu Lys Trp Met Gly Trp Ile Asn
305                 310                 315                 320

Thr Ser Thr Gly Glu Ser Thr Phe Ala Asp Asp Phe Lys Gly Arg Phe
                325                 330                 335

Asp Phe Ser Leu Glu Thr Ser Ala Asn Thr Ala Tyr Leu Gln Ile Asn
            340                 345                 350

Asn Leu Lys Ser Glu Asp Ser Ala Thr Tyr Phe Cys Ala Arg Trp Glu
        355                 360                 365

Val Tyr His Gly Tyr Val Pro Tyr Trp Gly Gln Gly Thr Thr Val Thr
    370                 375                 380

Val Ser Ser Gly Gly Gly Gly Ser Gly Gly Gly Ser Gly Gly Gly Gly
385                 390                 395                 400

Gly Ser Gly Gly Gly Gly Ser Gly Gly Gly Ser Asp Ile Gln Met
            405                 410                 415

Thr Gln Ser Pro Ser Ser Leu Ser Ala Ser Val Gly Asp Arg Val Thr
        420                 425                 430

Ile Thr Cys Lys Ala Ser Gln Asp Val Tyr Asn Ala Val Ala Trp Tyr
    435                 440                 445

Gln Gln Lys Pro Gly Gln Ser Pro Lys Leu Leu Ile Tyr Ser Ala Ser
    450                 455                 460

Ser Arg Tyr Thr Gly Val Pro Ser Arg Phe Thr Gly Ser Gly Ser Gly
465                 470                 475                 480

Pro Asp Phe Thr Phe Thr Ile Ser Ser Val Gln Ala Glu Asp Leu Ala
                485                 490                 495

Val Tyr Phe Cys Gln Gln His Phe Arg Thr Pro Phe Thr Phe Gly Ser
            500                 505                 510

Gly Thr Lys Leu Glu Ile Lys
        515

<210> SEQ ID NO 30
<211> LENGTH: 519
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 30

```
Met Arg Glu Phe Thr Leu Asp Phe Ser Thr Ala Arg Thr Tyr Val Asp
1               5                   10                  15

Ser Leu Asn Val Ile Arg Ser Ala Ile Gly Thr Pro Leu Gln Thr Ile
            20                  25                  30

Ser Ser Gly Gly Thr Ser Leu Leu Met Ile Asp Ser Gly Ile Gly Asp
        35                  40                  45

Asn Leu Phe Ala Val Asp Ile Leu Gly Phe Asp Phe Thr Leu Gly Arg
    50                  55                  60

Phe Asn Asn Leu Arg Leu Ile Val Glu Arg Asn Asn Leu Tyr Val Thr
65                  70                  75                  80

Gly Phe Val Asn Arg Thr Asn Asn Val Phe Tyr Arg Phe Ala Asp Phe
                85                  90                  95

Ser His Val Thr Phe Pro Gly Thr Thr Ala Val Thr Leu Ser Ala Asp
            100                 105                 110

Ser Ser Tyr Thr Thr Leu Gln Arg Val Ala Gly Ile Ser Arg Thr Gly
        115                 120                 125

Met Gln Ile Asn Arg His Ser Leu Thr Thr Ser Tyr Leu Ala Leu Met
130                 135                 140

Ser His Ser Gly Thr Ser Leu Thr Gln Ser Val Ala Arg Ala Met Leu
145                 150                 155                 160

Arg Phe Val Thr Val Thr Ala Glu Ala Leu Arg Phe Arg Gln Ile Gln
                165                 170                 175

Arg Gly Phe Arg Thr Thr Leu Asp Asp Leu Ser Gly Ala Ser Tyr Val
            180                 185                 190

Met Thr Ala Glu Asp Val Asp Leu Thr Leu Asn Trp Gly Arg Leu Ser
        195                 200                 205

Ser Val Leu Pro Asp Tyr His Gly Gln Asp Ser Val Arg Val Gly Arg
    210                 215                 220

Ile Ser Phe Gly Ser Ile Asn Ala Ile Leu Gly Ser Val Ala Leu Ile
225                 230                 235                 240

Leu Asn Ser His His His Ala Ser Ala Val Ala Ala Ser Pro Ser Thr
                245                 250                 255

Pro Pro Thr Pro Ser Pro Ser Thr Pro Pro Ala Ser Gln Val Gln Leu
            260                 265                 270

Val Gln Ser Gly Pro Glu Val Lys Lys Pro Gly Ala Ser Val Lys Val
        275                 280                 285

Ser Cys Lys Ala Ser Gly Tyr Pro Phe Thr Asn Tyr Gly Met Asn Trp
    290                 295                 300

Val Arg Gln Ala Pro Gly Gln Gly Leu Glu Trp Met Gly Trp Ile Asn
305                 310                 315                 320

Thr Ser Thr Gly Glu Ser Thr Phe Ala Asp Asp Phe Lys Gly Arg Val
                325                 330                 335

Thr Met Thr Thr Asp Thr Ser Thr Ser Thr Thr Tyr Met Glu Leu Arg
            340                 345                 350

Ser Leu Arg Pro Asp Asp Thr Ala Val Tyr Phe Cys Ala Arg Trp Glu
        355                 360                 365

Val Tyr His Gly Tyr Val Pro Tyr Trp Gly Gln Gly Thr Leu Val Thr
    370                 375                 380

Val Ser Ser Gly Gly Gly Gly Ser Gly Gly Gly Gly Ser Gly Gly Gly
385                 390                 395                 400
```

Gly Ser Gly Gly Gly Ser Gly Gly Gly Ser Asp Ile Gln Met
                405                 410                 415

Thr Gln Ser Pro Ser Ser Leu Ser Ala Ser Ile Gly Asp Arg Val Thr
            420                 425                 430

Ile Thr Cys Lys Ala Ser Gln Asp Val Tyr Asn Ala Val Ala Trp Tyr
            435                 440                 445

Gln Gln Lys Pro Gly Glu Ala Pro Lys Leu Leu Val Tyr Ser Ala Ser
        450                 455                 460

Ser Arg Tyr Thr Gly Val Pro Ser Arg Phe Ser Gly Ser Gly Ser Gly
465                 470                 475                 480

Thr Asp Phe Thr Phe Thr Ile Ser Ser Leu Gln Pro Glu Asp Ile Ala
                485                 490                 495

Thr Tyr Phe Cys Gln Gln His Phe Arg Thr Pro Phe Thr Phe Ala Pro
            500                 505                 510

Gly Thr Lys Leu Glu Ile Lys
        515

<210> SEQ ID NO 31
<211> LENGTH: 386
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 31

Met Lys Glu Phe Thr Leu Asp Phe Ser Thr Ala Lys Thr Tyr Val Asp
1               5                   10                  15

Ser Leu Asn Val Ile Arg Ser Ala Ile Gly Thr Pro Leu Gln Thr Ile
            20                  25                  30

Ser Ser Gly Gly Thr Ser Leu Leu Met Ile Asp Ser Gly Ile Gly Asp
        35                  40                  45

Asn Leu Phe Ala Val Asp Ile Leu Gly Phe Asp Phe Thr Leu Gly Arg
    50                  55                  60

Phe Asn Asn Leu Arg Leu Ile Val Glu Arg Asn Asn Leu Tyr Val Thr
65                  70                  75                  80

Gly Phe Val Asn Arg Thr Asn Asn Val Phe Tyr Arg Phe Ala Asp Phe
                85                  90                  95

Ser His Val Thr Phe Pro Gly Thr Thr Ala Val Thr Leu Ser Ala Asp
            100                 105                 110

Ser Ser Tyr Thr Thr Leu Gln Arg Val Ala Gly Ile Ser Arg Thr Gly
        115                 120                 125

Met Gln Ile Asn Arg His Ser Leu Thr Thr Ser Tyr Leu Asp Leu Met
    130                 135                 140

Ser His Ser Gly Thr Ser Leu Thr Gln Ser Val Ala Arg Ala Met Leu
145                 150                 155                 160

Arg Phe Val Thr Val Thr Ala Glu Ala Leu Arg Phe Arg Gln Ile Gln
                165                 170                 175

Arg Gly Phe Arg Thr Thr Leu Asp Asp Leu Ser Gly Ala Ser Tyr Val
            180                 185                 190

Met Thr Ala Glu Asp Val Asp Leu Thr Leu Asn Trp Gly Arg Leu Ser
        195                 200                 205

Ser Val Leu Pro Asp Tyr His Gly Gln Asp Ser Val Arg Val Gly Arg
    210                 215                 220

```
Ile Ser Phe Gly Ser Ile Asn Ala Ile Leu Gly Ser Val Ala Leu Ile
225                 230                 235                 240

Leu Asn Ser His His Ala Ser Ala Val Ala Ala His His Ser
            245                 250                 255

Glu Asp Pro Ser Ser Lys Ala Pro Lys Ala Pro Glu Val Gln Leu Val
                260                 265                 270

Glu Ser Gly Gly Gly Leu Val Gln Ala Gly Gly Ser Leu Arg Leu Ser
            275                 280                 285

Cys Ala Ala Ser Gly Ile Thr Phe Ser Ile Asn Thr Met Gly Trp Tyr
            290                 295                 300

Arg Gln Ala Pro Gly Lys Gln Arg Glu Leu Val Ala Leu Ile Ser Ser
305                 310                 315                 320

Ile Gly Asp Thr Tyr Tyr Ala Asp Ser Val Lys Gly Arg Phe Thr Ile
                325                 330                 335

Ser Arg Asp Asn Ala Lys Asn Thr Val Tyr Leu Gln Met Asn Ser Leu
                340                 345                 350

Lys Pro Glu Asp Thr Ala Val Tyr Tyr Cys Lys Arg Phe Arg Thr Ala
            355                 360                 365

Ala Gln Gly Thr Asp Tyr Trp Gly Gln Gly Thr Gln Val Thr Val Ser
370                 375                 380

Ser Ala
385

<210> SEQ ID NO 32
<211> LENGTH: 499
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 32

Met Lys Glu Phe Thr Leu Asp Phe Ser Thr Ala Lys Thr Tyr Val Asp
1               5                   10                  15

Ser Leu Asn Val Ile Arg Ser Ala Ile Gly Thr Pro Leu Gln Thr Ile
            20                  25                  30

Ser Ser Gly Gly Thr Ser Leu Leu Met Ile Asp Ser Gly Ile Gly Asp
        35                  40                  45

Asn Leu Phe Ala Val Asp Ile Leu Gly Phe Asp Phe Thr Leu Gly Arg
    50                  55                  60

Phe Asn Asn Leu Arg Leu Ile Val Glu Arg Asn Asn Leu Tyr Val Thr
65                  70                  75                  80

Gly Phe Val Asn Arg Thr Asn Asn Val Phe Tyr Arg Phe Ala Asp Phe
                85                  90                  95

Ser His Val Thr Phe Pro Gly Thr Thr Ala Val Thr Leu Ser Ala Asp
            100                 105                 110

Ser Ser Tyr Thr Thr Leu Gln Arg Val Ala Gly Ile Ser Arg Thr Gly
        115                 120                 125

Met Gln Ile Asn Arg His Ser Leu Thr Thr Ser Tyr Leu Asp Leu Met
130                 135                 140

Ser His Ser Gly Thr Ser Leu Thr Gln Ser Val Ala Arg Ala Met Leu
145                 150                 155                 160

Arg Phe Val Thr Val Thr Ala Glu Ala Leu Arg Phe Arg Gln Ile Gln
                165                 170                 175

Arg Gly Phe Arg Thr Thr Leu Asp Asp Leu Ser Gly Ala Ser Tyr Val
```

```
                180             185             190
Met Thr Ala Glu Asp Val Asp Leu Thr Leu Asn Trp Gly Arg Leu Ser
            195                 200                 205

Ser Val Leu Pro Asp Tyr His Gly Gln Asp Ser Val Arg Val Gly Arg
            210                 215                 220

Ile Ser Phe Gly Ser Ile Asn Ala Ile Leu Gly Ser Val Ala Leu Ile
225                 230                 235                 240

Leu Asn Ser His His His Ala Ser Ala Val Ala Ala Glu Phe Pro Lys
                245                 250                 255

Pro Ser Thr Pro Pro Gly Ser Ser Gly Gly Ala Pro Gln Val Gln Leu
            260                 265                 270

Gln Gln Ser Gly Pro Glu Leu Lys Lys Pro Gly Glu Thr Val Lys Ile
            275                 280                 285

Ser Cys Lys Ala Ser Gly Tyr Pro Phe Thr Asn Tyr Gly Met Asn Trp
            290                 295                 300

Val Lys Gln Ala Pro Gly Gln Gly Leu Lys Trp Met Gly Trp Ile Asn
305                 310                 315                 320

Thr Ser Thr Gly Glu Ser Thr Phe Ala Asp Asp Phe Lys Gly Arg Phe
                325                 330                 335

Asp Phe Ser Leu Glu Thr Ser Ala Asn Thr Ala Tyr Leu Gln Ile Asn
                340                 345                 350

Asn Leu Lys Ser Glu Asp Ser Ala Thr Tyr Phe Cys Ala Arg Trp Glu
            355                 360                 365

Val Tyr His Gly Tyr Val Pro Tyr Trp Gly Gln Gly Thr Thr Val Thr
            370                 375                 380

Val Ser Ser Gly Gly Gly Gly Ser Asp Ile Gln Met Thr Gln Ser Pro
385                 390                 395                 400

Ser Ser Leu Ser Ala Ser Val Gly Asp Arg Val Thr Ile Thr Cys Lys
                405                 410                 415

Ala Ser Gln Asp Val Tyr Asn Ala Val Ala Trp Tyr Gln Gln Lys Pro
                420                 425                 430

Gly Gln Ser Pro Lys Leu Leu Ile Tyr Ser Ala Ser Ser Arg Tyr Thr
            435                 440                 445

Gly Val Pro Ser Arg Phe Thr Gly Ser Gly Ser Gly Pro Asp Phe Thr
            450                 455                 460

Phe Thr Ile Ser Ser Val Gln Ala Glu Asp Leu Ala Val Tyr Phe Cys
465                 470                 475                 480

Gln Gln His Phe Arg Thr Pro Phe Thr Phe Gly Ser Gly Thr Lys Leu
                485                 490                 495

Glu Ile Lys

<210> SEQ ID NO 33
<211> LENGTH: 499
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 33

Met Lys Glu Phe Thr Leu Asp Phe Ser Thr Ala Lys Thr Tyr Val Asp
1               5                   10                  15

Ser Leu Asn Val Ile Arg Ser Ala Ile Gly Thr Pro Leu Gln Thr Ile
                20                  25                  30
```

```
Ser Ser Gly Thr Ser Leu Leu Met Ile Asp Ser Gly Ser Gly Asp
        35                  40                  45

Asn Leu Phe Ala Val Asp Val Arg Gly Ile Asp Pro Glu Glu Gly Arg
50                  55                  60

Phe Asn Asn Leu Arg Leu Ile Val Glu Arg Asn Asn Leu Tyr Val Thr
65                  70                  75                  80

Gly Phe Val Asn Arg Thr Asn Asn Val Phe Tyr Arg Phe Ala Asp Phe
                85                  90                  95

Ser His Val Thr Phe Pro Gly Thr Thr Ala Val Thr Leu Ser Gly Asp
                100                 105                 110

Ser Ser Tyr Thr Thr Leu Gln Arg Val Ala Gly Ile Ser Arg Thr Gly
            115                 120                 125

Met Gln Ile Asn Arg His Ser Leu Thr Thr Ser Tyr Leu Asp Leu Met
130                 135                 140

Ser His Ser Gly Thr Ser Leu Thr Gln Ser Val Ala Arg Ala Met Leu
145                 150                 155                 160

Arg Phe Val Thr Val Thr Ala Glu Ala Leu Arg Phe Arg Gln Ile Gln
                165                 170                 175

Arg Gly Phe Arg Thr Thr Leu Asp Asp Leu Ser Gly Arg Ser Tyr Val
            180                 185                 190

Met Thr Ala Glu Asp Val Asp Leu Thr Leu Asn Trp Gly Arg Leu Ser
            195                 200                 205

Ser Val Leu Pro Asp Tyr His Gly Gln Asp Ser Val Arg Val Gly Arg
        210                 215                 220

Ile Ser Phe Gly Ser Ile Asn Ala Ile Leu Gly Ser Val Ala Leu Ile
225                 230                 235                 240

Leu Asn Cys His His His Ala Ser Ala Val Ala Ala Glu Phe Pro Lys
                245                 250                 255

Pro Ser Thr Pro Pro Gly Ser Ser Gly Gly Ala Pro Gln Val Gln Leu
                260                 265                 270

Gln Gln Ser Gly Pro Glu Leu Lys Lys Pro Gly Glu Thr Val Lys Ile
            275                 280                 285

Ser Cys Lys Ala Ser Gly Tyr Pro Phe Thr Asn Tyr Gly Met Asn Trp
    290                 295                 300

Val Lys Gln Ala Pro Gly Gln Gly Leu Lys Trp Met Gly Trp Ile Asn
305                 310                 315                 320

Thr Ser Thr Gly Glu Ser Thr Phe Ala Asp Asp Phe Lys Gly Arg Phe
                325                 330                 335

Asp Phe Ser Leu Glu Thr Ser Ala Asn Thr Ala Tyr Leu Gln Ile Asn
            340                 345                 350

Asn Leu Lys Ser Glu Asp Ser Ala Thr Tyr Phe Cys Ala Arg Trp Glu
            355                 360                 365

Val Tyr His Gly Tyr Val Pro Tyr Trp Gly Gln Gly Thr Thr Val Thr
    370                 375                 380

Val Ser Ser Gly Gly Gly Gly Ser Asp Ile Gln Met Thr Gln Ser Pro
385                 390                 395                 400

Ser Ser Leu Ser Ala Ser Val Gly Asp Arg Val Thr Ile Thr Cys Lys
                405                 410                 415

Ala Ser Gln Asp Val Tyr Asn Ala Val Ala Trp Tyr Gln Gln Lys Pro
            420                 425                 430

Gly Gln Ser Pro Lys Leu Leu Ile Tyr Ser Ala Ser Ser Arg Tyr Thr
            435                 440                 445

Gly Val Pro Ser Arg Phe Thr Gly Ser Gly Ser Gly Pro Asp Phe Thr
```

```
            450                 455                 460
Phe Thr Ile Ser Ser Val Gln Ala Glu Asp Leu Ala Val Tyr Phe Cys
465                 470                 475                 480

Gln Gln His Phe Arg Thr Pro Phe Thr Phe Gly Ser Gly Thr Lys Leu
                485                 490                 495

Glu Ile Lys

<210> SEQ ID NO 34
<211> LENGTH: 371
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 34

Met Lys Glu Phe Thr Leu Asp Phe Ser Thr Ala Lys Thr Tyr Val Asp
1               5                   10                  15

Ser Leu Asn Val Ile Arg Ser Ala Ile Gly Thr Pro Leu Gln Thr Ile
                20                  25                  30

Ser Ser Gly Gly Thr Ser Leu Leu Met Ile Asp Ser Gly Ile Gly Asp
            35                  40                  45

Asn Leu Phe Ala Val Asp Ile Leu Gly Phe Asp Phe Thr Leu Gly Arg
50                  55                  60

Phe Asn Asn Leu Arg Leu Ile Val Glu Arg Asn Asn Leu Tyr Val Thr
65                  70                  75                  80

Gly Phe Val Asn Arg Thr Asn Asn Val Phe Tyr Arg Phe Ala Asp Phe
                85                  90                  95

Ser His Val Thr Phe Pro Gly Thr Thr Ala Val Thr Leu Ser Ala Asp
                100                 105                 110

Ser Ser Tyr Thr Thr Leu Gln Arg Val Ala Gly Ile Ser Arg Thr Gly
            115                 120                 125

Met Gln Ile Asn Arg His Ser Leu Thr Thr Ser Tyr Leu Asp Leu Met
130                 135                 140

Ser His Ser Gly Thr Ser Leu Thr Gln Ser Val Ala Arg Ala Met Leu
145                 150                 155                 160

Arg Phe Val Thr Val Thr Ala Glu Ala Leu Arg Phe Arg Gln Ile Gln
                165                 170                 175

Arg Gly Phe Arg Thr Thr Leu Asp Asp Leu Ser Gly Ala Ser Tyr Val
                180                 185                 190

Met Thr Ala Glu Asp Val Asp Leu Thr Leu Asn Trp Gly Arg Leu Ser
            195                 200                 205

Ser Val Leu Pro Asp Tyr His Gly Gln Asp Ser Val Arg Val Gly Arg
        210                 215                 220

Ile Ser Phe Gly Ser Ile Asn Ala Ile Leu Gly Ser Val Ala Leu Ile
225                 230                 235                 240

Leu Asn Ser His His His Ala Ser Ala Val Ala Glu Val Gln Leu
                245                 250                 255

Val Glu Ser Gly Gly Gly Leu Val Gln Ala Gly Gly Ser Leu Arg Leu
                260                 265                 270

Ser Cys Ala Ala Ser Gly Ile Thr Phe Ser Ile Asn Thr Met Gly Trp
            275                 280                 285

Tyr Arg Gln Ala Pro Gly Lys Gln Arg Glu Leu Val Ala Leu Ile Ser
        290                 295                 300
```

```
Ser Ile Gly Asp Thr Tyr Tyr Ala Asp Ser Val Lys Gly Arg Phe Thr
305                 310                 315                 320

Ile Ser Arg Asp Asn Ala Lys Asn Thr Val Tyr Leu Gln Met Asn Ser
            325                 330                 335

Leu Lys Pro Glu Asp Thr Ala Val Tyr Tyr Cys Lys Arg Phe Arg Thr
            340                 345                 350

Ala Ala Gln Gly Thr Asp Tyr Trp Gly Gln Gly Thr Gln Val Thr Val
            355                 360                 365

Ser Ser Ala
    370

<210> SEQ ID NO 35
<211> LENGTH: 373
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 35

Met Lys Glu Phe Thr Leu Asp Phe Ser Thr Ala Lys Thr Tyr Val Asp
1               5                   10                  15

Ser Leu Asn Val Ile Arg Ser Ala Ile Gly Thr Pro Leu Gln Thr Ile
            20                  25                  30

Ser Ser Gly Gly Thr Ser Leu Leu Met Ile Asp Ser Gly Ile Gly Asp
        35                  40                  45

Asn Leu Phe Ala Val Asp Ile Leu Gly Phe Asp Phe Thr Leu Gly Arg
50                  55                  60

Phe Asn Asn Leu Arg Leu Ile Val Glu Arg Asn Asn Leu Tyr Val Thr
65                  70                  75                  80

Gly Phe Val Asn Arg Thr Asn Asn Val Phe Tyr Arg Phe Ala Asp Phe
                85                  90                  95

Ser His Val Thr Phe Pro Gly Thr Thr Ala Val Thr Leu Ser Ala Asp
            100                 105                 110

Ser Ser Tyr Thr Thr Leu Gln Arg Val Ala Gly Ile Ser Arg Thr Gly
        115                 120                 125

Met Gln Ile Asn Arg His Ser Leu Thr Thr Ser Tyr Leu Ala Leu Met
130                 135                 140

Ser His Ser Gly Thr Ser Leu Thr Gln Ser Val Ala Arg Ala Met Leu
145                 150                 155                 160

Arg Phe Val Thr Val Thr Ala Glu Ala Leu Arg Phe Arg Gln Ile Gln
                165                 170                 175

Arg Gly Phe Arg Thr Thr Leu Asp Asp Leu Ser Gly Ala Ser Tyr Val
            180                 185                 190

Met Thr Ala Glu Asp Val Asp Leu Thr Leu Asn Trp Gly Arg Leu Ser
        195                 200                 205

Ser Val Leu Pro Asp Tyr His Gly Gln Asp Ser Val Arg Val Gly Arg
210                 215                 220

Ile Ser Phe Gly Ser Ile Asn Ala Ile Leu Gly Ser Val Ala Leu Ile
225                 230                 235                 240

Leu Asn Ser His His His Ala Ser Ala Val Ala Gln Val Gln Leu
                245                 250                 255

Gln Glu Ser Gly Gly Gly Ser Val Gln Ala Gly Gly Ser Leu Lys Leu
            260                 265                 270

Thr Cys Ala Ala Ser Gly Tyr Ile Phe Asn Ser Cys Gly Met Gly Trp
```

```
                    275                 280                 285
Tyr Arg Gln Ser Pro Gly Arg Glu Arg Glu Leu Val Ser Arg Ile Ser
    290                 295                 300

Gly Asp Gly Asp Thr Trp His Lys Glu Ser Val Lys Gly Arg Phe Thr
305                 310                 315                 320

Ile Ser Gln Asp Asn Val Lys Lys Thr Leu Tyr Leu Gln Met Asn Ser
                325                 330                 335

Leu Lys Pro Glu Asp Thr Ala Val Tyr Phe Cys Ala Val Cys Tyr Asn
            340                 345                 350

Leu Glu Thr Tyr Trp Gly Gln Gly Thr Gln Val Thr Val Ser Ser His
        355                 360                 365

His His His His His
        370

<210> SEQ ID NO 36
<211> LENGTH: 514
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 36

Met Lys Glu Phe Thr Leu Asp Phe Ser Thr Ala Lys Thr Tyr Val Asp
1               5                   10                  15

Ser Leu Asn Val Ile Arg Ser Ala Ile Gly Thr Pro Leu Gln Thr Ile
            20                  25                  30

Ser Ser Gly Gly Thr Ser Leu Leu Met Ile Asp Ser Gly Ile Gly Asp
        35                  40                  45

Asn Leu Phe Ala Val Asp Ile Leu Gly Phe Asp Phe Thr Leu Gly Arg
    50                  55                  60

Phe Asn Asn Leu Arg Leu Ile Val Glu Arg Asn Asn Leu Tyr Val Thr
65                  70                  75                  80

Gly Phe Val Asn Arg Thr Asn Asn Val Phe Tyr Arg Phe Ala Asp Phe
                85                  90                  95

Ser His Val Thr Phe Pro Gly Thr Thr Ala Val Thr Leu Ser Ala Asp
            100                 105                 110

Ser Ser Tyr Thr Thr Leu Gln Arg Val Ala Gly Ile Ser Arg Thr Gly
        115                 120                 125

Met Gln Ile Asn Arg His Ser Leu Thr Thr Ser Tyr Leu Asp Leu Met
130                 135                 140

Ser His Ser Gly Thr Ser Leu Thr Gln Ser Val Ala Arg Ala Met Leu
145                 150                 155                 160

Arg Phe Val Thr Val Thr Ala Glu Ala Leu Arg Phe Arg Gln Ile Gln
                165                 170                 175

Arg Gly Phe Arg Thr Thr Leu Asp Asp Leu Ser Gly Ala Ser Tyr Val
            180                 185                 190

Met Thr Ala Glu Asp Val Asp Leu Thr Leu Asn Trp Gly Arg Leu Ser
        195                 200                 205

Ser Val Leu Pro Asp Tyr His Gly Gln Asp Ser Val Arg Val Gly Arg
    210                 215                 220

Ile Ser Phe Gly Ser Ile Asn Ala Ile Leu Gly Ser Val Ala Leu Ile
225                 230                 235                 240

Leu Asn Ser His His His Ala Ser Ala Val Ala Glu Phe Pro Lys
                245                 250                 255
```

-continued

```
Pro Ser Thr Pro Pro Gly Ser Ser Gly Gly Ala Pro Gln Val Gln Leu
            260                 265                 270

Gln Gln Ser Gly Pro Glu Leu Lys Lys Pro Gly Glu Thr Val Lys Ile
        275                 280                 285

Ser Cys Lys Ala Ser Gly Tyr Pro Phe Thr Asn Tyr Gly Met Asn Trp
    290                 295                 300

Val Lys Gln Ala Pro Gly Gln Gly Leu Lys Trp Met Gly Trp Ile Asn
305                 310                 315                 320

Thr Ser Thr Gly Glu Ser Thr Phe Ala Asp Asp Phe Lys Gly Arg Phe
                325                 330                 335

Asp Phe Ser Leu Glu Thr Ser Ala Asn Thr Ala Tyr Leu Gln Ile Asn
            340                 345                 350

Asn Leu Lys Ser Glu Asp Ser Ala Thr Tyr Phe Cys Ala Arg Trp Glu
        355                 360                 365

Val Tyr His Gly Tyr Val Pro Tyr Trp Gly Gln Gly Thr Thr Val Thr
    370                 375                 380

Val Ser Ser Gly Gly Gly Gly Ser Gly Gly Gly Gly Ser Gly Gly Gly
385                 390                 395                 400

Gly Ser Gly Gly Gly Ser Asp Ile Gln Met Thr Gln Ser Pro Ser
                405                 410                 415

Ser Leu Ser Ala Ser Val Gly Asp Arg Val Thr Ile Thr Cys Lys Ala
            420                 425                 430

Ser Gln Asp Val Tyr Asn Ala Val Ala Trp Tyr Gln Gln Lys Pro Gly
        435                 440                 445

Gln Ser Pro Lys Leu Leu Ile Tyr Ser Ala Ser Ser Arg Tyr Thr Gly
    450                 455                 460

Val Pro Ser Arg Phe Thr Gly Ser Gly Ser Gly Pro Asp Phe Thr Phe
465                 470                 475                 480

Thr Ile Ser Ser Val Gln Ala Glu Asp Leu Ala Val Tyr Phe Cys Gln
                485                 490                 495

Gln His Phe Arg Thr Pro Phe Thr Phe Gly Ser Gly Thr Lys Leu Glu
            500                 505                 510

Ile Lys
```

<210> SEQ ID NO 37
<211> LENGTH: 251
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 37

```
Lys Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
            20                  25                  30

Ser Gly Gly Thr Ser Leu Leu Met Ile Asp Ser Gly Ser Gly Asp Asn
        35                  40                  45

Leu Phe Ala Val Asp Val Arg Gly Ile Asp Pro Glu Glu Gly Arg Phe
    50                  55                  60

Asn Asn Leu Arg Leu Ile Val Glu Arg Asn Asn Leu Tyr Val Thr Gly
65                  70                  75                  80

Phe Val Asn Arg Thr Asn Asn Val Phe Tyr Arg Phe Ala Asp Phe Ser
```

```
                85                  90                  95
His Val Thr Phe Pro Gly Thr Thr Ala Val Thr Leu Ser Gly Asp Ser
                100                 105                 110

Ser Tyr Thr Thr Leu Gln Arg Val Ala Gly Ile Ser Arg Thr Gly Met
                115                 120                 125

Gln Ile Asn Arg His Ser Leu Thr Thr Ser Tyr Leu Asp Leu Met Ser
                130                 135                 140

His Ser Gly Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Arg Thr Thr Leu Asp Asp Leu Ser Gly Arg Ser Tyr Val Met
                180                 185                 190

Thr Ala Glu Asp Val Asp Leu Thr Leu Asn Trp Gly Arg Leu Ser Ser
                195                 200                 205

Val Leu Pro Asp Tyr His Gly Gln Asp Ser Val Arg Val Gly Arg Ile
                210                 215                 220

Ser Phe Gly Ser Ile Asn Ala Ile Leu Gly Ser Val Ala Leu Ile Leu
225                 230                 235                 240

Asn Cys His His His Ala Ser Ala Val Ala Ala
                245                 250

<210> SEQ ID NO 38
<211> LENGTH: 1255
<212> TYPE: PRT
<213> ORGANISM: Homo sapiens

<400> SEQUENCE: 38

Met Glu Leu Ala Ala Leu Cys Arg Trp Gly Leu Leu Leu Ala Leu Leu
1               5                   10                  15

Pro Pro Gly Ala Ala Ser Thr Gln Val Cys Thr Gly Thr Asp Met Lys
                20                  25                  30

Leu Arg Leu Pro Ala Ser Pro Glu Thr His Leu Asp Met Leu Arg His
                35                  40                  45

Leu Tyr Gln Gly Cys Gln Val Val Gln Gly Asn Leu Glu Leu Thr Tyr
            50                  55                  60

Leu Pro Thr Asn Ala Ser Leu Ser Phe Leu Gln Asp Ile Gln Glu Val
65              70                  75                  80

Gln Gly Tyr Val Leu Ile Ala His Asn Gln Val Arg Gln Val Pro Leu
                85                  90                  95

Gln Arg Leu Arg Ile Val Arg Gly Thr Gln Leu Phe Glu Asp Asn Tyr
                100                 105                 110

Ala Leu Ala Val Leu Asp Asn Gly Asp Pro Leu Asn Asn Thr Thr Pro
                115                 120                 125

Val Thr Gly Ala Ser Pro Gly Gly Leu Arg Glu Leu Gln Leu Arg Ser
                130                 135                 140

Leu Thr Glu Ile Leu Lys Gly Gly Val Leu Ile Gln Arg Asn Pro Gln
145                 150                 155                 160

Leu Cys Tyr Gln Asp Thr Ile Leu Trp Lys Asp Ile Phe His Lys Asn
                165                 170                 175

Asn Gln Leu Ala Leu Thr Leu Ile Asp Thr Asn Arg Ser Arg Ala Cys
                180                 185                 190

His Pro Cys Ser Pro Met Cys Lys Gly Ser Arg Cys Trp Gly Glu Ser
                195                 200                 205
```

```
Ser Glu Asp Cys Gln Ser Leu Thr Arg Thr Val Cys Ala Gly Gly Cys
    210                 215                 220
Ala Arg Cys Lys Gly Pro Leu Pro Thr Asp Cys Cys His Glu Gln Cys
225                 230                 235                 240
Ala Ala Gly Cys Thr Gly Pro Lys His Ser Asp Cys Leu Ala Cys Leu
                245                 250                 255
His Phe Asn His Ser Gly Ile Cys Glu Leu His Cys Pro Ala Leu Val
            260                 265                 270
Thr Tyr Asn Thr Asp Thr Phe Glu Ser Met Pro Asn Pro Glu Gly Arg
            275                 280                 285
Tyr Thr Phe Gly Ala Ser Cys Val Thr Ala Cys Pro Tyr Asn Tyr Leu
290                 295                 300
Ser Thr Asp Val Gly Ser Cys Thr Leu Val Cys Pro Leu His Asn Gln
305                 310                 315                 320
Glu Val Thr Ala Glu Asp Gly Thr Gln Arg Cys Glu Lys Cys Ser Lys
                325                 330                 335
Pro Cys Ala Arg Val Cys Tyr Gly Leu Gly Met Glu His Leu Arg Glu
                340                 345                 350
Val Arg Ala Val Thr Ser Ala Asn Ile Gln Glu Phe Ala Gly Cys Lys
            355                 360                 365
Lys Ile Phe Gly Ser Leu Ala Phe Leu Pro Glu Ser Phe Asp Gly Asp
            370                 375                 380
Pro Ala Ser Asn Thr Ala Pro Leu Gln Pro Glu Gln Leu Gln Val Phe
385                 390                 395                 400
Glu Thr Leu Glu Glu Ile Thr Gly Tyr Leu Tyr Ile Ser Ala Trp Pro
                405                 410                 415
Asp Ser Leu Pro Asp Leu Ser Val Phe Gln Asn Leu Gln Val Ile Arg
                420                 425                 430
Gly Arg Ile Leu His Asn Gly Ala Tyr Ser Leu Thr Leu Gln Gly Leu
            435                 440                 445
Gly Ile Ser Trp Leu Gly Leu Arg Ser Leu Arg Glu Leu Gly Ser Gly
            450                 455                 460
Leu Ala Leu Ile His His Asn Thr His Leu Cys Phe Val His Thr Val
465                 470                 475                 480
Pro Trp Asp Gln Leu Phe Arg Asn Pro His Gln Ala Leu Leu His Thr
                485                 490                 495
Ala Asn Arg Pro Glu Asp Glu Cys Val Gly Glu Gly Leu Ala Cys His
                500                 505                 510
Gln Leu Cys Ala Arg Gly His Cys Trp Gly Pro Gly Pro Thr Gln Cys
            515                 520                 525
Val Asn Cys Ser Gln Phe Leu Arg Gly Gln Glu Cys Val Glu Glu Cys
            530                 535                 540
Arg Val Leu Gln Gly Leu Pro Arg Glu Tyr Val Asn Ala Arg His Cys
545                 550                 555                 560
Leu Pro Cys His Pro Glu Cys Gln Pro Gln Asn Gly Ser Val Thr Cys
                565                 570                 575
Phe Gly Pro Glu Ala Asp Gln Cys Val Ala Cys Ala His Tyr Lys Asp
                580                 585                 590
Pro Pro Phe Cys Val Ala Arg Cys Pro Ser Gly Val Lys Pro Asp Leu
            595                 600                 605
Ser Tyr Met Pro Ile Trp Lys Phe Pro Asp Glu Glu Gly Ala Cys Gln
            610                 615                 620
Pro Cys Pro Ile Asn Cys Thr His Ser Cys Val Asp Leu Asp Asp Lys
```

-continued

```
            625                 630                 635                 640
Gly Cys Pro Ala Glu Gln Arg Ala Ser Pro Leu Thr Ser Ile Ile Ser
                    645                 650                 655

Ala Val Val Gly Ile Leu Leu Val Val Leu Gly Val Val Phe Gly
                    660                 665                 670

Ile Leu Ile Lys Arg Arg Gln Gln Lys Ile Arg Lys Tyr Thr Met Arg
            675                 680                 685

Arg Leu Leu Gln Glu Thr Glu Leu Val Glu Pro Leu Thr Pro Ser Gly
            690                 695                 700

Ala Met Pro Asn Gln Ala Gln Met Arg Ile Leu Lys Glu Thr Glu Leu
705                 710                 715                 720

Arg Lys Val Lys Val Leu Gly Ser Gly Ala Phe Gly Thr Val Tyr Lys
                    725                 730                 735

Gly Ile Trp Ile Pro Asp Gly Glu Asn Val Lys Ile Pro Val Ala Ile
                    740                 745                 750

Lys Val Leu Arg Glu Asn Thr Ser Pro Lys Ala Asn Lys Glu Ile Leu
            755                 760                 765

Asp Glu Ala Tyr Val Met Ala Gly Val Gly Ser Pro Tyr Val Ser Arg
            770                 775                 780

Leu Leu Gly Ile Cys Leu Thr Ser Thr Val Gln Leu Val Thr Gln Leu
785                 790                 795                 800

Met Pro Tyr Gly Cys Leu Leu Asp His Val Arg Glu Asn Arg Gly Arg
                    805                 810                 815

Leu Gly Ser Gln Asp Leu Leu Asn Trp Cys Met Gln Ile Ala Lys Gly
                    820                 825                 830

Met Ser Tyr Leu Glu Asp Val Arg Leu Val His Arg Asp Leu Ala Ala
            835                 840                 845

Arg Asn Val Leu Val Lys Ser Pro Asn His Val Lys Ile Thr Asp Phe
            850                 855                 860

Gly Leu Ala Arg Leu Leu Asp Ile Asp Glu Thr Glu Tyr His Ala Asp
865                 870                 875                 880

Gly Gly Lys Val Pro Ile Lys Trp Met Ala Leu Glu Ser Ile Leu Arg
                    885                 890                 895

Arg Arg Phe Thr His Gln Ser Asp Val Trp Ser Tyr Gly Val Thr Val
                    900                 905                 910

Trp Glu Leu Met Thr Phe Gly Ala Lys Pro Tyr Asp Gly Ile Pro Ala
            915                 920                 925

Arg Glu Ile Pro Asp Leu Leu Glu Lys Gly Glu Arg Leu Pro Gln Pro
            930                 935                 940

Pro Ile Cys Thr Ile Asp Val Tyr Met Ile Met Val Lys Cys Trp Met
945                 950                 955                 960

Ile Asp Ser Glu Cys Arg Pro Arg Phe Arg Glu Leu Val Ser Glu Phe
                    965                 970                 975

Ser Arg Met Ala Arg Asp Pro Gln Arg Phe Val Val Ile Gln Asn Glu
                    980                 985                 990

Asp Leu Gly Pro Ala Ser Pro Leu Asp Ser Thr Phe Tyr Arg Ser Leu
            995                 1000                1005

Leu Glu Asp Asp Asp Met Gly Asp Leu Val Asp Ala Glu Glu Tyr
            1010                1015                1020

Leu Val Pro Gln Gln Gly Phe Phe Cys Pro Asp Pro Ala Pro Gly
            1025                1030                1035

Ala Gly Gly Met Val His His Arg His Arg Ser Ser Ser Thr Arg
            1040                1045                1050
```

```
Ser Gly Gly Gly Asp Leu Thr Leu Gly Leu Glu Pro Ser Glu Glu
    1055                1060                1065

Glu Ala Pro Arg Ser Pro Leu Ala Pro Ser Glu Gly Ala Gly Ser
    1070                1075                1080

Asp Val Phe Asp Gly Asp Leu Gly Met Gly Ala Ala Lys Gly Leu
    1085                1090                1095

Gln Ser Leu Pro Thr His Asp Pro Ser Pro Leu Gln Arg Tyr Ser
    1100                1105                1110

Glu Asp Pro Thr Val Pro Leu Pro Ser Glu Thr Asp Gly Tyr Val
    1115                1120                1125

Ala Pro Leu Thr Cys Ser Pro Gln Pro Glu Tyr Val Asn Gln Pro
    1130                1135                1140

Asp Val Arg Pro Gln Pro Pro Ser Pro Arg Glu Gly Pro Leu Pro
    1145                1150                1155

Ala Ala Arg Pro Ala Gly Ala Thr Leu Glu Arg Pro Lys Thr Leu
    1160                1165                1170

Ser Pro Gly Lys Asn Gly Val Val Lys Asp Val Phe Ala Phe Gly
    1175                1180                1185

Gly Ala Val Glu Asn Pro Glu Tyr Leu Thr Pro Gln Gly Gly Ala
    1190                1195                1200

Ala Pro Gln Pro His Pro Pro Pro Ala Phe Ser Pro Ala Phe Asp
    1205                1210                1215

Asn Leu Tyr Tyr Trp Asp Gln Asp Pro Pro Glu Arg Gly Ala Pro
    1220                1225                1230

Pro Ser Thr Phe Lys Gly Thr Pro Thr Ala Glu Asn Pro Glu Tyr
    1235                1240                1245

Leu Gly Leu Asp Val Pro Val
    1250                1255

<210> SEQ ID NO 39
<211> LENGTH: 630
<212> TYPE: PRT
<213> ORGANISM: Homo sapiens

<400> SEQUENCE: 39

Thr Gln Val Cys Thr Gly Thr Asp Met Lys Leu Arg Leu Pro Ala Ser
1               5                   10                  15

Pro Glu Thr His Leu Asp Met Leu Arg His Leu Tyr Gln Gly Cys Gln
                20                  25                  30

Val Val Gln Gly Asn Leu Glu Leu Thr Tyr Leu Pro Thr Asn Ala Ser
            35                  40                  45

Leu Ser Phe Leu Gln Asp Ile Gln Glu Val Gln Gly Tyr Val Leu Ile
        50                  55                  60

Ala His Asn Gln Val Arg Gln Val Pro Leu Gln Arg Leu Arg Ile Val
65                  70                  75                  80

Arg Gly Thr Gln Leu Phe Glu Asp Asn Tyr Ala Leu Ala Val Leu Asp
                85                  90                  95

Asn Gly Asp Pro Leu Asn Asn Thr Thr Pro Val Thr Gly Ala Ser Pro
            100                 105                 110

Gly Gly Leu Arg Glu Leu Gln Leu Arg Ser Leu Thr Glu Ile Leu Lys
        115                 120                 125

Gly Gly Val Leu Ile Gln Arg Asn Pro Gln Leu Cys Tyr Gln Asp Thr
    130                 135                 140

Ile Leu Trp Lys Asp Ile Phe His Lys Asn Asn Gln Leu Ala Leu Thr
```

```
        145                 150                 155                 160
Leu Ile Asp Thr Asn Arg Ser Arg Ala Cys His Pro Cys Ser Pro Met
                165                 170                 175
Cys Lys Gly Ser Arg Cys Trp Gly Glu Ser Ser Glu Asp Cys Gln Ser
                180                 185                 190
Leu Thr Arg Thr Val Cys Ala Gly Cys Ala Arg Cys Lys Gly Pro
                195                 200                 205
Leu Pro Thr Asp Cys Cys His Glu Gln Cys Ala Ala Gly Cys Thr Gly
210                 215                 220
Pro Lys His Ser Asp Cys Leu Ala Cys Leu His Phe Asn His Ser Gly
225                 230                 235                 240
Ile Cys Glu Leu His Cys Pro Ala Leu Val Thr Tyr Asn Thr Asp Thr
                245                 250                 255
Phe Glu Ser Met Pro Asn Pro Glu Gly Arg Tyr Thr Phe Gly Ala Ser
                260                 265                 270
Cys Val Thr Ala Cys Pro Tyr Asn Tyr Leu Ser Thr Asp Val Gly Ser
                275                 280                 285
Cys Thr Leu Val Cys Pro Leu His Asn Gln Glu Val Thr Ala Glu Asp
                290                 295                 300
Gly Thr Gln Arg Cys Glu Lys Cys Ser Lys Pro Cys Ala Arg Val Cys
305                 310                 315                 320
Tyr Gly Leu Gly Met Glu His Leu Arg Glu Val Arg Ala Val Thr Ser
                325                 330                 335
Ala Asn Ile Gln Glu Phe Ala Gly Cys Lys Lys Ile Phe Gly Ser Leu
                340                 345                 350
Ala Phe Leu Pro Glu Ser Phe Asp Gly Asp Pro Ala Ser Asn Thr Ala
                355                 360                 365
Pro Leu Gln Pro Glu Gln Leu Gln Val Phe Glu Thr Leu Glu Glu Ile
                370                 375                 380
Thr Gly Tyr Leu Tyr Ile Ser Ala Trp Pro Asp Ser Leu Pro Asp Leu
385                 390                 395                 400
Ser Val Phe Gln Asn Leu Gln Val Ile Arg Gly Arg Ile Leu His Asn
                405                 410                 415
Gly Ala Tyr Ser Leu Thr Leu Gln Gly Leu Gly Ile Ser Trp Leu Gly
                420                 425                 430
Leu Arg Ser Leu Arg Glu Leu Gly Ser Gly Leu Ala Leu Ile His His
                435                 440                 445
Asn Thr His Leu Cys Phe Val His Thr Val Pro Trp Asp Gln Leu Phe
450                 455                 460
Arg Asn Pro His Gln Ala Leu Leu His Thr Ala Asn Arg Pro Glu Asp
465                 470                 475                 480
Glu Cys Val Gly Glu Gly Leu Ala Cys His Gln Leu Cys Ala Arg Gly
                485                 490                 495
His Cys Trp Gly Pro Gly Pro Thr Gln Cys Val Asn Cys Ser Gln Phe
                500                 505                 510
Leu Arg Gly Gln Glu Cys Val Glu Glu Cys Arg Val Leu Gln Gly Leu
                515                 520                 525
Pro Arg Glu Tyr Val Asn Ala Arg His Cys Leu Pro Cys His Pro Glu
                530                 535                 540
Cys Gln Pro Gln Asn Gly Ser Val Thr Cys Phe Gly Pro Glu Ala Asp
545                 550                 555                 560
Gln Cys Val Ala Cys Ala His Tyr Lys Asp Pro Pro Phe Cys Val Ala
                565                 570                 575
```

-continued

Arg Cys Pro Ser Gly Val Lys Pro Asp Leu Ser Tyr Met Pro Ile Trp
            580                 585                 590

Lys Phe Pro Asp Glu Glu Gly Ala Cys Gln Pro Cys Pro Ile Asn Cys
            595                 600                 605

Thr His Ser Cys Val Asp Leu Asp Asp Lys Gly Cys Pro Ala Glu Gln
            610                 615                 620

Arg Ala Ser Pro Leu Thr
625             630

<210> SEQ ID NO 40
<211> LENGTH: 1255
<212> TYPE: PRT
<213> ORGANISM: Macaca fascicularis

<400> SEQUENCE: 40

Met Glu Leu Ala Ala Trp Tyr Arg Trp Gly Leu Leu Leu Ala Leu Leu
1               5                   10                  15

Pro Pro Gly Ala Ala Gly Thr Gln Val Cys Thr Gly Thr Asp Met Lys
            20                  25                  30

Leu Arg Leu Pro Ala Ser Pro Glu Thr His Leu Asp Met Leu Arg His
            35                  40                  45

Leu Tyr Gln Gly Cys Gln Val Val Gln Gly Asn Leu Glu Leu Thr Tyr
    50                  55                  60

Leu Pro Thr Asn Ala Ser Leu Ser Phe Leu Gln Asp Ile Gln Glu Val
65              70                  75                  80

Gln Gly Tyr Val Leu Ile Ala His Asn Gln Val Arg Gln Val Pro Leu
                85                  90                  95

Gln Arg Leu Arg Ile Val Arg Gly Thr Gln Leu Phe Glu Asp Asn Tyr
            100                 105                 110

Ala Leu Ala Val Leu Asp Asn Gly Asn Pro Leu Asn Asn Thr Thr Pro
            115                 120                 125

Val Thr Gly Ala Ser Pro Gly Gly Leu Arg Glu Leu Gln Leu Arg Ser
            130                 135                 140

Leu Thr Glu Ile Leu Lys Gly Gly Val Leu Ile Gln Arg Asn Pro Gln
145                 150                 155                 160

Leu Cys Tyr Gln Asp Thr Ile Leu Trp Lys Asp Ile Phe His Lys Asn
            165                 170                 175

Asn Gln Leu Ala Leu Thr Leu Ile Asp Thr Asn Arg Ser Arg Ala Cys
            180                 185                 190

His Pro Cys Ser Pro Val Cys Lys Gly Ser Arg Cys Trp Gly Glu Ser
            195                 200                 205

Ser Glu Asp Cys Gln Ser Leu Thr Arg Thr Val Cys Ala Gly Gly Cys
            210                 215                 220

Ala Arg Cys Lys Gly Pro Leu Pro Thr Asp Cys Cys His Glu Gln Cys
225                 230                 235                 240

Ala Ala Gly Cys Thr Gly Pro Lys His Ser Asp Cys Leu Ala Cys Leu
            245                 250                 255

His Phe Asn His Ser Gly Ile Cys Glu Leu His Cys Pro Ala Leu Val
            260                 265                 270

Thr Tyr Asn Thr Asp Thr Phe Glu Ser Met Pro Asn Pro Glu Gly Arg
            275                 280                 285

Tyr Thr Phe Gly Ala Ser Cys Val Thr Ala Cys Pro Tyr Asn Tyr Leu
            290                 295                 300

Ser Thr Asp Val Gly Ser Cys Thr Leu Val Cys Pro Leu His Asn Gln

```
       305                 310                 315                 320
Glu Val Thr Ala Glu Asp Gly Thr Gln Arg Cys Glu Lys Cys Ser Lys
                    325                 330                 335

Pro Cys Ala Arg Val Cys Tyr Gly Leu Gly Met Glu His Leu Arg Glu
                    340                 345                 350

Val Arg Ala Val Thr Ser Ala Asn Ile Gln Glu Phe Ala Gly Cys Lys
                    355                 360                 365

Lys Ile Phe Gly Ser Leu Ala Phe Leu Pro Glu Ser Phe Asp Gly Asp
                    370                 375                 380

Pro Ala Ser Asn Thr Ala Pro Leu Gln Pro Glu Gln Leu Arg Val Phe
385                 390                 395                 400

Glu Thr Leu Glu Glu Ile Thr Gly Tyr Leu Tyr Ile Ser Ala Trp Pro
                    405                 410                 415

Asp Ser Leu Pro Asp Leu Ser Val Leu Gln Asn Leu Gln Val Ile Arg
                    420                 425                 430

Gly Arg Ile Leu His Asn Gly Ala Tyr Ser Leu Thr Leu Gln Gly Leu
                    435                 440                 445

Gly Ile Ser Trp Leu Gly Leu Arg Ser Leu Arg Glu Leu Gly Ser Gly
                    450                 455                 460

Leu Ala Leu Ile His His Asn Thr Arg Leu Cys Phe Val His Thr Val
465                 470                 475                 480

Pro Trp Asp Gln Leu Phe Arg Asn Pro His Gln Ala Leu Leu His Thr
                    485                 490                 495

Ala Asn Arg Pro Glu Asp Glu Cys Val Gly Glu Gly Leu Ala Cys His
                    500                 505                 510

Gln Leu Cys Ala Arg Gly His Cys Trp Gly Pro Gly Pro Thr Gln Cys
                    515                 520                 525

Val Asn Cys Ser Gln Phe Leu Arg Gly Gln Glu Cys Val Glu Glu Cys
                    530                 535                 540

Arg Val Leu Gln Gly Leu Pro Arg Glu Tyr Val Asn Ala Arg His Cys
545                 550                 555                 560

Leu Pro Cys His Pro Glu Cys Gln Pro Gln Asn Gly Ser Val Thr Cys
                    565                 570                 575

Phe Gly Pro Glu Ala Asp Gln Cys Val Ala Cys Ala His Tyr Lys Asp
                    580                 585                 590

Pro Pro Phe Cys Val Ala Arg Cys Pro Ser Gly Val Lys Pro Asp Leu
                    595                 600                 605

Ser Tyr Met Pro Ile Trp Lys Phe Pro Asp Glu Glu Gly Thr Cys Gln
                    610                 615                 620

Ser Cys Pro Ile Asn Cys Thr His Ser Cys Val Asp Leu Asp Asp Lys
625                 630                 635                 640

Gly Cys Pro Ala Glu Gln Arg Ala Ser Pro Leu Thr Ser Ile Ile Ser
                    645                 650                 655

Ala Val Val Gly Ile Leu Leu Val Val Val Leu Gly Val Val Phe Gly
                    660                 665                 670

Ile Leu Ile Lys Arg Arg Gln Gln Lys Ile Arg Lys Tyr Thr Met Arg
                    675                 680                 685

Arg Leu Leu Gln Glu Thr Glu Leu Val Glu Pro Leu Thr Pro Ser Gly
                    690                 695                 700

Ala Met Pro Asn Gln Ala Gln Met Arg Ile Leu Lys Glu Thr Glu Leu
705                 710                 715                 720

Arg Lys Val Lys Val Leu Gly Ser Gly Ala Phe Gly Thr Val Tyr Lys
                    725                 730                 735
```

```
Gly Ile Trp Ile Pro Asp Gly Glu Asn Val Lys Ile Pro Val Ala Ile
            740                 745                 750

Lys Val Leu Arg Glu Asn Thr Ser Pro Lys Ala Asn Lys Glu Ile Leu
            755                 760                 765

Asp Glu Ala Tyr Val Met Ala Gly Val Gly Ser Pro Tyr Val Ser Arg
            770                 775                 780

Leu Leu Gly Ile Cys Leu Thr Ser Thr Val Gln Leu Val Thr Gln Leu
785                 790                 795                 800

Met Pro Tyr Gly Cys Leu Leu Asp His Val Arg Glu Asn Arg Gly Arg
                805                 810                 815

Leu Gly Ser Gln Asp Leu Leu Asn Trp Cys Met Gln Ile Ala Lys Gly
            820                 825                 830

Met Ser Tyr Leu Glu Asp Val Arg Leu Val His Arg Asp Leu Ala Ala
            835                 840                 845

Arg Asn Val Leu Val Lys Ser Pro Asn His Val Lys Ile Thr Asp Phe
850                 855                 860

Gly Leu Ala Arg Leu Leu Asp Ile Asp Glu Thr Glu Tyr His Ala Asp
865                 870                 875                 880

Gly Gly Lys Val Pro Ile Lys Trp Met Ala Leu Glu Ser Ile Leu Arg
                885                 890                 895

Arg Arg Phe Thr His Gln Ser Asp Val Trp Ser Tyr Gly Val Thr Val
                900                 905                 910

Trp Glu Leu Met Thr Phe Gly Ala Lys Pro Tyr Asp Gly Ile Pro Ala
            915                 920                 925

Arg Glu Ile Pro Asp Leu Leu Glu Lys Gly Glu Arg Leu Pro Gln Pro
            930                 935                 940

Pro Ile Cys Thr Ile Asp Val Tyr Met Ile Met Val Lys Cys Trp Met
945                 950                 955                 960

Ile Asp Ser Glu Cys Arg Pro Arg Phe Arg Glu Leu Val Ser Glu Phe
                965                 970                 975

Ser Arg Met Ala Arg Asp Pro Gln Arg Phe Val Val Ile Gln Asn Glu
            980                 985                 990

Asp Leu Gly Pro Ala Ser Pro Leu Asp Ser Thr Phe Tyr Arg Ser Leu
            995                 1000                1005

Leu Glu Asp Asp Asp Met Gly Asp Leu Val Asp Ala Glu Glu Tyr
    1010                1015                1020

Leu Val Pro Gln Gln Gly Phe Phe Cys Pro Asp Pro Ala Pro Gly
    1025                1030                1035

Thr Gly Gly Met Val His His Arg His Arg Ser Ser Ser Thr Arg
    1040                1045                1050

Ser Gly Gly Gly Asp Leu Thr Leu Gly Leu Glu Pro Ser Glu Glu
    1055                1060                1065

Glu Ala Pro Arg Ser Pro Arg Ala Pro Ser Glu Gly Thr Gly Ser
    1070                1075                1080

Asp Val Phe Asp Gly Asp Leu Gly Met Gly Ala Ala Lys Gly Leu
    1085                1090                1095

Gln Ser Leu Pro Ala His Asp Pro Ser Pro Leu Gln Arg Tyr Ser
    1100                1105                1110

Glu Asp Pro Thr Val Pro Leu Pro Ser Glu Thr Asp Gly Tyr Val
    1115                1120                1125

Ala Pro Leu Thr Cys Ser Pro Gln Pro Glu Tyr Val Asn Gln Pro
    1130                1135                1140
```

Asp Val Arg Pro Gln Pro Pro Leu Pro Gln Glu Gly Pro Leu Ser
1145                1150                1155

Pro Ala Arg Pro Thr Gly Ala Thr Leu Glu Arg Pro Lys Thr Leu
1160                1165                1170

Ser Pro Gly Lys Asn Gly Val Val Lys Asp Val Phe Ala Phe Gly
1175                1180                1185

Gly Ala Val Glu Asn Pro Glu Tyr Leu Ala Pro Arg Gly Gly Ala
1190                1195                1200

Ala Pro Gln Pro His Leu Pro Pro Ala Phe Ser Pro Ala Phe Asp
1205                1210                1215

Asn Leu Tyr Tyr Trp Asp Gln Asp Pro Ser Glu Arg Gly Ala Pro
1220                1225                1230

Pro Ser Thr Phe Lys Gly Thr Pro Thr Ala Glu Asn Pro Glu Tyr
1235                1240                1245

Leu Gly Leu Asp Val Pro Val
1250                1255

<210> SEQ ID NO 41
<211> LENGTH: 1255
<212> TYPE: PRT
<213> ORGANISM: Macaca mulatta

<400> SEQUENCE: 41

Met Glu Leu Ala Ala Trp Tyr Arg Trp Gly Leu Leu Leu Ala Leu Leu
1               5                   10                  15

Pro Pro Gly Ala Ala Gly Thr Gln Val Cys Thr Gly Thr Asp Met Lys
                20                  25                  30

Leu Arg Leu Pro Ala Ser Pro Glu Thr His Leu Asp Met Leu Arg His
            35                  40                  45

Leu Tyr Gln Gly Cys Gln Val Val Gln Gly Asn Leu Glu Leu Thr Tyr
        50                  55                  60

Leu Pro Thr Asn Ala Ser Leu Ser Phe Leu Gln Asp Ile Gln Glu Val
65                  70                  75                  80

Gln Gly Tyr Val Leu Ile Ala His Asn Gln Val Arg Gln Val Pro Leu
                85                  90                  95

Gln Arg Leu Arg Ile Val Arg Gly Thr Gln Leu Phe Glu Asp Asn Tyr
            100                 105                 110

Ala Leu Ala Val Leu Asp Asn Gly Asp Leu Leu Asn Asn Thr Thr Pro
        115                 120                 125

Val Thr Gly Ala Ser Pro Gly Gly Leu Arg Glu Leu Gln Leu Arg Ser
    130                 135                 140

Leu Thr Glu Ile Leu Lys Gly Gly Val Leu Ile Gln Arg Asn Pro Gln
145                 150                 155                 160

Leu Cys Tyr Gln Asp Thr Ile Leu Trp Lys Asp Ile Phe His Lys Asn
                165                 170                 175

Asn Gln Leu Ala Leu Thr Leu Ile Asp Thr Asn Arg Ser Arg Ala Cys
            180                 185                 190

His Pro Cys Ser Pro Val Cys Lys Gly Ser Arg Cys Trp Gly Glu Ser
        195                 200                 205

Ser Glu Asp Cys Gln Ser Leu Thr Arg Thr Val Cys Ala Gly Gly Cys
    210                 215                 220

Ala Arg Cys Lys Gly Pro Leu Pro Thr Asp Cys Cys His Glu Gln Cys
225                 230                 235                 240

Ala Ala Gly Cys Thr Gly Pro Lys His Ser Asp Cys Leu Ala Cys Leu
                245                 250                 255

```
His Phe Asn His Ser Gly Ile Cys Glu Leu His Cys Pro Ala Leu Val
            260                 265                 270

Thr Tyr Asn Thr Asp Thr Phe Glu Ser Met Pro Asn Pro Glu Gly Arg
            275                 280                 285

Tyr Thr Phe Gly Ala Ser Cys Val Thr Ala Cys Pro Tyr Asn Tyr Leu
            290                 295                 300

Ser Thr Asp Val Gly Ser Cys Thr Leu Val Cys Pro Leu His Asn Gln
305                 310                 315                 320

Glu Val Thr Ala Glu Asp Gly Thr Gln Arg Cys Glu Lys Cys Ser Lys
            325                 330                 335

Pro Cys Ala Arg Val Cys Tyr Gly Leu Gly Met Glu His Leu Arg Glu
            340                 345                 350

Val Arg Ala Val Thr Ser Ala Asn Ile Gln Glu Phe Ala Gly Cys Lys
            355                 360                 365

Lys Ile Phe Gly Ser Leu Ala Phe Leu Pro Glu Ser Phe Asp Gly Asp
            370                 375                 380

Pro Ala Ser Asn Thr Ala Pro Leu Gln Pro Glu Gln Leu Arg Val Phe
385                 390                 395                 400

Glu Thr Leu Glu Glu Ile Thr Gly Tyr Leu Tyr Ile Ser Ala Trp Pro
            405                 410                 415

Asp Ser Leu Pro Asp Leu Ser Val Leu Gln Asn Leu Gln Val Ile Arg
            420                 425                 430

Gly Arg Ile Leu His Asn Gly Ala Tyr Ser Leu Thr Leu Gln Gly Leu
            435                 440                 445

Gly Ile Ser Trp Leu Gly Leu Arg Ser Leu Arg Glu Leu Gly Ser Gly
            450                 455                 460

Leu Ala Leu Ile His His Asn Thr Arg Leu Cys Phe Val His Thr Val
465                 470                 475                 480

Pro Trp Asp Gln Leu Phe Arg Asn Pro His Gln Ala Leu Leu His Thr
            485                 490                 495

Ala Asn Arg Pro Glu Asp Glu Cys Val Gly Glu Gly Leu Ala Cys His
            500                 505                 510

Gln Leu Cys Ala Arg Gly His Cys Trp Gly Pro Gly Pro Thr Gln Cys
            515                 520                 525

Val Asn Cys Ser Gln Phe Leu Arg Gly Gln Glu Cys Val Glu Glu Cys
            530                 535                 540

Arg Val Leu Gln Gly Leu Pro Arg Glu Tyr Val Asn Ala Arg His Cys
545                 550                 555                 560

Leu Pro Cys His Pro Glu Cys Gln Pro Gln Asn Gly Ser Val Thr Cys
            565                 570                 575

Phe Gly Pro Glu Ala Asp Gln Cys Val Ala Cys Ala His Tyr Lys Asp
            580                 585                 590

Pro Pro Phe Cys Val Ala Arg Cys Pro Ser Gly Val Lys Pro Asp Leu
            595                 600                 605

Ser Tyr Met Pro Ile Trp Lys Phe Pro Asp Glu Glu Gly Thr Cys Gln
            610                 615                 620

Ser Cys Pro Ile Asn Cys Thr His Ser Cys Val Asp Leu Asp Asp Lys
625                 630                 635                 640

Gly Cys Pro Ala Glu Gln Arg Ala Ser Pro Leu Thr Ser Ile Ile Ser
            645                 650                 655

Ala Val Val Gly Ile Leu Leu Val Val Val Leu Gly Val Val Phe Gly
            660                 665                 670
```

-continued

```
Ile Leu Ile Lys Arg Arg Gln Gln Lys Ile Arg Lys Tyr Thr Met Arg
            675                 680                 685

Arg Leu Leu Gln Glu Thr Glu Leu Val Glu Pro Leu Thr Pro Ser Gly
    690                 695                 700

Ala Met Pro Asn Gln Ala Gln Met Arg Ile Leu Lys Glu Thr Glu Leu
705                 710                 715                 720

Arg Lys Val Lys Val Leu Gly Ser Gly Ala Phe Gly Thr Val Tyr Lys
                725                 730                 735

Gly Ile Trp Ile Pro Asp Gly Glu Asn Val Lys Ile Pro Val Ala Ile
            740                 745                 750

Lys Val Leu Arg Glu Asn Thr Ser Pro Lys Ala Asn Lys Glu Ile Leu
    755                 760                 765

Asp Glu Ala Tyr Val Met Ala Gly Val Gly Ser Pro Tyr Val Ser Arg
770                 775                 780

Leu Leu Gly Ile Cys Leu Thr Ser Thr Val Gln Leu Val Thr Gln Leu
785                 790                 795                 800

Met Pro Tyr Gly Cys Leu Leu Asp His Val Arg Glu Asn Arg Gly Arg
                805                 810                 815

Leu Gly Ser Gln Asp Leu Leu Asn Trp Cys Met Gln Ile Ala Lys Gly
            820                 825                 830

Met Ser Tyr Leu Glu Asp Val Arg Leu Val His Arg Asp Leu Ala Ala
    835                 840                 845

Arg Asn Val Leu Val Lys Ser Pro Asn His Val Lys Ile Thr Asp Phe
850                 855                 860

Gly Leu Ala Arg Leu Leu Asp Ile Asp Glu Thr Glu Tyr His Ala Asp
865                 870                 875                 880

Gly Gly Lys Val Pro Ile Lys Trp Met Ala Leu Glu Ser Ile Leu Arg
                885                 890                 895

Arg Arg Phe Thr His Gln Ser Asp Val Trp Ser Tyr Gly Val Thr Val
            900                 905                 910

Trp Glu Leu Met Thr Phe Gly Ala Lys Pro Tyr Asp Gly Ile Pro Ala
    915                 920                 925

Arg Glu Ile Pro Asp Leu Leu Glu Lys Gly Glu Arg Leu Pro Gln Pro
930                 935                 940

Pro Ile Cys Thr Ile Asp Val Tyr Met Ile Met Val Lys Cys Trp Met
945                 950                 955                 960

Ile Asp Ser Glu Cys Arg Pro Arg Phe Arg Glu Leu Val Ser Glu Phe
                965                 970                 975

Ser Arg Met Ala Arg Asp Pro Gln Arg Phe Val Val Ile Gln Asn Glu
            980                 985                 990

Asp Leu Gly Pro Ala Ser Pro Leu Asp Ser Thr Phe Tyr Arg Ser Leu
    995                 1000                1005

Leu Glu Asp Asp Asp Met Gly Asp Leu Val Asp Ala Glu Glu Tyr
    1010                1015                1020

Leu Val Pro Gln Gln Gly Phe Phe Cys Pro Asp Pro Ala Pro Gly
    1025                1030                1035

Thr Gly Gly Met Val His His Arg His Arg Ser Ser Ser Thr Arg
    1040                1045                1050

Ser Gly Gly Gly Asp Leu Thr Leu Gly Leu Glu Pro Ser Glu Glu
    1055                1060                1065

Glu Ala Pro Arg Ser Pro Arg Ala Pro Ser Glu Gly Thr Gly Ser
    1070                1075                1080

Asp Val Phe Asp Gly Asp Leu Gly Met Gly Ala Ala Lys Gly Leu
```

```
                1085                1090                1095

Gln Ser Leu Pro Ala His Asp Pro Ser Pro Leu Gln Arg Tyr Ser
        1100                1105                1110

Glu Asp Pro Thr Val Pro Leu Pro Ser Glu Thr Asp Gly Tyr Val
    1115                1120                1125

Ala Pro Leu Thr Cys Ser Pro Gln Pro Glu Tyr Val Asn Gln Pro
        1130                1135                1140

Asp Val Arg Pro Gln Pro Pro Ser Pro Gln Glu Gly Pro Leu Ser
    1145                1150                1155

Pro Ala Arg Pro Thr Gly Ala Thr Leu Glu Arg Pro Lys Thr Leu
        1160                1165                1170

Ser Pro Gly Lys Asn Gly Val Val Lys Asp Val Phe Ala Phe Gly
    1175                1180                1185

Gly Ala Val Glu Asn Pro Glu Tyr Leu Ala Pro Arg Gly Gly Ala
        1190                1195                1200

Ala Pro Gln Pro His Leu Pro Pro Ala Phe Ser Pro Ala Phe Asp
    1205                1210                1215

Asn Leu Tyr Tyr Trp Asp Gln Asp Pro Ser Glu Arg Gly Ala Pro
        1220                1225                1230

Pro Ser Thr Phe Lys Gly Thr Pro Thr Ala Glu Asn Pro Glu Tyr
    1235                1240                1245

Leu Gly Leu Asp Val Pro Val
        1250                1255

<210> SEQ ID NO 42
<211> LENGTH: 1256
<212> TYPE: PRT
<213> ORGANISM: Mus musculus

<400> SEQUENCE: 42

Met Glu Leu Ala Ala Trp Cys Arg Trp Gly Phe Leu Leu Ala Leu Leu
1               5                   10                  15

Ser Pro Gly Ala Ala Gly Thr Gln Val Cys Thr Gly Thr Asp Met Lys
            20                  25                  30

Leu Arg Leu Pro Ala Ser Pro Glu Thr His Leu Asp Met Leu Arg His
        35                  40                  45

Leu Tyr Gln Gly Cys Gln Val Val Gln Gly Asn Leu Glu Leu Thr Tyr
    50                  55                  60

Leu Pro Ala Asn Ala Ser Leu Ser Phe Leu Gln Asp Ile Gln Glu Val
65                  70                  75                  80

Gln Gly Tyr Met Leu Ile Ala His Asn Arg Val Lys His Val Pro Leu
                85                  90                  95

Gln Arg Leu Arg Ile Val Arg Gly Thr Gln Leu Phe Glu Asp Lys Tyr
            100                 105                 110

Ala Leu Ala Val Leu Asp Asn Arg Asp Pro Leu Asp Asn Val Thr Thr
        115                 120                 125

Ala Ala Pro Gly Arg Thr Pro Glu Gly Leu Arg Glu Leu Gln Leu Arg
    130                 135                 140

Ser Leu Thr Glu Ile Leu Lys Gly Gly Val Leu Ile Arg Gly Asn Pro
145                 150                 155                 160

Gln Leu Cys Tyr Gln Asp Met Val Leu Trp Lys Asp Val Leu Arg Lys
                165                 170                 175

Asn Asn Gln Leu Ala Pro Val Asp Met Asp Thr Asn Arg Ser Arg Ala
            180                 185                 190
```

```
Cys Pro Pro Cys Ala Pro Thr Cys Lys Asp Asn His Cys Trp Gly Glu
        195                 200                 205

Ser Pro Glu Asp Cys Gln Ile Leu Thr Gly Thr Ile Cys Thr Ser Gly
        210                 215                 220

Cys Ala Arg Cys Lys Gly Arg Leu Pro Thr Asp Cys Cys His Glu Gln
225                 230                 235                 240

Cys Ala Ala Gly Cys Thr Gly Pro Lys His Ser Asp Cys Leu Ala Cys
                245                 250                 255

Leu His Phe Asn His Ser Gly Ile Cys Glu Leu His Cys Pro Ala Leu
            260                 265                 270

Ile Thr Tyr Asn Thr Asp Thr Phe Glu Ser Met Leu Asn Pro Glu Gly
        275                 280                 285

Arg Tyr Thr Phe Gly Ala Ser Cys Val Thr Thr Cys Pro Tyr Asn Tyr
        290                 295                 300

Leu Ser Thr Glu Val Gly Ser Cys Thr Leu Val Cys Pro Pro Asn Asn
305                 310                 315                 320

Gln Glu Val Thr Ala Glu Asp Gly Thr Gln Arg Cys Glu Lys Cys Ser
                325                 330                 335

Lys Pro Cys Ala Gly Val Cys Tyr Gly Leu Gly Met Glu His Leu Arg
            340                 345                 350

Gly Ala Arg Ala Ile Thr Ser Asp Asn Ile Gln Glu Phe Ala Gly Cys
        355                 360                 365

Lys Lys Ile Phe Gly Ser Leu Ala Phe Leu Pro Glu Ser Phe Asp Gly
        370                 375                 380

Asn Pro Ser Ser Gly Val Ala Pro Leu Lys Pro Glu His Leu Gln Val
385                 390                 395                 400

Phe Glu Thr Leu Glu Glu Ile Thr Gly Tyr Leu Tyr Ile Ser Ala Trp
                405                 410                 415

Pro Glu Ser Phe Gln Asp Leu Ser Val Phe Gln Asn Leu Arg Val Ile
            420                 425                 430

Arg Gly Arg Ile Leu His Asp Gly Ala Tyr Ser Leu Thr Leu Gln Gly
        435                 440                 445

Leu Gly Ile His Ser Leu Gly Leu Arg Ser Leu Arg Glu Leu Gly Ser
        450                 455                 460

Gly Leu Ala Leu Ile His Arg Asn Thr His Leu Cys Phe Val Asn Thr
465                 470                 475                 480

Val Pro Trp Asp Gln Leu Phe Arg Asn Pro His Gln Ala Leu Leu His
                485                 490                 495

Ser Gly Asn Arg Pro Glu Glu Ala Cys Gly Leu Glu Gly Leu Val Cys
            500                 505                 510

Asn Ser Leu Cys Ala Arg Gly His Cys Trp Gly Pro Gly Pro Thr Gln
        515                 520                 525

Cys Val Asn Cys Ser Gln Phe Leu Arg Gly Gln Glu Cys Val Glu Glu
        530                 535                 540

Cys Arg Val Trp Lys Gly Leu Pro Arg Glu Tyr Val Arg Gly Lys His
545                 550                 555                 560

Cys Leu Pro Cys His Pro Glu Cys Gln Pro Gln Asn Ser Ser Glu Thr
                565                 570                 575

Cys Tyr Gly Ser Glu Ala Asp Gln Cys Glu Ala Cys Ala His Tyr Lys
            580                 585                 590

Asp Ser Ser Ser Cys Val Ala Arg Cys Pro Ser Gly Val Lys Pro Asp
        595                 600                 605

Leu Ser Tyr Met Pro Ile Trp Lys Tyr Pro Asp Glu Glu Gly Ile Cys
```

-continued

```
            610                 615                 620
Gln Pro Cys Pro Ile Asn Cys Thr His Ser Cys Val Asp Leu Asp Glu
625                 630                 635                 640

Arg Gly Cys Pro Ala Glu Gln Arg Ala Ser Pro Val Thr Phe Ile Ile
                    645                 650                 655

Ala Thr Val Val Gly Val Leu Leu Phe Leu Ile Ile Val Val Val Ile
                    660                 665                 670

Gly Ile Leu Ile Lys Arg Arg Gln Lys Ile Arg Lys Tyr Thr Met
                675                 680                 685

Arg Arg Leu Leu Gln Glu Thr Glu Leu Val Glu Pro Leu Thr Pro Ser
690                 695                 700

Gly Ala Val Pro Asn Gln Ala Gln Met Arg Ile Leu Lys Glu Thr Glu
705                 710                 715                 720

Leu Arg Lys Leu Lys Val Leu Gly Ser Gly Ala Phe Gly Thr Val Tyr
                    725                 730                 735

Lys Gly Ile Trp Ile Pro Asp Gly Glu Asn Val Lys Ile Pro Val Ala
                740                 745                 750

Ile Lys Val Leu Arg Glu Asn Thr Ser Pro Lys Ala Asn Lys Glu Ile
                755                 760                 765

Leu Asp Glu Ala Tyr Val Met Ala Gly Val Gly Ser Pro Tyr Val Ser
770                 775                 780

Arg Leu Leu Gly Ile Cys Leu Thr Ser Thr Val Gln Leu Val Thr Gln
785                 790                 795                 800

Leu Met Pro Tyr Gly Cys Leu Leu Asp His Val Arg Glu His Arg Gly
                    805                 810                 815

Arg Leu Gly Ser Gln Asp Leu Leu Asn Trp Cys Val Gln Ile Ala Lys
                820                 825                 830

Gly Met Ser Tyr Leu Glu Glu Val Arg Leu Val His Arg Asp Leu Ala
                835                 840                 845

Ala Arg Asn Val Leu Val Lys Ser Pro Asn His Val Lys Ile Thr Asp
850                 855                 860

Phe Gly Leu Ala Arg Leu Leu Asp Ile Asp Glu Thr Glu Tyr His Ala
865                 870                 875                 880

Asp Gly Gly Lys Val Pro Ile Lys Trp Met Ala Leu Glu Ser Ile Leu
                    885                 890                 895

Arg Arg Arg Phe Thr His Gln Ser Asp Val Trp Ser Tyr Gly Val Thr
                900                 905                 910

Val Trp Glu Leu Met Thr Phe Gly Ala Lys Pro Tyr Asp Gly Ile Pro
                915                 920                 925

Ala Arg Glu Ile Pro Asp Leu Leu Glu Lys Gly Glu Arg Leu Pro Gln
930                 935                 940

Pro Pro Ile Cys Thr Ile Asp Val Tyr Met Ile Met Val Lys Cys Trp
945                 950                 955                 960

Met Ile Asp Ser Glu Cys Arg Pro Arg Phe Arg Glu Leu Val Ser Glu
                    965                 970                 975

Phe Ser Arg Met Ala Arg Asp Pro Gln Arg Phe Val Val Ile Gln Asn
                980                 985                 990

Glu Asp Leu Gly Pro Ser Ser Pro  Met Asp Ser Thr Phe  Tyr Arg Ser
                995                 1000                 1005

Leu Leu  Glu Asp Asp Asp Met  Gly Glu Leu Val Asp  Ala Glu Glu
        1010                 1015                1020

Tyr Leu  Val Pro Gln Gln Gly  Phe Phe Ser Pro Asp  Pro Ala Leu
        1025                 1030                1035
```

Gly Thr Gly Ser Thr Ala His Arg Arg His Arg Ser Ser Ser Ala
            1040                    1045                    1050

Arg Ser Gly Gly Gly Glu Leu Thr Leu Gly Leu Glu Pro Ser Glu
    1055                    1060                    1065

Glu Glu Pro Pro Arg Ser Pro Leu Ala Pro Ser Glu Gly Ala Gly
    1070                    1075                    1080

Ser Asp Val Phe Asp Gly Asp Leu Ala Val Gly Val Thr Lys Gly
    1085                    1090                    1095

Leu Gln Ser Leu Ser Pro His Asp Leu Ser Pro Leu Gln Arg Tyr
    1100                    1105                    1110

Ser Glu Asp Pro Thr Leu Pro Leu Pro Pro Glu Thr Asp Gly Tyr
    1115                    1120                    1125

Val Ala Pro Leu Ala Cys Ser Pro Gln Pro Glu Tyr Val Asn Gln
    1130                    1135                    1140

Pro Glu Val Arg Pro Gln Ser Pro Leu Thr Pro Glu Gly Pro Pro
    1145                    1150                    1155

Pro Pro Ile Arg Pro Ala Gly Ala Thr Leu Glu Arg Pro Lys Thr
    1160                    1165                    1170

Leu Ser Pro Gly Lys Asn Gly Val Val Lys Asp Val Phe Ala Phe
    1175                    1180                    1185

Gly Gly Ala Val Glu Asn Pro Glu Tyr Leu Ala Pro Arg Ala Gly
    1190                    1195                    1200

Thr Ala Ser Gln Pro His Pro Ser Pro Ala Phe Ser Pro Ala Phe
    1205                    1210                    1215

Asp Asn Leu Tyr Tyr Trp Asp Gln Asn Ser Ser Glu Gln Gly Pro
    1220                    1225                    1230

Pro Pro Ser Thr Phe Glu Gly Thr Pro Thr Ala Glu Asn Pro Glu
    1235                    1240                    1245

Tyr Leu Gly Leu Asp Val Pro Val
    1250                    1255

<210> SEQ ID NO 43
<211> LENGTH: 260
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 43

Cys Ile Thr Gly Asp Ala Leu Val Ala Leu Pro Glu Gly Glu Ser Val
1               5                   10                  15

Arg Ile Ala Asp Ile Val Pro Gly Ala Arg Pro Asn Ser Asp Asn Ala
            20                  25                  30

Ile Asp Leu Lys Val Leu Asp Arg His Gly Asn Pro Val Leu Ala Asp
        35                  40                  45

Arg Leu Phe His Ser Gly Glu His Pro Val Tyr Thr Val Arg Thr Val
    50                  55                  60

Glu Gly Leu Arg Val Thr Gly Thr Ala Asn His Pro Leu Leu Cys Leu
65                  70                  75                  80

Val Asp Val Ala Gly Val Pro Thr Leu Leu Trp Lys Leu Ile Asp Glu
                85                  90                  95

Ile Lys Pro Gly Asp Tyr Ala Val Ile Gln Arg Ser Ala Phe Ser Val
            100                 105                 110

-continued

```
Asp Cys Ala Gly Phe Ala Arg Gly Lys Pro Glu Phe Ala Pro Thr Thr
            115                 120                 125

Tyr Thr Val Gly Val Pro Gly Leu Val Arg Phe Leu Glu Ala His His
        130                 135                 140

Arg Asp Pro Asp Ala Gln Ala Ile Ala Asp Glu Leu Thr Asp Gly Arg
145                 150                 155                 160

Phe Tyr Tyr Ala Lys Val Ala Ser Val Thr Asp Ala Gly Val Gln Pro
                165                 170                 175

Val Tyr Ser Leu Arg Val Asp Thr Ala Asp His Ala Phe Ile Thr Asn
            180                 185                 190

Gly Phe Val Ser His Ala Thr Gly Leu Thr Gly Leu Asn Ser Gly Leu
        195                 200                 205

Thr Thr Asn Pro Gly Val Ser Ala Trp Gln Val Asn Thr Ala Tyr Thr
    210                 215                 220

Ala Gly Gln Leu Val Thr Tyr Asn Gly Lys Thr Tyr Lys Cys Leu Gln
225                 230                 235                 240

Pro His Thr Ser Leu Ala Gly Trp Glu Pro Ser Asn Val Pro Ala Leu
                245                 250                 255

Trp Gln Leu Gln
            260

<210> SEQ ID NO 44
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 6xHis tag"

<400> SEQUENCE: 44

His His His His His His
1               5

<210> SEQ ID NO 45
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 45

Asp Thr Tyr Ile His
1               5

<210> SEQ ID NO 46
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 46

Arg Ile Tyr Pro Thr Asn Gly Tyr Thr Arg Tyr Ala Asp Ser Val Lys
1               5                   10                  15

Gly

<210> SEQ ID NO 47
```

```
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 47

Trp Gly Gly Asp Gly Phe Tyr Ala Met Asp Tyr
1               5                   10

<210> SEQ ID NO 48
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 48

Arg Ala Ser Gln Asp Val Asn Thr Ala Val Ala
1               5                   10

<210> SEQ ID NO 49
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 49

Ser Ala Ser Phe Leu Tyr Ser
1               5

<210> SEQ ID NO 50
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 50

Gln Gln His Tyr Thr Thr Pro Pro Thr
1               5

<210> SEQ ID NO 51
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 51

Ser Tyr Trp Ile Ala
1               5

<210> SEQ ID NO 52
<211> LENGTH: 17
<212> TYPE: PRT
<213> ORGANISM: Artificial Sequence
<220> FEATURE:
```

```
<221> NAME/KEY: source
<223> OTHER INFORMATION: /note="Description of Artificial Sequence:
      Synthetic peptide"

<400> SEQUENCE: 52

Leu Ile Tyr Pro Gly Asp Ser Asp Thr Lys Tyr Ser Pro Ser Phe Gln
1               5                   10                  15

Gly

<210> SEQ ID NO 53
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 53

His Asp Val Gly Tyr Cys Ser Ser Ser Asn Cys Ala Lys Trp Pro Glu
1               5                   10                  15

Tyr Phe Gln His
            20

<210> SEQ ID NO 54
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 54

Ser Gly Ser Ser Ser Asn Ile Gly Asn Asn Tyr Val Ser
1               5                   10

<210> SEQ ID NO 55
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 55

Ser Ala Ser Tyr Arg Tyr Thr
1               5

<210> SEQ ID NO 56
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 56

Gln Gln Tyr Tyr Ile Tyr Pro Tyr Thr
1               5

<210> SEQ ID NO 57
<211> LENGTH: 5
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic peptide"

<400> SEQUENCE: 57

Asn Tyr Gly Met Asn
1               5

<210> SEQ ID NO 58
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 58

Trp Ile Asn Thr Ser Thr Gly Glu Ser Thr Phe Ala Asp Asp Phe Lys
1               5                   10                  15

Gly

<210> SEQ ID NO 59
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 59

Trp Glu Val Tyr His Gly Tyr Val Pro Tyr
1               5                   10

<210> SEQ ID NO 60
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 60

Lys Ala Ser Gln Asp Val Tyr Asn Ala Val Ala
1               5                   10

<210> SEQ ID NO 61
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 61

Ser Ala Ser Ser Arg Tyr Thr
1               5

<210> SEQ ID NO 62
<211> LENGTH: 9
<212> TYPE: PRT
<213> ORGANISM: Artificial Sequence
<220> FEATURE:
<221> NAME/KEY: source
```

```
<223> OTHER INFORMATION: /note="Description of Artificial Sequence:
      Synthetic peptide"

<400> SEQUENCE: 62

Gln Gln His Phe Arg Thr Pro Phe Thr
1               5

<210> SEQ ID NO 63
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 63

Asp Tyr Thr Met Asp
1               5

<210> SEQ ID NO 64
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 64

Asp Val Asn Pro Asn Ser Gly Gly Ser Ile Tyr Asn Gln Arg Phe Lys
1               5                   10                  15

Gly

<210> SEQ ID NO 65
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 65

Asn Leu Gly Pro Ser Phe Tyr Phe Asp Tyr
1               5                   10

<210> SEQ ID NO 66
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 66

Lys Ala Ser Gln Asp Val Ser Ile Gly Val Ala
1               5                   10

<210> SEQ ID NO 67
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

<400> SEQUENCE: 67

Ser Ala Ser Tyr Arg Tyr Thr
1               5

<210> SEQ ID NO 68
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 68

Gln Gln Tyr Tyr Ile Tyr Pro Tyr Thr
1               5

<210> SEQ ID NO 69
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 69

Ile Asn Thr Met Gly
1               5

<210> SEQ ID NO 70
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 70

Leu Ile Ser Ser Ile Gly Asp Thr Tyr Tyr Ala Asp Ser Val Lys Gly
1               5                   10                  15

<210> SEQ ID NO 71
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 71

Phe Arg Thr Ala Ala Gln Gly Thr Asp Tyr
1               5                   10

<210> SEQ ID NO 72
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 72

Ser Cys Gly Met Gly

```
<210> SEQ ID NO 73
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 73

Arg Ile Ser Gly Asp Gly Asp Thr Trp His Lys Glu Ser Val Lys Gly
1               5                   10                  15

<210> SEQ ID NO 74
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 74

Cys Tyr Asn Leu Glu Thr Tyr
1               5

<210> SEQ ID NO 75
<211> LENGTH: 251
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 75

Lys Glu Phe Ile Leu Arg Phe Ser Val Ala His Lys Tyr Val Asp Ser
1               5                   10                  15

Leu Asn Val Ile Arg Ser Ala Ile Gly Thr Pro Leu Gln Thr Ile Ser
                20                  25                  30

Ser Gly Gly Thr Ser Leu Leu Met Ile Asp Ser Gly Ser Gly Asp Asn
            35                  40                  45

Leu Phe Ala Val Asp Val Arg Gly Ile Asp Pro Glu Glu Gly Arg Phe
        50                  55                  60

Asn Asn Leu Arg Leu Ile Val Glu Arg Asn Asn Leu Tyr Val Thr Gly
65                  70                  75                  80

Phe Val Asn Arg Thr Asn Asn Val Phe Tyr Arg Phe Ala Asp Phe Ser
                85                  90                  95

His Val Thr Phe Pro Gly Thr Thr Ala Val Thr Leu Ser Gly Asp Ser
            100                 105                 110

Ser Tyr Thr Thr Leu Gln Arg Val Ala Gly Ile Ser Arg Thr Gly Met
        115                 120                 125

Gln Ile Asn Arg His Ser Leu Thr Thr Ser Tyr Leu Asp Leu Met Ser
130                 135                 140

His Ser Gly Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Arg Thr Thr Leu Asp Asp Leu Ser Gly Arg Ser Tyr Val Met
            180                 185                 190
```

```
Thr Ala Glu Asp Val Asp Leu Thr Leu Asn Trp Gly Arg Leu Ser Ser
        195                 200                 205

Val Leu Pro Asp Tyr His Gly Gln Asp Ser Val Arg Val Gly Arg Ile
        210                 215                 220

Ser Phe Gly Ser Ile Asn Ala Ile Leu Gly Ser Val Ala Leu Ile Leu
225                 230                 235                 240

Asn Cys His His His Ala Ser Ala Val Ala Ala
                245                 250

<210> SEQ ID NO 76
<211> LENGTH: 251
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 76

Lys Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
            20                  25                  30

Ser Gly Gly Thr Ser Leu Leu Met Ile Asp Asn Leu Val Pro Met Val
        35                  40                  45

Ala Thr Val Val Asp Val Arg Gly Ile Asp Pro Glu Glu Gly Arg Phe
    50                  55                  60

Asn Asn Leu Arg Leu Ile Val Glu Arg Asn Leu Tyr Val Thr Gly
65                  70                  75                  80

Phe Val Asn Arg Thr Asn Asn Val Phe Tyr Arg Phe Ala Asp Phe Ser
                85                  90                  95

His Val Thr Phe Pro Gly Thr Thr Ala Val Thr Leu Ser Gly Asp Ser
            100                 105                 110

Ser Tyr Thr Thr Leu Gln Arg Val Ala Gly Ile Ser Arg Thr Gly Met
        115                 120                 125

Gln Ile Asn Arg His Ser Leu Thr Thr Ser Tyr Leu Asp Leu Met Ser
    130                 135                 140

His Ser Gly Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Arg Thr Thr Leu Asp Asp Leu Ser Gly Arg Ser Tyr Val Met
            180                 185                 190

Thr Ala Glu Asp Val Asp Leu Thr Leu Asn Trp Gly Arg Leu Ser Ser
        195                 200                 205

Val Leu Pro Asp Tyr His Gly Gln Asp Ser Val Arg Val Gly Arg Ile
        210                 215                 220

Ser Phe Gly Ser Ile Asn Ala Ile Leu Gly Ser Val Ala Leu Ile Leu
225                 230                 235                 240

Asn Cys His His His Ala Ser Ala Val Ala Ala
                245                 250

<210> SEQ ID NO 77
<211> LENGTH: 251
<212> TYPE: PRT
<213> ORGANISM: Artificial Sequence
<220> FEATURE:
```

```
<221> NAME/KEY: source
<223> OTHER INFORMATION: /note="Description of Artificial Sequence:
      Synthetic polypeptide"

<400> SEQUENCE: 77
```

Lys Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
            20                  25                  30

Ser Gly Gly Thr Ser Leu Leu Met Ile Asp Ser Asn Leu Val Pro Met
        35                  40                  45

Val Ala Thr Val Asp Val Arg Gly Ile Asp Pro Glu Glu Gly Arg Phe
    50                  55                  60

Asn Asn Leu Arg Leu Ile Val Glu Arg Asn Asn Leu Tyr Val Thr Gly
65                  70                  75                  80

Phe Val Asn Arg Thr Asn Asn Val Phe Tyr Arg Phe Ala Asp Phe Ser
                85                  90                  95

His Val Thr Phe Pro Gly Thr Thr Ala Val Thr Leu Ser Gly Asp Ser
            100                 105                 110

Ser Tyr Thr Thr Leu Gln Arg Val Ala Gly Ile Ser Arg Thr Gly Met
        115                 120                 125

Gln Ile Asn Arg His Ser Leu Thr Thr Ser Tyr Leu Asp Leu Met Ser
    130                 135                 140

His Ser Gly Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Arg Thr Thr Leu Asp Asp Leu Ser Gly Arg Ser Tyr Val Met
            180                 185                 190

Thr Ala Glu Asp Val Asp Leu Thr Leu Asn Trp Gly Arg Leu Ser Ser
        195                 200                 205

Val Leu Pro Asp Tyr His Gly Gln Asp Ser Val Arg Val Gly Arg Ile
    210                 215                 220

Ser Phe Gly Ser Ile Asn Ala Ile Leu Gly Ser Val Ala Leu Ile Leu
225                 230                 235                 240

Asn Cys His His His Ala Ser Ala Val Ala Ala
                245                 250

```
<210> SEQ ID NO 78
<211> LENGTH: 251
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 78
```

Lys Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
            20                  25                  30

Ser Gly Gly Thr Ser Leu Leu Met Ile Asp Ser Gly Ile Leu Gly Phe
        35                  40                  45

Val Phe Thr Leu Asp Val Arg Gly Ile Asp Pro Glu Glu Gly Arg Phe
    50                  55                  60

Asn Asn Leu Arg Leu Ile Val Glu Arg Asn Asn Leu Tyr Val Thr Gly

```
                65                  70                  75                  80
        Phe Val Asn Arg Thr Asn Asn Val Phe Tyr Arg Phe Ala Asp Phe Ser
                            85                  90                  95

His Val Thr Phe Pro Gly Thr Thr Ala Val Thr Leu Ser Gly Asp Ser
                        100                 105                 110

Ser Tyr Thr Thr Leu Gln Arg Val Ala Gly Ile Ser Arg Thr Gly Met
                        115                 120                 125

Gln Ile Asn Arg His Ser Leu Thr Thr Ser Tyr Leu Asp Leu Met Ser
                    130                 135                 140

His Ser Gly Thr Ser Leu Thr Gln Ser Val Ala Arg Ala Met Leu Arg
        145                 150                 155                 160

Phe Val Thr Val Thr Ala Glu Ala Leu Arg Phe Arg Gln Ile Gln Arg
                        165                 170                 175

Gly Phe Arg Thr Thr Leu Asp Asp Leu Ser Gly Arg Ser Tyr Val Met
                        180                 185                 190

Thr Ala Glu Asp Val Asp Leu Thr Leu Asn Trp Gly Arg Leu Ser Ser
                        195                 200                 205

Val Leu Pro Asp Tyr His Gly Gln Asp Ser Val Arg Val Gly Arg Ile
                    210                 215                 220

Ser Phe Gly Ser Ile Asn Ala Ile Leu Gly Ser Val Ala Leu Ile Leu
        225                 230                 235                 240

Asn Cys His His His Ala Ser Ala Val Ala Ala
                        245                 250

<210> SEQ ID NO 79
<211> LENGTH: 251
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 79

Lys Glu Phe Thr Leu Asp Phe Ser Thr Ala Lys Thr Tyr Val Asp Ser
        1               5                   10                  15

Leu Asn Val Ile Arg Ser Ala Ile Gly Thr Pro Leu Gln Thr Ile Ser
                        20                  25                  30

Ser Gly Gly Thr Ser Leu Leu Met Ile Asp Ser Gly Ser Gly Asp Asn
                    35                  40                  45

Leu Phe Ala Val Gly Ile Leu Gly Phe Asp Phe Thr Leu Gly Arg Phe
            50                  55                  60

Asn Asn Leu Arg Leu Ile Val Glu Arg Asn Asn Leu Tyr Val Thr Gly
        65                  70                  75                  80

Phe Val Asn Arg Thr Asn Asn Val Phe Tyr Arg Phe Ala Asp Phe Ser
                        85                  90                  95

His Val Thr Phe Pro Gly Thr Thr Ala Val Thr Leu Ser Gly Asp Ser
                        100                 105                 110

Ser Tyr Thr Thr Leu Gln Arg Val Ala Gly Ile Ser Arg Thr Gly Met
                        115                 120                 125

Gln Ile Asn Arg His Ser Leu Thr Thr Ser Tyr Leu Asp Leu Met Ser
                    130                 135                 140

His Ser Gly Thr Ser Leu Thr Gln Ser Val Ala Arg Ala Met Leu Arg
        145                 150                 155                 160

Phe Val Thr Val Thr Ala Glu Ala Leu Arg Phe Arg Gln Ile Gln Arg
                        165                 170                 175
```

Gly Phe Arg Thr Thr Leu Asp Asp Leu Ser Gly Arg Ser Tyr Val Met
            180                 185                 190

Thr Ala Glu Asp Val Asp Leu Thr Leu Asn Trp Gly Arg Leu Ser Ser
            195                 200                 205

Val Leu Pro Asp Tyr His Gly Gln Asp Ser Val Arg Val Gly Arg Ile
            210                 215                 220

Ser Phe Gly Ser Ile Asn Ala Ile Leu Gly Ser Val Ala Leu Ile Leu
225                 230                 235                 240

Asn Cys His His His Ala Ser Ala Val Ala Ala
                245                 250

<210> SEQ ID NO 80
<211> LENGTH: 251
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 80

Lys Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
            20                  25                  30

Ser Gly Gly Thr Ser Leu Leu Met Ile Asp Ser Gly Ser Gly Asp Asn
            35                  40                  45

Leu Phe Ala Val Asp Ile Leu Gly Phe Val Phe Thr Leu Gly Arg Phe
50                  55                  60

Asn Asn Leu Arg Leu Ile Val Glu Arg Asn Asn Leu Tyr Val Thr Gly
65                  70                  75                  80

Phe Val Asn Arg Thr Asn Asn Val Phe Tyr Arg Phe Ala Asp Phe Ser
            85                  90                  95

His Val Thr Phe Pro Gly Thr Thr Ala Val Thr Leu Ser Gly Asp Ser
            100                 105                 110

Ser Tyr Thr Thr Leu Gln Arg Val Ala Gly Ile Ser Arg Thr Gly Met
            115                 120                 125

Gln Ile Asn Arg His Ser Leu Thr Thr Ser Tyr Leu Asp Leu Met Ser
130                 135                 140

His Ser Gly Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
            165                 170                 175

Gly Phe Arg Thr Thr Leu Asp Asp Leu Ser Gly Arg Ser Tyr Val Met
            180                 185                 190

Thr Ala Glu Asp Val Asp Leu Thr Leu Asn Trp Gly Arg Leu Ser Ser
            195                 200                 205

Val Leu Pro Asp Tyr His Gly Gln Asp Ser Val Arg Val Gly Arg Ile
            210                 215                 220

Ser Phe Gly Ser Ile Asn Ala Ile Leu Gly Ser Val Ala Leu Ile Leu
225                 230                 235                 240

Asn Cys His His His Ala Ser Ala Val Ala Ala
                245                 250

<210> SEQ ID NO 81
<211> LENGTH: 251

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 81
```

Lys Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
            20                  25                  30

Ser Gly Gly Thr Ser Leu Leu Met Ile Asp Ser Gly Ser Gly Asp Asn
        35                  40                  45

Leu Phe Ala Val Asp Ile Leu Gly Phe Asp Thr Leu Gly Arg Phe
    50                  55                  60

Asn Asn Leu Arg Leu Ile Val Glu Arg Asn Asn Leu Tyr Val Thr Gly
65                  70                  75                  80

Phe Val Asn Arg Thr Asn Asn Val Phe Tyr Arg Phe Ala Asp Phe Ser
                85                  90                  95

His Val Thr Phe Pro Gly Thr Thr Ala Val Thr Leu Ser Gly Asp Ser
            100                 105                 110

Ser Tyr Thr Thr Leu Gln Arg Val Ala Gly Ile Ser Arg Thr Gly Met
        115                 120                 125

Gln Ile Asn Arg His Ser Leu Thr Thr Ser Tyr Leu Asp Leu Met Ser
    130                 135                 140

His Ser Gly Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Arg Thr Thr Leu Asp Asp Leu Ser Gly Arg Ser Tyr Val Met
            180                 185                 190

Thr Ala Glu Asp Val Asp Leu Thr Leu Asn Trp Gly Arg Leu Ser Ser
        195                 200                 205

Val Leu Pro Asp Tyr His Gly Gln Asp Ser Val Arg Val Gly Arg Ile
    210                 215                 220

Ser Phe Gly Ser Ile Asn Ala Ile Leu Gly Ser Val Ala Leu Ile Leu
225                 230                 235                 240

Asn Cys His His His Ala Ser Ala Val Ala Ala
                245                 250

```
<210> SEQ ID NO 82
<211> LENGTH: 251
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 82
```

Lys Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
            20                  25                  30

Ser Gly Gly Thr Ser Leu Leu Met Ile Asp Ser Gly Ser Gly Asp Asn
        35                  40                  45

Leu Phe Ala Val Gly Ile Leu Gly Phe Val Phe Thr Leu Gly Arg Phe

```
            50                  55                  60
Asn Asn Leu Arg Leu Ile Val Glu Arg Asn Asn Leu Tyr Val Thr Gly
 65                  70                  75                  80

Phe Val Asn Arg Thr Asn Asn Val Phe Tyr Arg Phe Ala Asp Phe Ser
                     85                  90                  95

His Val Thr Phe Pro Gly Thr Thr Ala Val Thr Leu Ser Gly Asp Ser
                    100                 105                 110

Ser Tyr Thr Thr Leu Gln Arg Val Ala Gly Ile Ser Arg Thr Gly Met
                115                 120                 125

Gln Ile Asn Arg His Ser Leu Thr Thr Ser Tyr Leu Asp Leu Met Ser
            130                 135                 140

His Ser Gly Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                    165                 170                 175

Gly Phe Arg Thr Thr Leu Asp Asp Leu Ser Gly Arg Ser Tyr Val Met
                180                 185                 190

Thr Ala Glu Asp Val Asp Leu Thr Leu Asn Trp Gly Arg Leu Ser Ser
            195                 200                 205

Val Leu Pro Asp Tyr His Gly Gln Asp Ser Val Arg Val Gly Arg Ile
210                 215                 220

Ser Phe Gly Ser Ile Asn Ala Ile Leu Gly Ser Val Ala Leu Ile Leu
225                 230                 235                 240

Asn Cys His His His Ala Ser Ala Val Ala Ala
                245                 250
```

<210> SEQ ID NO 83
<211> LENGTH: 251
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 83

```
Lys Glu Phe Ile Leu Asp Phe Ser Thr Ala Lys Thr Tyr Val Asp Ser
 1               5                  10                  15

Leu Asn Val Ile Arg Ser Ala Ile Gly Thr Pro Leu Gln Thr Ile Ser
                 20                  25                  30

Ser Gly Gly Thr Ser Leu Leu Met Ile Asp Ser Gly Ile Gly Asp Asn
             35                  40                  45

Leu Phe Ala Val Asp Val Arg Gly Ile Ala Pro Ile Glu Ala Arg Phe
 50                  55                  60

Asn Asn Leu Arg Leu Ile Val Glu Arg Asn Asn Leu Tyr Val Thr Gly
 65                  70                  75                  80

Phe Val Asn Arg Thr Asn Asn Val Phe Tyr Arg Phe Ala Asp Phe Ser
                     85                  90                  95

His Val Thr Phe Pro Gly Thr Thr Ala Val Thr Leu Ser Ala Asp Ser
                    100                 105                 110

Ser Tyr Thr Thr Leu Gln Arg Val Ala Gly Ile Ser Arg Thr Gly Met
                115                 120                 125

Gln Ile Asn Arg His Ser Leu Thr Thr Ser Tyr Leu Asp Leu Met Ser
            130                 135                 140

His Ser Ala Thr Ser Leu Thr Gln Ser Val Ala Arg Ala Met Leu Arg
145                 150                 155                 160
```

```
Phe Val Thr Val Thr Ala Glu Ala Leu Arg Phe Arg Gln Ile Gln Arg
            165                 170                 175

Gly Phe Arg Thr Thr Leu Ala Ala Leu Ser Gly Ala Ser Tyr Val Met
            180                 185                 190

Thr Ala Glu Asp Val Asp Leu Thr Leu Asn Trp Gly Arg Leu Ser Ser
            195                 200                 205

Val Leu Pro Asp Tyr His Gly Gln Asp Ser Val Arg Val Gly Arg Ile
        210                 215                 220

Ser Phe Gly Ser Ile Asn Ala Ile Leu Gly Ser Val Ala Leu Ile Leu
225                 230                 235                 240

Asn Ser His His His Ala Ser Ala Val Ala Ala
            245                 250
```

<210> SEQ ID NO 84
<211> LENGTH: 252
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 84

```
Lys Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
            20                  25                  30

Ser Gly Gly Thr Ser Leu Leu Met Ile Asp Ser Gly Ser Gly Asp Asn
        35                  40                  45

Leu Phe Ala Val Gly Ile Leu Gly Phe Val Phe Thr Leu Glu Gly Arg
    50                  55                  60

Phe Asn Asn Leu Arg Leu Ile Val Glu Arg Asn Asn Leu Tyr Val Thr
65                  70                  75                  80

Gly Phe Val Asn Arg Thr Asn Asn Val Phe Tyr Arg Phe Ala Asp Phe
                85                  90                  95

Ser His Val Thr Phe Pro Gly Thr Thr Ala Val Thr Leu Ser Gly Asp
            100                 105                 110

Ser Ser Tyr Thr Thr Leu Gln Arg Val Ala Gly Ile Ser Arg Thr Gly
        115                 120                 125

Met Gln Ile Asn Arg His Ser Leu Thr Thr Ser Tyr Leu Asp Leu Met
130                 135                 140

Ser His Ser Gly Thr Ser Leu Thr Gln Ser Val Ala Arg Ala Met Leu
145                 150                 155                 160

Arg Phe Val Thr Val Thr Ala Glu Ala Leu Arg Phe Arg Gln Ile Gln
                165                 170                 175

Arg Gly Phe Arg Thr Thr Leu Asp Asp Leu Ser Gly Arg Ser Tyr Val
            180                 185                 190

Met Thr Ala Glu Asp Val Asp Leu Thr Leu Asn Trp Gly Arg Leu Ser
        195                 200                 205

Ser Val Leu Pro Asp Tyr His Gly Gln Asp Ser Val Arg Val Gly Arg
    210                 215                 220

Ile Ser Phe Gly Ser Ile Asn Ala Ile Leu Gly Ser Val Ala Leu Ile
225                 230                 235                 240

Leu Asn Cys His His His Ala Ser Ala Val Ala Ala
                245                 250
```

```
<210> SEQ ID NO 85
<211> LENGTH: 251
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 85

Lys Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
            20                  25                  30

Ser Gly Gly Thr Ser Leu Leu Met Ile Asp Ser Gly Ser Gly Asp Asn
        35                  40                  45

Leu Phe Ala Val Asn Leu Val Pro Met Val Ala Thr Val Gly Arg Phe
    50                  55                  60

Asn Asn Leu Arg Leu Ile Val Glu Arg Asn Asn Leu Tyr Val Thr Gly
65                  70                  75                  80

Phe Val Asn Arg Thr Asn Asn Val Phe Tyr Arg Phe Ala Asp Phe Ser
                85                  90                  95

His Val Thr Phe Pro Gly Thr Thr Ala Val Thr Leu Ser Gly Asp Ser
            100                 105                 110

Ser Tyr Thr Thr Leu Gln Arg Val Ala Gly Ile Ser Arg Thr Gly Met
        115                 120                 125

Gln Ile Asn Arg His Ser Leu Thr Thr Ser Tyr Leu Asp Leu Met Ser
    130                 135                 140

His Ser Gly Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Arg Thr Thr Leu Asp Asp Leu Ser Gly Arg Ser Tyr Val Met
            180                 185                 190

Thr Ala Glu Asp Val Asp Leu Thr Leu Asn Trp Gly Arg Leu Ser Ser
        195                 200                 205

Val Leu Pro Asp Tyr His Gly Gln Asp Ser Val Arg Val Gly Arg Ile
    210                 215                 220

Ser Phe Gly Ser Ile Asn Ala Ile Leu Gly Ser Val Ala Leu Ile Leu
225                 230                 235                 240

Asn Cys His His His Ala Ser Ala Val Ala Ala
                245                 250

<210> SEQ ID NO 86
<211> LENGTH: 251
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 86

Lys Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
            20                  25                  30

Ser Gly Gly Thr Ser Leu Leu Met Ile Asp Ser Gly Ser Gly Asp Asn
```

```
                35                  40                  45
Leu Phe Ala Val Asp Val Arg Gly Ile Asp Pro Glu Glu Gly Arg Phe
    50                  55                  60
Asn Asn Leu Arg Leu Ile Val Glu Arg Asn Asn Leu Tyr Val Thr Gly
65                  70                  75                  80
Phe Val Asn Arg Thr Asn Asn Val Phe Tyr Arg Phe Ala Asp Phe Ser
                85                  90                  95
His Val Thr Phe Pro Gly Thr Asn Leu Val Pro Met Val Ala Thr Val
                100                 105                 110
Ser Tyr Thr Thr Leu Gln Arg Val Ala Gly Ile Ser Arg Thr Gly Met
                115                 120                 125
Gln Ile Asn Arg His Ser Leu Thr Thr Ser Tyr Leu Asp Leu Met Ser
                130                 135                 140
His Ser Gly Thr Ser Leu Thr Gln Ser Val Ala Arg Ala Met Leu Arg
145                 150                 155                 160
Phe Val Thr Val Thr Ala Glu Ala Leu Arg Phe Arg Gln Ile Gln Arg
                165                 170                 175
Gly Phe Arg Thr Thr Leu Asp Asp Leu Ser Gly Arg Ser Tyr Val Met
                180                 185                 190
Thr Ala Glu Asp Val Asp Leu Thr Leu Asn Trp Gly Arg Leu Ser Ser
                195                 200                 205
Val Leu Pro Asp Tyr His Gly Gln Asp Ser Val Arg Val Gly Arg Ile
                210                 215                 220
Ser Phe Gly Ser Ile Asn Ala Ile Leu Gly Ser Val Ala Leu Ile Leu
225                 230                 235                 240
Asn Cys His His His Ala Ser Ala Val Ala Ala
                245                 250

<210> SEQ ID NO 87
<211> LENGTH: 251
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 87

Lys Glu Phe Thr Leu Asp Phe Ser Thr Ala Lys Thr Tyr Val Asp Ser
1               5                   10                  15
Leu Asn Val Ile Arg Ser Ala Ile Gly Thr Pro Leu Gln Thr Ile Ser
                20                  25                  30
Ser Gly Gly Thr Ser Leu Leu Met Ile Asp Ser Gly Ser Gly Asp Asn
            35                  40                  45
Leu Phe Ala Val Asp Val Arg Gly Ile Asp Pro Glu Glu Gly Arg Phe
    50                  55                  60
Asn Asn Leu Arg Leu Ile Val Glu Arg Asn Asn Leu Tyr Val Thr Gly
65                  70                  75                  80
Phe Val Asn Arg Thr Asn Asn Val Phe Tyr Arg Phe Ala Asp Phe Ser
                85                  90                  95
His Val Thr Phe Pro Gly Thr Thr Ala Val Thr Leu Ser Gly Asp Ser
                100                 105                 110
Ser Tyr Thr Thr Leu Gln Arg Val Ala Gly Ile Ser Arg Thr Gly Met
                115                 120                 125
Gln Ile Asn Arg His Ser Leu Thr Thr Ser Tyr Leu Asp Leu Met Ser
                130                 135                 140
```

```
His Ser Gly Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Arg Gly Ile Leu Gly Asp Val Phe Thr Leu Ser Tyr Val Met
            180                 185                 190

Thr Ala Glu Asp Val Asp Leu Thr Leu Asn Trp Gly Arg Leu Ser Ser
                195                 200                 205

Val Leu Pro Asp Tyr His Gly Gln Asp Ser Val Arg Val Gly Arg Ile
            210                 215                 220

Ser Phe Gly Ser Ile Asn Ala Ile Leu Gly Ser Val Ala Leu Ile Leu
225                 230                 235                 240

Asn Ser His His His Ala Ser Ala Val Ala Ala
                245                 250

<210> SEQ ID NO 88
<211> LENGTH: 260
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 88

Lys Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
                20                  25                  30

Ser Gly Gly Thr Ser Leu Leu Met Ile Asp Ser Gly Ser Gly Asp Asn
            35                  40                  45

Leu Phe Ala Val Asp Val Arg Gly Ile Asp Pro Glu Glu Gly Arg Phe
50                  55                  60

Asn Asn Leu Arg Leu Ile Val Glu Arg Asn Asn Leu Tyr Val Thr Gly
65                  70                  75                  80

Phe Val Asn Arg Thr Asn Asn Val Phe Tyr Arg Phe Ala Asp Phe Ser
                85                  90                  95

His Val Thr Phe Pro Gly Thr Thr Ala Val Thr Leu Ser Gly Asp Ser
            100                 105                 110

Ser Tyr Thr Thr Leu Gln Arg Val Ala Gly Ile Ser Arg Thr Gly Met
            115                 120                 125

Gln Ile Asn Arg His Ser Leu Thr Thr Ser Tyr Leu Asp Leu Met Ser
130                 135                 140

His Ser Gly Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Arg Thr Thr Leu Asp Asp Leu Ser Gly Arg Ser Tyr Val Met
            180                 185                 190

Thr Ala Glu Asp Val Asp Leu Thr Leu Asn Trp Gly Arg Leu Ser Ser
                195                 200                 205

Val Leu Pro Asp Tyr His Gly Gln Asp Ser Val Arg Val Gly Arg Ile
            210                 215                 220

Ser Phe Gly Ser Ile Asn Ala Ile Leu Gly Ser Val Ala Leu Ile Leu
225                 230                 235                 240
```

```
Asn Cys His His His Ile Leu Arg Phe Ser Val Ala His Lys Ala Ser
                245                 250                 255

Ala Val Ala Ala
        260
```

<210> SEQ ID NO 89
<211> LENGTH: 262
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 89

```
Lys Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
                20                  25                  30

Ser Gly Gly Thr Ser Leu Leu Met Ile Asp Ser Gly Ser Gly Asp Asn
            35                  40                  45

Leu Phe Ala Val Asp Ile Leu Gly Phe Asp Phe Thr Leu Gly Arg Phe
    50                  55                  60

Asn Asn Leu Arg Leu Ile Val Glu Arg Asn Asn Leu Tyr Val Thr Gly
65                  70                  75                  80

Phe Val Asn Arg Thr Asn Asn Val Phe Tyr Arg Phe Ala Asp Phe Ser
                85                  90                  95

His Val Thr Phe Pro Gly Thr Thr Ala Val Thr Leu Ser Gly Asp Ser
                100                 105                 110

Ser Tyr Thr Thr Leu Gln Arg Val Ala Gly Ile Ser Arg Thr Gly Met
            115                 120                 125

Gln Ile Asn Arg His Ser Leu Thr Thr Ser Tyr Leu Asp Leu Met Ser
130                 135                 140

His Ser Gly Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Arg Thr Thr Leu Asp Asp Leu Ser Gly Arg Ser Tyr Val Met
            180                 185                 190

Thr Ala Glu Asp Val Asp Leu Thr Leu Asn Trp Gly Arg Leu Ser Ser
    195                 200                 205

Val Leu Pro Asp Tyr His Gly Gln Asp Ser Val Arg Val Gly Arg Ile
210                 215                 220

Ser Phe Gly Ser Ile Asn Ala Ile Leu Gly Ser Val Ala Leu Ile Leu
225                 230                 235                 240

Asn Cys His His His Ala Arg Asn Leu Val Pro Met Val Ala Thr Val
                245                 250                 255

Ala Ser Ala Val Ala Ala
        260
```

<210> SEQ ID NO 90
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

-continued

```
<400> SEQUENCE: 90

Glu Phe Pro Lys Pro Ser Thr Pro Pro Gly Ser Ser Gly Gly Ala Pro
1               5                   10                  15

<210> SEQ ID NO 91
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 91

Gly Gly Gly Gly Ser Gly Gly
1               5

<210> SEQ ID NO 92
<211> LENGTH: 25
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 92

Gly Gly Gly Gly Ser Gly Gly Gly Gly Ser Gly Gly Gly Ser Gly
1               5                   10                  15

Gly Gly Gly Ser Gly Gly Gly Gly Ser
            20                  25

<210> SEQ ID NO 93
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 93

Gly Ser Thr Ser Gly Ser Gly Lys Pro Gly Ser Gly Glu Gly Ser
1               5                   10                  15

<210> SEQ ID NO 94
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 94

Gly Gly Gly Gly Ser
1               5

<210> SEQ ID NO 95
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 95
```

```
Ala His His Ser Glu Asp Pro Ser Ser Lys Ala Pro Lys Ala Pro
1               5                   10                  15

<210> SEQ ID NO 96
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 96

Gly Ser Thr Ser Gly Ser Gly Lys Pro Gly Ser Gly Glu Gly Ser Thr
1               5                   10                  15

Lys Gly

<210> SEQ ID NO 97
<211> LENGTH: 500
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 97

Ala Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
                20                  25                  30

Ser Gly Gly Thr Ser Leu Leu Met Ile Asp Ser Gly Ile Gly Asp Asn
        35                  40                  45

Leu Phe Ala Val Asp Ile Leu Gly Phe Asp Phe Thr Leu Gly Arg Phe
    50                  55                  60

Asn Asn Leu Arg Leu Ile Val Glu Arg Asn Asn Leu Tyr Val Thr Gly
65                  70                  75                  80

Phe Val Asn Arg Thr Asn Asn Val Phe Tyr Arg Phe Ala Asp Phe Ser
                85                  90                  95

His Val Thr Phe Pro Gly Thr Thr Ala Val Thr Leu Ser Ala Asp Ser
                100                 105                 110

Ser Tyr Thr Thr Leu Gln Arg Val Ala Gly Ile Ser Arg Thr Gly Met
            115                 120                 125

Gln Ile Asn Arg His Ser Leu Thr Thr Ser Tyr Leu Asp Leu Met Ser
        130                 135                 140

His Ser Ala Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Arg Thr Thr Leu Asp Asp Leu Ser Gly Arg Ser Tyr Val Met
            180                 185                 190

Thr Ala Glu Asp Val Asp Leu Thr Leu Asn Trp Gly Arg Leu Ser Ser
        195                 200                 205

Val Leu Pro Asp Tyr His Gly Gln Asp Ser Val Arg Val Gly Arg Ile
    210                 215                 220

Ser Phe Gly Ser Ile Asn Ala Ile Leu Gly Ser Val Ala Leu Ile Leu
225                 230                 235                 240

Asn Ser His His His Ala Ser Ala Val Ala Ala Glu Phe Pro Lys Pro
```

```
                    245                 250                 255
Ser Thr Pro Pro Gly Ser Ser Gly Gly Ala Pro Asp Ile Gln Met Thr
            260                 265                 270

Gln Ser Pro Ser Ser Leu Ser Ala Ser Val Gly Asp Arg Val Thr Ile
        275                 280                 285

Thr Cys Arg Ala Ser Gln Asp Val Asn Thr Ala Val Ala Trp Tyr Gln
    290                 295                 300

Gln Lys Pro Gly Lys Ala Pro Lys Leu Leu Ile Tyr Ser Ala Ser Phe
305                 310                 315                 320

Leu Tyr Ser Gly Val Pro Ser Arg Phe Ser Gly Ser Arg Ser Gly Thr
                325                 330                 335

Asp Phe Thr Leu Thr Ile Ser Ser Leu Gln Pro Glu Asp Phe Ala Thr
            340                 345                 350

Tyr Tyr Cys Gln Gln His Tyr Thr Thr Pro Pro Thr Phe Gly Gln Gly
        355                 360                 365

Thr Lys Val Glu Ile Lys Gly Gly Gly Ser Glu Val Gln Leu Val
    370                 375                 380

Glu Ser Gly Gly Gly Leu Val Gln Pro Gly Gly Ser Leu Arg Leu Ser
385                 390                 395                 400

Cys Ala Ala Ser Gly Phe Asn Ile Lys Asp Thr Tyr Ile His Trp Val
                405                 410                 415

Arg Gln Ala Pro Gly Lys Gly Leu Glu Trp Val Ala Arg Ile Tyr Pro
            420                 425                 430

Thr Asn Gly Tyr Thr Arg Tyr Ala Asp Ser Val Lys Gly Arg Phe Thr
        435                 440                 445

Ile Ser Ala Asp Thr Ser Lys Asn Thr Ala Tyr Leu Gln Met Asn Ser
    450                 455                 460

Leu Arg Ala Glu Asp Thr Ala Val Tyr Tyr Cys Ser Arg Trp Gly Gly
465                 470                 475                 480

Asp Gly Phe Tyr Ala Met Asp Tyr Trp Gly Gln Gly Thr Leu Val Thr
                485                 490                 495

Val Ser Ser Ala
            500

<210> SEQ ID NO 98
<211> LENGTH: 512
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 98

Ala Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
            20                  25                  30

Ser Gly Gly Thr Ser Leu Leu Met Ile Asp Ser Gly Ile Gly Asp Asn
        35                  40                  45

Leu Phe Ala Val Asp Ile Leu Gly Phe Asp Phe Thr Leu Gly Arg Phe
    50                  55                  60

Asn Asn Leu Arg Leu Ile Val Glu Arg Asn Asn Leu Tyr Val Thr Gly
65                  70                  75                  80

Phe Val Asn Arg Thr Asn Asn Val Phe Tyr Arg Phe Ala Asp Phe Ser
                85                  90                  95
```

-continued

His Val Thr Phe Pro Gly Thr Ala Val Thr Leu Ser Ala Asp Ser
              100                 105                 110

Ser Tyr Thr Thr Leu Gln Arg Val Ala Gly Ile Ser Arg Thr Gly Met
              115                 120                 125

Gln Ile Asn Arg His Ser Leu Thr Thr Ser Tyr Leu Asp Leu Met Ser
    130                 135                 140

His Ser Ala Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Arg Thr Thr Leu Asp Asp Leu Ser Gly Arg Ser Tyr Val Met
            180                 185                 190

Thr Ala Glu Asp Val Asp Leu Thr Leu Asn Trp Gly Arg Leu Ser Ser
        195                 200                 205

Val Leu Pro Asp Tyr His Gly Gln Asp Ser Val Arg Val Gly Arg Ile
    210                 215                 220

Ser Phe Gly Ser Ile Asn Ala Ile Leu Gly Ser Val Ala Leu Ile Leu
225                 230                 235                 240

Asn Ser His His His Ala Ser Ala Val Ala Ala Glu Phe Pro Lys Pro
                245                 250                 255

Ser Thr Pro Pro Gly Ser Ser Gly Ala Pro Gln Val Gln Leu Leu
            260                 265                 270

Gln Ser Gly Ala Glu Leu Lys Lys Pro Gly Glu Ser Leu Lys Ile Ser
    275                 280                 285

Cys Lys Gly Ser Gly Tyr Ser Phe Thr Ser Tyr Trp Ile Ala Trp Val
    290                 295                 300

Arg Gln Met Pro Gly Lys Gly Leu Glu Tyr Met Gly Leu Ile Tyr Pro
305                 310                 315                 320

Gly Asp Ser Asp Thr Lys Tyr Ser Pro Ser Phe Gln Gly Gln Val Thr
                325                 330                 335

Ile Ser Val Asp Lys Ser Val Ser Thr Ala Tyr Leu Gln Trp Ser Ser
            340                 345                 350

Leu Lys Pro Ser Asp Ser Ala Val Tyr Phe Cys Ala Arg His Asp Val
        355                 360                 365

Gly Tyr Cys Ser Ser Ser Asn Cys Ala Lys Trp Pro Glu Tyr Phe Gln
    370                 375                 380

His Trp Gly Gln Gly Thr Leu Val Thr Val Ser Ser Gly Gly Gly Gly
385                 390                 395                 400

Ser Gln Ser Val Leu Thr Gln Pro Pro Ser Val Ser Ala Ala Pro Gly
                405                 410                 415

Gln Lys Val Thr Ile Ser Cys Ser Gly Ser Ser Ser Asn Ile Gly Asn
            420                 425                 430

Asn Tyr Val Ser Trp Tyr Gln Gln Leu Pro Gly Thr Ala Pro Lys Leu
        435                 440                 445

Leu Ile Tyr Gly His Thr Asn Arg Pro Ala Gly Val Pro Asp Arg Phe
    450                 455                 460

Ser Gly Ser Lys Ser Gly Thr Ser Ala Ser Leu Ala Ile Ser Gly Phe
465                 470                 475                 480

Arg Ser Glu Asp Glu Ala Asp Tyr Tyr Cys Ala Ala Trp Asp Asp Ser
                485                 490                 495

Leu Ser Gly Trp Val Phe Gly Gly Gly Thr Lys Leu Thr Val Leu Ala
            500                 505                 510

<210> SEQ ID NO 99
<211> LENGTH: 498
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 99

```
Ala Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
            20                  25                  30

Ser Gly Gly Thr Ser Leu Leu Met Ile Asp Ser Gly Ile Gly Asp Asn
        35                  40                  45

Leu Phe Ala Val Asp Ile Leu Gly Phe Asp Phe Thr Leu Gly Arg Phe
    50                  55                  60

Asn Asn Leu Arg Leu Ile Val Glu Arg Asn Asn Leu Tyr Val Thr Gly
65                  70                  75                  80

Phe Val Asn Arg Thr Asn Asn Val Phe Tyr Arg Phe Ala Asp Phe Ser
                85                  90                  95

His Val Thr Phe Pro Gly Thr Thr Ala Val Thr Leu Ser Ala Asp Ser
            100                 105                 110

Ser Tyr Thr Thr Leu Gln Arg Val Ala Gly Ile Ser Arg Thr Gly Met
        115                 120                 125

Gln Ile Asn Arg His Ser Leu Thr Thr Ser Tyr Leu Asp Leu Met Ser
    130                 135                 140

His Ser Ala Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Arg Thr Thr Leu Asp Asp Leu Ser Gly Arg Ser Tyr Val Met
            180                 185                 190

Thr Ala Glu Asp Val Asp Leu Thr Leu Asn Trp Gly Arg Leu Ser Ser
        195                 200                 205

Val Leu Pro Asp Tyr His Gly Gln Asp Ser Val Arg Val Gly Arg Ile
    210                 215                 220

Ser Phe Gly Ser Ile Asn Ala Ile Leu Gly Ser Val Ala Leu Ile Leu
225                 230                 235                 240

Asn Ser His His His Ala Ser Ala Val Ala Ala Glu Phe Pro Lys Pro
                245                 250                 255

Ser Thr Pro Pro Gly Ser Ser Gly Ala Pro Gln Val Gln Leu Gln
            260                 265                 270

Gln Ser Gly Pro Glu Leu Lys Lys Pro Gly Glu Thr Val Lys Ile Ser
        275                 280                 285

Cys Lys Ala Ser Gly Tyr Pro Phe Thr Asn Tyr Gly Met Asn Trp Val
    290                 295                 300

Lys Gln Ala Pro Gly Gln Gly Leu Lys Trp Met Gly Trp Ile Asn Thr
305                 310                 315                 320

Ser Thr Gly Glu Ser Thr Phe Ala Asp Asp Phe Lys Gly Arg Phe Asp
                325                 330                 335

Phe Ser Leu Glu Thr Ser Ala Asn Thr Ala Tyr Leu Gln Ile Asn Asn
            340                 345                 350

Leu Lys Ser Glu Asp Ser Ala Thr Tyr Phe Cys Ala Arg Trp Glu Val
```

```
                    355                 360                 365
Tyr His Gly Tyr Val Pro Tyr Trp Gly Gln Gly Thr Thr Val Thr Val
    370                 375                 380

Ser Ser Gly Gly Gly Ser Asp Ile Gln Leu Thr Gln Ser His Lys
385                 390                 395                 400

Phe Leu Ser Thr Ser Val Gly Asp Arg Val Ser Ile Thr Cys Lys Ala
                405                 410                 415

Ser Gln Asp Val Tyr Asn Ala Val Ala Trp Tyr Gln Lys Pro Gly
            420                 425                 430

Gln Ser Pro Lys Leu Leu Ile Tyr Ser Ala Ser Arg Tyr Thr Gly
                435                 440                 445

Val Pro Ser Arg Phe Thr Gly Ser Gly Ser Gly Pro Asp Phe Thr Phe
        450                 455                 460

Thr Ile Ser Ser Val Gln Ala Glu Asp Leu Ala Val Tyr Phe Cys Gln
465                 470                 475                 480

Gln His Phe Arg Thr Pro Phe Thr Phe Gly Ser Gly Thr Lys Leu Glu
                485                 490                 495

Ile Lys

<210> SEQ ID NO 100
<211> LENGTH: 499
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 100

Ala Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
            20                  25                  30

Ser Gly Gly Thr Ser Leu Leu Met Ile Asp Ser Gly Ile Gly Asp Asn
        35                  40                  45

Leu Phe Ala Val Asp Ile Leu Gly Phe Asp Phe Thr Leu Gly Arg Phe
    50                  55                  60

Asn Asn Leu Arg Leu Ile Val Glu Arg Asn Asn Leu Tyr Val Thr Gly
65                  70                  75                  80

Phe Val Asn Arg Thr Asn Asn Val Phe Tyr Arg Phe Ala Asp Phe Ser
                85                  90                  95

His Val Thr Phe Pro Gly Thr Thr Ala Val Thr Leu Ser Ala Asp Ser
            100                 105                 110

Ser Tyr Thr Thr Leu Gln Arg Val Ala Gly Ile Ser Arg Thr Gly Met
        115                 120                 125

Gln Ile Asn Arg His Ser Leu Thr Thr Ser Tyr Leu Asp Leu Met Ser
130                 135                 140

His Ser Ala Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Arg Thr Thr Leu Asp Asp Leu Ser Gly Arg Ser Tyr Val Met
            180                 185                 190

Thr Ala Glu Asp Val Asp Leu Thr Leu Asn Trp Gly Arg Leu Ser Ser
        195                 200                 205
```

Val Leu Pro Asp Tyr His Gly Gln Asp Ser Val Arg Val Gly Arg Ile
    210                 215                 220

Ser Phe Gly Ser Ile Asn Ala Ile Leu Gly Ser Val Ala Leu Ile Leu
225                 230                 235                 240

Asn Ser His His His Ala Ser Ala Val Ala Ala Glu Phe Pro Lys Pro
                245                 250                 255

Ser Thr Pro Pro Gly Ser Ser Gly Ala Pro Asp Ile Gln Met Thr
            260                 265                 270

Gln Ser Pro Ser Ser Leu Ser Ala Ser Val Gly Asp Arg Val Thr Ile
            275                 280                 285

Thr Cys Lys Ala Ser Gln Asp Val Ser Ile Gly Val Ala Trp Tyr Gln
    290                 295                 300

Gln Lys Pro Gly Lys Ala Pro Lys Leu Leu Ile Tyr Ser Ala Ser Tyr
305                 310                 315                 320

Arg Tyr Thr Gly Val Pro Ser Arg Phe Ser Gly Ser Gly Ser Gly Thr
                325                 330                 335

Asp Phe Thr Leu Thr Ile Ser Ser Leu Gln Pro Glu Asp Phe Ala Thr
            340                 345                 350

Tyr Tyr Cys Gln Gln Tyr Tyr Ile Tyr Pro Tyr Thr Phe Gly Gln Gly
        355                 360                 365

Thr Lys Val Glu Ile Lys Gly Gly Gly Ser Glu Val Gln Leu Val
370                 375                 380

Glu Ser Gly Gly Gly Leu Val Gln Pro Gly Gly Ser Leu Arg Leu Ser
385                 390                 395                 400

Cys Ala Ala Ser Gly Phe Thr Phe Thr Asp Tyr Thr Met Asp Trp Val
                405                 410                 415

Arg Gln Ala Pro Gly Lys Gly Leu Glu Trp Val Ala Asp Val Asn Pro
            420                 425                 430

Asn Ser Gly Gly Ser Ile Tyr Asn Gln Arg Phe Lys Gly Arg Phe Thr
        435                 440                 445

Leu Ser Val Asp Arg Ser Lys Asn Thr Leu Tyr Leu Gln Met Asn Ser
    450                 455                 460

Leu Arg Ala Glu Asp Thr Ala Val Tyr Tyr Cys Ala Arg Asn Leu Gly
465                 470                 475                 480

Pro Ser Phe Tyr Phe Asp Tyr Trp Gly Gln Gly Thr Leu Val Thr Val
                485                 490                 495

Ser Ser Ala

<210> SEQ ID NO 101
<211> LENGTH: 519
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 101

Lys Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
            20                  25                  30

Ser Gly Gly Thr Ser Leu Leu Met Ile Asp Ser Gly Ile Gly Asp Asn
        35                  40                  45

Leu Phe Ala Val Asp Ile Leu Gly Phe Asp Phe Thr Leu Gly Arg Phe
    50                  55                  60

```
Asn Asn Leu Arg Leu Ile Val Glu Arg Asn Asn Leu Tyr Val Thr Gly
 65                  70                  75                  80

Phe Val Asn Arg Thr Asn Asn Val Phe Tyr Arg Phe Ala Asp Phe Ser
                 85                  90                  95

His Val Thr Phe Pro Gly Thr Thr Ala Val Thr Leu Ser Ala Asp Ser
                100                 105                 110

Ser Tyr Thr Thr Leu Gln Arg Val Ala Gly Ile Ser Arg Thr Gly Met
                115                 120                 125

Gln Ile Asn Arg His Ser Leu Thr Thr Ser Tyr Leu Asp Leu Met Ser
130                 135                 140

His Ser Gly Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Arg Thr Thr Leu Asp Asp Leu Ser Gly Ala Ser Tyr Val Met
                180                 185                 190

Thr Ala Glu Asp Val Asp Leu Thr Leu Asn Trp Gly Arg Leu Ser Ser
                195                 200                 205

Val Leu Pro Asp Tyr His Gly Gln Asp Ser Val Arg Val Gly Arg Ile
210                 215                 220

Ser Phe Gly Ser Ile Asn Ala Ile Leu Gly Ser Val Ala Leu Ile Leu
225                 230                 235                 240

Asn Ser His His His Ala Ser Ala Val Ala Ala Glu Phe Pro Lys Pro
                245                 250                 255

Ser Thr Pro Pro Gly Ser Ser Gly Gly Ala Pro Asp Ile Gln Met Thr
                260                 265                 270

Gln Ser Pro Ser Ser Leu Ser Ala Ser Val Gly Asp Arg Val Thr Ile
                275                 280                 285

Thr Cys Arg Ala Ser Gln Asp Val Asn Thr Ala Val Ala Trp Tyr Gln
                290                 295                 300

Gln Lys Pro Gly Lys Ala Pro Lys Leu Leu Ile Tyr Ser Ala Ser Phe
305                 310                 315                 320

Leu Tyr Ser Gly Val Pro Ser Arg Phe Ser Gly Ser Arg Ser Gly Thr
                325                 330                 335

Asp Phe Thr Leu Thr Ile Ser Ser Leu Gln Pro Glu Asp Phe Ala Thr
                340                 345                 350

Tyr Tyr Cys Gln Gln His Tyr Thr Thr Pro Pro Thr Phe Gly Gln Gly
                355                 360                 365

Thr Lys Val Glu Ile Lys Gly Gly Gly Gly Ser Gly Gly Gly Gly Ser
                370                 375                 380

Gly Gly Gly Gly Ser Gly Gly Gly Gly Ser Gly Gly Gly Gly Ser Glu
385                 390                 395                 400

Val Gln Leu Val Glu Ser Gly Gly Gly Leu Val Gln Pro Gly Gly Ser
                405                 410                 415

Leu Arg Leu Ser Cys Ala Ala Ser Gly Phe Asn Ile Lys Asp Thr Tyr
                420                 425                 430

Ile His Trp Val Arg Gln Ala Pro Gly Lys Gly Leu Glu Trp Val Ala
                435                 440                 445

Arg Ile Tyr Pro Thr Asn Gly Tyr Thr Arg Tyr Ala Asp Ser Val Lys
                450                 455                 460

Gly Arg Phe Thr Ile Ser Ala Asp Thr Ser Lys Asn Thr Ala Tyr Leu
465                 470                 475                 480
```

```
Gln Met Asn Ser Leu Arg Ala Glu Asp Thr Ala Val Tyr Tyr Cys Ser
                485                 490                 495

Arg Trp Gly Gly Asp Gly Phe Tyr Ala Met Asp Tyr Trp Gly Gln Gly
            500                 505                 510

Thr Leu Val Thr Val Ser Ser
        515

<210> SEQ ID NO 102
<211> LENGTH: 518
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 102

Lys Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
            20                  25                  30

Ser Gly Gly Thr Ser Leu Leu Met Ile Asp Ser Gly Ile Gly Asp Asn
        35                  40                  45

Leu Phe Ala Val Asp Ile Leu Gly Phe Asp Phe Thr Leu Gly Arg Phe
    50                  55                  60

Asn Asn Leu Arg Leu Ile Val Glu Arg Asn Asn Leu Tyr Val Thr Gly
65                  70                  75                  80

Phe Val Asn Arg Thr Asn Asn Val Phe Tyr Arg Phe Ala Asp Phe Ser
                85                  90                  95

His Val Thr Phe Pro Gly Thr Thr Ala Val Thr Leu Ser Ala Asp Ser
            100                 105                 110

Ser Tyr Thr Thr Leu Gln Arg Val Ala Gly Ile Ser Arg Thr Gly Met
        115                 120                 125

Gln Ile Asn Arg His Ser Leu Thr Thr Ser Tyr Leu Asp Leu Met Ser
    130                 135                 140

His Ser Gly Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Arg Thr Thr Leu Asp Asp Leu Ser Gly Ala Ser Tyr Val Met
            180                 185                 190

Thr Ala Glu Asp Val Asp Leu Thr Leu Asn Trp Gly Arg Leu Ser Ser
        195                 200                 205

Val Leu Pro Asp Tyr His Gly Gln Asp Ser Val Arg Val Gly Arg Ile
    210                 215                 220

Ser Phe Gly Ser Ile Asn Ala Ile Leu Gly Ser Val Ala Leu Ile Leu
225                 230                 235                 240

Asn Ser His His His Ala Ser Ala Val Ala Ala Glu Phe Pro Lys Pro
                245                 250                 255

Ser Thr Pro Pro Gly Ser Ser Gly Ala Pro Gln Val Gln Leu Gln
            260                 265                 270

Gln Ser Gly Pro Glu Leu Lys Lys Pro Gly Glu Thr Val Lys Ile Ser
        275                 280                 285

Cys Lys Ala Ser Gly Tyr Pro Phe Thr Asn Tyr Gly Met Asn Trp Val
    290                 295                 300

Lys Gln Ala Pro Gly Gln Gly Leu Lys Trp Met Gly Trp Ile Asn Thr
```

```
                305                 310                 315                 320
Ser Thr Gly Glu Ser Thr Phe Ala Asp Asp Phe Lys Gly Arg Phe Asp
                325                 330                 335

Phe Ser Leu Glu Thr Ser Ala Asn Thr Ala Tyr Leu Gln Ile Asn Asn
                340                 345                 350

Leu Lys Ser Glu Asp Ser Ala Thr Tyr Phe Cys Ala Arg Trp Glu Val
                355                 360                 365

Tyr His Gly Tyr Val Pro Tyr Trp Gly Gln Gly Thr Thr Val Thr Val
                370                 375                 380

Ser Ser Gly Gly Gly Gly Ser Gly Gly Gly Gly Ser Gly Gly Gly Gly
385                 390                 395                 400

Ser Gly Gly Gly Gly Ser Gly Gly Gly Gly Ser Asp Ile Gln Met Thr
                405                 410                 415

Gln Ser Pro Ser Ser Leu Ser Ala Ser Val Gly Asp Arg Val Thr Ile
                420                 425                 430

Thr Cys Lys Ala Ser Gln Asp Val Tyr Asn Ala Val Ala Trp Tyr Gln
                435                 440                 445

Gln Lys Pro Gly Gln Ser Pro Lys Leu Leu Ile Tyr Ser Ala Ser Ser
                450                 455                 460

Arg Tyr Thr Gly Val Pro Ser Arg Phe Thr Gly Ser Gly Ser Gly Pro
465                 470                 475                 480

Asp Phe Thr Phe Thr Ile Ser Ser Val Gln Ala Glu Asp Leu Ala Val
                485                 490                 495

Tyr Phe Cys Gln Gln His Phe Arg Thr Pro Phe Thr Phe Gly Ser Gly
                500                 505                 510

Thr Lys Leu Glu Ile Lys
                515

<210> SEQ ID NO 103
<211> LENGTH: 518
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 103

Arg Glu Phe Thr Leu Asp Phe Ser Thr Ala Arg Thr Tyr Val Asp Ser
1               5                   10                  15

Leu Asn Val Ile Arg Ser Ala Ile Gly Thr Pro Leu Gln Thr Ile Ser
                20                  25                  30

Ser Gly Gly Thr Ser Leu Leu Met Ile Asp Ser Gly Ile Gly Asp Asn
                35                  40                  45

Leu Phe Ala Val Asp Ile Leu Gly Phe Asp Phe Thr Leu Gly Arg Phe
            50                  55                  60

Asn Asn Leu Arg Leu Ile Val Glu Arg Asn Asn Leu Tyr Val Thr Gly
65                  70                  75                  80

Phe Val Asn Arg Thr Asn Asn Val Phe Tyr Arg Phe Ala Asp Phe Ser
                85                  90                  95

His Val Thr Phe Pro Gly Thr Thr Ala Val Thr Leu Ser Ala Asp Ser
                100                 105                 110

Ser Tyr Thr Thr Leu Gln Arg Val Ala Gly Ile Ser Arg Thr Gly Met
            115                 120                 125

Gln Ile Asn Arg His Ser Leu Thr Thr Ser Tyr Leu Ala Leu Met Ser
            130                 135                 140
```

```
His Ser Gly Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Arg Thr Thr Leu Asp Asp Leu Ser Gly Ala Ser Tyr Val Met
            180                 185                 190

Thr Ala Glu Asp Val Asp Leu Thr Leu Asn Trp Gly Arg Leu Ser Ser
        195                 200                 205

Val Leu Pro Asp Tyr His Gly Gln Asp Ser Val Arg Val Gly Arg Ile
    210                 215                 220

Ser Phe Gly Ser Ile Asn Ala Ile Leu Gly Ser Val Ala Leu Ile Leu
225                 230                 235                 240

Asn Ser His His His Ala Ser Ala Val Ala Ala Ser Pro Ser Thr Pro
                245                 250                 255

Pro Thr Pro Ser Pro Ser Thr Pro Pro Ala Ser Gln Val Gln Leu Val
            260                 265                 270

Gln Ser Gly Pro Glu Val Lys Lys Pro Gly Ala Ser Val Lys Val Ser
        275                 280                 285

Cys Lys Ala Ser Gly Tyr Pro Phe Thr Asn Tyr Gly Met Asn Trp Val
290                 295                 300

Arg Gln Ala Pro Gly Gln Gly Leu Glu Trp Met Gly Trp Ile Asn Thr
305                 310                 315                 320

Ser Thr Gly Glu Ser Thr Phe Ala Asp Asp Phe Lys Gly Arg Val Thr
                325                 330                 335

Met Thr Thr Asp Thr Ser Thr Ser Thr Tyr Met Glu Leu Arg Ser
            340                 345                 350

Leu Arg Pro Asp Asp Thr Ala Val Tyr Phe Cys Ala Arg Trp Glu Val
        355                 360                 365

Tyr His Gly Tyr Val Pro Tyr Trp Gly Gln Gly Thr Leu Val Thr Val
    370                 375                 380

Ser Ser Gly Gly Gly Gly Ser Gly Gly Gly Gly Ser Gly Gly Gly Gly
385                 390                 395                 400

Ser Gly Gly Gly Gly Ser Gly Gly Gly Gly Ser Asp Ile Gln Met Thr
                405                 410                 415

Gln Ser Pro Ser Ser Leu Ser Ala Ser Ile Gly Asp Arg Val Thr Ile
            420                 425                 430

Thr Cys Lys Ala Ser Gln Asp Val Tyr Asn Ala Val Ala Trp Tyr Gln
        435                 440                 445

Gln Lys Pro Gly Glu Ala Pro Lys Leu Leu Val Tyr Ser Ala Ser Ser
    450                 455                 460

Arg Tyr Thr Gly Val Pro Ser Arg Phe Ser Gly Ser Gly Ser Gly Thr
465                 470                 475                 480

Asp Phe Thr Phe Thr Ile Ser Ser Leu Gln Pro Glu Asp Ile Ala Thr
                485                 490                 495

Tyr Phe Cys Gln Gln His Phe Arg Thr Pro Phe Thr Phe Ala Pro Gly
            500                 505                 510

Thr Lys Leu Glu Ile Lys
        515

<210> SEQ ID NO 104
<211> LENGTH: 385
<212> TYPE: PRT
<213> ORGANISM: Artificial Sequence
<220> FEATURE:
```

```
<221> NAME/KEY: source
<223> OTHER INFORMATION: /note="Description of Artificial Sequence:
      Synthetic polypeptide"

<400> SEQUENCE: 104
```

Lys Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
            20                  25                  30

Ser Gly Gly Thr Ser Leu Leu Met Ile Asp Ser Gly Ile Gly Asp Asn
        35                  40                  45

Leu Phe Ala Val Asp Ile Leu Gly Phe Asp Phe Thr Leu Gly Arg Phe
    50                  55                  60

Asn Asn Leu Arg Leu Ile Val Glu Arg Asn Asn Leu Tyr Val Thr Gly
65                  70                  75                  80

Phe Val Asn Arg Thr Asn Asn Val Phe Tyr Arg Phe Ala Asp Phe Ser
                85                  90                  95

His Val Thr Phe Pro Gly Thr Thr Ala Val Thr Leu Ser Ala Asp Ser
            100                 105                 110

Ser Tyr Thr Thr Leu Gln Arg Val Ala Gly Ile Ser Arg Thr Gly Met
        115                 120                 125

Gln Ile Asn Arg His Ser Leu Thr Thr Ser Tyr Leu Asp Leu Met Ser
130                 135                 140

His Ser Gly Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Arg Thr Thr Leu Asp Asp Leu Ser Gly Ala Ser Tyr Val Met
            180                 185                 190

Thr Ala Glu Asp Val Asp Leu Thr Leu Asn Trp Gly Arg Leu Ser Ser
        195                 200                 205

Val Leu Pro Asp Tyr His Gly Gln Asp Ser Val Arg Val Gly Arg Ile
    210                 215                 220

Ser Phe Gly Ser Ile Asn Ala Ile Leu Gly Ser Val Ala Leu Ile Leu
225                 230                 235                 240

Asn Ser His His His Ala Ser Ala Val Ala Ala His His Ser Glu
                245                 250                 255

Asp Pro Ser Ser Lys Ala Pro Lys Ala Pro Glu Val Gln Leu Val Glu
            260                 265                 270

Ser Gly Gly Gly Leu Val Gln Ala Gly Gly Ser Leu Arg Leu Ser Cys
        275                 280                 285

Ala Ala Ser Gly Ile Thr Phe Ser Ile Asn Thr Met Gly Trp Tyr Arg
    290                 295                 300

Gln Ala Pro Gly Lys Gln Arg Glu Leu Val Ala Leu Ile Ser Ser Ile
305                 310                 315                 320

Gly Asp Thr Tyr Tyr Ala Asp Ser Val Lys Gly Arg Phe Thr Ile Ser
                325                 330                 335

Arg Asp Asn Ala Lys Asn Thr Val Tyr Leu Gln Met Asn Ser Leu Lys
            340                 345                 350

Pro Glu Asp Thr Ala Val Tyr Tyr Cys Lys Arg Phe Arg Thr Ala Ala
        355                 360                 365

Gln Gly Thr Asp Tyr Trp Gly Gln Gly Thr Gln Val Thr Val Ser Ser
    370                 375                 380

Ala

<210> SEQ ID NO 105
<211> LENGTH: 498
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 105

| | | | | | | | | | | | | | | |
|---|---|---|---|---|---|---|---|---|---|---|---|---|---|---|
| Lys | Glu | Phe | Thr | Leu | Asp | Phe | Ser | Thr | Ala | Lys | Thr | Tyr | Val | Asp | Ser |
| 1 | | | | 5 | | | | | 10 | | | | | 15 | |
| Leu | Asn | Val | Ile | Arg | Ser | Ala | Ile | Gly | Thr | Pro | Leu | Gln | Thr | Ile | Ser |
| | | | 20 | | | | | 25 | | | | | 30 | | |
| Ser | Gly | Gly | Thr | Ser | Leu | Leu | Met | Ile | Asp | Ser | Gly | Ile | Gly | Asp | Asn |
| | | 35 | | | | | 40 | | | | | 45 | | | |
| Leu | Phe | Ala | Val | Asp | Ile | Leu | Gly | Phe | Asp | Phe | Thr | Leu | Gly | Arg | Phe |
| 50 | | | | | 55 | | | | | 60 | | | | | |
| Asn | Asn | Leu | Arg | Leu | Ile | Val | Glu | Arg | Asn | Asn | Leu | Tyr | Val | Thr | Gly |
| 65 | | | | | 70 | | | | | 75 | | | | | 80 |
| Phe | Val | Asn | Arg | Thr | Asn | Asn | Val | Phe | Tyr | Arg | Phe | Ala | Asp | Phe | Ser |
| | | | | 85 | | | | | 90 | | | | | 95 | |
| His | Val | Thr | Phe | Pro | Gly | Thr | Thr | Ala | Val | Thr | Leu | Ser | Ala | Asp | Ser |
| | | | | 100 | | | | | 105 | | | | | 110 | |
| Ser | Tyr | Thr | Thr | Leu | Gln | Arg | Val | Ala | Gly | Ile | Ser | Arg | Thr | Gly | Met |
| | | | 115 | | | | | 120 | | | | | 125 | | |
| Gln | Ile | Asn | Arg | His | Ser | Leu | Thr | Thr | Ser | Tyr | Leu | Asp | Leu | Met | Ser |
| | 130 | | | | | 135 | | | | | 140 | | | | |
| His | Ser | Gly | Thr | Ser | Leu | Thr | Gln | Ser | Val | Ala | Arg | Ala | Met | Leu | Arg |
| 145 | | | | | 150 | | | | | 155 | | | | | 160 |
| Phe | Val | Thr | Val | Thr | Ala | Glu | Ala | Leu | Arg | Phe | Arg | Gln | Ile | Gln | Arg |
| | | | | 165 | | | | | 170 | | | | | 175 | |
| Gly | Phe | Arg | Thr | Thr | Leu | Asp | Asp | Leu | Ser | Gly | Ala | Ser | Tyr | Val | Met |
| | | | 180 | | | | | 185 | | | | | 190 | | |
| Thr | Ala | Glu | Asp | Val | Asp | Leu | Thr | Leu | Asn | Trp | Gly | Arg | Leu | Ser | Ser |
| | | | 195 | | | | | 200 | | | | | 205 | | |
| Val | Leu | Pro | Asp | Tyr | His | Gly | Gln | Asp | Ser | Val | Arg | Val | Gly | Arg | Ile |
| 210 | | | | | 215 | | | | | 220 | | | | | |
| Ser | Phe | Gly | Ser | Ile | Asn | Ala | Ile | Leu | Gly | Ser | Val | Ala | Leu | Ile | Leu |
| 225 | | | | | 230 | | | | | 235 | | | | | 240 |
| Asn | Ser | His | His | His | Ala | Ser | Ala | Val | Ala | Ala | Glu | Phe | Pro | Lys | Pro |
| | | | | 245 | | | | | 250 | | | | | 255 | |
| Ser | Thr | Pro | Pro | Gly | Ser | Ser | Gly | Gly | Ala | Pro | Gln | Val | Gln | Leu | Gln |
| | | | 260 | | | | | 265 | | | | | 270 | | |
| Gln | Ser | Gly | Pro | Glu | Leu | Lys | Lys | Pro | Gly | Glu | Thr | Val | Lys | Ile | Ser |
| | | 275 | | | | | 280 | | | | | 285 | | | |
| Cys | Lys | Ala | Ser | Gly | Tyr | Pro | Phe | Thr | Asn | Tyr | Gly | Met | Asn | Trp | Val |
| 290 | | | | | 295 | | | | | 300 | | | | | |
| Lys | Gln | Ala | Pro | Gly | Gln | Gly | Leu | Lys | Trp | Met | Gly | Trp | Ile | Asn | Thr |
| 305 | | | | | 310 | | | | | 315 | | | | | 320 |
| Ser | Thr | Gly | Glu | Ser | Thr | Phe | Ala | Asp | Asp | Phe | Lys | Gly | Arg | Phe | Asp |
| | | | | 325 | | | | | 330 | | | | | 335 | |
| Phe | Ser | Leu | Glu | Thr | Ser | Ala | Asn | Thr | Ala | Tyr | Leu | Gln | Ile | Asn | Asn |
| | | | 340 | | | | | 345 | | | | | 350 | | |

```
Leu Lys Ser Glu Asp Ser Ala Thr Tyr Phe Cys Ala Arg Trp Glu Val
        355                 360                 365

Tyr His Gly Tyr Val Pro Tyr Trp Gly Gln Gly Thr Thr Val Thr Val
    370                 375                 380

Ser Ser Gly Gly Gly Gly Ser Asp Ile Gln Met Thr Gln Ser Pro Ser
385                 390                 395                 400

Ser Leu Ser Ala Ser Val Gly Asp Arg Val Thr Ile Thr Cys Lys Ala
                405                 410                 415

Ser Gln Asp Val Tyr Asn Ala Val Ala Trp Tyr Gln Lys Pro Gly
            420                 425                 430

Gln Ser Pro Lys Leu Leu Ile Tyr Ser Ala Ser Ser Arg Tyr Thr Gly
        435                 440                 445

Val Pro Ser Arg Phe Thr Gly Ser Gly Ser Gly Pro Asp Phe Thr Phe
    450                 455                 460

Thr Ile Ser Ser Val Gln Ala Glu Asp Leu Ala Val Tyr Phe Cys Gln
465                 470                 475                 480

Gln His Phe Arg Thr Pro Phe Thr Phe Gly Ser Gly Thr Lys Leu Glu
                485                 490                 495

Ile Lys

<210> SEQ ID NO 106
<211> LENGTH: 370
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 106

Lys Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
            20                  25                  30

Ser Gly Gly Thr Ser Leu Leu Met Ile Asp Ser Gly Ile Gly Asp Asn
        35                  40                  45

Leu Phe Ala Val Asp Ile Leu Gly Phe Asp Phe Thr Leu Gly Arg Phe
    50                  55                  60

Asn Asn Leu Arg Leu Ile Val Glu Arg Asn Asn Leu Tyr Val Thr Gly
65                  70                  75                  80

Phe Val Asn Arg Thr Asn Asn Val Phe Tyr Arg Phe Ala Asp Phe Ser
                85                  90                  95

His Val Thr Phe Pro Gly Thr Thr Ala Val Thr Leu Ser Ala Asp Ser
                100                 105                 110

Ser Tyr Thr Thr Leu Gln Arg Val Ala Gly Ile Ser Arg Thr Gly Met
            115                 120                 125

Gln Ile Asn Arg His Ser Leu Thr Thr Ser Tyr Leu Asp Leu Met Ser
        130                 135                 140

His Ser Gly Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Arg Thr Thr Leu Asp Asp Leu Ser Gly Ala Ser Tyr Val Met
                180                 185                 190

Thr Ala Glu Asp Val Asp Leu Thr Leu Asn Trp Gly Arg Leu Ser Ser
```

```
                195                 200                 205
Val Leu Pro Asp Tyr His Gly Gln Asp Ser Val Arg Val Gly Arg Ile
210                 215                 220

Ser Phe Gly Ser Ile Asn Ala Ile Leu Gly Ser Val Ala Leu Ile Leu
225                 230                 235                 240

Asn Ser His His His Ala Ser Ala Val Ala Ala Glu Val Gln Leu Val
                245                 250                 255

Glu Ser Gly Gly Gly Leu Val Gln Ala Gly Gly Ser Leu Arg Leu Ser
            260                 265                 270

Cys Ala Ala Ser Gly Ile Thr Phe Ser Ile Asn Thr Met Gly Trp Tyr
            275                 280                 285

Arg Gln Ala Pro Gly Lys Gln Arg Glu Leu Val Ala Leu Ile Ser Ser
        290                 295                 300

Ile Gly Asp Thr Tyr Tyr Ala Asp Ser Val Lys Gly Arg Phe Thr Ile
305                 310                 315                 320

Ser Arg Asp Asn Ala Lys Asn Thr Val Tyr Leu Gln Met Asn Ser Leu
                325                 330                 335

Lys Pro Glu Asp Thr Ala Val Tyr Tyr Cys Lys Arg Phe Arg Thr Ala
            340                 345                 350

Ala Gln Gly Thr Asp Tyr Trp Gly Gln Gly Thr Gln Val Thr Val Ser
        355                 360                 365

Ser Ala
    370

<210> SEQ ID NO 107
<211> LENGTH: 366
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 107

Lys Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
            20                  25                  30

Ser Gly Gly Thr Ser Leu Leu Met Ile Asp Ser Gly Ile Gly Asp Asn
        35                  40                  45

Leu Phe Ala Val Asp Ile Leu Gly Phe Asp Phe Thr Leu Gly Arg Phe
    50                  55                  60

Asn Asn Leu Arg Leu Ile Val Glu Arg Asn Asn Leu Tyr Val Thr Gly
65                  70                  75                  80

Phe Val Asn Arg Thr Asn Asn Val Phe Tyr Arg Phe Ala Asp Phe Ser
                85                  90                  95

His Val Thr Phe Pro Gly Thr Thr Ala Val Thr Leu Ser Ala Asp Ser
            100                 105                 110

Ser Tyr Thr Thr Leu Gln Arg Val Ala Gly Ile Ser Arg Thr Gly Met
        115                 120                 125

Gln Ile Asn Arg His Ser Leu Thr Thr Ser Tyr Leu Ala Leu Met Ser
    130                 135                 140

His Ser Gly Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175
```

```
Gly Phe Arg Thr Thr Leu Asp Asp Leu Ser Gly Ala Ser Tyr Val Met
            180                 185                 190

Thr Ala Glu Asp Val Asp Leu Thr Leu Asn Trp Gly Arg Leu Ser Ser
            195                 200                 205

Val Leu Pro Asp Tyr His Gly Gln Asp Ser Val Arg Val Gly Arg Ile
            210                 215                 220

Ser Phe Gly Ser Ile Asn Ala Ile Leu Gly Ser Val Ala Leu Ile Leu
225                 230                 235                 240

Asn Ser His His His Ala Ser Ala Val Ala Ala Gln Val Gln Leu Gln
                245                 250                 255

Glu Ser Gly Gly Gly Ser Val Gln Ala Gly Gly Ser Leu Lys Leu Thr
            260                 265                 270

Cys Ala Ala Ser Gly Tyr Ile Phe Asn Ser Cys Gly Met Gly Trp Tyr
            275                 280                 285

Arg Gln Ser Pro Gly Arg Glu Arg Glu Leu Val Ser Arg Ile Ser Gly
            290                 295                 300

Asp Gly Asp Thr Trp His Lys Glu Ser Val Lys Gly Arg Phe Thr Ile
305                 310                 315                 320

Ser Gln Asp Asn Val Lys Lys Thr Leu Tyr Leu Gln Met Asn Ser Leu
                325                 330                 335

Lys Pro Glu Asp Thr Ala Val Tyr Phe Cys Ala Val Cys Tyr Asn Leu
            340                 345                 350

Glu Thr Tyr Trp Gly Gln Gly Thr Gln Val Thr Val Ser Ser
            355                 360                 365

<210> SEQ ID NO 108
<211> LENGTH: 513
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 108

Lys Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
            20                  25                  30

Ser Gly Gly Thr Ser Leu Leu Met Ile Asp Ser Gly Ile Gly Asp Asn
        35                  40                  45

Leu Phe Ala Val Asp Ile Leu Gly Phe Asp Phe Thr Leu Gly Arg Phe
    50                  55                  60

Asn Asn Leu Arg Leu Ile Val Glu Arg Asn Asn Leu Tyr Val Thr Gly
65                  70                  75                  80

Phe Val Asn Arg Thr Asn Asn Val Phe Tyr Arg Phe Ala Asp Phe Ser
                85                  90                  95

His Val Thr Phe Pro Gly Thr Thr Ala Val Thr Leu Ser Ala Asp Ser
            100                 105                 110

Ser Tyr Thr Thr Leu Gln Arg Val Ala Gly Ile Ser Arg Thr Gly Met
            115                 120                 125

Gln Ile Asn Arg His Ser Leu Thr Thr Ser Tyr Leu Asp Leu Met Ser
        130                 135                 140

His Ser Gly Thr Ser Leu Thr Gln Ser Val Ala Arg Ala Met Leu Arg
145                 150                 155                 160
```

```
Phe Val Thr Val Thr Ala Glu Ala Leu Arg Phe Arg Gln Ile Gln Arg
                165                 170                 175
Gly Phe Arg Thr Thr Leu Asp Asp Leu Ser Gly Ala Ser Tyr Val Met
            180                 185                 190
Thr Ala Glu Asp Val Asp Leu Thr Leu Asn Trp Gly Arg Leu Ser Ser
        195                 200                 205
Val Leu Pro Asp Tyr His Gly Gln Asp Ser Val Arg Val Gly Arg Ile
210                 215                 220
Ser Phe Gly Ser Ile Asn Ala Ile Leu Gly Ser Val Ala Leu Ile Leu
225                 230                 235                 240
Asn Ser His His His Ala Ser Ala Val Ala Ala Glu Phe Pro Lys Pro
                245                 250                 255
Ser Thr Pro Pro Gly Ser Ser Gly Ala Pro Gln Val Gln Leu Gln
            260                 265                 270
Gln Ser Gly Pro Glu Leu Lys Lys Pro Gly Glu Thr Val Lys Ile Ser
        275                 280                 285
Cys Lys Ala Ser Gly Tyr Pro Phe Thr Asn Tyr Gly Met Asn Trp Val
290                 295                 300
Lys Gln Ala Pro Gly Gln Gly Leu Lys Trp Met Gly Trp Ile Asn Thr
305                 310                 315                 320
Ser Thr Gly Glu Ser Thr Phe Ala Asp Asp Phe Lys Gly Arg Phe Asp
                325                 330                 335
Phe Ser Leu Glu Thr Ser Ala Asn Thr Ala Tyr Leu Gln Ile Asn Asn
            340                 345                 350
Leu Lys Ser Glu Asp Ser Ala Thr Tyr Phe Cys Ala Arg Trp Glu Val
        355                 360                 365
Tyr His Gly Tyr Val Pro Tyr Trp Gly Gln Gly Thr Thr Val Thr Val
370                 375                 380
Ser Ser Gly Gly Gly Ser Gly Gly Gly Ser Gly Gly Gly
385                 390                 395                 400
Ser Gly Gly Gly Ser Asp Ile Gln Met Thr Gln Ser Pro Ser Ser
                405                 410                 415
Leu Ser Ala Ser Val Gly Asp Arg Val Thr Ile Thr Cys Lys Ala Ser
            420                 425                 430
Gln Asp Val Tyr Asn Ala Val Ala Trp Tyr Gln Gln Lys Pro Gly Gln
        435                 440                 445
Ser Pro Lys Leu Leu Ile Tyr Ser Ala Ser Ser Arg Tyr Thr Gly Val
450                 455                 460
Pro Ser Arg Phe Thr Gly Ser Gly Ser Gly Pro Asp Phe Thr Phe Thr
465                 470                 475                 480
Ile Ser Ser Val Gln Ala Glu Asp Leu Ala Val Tyr Phe Cys Gln Gln
                485                 490                 495
His Phe Arg Thr Pro Phe Thr Phe Gly Ser Gly Thr Lys Leu Glu Ile
            500                 505                 510
Lys

<210> SEQ ID NO 109
<211> LENGTH: 4
<212> TYPE: PRT
<213> ORGANISM: Unknown
<220> FEATURE:
<221> NAME/KEY: source
<223> OTHER INFORMATION: /note="Description of Unknown:
      'KDEL' family motif peptide"

<400> SEQUENCE: 109
```

Lys Asp Glu Leu
1

<210> SEQ ID NO 110
<211> LENGTH: 4
<212> TYPE: PRT
<213> ORGANISM: Unknown
<220> FEATURE:
<221> NAME/KEY: source
<223> OTHER INFORMATION: /note="Description of Unknown:
      'KDEL' family motif peptide"

<400> SEQUENCE: 110

His Asp Glu Phe
1

<210> SEQ ID NO 111
<211> LENGTH: 4
<212> TYPE: PRT
<213> ORGANISM: Unknown
<220> FEATURE:
<221> NAME/KEY: source
<223> OTHER INFORMATION: /note="Description of Unknown:
      'KDEL' family motif peptide"

<400> SEQUENCE: 111

His Asp Glu Leu
1

<210> SEQ ID NO 112
<211> LENGTH: 4
<212> TYPE: PRT
<213> ORGANISM: Unknown
<220> FEATURE:
<221> NAME/KEY: source
<223> OTHER INFORMATION: /note="Description of Unknown:
      'KDEL' family motif peptide"

<400> SEQUENCE: 112

Arg Asp Glu Phe
1

<210> SEQ ID NO 113
<211> LENGTH: 4
<212> TYPE: PRT
<213> ORGANISM: Unknown
<220> FEATURE:
<221> NAME/KEY: source
<223> OTHER INFORMATION: /note="Description of Unknown:
      'KDEL' family motif peptide"

<400> SEQUENCE: 113

Arg Asp Glu Leu
1

<210> SEQ ID NO 114
<211> LENGTH: 4
<212> TYPE: PRT
<213> ORGANISM: Unknown
<220> FEATURE:
<221> NAME/KEY: source
<223> OTHER INFORMATION: /note="Description of Unknown:
      'KDEL' family motif peptide"

<400> SEQUENCE: 114

Trp Asp Glu Leu
1

```
<210> SEQ ID NO 115
<211> LENGTH: 4
<212> TYPE: PRT
<213> ORGANISM: Unknown
<220> FEATURE:
<221> NAME/KEY: source
<223> OTHER INFORMATION: /note="Description of Unknown:
      'KDEL' family motif peptide"

<400> SEQUENCE: 115

Tyr Asp Glu Leu
1

<210> SEQ ID NO 116
<211> LENGTH: 4
<212> TYPE: PRT
<213> ORGANISM: Unknown
<220> FEATURE:
<221> NAME/KEY: source
<223> OTHER INFORMATION: /note="Description of Unknown:
      'KDEL' family motif peptide"

<400> SEQUENCE: 116

His Glu Glu Phe
1

<210> SEQ ID NO 117
<211> LENGTH: 4
<212> TYPE: PRT
<213> ORGANISM: Unknown
<220> FEATURE:
<221> NAME/KEY: source
<223> OTHER INFORMATION: /note="Description of Unknown:
      'KDEL' family motif peptide"

<400> SEQUENCE: 117

His Glu Glu Leu
1

<210> SEQ ID NO 118
<211> LENGTH: 4
<212> TYPE: PRT
<213> ORGANISM: Unknown
<220> FEATURE:
<221> NAME/KEY: source
<223> OTHER INFORMATION: /note="Description of Unknown:
      'KDEL' family motif peptide"

<400> SEQUENCE: 118

Lys Glu Glu Leu
1

<210> SEQ ID NO 119
<211> LENGTH: 4
<212> TYPE: PRT
<213> ORGANISM: Unknown
<220> FEATURE:
<221> NAME/KEY: source
<223> OTHER INFORMATION: /note="Description of Unknown:
      'KDEL' family motif peptide"

<400> SEQUENCE: 119

Arg Glu Glu Leu
1

<210> SEQ ID NO 120
<211> LENGTH: 4
<212> TYPE: PRT
```

```
<213> ORGANISM: Unknown
<220> FEATURE:
<221> NAME/KEY: source
<223> OTHER INFORMATION: /note="Description of Unknown:
      'KDEL' family motif peptide"

<400> SEQUENCE: 120

Lys Ala Glu Leu
1

<210> SEQ ID NO 121
<211> LENGTH: 4
<212> TYPE: PRT
<213> ORGANISM: Unknown
<220> FEATURE:
<221> NAME/KEY: source
<223> OTHER INFORMATION: /note="Description of Unknown:
      'KDEL' family motif peptide"

<400> SEQUENCE: 121

Lys Cys Glu Leu
1

<210> SEQ ID NO 122
<211> LENGTH: 4
<212> TYPE: PRT
<213> ORGANISM: Unknown
<220> FEATURE:
<221> NAME/KEY: source
<223> OTHER INFORMATION: /note="Description of Unknown:
      'KDEL' family motif peptide"

<400> SEQUENCE: 122

Lys Phe Glu Leu
1

<210> SEQ ID NO 123
<211> LENGTH: 4
<212> TYPE: PRT
<213> ORGANISM: Unknown
<220> FEATURE:
<221> NAME/KEY: source
<223> OTHER INFORMATION: /note="Description of Unknown:
      'KDEL' family motif peptide"

<400> SEQUENCE: 123

Lys Gly Glu Leu
1

<210> SEQ ID NO 124
<211> LENGTH: 4
<212> TYPE: PRT
<213> ORGANISM: Unknown
<220> FEATURE:
<221> NAME/KEY: source
<223> OTHER INFORMATION: /note="Description of Unknown:
      'KDEL' family motif peptide"

<400> SEQUENCE: 124

Lys His Glu Leu
1

<210> SEQ ID NO 125
<211> LENGTH: 4
<212> TYPE: PRT
<213> ORGANISM: Unknown
<220> FEATURE:
<221> NAME/KEY: source
<223> OTHER INFORMATION: /note="Description of Unknown:
```

```
       'KDEL' family motif peptide"

<400> SEQUENCE: 125

Lys Leu Glu Leu
1

<210> SEQ ID NO 126
<211> LENGTH: 4
<212> TYPE: PRT
<213> ORGANISM: Unknown
<220> FEATURE:
<221> NAME/KEY: source
<223> OTHER INFORMATION: /note="Description of Unknown:
       'KDEL' family motif peptide"

<400> SEQUENCE: 126

Lys Asn Glu Leu
1

<210> SEQ ID NO 127
<211> LENGTH: 4
<212> TYPE: PRT
<213> ORGANISM: Unknown
<220> FEATURE:
<221> NAME/KEY: source
<223> OTHER INFORMATION: /note="Description of Unknown:
       'KDEL' family motif peptide"

<400> SEQUENCE: 127

Lys Gln Glu Leu
1

<210> SEQ ID NO 128
<211> LENGTH: 4
<212> TYPE: PRT
<213> ORGANISM: Unknown
<220> FEATURE:
<221> NAME/KEY: source
<223> OTHER INFORMATION: /note="Description of Unknown:
       'KDEL' family motif peptide"

<400> SEQUENCE: 128

Lys Arg Glu Leu
1

<210> SEQ ID NO 129
<211> LENGTH: 4
<212> TYPE: PRT
<213> ORGANISM: Unknown
<220> FEATURE:
<221> NAME/KEY: source
<223> OTHER INFORMATION: /note="Description of Unknown:
       'KDEL' family motif peptide"

<400> SEQUENCE: 129

Lys Ser Glu Leu
1

<210> SEQ ID NO 130
<211> LENGTH: 4
<212> TYPE: PRT
<213> ORGANISM: Unknown
<220> FEATURE:
<221> NAME/KEY: source
<223> OTHER INFORMATION: /note="Description of Unknown:
       'KDEL' family motif peptide"

<400> SEQUENCE: 130
```

Lys Val Glu Leu
1

<210> SEQ ID NO 131
<211> LENGTH: 4
<212> TYPE: PRT
<213> ORGANISM: Unknown
<220> FEATURE:
<221> NAME/KEY: source
<223> OTHER INFORMATION: /note="Description of Unknown:
      'KDEL' family motif peptide"

<400> SEQUENCE: 131

Lys Trp Glu Leu
1

<210> SEQ ID NO 132
<211> LENGTH: 4
<212> TYPE: PRT
<213> ORGANISM: Unknown
<220> FEATURE:
<221> NAME/KEY: source
<223> OTHER INFORMATION: /note="Description of Unknown:
      'KDEL' family motif peptide"

<400> SEQUENCE: 132

Lys Tyr Glu Leu
1

<210> SEQ ID NO 133
<211> LENGTH: 4
<212> TYPE: PRT
<213> ORGANISM: Unknown
<220> FEATURE:
<221> NAME/KEY: source
<223> OTHER INFORMATION: /note="Description of Unknown:
      'KDEL' family motif peptide"

<400> SEQUENCE: 133

Lys Glu Asp Leu
1

<210> SEQ ID NO 134
<211> LENGTH: 4
<212> TYPE: PRT
<213> ORGANISM: Unknown
<220> FEATURE:
<221> NAME/KEY: source
<223> OTHER INFORMATION: /note="Description of Unknown:
      'KDEL' family motif peptide"

<400> SEQUENCE: 134

Lys Ile Glu Leu
1

<210> SEQ ID NO 135
<211> LENGTH: 4
<212> TYPE: PRT
<213> ORGANISM: Unknown
<220> FEATURE:
<221> NAME/KEY: source
<223> OTHER INFORMATION: /note="Description of Unknown:
      'KDEL' family motif peptide"

<400> SEQUENCE: 135

Asp Lys Glu Leu
1

```
<210> SEQ ID NO 136
<211> LENGTH: 4
<212> TYPE: PRT
<213> ORGANISM: Unknown
<220> FEATURE:
<221> NAME/KEY: source
<223> OTHER INFORMATION: /note="Description of Unknown:
      'KDEL' family motif peptide"

<400> SEQUENCE: 136

Phe Asp Glu Leu
1

<210> SEQ ID NO 137
<211> LENGTH: 4
<212> TYPE: PRT
<213> ORGANISM: Unknown
<220> FEATURE:
<221> NAME/KEY: source
<223> OTHER INFORMATION: /note="Description of Unknown:
      'KDEL' family motif peptide"

<400> SEQUENCE: 137

Lys Asp Glu Phe
1

<210> SEQ ID NO 138
<211> LENGTH: 4
<212> TYPE: PRT
<213> ORGANISM: Unknown
<220> FEATURE:
<221> NAME/KEY: source
<223> OTHER INFORMATION: /note="Description of Unknown:
      'KDEL' family motif peptide"

<400> SEQUENCE: 138

Lys Lys Glu Leu
1

<210> SEQ ID NO 139
<211> LENGTH: 4
<212> TYPE: PRT
<213> ORGANISM: Unknown
<220> FEATURE:
<221> NAME/KEY: source
<223> OTHER INFORMATION: /note="Description of Unknown:
      'KDEL' family motif peptide"

<400> SEQUENCE: 139

His Ala Asp Leu
1

<210> SEQ ID NO 140
<211> LENGTH: 4
<212> TYPE: PRT
<213> ORGANISM: Unknown
<220> FEATURE:
<221> NAME/KEY: source
<223> OTHER INFORMATION: /note="Description of Unknown:
      'KDEL' family motif peptide"

<400> SEQUENCE: 140

His Ala Glu Leu
1

<210> SEQ ID NO 141
<211> LENGTH: 4
<212> TYPE: PRT
<213> ORGANISM: Unknown
```

<220> FEATURE:
<221> NAME/KEY: source
<223> OTHER INFORMATION: /note="Description of Unknown:
      'KDEL' family motif peptide"

<400> SEQUENCE: 141

His Ile Glu Leu
1

<210> SEQ ID NO 142
<211> LENGTH: 4
<212> TYPE: PRT
<213> ORGANISM: Unknown
<220> FEATURE:
<221> NAME/KEY: source
<223> OTHER INFORMATION: /note="Description of Unknown:
      'KDEL' family motif peptide"

<400> SEQUENCE: 142

His Asn Glu Leu
1

<210> SEQ ID NO 143
<211> LENGTH: 4
<212> TYPE: PRT
<213> ORGANISM: Unknown
<220> FEATURE:
<221> NAME/KEY: source
<223> OTHER INFORMATION: /note="Description of Unknown:
      'KDEL' family motif peptide"

<400> SEQUENCE: 143

His Thr Glu Leu
1

<210> SEQ ID NO 144
<211> LENGTH: 4
<212> TYPE: PRT
<213> ORGANISM: Unknown
<220> FEATURE:
<221> NAME/KEY: source
<223> OTHER INFORMATION: /note="Description of Unknown:
      'KDEL' family motif peptide"

<400> SEQUENCE: 144

Lys Thr Glu Leu
1

<210> SEQ ID NO 145
<211> LENGTH: 4
<212> TYPE: PRT
<213> ORGANISM: Unknown
<220> FEATURE:
<221> NAME/KEY: source
<223> OTHER INFORMATION: /note="Description of Unknown:
      'KDEL' family motif peptide"

<400> SEQUENCE: 145

His Val Glu Leu
1

<210> SEQ ID NO 146
<211> LENGTH: 4
<212> TYPE: PRT
<213> ORGANISM: Unknown
<220> FEATURE:
<221> NAME/KEY: source
<223> OTHER INFORMATION: /note="Description of Unknown:
      'KDEL' family motif peptide"

```
<400> SEQUENCE: 146

Asn Asp Glu Leu
1

<210> SEQ ID NO 147
<211> LENGTH: 4
<212> TYPE: PRT
<213> ORGANISM: Unknown
<220> FEATURE:
<221> NAME/KEY: source
<223> OTHER INFORMATION: /note="Description of Unknown:
      'KDEL' family motif peptide"

<400> SEQUENCE: 147

Gln Asp Glu Leu
1

<210> SEQ ID NO 148
<211> LENGTH: 4
<212> TYPE: PRT
<213> ORGANISM: Unknown
<220> FEATURE:
<221> NAME/KEY: source
<223> OTHER INFORMATION: /note="Description of Unknown:
      'KDEL' family motif peptide"

<400> SEQUENCE: 148

Arg Glu Asp Leu
1

<210> SEQ ID NO 149
<211> LENGTH: 4
<212> TYPE: PRT
<213> ORGANISM: Unknown
<220> FEATURE:
<221> NAME/KEY: source
<223> OTHER INFORMATION: /note="Description of Unknown:
      'KDEL' family motif peptide"

<400> SEQUENCE: 149

Arg Asn Glu Leu
1

<210> SEQ ID NO 150
<211> LENGTH: 4
<212> TYPE: PRT
<213> ORGANISM: Unknown
<220> FEATURE:
<221> NAME/KEY: source
<223> OTHER INFORMATION: /note="Description of Unknown:
      'KDEL' family motif peptide"

<400> SEQUENCE: 150

Arg Thr Asp Leu
1

<210> SEQ ID NO 151
<211> LENGTH: 4
<212> TYPE: PRT
<213> ORGANISM: Unknown
<220> FEATURE:
<221> NAME/KEY: source
<223> OTHER INFORMATION: /note="Description of Unknown:
      'KDEL' family motif peptide"

<400> SEQUENCE: 151

Arg Thr Glu Leu
```

<210> SEQ ID NO 152
<211> LENGTH: 4
<212> TYPE: PRT
<213> ORGANISM: Unknown
<220> FEATURE:
<221> NAME/KEY: source
<223> OTHER INFORMATION: /note="Description of Unknown:
      'KDEL' family motif peptide"

<400> SEQUENCE: 152

Ser Asp Glu Leu
1

<210> SEQ ID NO 153
<211> LENGTH: 4
<212> TYPE: PRT
<213> ORGANISM: Unknown
<220> FEATURE:
<221> NAME/KEY: source
<223> OTHER INFORMATION: /note="Description of Unknown:
      'KDEL' family motif peptide"

<400> SEQUENCE: 153

Thr Asp Glu Leu
1

<210> SEQ ID NO 154
<211> LENGTH: 4
<212> TYPE: PRT
<213> ORGANISM: Unknown
<220> FEATURE:
<221> NAME/KEY: source
<223> OTHER INFORMATION: /note="Description of Unknown:
      'KDEL' family motif peptide"

<400> SEQUENCE: 154

Ser Lys Glu Leu
1

<210> SEQ ID NO 155
<211> LENGTH: 4
<212> TYPE: PRT
<213> ORGANISM: Unknown
<220> FEATURE:
<221> NAME/KEY: source
<223> OTHER INFORMATION: /note="Description of Unknown:
      'KDEL' family motif peptide"

<400> SEQUENCE: 155

Ser Thr Glu Leu
1

<210> SEQ ID NO 156
<211> LENGTH: 4
<212> TYPE: PRT
<213> ORGANISM: Unknown
<220> FEATURE:
<221> NAME/KEY: source
<223> OTHER INFORMATION: /note="Description of Unknown:
      'KDEL' family motif peptide"

<400> SEQUENCE: 156

Glu Asp Glu Leu
1

<210> SEQ ID NO 157

```
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 157

Arg Val Lys Arg
1

<210> SEQ ID NO 158
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 158

Ala Ser Gly Gly Pro Glu
1               5

<210> SEQ ID NO 159
<211> LENGTH: 54
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: SITE
<222> LOCATION: (3)..(6)
<223> OTHER INFORMATION: /note="This region may encompass 2-4 residues"
<220> FEATURE:
<221> NAME/KEY: SITE
<222> LOCATION: (8)..(11)
<223> OTHER INFORMATION: /note="This region may encompass 2-4 residues"
<220> FEATURE:
<221> NAME/KEY: SITE
<222> LOCATION: (13)..(16)
<223> OTHER INFORMATION: /note="This region may encompass 2-4 residues"
<220> FEATURE:
<221> NAME/KEY: SITE
<222> LOCATION: (18)..(21)
<223> OTHER INFORMATION: /note="This region may encompass 2-4 residues"
<220> FEATURE:
<221> NAME/KEY: SITE
<222> LOCATION: (23)..(26)
<223> OTHER INFORMATION: /note="This region may encompass 2-4 residues"
<220> FEATURE:
<221> NAME/KEY: SITE
<222> LOCATION: (28)..(31)
<223> OTHER INFORMATION: /note="This region may encompass 2-4 residues"
<220> FEATURE:
<221> NAME/KEY: SITE
<222> LOCATION: (33)..(36)
<223> OTHER INFORMATION: /note="This region may encompass 2-4 residues"
<220> FEATURE:
<221> NAME/KEY: SITE
<222> LOCATION: (38)..(41)
<223> OTHER INFORMATION: /note="This region may encompass 2-4 residues"
<220> FEATURE:
<221> NAME/KEY: SITE
<222> LOCATION: (43)..(46)
<223> OTHER INFORMATION: /note="This region may encompass 2-4 residues"
<220> FEATURE:
<221> NAME/KEY: SITE
<222> LOCATION: (48)..(51)
<223> OTHER INFORMATION: /note="This region may encompass 2-4 residues"
<220> FEATURE:
<221> NAME/KEY: SITE
```

```
<222> LOCATION: (3)..(52)
<223> OTHER INFORMATION: /note="This region may encompass 1 to 6
      'Gly(x) Ser' repeating units wherein x = 2 to 4"

<400> SEQUENCE: 159

Ala Met Gly Gly Gly Gly Ser Gly Gly Gly Ser Gly Gly Gly Gly
1               5                   10                  15

Ser Gly Gly Gly Gly Ser Gly Gly Gly Gly Ser Gly Gly Gly Ser
                20                  25                  30

Gly Gly Gly Gly Ser Gly Gly Gly Gly Ser Gly Gly Gly Ser Gly
            35                  40                  45

Gly Gly Gly Ser Ala Met
            50

<210> SEQ ID NO 160
<211> LENGTH: 210
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: SITE
<222> LOCATION: (1)..(6)
<223> OTHER INFORMATION: /note="This region may encompass 1-6 residues"
<220> FEATURE:
<221> NAME/KEY: SITE
<222> LOCATION: (8)..(13)
<223> OTHER INFORMATION: /note="This region may encompass 1-6 residues"
<220> FEATURE:
<221> NAME/KEY: SITE
<222> LOCATION: (15)..(20)
<223> OTHER INFORMATION: /note="This region may encompass 1-6 residues"
<220> FEATURE:
<221> NAME/KEY: SITE
<222> LOCATION: (22)..(27)
<223> OTHER INFORMATION: /note="This region may encompass 1-6 residues"
<220> FEATURE:
<221> NAME/KEY: SITE
<222> LOCATION: (29)..(34)
<223> OTHER INFORMATION: /note="This region may encompass 1-6 residues"
<220> FEATURE:
<221> NAME/KEY: SITE
<222> LOCATION: (36)..(41)
<223> OTHER INFORMATION: /note="This region may encompass 1-6 residues"
<220> FEATURE:
<221> NAME/KEY: SITE
<222> LOCATION: (43)..(48)
<223> OTHER INFORMATION: /note="This region may encompass 1-6 residues"
<220> FEATURE:
<221> NAME/KEY: SITE
<222> LOCATION: (50)..(55)
<223> OTHER INFORMATION: /note="This region may encompass 1-6 residues"
<220> FEATURE:
<221> NAME/KEY: SITE
<222> LOCATION: (57)..(62)
<223> OTHER INFORMATION: /note="This region may encompass 1-6 residues"
<220> FEATURE:
<221> NAME/KEY: SITE
<222> LOCATION: (64)..(69)
<223> OTHER INFORMATION: /note="This region may encompass 1-6 residues"
<220> FEATURE:
<221> NAME/KEY: SITE
<222> LOCATION: (71)..(76)
<223> OTHER INFORMATION: /note="This region may encompass 1-6 residues"
<220> FEATURE:
<221> NAME/KEY: SITE
<222> LOCATION: (78)..(83)
<223> OTHER INFORMATION: /note="This region may encompass 1-6 residues"
<220> FEATURE:
<221> NAME/KEY: SITE
<222> LOCATION: (85)..(90)
<223> OTHER INFORMATION: /note="This region may encompass 1-6 residues"
```

```
<220> FEATURE:
<221> NAME/KEY: SITE
<222> LOCATION: (92)..(97)
<223> OTHER INFORMATION: /note="This region may encompass 1-6 residues"
<220> FEATURE:
<221> NAME/KEY: SITE
<222> LOCATION: (99)..(104)
<223> OTHER INFORMATION: /note="This region may encompass 1-6 residues"
<220> FEATURE:
<221> NAME/KEY: SITE
<222> LOCATION: (106)..(111)
<223> OTHER INFORMATION: /note="This region may encompass 1-6 residues"
<220> FEATURE:
<221> NAME/KEY: SITE
<222> LOCATION: (113)..(118)
<223> OTHER INFORMATION: /note="This region may encompass 1-6 residues"
<220> FEATURE:
<221> NAME/KEY: SITE
<222> LOCATION: (120)..(125)
<223> OTHER INFORMATION: /note="This region may encompass 1-6 residues"
<220> FEATURE:
<221> NAME/KEY: SITE
<222> LOCATION: (127)..(132)
<223> OTHER INFORMATION: /note="This region may encompass 1-6 residues"
<220> FEATURE:
<221> NAME/KEY: SITE
<222> LOCATION: (134)..(139)
<223> OTHER INFORMATION: /note="This region may encompass 1-6 residues"
<220> FEATURE:
<221> NAME/KEY: SITE
<222> LOCATION: (141)..(146)
<223> OTHER INFORMATION: /note="This region may encompass 1-6 residues"
<220> FEATURE:
<221> NAME/KEY: SITE
<222> LOCATION: (148)..(153)
<223> OTHER INFORMATION: /note="This region may encompass 1-6 residues"
<220> FEATURE:
<221> NAME/KEY: SITE
<222> LOCATION: (155)..(160)
<223> OTHER INFORMATION: /note="This region may encompass 1-6 residues"
<220> FEATURE:
<221> NAME/KEY: SITE
<222> LOCATION: (162)..(167)
<223> OTHER INFORMATION: /note="This region may encompass 1-6 residues"
<220> FEATURE:
<221> NAME/KEY: SITE
<222> LOCATION: (169)..(174)
<223> OTHER INFORMATION: /note="This region may encompass 1-6 residues"
<220> FEATURE:
<221> NAME/KEY: SITE
<222> LOCATION: (176)..(181)
<223> OTHER INFORMATION: /note="This region may encompass 1-6 residues"
<220> FEATURE:
<221> NAME/KEY: SITE
<222> LOCATION: (183)..(188)
<223> OTHER INFORMATION: /note="This region may encompass 1-6 residues"
<220> FEATURE:
<221> NAME/KEY: SITE
<222> LOCATION: (190)..(195)
<223> OTHER INFORMATION: /note="This region may encompass 1-6 residues"
<220> FEATURE:
<221> NAME/KEY: SITE
<222> LOCATION: (197)..(202)
<223> OTHER INFORMATION: /note="This region may encompass 1-6 residues"
<220> FEATURE:
<221> NAME/KEY: SITE
<222> LOCATION: (204)..(209)
<223> OTHER INFORMATION: /note="This region may encompass 1-6 residues"
<220> FEATURE:
<221> NAME/KEY: SITE
<222> LOCATION: (1)..(210)
<223> OTHER INFORMATION: /note="This sequence may encompass 1 to 30
      'Gly(x) Ser' repeating units wherein x = 1 to 6"
<220> FEATURE:
<223> OTHER INFORMATION: See specification as filed for detailed
      description of substitutions and preferred embodiments

<400> SEQUENCE: 160
```

Gly Gly Gly Gly Gly Ser Gly Gly Gly Gly Gly Ser Gly Gly
1               5                   10                  15
Gly Gly Gly Gly Ser Gly Gly Gly Gly Ser Gly Gly Gly
            20                  25              30
Gly Gly Ser Gly Gly Gly Gly Gly Ser Gly Gly Gly Gly Gly
        35                      40                  45
Ser Gly Gly Gly Gly Gly Ser Gly Gly Gly Gly Ser Gly
50                      55                  60
Gly Gly Gly Gly Ser Gly Gly Gly Gly Gly Ser Gly Gly Gly
65                  70                  75                  80
Gly Gly Gly Ser Gly Gly Gly Gly Gly Ser Gly Gly Gly Gly
            85                      90                  95
Gly Ser Gly Gly Gly Gly Gly Ser Gly Gly Gly Gly Gly Ser
        100                     105                 110
Gly Gly Gly Gly Gly Ser Gly Gly Gly Gly Gly Ser Gly Gly
        115                     120                 125
Gly Gly Gly Gly Ser Gly Gly Gly Gly Gly Ser Gly Gly Gly
        130                     135             140
Gly Gly Ser Gly Gly Gly Gly Gly Ser Gly Gly Gly Gly Gly
145             150                     155                 160
Ser Gly Gly Gly Gly Gly Ser Gly Gly Gly Gly Gly Ser Gly
            165                 170                 175
Gly Gly Gly Gly Ser Gly Gly Gly Gly Gly Ser Gly Gly Gly
            180                 185                 190
Gly Gly Gly Ser Gly Gly Gly Gly Gly Ser Gly Gly Gly Gly
        195                     200                 205
Gly Ser
    210

```
<210> SEQ ID NO 161
<211> LENGTH: 210
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: SITE
<222> LOCATION: (1)..(6)
<223> OTHER INFORMATION: /note="This region may encompass 1-6 residues"
<220> FEATURE:
<221> NAME/KEY: SITE
<222> LOCATION: (8)..(13)
<223> OTHER INFORMATION: /note="This region may encompass 1-6 residues"
<220> FEATURE:
<221> NAME/KEY: SITE
<222> LOCATION: (15)..(20)
<223> OTHER INFORMATION: /note="This region may encompass 1-6 residues"
<220> FEATURE:
<221> NAME/KEY: SITE
<222> LOCATION: (22)..(27)
<223> OTHER INFORMATION: /note="This region may encompass 1-6 residues"
<220> FEATURE:
<221> NAME/KEY: SITE
<222> LOCATION: (29)..(34)
<223> OTHER INFORMATION: /note="This region may encompass 1-6 residues"
<220> FEATURE:
<221> NAME/KEY: SITE
<222> LOCATION: (36)..(41)
<223> OTHER INFORMATION: /note="This region may encompass 1-6 residues"
<220> FEATURE:
<221> NAME/KEY: SITE
<222> LOCATION: (43)..(48)
<223> OTHER INFORMATION: /note="This region may encompass 1-6 residues"
```

-continued

```
<220> FEATURE:
<221> NAME/KEY: SITE
<222> LOCATION: (50)..(55)
<223> OTHER INFORMATION: /note="This region may encompass 1-6 residues"
<220> FEATURE:
<221> NAME/KEY: SITE
<222> LOCATION: (57)..(62)
<223> OTHER INFORMATION: /note="This region may encompass 1-6 residues"
<220> FEATURE:
<221> NAME/KEY: SITE
<222> LOCATION: (64)..(69)
<223> OTHER INFORMATION: /note="This region may encompass 1-6 residues"
<220> FEATURE:
<221> NAME/KEY: SITE
<222> LOCATION: (71)..(76)
<223> OTHER INFORMATION: /note="This region may encompass 1-6 residues"
<220> FEATURE:
<221> NAME/KEY: SITE
<222> LOCATION: (78)..(83)
<223> OTHER INFORMATION: /note="This region may encompass 1-6 residues"
<220> FEATURE:
<221> NAME/KEY: SITE
<222> LOCATION: (85)..(90)
<223> OTHER INFORMATION: /note="This region may encompass 1-6 residues"
<220> FEATURE:
<221> NAME/KEY: SITE
<222> LOCATION: (92)..(97)
<223> OTHER INFORMATION: /note="This region may encompass 1-6 residues"
<220> FEATURE:
<221> NAME/KEY: SITE
<222> LOCATION: (99)..(104)
<223> OTHER INFORMATION: /note="This region may encompass 1-6 residues"
<220> FEATURE:
<221> NAME/KEY: SITE
<222> LOCATION: (106)..(111)
<223> OTHER INFORMATION: /note="This region may encompass 1-6 residues"
<220> FEATURE:
<221> NAME/KEY: SITE
<222> LOCATION: (113)..(118)
<223> OTHER INFORMATION: /note="This region may encompass 1-6 residues"
<220> FEATURE:
<221> NAME/KEY: SITE
<222> LOCATION: (120)..(125)
<223> OTHER INFORMATION: /note="This region may encompass 1-6 residues"
<220> FEATURE:
<221> NAME/KEY: SITE
<222> LOCATION: (127)..(132)
<223> OTHER INFORMATION: /note="This region may encompass 1-6 residues"
<220> FEATURE:
<221> NAME/KEY: SITE
<222> LOCATION: (134)..(139)
<223> OTHER INFORMATION: /note="This region may encompass 1-6 residues"
<220> FEATURE:
<221> NAME/KEY: SITE
<222> LOCATION: (141)..(146)
<223> OTHER INFORMATION: /note="This region may encompass 1-6 residues"
<220> FEATURE:
<221> NAME/KEY: SITE
<222> LOCATION: (148)..(153)
<223> OTHER INFORMATION: /note="This region may encompass 1-6 residues"
<220> FEATURE:
<221> NAME/KEY: SITE
<222> LOCATION: (155)..(160)
<223> OTHER INFORMATION: /note="This region may encompass 1-6 residues"
<220> FEATURE:
<221> NAME/KEY: SITE
<222> LOCATION: (162)..(167)
<223> OTHER INFORMATION: /note="This region may encompass 1-6 residues"
<220> FEATURE:
<221> NAME/KEY: SITE
<222> LOCATION: (169)..(174)
<223> OTHER INFORMATION: /note="This region may encompass 1-6 residues"
<220> FEATURE:
<221> NAME/KEY: SITE
<222> LOCATION: (176)..(181)
<223> OTHER INFORMATION: /note="This region may encompass 1-6 residues"
<220> FEATURE:
<221> NAME/KEY: SITE
<222> LOCATION: (183)..(188)
```

<223> OTHER INFORMATION: /note="This region may encompass 1-6 residues"
<220> FEATURE:
<221> NAME/KEY: SITE
<222> LOCATION: (190)..(195)
<223> OTHER INFORMATION: /note="This region may encompass 1-6 residues"
<220> FEATURE:
<221> NAME/KEY: SITE
<222> LOCATION: (197)..(202)
<223> OTHER INFORMATION: /note="This region may encompass 1-6 residues"
<220> FEATURE:
<221> NAME/KEY: SITE
<222> LOCATION: (204)..(209)
<223> OTHER INFORMATION: /note="This region may encompass 1-6 residues"
<220> FEATURE:
<221> NAME/KEY: SITE
<222> LOCATION: (1)..(210)
<223> OTHER INFORMATION: /note="This sequence may encompass 1 to 30 'Ser(x) Gly' repeating units wherein x = 1 to 6"
<220> FEATURE:
<223> OTHER INFORMATION: See specification as filed for detailed description of substitutions and preferred embodiments

<400> SEQUENCE: 161

Ser Ser Ser Ser Ser Gly Ser Ser Ser Ser Ser Gly Ser Ser
1               5                   10                  15

Ser Ser Ser Ser Gly Ser Ser Ser Ser Ser Gly Ser Ser Ser
            20                  25                  30

Ser Ser Gly Ser Ser Ser Ser Ser Gly Ser Ser Ser Ser Ser
        35                  40                  45

Gly Ser Ser Ser Ser Ser Gly Ser Ser Ser Ser Ser Gly Ser
    50                  55                  60

Ser Ser Ser Ser Gly Ser Ser Ser Ser Ser Gly Ser Ser Ser
65              70                  75                  80

Ser Ser Ser Gly Ser Ser Ser Ser Ser Gly Ser Ser Ser Ser
            85                  90                  95

Ser Gly Ser Ser Ser Ser Ser Gly Ser Ser Ser Ser Ser Gly
                100                 105                 110

Ser Ser Ser Ser Ser Gly Ser Ser Ser Ser Ser Gly Ser Ser
        115                 120                 125

Ser Ser Ser Ser Gly Ser Ser Ser Ser Ser Gly Ser Ser Ser
130                 135                 140

Ser Ser Gly Ser Ser Ser Ser Ser Gly Ser Ser Ser Ser Ser
145                 150                 155                 160

Gly Ser Ser Ser Ser Ser Gly Ser Ser Ser Ser Ser Gly Ser
                165                 170                 175

Ser Ser Ser Ser Gly Ser Ser Ser Ser Ser Gly Ser Ser Ser
            180                 185                 190

Ser Ser Ser Gly Ser Ser Ser Ser Ser Gly Ser Ser Ser Ser
        195                 200                 205

Ser Gly
    210

<210> SEQ ID NO 162
<211> LENGTH: 150
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"
<220> FEATURE:
<221> NAME/KEY: SITE
<222> LOCATION: (1)..(150)
<223> OTHER INFORMATION: /note="This sequence may encompass 1-30

'Gly Gly Gly Gly Ser' repeating units"

<400> SEQUENCE: 162

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Gly Gly Gly Gly Ser Gly Gly Gly Gly Ser Gly Gly Gly
        35                  40                  45

Gly Ser Gly Gly Gly Gly Ser Gly Gly Gly Gly Ser Gly Gly Gly Gly
    50                  55                  60

Ser Gly Gly Gly Gly Ser Gly Gly Gly Gly Ser Gly Gly Gly Gly Ser
65                  70                  75                  80

Gly Gly Gly Gly Ser Gly Gly Gly Gly Ser Gly Gly Gly Gly Ser Gly
                85                  90                  95

Gly Gly Gly Ser Gly Gly Gly Gly Ser Gly Gly Gly Gly Ser Gly Gly
            100                 105                 110

Gly Gly Ser Gly Gly Gly Gly Ser Gly Gly Gly Gly Ser Gly Gly Gly
        115                 120                 125

Gly Ser Gly Gly Gly Gly Ser Gly Gly Gly Gly Ser Gly Gly Gly Gly
    130                 135                 140

Ser Gly Gly Gly Gly Ser
145                 150

<210> SEQ ID NO 163
<211> LENGTH: 30
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: SITE
<222> LOCATION: (1)..(30)
<223> OTHER INFORMATION: /note="This sequence may encompass 1-30
      residues"

<400> SEQUENCE: 163

Gly Gly Gly Gly Gly Gly Gly Gly Gly Gly Gly Gly Gly Gly Gly Gly
1               5                   10                  15

Gly Gly Gly Gly Gly Gly Gly Gly Gly Gly Gly Gly Gly Gly
            20                  25                  30

<210> SEQ ID NO 164
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 164

Gly Lys Ser Ser Gly Ser Gly Ser Glu Ser Lys Ser
1               5                   10

<210> SEQ ID NO 165
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 165

Glu Gly Lys Ser Ser Gly Ser Gly Ser Glu Ser Lys Glu Phe
1               5                   10

<210> SEQ ID NO 166
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 166

Gly Ser Thr Ser Gly Ser Gly Lys Ser Ser Glu Gly Lys Gly
1               5                   10

<210> SEQ ID NO 167
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 167

Gly Ser Thr Ser Gly Ser Gly Lys Ser Ser Glu Gly Ser Gly Ser Thr
1               5                   10                  15

Lys Gly

<210> SEQ ID NO 168
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 168

Ser Arg Ser Ser Gly
1               5

<210> SEQ ID NO 169
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 169

Ser Gly Ser Ser Cys
1               5

<210> SEQ ID NO 170
<211> LENGTH: 28
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 170

Ala Met Gly Arg Ser Gly Gly Gly Cys Ala Gly Asn Arg Val Gly Ser
1               5                   10                  15

Ser Leu Ser Cys Gly Gly Leu Asn Leu Gln Ala Met
            20                  25

<210> SEQ ID NO 171
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 171

Gly Gly Gly Gly Ser Gly Gly Gly Ser Gly Gly Gly Gly Ser
1               5                   10                  15

<210> SEQ ID NO 172
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 172

Gly Gly Gly Ser
1

<210> SEQ ID NO 173
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 173

Gly Gly Gly Gly Ser Gly Gly Gly
1               5

<210> SEQ ID NO 174
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 174

Gly Gly Ser Gly Gly Gly Gly
1               5

<210> SEQ ID NO 175
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

```
<400> SEQUENCE: 175

Gly Ser Thr Ser Gly Gly Gly Ser Gly Gly Gly Ser Gly Gly Gly Gly
1               5                   10                  15

Ser Ser

<210> SEQ ID NO 176
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 176

Gly Ser Thr Ser Gly Ser Gly Lys Pro Gly Ser Ser Glu Gly Ser Thr
1               5                   10                  15

Lys Gly

<210> SEQ ID NO 177
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 177

Gly Gly Gly Gly Ser Gly Gly Gly Ser Gly Gly Gly Ser Gly
1               5                   10                  15

Gly Gly Gly Ser
            20

<210> SEQ ID NO 178
<211> LENGTH: 30
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 178

Gly Gly Gly Gly Ser Gly Gly Gly Ser Gly Gly Gly Ser Gly
1               5                   10                  15

Gly Gly Gly Ser Gly Gly Gly Ser Gly Gly Gly Ser
            20                  25                  30

<210> SEQ ID NO 179
<211> LENGTH: 35
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 179

Gly Gly Gly Gly Ser Gly Gly Gly Ser Gly Gly Gly Ser Gly
1               5                   10                  15

Gly Gly Gly Ser Gly Gly Gly Ser Gly Gly Gly Ser Gly Gly
            20                  25                  30

Gly Gly Ser
```

```
<210> SEQ ID NO 180
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 180

Gly Gly Gly Gly Ser Gly Gly Gly Gly Ser Gly Gly Gly Gly Ser
1               5                   10                  15

<210> SEQ ID NO 181
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 181

Ser Pro Ser Thr Pro Pro Thr Pro Ser Pro Ser Thr Pro Pro Ala
1               5                   10                  15
```

HER2-TARGETING MOLECULES COMPRISING DE-IMMUNIZED, SHIGA TOXIN A SUBUNIT SCAFFOLDS

CROSS-REFERENCE TO RELATED APPLICATIONS

This application is a Continuation Application of International Application No. PCT/US2019/027627, filed Apr. 16, 2019, which claims benefit under 35 U.S.C. § 119(e) to U.S. Provisional Patent Application No. 62/659,116, filed Apr. 17, 2018, the contents of each of which are incorporated herein by reference in their entirety.

SEQUENCE LISTING

The instant application contains a Sequence Listing which has been submitted electronically in ASCII format and is hereby incorporated by reference in its entirety. Said ASCII copy, created on Apr. 16, 2019, is named PCT-Sequence-Listing-as-filed-P61033WO.txt and is 290485 bytes in size.

TECHNICAL FIELD

The present invention relates to HER2-targeting molecules comprising Shiga toxin effector polypeptides, derived from the A Subunits of naturally occurring Shiga toxins, that comprise a combination of mutations providing (1) de-immunization, (2) a reduction in protease sensitivity, and/or (3) an embedded, T-cell epitope(s); wherein the Shiga toxin effector polypeptides retain one or more Shiga toxin functions, such as, e.g., potent cytotoxicity. The HER2-targeting molecules of the present invention are useful for administration to multicellular organisms, such as, e.g., when it is desirable to (1) eliminate or reduce non-specific toxicities and/or (2) eliminate or reduce certain immune responses. The HER2-targeting molecules of the present invention are useful (1) for selectively killing specific HER2-positive cell type(s) amongst other cells and (2) as therapeutic molecules for treating a variety of diseases, disorders, and conditions involving HER2-expressing cells, including cancers and tumors.

BACKGROUND

HER2 is a particularly attractive molecular target for therapeutics because of its overexpression on the surfaces of tumor and/or cancer cells, its correlation with poor prognoses, and its functional roles in tumorigenesis and cancer development, such as invasiveness and metastasis, and anti-neoplastic drug resistance (Nielsen D et al., Breast 22: 1-12 (2013); Ocafia A, Pandiella A, Curr Pharm Des 19: 808-17 (2013)).

HER2 (human epidermal growth factor receptor 2) is a type I transmembrane tyrosine kinase receptor of the ErbB family (Yamamoto T et al., Nature 319: 230-4 (1986); Slamon D et al., Science 235: 177-82 (1987)). Members of the ErbB family are integral glycoproteins which regulate cell growth, differentiation, and survival by binding to growth factor ligands as dimers (Chantry A, J Biol Chem 270: 3068-73 (1995)).

HER2 is prominently associated with the pathogenesis, progression, and prognosis of certain breast cancers, among other cancers (Citri A, Yarden Y, Nat Rev Mol Cell Biol 7: 505-16 (2006)). The proto-oncogene HER2, which encodes HER2, was found to be amplified and overexpressed in breast cancer cells (King et al., Science 229: 974-6 (1985); Slamon et al. Science 235: 177-82 (1987)). Amplification and/or over-expression of HER2 occurs in approximately 15-30% of breast cancers, and the presence of HER2 in breast cancer is strongly associated with aggressive malignancy, increased disease recurrence, and poor prognosis (Slamon D et al., Science 244: 707-12 (1989)); Bernstein H, N Engl J Med 353: 1652-4 (2005); Pritchard I et al., N Engl J Med 354: 2103-11 (2006); Tan M, Yu D, Adv Exp Med Biol 608: 119-29 (2007); Mitri Z et al., Chemother Res Pract 2012: 743193 (2012)).

HER2 is overexpressed in many other diverse cancers and may functionally contribute to tumorigenesis generally. HER2 overexpression has been observed in breast, colorectal, endometrial, esophageal, gastric, head and neck, lung, ovarian, prostate, pancreatic, and testicular germ cell tumor cells (Kern J et al., Cancer Res 50: 5184-7 (1990); Natali P et al., Int J Cancer 45: 457-61 (1990); Jaehne J et al., J Cancer Res Clin Oncol 118: 474-9 (1992); Signoretti S et al., J Natl Cancer Inst 92: 1918-25 (2000); Di Lorenzo G et al., Clin Cancer Res 8: 3438-44 (2002); Owens M et al., Clin Breast Cancer 5: 63-9 (2004); Roskoski R, Biochem Biophys Res Commun 319: 1-11 (2004); Cohen G et al., Cancer Res 66: 5656-64 (2006); Santin A et al., Int J Gynaecol Obstet 102: 128-31 (2008); Vermeij J et al., BMC Cancer 8: 3 (2008); Chen P et al., J Clin Pathol 66: 113-9 (2013); Chou et al., Genome Med 5: 78 (2013); Cros J et al., Ann Oncol 24: 2624-9 (2013); Konig A et al., Anticancer Res 33: 4975-82 (2013); Sugishita Y et al., Int J Oncol 42: 1589-96 (2013)). In addition, overexpression of HER2 in a tumor cell can confer drug resistance to anti-neoplastic agents (Koutras A et al., Crit Rev Oncol Hematol 74: 73-8 (2010)).

There is an urgent need for new therapeutics to supplement present day therapies for HER2-bearing neoplasms. Thus, it would be desirable to have cytotoxic cell-targeting molecules which target HER2 for use as therapeutic molecules to treat a variety of diseases, such as, e.g., cancers and tumors, that can be treated by selective killing of, or selective delivery of a beneficial agent into, a HER2 positive cell. In particular, it would be desirable to have HER2-binding, cytotoxic, cell-targeting molecules exhibiting low antigenicity and/or immunogenicity, low off-target toxicity, and potent cytotoxicity. Furthermore, it would be desirable to have HER2-targeting therapeutic and/or diagnostic molecules exhibiting low antigenicity and/or immunogenicity, low off-target toxicity, high stability, and/or the ability to deliver peptide-epitope cargos for presentation by the MHC class I system of a target cell. For example, it would be desirable to have cytotoxic HER2-targeting molecules comprising Shiga toxin A Subunit derived components which maintain potent cytotoxicity to target cells while 1) reducing the potential for unwanted antigenicities and/or immunogenicities, 2) reducing the potential for non-specific toxicities, 3) allowing for drug tolerability over a wide range of dosages, 4) allowing for drug tolerance after repeated administration, and 5) retaining effectiveness in the presence of one or more additional HER2-targeted therapies.

SUMMARY OF THE INVENTION

The Shiga toxin A Subunit derived components of the HER2-targeting molecules of the present invention each comprise a combination of features (e.g., de-immunized sub-region(s) and a protease-cleavage resistant sub-region). Certain combination Shiga toxin effector polypeptides of the present invention are more useful because they provide several Shiga toxin effector functions in a single polypeptide, such as, e.g., promoting cellular internalization, directing sub-cellular routing to the cytosol, ribosome inactivation, and/or delivering cargos to subcellular compartments. Certain HER2-targeting molecules of the present invention are more useful because they provide a combination of several properties in a single molecule, such as, e.g., efficient cellular internalization, potent cell-targeted cytotoxicity, selective cytotoxicity, de-immunization, low non-specific toxicity at high dosages, high stability, CD8+ T-cell hyper-immunization, and/or 5) retention of effectiveness in the presence of one or more additional HER2-targeted therapies. Different embodiments of the HER2-targeting molecules of the present invention are described below with reference to sets of embodiments numbered #1-3.

Embodiment Set #1—HER2-Targeting Molecule Comprising a De-Immunized Shiga Toxin Effector Polypeptide Comprising an Embedded or Inserted, Heterologous, T-Cell Epitope and a Non-Overlapping De-Immunized Sub-Region The present invention provides cell-targeting molecules, each comprising (i) a binding region capable of specifically binding an extracellular target biomolecule (HER2/neu/ErbB2) and (ii) a de-immunized, Shiga toxin A Subunit effector polypeptide. For example, certain embodiments of Set #1 is the cell-targeting molecule comprising (i) a binding region capable of specifically binding an extracellular target biomolecule and (ii) a de-immunized, Shiga toxin effector polypeptide comprising a Shiga toxin A1 fragment region and a carboxy-terminus, wherein the Shiga toxin A subunit effector polypeptide comprises: (a) at least one inserted or embedded, heterologous epitope; and (b) at least one disrupted, endogenous, B-cell and/or CD4+ T-cell epitope region which does not overlap with the embedded or inserted, heterologous, T-cell epitope. For certain further embodiments, the Shiga toxin effector polypeptide is capable of exhibiting at least one Shiga toxin effector function, such as, e.g., directing intracellular routing to the endoplasmic reticulum and/or cytosol of a cell in which the polypeptide is present, inhibiting a ribosome function, enzymatically inactivating a ribosome, causing cytostasis, and/or causing cytotoxicity. The Shiga toxin effector polypeptide of Embodiment Set #1 may be truncated at its carboxy-terminus, relative to a wild-type Shiga toxin A Subunit, resulting in the elimination of one or more endogenous, B-cell and/or CD4+ T-cell epitope regions. The Shiga toxin effector polypeptide of Embodiment Set #1 may comprise a disrupted furin-cleavage motif at the carboxy-terminus of the A1 fragment region. In certain embodiments, the furin-cleavage motif is disrupted by a carboxy-terminal truncation of the Shiga toxin effector polypeptide as compared to the carboxy-terminus of a wild-type Shiga toxin A Subunit. For example, the present invention provides a Shiga toxin effector polypeptide comprising a Shiga toxin A1 fragment region and a carboxy-terminus, wherein the Shiga toxin A subunit effector polypeptide comprises: (a) an embedded or inserted, heterologous, epitope; (b) a disruption of at least one, endogenous, B-cell and/or CD4+ T-cell epitope region; and (c) a disrupted furin-cleavage motif at the carboxy-terminus of the Shiga toxin A1 fragment region; wherein the Shiga toxin A subunit effector polypeptide is capable of exhibiting a Shiga toxin effector function. In a further example, the present invention provides a Shiga toxin A subunit effector polypeptide comprising a Shiga toxin A1 fragment region and a carboxy-terminus, wherein the Shiga toxin A subunit effector polypeptide comprises (a) an embedded or inserted, heterologous, CD8+ T-cell epitope which disrupts an endogenous, B-cell and/or CD4+ T-cell epitope region; (b) a disruption of at least four, endogenous, B-cell and/or CD4+ T-cell epitope regions which do not overlap with the embedded or inserted, heterologous, CD8+ T-cell epitope; and (c) a disrupted furin-cleavage motif at the carboxy-terminus of the Shiga toxin A1 fragment region; and wherein the Shiga toxin A subunit effector polypeptide is truncated at its carboxy-terminus, relative to a wild-type Shiga toxin A subunit, resulting in the elimination of one or more endogenous, B-cell and/or CD4+ T-cell epitope regions; wherein the Shiga toxin A subunit effector polypeptide is capable of exhibiting a Shiga toxin effector function. Accordingly, the present invention provides a HER2-targeting molecule that comprises: (i) an immunoglobulin binding region capable of specifically binding an extracellular part of HER2/neu/ErbB2, and comprising one or more of: an antibody variable fragment, a single-domain antibody fragment, a single-chain variable fragment, a Fd fragment, an antigen-binding fragment, an autonomous VH domain, a $V_HH$ fragment derived from a camelid antibody, a heavy-chain antibody domain derived from a cartilaginous fish antibody, a VNAR fragment, and an immunoglobulin new antigen receptor; and ii) a Shiga toxin A subunit effector polypeptide comprising a Shiga toxin A1 fragment region and a carboxy-terminus, wherein the Shiga toxin A subunit effector polypeptide comprises: (a) an embedded or inserted, heterologous, CD8+ T-cell epitope which disrupts an endogenous, B-cell and/or CD4+ T-cell epitope region; (b) a disruption of at least four, endogenous, B-cell and/or CD4+ T-cell epitope regions which do not overlap with the embedded or inserted, heterologous, CD8+ T-cell epitope; and (c) a disrupted furin-cleavage motif at the carboxy-terminus of the Shiga toxin A1 fragment region; and wherein the Shiga toxin A subunit effector polypeptide is truncated at its carboxy-terminus, relative to a wild-type Shiga toxin A subunit, resulting in the elimination of one or more endogenous, B-cell and/or CD4+ T-cell epitope regions; wherein the Shiga toxin A subunit effector polypeptide is capable of exhibiting a Shiga toxin effector function. For certain further embodiments, the cell-targeting molecule is capable when introduced to cells of exhibiting a cytotoxicity comparable or better than a reference molecule, such as, e.g., a second cell-targeting molecule consisting of the cell-targeting molecule except for all of its Shiga toxin effector polypeptide components comprise a wild-type Shiga toxin furin-cleavage site at the carboxy terminus of its A1 fragment region.

For certain embodiments of Embodiment Set #1, the cell-targeting molecule exhibits reduced relative antigenicity and/or relative immunogenicity as compared to a reference molecule, such as, e.g., a wild-type Shiga toxin A Subunit or a third cell-targeting molecule consisting of the cell-targeting molecule except for all of its Shiga toxin effector polypeptide component(s) each comprise a wild-type Shiga toxin A1 fragment.

In certain embodiments of Embodiment Set #1, the binding region and Shiga toxin effector polypeptide are linked together, either directly or indirectly.

In certain embodiments of Embodiment Set #1, the binding region comprises a polypeptide comprising an immunoglobulin or immunoglobulin-type binding region. In certain further embodiments, the binding region comprising a polypeptide selected from the group consisting of: an autonomous $V_H$ domain, single-domain antibody fragment (sdAb), Nanobody®, heavy chain-antibody domain derived from a camelid antibody ($V_HH$ or $V_H$ domain fragment), heavy-chain antibody domain derived from a cartilaginous fish antibody ($V_HH$ or $V_H$ domain fragment), immunoglobulin new antigen receptor (IgNAR), $V_{NAR}$ fragment, single-chain variable fragment (scFv), antibody variable fragment (Fv), complementary determining region 3 fragment (CDR3), constrained FR3-CDR3-FR4 polypeptide (FR3-CDR3-FR4), Fd fragment, small modular immunopharmaceutical (SMIP) domain, antigen-binding fragment (Fab), Armadillo repeat polypeptide (ArmRP), fibronectin-derived $10^{th}$ fibronectin type III domain (10Fn3), tenascin type III domain (TNfn3), ankyrin repeat motif domain, low-density-lipoprotein-receptor-derived A-domain (LDLR-A), lipocalin (anticalin), Kunitz domain, Protein-A-derived Z domain, gamma-B crystallin-derived domain, ubiquitin-derived domain, Sac7d-derived polypeptide (affitin), Fyn-derived SH2 domain, miniprotein, C-type lectin-like domain scaffold, engineered antibody mimic, and any genetically manipulated counterparts of any of the foregoing which retain binding functionality. In certain embodiments, the binding region comprises a polypeptide selected from the group consisting of: an autonomous $V_H$ domain, single-domain antibody fragment (sdAb), Nanobody®, heavy chain-antibody domain derived from a camelid antibody ($V_HH$ or $V_H$ domain fragment), heavy-chain antibody domain derived from a cartilaginous fish antibody ($V_HH$ or $V_H$ domain fragment), immunoglobulin new antigen receptor (IgNAR), $V_{NAR}$ fragment, single-chain variable fragment (scFv), antibody variable fragment (Fv), Fd fragment, and antigen-binding fragment (Fab). In certain embodiments, the cell-targeting molecule of the present invention comprises an immunoglobulin binding region capable of specifically binding an extracellular part of HER2/neu/ErbB2, and comprising one or more of: an antibody variable fragment, a single-domain antibody fragment, a single-chain variable fragment, a Fd fragment, an antigen-binding fragment, an autonomous $V_H$ domain, a $V_HH$ fragment derived from a camelid antibody, a heavy-chain antibody domain derived from a cartilaginous fish antibody, a VNAR fragment, and an immunoglobulin new antigen receptor. In certain embodiments, the binding region comprises, consists essentially of, or consists of a single-chain variable fragment (scFv). In certain embodiments, the binding region comprises a single-chain variable fragment (scFv). In certain embodiments, the binding region comprises, consists essentially of, or consists of a $V_HH$ fragment derived from a camelid antibody.

In certain embodiments of Embodiment Set #1, the binding region and the Shiga toxin effector polypeptide are fused, either directly or indirectly, forming a continuous polypeptide such that the binding region is associated, either directly or indirectly, with the carboxy-terminus of the Shiga toxin effector polypeptide.

For certain embodiments of Embodiment Set #1, the cell-targeting molecule of the present invention is capable of exhibiting (i) a catalytic activity level comparable to a wild-type Shiga toxin A1 fragment or wild-type Shiga toxin effector polypeptide, (ii) a ribosome inhibition activity with a half-maximal inhibitory concentration ($IC_{50}$) value of 10,000 picomolar or less, and/or (iii) a significant level of Shiga toxin catalytic activity.

For certain embodiments of Embodiment Set #1, the cell-targeting molecule of the present invention and/or its Shiga toxin effector polypeptide is (i) capable of exhibiting subcellular routing efficiency comparable to a reference cell-targeting molecule, such as, e.g., a third cell-targeting molecule consisting of the cell-targeting molecule except for all of its Shiga toxin effector polypeptide component(s) each comprise a wild-type Shiga toxin A1 fragment, and/or (ii) capable of exhibiting a significant level of intracellular routing activity to the endoplasmic reticulum and/or cytosol from an endosomal starting location of a cell.

For certain embodiments of Embodiment Set #1, whereby administration of the cell-targeting molecule of the present invention to a cell physically coupled with the extracellular target biomolecule of the cell-targeting molecule's binding region, the cell-targeting molecule is capable of causing death of the cell. For certain further embodiments, administration of the cell-targeting molecule of the invention to two different populations of cell types which differ with respect to the presence or level of the extracellular target biomolecule, the cell-targeting molecule is capable of causing cell death to the cell-types physically coupled with an extracellular target biomolecule of the cytotoxic cell-targeting molecule's binding region at a CD50 at least three times or less than the CD50 to cell types which are not physically coupled with an extracellular target biomolecule of the cell-targeting molecule's binding region. For certain embodiments, whereby administration of the cell-targeting molecule of the present invention to a first populations of cells whose members are physically coupled to extracellular target biomolecules of the cell-targeting molecule's binding region, and a second population of cells whose members are not physically coupled to any extracellular target biomolecule of the binding region, the cytotoxic effect of the cell-targeting molecule to members of said first population of cells relative to members of said second population of cells is at least 3-fold greater. For certain embodiments, whereby administration of the cell-targeting molecule of the present invention to a first populations of cells whose members are physically coupled to a significant amount of the extracellular target biomolecule of the cell-targeting molecule's binding region, and a second population of cells whose members are not physically coupled to a significant amount of any extracellular target biomolecule of the binding region, the cytotoxic effect of the cell-targeting molecule to members of said first population of cells relative to members of said second population of cells is at least 3-fold greater. For certain embodiments, whereby administration of the cell-targeting molecule of the present invention to a first population of target biomolecule positive cells, and a second population of cells whose members do not express a significant amount of a target biomolecule of the cell-targeting molecule's binding region at a cellular surface, the cytotoxic effect of the cell-targeting molecule to members of the first population of cells relative to members of the second population of cells is at least 3-fold greater.

For certain embodiments of Embodiment Set #1, the cell-targeting molecule of the present invention is capable when introduced to cells of exhibiting a cytotoxicity with a half-maximal inhibitory concentration (CD50) value of 300 nM or less and/or capable of exhibiting a significant level of Shiga toxin cytotoxicity. For certain further embodiments, the cell-targeting molecule exhibits reduced relative antigenicity and/or relative immunogenicity as compared to a reference molecule, such as, e.g., a wild-type Shiga toxin A Subunit or a third cell-targeting molecule consisting of the cell-targeting molecule except for all of its Shiga toxin effector polypeptide component(s) each comprise a wild-type Shiga toxin A1 fragment.

In certain embodiments of Embodiment Set #1, the heterologous, T-cell epitope is a CD8+ T-cell epitope, such as, e.g., with regard to a human immune system. For certain further embodiments, the heterologous, T-cell epitope is capable of being presented by a MHC class I molecule of a cell. In certain further embodiments, the cell-targeting molecule of the present invention is capable of one or more the following: entering a cell, inhibiting a ribosome function, causing cytostasis, causing cell death, and/or delivering the embedded or inserted, heterologous, T-cell epitope to a MHC class I molecule for presentation on a cellular surface. For certain further embodiments, the cell-targeting molecule is capable when introduced to cells of exhibiting a cytotoxicity comparable or better than a reference molecule, such as, e.g., a third cell-targeting molecule consisting of the cell-targeting molecule except for all of its Shiga toxin effector polypeptide component(s) each comprise a wild-type Shiga toxin A1 fragment.

For certain embodiments of Embodiment Set #1, the cell-targeting molecule of the present invention is capable of delivering an embedded or inserted, heterologous, CD8+ T-cell epitope to a MHC class I presentation pathway of a cell for cell-surface presentation of the epitope bound by a MHC class I molecule.

In certain embodiments of Embodiment Set #1, the cell-targeting molecule comprises a molecular moiety located carboxy-terminal to the carboxy-terminus of the Shiga toxin A1 fragment region.

For certain embodiments of Embodiment Set #1, the cell-targeting molecule of the present invention is capable when introduced to a chordate of exhibiting improved in vivo tolerability and/or stability compared to a reference molecule, such as, e.g., a fourth cell-targeting molecule consisting of the cell-targeting molecule except for all of its Shiga toxin effector polypeptide component(s) each comprise a wild-type Shiga toxin A1 fragment and/or wild-type Shiga toxin furin-cleavage site at the carboxy terminus of its A1 fragment region. In certain further embodiments, the Shiga toxin effector polypeptide is not cytotoxic and the molecular moiety is cytotoxic.

In certain embodiments of Embodiment Set #1, the cell-targeting molecule comprises a molecular moiety associated with the carboxy-terminus of the Shiga toxin effector polypeptide. In certain embodiments, the molecular moiety comprises or consists of the binding region. In certain embodiments, the molecular moiety comprises at least one amino acid and the Shiga toxin effector polypeptide is linked to at least one amino acid residue of the molecular moiety. In certain further embodiments, the molecular moiety and the Shiga toxin effector polypeptide are fused forming a continuous polypeptide.

In certain embodiments of Embodiment Set #1, the cell-targeting molecule further comprises a cytotoxic molecular moiety associated with the carboxy-terminus of the Shiga toxin effector polypeptide. For certain embodiments, the cytotoxic molecular moiety is a cytotoxic agent, such as, e.g., a small molecule chemotherapeutic agent, anti-neoplastic agent, cytotoxic antibiotic, alkylating agent, antimetabolite, topoisomerase inhibitor, and/or tubulin inhibitor known to the skilled worker and/or described herein. For certain further embodiments, the cytotoxic molecular moiety is cytotoxic at concentrations of less than 10,000, 5,000, 1,000, 500, or 200 pM.

In certain embodiments of Embodiment Set #1, the binding region is linked, either directly or indirectly, to the Shiga toxin effector polypeptide by at least one covalent bond which is not a disulfide bond. In certain further embodiments, the binding region is fused, either directly or indirectly, to the carboxy-terminus of the Shiga toxin effector polypeptide to form a single, continuous polypeptide. In certain further embodiments, the binding region is an immunoglobulin or immunoglobulin-type binding region.

In certain embodiments of Embodiment Set #1, the disrupted furin-cleavage motif comprises one or more mutations in the minimal, furin-cleavage site relative to a wild-type Shiga toxin A Subunit. In certain embodiments, the disrupted furin-cleavage motif is not an amino-terminal truncation of sequences that overlap with part or all of at least one amino acid residue of the minimal furin-cleavage site. In certain embodiments, the mutation in the minimal, furin-cleavage site is an amino acid deletion, insertion, and/or substitution of at least one amino acid residue in the R/Y-x-x-R furin cleavage motif. In certain further embodiments, the disrupted furin-cleavage motif comprises at least one mutation relative to a wild-type Shiga toxin A Subunit, the mutation altering at least one amino acid residue in the region natively positioned (1) at 248-251 of the A Subunit of Shiga-like toxin 1 (SEQ ID NO:1), Shiga toxin (SEQ ID NO:2), or another Shiga toxin 1 variant sequence (e.g. SEQ ID NOs: 4-6); or (2) at 247-250 of the A Subunit of Shiga-like toxin 2 (SEQ ID NO:3) or a Shiga-like toxin 2 variant sequence (e.g. SEQ ID NOs: 7-18), or the equivalent amino acid sequence position in any Shiga toxin A Subunit. In certain further embodiments, the mutation is an amino acid residue substitution of an arginine residue with a non-positively charged, amino acid residue.

In certain embodiments of Embodiment Set #1, the Shiga toxin effector polypeptide comprises, consists essentially of, or consists of: (i) amino acids 75 to 251 of any one of SEQ ID NOs: 1-6 and 37; (ii) amino acids 1 to 241 of any one of SEQ ID NOs: 1-18 and 75-89; (iii) amino acids 1 to 251 of any one of SEQ ID NOs: 1-6, 37, and 75-89; or (iv) amino acids 1 to 261 of any one of SEQ ID NOs: 1-3; wherein the Shiga toxin effector polypeptide comprises at least one embedded or inserted, heterologous T-cell epitope and at least one (two, three, four or more) disrupted, endogenous, B-cell and/or CD4+ T-cell epitope region(s) which does not overlap with the embedded or inserted, heterologous, T-cell epitope.

In certain embodiments of Embodiment Set #1, the cell-targeting molecule of the present invention is capable when introduced to cells of exhibiting cytotoxicity comparable to a cytotoxicity of a reference molecule, such as, e.g., a third cell-targeting molecule consisting of the cell-targeting molecule except for all of its Shiga toxin effector polypeptide component(s) each comprise a wild-type Shiga toxin A1 fragment.

In certain embodiments of Embodiment Set #1, the binding region may comprise at least one heavy-chain variable domain polypeptide comprising (i) the HCDR1, HCDR2, and HCDR3 amino acid sequences shown in SEQ ID NOs: 51, SEQ ID NO:52, and SEQ ID NO:53, respectively; and at least one light-chain variable domain polypeptide comprising: (i) the LCDR1, LCDR2, and LCDR3 amino acid sequences shown in SEQ ID NO:54, SEQ ID NO:55, and SEQ ID NO:56, respectively. For example, the binding region may comprises at least one heavy-chain variable domain polypeptide comprising (i) the HCDR1, HCDR2, and HCDR3 amino acid sequences shown in SEQ ID NOs: 57, SEQ ID NO:58, and SEQ ID NO:59, respectively; and at least one light-chain variable domain polypeptide comprising (i) the LCDR1, LCDR2, and LCDR3 amino acid sequences shown in SEQ ID NO:60, SEQ ID NO:61, and SEQ ID NO:62, respectively. For example, the binding region may comprises at least one heavy-chain variable domain polypeptide comprising (i) the HCDR1, HCDR2, and HCDR3 amino acid sequences shown in SEQ ID NOs: 63, SEQ ID NO:64, and SEQ ID NO:65, respectively; and at least one light-chain variable domain polypeptide comprising (i) the LCDR1, LCDR2, and LCDR3 amino acid sequences shown in SEQ ID NO:66, SEQ ID NO:67, and SEQ ID NO:68, respectively. The binding region having these CDRs may be an immunoglobulin binding region comprising a single-chain variable fragment.

In certain embodiments of Embodiment Set #1, the binding region may comprises the binding region comprises a polypeptide selected from the group consisting of: a) a heavy chain only variable ($V_HH$) domain comprising (i) a HCDR1 comprising or consisting essentially of the amino acid sequences as shown in SEQ ID NO:69 or SEQ ID NO:72; (ii) a HCDR2 comprising or consisting essentially of the amino acid sequence as shown in SEQ ID NO:70 or SEQ ID NO:73; and (iii) a HCDR3 comprising or consisting essentially of the amino acid sequence as shown in SEQ ID NO:71 or SEQ ID NO:74. The binding region having these CDRs may be an immunoglobulin binding region comprising a heavy chain only variable ($V_HH$) domain derived from a camelid antibody.

In certain embodiments of Embodiment Set #1, the binding region may comprise: (a) at least one heavy chain variable ($V_H$) domain comprising, consisting essentially of, or consisting of: amino acids 269 to 387 of SEQ ID NOs: 26, 29, 30, or 36; amino acids 269 to 397 of SEQ ID NO:25; amino acids 381 to 500 of SEQ ID NO: 24 or 27; amino acids 401 to 522 of SEQ ID NO:36, or amino acids 401 to 520 of SEQ ID NO:28; and (b) at least one light chain variable ($V_L$) domain comprising, consisting essentially of, or consisting of: amino acids 269 to 375 of SEQ ID NO: 24, 27, or 28; amino acids 393 to 499 of SEQ ID NO:26; amino acids 403 to 513 of SEQ ID NO:25; amino acids 408 to 514 of SEQ ID NO:36; and amino acids 413 to 519 of SEQ ID NO: 29 or 30. For example, the binding region may comprise (a) at least one heavy chain variable ($V_H$) domain comprising, consisting essentially of, or consisting of amino acids 269 to 387 of SEQ ID NO:29; and (b) at least one light chain variable ($V_L$) domain comprising, consisting essentially of, or consisting of amino acids 413 to 519 of SEQ ID NO:29. For example, the binding region may comprise (a) at least one heavy chain variable ($V_H$) domain comprising, consisting essentially of, or consisting of amino acids 269 to 387 of SEQ ID NO:36; and (b) at least one light chain variable ($V_L$) domain comprising, consisting essentially of, or consisting of amino acids 408 to 514 of SEQ ID NO:36

In certain embodiments of Embodiment Set #1, the binding region comprises, consists essentially of, or consists of the polypeptide represented by any one of the following polypeptide sequences: amino acids 269 to 513 of SEQ ID NO:25; amino acids 269 to 499 of SEQ ID NO:26; amino acids 269 to 519 of SEQ ID NO:29 or SEQ ID NO:30; amino acids 268 to 386 of SEQ ID NO:31; amino acids 253 to 370 of SEQ ID NO:34; amino acids 253 to 367 of SEQ ID NO:35; or amino acids 269 to 514 of SEQ ID NO:36. For example, the binding region comprises, consists essentially of, or consists of the polypeptide represented by amino acids 269 to 519 of SEQ ID NO:29. For example, the binding region comprises, consists essentially of, or consists of the polypeptide represented by amino acids 268 to 518 of SEQ ID NO:102. For example, the binding region comprises, consists essentially of, or consists of the polypeptide represented by amino acids 268 to 386 of SEQ ID NO:31. For example, the binding region comprises, consists essentially of, or consists of the polypeptide represented by amino acids 253 to 370 of SEQ ID NO:34. For example, the binding region comprises, consists essentially of, or consists of the polypeptide represented by amino acids 253 to 367 of SEQ ID NO:35. For example, the binding region comprises, consists essentially of, or consists of the polypeptide represented by amino acids 269 to 514 of SEQ ID NO:36.

In certain embodiments of Embodiment Set #1, the cell-targeting molecule of the present invention comprises, consists essentially of, or consists of the polypeptide shown in any one of SEQ ID NOs: 22-36 and 97-108. In certain embodiments of Embodiment Set #1, the cell-targeting molecule of the present invention comprises, consists essentially of, or consists of the polypeptide shown in any one of SEQ ID NOs: 29, 31, 34, 35, 36, 102, 104, and 106-108. In certain further embodiments, the cell-targeting molecule of the present invention further comprises an amino terminal methionine residue. In certain further embodiments, the cell-targeting molecule of the present invention comprises, consists essentially of, or consists of the polypeptide shown in SEQ ID NO: 29 or 102.

In certain embodiments of Embodiment Set #1, the binding region sterically covers the carboxy-terminus of the A1 fragment region.

In certain embodiments of Embodiment Set #1, the molecular moiety sterically covers the carboxy-terminus of the A1 fragment region. In certain further embodiments, the molecular moiety comprises the binding region.

In certain embodiments of Embodiment Set #1, the cell-targeting molecule of the present invention comprises a binding region and/or molecular moiety located carboxy-terminal to the carboxy-terminus of the Shiga toxin A1 fragment region. In certain further embodiments, the mass of the binding region and/or molecular moiety is at least 4.5 kDa, 6, kDa, 9 kDa, 12 kDa, 15 kDa, 20 kDa, 25 kDa, 28 kDa, 30 kDa, 41 kDa, 50 kDa, 100 kDa, or greater.

In certain embodiments of Embodiment Set #1, the cell-targeting molecule comprises a binding region with a mass of at least 4.5 kDa, 6, kDa, 9 kDa, 12 kDa, 15 kDa, 20 kDa, 25 kDa, 28 kDa, 30 kDa, 41 kDa, 50 kDa, 100 kDa, or greater, as long as the cell-targeting molecule retains the appropriate level of the Shiga toxin biological activity noted herein (e.g., cytotoxicity and/or intracellular routing).

In certain embodiments of Embodiment Set #1, the binding region is comprised within a relatively large, molecular moiety comprising such as, e.g., a molecular moiety with a mass of at least 4.5 kDa, 6, kDa, 9 kDa, 12 kDa, 15 kDa, 20 kDa, 25 kDa, 28 kDa, 30 kDa, 41 kDa, 50 kDa, 100 kDa, or greater, as long as the cell-targeting molecule retains the appropriate level of the Shiga toxin biological activity noted herein.

In certain embodiments of Embodiment Set #1, the amino-terminus of the Shiga toxin effector polypeptide is at and/or proximal to an amino-terminus of a polypeptide component of the cell-targeting molecule. In certain further embodiments, the binding region is not located proximally to the amino-terminus of the cell-targeting molecule relative to the Shiga toxin effector polypeptide. In certain further embodiments, the binding region and Shiga toxin effector polypeptide are physically arranged or oriented within the cell-targeting molecule such that the binding region is not located proximally to the amino-terminus of the Shiga toxin effector polypeptide. In certain further embodiments, the binding region is located within the cell-targeting molecule more proximal to the carboxy-terminus of the Shiga toxin effector polypeptide than to the amino-terminus of the Shiga toxin effector polypeptide. For certain further embodiments, the cell-targeting molecule of the present invention is capable when introduced to cells of exhibiting cytotoxicity that is greater than that of a third cell-targeting molecule having an amino-terminus and comprising the binding region and the Shiga toxin effector polypeptide which is not positioned at or proximal to the amino-terminus of the third cell-targeting molecule. For certain further embodiments, the cell-targeting molecule of the present invention exhibits cytotoxicity with better optimized, cytotoxic potency, such as, e.g., 4-fold, 5-fold, 6-fold, 9-fold, or greater cytotoxicity as compared to the cytotoxicity of the third cell-targeting molecule. For certain further embodiments, the cytotoxicity of the cell-targeting molecule of the present invention to a population of target positive cells is 3-fold, 4-fold, 5-fold, 6-fold, 7-fold, 8-fold, 9-fold, 10-fold or greater than the cytotoxicity of the third cell-targeting molecule to a second population of target positive cells as assayed by $CD_{50}$ values. In certain further embodiments, the third cell-targeting molecule does not comprise any carboxy-terminal, endoplasmic reticulum retention/retrieval signal motif of the KDEL family (e.g. SEQ ID NO:109).

In certain embodiments of Embodiment Set #1, the amino-terminus of the Shiga toxin effector polypeptide is at and/or proximal to an amino-terminus of a polypeptide component of the cell-targeting molecule. In certain further embodiments, the binding region is not located proximally to the amino-terminus of the cell-targeting molecule relative to the Shiga toxin effector polypeptide. In certain further embodiments, the binding region and Shiga toxin effector polypeptide are physically arranged or oriented within the cell-targeting molecule such that the binding region is not located proximally to the amino-terminus of the Shiga toxin effector polypeptide. In certain further embodiments, the binding region is located within the cell-targeting molecule more proximal to the carboxy-terminus of the Shiga toxin effector polypeptide than to the amino-terminus of the Shiga toxin effector polypeptide. For certain further embodiments, the cell-targeting molecule of the present invention is not cytotoxic and is capable when introduced to cells of exhibiting a greater subcellular routing efficiency from an extracellular space to a subcellular compartment of an endoplasmic reticulum and/or cytosol as compared to the cytotoxicity of a reference molecule, such as, e.g., a fifth cell-targeting molecule having an amino-terminus and comprising the binding region and the Shiga toxin effector polypeptide which is not positioned at or proximal to the amino-terminus of the fifth cell-targeting molecule. In certain further embodiments, the fifth cell-targeting molecule does not comprise any carboxy-terminal, endoplasmic reticulum retention/retrieval signal motif of the KDEL family.

In certain embodiments of Embodiment Set #1, the amino-terminus of the Shiga toxin effector polypeptide is at and/or proximal to an amino-terminus of a polypeptide component of the cell-targeting molecule. In certain further embodiments, the binding region is not located proximally to the amino-terminus of the cell-targeting molecule relative to the Shiga toxin effector polypeptide. In certain further embodiments, the binding region and Shiga toxin effector polypeptide are physically arranged or oriented within the cell-targeting molecule such that the binding region is not located proximally to the amino-terminus of the Shiga toxin effector polypeptide. In certain further embodiments, the binding region is located within the cell-targeting molecule more proximal to the carboxy-terminus of the Shiga toxin effector polypeptide than to the amino-terminus of the Shiga toxin effector polypeptide. For certain further embodiments, the cell-targeting molecule of the present invention exhibits low cytotoxic potency (i.e. is not capable when introduced to certain positive target cell types of exhibiting a cytotoxicity greater than 1% cell death of a cell population at a cell-targeting molecule concentration of 1000 nM, 500 nM, 100 nM, 75 nM, or 50 nM) and is capable when introduced to cells of exhibiting a greater subcellular routing efficiency from an extracellular space to a subcellular compartment of an endoplasmic reticulum and/or cytosol as compared to the cytotoxicity of a reference cell-targeting molecule, such as, e.g., a fifth cell-targeting molecule having an amino-terminus and comprising the binding region and the Shiga toxin effector polypeptide which is not positioned at or proximal to the amino-terminus of the fifth cell-targeting molecule. In certain further embodiments, the fifth cell-targeting molecule does not comprise any carboxy-terminal, endoplasmic reticulum retention/retrieval signal motif of the KDEL family.

In certain embodiments of Embodiment Set #1, the cell-targeting molecule of the present invention, or a polypeptide component thereof, comprises a carboxy-terminal, endoplasmic reticulum retention/retrieval signal motif of a member of the KDEL family. For certain further embodiments, the carboxy-terminal endoplasmic reticulum retention/retrieval signal motif is selected from the group consisting of: KDEL (SEQ ID NO:109), HDEF (SEQ ID NO:110), HDEL (SEQ ID NO:111), RDEF (SEQ ID NO:112), RDEL (SEQ ID NO:113), WDEL (SEQ ID NO:114), YDEL (SEQ ID NO:115), HEEF (SEQ ID NO:116), HEEL (SEQ ID NO:117), KEEL (SEQ ID NO:118), REEL (SEQ ID NO:119), KAEL (SEQ ID NO:120), KCEL (SEQ ID NO:121), KFEL (SEQ ID NO:122), KGEL (SEQ ID NO:123), KHEL (SEQ ID NO:124), KLEL (SEQ ID NO:125), KNEL (SEQ ID NO:126), KQEL (SEQ ID NO:127), KREL (SEQ ID NO:128), KSEL (SEQ ID NO:129), KVEL (SEQ ID NO:130), KWEL (SEQ ID NO:131), KYEL (SEQ ID NO:132), KEDL (SEQ ID NO:133), KIEL (SEQ ID NO:134), DKEL (SEQ ID NO:135), FDEL (SEQ ID NO:136), KDEF (SEQ ID NO:137), KKEL (SEQ ID NO:138), HADL (SEQ ID NO:139), HAEL (SEQ ID NO:140), HIEL (SEQ ID NO:141), HNEL (SEQ ID NO:142), HTEL (SEQ ID NO:143), KTEL (SEQ ID NO:144), HVEL (SEQ ID NO:145), NDEL (SEQ ID NO:146), QDEL (SEQ ID NO:147), REDL (SEQ ID NO:148), RNEL (SEQ ID NO:149), RTDL (SEQ ID NO:150), RTEL (SEQ ID NO:151), SDEL (SEQ ID NO:152), TDEL (SEQ ID NO:153), SKEL (SEQ ID NO:154), STEL (SEQ ID NO:155), and EDEL (SEQ ID NO:156). In certain further embodiments, the cell-targeting molecule of the present invention is capable when introduced to cells of exhibiting cytotoxicity that is greater than that of a reference molecule, such as, e.g., a sixth cell-targeting molecule consisting of the cell-targeting molecule except for it does not comprise any carboxy-terminal, endoplasmic reticulum retention/retrieval signal motif of the KDEL family. In certain further embodiments, the cell-targeting molecule of the present invention is capable of exhibiting a cytotoxicity with better optimized, cytotoxic potency, such as, e.g., 4-fold, 5-fold, 6-fold, 9-fold, or greater cytotoxicity as compared to the sixth cell-targeting molecule. In certain further embodiments, the cell-targeting molecule of the present invention is capable of exhibiting a cytotoxicity with better optimized, cytotoxic potency, such as, e.g., 4-fold, 5-fold, 6-fold, 9-fold, or greater cytotoxicity as compared to the sixth cell-targeting molecule. In certain further embodiments, the cytotoxicity of the cell-targeting molecule of the present invention to a population of target positive cells is 3-fold, 4-fold, 5-fold, 6-fold, 7-fold, 8-fold, 9-fold, 10-fold or greater than the cytotoxicity of the sixth cell-targeting molecule to a second population of target positive cells as assayed by $CD_{50}$ values.

Embodiment Set #2—HER2-Targeting Molecule Comprising a Shiga Toxin Effector Polypeptide Comprising (i) an Embedded or Inserted, Heterologous, T-Cell Epitope and (ii) a Disrupted, Furin-Cleavage Motif The present invention provides cell-targeting molecules, each comprising (i) a binding region capable of specifically binding an extracellular target biomolecule (HER2/neu/ErbB2) and (ii) a Shiga toxin A Subunit effector polypeptide comprising an inserted or embedded, heterologous, epitope; and (iii) a disrupted furin-cleavage motif. In certain embodiments, the cell-targeting molecule of the present invention comprises (i) a binding region capable of specifically binding an extracellular target biomolecule; (ii) a Shiga toxin effector polypeptide comprising a Shiga toxin A1 fragment derived region and a carboxy terminus, wherein the Shiga toxin effector polypeptide comprises: (a) an inserted or embedded, heterologous, epitope; and (b) a disrupted furin-cleavage motif at the carboxy-terminus of the A1 fragment region. For certain further embodiments, the Shiga toxin effector polypeptide is capable of exhibiting at least one Shiga toxin effector function, such as, e.g., directing intracellular routing to the endoplasmic reticulum and/or cytosol of a cell in which the polypeptide is present, inhibiting a ribosome function, enzymatically inactivating a ribosome, causing cytostasis, and/or causing cytotoxicity. In certain embodiments, the furin-cleavage motif is disrupted by a carboxy-terminal truncation of the Shiga toxin effector polypeptide as compared to the carboxy-terminus of a wild-type Shiga toxin A Subunit. The Shiga toxin effector polypeptide may be truncated at its carboxy-terminus, relative to a wild-type Shiga toxin A subunit, resulting in the elimination of one or more endogenous, B-cell and/or CD4+ T-cell epitope regions. The Shiga toxin effector polypeptide of Embodiment Set #2 may further comprise at least one disrupted, endogenous, B-cell and/or CD4+ T-cell epitope region. In certain embodiments, the at least one disrupted, endogenous, B-cell and/or CD4+ T-cell epitope region does not overlap with the embedded or inserted, heterologous, epitope. For example, the present invention provides a Shiga toxin effector polypeptide comprising a Shiga toxin A1 fragment region and a carboxy-terminus, wherein the Shiga toxin A subunit effector polypeptide comprises: (a) an embedded or inserted, heterologous, epitope; (b) a disruption of at least one, endogenous, B-cell and/or CD4+ T-cell epitope region; and (c) a disrupted furin-cleavage motif at the carboxy-terminus of the Shiga toxin A1 fragment region; wherein the Shiga toxin A subunit effector polypeptide is capable of exhibiting a Shiga toxin effector function. In a further example, the present invention provides a Shiga toxin A subunit effector polypeptide comprising a Shiga toxin A1 fragment region and a carboxy-terminus, wherein the Shiga toxin A subunit effector polypeptide comprises (a) an embedded or inserted, heterologous, CD8+ T-cell epitope which disrupts an endogenous, B-cell and/or CD4+ T-cell epitope region; (b) a disruption of at least four, endogenous, B-cell and/or CD4+ T-cell epitope regions which do not overlap with the embedded or inserted, heterologous, CD8+ T-cell epitope; and (c) a disrupted furin-cleavage motif at the carboxy-terminus of the Shiga toxin A1 fragment region; wherein the Shiga toxin A subunit effector polypeptide is truncated at its carboxy-terminus, relative to a wild-type Shiga toxin A subunit, resulting in the elimination of one or more endogenous, B-cell and/or CD4+ T-cell epitope regions; and wherein the Shiga toxin A subunit effector polypeptide is capable of exhibiting a Shiga toxin effector function. In certain further embodiments, the heterologous, T-cell epitope is a CD8+ T-cell epitope, such as, e.g., with regard to a human immune system. For certain further embodiments, the heterologous, T-cell epitope is capable of being presented by a MHC class I molecule of a cell. In certain further embodiments, the cell-targeting molecule of the present invention is capable of one or more the following: entering a cell, inhibiting a ribosome function, causing cytostasis, causing cell death, and/or delivering the embedded or inserted, heterologous, T-cell epitope to a MHC class I molecule for presentation on a cellular surface. For certain further embodiments, the cell-targeting molecule is capable when introduced to cells of exhibiting a cytotoxicity comparable or better than a reference molecule, such as, e.g., a second cell-targeting molecule consisting of the cell-targeting molecule except for all of its Shiga toxin effector polypeptide components comprise a wild-type Shiga toxin furin-cleavage site at the carboxy terminus of its A1 fragment region.

In certain embodiments of Embodiment Set #2, the binding region and Shiga toxin effector polypeptide are linked together, either directly or indirectly.

In certain embodiments of Embodiment Set #2, the binding region comprises a polypeptide comprising an immunoglobulin or immunoglobulin-type binding region. In certain further embodiments, the binding region comprising a polypeptide selected from the group consisting of: an autonomous $V_H$ domain, single-domain antibody fragment (sdAb), Nanobody®, heavy chain-antibody domain derived from a camelid antibody ($V_HH$ or $V_H$ domain fragment), heavy-chain antibody domain derived from a cartilaginous fish antibody ($V_HH$ or $V_H$ domain fragment), immunoglobulin new antigen receptor (IgNAR), $V_{NAR}$ fragment, single-chain variable fragment (scFv), antibody variable fragment (Fv), complementary determining region 3 fragment (CDR3), constrained FR3-CDR3-FR4 polypeptide (FR3-CDR3-FR4), Fd fragment, small modular immunopharmaceutical (SMIP) domain, antigen-binding fragment (Fab), Armadillo repeat polypeptide (ArmRP), fibronectin-derived 10$^{th}$ fibronectin type III domain (10Fn3), tenascin type III domain (TNfn3), ankyrin repeat motif domain, low-density-lipoprotein-receptor-derived A-domain (LDLR-A), lipocalin (anticalin), Kunitz domain, Protein-A-derived Z domain, gamma-B crystallin-derived domain, ubiquitin-derived domain, Sac7d-derived polypeptide (affitin), Fyn-derived SH2 domain, miniprotein, C-type lectin-like domain scaffold, engineered antibody mimic, and any genetically manipulated counterparts of any of the foregoing which retain binding functionality. In certain embodiments, the binding region comprises a polypeptide selected from the group consisting of: an autonomous $V_H$ domain, single-domain antibody fragment (sdAb), Nanobody®, heavy chain-antibody domain derived from a camelid antibody ($V_HH$ or $V_H$ domain fragment), heavy-chain antibody domain derived from a cartilaginous fish antibody ($V_HH$ or $V_H$ domain fragment), immunoglobulin new antigen receptor (IgNAR), VNAR fragment, single-chain variable fragment (scFv), antibody variable fragment (Fv), Fd fragment, and antigen-binding fragment (Fab). In certain embodiments, the cell-targeting molecule of the present invention comprises an immunoglobulin binding region capable of specifically binding an extracellular part of HER2/neu/ErbB2, and comprising one or more of: an antibody variable fragment, a single-domain antibody fragment, a single-chain variable fragment, a Fd fragment, an antigen-binding fragment, an autonomous $V_H$ domain, a $V_HH$ fragment derived from a camelid antibody, a heavy-chain antibody domain derived from a cartilaginous fish antibody, a VNAR fragment, and an immunoglobulin new antigen receptor. In certain embodiments, the binding region comprises, consists essentially of, or consists of a single-chain variable fragment (scFv). In certain embodiments, the binding region comprises a single-chain variable fragment (scFv). In certain embodiments, the binding region comprises, consists essentially of, or consists of a $V_H H$ fragment derived from a camelid antibody.

In certain embodiments of Embodiment Set #2, the binding region and the Shiga toxin effector polypeptide are fused, either directly or indirectly, forming a continuous polypeptide such that the binding region is associated, either directly or indirectly, with the carboxy-terminus of the Shiga toxin effector polypeptide.

In certain embodiments of Embodiment Set #2, the embedded or inserted, heterologous, T-cell epitope disrupts the endogenous, B-cell and/or CD4+ T-cell epitope region selected from the group of natively positioned Shiga toxin A Subunit regions consisting of: (i) 1-15 of SEQ ID NO:1 or SEQ ID NO:2; 3-14 of SEQ ID NO:3; 26-37 of SEQ ID NO:3; 27-37 of SEQ ID NO:1 or SEQ ID NO:2; 39-48 of SEQ ID NO:1 or SEQ ID NO:2; 42-48 of SEQ ID NO:3; and 53-66 of SEQ ID NO:1, SEQ ID NO:2, or SEQ ID NO:3, or the equivalent region in a Shiga toxin A Subunit or derivative thereof (ii) 94-115 of SEQ ID NO:1, SEQ ID NO:2, or SEQ ID NO:3; 141-153 of SEQ ID NO:1 or SEQ ID NO:2; 140-156 of SEQ ID NO:3; 179-190 of SEQ ID NO:1 or SEQ ID NO:2; 179-191 of SEQ ID NO:3; 204 of SEQ ID NO:3; 205 of SEQ ID NO:1 or SEQ ID NO:2; and 210-218 of SEQ ID NO:3; and (iii) 240-260 of SEQ ID NO:3; 243-257 of SEQ ID NO:1 or SEQ ID NO:2; 254-268 of SEQ ID NO:1 or SEQ ID NO:2; 262-278 of SEQ ID NO:3; 281-297 of SEQ ID NO:3; and 285-293 of SEQ ID NO:1 or SEQ ID NO:2, or the equivalent region in a Shiga toxin A Subunit or derivative thereof.

In certain embodiments of Embodiment Set #2, the disrupted furin-cleavage motif comprises one or more mutations, relative to a wild-type Shiga toxin A Subunit, the mutation altering at least one amino acid residue in a region natively positioned at (1) at 248-251 of the A Subunit of Shiga-like toxin 1 (SEQ ID NO:1), Shiga toxin (SEQ ID NO:2), or another Shiga toxin 1 variant sequence (e.g. SEQ ID NOs: 4-6); or (2) at 247-250 of the A Subunit of Shiga-like toxin 2 (SEQ ID NO:3) or a Shiga-like toxin 2 variant sequence (e.g. SEQ ID NOs: 7-18); or the equivalent region in a Shiga toxin A Subunit or derivative thereof. In certain further embodiments, the disrupted furin-cleavage motif comprises one or more mutations, relative to a wild-type Shiga toxin A Subunit, in a minimal furin cleavage site of the furin-cleavage motif. In certain further embodiments the minimal furin cleavage site is represented by the consensus amino acid sequence R/Y-x-x-R and/or R-x-x-R.

In certain embodiments of Embodiment Set #2, the Shiga toxin effector polypeptide comprises, consists essentially of, or consists of: (i) amino acids 75 to 251 of any one of SEQ ID NOs: 1-6 and 37; (ii) amino acids 1 to 241 of any one of SEQ ID NOs: 1-18 and 75-89; (iii) amino acids 1 to 251 of any one of SEQ ID NOs: 1-6, 37, and 75-89; or (iv) amino acids 1 to 261 of any one of SEQ ID NOs: 1-3; wherein the Shiga toxin effector polypeptide comprises at least one embedded or inserted, heterologous T-cell epitope and a disrupted furin-cleavage motif at the carboxy-terminus of a Shiga toxin A1 fragment derived region.

In certain embodiments of Embodiment Set #2, the cell-targeting molecule comprises a molecular moiety located carboxy-terminal to the carboxy-terminus of the Shiga toxin A1 fragment region.

In certain embodiments of Embodiment Set #2, the binding region sterically covers the carboxy-terminus of the A1 fragment region.

In certain embodiments of Embodiment Set #2, the molecular moiety sterically covers the carboxy-terminus of the A1 fragment region. In certain further embodiments, the molecular moiety comprises the binding region.

In certain embodiments of Embodiment Set #2, the cell-targeting molecule of the present invention comprises a binding region and/or molecular moiety located carboxy-terminal to the carboxy-terminus of the Shiga toxin A1 fragment region. In certain further embodiments, the mass of the binding region and/or molecular moiety is at least 4.5 kDa, 6, kDa, 9 kDa, 12 kDa, 15 kDa, 20 kDa, 25 kDa, 28 kDa, 30 kDa, 41 kDa, 50 kDa, 100 kDa, or greater.

In certain embodiments of Embodiment Set #2, the cell-targeting molecule comprises a binding region with a mass of at least 4.5 kDa, 6, kDa, 9 kDa, 12 kDa, 15 kDa, 20 kDa, 25 kDa, 28 kDa, 30 kDa, 41 kDa, 50 kDa, 100 kDa, or greater, as long as the cell-targeting molecule retains the appropriate level of the Shiga toxin biological activity noted herein (e.g., cytotoxicity and/or intracellular routing).

In certain embodiments of Embodiment Set #2, the binding region is comprised within a relatively large, molecular moiety comprising such as, e.g., a molecular moiety with a mass of at least 4.5 kDa, 6, kDa, 9 kDa, 12 kDa, 15 kDa, 20 kDa, 25 kDa, 28 kDa, 30 kDa, 41 kDa, 50 kDa, 100 kDa, or greater, as long as the cell-targeting molecule retains the appropriate level of the Shiga toxin biological activity noted herein.

In certain embodiments of Embodiment Set #2, the binding region may comprise at least one heavy-chain variable domain polypeptide comprising (i) the HCDR1, HCDR2, and HCDR3 amino acid sequences shown in SEQ ID NOs: 51, SEQ ID NO:52, and SEQ ID NO:53, respectively; and at least one light-chain variable domain polypeptide comprising: (i) the LCDR1, LCDR2, and LCDR3 amino acid sequences shown in SEQ ID NO:54, SEQ ID NO:55, and SEQ ID NO:56, respectively. For example, the binding region may comprises at least one heavy-chain variable domain polypeptide comprising (i) the HCDR1, HCDR2, and HCDR3 amino acid sequences shown in SEQ ID NOs: 57, SEQ ID NO:58, and SEQ ID NO:59, respectively; and at least one light-chain variable domain polypeptide comprising (i) the LCDR1, LCDR2, and LCDR3 amino acid sequences shown in SEQ ID NO:60, SEQ ID NO:61, and SEQ ID NO:62, respectively. For example, the binding region may comprises at least one heavy-chain variable domain polypeptide comprising (i) the HCDR1, HCDR2, and HCDR3 amino acid sequences shown in SEQ ID NOs: 63, SEQ ID NO:64, and SEQ ID NO:65, respectively; and at least one light-chain variable domain polypeptide comprising (i) the LCDR1, LCDR2, and LCDR3 amino acid sequences shown in SEQ ID NO:66, SEQ ID NO:67, and SEQ ID NO:68, respectively. The binding region having these CDRs may be an immunoglobulin binding region comprising a single-chain variable fragment.

In certain embodiments of Embodiment Set #2, the binding region may comprises the binding region comprises a polypeptide selected from the group consisting of: a) a heavy chain only variable ($V_H H$) domain comprising (i) a HCDR1 comprising or consisting essentially of the amino acid sequences as shown in SEQ ID NO:69 or SEQ ID NO:72; (ii) a HCDR2 comprising or consisting essentially of the amino acid sequence as shown in SEQ ID NO:70 or SEQ ID NO:73; and (iii) a HCDR3 comprising or consisting essentially of the amino acid sequence as shown in SEQ ID NO:71 or SEQ ID NO:74. The binding region having these CDRs may be an immunoglobulin binding region comprising a heavy chain only variable ($V_H$H) domain derived from a camelid antibody.

In certain embodiments of Embodiment Set #2, the binding region may comprise: (a) at least one heavy chain variable ($V_H$) domain comprising, consisting essentially of, or consisting of: amino acids 269 to 387 of SEQ ID NOs: 26, 29, 30, or 36; amino acids 269 to 397 of SEQ ID NO:25; amino acids 381 to 500 of SEQ ID NO: 24 or 27; amino acids 401 to 522 of SEQ ID NO:36, or amino acids 401 to 520 of SEQ ID NO:28; and (b) at least one light chain variable ($V_L$) domain comprising, consisting essentially of, or consisting of: amino acids 269 to 375 of SEQ ID NO: 24, 27, or 28; amino acids 393 to 499 of SEQ ID NO:26; amino acids 403 to 513 of SEQ ID NO:25; amino acids 408 to 514 of SEQ ID NO:36; and amino acids 413 to 519 of SEQ ID NO: 29 or 30. For example, the binding region may comprise (a) at least one heavy chain variable ($V_H$) domain comprising, consisting essentially of, or consisting of amino acids 269 to 387 of SEQ ID NO:29; and (b) at least one light chain variable ($V_L$) domain comprising, consisting essentially of, or consisting of amino acids 413 to 519 of SEQ ID NO:29. For example, the binding region may comprise (a) at least one heavy chain variable ($V_H$) domain comprising, consisting essentially of, or consisting of amino acids 269 to 387 of SEQ ID NO:36; and (b) at least one light chain variable ($V_L$) domain comprising, consisting essentially of, or consisting of amino acids 408 to 514 of SEQ ID NO:36

In certain embodiments of Embodiment Set #2, the binding region comprises, consists essentially of, or consists of the polypeptide represented by any one of the following polypeptide sequences: amino acids 269 to 513 of SEQ ID NO:25; amino acids 269 to 499 of SEQ ID NO:26; amino acids 269 to 519 of SEQ ID NO:29 or SEQ ID NO:30; amino acids 268 to 386 of SEQ ID NO:31; amino acids 253 to 370 of SEQ ID NO:34; amino acids 253 to 367 of SEQ ID NO:35; or amino acids 269 to 514 of SEQ ID NO:36. For example, the binding region comprises, consists essentially of, or consists of the polypeptide represented by amino acids 269 to 519 of SEQ ID NO:29. For example, the binding region comprises, consists essentially of, or consists of the polypeptide represented by amino acids 268 to 518 of SEQ ID NO:102. For example, the binding region comprises, consists essentially of, or consists of the polypeptide represented by amino acids 268 to 386 of SEQ ID NO:31. For example, the binding region comprises, consists essentially of, or consists of the polypeptide represented by amino acids 253 to 370 of SEQ ID NO:34. For example, the binding region comprises, consists essentially of, or consists of the polypeptide represented by amino acids 253 to 367 of SEQ ID NO:35. For example, the binding region comprises, consists essentially of, or consists of the polypeptide represented by amino acids 269 to 514 of SEQ ID NO:36.

In certain embodiments of Embodiment Set #2, the cell-targeting molecule of the present invention comprises, consists essentially of, or consists of the polypeptide shown in any one of SEQ ID NOs: 22-36 and 97-108. In certain embodiments of Embodiment Set #2, the cell-targeting molecule of the present invention comprises, consists essentially of, or consists of the polypeptide shown in any one of SEQ ID NOs: 29, 31, 34, 35, 36, 102, 104, and 106-108. In certain further embodiments, the cell-targeting molecule of the present invention further comprises an amino terminal methionine residue. In certain further embodiments, the cell-targeting molecule of the present invention comprises, consists essentially of, or consists of the polypeptide shown in SEQ ID NO: 29 or 102.

In certain embodiments of Embodiment Set #2, the disrupted furin-cleavage motif comprises an amino acid residue substitution in the furin-cleavage motif relative to a wild-type Shiga toxin A Subunit. In certain further embodiments, the substitution of the amino acid residue in the furin-cleavage motif is of an arginine residue with a non-positively charged, amino acid residue selected from the group consisting of: alanine, glycine, proline, serine, threonine, aspartate, asparagine, glutamate, glutamine, cysteine, isoleucine, leucine, methionine, valine, phenylalanine, tryptophan, and tyrosine. In certain embodiments, the substitution of the amino acid residue in the furin-cleavage motif is of an arginine residue with a histidine.

In certain embodiments of Embodiment Set #2, the cell-targeting molecule is capable when introduced to cells of exhibiting cytotoxicity comparable to the cytotoxicity of a reference cell-targeting molecule, such as, e.g., a fourth cell-targeting molecule consisting of the cell-targeting molecule except for all of its Shiga toxin effector polypeptide component(s) each comprise a wild-type Shiga toxin A1 fragment and/or wild-type Shiga toxin furin-cleavage site at the carboxy terminus of its A1 fragment region. In certain further embodiments, the cell-targeting molecule of the present invention is capable when introduced to cells of exhibiting cytotoxicity that is in a range of from 0.1-fold, 0.5-fold, or 0.75-fold to 1.2-fold, 1.5-fold, 1.75-fold, 2-fold, 3-fold, 4-fold, or 5-fold of the cytotoxicity exhibited by the fourth cell-targeting molecule.

In certain embodiments of Embodiment Set #2, the cell-targeting molecule is capable when introduced to a chordate of exhibiting improved, in vivo tolerability compared to in vivo tolerability of a reference molecule, such as, e.g., a fourth cell-targeting molecule consisting of the cell-targeting molecule except for all of its Shiga toxin effector polypeptide component(s) each comprise a wild-type Shiga toxin A1 fragment and/or wild-type Shiga toxin furin-cleavage site at the carboxy terminus of its A1 fragment region.

In certain embodiments of Embodiment Set #2, the cell-targeting molecule is de-immunized due to the embedded or inserted, heterologous, epitope. In certain further embodiments, the cell-targeting molecule is capable of exhibiting less relative antigenicity and/or relative immunogenicity as compared to a reference molecule, such as, e.g., a seventh cell-targeting molecule consisting of the cell-targeting molecule except for it lacks one or more embedded or inserted epitopes present in the cell targeting molecule.

In certain embodiments of Embodiment Set #2, the cell-targeting molecule is de-immunized due to the furin-cleavage motif disruption. In certain further embodiments, the cell-targeting molecule is capable of exhibiting less relative antigenicity and/or relative immunogenicity as compared to a reference molecule, such as, e.g., fourth cell-targeting molecule consisting of the cell-targeting molecule except for all of its Shiga toxin effector polypeptide component(s) each comprise a wild-type Shiga toxin A1 fragment and/or wild-type Shiga toxin furin-cleavage site at the carboxy terminus of its A1 fragment region.

For certain embodiments of Embodiment Set #2, the cell-targeting molecule exhibits reduced relative antigenicity and/or relative immunogenicity as compared to a reference molecule, such as, e.g., a wild-type Shiga toxin A Subunit or a third cell-targeting molecule consisting of the cell-targeting molecule except for all of its Shiga toxin effector polypeptide component(s) each comprise a wild-type Shiga toxin A1 fragment.

Embodiment Set #3—HER2-Targeting Molecule Comprising a De-Immunized Shiga Toxin Effector Polypeptide Comprising a Disrupted, Furin-Cleavage Motif The present invention provides cell-targeting molecules, each comprising (i) a binding region capable of specifically binding an extracellular target biomolecule (HER2/neu/ErbB2) and (ii) a de-immunized, Shiga toxin A Subunit effector polypeptide comprising a disrupted furin-cleavage motif. In certain embodiments, the cell-targeting molecule of the present invention comprises (i) a binding region capable of specifically binding an extracellular target biomolecule and (ii) a de-immunized, Shiga toxin effector polypeptide comprising a Shiga toxin A1 fragment derived region and a carboxy terminus, wherein the Shiga toxin effector polypeptide comprises (a) a disrupted furin-cleavage motif at the carboxy-terminus of the A1 fragment region, and (b) at least one disrupted, endogenous, B-cell and/or CD4+ T-cell epitope and/or epitope region. For certain further embodiments, the Shiga toxin effector polypeptide is capable of exhibiting at least one Shiga toxin effector function, such as, e.g., directing intracellular routing to the endoplasmic reticulum and/or cytosol of a cell in which the polypeptide is present, inhibiting a ribosome function, enzymatically inactivating a ribosome, causing cytostasis, and/or causing cytotoxicity. In certain further embodiments, the cell-targeting molecule of the present invention is capable of one or more the following: entering a cell, inhibiting a ribosome function, causing cytostasis, and/or causing cell death. In certain embodiments, the furin-cleavage motif is disrupted by a carboxy-terminal truncation of the Shiga toxin effector polypeptide as compared to the carboxy-terminus of a wild-type Shiga toxin A Subunit. The Shiga toxin effector polypeptide may be truncated at its carboxy-terminus, relative to a wild-type Shiga toxin A subunit, resulting in the elimination of one or more endogenous, B-cell and/or CD4+ T-cell epitope regions. The Shiga toxin effector polypeptide of Embodiment Set #3 may further comprise an inserted or embedded, heterologous, epitope; such as an embedded or inserted, heterologous, CD8+ T-cell epitope. The embedded or inserted, heterologous, CD8+ T-cell epitope may disrupt an endogenous, B-cell and/or CD4+ T-cell epitope region. For example, the present invention provides a Shiga toxin effector polypeptide comprising a Shiga toxin A1 fragment region and a carboxy-terminus, wherein the Shiga toxin A subunit effector polypeptide comprises: a) an embedded or inserted, heterologous, epitope; (b) a disruption of at least one, endogenous, B-cell and/or CD4+ T-cell epitope region; and (c) a disrupted furin-cleavage motif at the carboxy-terminus of the Shiga toxin A1 fragment region; and wherein the Shiga toxin A subunit effector polypeptide is capable of exhibiting a Shiga toxin effector function. In a further example, the present invention provides a Shiga toxin A subunit effector polypeptide comprising a Shiga toxin A1 fragment region and a carboxy-terminus, wherein the Shiga toxin A subunit effector polypeptide comprises: (a) an embedded or inserted, heterologous, CD8+ T-cell epitope which disrupts an endogenous, B-cell and/or CD4+ T-cell epitope region; (b) a disruption of at least four, endogenous, B-cell and/or CD4+ T-cell epitope regions which do not overlap with the embedded or inserted, heterologous, CD8+ T-cell epitope; and (c) a disrupted furin-cleavage motif at the carboxy-terminus of the Shiga toxin A1 fragment region; and wherein the Shiga toxin A subunit effector polypeptide is truncated at its carboxy-terminus, relative to a wild-type Shiga toxin A subunit, resulting in the elimination of one or more endogenous, B-cell and/or CD4+ T-cell epitope regions; wherein the Shiga toxin A subunit effector polypeptide is capable of exhibiting a Shiga toxin effector function.

For certain embodiments of Embodiment Set #3, the cell-targeting molecule exhibits reduced relative antigenicity and/or relative immunogenicity as compared to a reference molecule, such as, e.g., a wild-type Shiga toxin A Subunit or a third cell-targeting molecule consisting of the cell-targeting molecule except for all of its Shiga toxin effector polypeptide component(s) each comprise a wild-type Shiga toxin A1 fragment.

In certain embodiments of Embodiment Set #3, the binding region and Shiga toxin effector polypeptide are linked together, either directly or indirectly.

In certain embodiments of Embodiment Set #3, the binding region comprises a polypeptide comprising an immunoglobulin or immunoglobulin-type binding region. In certain further embodiments, the binding region comprising a polypeptide selected from the group consisting of: an autonomous $V_H$ domain, single-domain antibody fragment (sdAb), Nanobody®, heavy chain-antibody domain derived from a camelid antibody ($V_HH$ or $V_H$ domain fragment), heavy-chain antibody domain derived from a cartilaginous fish antibody ($V_HH$ or $V_H$ domain fragment), immunoglobulin new antigen receptor (IgNAR), $V_{NAR}$ fragment, single-chain variable fragment (scFv), antibody variable fragment (Fv), complementary determining region 3 fragment (CDR3), constrained FR3-CDR3-FR4 polypeptide (FR3-CDR3-FR4), Fd fragment, small modular immunopharmaceutical (SMIP) domain, antigen-binding fragment (Fab), Armadillo repeat polypeptide (ArmRP), fibronectin-derived $10^{th}$ fibronectin type III domain (10Fn3), tenascin type III domain (TNfn3), ankyrin repeat motif domain, low-density-lipoprotein-receptor-derived A-domain (LDLR-A), lipocalin (anticalin), Kunitz domain, Protein-A-derived Z domain, gamma-B crystallin-derived domain, ubiquitin-derived domain, Sac7d-derived polypeptide (affitin), Fyn-derived SH2 domain, miniprotein, C-type lectin-like domain scaffold, engineered antibody mimic, and any genetically manipulated counterparts of any of the foregoing which retain binding functionality. In certain embodiments, the binding region comprises a polypeptide selected from the group consisting of: an autonomous $V_H$ domain, single-domain antibody fragment (sdAb), Nanobody®, heavy chain-antibody domain derived from a camelid antibody ($V_HH$ or $V_H$ domain fragment), heavy-chain antibody domain derived from a cartilaginous fish antibody ($V_HH$ or $V_H$ domain fragment), immunoglobulin new antigen receptor (IgNAR), VNAR fragment, single-chain variable fragment (scFv), antibody variable fragment (Fv), Fd fragment, and antigen-binding fragment (Fab). In certain embodiments, the cell-targeting molecule of the present invention comprises an immunoglobulin binding region capable of specifically binding an extracellular part of HER2/neu/ErbB2, and comprising one or more of: an antibody variable fragment, a single-domain antibody fragment, a single-chain variable fragment, a Fd fragment, an antigen-binding fragment, an autonomous $V_H$ domain, a $V_HH$ fragment derived from a camelid antibody, a heavy-chain antibody domain derived from a cartilaginous fish antibody, a VNAR fragment, and an immunoglobulin new antigen receptor. In certain embodiments, the binding region comprises, consists essentially of, or consists of a single-chain variable fragment (scFv). In certain embodiments, the binding region comprises a single-chain variable fragment (scFv). In certain embodiments, the binding region comprises, consists essentially of, or consists of a V$_H$H fragment derived from a camelid antibody.

In certain embodiments of Embodiment Set #3, the binding region and the Shiga toxin effector polypeptide are fused, either directly or indirectly, forming a continuous polypeptide such that the binding region is associated, either directly or indirectly, with the carboxy-terminus of the Shiga toxin effector polypeptide.

For certain embodiments of Embodiment Set #1, the cell-targeting molecule of the present invention is capable when introduced to cells of exhibiting a cytotoxicity with a half-maximal inhibitory concentration (CD50) value of 300 nM or less and/or capable of exhibiting a significant level of Shiga toxin cytotoxicity. For certain further embodiments, the cell-targeting molecule exhibits reduced relative antigenicity and/or relative immunogenicity as compared to a reference molecule, such as, e.g., a wild-type Shiga toxin A Subunit or a third cell-targeting molecule consisting of the cell-targeting molecule except for all of its Shiga toxin effector polypeptide component(s) each comprise a wild-type Shiga toxin A1 fragment.

For certain further embodiments, the cell-targeting molecule is capable when introduced to cells of exhibiting a cytotoxicity comparable or better than a reference molecule, such as, e.g., a second cell-targeting molecule consisting of the cell-targeting molecule except for all of its Shiga toxin effector polypeptide components comprise a wild-type Shiga toxin furin-cleavage site at the carboxy terminus of its A1 fragment region.

In certain embodiments of Embodiment Set #3, the Shiga toxin effector polypeptide comprises a mutation, relative to a wild-type Shiga toxin A Subunit, in the B-cell and/or CD4+ T-cell epitope region selected from the group of natively positioned Shiga toxin A Subunit regions consisting of: 1-15 of SEQ ID NO:1 or SEQ ID NO:2; 3-14 of SEQ ID NO:3; 26-37 of SEQ ID NO:3; 27-37 of SEQ ID NO:1 or SEQ ID NO:2; 39-48 of SEQ ID NO:1 or SEQ ID NO:2; 42-48 of SEQ ID NO:3; 53-66 of SEQ ID NO:1, SEQ ID NO:2, or SEQ ID NO:3; 94-115 of SEQ ID NO:1, SEQ ID NO:2, or SEQ ID NO:3; 141-153 of SEQ ID NO:1 or SEQ ID NO:2; 140-156 of SEQ ID NO:3; 179-190 of SEQ ID NO:1 or SEQ ID NO:2; 179-191 of SEQ ID NO:3; 204 of SEQ ID NO:3; 205 of SEQ ID NO:1 or SEQ ID NO:2, and 210-218 of SEQ ID NO:3; 240-260 of SEQ ID NO:3; 243-257 of SEQ ID NO:1 or SEQ ID NO:2; 254-268 of SEQ ID NO:1 or SEQ ID NO:2; 262-278 of SEQ ID NO:3; 281-297 of SEQ ID NO:3; 285-293 of SEQ ID NO:1 or SEQ ID NO:2; 4-33 of SEQ ID NO:1 or SEQ ID NO:2; 34-78 of SEQ ID NO:1 or SEQ ID NO:2; 77-103 of SEQ ID NO:1 or SEQ ID NO:2; 128-168 of SEQ ID NO:1 or SEQ ID NO:2; 160-183 of SEQ ID NO:1 or SEQ ID NO:2; 236-258 of SEQ ID NO:1 or SEQ ID NO:2; and 274-293 of SEQ ID NO:1 or SEQ ID NO:2; or the equivalent region in a Shiga toxin A Subunit or derivative thereof. In certain further embodiments, there is no disruption which is a carboxy-terminal truncation of amino acid residues that overlap with part or all of at least one disrupted, endogenous, B-cell and/or CD4+ T-cell epitope and/or epitope region (which may also disrupt an additional, different, endogenous, B-cell and/or CD4+ T-cell epitope region(s)).

In certain embodiments of Embodiment Set #3, the disrupted furin-cleavage motif comprises one or more mutations, relative to a wild-type Shiga toxin A Subunit, the mutation altering at least one amino acid residue in a region natively positioned at (1) at 248-251 of the A Subunit of Shiga-like toxin 1 (SEQ ID NO:1), Shiga toxin (SEQ ID NO:2), or another Shiga toxin 1 variant sequence (e.g. SEQ ID NOs: 4-6); or (2) at 247-250 of the A Subunit of Shiga-like toxin 2 (SEQ ID NO:3) or a Shiga-like toxin 2 variant sequence (e.g. SEQ ID NOs: 7-18); or the equivalent region in a Shiga toxin A Subunit or derivative thereof. In certain further embodiments, the disrupted furin-cleavage motif comprises one or more mutations, relative to a wild-type Shiga toxin A Subunit, in a minimal furin cleavage site of the furin-cleavage motif. In certain further embodiments the minimal furin cleavage site is represented by the consensus amino acid sequence R/Y-x-x-R and/or R-x-x-R.

In certain embodiments of Embodiment Set #3, the cell-targeting molecule comprises a molecular moiety located carboxy-terminal to the carboxy-terminus of the Shiga toxin A1 fragment region.

In certain embodiments of Embodiment Set #3, the binding region sterically covers the carboxy-terminus of the A1 fragment region.

In certain embodiments of Embodiment Set #3, the molecular moiety sterically covers the carboxy-terminus of the A1 fragment region. In certain further embodiments, the molecular moiety comprises the binding region.

In certain embodiments of Embodiment Set #3, the cell-targeting molecule of the present invention comprises a binding region and/or molecular moiety located carboxy-terminal to the carboxy-terminus of the Shiga toxin A1 fragment region. In certain further embodiments, the mass of the binding region and/or molecular moiety is at least 4.5 kDa, 6, kDa, 9 kDa, 12 kDa, 15 kDa, 20 kDa, 25 kDa, 28 kDa, 30 kDa, 41 kDa, 50 kDa, 100 kDa, or greater.

In certain embodiments of Embodiment Set #3, the cell-targeting molecule comprises a binding region with a mass of at least 4.5 kDa, 6, kDa, 9 kDa, 12 kDa, 15 kDa, 20 kDa, 25 kDa, 28 kDa, 30 kDa, 41 kDa, 50 kDa, 100 kDa, or greater, as long as the cell-targeting molecule retains the appropriate level of the Shiga toxin biological activity noted herein (e.g., cytotoxicity and/or intracellular routing).

In certain embodiments of Embodiment Set #3, the binding region is comprised within a relatively large, molecular moiety comprising such as, e.g., a molecular moiety with a mass of at least 4.5 kDa, 6, kDa, 9 kDa, 12 kDa, 15 kDa, 20 kDa, 25 kDa, 28 kDa, 30 kDa, 41 kDa, 50 kDa, 100 kDa, or greater, as long as the cell-targeting molecule retains the appropriate level of the Shiga toxin biological activity noted herein.

In certain embodiments of Embodiment Set #3, the disrupted furin-cleavage motif comprises an amino acid residue substitution in the furin-cleavage motif relative to a wild-type Shiga toxin A Subunit. In certain further embodiments, the substitution of the amino acid residue in the furin-cleavage motif is of an arginine residue with a non-positively charged, amino acid residue selected from the group consisting of: alanine, glycine, proline, serine, threonine, aspartate, asparagine, glutamate, glutamine, cysteine, isoleucine, leucine, methionine, valine, phenylalanine, tryptophan, and tyrosine. In certain embodiments, the substitution of the amino acid residue in the furin-cleavage motif is of an arginine residue with a histidine.

In certain embodiments of Embodiment Set #3, the Shiga toxin effector polypeptide comprises, consists essentially of, or consists of: (i) amino acids 75 to 251 of any one of SEQ ID NOs: 1-6 and 37; (ii) amino acids 1 to 241 of any one of SEQ ID NOs: 1-18 and 75-89; (iii) amino acids 1 to 251 of any one of SEQ ID NOs: 1-6, 37, and 75-89; or (iv) amino acids 1 to 261 of any one of SEQ ID NOs: 1-3; wherein the Shiga toxin effector polypeptide comprises at least one at least one (two, three, four or more) disrupted, endogenous, B-cell and/or CD4+ T-cell epitope and/or epitope region(s) and a disrupted furin-cleavage motif at the carboxy-terminus of a Shiga toxin A1 fragment derived region.

In certain embodiments of Embodiment Set #3, the binding region may comprise at least one heavy-chain variable domain polypeptide comprising (i) the HCDR1, HCDR2, and HCDR3 amino acid sequences shown in SEQ ID NOs: 51, SEQ ID NO:52, and SEQ ID NO:53, respectively; and at least one light-chain variable domain polypeptide comprising: (i) the LCDR1, LCDR2, and LCDR3 amino acid sequences shown in SEQ ID NO:54, SEQ ID NO:55, and SEQ ID NO:56, respectively. For example, the binding region may comprises at least one heavy-chain variable domain polypeptide comprising (i) the HCDR1, HCDR2, and HCDR3 amino acid sequences shown in SEQ ID NOs: 57, SEQ ID NO:58, and SEQ ID NO:59, respectively; and at least one light-chain variable domain polypeptide comprising (i) the LCDR1, LCDR2, and LCDR3 amino acid sequences shown in SEQ ID NO:60, SEQ ID NO:61, and SEQ ID NO:62, respectively. For example, the binding region may comprises at least one heavy-chain variable domain polypeptide comprising (i) the HCDR1, HCDR2, and HCDR3 amino acid sequences shown in SEQ ID NOs: 63, SEQ ID NO:64, and SEQ ID NO:65, respectively; and at least one light-chain variable domain polypeptide comprising (i) the LCDR1, LCDR2, and LCDR3 amino acid sequences shown in SEQ ID NO:66, SEQ ID NO:67, and SEQ ID NO:68, respectively. The binding region having these CDRs may be an immunoglobulin binding region comprising a single-chain variable fragment.

In certain embodiments of Embodiment Set #3, the binding region may comprises the binding region comprises a polypeptide selected from the group consisting of: a) a heavy chain only variable ($V_HH$) domain comprising (i) a HCDR1 comprising or consisting essentially of the amino acid sequences as shown in SEQ ID NO:69 or SEQ ID NO:72; (ii) a HCDR2 comprising or consisting essentially of the amino acid sequence as shown in SEQ ID NO:70 or SEQ ID NO:73; and (iii) a HCDR3 comprising or consisting essentially of the amino acid sequence as shown in SEQ ID NO:71 or SEQ ID NO:74. The binding region having these CDRs may be an immunoglobulin binding region comprising a heavy chain only variable ($V_HH$) domain derived from a camelid antibody.

In certain embodiments of Embodiment Set #3, the binding region may comprise: (a) at least one heavy chain variable ($V_H$) domain comprising, consisting essentially of, or consisting of: amino acids 269 to 387 of SEQ ID NOs: 26, 29, 30, or 36; amino acids 269 to 397 of SEQ ID NO:25; amino acids 381 to 500 of SEQ ID NO: 24 or 27; amino acids 401 to 522 of SEQ ID NO:36, or amino acids 401 to 520 of SEQ ID NO:28; and (b) at least one light chain variable ($V_L$) domain comprising, consisting essentially of, or consisting of: amino acids 269 to 375 of SEQ ID NO: 24, 27, or 28; amino acids 393 to 499 of SEQ ID NO:26; amino acids 403 to 513 of SEQ ID NO:25; amino acids 408 to 514 of SEQ ID NO:36; and amino acids 413 to 519 of SEQ ID NO: 29 or 30. For example, the binding region may comprise (a) at least one heavy chain variable ($V_H$) domain comprising, consisting essentially of, or consisting of amino acids 269 to 387 of SEQ ID NO:29; and (b) at least one light chain variable ($V_L$) domain comprising, consisting essentially of, or consisting of amino acids 413 to 519 of SEQ ID NO:29. For example, the binding region may comprise (a) at least one heavy chain variable ($V_H$) domain comprising, consisting essentially of, or consisting of amino acids 269 to 387 of SEQ ID NO:36; and (b) at least one light chain variable ($V_L$) domain comprising, consisting essentially of, or consisting of amino acids 408 to 514 of SEQ ID NO:36

In certain embodiments of Embodiment Set #3, the binding region comprises, consists essentially of, or consists of the polypeptide represented by any one of the following polypeptide sequences: amino acids 269 to 513 of SEQ ID NO:25; amino acids 269 to 499 of SEQ ID NO:26; amino acids 269 to 519 of SEQ ID NO:29 or SEQ ID NO:30; amino acids 268 to 386 of SEQ ID NO:31; amino acids 253 to 370 of SEQ ID NO:34; amino acids 253 to 367 of SEQ ID NO:35; or amino acids 269 to 514 of SEQ ID NO:36. For example, the binding region comprises, consists essentially of, or consists of the polypeptide represented by amino acids 269 to 519 of SEQ ID NO:29. For example, the binding region comprises, consists essentially of, or consists of the polypeptide represented by amino acids 268 to 518 of SEQ ID NO:102. For example, the binding region comprises, consists essentially of, or consists of the polypeptide represented by amino acids 268 to 386 of SEQ ID NO:31. For example, the binding region comprises, consists essentially of, or consists of the polypeptide represented by amino acids 253 to 370 of SEQ ID NO:34. For example, the binding region comprises, consists essentially of, or consists of the polypeptide represented by amino acids 253 to 367 of SEQ ID NO:35. For example, the binding region comprises, consists essentially of, or consists of the polypeptide represented by amino acids 269 to 514 of SEQ ID NO:36.

In certain embodiments of Embodiment Set #3, the cell-targeting molecule of the present invention comprises, consists essentially of, or consists of the polypeptide shown in any one of SEQ ID NOs: 22-36 and 97-108. In certain embodiments of Embodiment Set #3, the cell-targeting molecule of the present invention comprises, consists essentially of, or consists of the polypeptide shown in any one of SEQ ID NOs: 29, 31, 34, 35, 36, 102, 104, and 106-108. In certain further embodiments, the cell-targeting molecule of the present invention further comprises an amino terminal methionine residue. In certain further embodiments, the cell-targeting molecule of the present invention comprises, consists essentially of, or consists of the polypeptide shown in SEQ ID NO: 29 or 102.

In certain embodiments of Embodiment Set #3, the cell-targeting molecule is capable when introduced to cells of exhibiting cytotoxicity comparable to the cytotoxicity of a reference molecule, such as, e.g., a fourth cell-targeting molecule consisting of the cell-targeting molecule except for all of its Shiga toxin effector polypeptide component(s) each comprise a wild-type Shiga toxin A1 fragment and/or wild-type Shiga toxin furin-cleavage site at the carboxy terminus of its A1 fragment region. In certain further embodiments, the cell-targeting molecule of the present invention is capable when introduced to cells of exhibiting cytotoxicity that is in a range of from 0.1-fold, 0.5-fold, or 0.75-fold to 1.2-fold, 1.5-fold, 1.75-fold, 2-fold, 3-fold, 4-fold, or 5-fold of the cytotoxicity exhibited by the fourth cell-targeting molecule.

In certain embodiments of Embodiment Set #3, the cell-targeting molecule is capable when introduced to a chordate of exhibiting improved, in vivo tolerability compared to in vivo tolerability of a reference molecule, such as, e.g., a fourth cell-targeting molecule consisting of the cell-targeting molecule except for all of its Shiga toxin effector polypeptide component(s) each comprise a wild-type Shiga toxin A1 fragment and/or wild-type Shiga toxin furin-cleavage site at the carboxy terminus of its A1 fragment region.

In certain embodiments of Embodiment Set #3, the cell-targeting molecule is de-immunized due to the furin-cleavage motif disruption. In certain further embodiments, the cell-targeting molecule is capable of exhibiting less relative antigenicity and/or relative immunogenicity as compared to a reference cell-targeting molecule, such as, e.g., a fourth cell-targeting molecule consisting of the cell-targeting molecule except for all of its Shiga toxin effector polypeptide component(s) each comprise a wild-type Shiga toxin A1 fragment and/or wild-type Shiga toxin furin-cleavage site at the carboxy terminus of its A1 fragment region.

Further Embodiments of Embodiment Sets #1-#3

In certain embodiments of Embodiment Sets #1 to #3, the Shiga toxin effector polypeptide is truncated at its carboxy-terminus, relative to a wild-type Shiga toxin A subunit, resulting in the elimination of one or more endogenous, B-cell and/or CD4+ T-cell epitope regions.

In certain embodiments of Embodiment Sets #1 to #3, the Shiga toxin effector polypeptide has a Shiga toxin A1 fragment derived region having a carboxy terminus and further comprises a disrupted furin-cleavage motif at the carboxy-terminus of the A1 fragment region. In certain embodiments, the furin-cleavage motif is disrupted by a carboxy-terminal truncation of the Shiga toxin effector polypeptide as compared to the carboxy-terminus of a wild-type Shiga toxin A Subunit. For example, the Shiga toxin effector polypeptide of the present invention may comprise a Shiga toxin A1 fragment derived region wherein the Shiga toxin A1 fragment region comprises a disrupted furin-cleavage motif at the carboxy-terminus of the Shiga toxin A1 fragment region, and wherein said furin-cleavage motif is disrupted by a carboxy-terminal truncation of the Shiga toxin effector polypeptide as compared to the carboxy-terminus of a wild-type Shiga toxin A Subunit.

In certain embodiments of Embodiment Sets #1 to #3, the Shiga toxin effector polypeptide further comprises at least one inserted or embedded, heterologous epitope. In certain embodiments of Embodiment Sets #1 to #3, the Shiga toxin effector polypeptide comprises at least one embedded, heterologous epitope. In certain embodiments, the at least one inserted or embedded, heterologous epitope is a CD8+ T-cell epitope. In certain embodiments, the Shiga toxin effector polypeptide of the present invention comprises at least one inserted or embedded, heterologous CD8+ T-cell epitope. In certain embodiments, the embedded or inserted, heterologous, CD8+ T-cell epitope disrupts an endogenous, B-cell and/or CD4+ T-cell epitope region.

In certain embodiments of Embodiment Sets #1 to #3, the amino-terminus of the Shiga toxin effector polypeptide is at and/or proximal to an amino-terminus of a polypeptide component of the cell-targeting molecule. In certain further embodiments, the binding region is not located proximally to the amino-terminus of the cell-targeting molecule relative to the Shiga toxin effector polypeptide. In certain further embodiments, the binding region and Shiga toxin effector polypeptide are physically arranged or oriented within the cell-targeting molecule such that the binding region is not located proximally to the amino-terminus of the Shiga toxin effector polypeptide. In certain further embodiments, the binding region is located within the cell-targeting molecule more proximal to the carboxy-terminus of the Shiga toxin effector polypeptide than to the amino-terminus of the Shiga toxin effector polypeptide. For certain further embodiments, the cell-targeting molecule of the present invention is not cytotoxic and is capable when introduced to cells of exhibiting a greater subcellular routing efficiency from an extracellular space to a subcellular compartment of an endoplasmic reticulum and/or cytosol as compared to the cytotoxicity of a reference molecule, such as, e.g., an fifth cell-targeting molecule having an amino-terminus and comprising the binding region and the Shiga toxin effector polypeptide which is not positioned at or proximal to the amino-terminus of the fifth cell-targeting molecule. For certain further embodiments, the cell-targeting molecule of the present invention exhibits cytotoxicity with better optimized, cytotoxic potency, such as, e.g., 4-fold, 5-fold, 6-fold, 9-fold, or greater cytotoxicity as compared to the cytotoxicity of the fifth cell-targeting molecule. For certain further embodiments, the cytotoxicity of the cell-targeting molecule of the present invention to a population of target positive cells is 3-fold, 4-fold, 5-fold, 6-fold, 7-fold, 8-fold, 9-fold, 10-fold or greater than the cytotoxicity of the fifth cell-targeting molecule to a second population of target positive cells as assayed by $CD_{50}$ values. In certain further embodiments, the fifth cell-targeting molecule does not comprise any carboxy-terminal, endoplasmic reticulum retention/retrieval signal motif of the KDEL family.

In certain embodiments of Embodiment Sets #1 to #3, the cell-targeting molecule comprises a molecular moiety located carboxy-terminal to the carboxy-terminus of the Shiga toxin A1 fragment region.

In certain embodiments of Embodiment Sets #1 to #3, the cell-targeting molecule of the present invention, or a polypeptide component thereof, comprises a carboxy-terminal, endoplasmic reticulum retention/retrieval signal motif of a member of the KDEL family. In certain further embodiments, the carboxy-terminal endoplasmic reticulum retention/retrieval signal motif is selected from the group consisting of: KDEL (SEQ ID NO:109), HDEF (SEQ ID NO:110), HDEL (SEQ ID NO:111), RDEF (SEQ ID NO:112), RDEL (SEQ ID NO:113), WDEL (SEQ ID NO:114), YDEL (SEQ ID NO:115), HEEF (SEQ ID NO:116), HEEL (SEQ ID NO:117), KEEL (SEQ ID NO:118), REEL (SEQ ID NO:119), KAEL (SEQ ID NO:120), KCEL (SEQ ID NO:121), KFEL (SEQ ID NO:122), KGEL (SEQ ID NO:123), KHEL (SEQ ID NO:124), KLEL (SEQ ID NO:125), KNEL (SEQ ID NO:126), KQEL (SEQ ID NO:127), KREL (SEQ ID NO:128), KSEL (SEQ ID NO:129), KVEL (SEQ ID NO:130), KWEL (SEQ ID NO:131), KYEL (SEQ ID NO:132), KEDL (SEQ ID NO:133), KIEL (SEQ ID NO:134), DKEL (SEQ ID NO:135), FDEL (SEQ ID NO:136), KDEF (SEQ ID NO:137), KKEL (SEQ ID NO:138), HADL (SEQ ID NO:139), HAEL (SEQ ID NO:140), HIEL (SEQ ID NO:141), HNEL (SEQ ID NO:142), HTEL (SEQ ID NO:143), KTEL (SEQ ID NO:144), HVEL (SEQ ID NO:145), NDEL (SEQ ID NO:146), QDEL (SEQ ID NO:147), REDL (SEQ ID NO:148), RNEL (SEQ ID NO:149), RTDL (SEQ ID NO:150), RTEL (SEQ ID NO:151), SDEL (SEQ ID NO:152), TDEL (SEQ ID NO:153), SKEL (SEQ ID NO:154), STEL (SEQ ID NO:155), and EDEL (SEQ ID NO:156). In certain further embodiments, the cell-targeting molecule of the present invention is capable when introduced to cells of exhibiting cytotoxicity that is greater than that of a reference molecule, such as, e.g., a sixth cell-targeting molecule consisting of the cell-targeting molecule except for it does not comprise any carboxy-terminal, endoplasmic reticulum retention/retrieval signal motif of the KDEL family. In certain further embodiments, the cell-targeting molecule of the present invention is capable of exhibiting a cytotoxicity with better optimized, cytotoxic potency, such as, e.g., 4-fold, 5-fold, 6-fold, 9-fold, or greater cytotoxicity as compared to a reference molecule, such as, e.g., a sixth cell-targeting molecule consisting of the cell-targeting molecule except for it does not comprise any carboxy-terminal, endoplasmic reticulum retention/retrieval signal motif of the KDEL family. In certain further embodiments, the cytotoxicity of the cell-targeting molecule of the present invention to a population of target positive cells is 3-fold, 4-fold, 5-fold, 6-fold, 7-fold, 8-fold, 9-fold, 10-fold or greater than the cytotoxicity of the sixth cell-targeting molecule to a second population of target positive cells as assayed by $CD_{50}$ values.

In certain embodiments of Embodiment Sets #1 to #3, the Shiga toxin effector polypeptide further comprises at least one, two, three, four, five, six, seven, or eight disrupted, endogenous, B-cell and/or T-cell epitope regions. In certain further embodiments, the Shiga toxin effector polypeptide comprises a disruption of at least one, two, three, four, five, six, seven, or eight endogenous, B-cell and/or CD4+ T-cell epitopes and/or epitope regions described herein. In certain further embodiments, the Shiga toxin effector polypeptide further comprises at least one (such as at least two, three, four, five, six, seven, or eight) disrupted, endogenous, B-cell and/or CD4+ T-cell epitope region which does not overlap with at least one inserted or embedded, heterologous epitope, which may also disrupt an additional, different, endogenous, B-cell and/or CD4+ T-cell epitope region(s). In certain embodiments, the Shiga toxin effector polypeptide comprises a disruption of at least three, endogenous, B-cell and/or CD4+ T-cell epitope regions which do not overlap with the embedded or inserted, heterologous, CD8+ T-cell epitope, which may also disrupt an additional, different, endogenous, B-cell and/or CD4+ T-cell epitope region(s).

In certain embodiments of Embodiment Sets #1 to #3, the Shiga toxin effector polypeptide further comprises a disruption in the endogenous, B-cell and/or CD4+ T-cell epitope region selected from the group of natively positioned Shiga toxin A Subunit regions consisting of: 1-15 of SEQ ID NO:1 or SEQ ID NO:2; 3-14 of SEQ ID NO:3; 26-37 of SEQ ID NO:3; 27-37 of SEQ ID NO:1 or SEQ ID NO:2; 39-48 of SEQ ID NO:1 or SEQ ID NO:2; 42-48 of SEQ ID NO:3; 53-66 of SEQ ID NO:1, SEQ ID NO:2, or SEQ ID NO:3; 94-115 of SEQ ID NO:1, SEQ ID NO:2, or SEQ ID NO:3; 141-153 of SEQ ID NO:1 or SEQ ID NO:2; 140-156 of SEQ ID NO:3; 179-190 of SEQ ID NO:1 or SEQ ID NO:2; 179-191 of SEQ ID NO:3; 197 of SEQ ID NO:3; 198 of SEQ ID NO:1 or SEQ ID NO:2; 204 of SEQ ID NO:3; 205 of SEQ ID NO:1 or SEQ ID NO:2, and 210-218 of SEQ ID NO:3; 240-260 of SEQ ID NO:3; 243-257 of SEQ ID NO:1 or SEQ ID NO:2; 254-268 of SEQ ID NO:1 or SEQ ID NO:2; 262-278 of SEQ ID NO:3; 281-297 of SEQ ID NO:3; 285-293 of SEQ ID NO:1 or SEQ ID NO:2; 4-33 of SEQ ID NO:1 or SEQ ID NO:2; 34-78 of SEQ ID NO:1 or SEQ ID NO:2; 77-103 of SEQ ID NO:1 or SEQ ID NO:2; 128-168 of SEQ ID NO:1 or SEQ ID NO:2; 160-183 of SEQ ID NO:1 or SEQ ID NO:2; 236-258 of SEQ ID NO:1 or SEQ ID NO:2; and 274-293 of SEQ ID NO:1 or SEQ ID NO:2; or the equivalent region in a Shiga toxin A Subunit or derivative thereof. In certain further embodiments, there is no disruption which is a carboxy-terminal truncation of amino acid residues that overlap with part or all of at least one disrupted, endogenous, B-cell and/or CD4+ T-cell epitope and/or epitope region.

In certain embodiments of Embodiment Sets #1 to #3, the Shiga toxin effector polypeptide further comprises a disruption of at least one (such as at least two, three, four, five, six, seven, eight or more) endogenous, B-cell and/or CD4+ T-cell epitope region, wherein the B-cell region is selected from the group of natively positioned Shiga toxin A Subunit regions consisting of: 1-15 of SEQ ID NO:1 or SEQ ID NO:2; 3-14 of SEQ ID NO:3; 26-37 of SEQ ID NO:3; 27-37 of SEQ ID NO:1 or SEQ ID NO:2; 39-48 of SEQ ID NO:1 or SEQ ID NO:2; 42-48 of SEQ ID NO:3; 53-66 of SEQ ID NO:1, SEQ ID NO:2, or SEQ ID NO:3; 94-115 of SEQ ID NO:1, SEQ ID NO:2, or SEQ ID NO:3; 141-153 of SEQ ID NO:1 or SEQ ID NO:2; 140-156 of SEQ ID NO:3; 179-190 of SEQ ID NO:1 or SEQ ID NO:2; 179-191 of SEQ ID NO:3; 204 of SEQ ID NO:3; 205 of SEQ ID NO:1 or SEQ ID NO:2; 197 of SEQ ID NO:3; 198 of SEQ ID NO:1 or SEQ ID NO:2; 210-218 of SEQ ID NO:3; 240-260 of SEQ ID NO:3; 243-257 of SEQ ID NO:1 or SEQ ID NO:2; 254-268 of SEQ ID NO:1 or SEQ ID NO:2; 262-278 of SEQ ID NO:3; 281-297 of SEQ ID NO:3; and 285-293 of SEQ ID NO:1 or SEQ ID NO:2; or the equivalent region in a Shiga toxin A Subunit or derivative thereof (such as the equivalent region in the Shiga toxin effector polypeptides SEQ ID NOs: 4-18); and the CD4+ T-cell epitope region is selected from the group of natively positioned Shiga toxin A Subunit regions consisting of: 4-33 of SEQ ID NO:1 or SEQ ID NO:2; 34-78 of SEQ ID NO:1 or SEQ ID NO:2; 77-103 of SEQ ID NO:1 or SEQ ID NO:2; 128-168 of SEQ ID NO:1 or SEQ ID NO:2; 160-183 of SEQ ID NO:1 or SEQ ID NO:2; 236-258 of SEQ ID NO:1 or SEQ ID NO:2; and 274-293 of SEQ ID NO:1 or SEQ ID NO:2; or the equivalent region in a Shiga toxin A Subunit or derivative thereof (such as the equivalent region in the Shiga toxin effector polypeptides SEQ ID NOs: 4-18). In certain embodiments, the B-cell epitope region is selected from the group of natively positioned Shiga toxin A Subunit regions consisting of: 1-15 of SEQ ID NO:1 or SEQ ID NO:2; 3-14 of SEQ ID NO:3; 26-37 of SEQ ID NO:3; 27-37 of SEQ ID NO:1 or SEQ ID NO:2; 39-48 of SEQ ID NO:1 or SEQ ID NO:2; 42-48 of SEQ ID NO:3; 53-66 of SEQ ID NO:1, SEQ ID NO:2, or SEQ ID NO:3; 94-115 of SEQ ID NO:1, SEQ ID NO:2, or SEQ ID NO:3; 141-153 of SEQ ID NO:1 or SEQ ID NO:2; 140-156 of SEQ ID NO:3; 179-190 of SEQ ID NO:1 or SEQ ID NO:2; 179-191 of SEQ ID NO:3; 197 of SEQ ID NO:3; 198 of SEQ ID NO:1 or SEQ ID NO:2; 204 of SEQ ID NO:3; 205 of SEQ ID NO:1 or SEQ ID NO:2; 210-218 of SEQ ID NO:3; and 243-257 of SEQ ID NO:1 or SEQ ID NO:2; or the equivalent region in a Shiga toxin A Subunit or derivative thereof (such as the equivalent region in the Shiga toxin effector polypeptides SEQ ID NOs: 4-18); and the CD4+ T-cell epitope region is selected from the group of natively positioned Shiga toxin A Subunit regions consisting of: 4-33 of SEQ ID NO:1 or SEQ ID NO:2; 34-78 of SEQ ID NO:1 or SEQ ID NO:2; 77-103 of SEQ ID NO:1 or SEQ ID NO:2; 128-168 of SEQ ID NO:1 or SEQ ID NO:2; 160-183 of SEQ ID NO:1 or SEQ ID NO:2; and 236-258 of SEQ ID NO:1 or SEQ ID NO:2; or the equivalent region in a Shiga toxin A Subunit or derivative thereof (such as the equivalent region in the Shiga toxin effector polypeptides SEQ ID NOs: 4-18). For example, the B-cell epitope region may be selected from the group of natively positioned Shiga toxin A Subunit regions consisting of: 39-48 of SEQ ID NO:1 or SEQ ID NO:2; 42-48 of SEQ ID NO:3; 53-66 of SEQ ID NO:1, SEQ ID NO:2, or SEQ ID NO:3; 94-115 of SEQ ID NO:1, SEQ ID NO:2, or SEQ ID NO:3; 179-190 of SEQ ID NO:1 or SEQ ID NO:2; and 179-191 of SEQ ID NO:3; or the equivalent region in a Shiga toxin A Subunit or derivative thereof (such as the equivalent region in the Shiga toxin effector polypeptides SEQ ID NOs: 4-18); and the CD4+ T-cell epitope region is 236-258 of SEQ ID NO:1 or SEQ ID NO:2; or the equivalent region in a Shiga toxin A Subunit or derivative thereof (such as the equivalent region in the Shiga toxin effector polypeptides SEQ ID NOs: 4-18).

In certain embodiments of Embodiment Sets #1 to #3, the Shiga toxin effector polypeptide comprises a disruption of at least four, endogenous, B-cell and/or CD4+ T-cell epitope regions, wherein the disruption comprises a mutation, relative to a wild-type Shiga toxin A Subunit, in the B-cell epitope region selected from the group of natively positioned Shiga toxin A Subunit regions consisting of: 1-15 of SEQ ID NO:1 or SEQ ID NO:2; 3-14 of SEQ ID NO:3; 26-37 of SEQ ID NO:3; 27-37 of SEQ ID NO:1 or SEQ ID NO:2; 39-48 of SEQ ID NO:1 or SEQ ID NO:2; 42-48 of SEQ ID NO:3; 53-66 of SEQ ID NO:1, SEQ ID NO:2, or SEQ ID NO:3; 94-115 of SEQ ID NO:1, SEQ ID NO:2, or SEQ ID NO:3; 141-153 of SEQ ID NO:1 or SEQ ID NO:2; 140-156 of SEQ ID NO:3; 179-190 of SEQ ID NO:1 or SEQ ID NO:2; 179-191 of SEQ ID NO:3; 197 of SEQ ID NO:3; 198 of SEQ ID NO:1 or SEQ ID NO:2; 204 of SEQ ID NO:3; 205 of SEQ ID NO:1 or SEQ ID NO:2; 210-218 of SEQ ID NO:3; and 243-257 of SEQ ID NO:1 or SEQ ID NO:2; or the equivalent region in a Shiga toxin A Subunit or derivative thereof (such as the equivalent region in the Shiga toxin effector polypeptides SEQ ID NOs: 4-18); and/or the CD4+ T-cell epitope region selected from the group of natively positioned Shiga toxin A Subunit regions consisting of: 4-33 of SEQ ID NO:1 or SEQ ID NO:2; 34-78 of SEQ ID NO:1 or SEQ ID NO:2; 77-103 of SEQ ID NO:1 or SEQ ID NO:2; 128-168 of SEQ ID NO:1 or SEQ ID NO:2; 160-183 of SEQ ID NO:1 or SEQ ID NO:2; and 236-258 of SEQ ID NO:1 or SEQ ID NO:2; or the equivalent region in a Shiga toxin A Subunit or derivative thereof (such as the equivalent region in the Shiga toxin effector polypeptides SEQ ID NOs: 4-18).

In certain embodiments of Embodiment Sets #1 to #3, the Shiga toxin effector polypeptide further comprises a mutation, relative to a wild-type Shiga toxin A Subunit, in the B-cell immunogenic amino acid residue selected from the group of natively positioned Shiga toxin A Subunit amino acid residues: L49, D197, D198, R204, and R205.

In certain embodiments of Embodiment Sets #1 to #3, the embedded or inserted, heterologous, T-cell epitope disrupts the endogenous, B-cell and/or CD4+ T-cell epitope region is selected from the group of natively positioned Shiga toxin A Subunit regions consisting of: (i) 1-15 of SEQ ID NO:1 or SEQ ID NO:2; 3-14 of SEQ ID NO:3; 26-37 of SEQ ID NO:3; 27-37 of SEQ ID NO:1 or SEQ ID NO:2; 39-48 of SEQ ID NO:1 or SEQ ID NO:2; 42-48 of SEQ ID NO:3; and 53-66 of SEQ ID NO:1, SEQ ID NO:2, or SEQ ID NO:3; or the equivalent region in a Shiga toxin A Subunit or derivative thereof (such as the equivalent region in any one of the Shiga toxin 1 effector polypeptide variants shown in SEQ ID NOs: 4-6 and any one of the Shiga-like toxin 2 effector polypeptide variants shown in SEQ ID NOs: 7-18), wherein there is no disruption which is an amino-terminal truncation of sequences that overlap with part or all of at least one disrupted epitope region; (ii) 94-115 of SEQ ID NO:1, SEQ ID NO:2, or SEQ ID NO:3; 141-153 of SEQ ID NO:1 or SEQ ID NO:2; 140-156 of SEQ ID NO:3; 179-190 of SEQ ID NO:1 or SEQ ID NO:2; 179-191 of SEQ ID NO:3; 197 of SEQ ID NO:3; 198 of SEQ ID NO:1 or SEQ ID NO:2; 204 of SEQ ID NO:3; 205 of SEQ ID NO:1 or SEQ ID NO:2; and 210-218 of SEQ ID NO:3; and (iii) 240-260 of SEQ ID NO:3; 243-257 of SEQ ID NO:1 or SEQ ID NO:2; 254-268 of SEQ ID NO:1 or SEQ ID NO:2; 262-278 of SEQ ID NO:3; 281-297 of SEQ ID NO:3; and 285-293 of SEQ ID NO:1 or SEQ ID NO:2; or the equivalent region in a Shiga toxin A Subunit or derivative thereof (such as the equivalent region in any one of the Shiga toxin 1 effector polypeptide variants shown in SEQ ID NOs: 4-6 and any one of the Shiga-like toxin 2 effector polypeptide variants shown in SEQ ID NOs: 7-18).

In certain embodiments of Embodiment Sets #1 to #3, the Shiga toxin effector polypeptide comprises a mutation, relative to a wild-type Shiga toxin A Subunit, in the B-cell and/or CD4+ T-cell epitope region selected from the group of natively positioned Shiga toxin A Subunit regions consisting of: (i) 1-15 of SEQ ID NO:1 or SEQ ID NO:2; 3-14 of SEQ ID NO:3; 26-37 of SEQ ID NO:3; 27-37 of SEQ ID NO:1 or SEQ ID NO:2; 39-48 of SEQ ID NO:1 or SEQ ID NO:2; 42-48 of SEQ ID NO:3; and 53-66 of SEQ ID NO:1, SEQ ID NO:2, or SEQ ID NO:3; or the equivalent region in a Shiga toxin A Subunit or derivative thereof (such as the equivalent region in any one of the Shiga toxin 1 effector polypeptide variants shown in SEQ ID NOs: 4-6 and any one of the Shiga-like toxin 2 effector polypeptide variants shown in SEQ ID NOs: 7-18), wherein there is no disruption which is an amino-terminal truncation of sequences that overlap with part or all of at least one disrupted epitope region; (ii) 94-115 of SEQ ID NO:1, SEQ ID NO:2, or SEQ ID NO:3; 141-153 of SEQ ID NO:1 or SEQ ID NO:2; 140-156 of SEQ ID NO:3; 179-190 of SEQ ID NO:1 or SEQ ID NO:2; 179-191 of SEQ ID NO:3; 197 of SEQ ID NO:3; 198 of SEQ ID NO:1 or SEQ ID NO:2; 204 of SEQ ID NO:3; 205 of SEQ ID NO:1 or SEQ ID NO:2; and 210-218 of SEQ ID NO:3; and (iii) 240-260 of SEQ ID NO:3; 243-257 of SEQ ID NO:1 or SEQ ID NO:2; 254-268 of SEQ ID NO:1 or SEQ ID NO:2; 262-278 of SEQ ID NO:3; 281-297 of SEQ ID NO:3; and 285-293 of SEQ ID NO:1 or SEQ ID NO:2; or the equivalent region in a Shiga toxin A Subunit or derivative thereof (such as the equivalent region in any one of the Shiga toxin 1 effector polypeptide variants shown in SEQ ID NOs: 4-6 and any one of the Shiga-like toxin 2 effector polypeptide variants shown in SEQ ID NOs: 7-18), wherein there is no disruption which is an amino-terminal truncation of sequences that overlap with part or all of at least one disrupted epitope region.

In certain embodiments of Embodiment Sets #1 to #3, the embedded or inserted, heterologous, CD8+ T-cell epitope disrupts an endogenous, B-cell epitope region selected from the group of natively positioned Shiga toxin A Subunit regions consisting of: 1-15 of SEQ ID NO:1 or SEQ ID NO:2; 3-14 of SEQ ID NO:3; 26-37 of SEQ ID NO:3; 27-37 of SEQ ID NO:1 or SEQ ID NO:2; 39-48 of SEQ ID NO:1 or SEQ ID NO:2; 42-48 of SEQ ID NO:3; and 53-66 of SEQ ID NO:1, SEQ ID NO:2, or SEQ ID NO:3, 94-115 of SEQ ID NO:1, SEQ ID NO:2, or SEQ ID NO:3; 141-153 of SEQ ID NO:1 or SEQ ID NO:2; 140-156 of SEQ ID NO:3; 179-190 of SEQ ID NO:1 or SEQ ID NO:2; 179-191 of SEQ ID NO:3; 197 of SEQ ID NO:3; 198 of SEQ ID NO:1 or SEQ ID NO:2; 204 of SEQ ID NO:3; 205 of SEQ ID NO:1 or SEQ ID NO:2; and 210-218 of SEQ ID NO:3; 240-260 of SEQ ID NO:3; 243-257 of SEQ ID NO:1 or SEQ ID NO:2; 254-268 of SEQ ID NO:1 or SEQ ID NO:2; 262-278 of SEQ ID NO:3; 281-297 of SEQ ID NO:3; and 285-293 of SEQ ID NO:1 or SEQ ID NO:2, or the equivalent region in a Shiga toxin A Subunit or derivative thereof (such as the equivalent region in any one of the Shiga toxin 1 effector polypeptide variants shown in SEQ ID NOs: 4-6 and any one of the Shiga-like toxin 2 effector polypeptide variants shown in SEQ ID NOs: 7-18); and/or an endogenous CD4+ T-cell epitope region selected from the group of natively positioned Shiga toxin A Subunit regions consisting of: 4-33 of SEQ ID NO:1 or SEQ ID NO:2; 34-78 of SEQ ID NO:1 or SEQ ID NO:2; 77-103 of SEQ ID NO:1 or SEQ ID NO:2; 128-168 of SEQ ID NO:1 or SEQ ID NO:2; 160-183 of SEQ ID NO:1 or SEQ ID NO:2; 236-258 of SEQ ID NO:1 or SEQ ID NO:2; and 274-293 of SEQ ID NO:1 or SEQ ID NO:2 or the equivalent region in a Shiga toxin A Subunit or derivative thereof (such as the equivalent region in any one of the Shiga toxin 1 effector polypeptide variants shown in SEQ ID NOs: 4-6 and any one of the Shiga-like toxin 2 effector polypeptide variants shown in SEQ ID NOs: 7-18).

In certain embodiments of Embodiment Sets #1 to #3, the embedded or inserted, heterologous, CD8+ T-cell epitope disrupts an endogenous, B-cell epitope region selected from the group of natively positioned Shiga toxin A Subunit regions consisting of: 1-15 of SEQ ID NO:1 or SEQ ID NO:2; 3-14 of SEQ ID NO:3; 26-37 of SEQ ID NO:3; 27-37 of SEQ ID NO:1 or SEQ ID NO:2; 39-48 of SEQ ID NO:1 or SEQ ID NO:2; 42-48 of SEQ ID NO:3; and 53-66 of SEQ ID NO:1, SEQ ID NO:2, or SEQ ID NO:3, 94-115 of SEQ ID NO:1, SEQ ID NO:2, or SEQ ID NO:3; 141-153 of SEQ ID NO:1 or SEQ ID NO:2; 140-156 of SEQ ID NO:3; 179-190 of SEQ ID NO:1 or SEQ ID NO:2; 179-191 of SEQ ID NO:3; 197 of SEQ ID NO:3; 198 of SEQ ID NO:1 or SEQ ID NO:2; 204 of SEQ ID NO:3; 205 of SEQ ID NO:1 or SEQ ID NO:2; and 210-218 of SEQ ID NO:3; 240-260 of SEQ ID NO:3; and 243-257 of SEQ ID NO:1 or SEQ ID NO:2, or the equivalent region in a Shiga toxin A Subunit or derivative thereof (such as the equivalent region in any one of the Shiga toxin 1 effector polypeptide variants shown in SEQ ID NOs: 4-6 and any one of the Shiga-like toxin 2 effector polypeptide variants shown in SEQ ID NOs: 7-18); and/or an endogenous CD4+ T-cell epitope region selected from the group of natively positioned Shiga toxin A Subunit regions consisting of: 4-33 of SEQ ID NO:1 or SEQ ID NO:2; 34-78 of SEQ ID NO:1 or SEQ ID NO:2; 77-103 of SEQ ID NO:1 or SEQ ID NO:2; 128-168 of SEQ ID NO:1 or SEQ ID NO:2; 160-183 of SEQ ID NO:1 or SEQ ID NO:2; and 236-258 of SEQ ID NO:1 or SEQ ID NO:2; or the equivalent region in a Shiga toxin A Subunit or derivative thereof (such as the equivalent region in any one of the Shiga toxin 1 effector polypeptide variants shown in SEQ ID NOs: 4-6 and any one of the Shiga-like toxin 2 effector polypeptide variants shown in SEQ ID NOs: 7-18).

In certain embodiments of Embodiment Sets #1 to #3, the Shiga toxin effector polypeptide comprises a disruption of at least one endogenous epitope region selected from the group of natively positioned Shiga toxin A Subunits consisting of: 94-115 of SEQ ID NO:1, SEQ ID NO:2, or SEQ ID NO:3; 141-153 of SEQ ID NO:1 or SEQ ID NO:2; 140-156 of SEQ ID NO:3; 179-190 of SEQ ID NO:1 or SEQ ID NO:2; 179-191 of SEQ ID NO:3; 197 of SEQ ID NO:3; 198 of SEQ ID NO:1 or SEQ ID NO:2; 204 of SEQ ID NO:3; 205 of SEQ ID NO:1 or SEQ ID NO:2; or 210-218 of SEQ ID NO:3 or the equivalent region in a Shiga toxin A Subunit or derivative thereof (such as in any one of the Shiga toxin 1 effector polypeptide variants shown in SEQ ID NOs: 4-6 and in any one of the Shiga-like toxin 2 effector polypeptide variants shown in SEQ ID NOs: 7-18).

In certain embodiments of Embodiment Sets #1 to #3, the Shiga toxin effector polypeptide does not comprise a heterologous, MHC class I-restricted, T-cell epitope. MHC class I-restricted, T-cell epitopes are known in the art or can be predicted by the skilled worker. The term heterologous refers to MHC class I-restricted, T-cell epitopes which are not natively present in wild-type Shiga toxin A Subunits, such as, e.g., the wild-type Shiga toxin A Subunit which is most closely related to the Shiga toxin effector polypeptide of interest.

In certain embodiments of Embodiment Sets #1 to #3, the Shiga toxin effector polypeptide comprises disruptions of at least two, three, four, five, six, seven, eight or more endogenous, B-cell and/or T-cell epitope regions. In certain embodiments of Embodiment Sets #1 to #3, the Shiga toxin effector polypeptide comprises disruptions of at least four endogenous, B-cell and/or T-cell epitope regions. In certain embodiments, the Shiga toxin effector polypeptide comprises disruptions of at least five endogenous, B-cell and/or CD4+ T-cell epitope regions. For example in certain embodiments, the Shiga toxin effector polypeptide comprises disruptions of at least six endogenous, B-cell and/or CD4+ T-cell epitope regions. In certain further embodiments, the two, three, four, five, six, seven, eight or more disrupted epitope regions do not overlap with the embedded or inserted, heterologous, CD8+ T-cell epitope, which may also disrupt an additional, different, endogenous, B-cell and/or CD4+ T-cell epitope region(s).

In certain embodiments of Embodiment Sets #1 to #3, one or more disruptions comprises an amino acid residue substitution relative to a wild-type Shiga toxin A Subunit.

In certain embodiments of Embodiment Sets #1 to #3, one or more endogenous, B-cell and/or T-cell epitope regions comprises a plurality of amino acid residue substitutions relative to a wild-type Shiga toxin A Subunit. In certain embodiments, at least three, four, five or more of the B-cell and/or CD4+ T-cell epitope region disruptions comprise an amino acid residue substitution relative to a wild-type Shiga toxin A Subunit.

In certain embodiments of Embodiment Sets #1 to #3, at least one, two, three, or four disruptions comprise a plurality of amino acid residue substitutions in the endogenous, B-cell and/or T-cell epitope region relative to a wild-type Shiga toxin A Subunit.

In certain embodiments of Embodiment Sets #1 to #3, at least one disruption comprises at least one, two, three, four, five, six, seven, eight or more amino acid residue substitutions relative to a wild-type Shiga toxin A Subunit, and optionally wherein at least one substitution occurs at the natively positioned Shiga toxin A Subunit amino acid residue selected from the group consisting of: 1 of SEQ ID NO:1 or SEQ ID NO:2; 4 of SEQ ID NO:1, SEQ ID NO:2, or SEQ ID NO:3; 6 of SEQ ID NO:1, SEQ ID NO:2, or SEQ ID NO:3; 8 of SEQ ID NO:1, SEQ ID NO:2, or SEQ ID NO:3; 9 of SEQ ID NO:1, SEQ ID NO:2, or SEQ ID NO:3; 11 of SEQ ID NO:1, SEQ ID NO:2, or SEQ ID NO:3; 12 of SEQ ID NO:1, SEQ ID NO:2, or SEQ ID NO:3; 33 of SEQ ID NO:1 or SEQ ID NO:2; 43 of SEQ ID NO:1 or SEQ ID NO:2; 44 of SEQ ID NO:1 or SEQ ID NO:2; 45 of SEQ ID NO:1 or SEQ ID NO:2; 46 of SEQ ID NO:1, SEQ ID NO:2, or SEQ ID NO:3; 47 of SEQ ID NO:1 or SEQ ID NO:2; 48 of SEQ ID NO:1, SEQ ID NO:2, or SEQ ID NO:3; 49 of SEQ ID NO:1, SEQ ID NO:2, or SEQ ID NO:3; 50 of SEQ ID NO:1 or SEQ ID NO:2; 51 of SEQ ID NO:1 or SEQ ID NO:2; 53 of SEQ ID NO:1 or SEQ ID NO:2; 54 of SEQ ID NO:1, SEQ ID NO:2, or SEQ ID NO:3; 55 of SEQ ID NO:1 or SEQ ID NO:2; 56 of SEQ ID NO:1, SEQ ID NO:2, or SEQ ID NO:3; 57 of SEQ ID NO:1, SEQ ID NO:2, or SEQ ID NO:3; 58 of SEQ ID NO:1, SEQ ID NO:2, or SEQ ID NO:3; 59 of SEQ ID NO:1, SEQ ID NO:2, or SEQ ID NO:3; 60 of SEQ ID NO:1 or SEQ ID NO:2; 61 of SEQ ID NO:1 or SEQ ID NO:2; 62 of SEQ ID NO:1 or SEQ ID NO:2; 84 of SEQ ID NO:1 or SEQ ID NO:2; 88 of SEQ ID NO:1, SEQ ID NO:2, or SEQ ID NO:3; 94 of SEQ ID NO:1, SEQ ID NO:2, or SEQ ID NO:3; 96 of SEQ ID NO:1, SEQ ID NO:2, or SEQ ID NO:3; 104 of SEQ ID NO:1 or SEQ ID NO:2; 105 of SEQ ID NO:1 or SEQ ID NO:2; 107 of SEQ ID NO:1, SEQ ID NO:2, or SEQ ID NO:3; 108 of SEQ ID NO:1 or SEQ ID NO:2; 109 of SEQ ID NO:1, SEQ ID NO:2, or SEQ ID NO:3; 110 of SEQ ID NO:1 or SEQ ID NO:2; 111 of SEQ ID NO:1, SEQ ID NO:2, or SEQ ID NO:3; 112 of SEQ ID NO:1, SEQ ID NO:2, or SEQ ID NO:3; 141 of SEQ ID NO:1, SEQ ID NO:2, or SEQ ID NO:3; 147 of SEQ ID NO:1, SEQ ID NO:2, or SEQ ID NO:3; 154 of SEQ ID NO:1 or SEQ ID NO:2; 179 of SEQ ID NO:1, SEQ ID NO:2, or SEQ ID NO:3; 180 of SEQ ID NO:1 or SEQ ID NO:2; 181 of SEQ ID NO:1 or SEQ ID NO:2; 183 of SEQ ID NO:1, SEQ ID NO:2, or SEQ ID NO:3; 184 of SEQ ID NO:1, SEQ ID NO:2, or SEQ ID NO:3; 185 of SEQ ID NO:1 or SEQ ID NO:2; 186 of SEQ ID NO:1, SEQ ID NO:2, or SEQ ID NO:3; 187 of SEQ ID NO:1 or SEQ ID NO:2; 188 of SEQ ID NO:1 or SEQ ID NO:2; 189 of SEQ ID NO:1 or SEQ ID NO:2; 197 of SEQ ID NO:3; 198 of SEQ ID NO:1 or SEQ ID NO:2; 204 of SEQ ID NO:3; 205 of SEQ ID NO:1 or SEQ ID NO:2; 242 of SEQ ID NO: 1 or SEQ ID NO:2; 247 of SEQ ID NO:1 or SEQ ID NO:2; 247 of SEQ ID NO:3; 248 of SEQ ID NO:1 or SEQ ID NO:2; 250 of SEQ ID NO:3; 251 of SEQ ID NO:1 or SEQ ID NO:2; 264 of SEQ ID NO:1, SEQ ID NO:2, or SEQ ID NO:3; 265 of SEQ ID NO:1 or SEQ ID NO:2; and 286 of SEQ ID NO:1 or SEQ ID NO:2; or the equivalent amino acid residue in a Shiga toxin A Subunit or derivative thereof (such as the equivalent region in any one of the Shiga toxin 1 effector polypeptide variants shown in SEQ ID NOs: 4-6 and in any one of the Shiga-like toxin 2 effector polypeptide variants shown in SEQ ID NOs: 7-18).

In certain embodiments of Embodiment Sets #1 to #3, at least one disruption comprises at least one, two, three, four, five, six, seven, eight, or more amino acid residue substitutions relative to a wild-type Shiga toxin A Subunit, and optionally wherein at least one substitution (such as at least two, three, four, five, six, seven, eight or more amino acid residue substitutions) occurs at the natively positioned Shiga toxin A Subunit amino acid residue selected from the group consisting of: 1 of SEQ ID NO:1 or SEQ ID NO:2; 4 of SEQ ID NO:1, SEQ ID NO:2, or SEQ ID NO:3; 6 of SEQ ID NO:1, SEQ ID NO:2, or SEQ ID NO:3; 8 of SEQ ID NO:1, SEQ ID NO:2, or SEQ ID NO:3; 9 of SEQ ID NO:1, SEQ ID NO:2, or SEQ ID NO:3; 11 of SEQ ID NO:1, SEQ ID NO:2, or SEQ ID NO:3; 12 of SEQ ID NO:1, SEQ ID NO:2, or SEQ ID NO:3; 33 of SEQ ID NO:1 or SEQ ID NO:2; 43 of SEQ ID NO:1 or SEQ ID NO:2; 44 of SEQ ID NO:1 or SEQ ID NO:2; 45 of SEQ ID NO:1 or SEQ ID NO:2; 46 of SEQ ID NO:1, SEQ ID NO:2, or SEQ ID NO:3; 47 of SEQ ID NO:1 or SEQ ID NO:2; 48 of SEQ ID NO:1, SEQ ID NO:2, or SEQ ID NO:3; 49 of SEQ ID NO:1, SEQ ID NO:2, or SEQ ID NO:3; 50 of SEQ ID NO:1 or SEQ ID NO:2; 51 of SEQ ID NO:1 or SEQ ID NO:2; 53 of SEQ ID NO:1 or SEQ ID NO:2; 54 of SEQ ID NO:1, SEQ ID NO:2, or SEQ ID NO:3; 55 of SEQ ID NO:1 or SEQ ID NO:2; 56 of SEQ ID NO:1, SEQ ID NO:2, or SEQ ID NO:3; 57 of SEQ ID NO:1, SEQ ID NO:2, or SEQ ID NO:3; 58 of SEQ ID NO:1, SEQ ID NO:2, or SEQ ID NO:3; 59 of SEQ ID NO:1, SEQ ID NO:2, or SEQ ID NO:3; 60 of SEQ ID NO:1 or SEQ ID NO:2; 61 of SEQ ID NO:1 or SEQ ID NO:2; 62 of SEQ ID NO:1 or SEQ ID NO:2; 84 of SEQ ID NO:1 or SEQ ID NO:2; 88 of SEQ ID NO:1, SEQ ID NO:2, or SEQ ID NO:3; 94 of SEQ ID NO:1, SEQ ID NO:2, or SEQ ID NO:3; 96 of SEQ ID NO:1, SEQ ID NO:2, or SEQ ID NO:3; 104 of SEQ ID NO:1 or SEQ ID NO:2; 105 of SEQ ID NO:1 or SEQ ID NO:2; 107 of SEQ ID NO:1, SEQ ID NO:2, or SEQ ID NO:3; 108 of SEQ ID NO:1 or SEQ ID NO:2; 109 of SEQ ID NO:1, SEQ ID NO:2, or SEQ ID NO:3; 110 of SEQ ID NO:1 or SEQ ID NO:2; 111 of SEQ ID NO:1, SEQ ID NO:2, or SEQ ID NO:3; 112 of SEQ ID NO:1, SEQ ID NO:2, or SEQ ID NO:3; 141 of SEQ ID NO:1, SEQ ID NO:2, or SEQ ID NO:3; 147 of SEQ ID NO:1, SEQ ID NO:2, or SEQ ID NO:3; 154 of SEQ ID NO:1 or SEQ ID NO:2; 179 of SEQ ID NO:1, SEQ ID NO:2, or SEQ ID NO:3; 180 of SEQ ID NO:1 or SEQ ID NO:2; 181 of SEQ ID NO:1 or SEQ ID NO:2; 183 of SEQ ID NO:1, SEQ ID NO:2, or SEQ ID NO:3; 184 of SEQ ID NO:1, SEQ ID NO:2, or SEQ ID NO:3; 185 of SEQ ID NO:1 or SEQ ID NO:2; 186 of SEQ ID NO:1, SEQ ID NO:2, or SEQ ID NO:3; 187 of SEQ ID NO:1 or SEQ ID NO:2; 188 of SEQ ID NO:1 or SEQ ID NO:2; 189 of SEQ ID NO:1 or SEQ ID NO:2; 197 of SEQ ID NO:3; 198 of SEQ ID NO:1 or SEQ ID NO:2; 204 of SEQ ID NO:3; 205 of SEQ ID NO:1 or SEQ ID NO:2; 242 of SEQ ID NO:1 or SEQ ID NO:2; 247 of SEQ ID NO:1 or SEQ ID NO:2; 247 of SEQ ID NO:3; 248 of SEQ ID NO:1 or SEQ ID NO:2; 250 of SEQ ID NO:3; and 251 of SEQ ID NO:1 or SEQ ID NO:2; or the equivalent amino acid residue in a Shiga toxin A Subunit or derivative thereof (such as the equivalent region in any one of the Shiga toxin 1 effector polypeptide variants shown in SEQ ID NOs: 4-6 and any one of the Shiga-like toxin 2 effector polypeptide variants shown in SEQ ID NOs: 7-18). In certain embodiments, the at least one substitution occurs at the natively positioned Shiga toxin A Subunit amino acid residues: 45 of SEQ ID NO:1 or SEQ ID NO:2; 54 of SEQ ID NO:1, SEQ ID NO:2; 55 of SEQ ID NO:1 or SEQ ID NO:2; 57 of SEQ ID NO:1, SEQ ID NO:2; 59 of SEQ ID NO:1, SEQ ID NO:2; 60 of SEQ ID NO:1 or SEQ ID NO:2; 61 of SEQ ID NO:1 or SEQ ID NO:2; 110 of SEQ ID NO:1 or SEQ ID NO:2; 141 of SEQ ID NO:1 or SEQ ID NO:2; 188 of SEQ ID NO:1 or SEQ ID NO:2; 242 of SEQ ID NO:1 or SEQ ID NO:2; 248 of SEQ ID NO:1 or SEQ ID NO:2; and 251 of SEQ ID NO:1 or SEQ ID NO:2.

In certain further embodiments, at least two disruptions each comprise at least one amino acid residue substitutions relative to a wild-type Shiga toxin A Subunit selected form the group consisting of: 1 of SEQ ID NO:1 or SEQ ID NO:2; 4 of SEQ ID NO:1, SEQ ID NO:2, or SEQ ID NO:3; 8 of SEQ ID NO:1, SEQ ID NO:2, or SEQ ID NO:3; 9 of SEQ ID NO:1, SEQ ID NO:2, or SEQ ID NO:3; 11 of SEQ ID NO:1, SEQ ID NO:2, or SEQ ID NO:3; 33 of SEQ ID NO:1 or SEQ ID NO:2; 43 of SEQ ID NO:1 or SEQ ID NO:2; 45 of SEQ ID NO:1 or SEQ ID NO:2; 47 of SEQ ID NO:1 or SEQ ID NO:2; 48 of SEQ ID NO:1, SEQ ID NO:2, or SEQ ID NO:3; 49 of SEQ ID NO:1 or SEQ ID NO:2; 53 of SEQ ID NO:1 or SEQ ID NO:2; 55 of SEQ ID NO:1 or SEQ ID NO:2; 58 of SEQ ID NO:1, SEQ ID NO:2, or SEQ ID NO:3; 59 of SEQ ID NO:1, SEQ ID NO:2, or SEQ ID NO:3; 60 of SEQ ID NO:1 or SEQ ID NO:2; 61 of SEQ ID NO:1 or SEQ ID NO:2; 62 of SEQ ID NO:1 or SEQ ID NO:2; 94 of SEQ ID NO:1, SEQ ID NO:2, or SEQ ID NO:3; 96 of SEQ ID NO:1, SEQ ID NO:2, or SEQ ID NO:3; 109 of SEQ ID NO:1, SEQ ID NO:2, or SEQ ID NO:3; 110 of SEQ ID NO:1 or SEQ ID NO:2; 112 of SEQ ID NO:1, SEQ ID NO:2, or SEQ ID NO:3; 147 of SEQ ID NO:1, SEQ ID NO:2, or SEQ ID NO:3; 179 of SEQ ID NO:1, SEQ ID NO:2, or SEQ ID NO:3; 180 of SEQ ID NO:1 or SEQ ID NO:2; 181 of SEQ ID NO:1 or SEQ ID NO:2; 183 of SEQ ID NO:1, SEQ ID NO:2, or SEQ ID NO:3; 184 of SEQ ID NO:1, SEQ ID NO:2, or SEQ ID NO:3; 185 of SEQ ID NO:1, SEQ ID NO:2, or SEQ ID NO:3; 186 of SEQ ID NO:1, SEQ ID NO:2, or SEQ ID NO:3; 187 of SEQ ID NO:1 or SEQ ID NO:2; 188 of SEQ ID NO:1 or SEQ ID NO:2; 189 of SEQ ID NO:1 or SEQ ID NO:2; 197 of SEQ ID NO:3; 198 of SEQ ID NO:1 or SEQ ID NO:2; 204 of SEQ ID NO:3; 205 of SEQ ID NO:1 or SEQ ID NO:2; 242 of SEQ ID NO:1 or SEQ ID NO:2; 247 of SEQ ID NO:3; 250 of SEQ ID NO:3; 264 of SEQ ID NO:1, SEQ ID NO:2, or SEQ ID NO:3; 265 of SEQ ID NO:1 or SEQ ID NO:2; and 286 of SEQ ID NO:1 or SEQ ID NO:2; or the equivalent amino acid residue in a Shiga toxin A Subunit or derivative thereof (such as the equivalent region in any one of the Shiga toxin 1 effector polypeptide variants shown in SEQ ID NOs: 4-6 and any one of the Shiga-like toxin 2 effector polypeptide variants shown in SEQ ID NOs: 7-18).

In certain embodiments of Embodiment Sets #1 to #3, the Shiga toxin effector polypeptide comprises disruption of at least three, endogenous, B-cell and/or CD4+ T-cell epitope regions selected from the group of consisting of: (i) 1-15 of SEQ ID NO:1 or SEQ ID NO:2; 3-14 of SEQ ID NO:3; 26-37 of SEQ ID NO:3; 27-37 of SEQ ID NO:1 or SEQ ID NO:2; 39-48 of SEQ ID NO:1 or SEQ ID NO:2; 42-48 of SEQ ID NO:3; and 53-66 of SEQ ID NO:1, SEQ ID NO:2, or SEQ ID NO:3, or the equivalent region in a Shiga toxin A Subunit or derivative thereof (such as the equivalent region in any one of the Shiga toxin 1 effector polypeptide variants shown in SEQ ID NOs: 4-6 and any one of the Shiga-like toxin 2 effector polypeptide variants shown in SEQ ID NOs: 7-18), wherein there is no disruption which is an amino-terminal truncation of amino acid residues that overlap with part or all of at least one disrupted, endogenous, B-cell and/or CD4+ T-cell epitope region; (ii) 94-115 of SEQ ID NO:1, SEQ ID NO:2, or SEQ ID NO:3; 141-153 of SEQ ID NO:1 or SEQ ID NO:2; 140-156 of SEQ ID NO:3; 179-190 of SEQ ID NO:1 or SEQ ID NO:2; 179-191 of SEQ ID NO:3; 197 of SEQ ID NO:3; 198 of SEQ ID NO:1 or SEQ ID NO:2; 204 of SEQ ID NO:3; 205 of SEQ ID NO:1 or SEQ ID NO:2; and 210-218 of SEQ ID NO:3; and (iii) 240-260 of SEQ ID NO:3; 243-257 of SEQ ID NO:1 or SEQ ID NO:2; 254-268 of SEQ ID NO:1 or SEQ ID NO:2; 262-278 of SEQ ID NO:3; 281-297 of SEQ ID NO:3; and 285-293 of SEQ ID NO:1 or SEQ ID NO:2; or the equivalent region in a Shiga toxin A Subunit or derivative thereof (such as the equivalent region in any one of the Shiga toxin 1 effector polypeptide variants shown in SEQ ID NOs: 4-6 and any one of the Shiga-like toxin 2 effector polypeptide variants shown in SEQ ID NOs: 7-18), wherein there is no disruption which is a carboxy-terminal truncation of amino acid residues that overlap with part or all of at least one disrupted, endogenous, B-cell and/or CD4+ T-cell epitope and/or epitope region.

In certain embodiments of Embodiment Sets #1 to #3, the Shiga toxin effector polypeptide comprises disruptions of at least two, endogenous, B-cell and/or CD4+ T-cell epitope regions, wherein each disruption comprises one or more amino acid residue substitutions, and wherein the endogenous, B-cell and/or CD4+ T-cell epitope regions are selected from the group of natively positioned Shiga toxin A Subunit regions consisting of: 3-14 of SEQ ID NO:3; 26-37 of SEQ ID NO:3; 27-37 of SEQ ID NO:1 or SEQ ID NO:2; 39-48 of SEQ ID NO:1 or SEQ ID NO:2; 42-48 of SEQ ID NO:3; 53-66 of SEQ ID NO:1, SEQ ID NO:2, or SEQ ID NO:3; or the equivalent region in a Shiga toxin A Subunit or derivative thereof (such as the equivalent region in any one of the Shiga toxin 1 effector polypeptide variants shown in SEQ ID NOs: 4-6 and any one of the Shiga-like toxin 2 effector polypeptide variants shown in SEQ ID NOs: 7-18).

In certain embodiments of Embodiment Sets #1 to #3, the embedded or inserted, heterologous, T-cell epitope does not disrupt any endogenous, B-cell and/or CD4+ T-cell epitope region described herein.

In certain embodiments of Embodiment Sets #1 to #3, at least one disruption comprises one or more amino acid residue substitutions relative to a wild-type Shiga toxin A Subunit is selected from the group consisting of: D to A, D to G, D to V, D to L, D to I, D to F, D to S, D to Q, D to M, D to R, E to A, E to G, E to V, E to L, E to I, E to F, E to S, E to Q, E to N, E to D, E to M, E to R, F to A, F to G, F to V, F to L, F to I, G to A, G to P, H to A, H to G, H to V, H to L, H to I, H to F, H to M, I to A, I to V, I to G, I to C, K to A, K to G, K to V, K to L, K to I, K to M, K to H, L to A, L to V, L to G, L to C, N to A, N to G, N to V, N to L, N to I, N to F, P to A, P to G, P to F, R to A, R to G, R to V, R to L, R to I, R to F, R to M, R to Q, R to S, R to K, R to H, S to A, S to G, S to V, S to L, S to I, S to F, S to M, T to A, T to G, T to V, T to L, T to I, T to F, T to M, T to S, V to A, V to G, Y to A, Y to G, Y to V, Y to L, Y to I, Y to F, Y to M, and Y to T. In certain further embodiments, the one or more amino acid residue substitutions relative to a wild-type Shiga toxin A Subunit is selected from the group consisting of: D to A, D to G, D to V, D to L, D to I, D to F, D to S, D to Q, E to A, E to G, E to V, E to L, E to I, E to F, E to S, E to Q, E to N, E to D, E to M, E to R, G to A, H to A, H to G, H to V, H to L, H to I, H to F, H to M, K to A, K to G, K to V, K to L, K to I, K to M, K to H, L to A, L to G, N to A, N to G, N to V, N to L, N to I, N to F, P to A, P to G, P to F, R to A, R to G, R to V, R to L, R to I, R to F, R to M, R to Q, R to S, R to K, R to H, S to A, S to G, S to V, S to L, S to I, S to F, S to M, T to A, T to G, T to V, T to L, T to I, T to F, T to M, T to S, Y to A, Y to G, Y to V, Y to L, Y to I, Y to F, and Y to M.

In certain embodiments of Embodiment Sets #1 to #3, at least one of the disruption(s) comprises one or more amino acid residue substitutions relative to a wild-type Shiga toxin A Subunit selected from the group consisting of: K1 to A, G, V, L, I, F, M and H; T4 to A, G, V, L, I, F, M, and S; D6 to A, G, V, L, I, F, S, Q and R; T8 to A, G, V, I, L, F, and M; S8 to A, G, V, I, L, F, and M; T9 to A, G, V, I, L, F, M, and S; S9 to A, G, V, L, I, F, and M; K11 to A, G, V, L, I, F, M and H; T12 to A, G, V, I, L, F, M, S, and K; S12 to A, G, V, I, L, F, and M; S33 to A, G, V, L, I, F, M, and C; S43 to A, G, V, L, I, F, and M; G44 to A or L; S45 to A, G, V, L, I, F, and M; T45 to A, G, V, L, I, F, and M; G46 to A and P; D47 to A, G, V, L, I, F, S, M, and Q; N48 to A, G, V, L, M and F; L49 to A, V, C, and G; Y49 to A, G, V, L, I, F, M, and T; F50 to A, G, V, L, I, and T; D53 to A, G, V, L, I, F, S, and Q; V54 to A, G, I, and L; R55 to A, G, V, L, I, F, M, Q, S, K, and H; G56 to A and P; I57 to A, G, V, and M; L57 to A, V, C, G, M, and F; D58 to A, G, V, L, I, F, S, and Q; P59 to A, G, and F; E60 to A, G, V, L, I, F, S, Q, N, D, M, T, and R; E61 to A, G, V, L, I, F, S, Q, N, D, M, and R; G62 to A; R84 to A, G, V, L, I, F, M, Q, S, K, and H; V88 to A and G; I88 to A, V, C, and G; D94 to A, G, V, L, I, F, S, and Q; S96 to A, G, V, I, L, F, and M; T104 to A, G, V, L, I, F, M; and N; A105 to L; T107 to A, G, V, L, I, F, M, and P; S107 to A, G, V, L, I, F, M, and P; L108 to A, V, C, and G; S109 to A, G, V, I, L, F, and M; T109 to A, G, V, I, L, F, M, and S; G110 to A; S112 to A, G, V, L, I, F, and M; D111 to A, G, V, L, I, F, S, Q, and T; S112 to A, G, V, L, I, F, and M; D141 to A, G, V, L, I, F, S, and Q; G147 to A; V154 to A and G; R179 to A, G, V, L, I, F, M, Q, S, K, and H; T180 to A, G, V, L, I, F, M, and S; T181 to A, G, V, L, I, F, M, and S; D183 to A, G, V, L, I, F, S, and Q; D184 to A, G, V, L, I, F, S, and Q; L185 to A, G, V and C; S186 to A, G, V, I, L, F, and M; G187 to A; R188 to A, G, V, L, I, F, M, Q, S, K, and H; S189 to A, G, V, I, L, F, and M; D197 to A, G, V, L, I, F, S, and Q; D198 to A, G, V, L, I, F, S, and Q; R204 to A, G, V, L, I, F, M, Q, S, K, and H; R205 to A, G, V, L, I, F, M, Q, S, K and H; C242 to A, G and V; S247 to A, G, V, I, L, F, and M; Y247 to A, G, V, L, I, F, and M; R247 to A, G, V, L, I, F, M, Q, S, K, and H; R248 to A, G, V, L, I, F, M, Q, S, K, and H; R250 to A, G, V, L, I, F, M, Q, S, K, and H; R25I to A, G, V, L, I, F, M, Q, S, K, and H; D264 to A, G, V, L, I, F, S, and Q; G264 to A; and T286 to A, G, V, L, I, F, M, and S. In certain embodiments of Embodiment Sets #1 to #3, the one or more substitutions are selected from the group of substitutions at native positions in a Shiga toxin A Subunit consisting of: K1A, K1M, T4I, D6R, S8I, TBV, T9I, S9I, K11A, K11H, T12K, S33I, S33C, S43N, G44L, S45V, S45I, T45V, T45I, G46P, D47M, D47G, N48V, N48F, L49A, F50T, D53A, D53N, D53G, V54L, V54I, R55A, R55V, R55L, G56P, I57F, I57M, D58A, D58V, D58F, P59A, P59F, E60I, E60T, E60R, E61A, E61V, E61L, G62A, R84A, V88A, D94A, S96I, T104N, A105L, T107P, L108M, S109V, T109V, G110A, D111T, S112V, D141A, G147A, V154A, R179A, T180G, T181I, D183A, D183G, D184A, D184A, D184F, L185V, L185D, S186A, S186F, G187A, G187T, R188A, R188L, S189A, D197A, D198A, R204A, R205A, C242A, S247I, Y247A, R247A, R248A, R250A, R251A, D264A, G264A, T286A, and T286I. In certain embodiments, the one or more substitutions are selected from the group of substitutions at native positions in a Shiga toxin A Subunit consisting of: K1A, S45I, V54I, R55L, I57F, P59F, E60T, E61L, G110A, D141A, G147A, R188A, C242S, R248A, and R251A. In certain further embodiments, the Shiga toxin effector polypeptide comprises one or more substitutions selected from the group of substitutions at native positions in a Shiga toxin A Subunit consisting of: K1R and K11R. In certain further embodiments, the Shiga toxin effector polypeptide comprises all the following substitutions: S45I, V54I, R55L, I57F, P59F, E60T, E61L, G110A, R188A, C242S, R248A, and R251A. In certain other further embodiments, the Shiga toxin effector polypeptide comprises all the following substitutions: K1A, S45I, V54I, R55L, I57F, P59F, E60T, E61L, G110A, G147A, C242S, R248A, and R251A. In certain other further embodiments, the Shiga toxin effector polypeptide comprises all the following substitutions: S45I, V54I, R55L, I57F, P59F, E60T, E61L, G110A, D141A, R188A, C242S, R248A, and R251A. In certain further embodiments, the Shiga toxin effector polypeptide comprises all the following substitutions: K1R, K11R, S45I, V54I, R55L, I57F, P59F, E60T, E61L, G110A, D141A, R188A, C242S, R248A, and R251A. In certain further embodiments, the Shiga toxin effector polypeptide further comprises one or more additional substitutions selected from the group of substitutions at native positions in a Shiga toxin A Subunit consisting of: K1A, K1M, T4I, D6R, S8I, T8V, T9I, S9I, K11A, K11H, T12K, S33I, S33C, S43N, G44L, S45V, S45I, T45V, T45I, G46P, D47M, D47G, N48V, N48F, L49A, F50T, A51V, D53A, D53N, D53G, V54L, V54I, R55A, R55V, R55L, G56P, I57F, I57M, D58A, D58V, D58F, P59A, P59F, E60I, E60T, E60R, E61A, E61V, E61L, G62A, R84A, V88A, D94A, S96I, T104N, A105L, T107P, L108M, S109V, T109V, G110A, D111T, S112V, D141A, G147A, V154A, R179A, T180G, T181I, D183A, D183G, D184A, D184A, D184F, L185V, L185D, S186A, S186F, G187A, G187T, R188A, R188L, S189A, D197A, D198A, R204A, R205A, C242A, S247I, R247A, Y247A, R248A, R250A, and R251A.

In certain embodiments of Embodiment Sets #1 to #3, the cell-targeting molecule of the present invention comprises the Shiga toxin effector polypeptide comprising, consisting essentially of, or consisting of an amino acid sequence that is at least 85% (such as at least 90%, 91%, 92%, 93%, 94%, 95%, 96%, 97%, 98%, 99% or more) identical to an amino acid sequence selected from any one of SEQ ID NOs: 19-21 and 75-89. In certain embodiments of Embodiment Sets #1 to #3, the cell-targeting molecule of the present invention comprises the Shiga toxin effector polypeptide comprising, consisting essentially of, or consisting of an amino acid sequence that is at least 85% (such as at least 90%, 91%, 92%, 93%, 94%, 95%, 96%, 97%, 98%, 99% or more) identical to an amino acid sequence selected from any one of SEQ ID NOs: 19-21. In certain embodiments of Embodiment Sets #1 to #3, the cell-targeting molecule of the present invention comprises the Shiga toxin effector polypeptide comprising, consisting essentially of, or consisting of the polypeptide shown in any one of SEQ ID NOs: 19-21 and 75-89. In certain embodiments, the cell-targeting molecule of the present invention comprises the Shiga toxin effector polypeptide comprising, consisting essentially of, or consisting of the polypeptide shown in any one of SEQ ID NOs: 19-21. For example, the Shiga toxin effector polypeptide comprises, consists essentially of, or consists of the polypeptide shown in SEQ ID NO:20.

For certain embodiments of Embodiment Sets #1 to #3, the cell-targeting molecule of the present invention is capable when introduced to a chordate of exhibiting improved in vivo tolerability and/or stability compared to a reference molecule, such as, e.g., a fourth cell-targeting molecule consisting of the cell-targeting molecule except for all of its Shiga toxin effector polypeptide component(s) each comprise a wild-type Shiga toxin A1 fragment and/or wild-type Shiga toxin furin-cleavage site at the carboxy terminus of its A1 fragment region. In certain further embodiments, the Shiga toxin effector polypeptide is not cytotoxic and the molecular moiety is cytotoxic.

In certain embodiments of Embodiment Sets #1 to #3, the binding region and Shiga toxin effector polypeptide are linked together, either directly or indirectly.

In certain embodiments of Embodiment Sets #1 to #3, the Shiga toxin effector polypeptide is fused to the binding region, either directly or indirectly, such as, e.g., via a linker known to the skilled worker. The binding region and Shiga toxin effector polypeptide may be fused by a proteinaceous linker comprising one or more amino acids. For example, the linker may comprise, consist essentially of, or consist of an amino acid sequence selected from GST-SGSGKPGSGEGS (SEQ ID NO:93), AHHSEDPSSKAPKAP (SEQ ID NO:95), SPSTPPTPSP-STPPA (SEQ ID NO:181), EFPKPSTPPGSSGGAP (SEQ ID NO:90), and GSTSGSGKPGSGEGSTKG (SEQ ID NO:96). The binding region and the Shiga toxin effector polypeptide may be indirectly fused together by the presence of an intervening single amino acid residue, such as, e.g., an alanine residue.

In certain embodiments of Embodiment Sets #1 to #3, the binding region comprises at least one peptide and/or polypeptide. In certain further embodiments, the binding region is or comprises an immunoglobulin or immunoglobulin-type binding region. In certain further embodiments, the binding region comprising a polypeptide selected from the group consisting of: an autonomous $V_H$ domain, single-domain antibody fragment (sdAb), Nanobody®, heavy chain-antibody domain derived from a camelid ($V_HH$ or $V_H$ domain fragment), heavy-chain antibody domain derived from a cartilaginous fish antibody ($V_HH$ or $V_H$ domain fragment), immunoglobulin new antigen receptor (IgNAR), VNAR fragment, single-chain variable fragment (scFv), antibody variable fragment (Fv), complementary determining region 3 fragment (CDR3), constrained FR3-CDR3-FR4 polypeptide (FR3-CDR3-FR4), Fd fragment, small modular immunopharmaceutical (SMIP) domain, antigen-binding fragment (Fab), Armadillo repeat polypeptide (ArmRP), fibronectin-derived 10$^{th}$ fibronectin type III domain (10Fn3), tenascin type III domain (TNfn3), ankyrin repeat motif domain, low-density-lipoprotein-receptor-derived A-domain (LDLR-A), lipocalin (anticalin), Kunitz domain, Protein-A-derived Z domain, gamma-B crystallin-derived domain, ubiquitin-derived domain, Sac7d-derived polypeptide (affitin), Fyn-derived SH2 domain, miniprotein, C-type lectin-like domain scaffold, engineered antibody mimic, and any genetically manipulated counterparts of any of the foregoing which retain binding functionality. In certain embodiments of Embodiment Sets #1 to #3, the binding region comprises a polypeptide selected from the group consisting of: autonomous $V_H$ domain, single-domain antibody fragment (sdAb), Nanobody®, heavy chain-antibody domain derived from a camelid ($V_HH$ or $V_H$ domain fragment), heavy-chain antibody domain derived from a cartilaginous fish antibody ($V_HH$ or $V_H$ domain fragment), immunoglobulin new antigen receptor (IgNAR), VNAR fragment, single-chain variable fragment (scFv), antibody variable fragment (Fv), complementary determining region 3 fragment (CDR3), constrained FR3-CDR3-FR4 polypeptide (FR3-CDR3-FR4), Fd fragment, and antigen-binding fragment (Fab). In certain embodiments of Embodiment Sets #1 to #3, the binding region comprises a polypeptide selected from the group consisting of: an autonomous $V_H$ domain, single-domain antibody fragment (sdAb), Nanobody®, heavy chain-antibody domain derived from a camelid ($V_HH$ or $V_H$ domain fragment), heavy-chain antibody domain derived from a cartilaginous fish antibody ($V_HH$ or $V_H$ domain fragment), immunoglobulin new antigen receptor (IgNAR), $V_{NAR}$ fragment, single-chain variable fragment (scFv), antibody variable fragment (Fv), Fd fragment, and antigen-binding fragment (Fab). In certain embodiments of Embodiment Sets #1 to #3, the binding region comprises a single-chain variable fragment (scFv). The binding region may comprise a polypeptide selected from the group consisting of: an autonomous $V_H$ domain, single-domain antibody fragment (sdAb), Nanobody®, heavy chain-antibody domain derived from a camelid ($V_HH$ or $V_H$ domain fragment), heavy-chain antibody domain derived from a cartilaginous fish antibody ($V_HH$ or $V_H$ domain fragment), immunoglobulin new antigen receptor (IgNAR), $V_{NAR}$ fragment, single-chain variable fragment (scFv), antibody variable fragment (Fv), complementary determining region 3 fragment (CDR3), constrained FR3-CDR3-FR4 polypeptide (FR3-CDR3-FR4), Fd fragment, and antigen-binding fragment (Fab). For example, the cell-targeting molecule of the present invention comprises a binding region comprising one or more of: an antibody variable fragment, a single-domain antibody fragment, a single-chain variable fragment, a Fd fragment, an antigen-binding fragment, an autonomous $V_H$ domain, a $V_HH$ fragment derived from a camelid antibody, a heavy-chain antibody domain derived from a cartilaginous fish antibody, a VNAR fragment, and an immunoglobulin new antigen receptor. In a further example, the binding region comprises a single-chain variable fragment and/or a $V_HH$ fragment derived from a camelid antibody. In yet a further example, the binding region comprises a single-chain variable fragment. In yet a further example, the binding region comprises a $V_HH$ fragment derived from a camelid antibody.

In certain embodiments of Embodiment Sets #1 to #3, the binding region comprises an immunoglobulin binding region comprising at least one heavy-chain variable domain polypeptide linked to at least one light-chain variable domain polypeptide by a linker comprising a non-branched sequence of thirteen or more amino acid residues, optionally wherein the linker comprises an amino acid sequence selected from any one of $(G_4S)_3$ (SEQ ID NO:180), $(G_4S)_4$ (SEQ ID NO:177), $(G_4S)_5$ (SEQ ID NO:92), $(G_4S)_6$ (SEQ ID NO:178), or $(G4S)_7$ (SEQ ID NO:179).

For certain embodiments of Embodiment Sets #1 to #3, the cell-targeting molecule of the present invention is capable of exhibiting (i) a catalytic activity level comparable to a wild-type Shiga toxin A1 fragment or wild-type Shiga toxin effector polypeptide, (ii) a ribosome inhibition activity with a half-maximal inhibitory concentration ($IC_{50}$) value of 10,000 picomolar or less, and/or (iii) a significant level of Shiga toxin catalytic activity.

For certain embodiments of Embodiment Sets #1 to #3, the cell-targeting molecule of the present invention and/or its Shiga toxin effector polypeptide is capable of exhibiting subcellular routing efficiency comparable to a reference cell-targeting molecule comprising a wild-type Shiga toxin A1 fragment or wild-type Shiga toxin effector polypeptide and/or capable of exhibiting a significant level of intracellular routing activity to the endoplasmic reticulum and/or cytosol from an endosomal starting location of a cell.

For certain embodiments of Embodiment Sets #1 to #3, whereby administration of the cell-targeting molecule of the present invention to a cell physically coupled with the extracellular target biomolecule of the cell-targeting molecule's binding region, the cell-targeting molecule is capable of causing death of the cell. For certain further embodiments, administration of the cell-targeting molecule of the invention to two different populations of cell types which differ with respect to the presence or level of the extracellular target biomolecule, the cell-targeting molecule is capable of causing cell death to the cell-types physically coupled with an extracellular target biomolecule of the cytotoxic cell-targeting molecule's binding region at a CD50 at least three times or less than the CD50 to cell types which are not physically coupled with an extracellular target biomolecule of the cell-targeting molecule's binding region. For certain embodiments, whereby administration of the cell-targeting molecule of the present invention to a first population of cells whose members are physically coupled to extracellular target biomolecules of the cell-targeting molecule's binding region, and a second population of cells whose members are not physically coupled to any extracellular target biomolecule of the binding region, the cytotoxic effect of the cell-targeting molecule to members of said first population of cells relative to members of said second population of cells is at least 3-fold greater. For certain embodiments, whereby administration of the cell-targeting molecule of the present invention to a first populations of cells whose members are physically coupled to a significant amount of the extracellular target biomolecule of the cell-targeting molecule's binding region, and a second population of cells whose members are not physically coupled to a significant amount of any extracellular target biomolecule of the binding region, the cytotoxic effect of the cell-targeting molecule to members of said first population of cells relative to members of said second population of cells is at least 3-fold greater. For certain embodiments, whereby administration of the cell-targeting molecule of the present invention to a first population of target biomolecule positive cells, and a second population of cells whose members do not express a significant amount of a target biomolecule of the cell-targeting molecule's binding region at a cellular surface, the cytotoxic effect of the cell-targeting molecule to members of the first population of cells relative to members of the second population of cells is at least 3-fold greater.

For certain embodiments of Embodiment Sets #1 to #3, the cell-targeting molecule of the present invention is capable when introduced to cells of exhibiting a cytotoxicity with a half-maximal inhibitory concentration (CD50) value of 300 nM or less and/or capable of exhibiting a significant level of Shiga toxin cytotoxicity.

For certain embodiments of Embodiment Sets #1 to #3, the cell-targeting molecule of the present invention is capable of delivering an embedded or inserted, heterologous, CD8+ T-cell epitope to a MHC class I presentation pathway of a cell for cell-surface presentation of the epitope bound by a MHC class I molecule.

In certain embodiments of Embodiment Sets #1 to #3, the cell-targeting molecule comprises a molecular moiety associated with the carboxy-terminus of the Shiga toxin effector polypeptide. In certain embodiments, the molecular moiety comprises or consists of the binding region. In certain embodiments, the molecular moiety comprises at least one amino acid and the Shiga toxin effector polypeptide is linked to at least one amino acid residue of the molecular moiety. In certain further embodiments, the molecular moiety and the Shiga toxin effector polypeptide are fused forming a continuous polypeptide.

In certain embodiments of Embodiment Sets #1 to #3, the cell-targeting molecule further comprises a cytotoxic molecular moiety associated with the carboxy-terminus of the Shiga toxin effector polypeptide. For certain embodiments, the cytotoxic molecular moiety is a cytotoxic agent, such as, e.g., a small molecule chemotherapeutic agent, anti-neoplastic agent, cytotoxic antibiotic, alkylating agent, antimetabolite, topoisomerase inhibitor, and/or tubulin inhibitor known to the skilled worker and/or described herein. For certain further embodiments, the cytotoxic molecular moiety is cytotoxic at concentrations of less than 10,000, 5,000, 1,000, 500, or 200 pM.

In certain embodiments of Embodiment Sets #1 to #3, the binding region is linked, either directly or indirectly, to the Shiga toxin effector polypeptide by at least one covalent bond which is not a disulfide bond. In certain further embodiments, the binding region is fused, either directly or indirectly, to the carboxy-terminus of the Shiga toxin effector polypeptide to form a single, continuous polypeptide. In certain further embodiments, the binding region is an immunoglobulin or immunoglobulin-type binding region. For example, in the cell-targeting molecule of the present invention, the binding region and the Shiga toxin effector polypeptide may be fused forming a continuous polypeptide such that the binding region is associated with the carboxy-terminus of the Shiga toxin A subunit effector polypeptide In certain embodiments of Embodiment Sets #1 to #3, the disrupted furin-cleavage motif comprises one or more mutations in the minimal, furin-cleavage site relative to a wild-type Shiga toxin A Subunit. In certain embodiments, the disrupted furin-cleavage motif is not an amino-terminal truncation of sequences that overlap with part or all of at least one amino acid residue of the minimal furin-cleavage site. In certain embodiments, the mutation in the minimal, furin-cleavage site is an amino acid deletion, insertion, and/or substitution of at least one amino acid residue in the R/Y-x-x-R furin cleavage motif. In certain further embodiments, the disrupted furin-cleavage motif comprises at least one mutation relative to a wild-type Shiga toxin A Subunit, the mutation altering at least one amino acid residue in the region natively positioned (1) at 248-251 of the A Subunit of Shiga-like toxin 1 (SEQ ID NO:1), Shiga toxin (SEQ ID NO:2), or another Shiga toxin 1 variant sequence (e.g. SEQ ID NOs: 4-6); or (2) at 247-250 of the A Subunit of Shiga-like toxin 2 (SEQ ID NO:3) or a Shiga-like toxin 2 variant sequence (e.g. SEQ ID NOs: 7-18); or the equivalent amino acid sequence position in any Shiga toxin A Subunit. In certain further embodiments, the mutation is an amino acid residue substitution of an arginine residue with a non-positively charged, amino acid residue. In certain embodiments, the Shiga toxin effector polypeptide comprises a disrupted furin-cleavage motif at the carboxy-terminus of the Shiga toxin A1 fragment derived region, wherein said disrupted furin-cleavage motif comprises (i) a carboxy-terminal truncation of as compared to the carboxy-terminus of a wild-type Shiga toxin A Subunit and (ii) at least one amino acid substitution in the furin-cleavage site relative to a wild-type Shiga toxin A Subunit, at the natively positioned amino acid residues 248 and 251 of the A Subunit of Shiga-like toxin 1 (SEQ ID NO:1), Shiga toxin (SEQ ID NO:2), or another Shiga toxin 1 effector polypeptide variant (SEQ ID NOs: 4-6); or at the natively positioned amino acid residues 247 and 250 of the A Subunit of Shiga-like toxin 2 (SEQ ID NO:3) or a Shiga-like toxin 2 effector polypeptide variant (SEQ ID NOs: 7-18). In certain embodiments, the disrupted furin-cleavage motif comprises a carboxy-terminal truncation as compared to a wild-type Shiga toxin A Subunit; and an amino acid substitution in the furin-cleavage motif relative to a wild-type Shiga toxin A Subunit, at the natively positioned amino acid residues 248 and 251 of the A Subunit of Shiga-like toxin 1 (SEQ ID NO:1) or Shiga toxin (SEQ ID NO:2); or at the natively positioned amino acid residues 247 and 250 of the A Subunit of Shiga-like toxin 2 (SEQ ID NO:3). In certain embodiments, the substitution of the amino acid residue in the furin-cleavage motif is of an arginine residue with an alanine residue.

In certain embodiments of Embodiment Sets #1 to #3, the cell-targeting molecule of the present invention comprises the Shiga toxin effector polypeptide comprising or consisting essentially of the polypeptide shown in any one of SEQ ID NOs: 19-21 and 75-89.

In certain embodiments of Embodiment Sets #1 to #3, the cell-targeting molecule of the present invention is capable when introduced to cells of exhibiting cytotoxicity comparable to a cytotoxicity of a reference molecule, such as, e.g., a third cell-targeting molecule consisting of the cell-targeting molecule except for all of its Shiga toxin effector polypeptide component(s) each comprise a wild-type Shiga toxin A1 fragment.

In certain embodiments of Embodiment Sets #1 to #3, the binding region comprises the peptide or polypeptide shown in any one of SEQ ID NOs: 45-74, 91-92, or 94.

In certain embodiments of Embodiment Sets #1 to #3, the binding region comprises, consists essentially of, or consists of an amino acid sequence that is at least 85% (such as at least 90%, 91%, 92%, 93%, 94%, 95%, 96%, 97%, 98%, 99% or more) identical to the amino acid sequence of: amino acids 269 to 501 of SEQ ID NO:24; amino acids 269 to 513 of SEQ ID NO:25; amino acids 269 to 499 of SEQ ID NO:26; amino acids 269 to 500 of SEQ ID NO:27; amino acids 269-520 of SEQ ID NO:28; amino acids 269 to 519 of SEQ ID NO:29 or SEQ ID NO:30; amino acids 268 to 386 of SEQ ID NO:31; amino acids 269 to 499 of SEQ ID NO:32; amino acids 269 to 499 of SEQ ID NO:33; amino acids 253 to 370 of SEQ ID NO:34; amino acids 253 to 367 of SEQ ID NO:35; amino acids 269 to 514 of SEQ ID NO:36; amino acids 268 to 500 of SEQ ID NO:97; amino acids 268 to 512 of SEQ ID NO:98; amino acids 268 to 498 of SEQ ID NO:99; amino acids 268 to 499 of SEQ ID NO:100; amino acids 268-519 of SEQ ID NO:101; or amino acids 268 to 518 of SEQ ID NO:102 or SEQ ID NO:103. In certain embodiments, the binding region comprises, consists essentially of, or consists of an amino acid sequence that is at least 85% (such as at least 90%, 91%, 92%, 93%, 94%, 95%, 96%, 97%, 98%, 99% or more) identical to the amino acid sequence of: amino acids 269 to 501 of SEQ ID NO:24; amino acids 269 to 513 of SEQ ID NO:25; amino acids 269 to 499 of SEQ ID NO:26; amino acids 269 to 500 of SEQ ID NO:27; amino acids 269-520 of SEQ ID NO:28; amino acids 269 to 519 of SEQ ID NO:29 or SEQ ID NO:30; amino acids 268 to 386 of SEQ ID NO:31; amino acids 269 to 499 of SEQ ID NO:32; amino acids 269 to 499 of SEQ ID NO:33; amino acids 253 to 370 of SEQ ID NO:34; amino acids 253 to 367 of SEQ ID NO:35; or amino acids 269 to 514 of SEQ ID NO:36. In certain embodiments, the binding region comprises, consists essentially of, or consists of an amino acid sequence that is at least 85% (such as at least 90%, 91%, 92%, 93%, 94%, 95%, 96%, 97%, 98%, 99% or more) identical to the amino acid sequence of: amino acids 269 to 513 of SEQ ID NO:25; amino acids 269 to 499 of SEQ ID NO:26; amino acids 269 to 519 of SEQ ID NO:29 or SEQ ID NO:30; amino acids 268 to 386 of SEQ ID NO:31; amino acids 269 to 499 of SEQ ID NO:32; amino acids 269 to 499 of SEQ ID NO:33; amino acids 253 to 370 of SEQ ID NO:34; amino acids 253 to 367 of SEQ ID NO:35; or amino acids 269 to 514 of SEQ ID NO:36.

In certain embodiments of Embodiment Sets #1 to #3, the binding region comprises the peptide or polypeptide shown in any one of SEQ ID NOs: 45-74 and 90-96.

In certain embodiments of Embodiment Set #1 to #3, the binding region comprises, consists essentially of, or consists of the polypeptide represented by any of the following: amino acids 269 to 501 of SEQ ID NO:24; amino acids 269 to 513 of SEQ ID NO:25; amino acids 269 to 499 of SEQ ID NO:26; amino acids 269 to 500 of SEQ ID NO:27; amino acids 269-520 of SEQ ID NO:28; amino acids 269 to 519 of SEQ ID NO:29 or SEQ ID NO:30; amino acids 268 to 386 of SEQ ID NO:31; amino acids 269 to 499 of SEQ ID NO:32; amino acids 269 to 499 of SEQ ID NO:33; amino acids 253 to 370 of SEQ ID NO:34; amino acids 253 to 367 of SEQ ID NO:35; amino acids 269 to 514 of SEQ ID NO:36; amino acids 268 to 500 of SEQ ID NO:97; amino acids 268 to 512 of SEQ ID NO:98; amino acids 268 to 498 of SEQ ID NO:99; amino acids 268 to 499 of SEQ ID NO:100; amino acids 268-519 of SEQ ID NO:101; and amino acids 268 to 518 of SEQ ID NO:102 or SEQ ID NO:103. In certain embodiments, the binding region comprises, consists essentially of, or consists of the polypeptide represented by any of the following: amino acids 269 to 501 of SEQ ID NO:24; amino acids 269 to 513 of SEQ ID NO:25; amino acids 269 to 499 of SEQ ID NO:26; amino acids 269 to 500 of SEQ ID NO:27; amino acids 269-520 of SEQ ID NO:28; amino acids 269 to 519 of SEQ ID NO:29 or SEQ ID NO:30; amino acids 268 to 386 of SEQ ID NO:31; amino acids 269 to 499 of SEQ ID NO:32; amino acids 269 to 499 of SEQ ID NO:33; amino acids 253 to 370 of SEQ ID NO:34; amino acids 253 to 367 of SEQ ID NO:35; and amino acids 269 to 514 of SEQ ID NO:36. In certain embodiments, the binding region comprises, consists essentially of, or consists of the polypeptide represented by any of the following: amino acids 269 to 513 of SEQ ID NO:25; amino acids 269 to 499 of SEQ ID NO:26; amino acids 269 to 519 of SEQ ID NO:29 or SEQ ID NO:30; amino acids 268 to 386 of SEQ ID NO:31; amino acids 269 to 499 of SEQ ID NO 2; amino acids 269 to 499 of SEQ ID NO:33; amino acids 253 to 370 of SEQ ID NO:34; amino acids 253 to 367 of SEQ ID NO:35; and amino acids 269 to 514 of SEQ ID NO:36. In certain embodiments, the binding region comprises, consists essentially of, or consists of the polypeptide represented by amino acids 269 to 519 of SEQ ID NO:29, amino acids 268 to 386 of SEQ ID NO:31; amino acids 253 to 370 of SEQ ID NO:34; or amino acids 253 to 367 of SEQ ID NO:35. In certain embodiments, the binding region comprises, consists essentially of, or consists of the polypeptide represented by amino acids 269 to 519 of SEQ ID NO:29. In certain, embodiments, the binding region comprises, consists essentially of, or consists of the polypeptide represented by amino acids 268 to 386 of SEQ ID NO:31. In certain, embodiments, the binding region comprises, consists essentially of, or consists of the polypeptide represented by amino acids 253 to 370 of SEQ ID NO:34. In certain embodiments, the binding region comprises, consists essentially of, or consists of the polypeptide represented by amino acids 253 to 367 of SEQ ID NO:35.

In certain embodiments of Embodiment Set #1 to #3, the cell-targeting molecule of the present invention comprises, consists essentially of, or consists of the polypeptide shown in any one of SEQ ID NOs: 22-36 and 97-108. In certain embodiments, the cell-targeting molecule of the present invention comprises, consists essentially of, or consists of the polypeptide shown in any one of SEQ ID NOs: 25-27 and 29-36. In certain embodiments, the cell-targeting molecule of the present invention comprises, consists essentially of, or consists of the polypeptide shown in any one of SEQ ID NOs: 29, 31, 34 and 35. In certain embodiments, the cell-targeting molecule of the present invention comprises, consists essentially of, or consists of the polypeptide shown in SEQ ID NO:29. In certain embodiments, the cell-targeting molecule of the present invention comprises, consists essentially of, or consists of the polypeptide shown in SEQ ID NO:31. In certain embodiments, the cell-targeting molecule of the present invention comprises, consists essentially of, or consists of the polypeptide shown in SEQ ID NO:34. In certain embodiments, the cell-targeting molecule of the present invention comprises, consists essentially of, or consists of the polypeptide shown in SEQ ID NO:35. In certain embodiments, the cell-targeting molecule of the present invention comprises, consists essentially of, or consists of the polypeptide shown in SEQ ID NO:102.

In certain embodiments of Embodiment Set #1 to #3, the cell-targeting molecule of the present invention comprises, consists essentially of, or consists of an amino acid sequence that is at least 85% (such as at least 90%, 91%, 92%, 93%, 94%, 95%, 96%, 97%, 98%, 99% or more) identical to the amino acid sequence shown in any one of SEQ ID NOs: 22-36 and 97-108. In certain embodiments of Embodiment Set #1 to #3, the cell-targeting molecule of the present invention comprises, consists essentially of, or consists of an amino acid sequence that is at least 85% (such as at least 90%, 91%, 92%, 93%, 94%, 95%, 96%, 97%, 98%, 99% or more) identical to the amino acid sequence shown in any one of SEQ ID NOs: 25-27 and 29-36. In certain embodiments of Embodiment Set #1 to #3, the cell-targeting molecule of the present invention comprises, consists essentially of, or consists of an amino acid sequence that is at least 85% (such as at least 90%, 91%, 92%, 93%, 94%, 95%, 96%, 97%, 98%, 99% or more) identical to the amino acid sequence shown in any one of SEQ ID NOs: 29, 31, 34 and 35. In certain embodiments of Embodiment Set #1 to #3, the cell-targeting molecule of the present invention comprises, consists essentially of, or consists of an amino acid sequence that is at least 85% (such as at least 90%, 91%, 92%, 93%, 94%, 95%, 96%, 97%, 98%, 99% or more) identical to the amino acid sequence of SEQ ID NO: 29. In certain embodiments of Embodiment Set #1 to #3, the cell-targeting molecule of the present invention comprises, consists essentially of, or consists of an amino acid sequence that is at least 85% (such as at least 90%, 91%, 92%, 93%, 94%, 95%, 96%, 97%, 98%, 99% or more) identical to the amino acid sequence of SEQ ID NO:31. In certain embodiments of Embodiment Set #1 to #3, the cell-targeting molecule of the present invention comprises, consists essentially of, or consists of an amino acid sequence that is at least 85% (such as at least 90%, 91%, 92%, 93%, 94%, 95%, 96%, 97%, 98%, 99% or more) identical to the amino acid sequence of SEQ ID NO:34. In certain embodiments of Embodiment Set #1 to #3, the cell-targeting molecule of the present invention comprises, consists essentially of, or consists of an amino acid sequence that is at least 85% (such as at least 90%, 91%, 92%, 93%, 94%, 95%, 96%, 97%, 98%, 99% or more) identical to the amino acid sequence of SEQ ID NO:35.

In certain embodiments of Embodiment Set #1 to #3, the binding region comprises, consists essentially of, or consists of the polypeptide represented by any of the following: amino acids 269 to 501 of SEQ ID NO:24; amino acids 269 to 513 of SEQ ID NO:25; amino acids 269 to 499 of SEQ ID NO:26; amino acids 269 to 500 of SEQ ID NO:27; amino acids 269-520 of SEQ ID NO:28; amino acids 269 to 519 of SEQ ID NO:29 or SEQ ID NO:30; amino acids 268 to 386 of SEQ ID NO:31; amino acids 269 to 499 of SEQ ID NO:32; amino acids 269 to 499 of SEQ ID NO:33; amino acids 253 to 370 of SEQ ID NO:34; amino acids 253 to 367 of SEQ ID NO:35; amino acids 269 to 514 of SEQ ID NO:36; amino acids 268 to 500 of SEQ ID NO:97; amino acids 268 to 512 of SEQ ID NO:98; amino acids 268 to 498 of SEQ ID NO:99; amino acids 268 to 499 of SEQ ID NO:100; amino acids 268-519 of SEQ ID NO:101; amino acids 268 to 518 of SEQ ID NO:102 or SEQ ID NO:103; amino acids 267 to 384 of SEQ ID NO:104; amino acids 268 to 498 of SEQ ID NO:105; amino acids 252 to 370 of SEQ ID NO:106; amino acids 252 to 366 of SEQ ID NO:107; and amino acids 268 to 513 of SEQ ID NO:108. In certain embodiments, the binding region comprises, consists essentially of, or consists of the polypeptide represented by any of the following: amino acids 269 to 501 of SEQ ID NO:24; amino acids 269 to 513 of SEQ ID NO:25; amino acids 269 to 499 of SEQ ID NO:26; amino acids 269 to 500 of SEQ ID NO:27; amino acids 269-520 of SEQ ID NO:28; amino acids 269 to 519 of SEQ ID NO:29 or SEQ ID NO:30; amino acids 268 to 386 of SEQ ID NO:31; amino acids 269 to 499 of SEQ ID NO:32; amino acids 269 to 499 of SEQ ID NO:33; amino acids 253 to 370 of SEQ ID NO:34; amino acids 253 to 367 of SEQ ID NO:35; and amino acids 269 to 514 of SEQ ID NO:36. In certain embodiments, the binding region comprises, consists essentially of, or consists of the polypeptide represented by any of the following: amino acids 269 to 513 of SEQ ID NO:25; amino acids 269 to 499 of SEQ ID NO:26; amino acids 269 to 519 of SEQ ID NO:29 or SEQ ID NO:30; amino acids 268 to 386 of SEQ ID NO:31; amino acids 269 to 499 of SEQ ID NO:32; amino acids 269 to 499 of SEQ ID NO:33; amino acids 253 to 370 of SEQ ID NO:34; amino acids 253 to 367 of SEQ ID NO:35; and amino acids 269 to 514 of SEQ ID NO:36. In certain embodiments, the binding region comprises, consists essentially of, or consists of the polypeptide represented by amino acids 269 to 519 of SEQ ID NO:29, amino acids 268 to 386 of SEQ ID NO:31; amino acids 253 to 370 of SEQ ID NO:34; or amino acids 253 to 367 of SEQ ID NO:35. In certain embodiments, the binding region comprises, consists essentially of, or consists of the polypeptide represented by amino acids 269 to 519 of SEQ ID NO:29. In certain, embodiments, the binding region comprises, consists essentially of, or consists of the polypeptide represented by amino acids 268 to 386 of SEQ ID NO:31. In certain, embodiments, the binding region comprises, consists essentially of, or consists of the polypeptide represented by amino acids 253 to 370 of SEQ ID NO:34. In certain embodiments, the binding region comprises, consists essentially of, or consists of the polypeptide represented by amino acids 253 to 367 of SEQ ID NO:35.

In certain embodiments of Embodiment Set #1 to #3, the cell-targeting molecule of the present invention comprises, consists essentially of, or consists of the polypeptide shown in any one of SEQ ID NOs: 22-36 and 97-108. In certain embodiments, the cell-targeting molecule of the present invention comprises, consists essentially of, or consists of the polypeptide shown in any one of SEQ ID NOs: 25-27 and 29-36. In certain embodiments, the cell-targeting molecule of the present invention comprises, consists essentially of, or consists of the polypeptide shown in any one of SEQ ID NOs: 29, 31, 34 and 35. In certain embodiments, the cell-targeting molecule of the present invention comprises, consists essentially of, or consists of the polypeptide shown in SEQ ID NO:29. In certain embodiments, the cell-targeting molecule of the present invention comprises, consists essentially of, or consists of the polypeptide shown in SEQ ID NO:31. In certain embodiments, the cell-targeting molecule of the present invention comprises, consists essentially of, or consists of the polypeptide shown in SEQ ID NO:34. In certain embodiments, the cell-targeting molecule of the present invention comprises, consists essentially of, or consists of the polypeptide shown in SEQ ID NO:35.

In certain embodiments of Embodiment Set #1 to #3, the cell-targeting molecule of the present invention comprises, consists essentially of, or consists of an amino acid sequence that is at least 85% (such as at least 90%, 91%, 92%, 93%, 94%, 95%, 96%, 97%, 98%, 99% or more) identical to the amino acid sequence shown in any one of SEQ ID NOs: 22-36 and 97-108. In certain embodiments of Embodiment Set #1 to #3, the cell-targeting molecule of the present invention comprises, consists essentially of, or consists of an amino acid sequence that is at least 85% (such as at least 90%, 91%, 92%, 93%, 94%, 95%, 96%, 97%, 98%, 99% or more) identical to the amino acid sequence shown in any one of SEQ ID NOs: 25-27 and 29-36. In certain embodiments of Embodiment Set #1 to #3, the cell-targeting molecule of the present invention comprises, consists essentially of, or consists of an amino acid sequence that is at least 85% (such as at least 90%, 91%, 92%, 93%, 94%, 95%, 96%, 97%, 98%, 99% or more) identical to the amino acid sequence shown in any one of SEQ ID NOs: 29, 31, 34 and 35. In certain embodiments of Embodiment Set #1 to #3, the cell-targeting molecule of the present invention comprises, consists essentially of, or consists of an amino acid sequence that is at least 85% (such as at least 90%, 91%, 92%, 93%, 94%, 95%, 96%, 97%, 98%, 99% or more) identical to the amino acid sequence of SEQ ID NO: 29. In certain embodiments of Embodiment Set #1 to #3, the cell-targeting molecule of the present invention comprises, consists essentially of, or consists of an amino acid sequence that is at least 85% (such as at least 90%, 91%, 92%, 93%, 94%, 95%, 96%, 97%, 98%, 99% or more) identical to the amino acid sequence of SEQ ID NO:31. In certain embodiments of Embodiment Set #1 to #3, the cell-targeting molecule of the present invention comprises, consists essentially of, or consists of an amino acid sequence that is at least 85% (such as at least 90%, 91%, 92%, 93%, 94%, 95%, 96%, 97%, 98%, 99% or more) identical to the amino acid sequence of SEQ ID NO:34. In certain embodiments of Embodiment Set #1 to #3, the cell-targeting molecule of the present invention comprises, consists essentially of, or consists of an amino acid sequence that is at least 85% (such as at least 90%, 91%, 92%, 93%, 94%, 95%, 96%, 97%, 98%, 99% or more) identical to the amino acid sequence of SEQ ID NO:35.

In certain embodiments of Embodiment Sets #1 to #3, the binding region sterically covers the carboxy-terminus of the A1 fragment region.

In certain embodiments of Embodiment Sets #1 to #3, the molecular moiety sterically covers the carboxy-terminus of the A1 fragment region. In certain further embodiments, the molecular moiety comprises the binding region.

In certain embodiments of Embodiment Sets #1 to #3, the cell-targeting molecule of the present invention comprises a binding region and/or molecular moiety located carboxy-terminal to the carboxy-terminus of the Shiga toxin A1 fragment region. In certain further embodiments, the mass of the binding region and/or molecular moiety is at least 4.5 kDa, 6, kDa, 9 kDa, 12 kDa, 15 kDa, 20 kDa, 25 kDa, 28 kDa, 30 kDa, 41 kDa, 50 kDa, 100 kDa, or greater.

In certain embodiments of Embodiment Sets #1 to #3, the cell-targeting molecule comprises a binding region with a mass of at least 4.5 kDa, 6, kDa, 9 kDa, 12 kDa, 15 kDa, 20 kDa, 25 kDa, 28 kDa, 30 kDa, 41 kDa, 50 kDa, 100 kDa, or greater, as long as the cell-targeting molecule retains the appropriate level of the Shiga toxin biological activity noted herein (e.g., cytotoxicity and/or intracellular routing).

In certain embodiments of Embodiment Sets #1 to #3, the binding region is comprised within a relatively large, molecular moiety comprising such as, e.g., a molecular moiety with a mass of at least 4.5 kDa, 6, kDa, 9 kDa, 12 kDa, 15 kDa, 20 kDa, 25 kDa, 28 kDa, 30 kDa, 41 kDa, 50 kDa, 100 kDa, or greater, as long as the cell-targeting molecule retains the appropriate level of the Shiga toxin biological activity noted herein.

In certain embodiments of Embodiment Sets #1 to #3, the cell-targeting molecule of the present invention comprises or consists essentially of the polypeptide shown in any one of SEQ ID NOs: 22-37 and 97-108, and optionally the cell-targeting molecule comprises an amino-terminal methionine residue.

For certain embodiments of Embodiment Sets #1 to #3, the cell-targeting molecule of the present invention exhibits low cytotoxic potency (i.e. is not capable when introduced to certain positive target cell types of exhibiting a cytotoxicity greater than 1% cell death of a cell population at a cell-targeting molecule concentration of 1000 nM, 500 nM, 100 nM, 75 nM, or 50 nM) and is capable when introduced to cells of exhibiting a greater subcellular routing efficiency from an extracellular space to a subcellular compartment of an endoplasmic reticulum and/or cytosol as compared to the cytotoxicity of a reference molecule, such as, e.g., a fifth cell-targeting molecule having an amino-terminus and comprising the binding region and the Shiga toxin effector polypeptide which is not positioned at or proximal to the amino-terminus of the fifth cell-targeting molecule. In certain further embodiments, the fifth cell-targeting molecule does not comprise any carboxy-terminal, endoplasmic reticulum retention/retrieval signal motif of the KDEL family.

In certain embodiments of Embodiment Sets #1 to #3, the molecular moiety comprises a peptide and/or polypeptide derived from the Shiga toxin A2 fragment of a naturally occurring Shiga toxin.

The embodiments of the present invention are not intended to cover any naturally-occurring Shiga holotoxin or Shiga toxin A Subunit. In certain embodiments of Embodiment Sets #1 to #3, the cell-targeting molecule of the present invention does not comprise a naturally occurring Shiga toxin B Subunit. In certain further embodiments, the cell-targeting molecule of the invention does not comprise any polypeptide comprising, consisting essentially of, or consisting of a functional binding domain of a native Shiga toxin B subunit. Rather, in certain embodiments of the cell-targeting molecules of the invention, the Shiga toxin A Subunit derived regions are functionally associated with heterologous binding regions to effectuate cell-targeting.

In certain embodiments of Embodiment Sets #1 to #3, the Shiga toxin effector polypeptide comprises at least two, embedded or inserted, heterologous epitopes.

In certain embodiments of Embodiment Sets #1 to #3, the Shiga toxin effector polypeptide does not comprise the set of amino acid residue substitutions relative to a wild-type Shiga toxin A Subunit selected from the following sets: (1) R248H and R251H; (2) R248G and R251G; (3) A246G, S247A, A253G, and S254A; and (4) A246G, S247A, R248G, R251G, A253G, and S254A.

In certain embodiments of Embodiment Sets #1 to #3, the Shiga toxin effector polypeptide does not comprise a deletion of the region natively positioned at 247-252 in a wild-type Shiga toxin A Subunit. In certain embodiments of Embodiment Sets #1 to #3, the Shiga toxin effector polypeptide does not comprise deletions of the regions natively positioned at 245-247 and 253-255 in a wild-type Shiga toxin A Subunit.

In certain embodiments of Embodiment Sets #1 to #3, the Shiga toxin effector polypeptide comprises one or more mutations relative to a naturally occurring (or wild-type) A Subunit of a member of the Shiga toxin family which changes an enzymatic activity of the Shiga toxin effector polypeptide, the mutation selected from at least one amino acid residue deletion, insertion, or substitution. In certain further embodiments, the mutation relative to the naturally occurring A Subunit reduces or eliminates a cytotoxic activity of the Shiga toxin effector polypeptide but the Shiga toxin effector polypeptide retains at least one other Shiga toxin effector function, such as, e.g., promoting cellular internalization and/or directing intracellular routing to a certain subcellular compartment(s). In certain further embodiments, the mutation relative to the naturally occurring (or wild-type) A Subunit is selected from at least one amino acid residue substitution, such as, e.g., A231E, R75A, Y77S, Y114S, E167D, R170A, R176K, and/or W203A in SEQ ID NO:1, SEQ ID NO:2, or SEQ ID NO:3.

For certain embodiments of Embodiment Sets #1 to #3, the Shiga toxin effector polypeptide is capable of: (i) routing to a subcellular compartment of a cell in which the Shiga toxin effector polypeptide is present selected from the following: cytosol, endoplasmic reticulum, and lysosome; (ii) intracellular delivery of the epitope from an early endosomal compartment to a proteasome of a cell in which the Shiga toxin effector polypeptide is present; and/or (iii) intracellular delivery of the epitope to a MHC class I molecule from an early endosomal compartment of a cell in which the Shiga toxin effector polypeptide is present. In certain further embodiments, the Shiga toxin effector polypeptide is capable of intracellular delivery of the CD 8+ T-cell epitope for presentation by a MHC class I molecule on the surface of a cell in which the Shiga toxin effector polypeptide is present.

In certain embodiments, the molecule of the present invention does not comprise, at a position carboxy-terminal of the Shiga toxin effector polypeptide and/or the carboxy-terminus of the Shiga toxin A1 fragment region, any additional exogenous material representing an antigen and/or heterologous, CD8+, T-cell epitope-peptide.

In certain embodiments of Embodiment Sets #1 to #3, the binding region does not comprise a ligand.

In certain embodiments of Embodiment Sets #1 to #3, the cell-targeting molecule is de-immunized due to the embedded or inserted, heterologous, epitope, and exhibits reduced relative antigenicity and/or relative immunogenicity. The cell-targeting molecule exhibits reduced relative antigenicity and/or relative immunogenicity as compared to a reference molecule, such as, e.g., a seventh cell-targeting molecule consisting of the cell-targeting molecule except for it lacks one or more embedded or inserted epitopes present in the cell targeting molecule.

In certain embodiments of Embodiment Sets #1 to #3, the cell-targeting molecule is de-immunized due to the furin-cleavage motif disruption, and exhibits reduced relative antigenicity and/or relative immunogenicity. The cell-targeting molecule exhibits reduced relative antigenicity and/or relative immunogenicity as compared to a reference cell-targeting molecule consisting of the cell-targeting molecule except for the furin-cleavage motif is wild-type and/or all the Shiga toxin effector polypeptide components consist of a wild-type Shiga toxin A1 fragment.

In certain embodiments of Embodiment Sets #1 to #3, the cell-targeting molecule is de-immunized due to the plurality of disrupted B-cell and/or CD4+ T-cell epitope regions and exhibits reduced relative B-cell and/or CD4+ T-cell antigenicity and/or reduced relative B-cell and/or CD4+ T-cell immunogenicity. In certain further embodiments, the cell-targeting molecule exhibits reduced relative B-cell antigenicity and/or relative B-cell immunogenicity as compared to a reference molecule, such as, e.g., a wild-type Shiga toxin A1 fragment or cell-targeting molecule comprising the aforementioned, such as a third cell-targeting molecule consisting of the cell-targeting molecule except for all of its Shiga toxin effector polypeptide component(s) each comprise a wild-type Shiga toxin A1 fragment. In certain further embodiments, the cell-targeting molecule exhibits reduced relative CD4+ T-cell antigenicity and/or relative CD4+ T-cell immunogenicity as compared to a reference cell-targeting molecule consisting of the cell-targeting molecule except for the Shiga toxin effector polypeptide component(s) comprises a wild-type Shiga toxin A1 fragment sequence.

In certain embodiments of Embodiment Sets #1 to #3, the cell-targeting molecule is in the form of a pharmaceutically acceptable salt or solvate. Among certain embodiments of the present invention is a pharmaceutical composition comprising any one of the above Shiga toxin effector polypeptides of the present invention and/or any one of the above cell-targeting molecules of the present invention; and at least one pharmaceutically acceptable excipient or carrier. The at least one pharmaceutically acceptable carrier may include a solvent, a dispersion medium, a coating, an antimicrobial agent, an isotonic agent, or an absorption delaying agent; and/or wherein the pharmaceutical composition further comprises an aqueous or non-aqueous carrier; a surfactant; a stabilizer, a preservative, a buffer, an antioxidant, a wetting agent, an emulsifying agent, a dispersing agent; an isotonic agent; and/or an antibacterial or antifungal agent.

Among certain embodiments of the present invention is a diagnostic composition comprising any one of the above cell-targeting molecules of the present invention and a detection promoting agent. Certain further embodiments are cell-targeting molecules of the present invention wherein the detection promoting agent is a heterologous epitope and the cell-targeting molecule comprises the heterologous epitope.

Beyond the Shiga toxin effector polypeptides of the present invention, cell-targeting molecules of the present invention, and compositions thereof, polynucleotides capable of encoding a cell-targeting molecule of the present invention are within the scope of the present invention, as well as expression vectors which comprise a polynucleotide of the present invention and host cells comprising any polynucleotide and/or expression vector of the present invention. Host cells comprising an expression vector may be used, e.g., in methods for producing a molecule of the present invention or a polypeptide component or fragment thereof by recombinant expression.

Among certain embodiments of the present invention is a method of killing a cell (e.g. a HER2-expressing cell), the method comprising the step of contacting the cell with any of the above cell-targeting molecules of the present invention or the above pharmaceutical compositions of the present invention. In certain embodiments, the step of contacting the cell(s) occurs in vitro. In certain embodiments, the cell expresses muc-4 and/or CD44. In certain embodiments, the cell is resistant to cytotoxicity caused by T-DM1 (trastuzumab emtansine) and/or trastuzumab. In further embodiments of the cell-killing methods, the method is capable of selectively killing cell(s) and/or cell types preferentially over other cell(s) and/or cell types when contacting a mixture of cells which differ with respect to the extracellular presence and/or expression level of a target HER2/neu/ErbB2 of the binding region of the cell-targeting molecule. In certain further embodiments the cell(s) are in the presence of pertuzumab, T-DM1 (trastuzumab emtansine), and/or lapatinib and/or had previously been contacted with pertuzumab, T-DM1 (trastuzumab emtansine), and/or lapatinib. In certain embodiments, the step of contacting the cell(s) occurs or in vivo. In further embodiments of the cell-killing methods, the method is capable of selectively killing cell(s) and/or cell types preferentially over other cell(s) and/or cell types when contacting a mixture of cells which differ with respect to the extracellular presence and/or expression level of an extracellular target biomolecule of the binding region of the cell-targeting molecule.

Among certain embodiments of the present invention is a method of killing a cell (e.g. a HER2-expressing cell), the method comprising the step of contacting the cell with any of the above cell-targeting molecules of the present invention or the above pharmaceutical compositions of the present invention. In certain embodiments, the step of contacting the cell(s) occurs in vitro. In certain other embodiments, the step of contacting the cell(s) occurs or in vivo. In certain embodiments, the cell expresses muc-4 and/or CD44. In certain embodiments, the cell is resistant to cytotoxicity caused by T-DM1 (trastuzumab emtansine) and/or trastuzumab. In further embodiments of the cell-killing methods, the method is capable of selectively killing cell(s) and/or cell types preferentially over other cell(s) and/or cell types when contacting a mixture of cells which differ with respect to the extracellular presence and/or expression level of an extracellular target biomolecule of the binding region of the cell-targeting molecule. In certain further embodiments the cell(s) are in the presence of pertuzumab, T-DM1 (trastuzumab emtansine), and/or lapatinib and/or had previously been contacted with pertuzumab, T-DM1 (trastuzumab emtansine), and/or lapatinib.

Among certain embodiments of the present invention is a method of killing a cell (e.g. a HER2-expressing cell), the method comprising the step of contacting the cell with any of the above cell-targeting molecules of the present invention or the above pharmaceutical compositions of the present invention wherein the cell is in the presence of pertuzumab, T-DM1 (trastuzumab emtansine), and/or lapatinib and/or had previously been contacted with pertuzumab, T-DM1 (trastuzumab emtansine), and/or lapatinib. In certain embodiments, the step of contacting the cell(s) occurs in vitro. In certain other embodiments, the step of contacting the cell(s) occurs or in vivo. In certain embodiments, the cell expresses muc-4 and/or CD44. In certain embodiments, the cell is resistant to cytotoxicity caused by T-DM1 (trastuzumab emtansine) and/or trastuzumab. In further embodiments of the cell-killing methods, the method is capable of selectively killing cell(s) and/or cell types preferentially over other cell(s) and/or cell types when contacting a mixture of cells which differ with respect to the extracellular presence and/or expression level of an extracellular target biomolecule of the binding region of the cell-targeting molecule.

The present invention further provides methods of treating diseases, disorders, and/or conditions in patients, the methods each comprising the step of administering to a patient in need thereof a therapeutically effective amount of a cell-targeting molecule of the present invention and/or pharmaceutical composition of the present invention. For certain embodiments, the method of treating diseases, disorders, and/or conditions in a patient in need thereof further comprises administering to the patient in need thereof a therapeutically effective amount of one or more additional HER2-targeting therapeutic agent as described herein. For certain embodiments, the patient in need thereof has been previously treated with one or more additional HER2-targeting therapeutic agent and/or does not respond to, or does not benefit from, treatment with one or more additional HER2-targeting therapeutic agent.

For certain embodiments, the disease, disorder, or condition to be treated using a method of the invention is selected from: a cancer, tumor, growth abnormality, immune disorder, or microbial infection. In certain embodiments of these methods, the cancer to be treated is selected from the group consisting of: bone cancer, breast cancer, central/peripheral nervous system cancer, gastrointestinal cancer, germ cell cancer, glandular cancer, head-neck cancer, hematological cancer, kidney-urinary tract cancer, liver cancer, lung/pleura cancer, prostate cancer, sarcoma, skin cancer, and uterine cancer, such as, e.g., breast cancer, gastric cancer, urothelial cancer, bladder cancer, urothelial bladder cancer, serous uterine cancer, extrahepatic biliary tract cancer, or biliary carcinoma. For certain embodiments, the cancer being treated is breast cancer and/or gastrointestinal cancer. For certain embodiments of these methods, the immune disorder to be treated is an immune disorder associated with a disease selected from the group consisting of: amyloidosis, ankylosing spondylitis, asthma, Crohn's disease, diabetes, graft rejection, graft-versus-host disease, Hashimoto's thyroiditis, hemolytic uremic syndrome, HIV-related disease, lupus erythematosus, multiple sclerosis, polyarteritis nodosa, polyarthritis, psoriasis, psoriatic arthritis, rheumatoid arthritis, scleroderma, septic shock, Sjögren's syndrome, ulcerative colitis, and vasculitis.

The use of any composition of matter of the present invention for the treatment or prevention of a cancer, tumor, growth abnormality, and/or immune disorder is within the scope of the present invention. Among certain embodiments of the present invention is a cell-targeting molecule of the present invention and/or a pharmaceutical composition of the invention for use in the treatment or prevention of a disease, disorder or condition in a patient in need thereof. Furthermore, the diagnostic composition, polynucleotide, expression vector, and host cell of the present invention are for use in the treatment or prevention of a disease, disorder or condition in a patient in need thereof. Among certain embodiments of the present invention is a cell-targeting molecule of the present invention and/or a pharmaceutical composition thereof for the treatment or prevention of a cancer, tumor, growth abnormality, immune disorder, and/or microbial infection. Among certain embodiments of the present invention is the use of a cell-targeting molecule of the present invention and/or pharmaceutical composition of the present invention in the manufacture of a medicament for the treatment or prevention of a disease, disorder or condition in a patient in need thereof. Furthermore, the present invention provides the use of the diagnostic composition, polynucleotide, expression vector, and host cell of the present invention in the manufacture of a medicament for the treatment or prevention of a disease, disorder or condition in a patient in need thereof. Among certain embodiments of the present invention is the use of a cell-targeting molecule of the present invention and/or pharmaceutical composition thereof in the manufacture of a medicament for the treatment or prevention of a cancer, tumor, growth abnormality, immune disorder, or microbial infection. Furthermore, the present invention provides the use of the diagnostic composition, polynucleotide, expression vector, and host cell of the present invention in the manufacture of a medicament for the treatment or prevention of a cancer, tumor, growth abnormality, immune disorder, or microbial infection. The "disease, disorder or condition" or the "cancer, tumor, growth abnormality, immune disorder, or microbial infection" may be characterized by cells that are physically coupled with HER2/neu/ErbB2. The HER2/neu/ErbB2 target biomolecule can be physically coupled to the surface of the cells. In certain embodiments, the disease, disorder or condition may be characterized by cells that express the HER2/neu/ErbB2 target biomolecule (including cells that overexpress HER2). The HER2/neu/ErbB2 can be expressed (including overexpressed) at the surface of the cells.

Certain embodiments of the cell-targeting molecules of the present invention may be utilized for the delivery of additional exogenous material into a cell physically coupled with an extracellular target biomolecule of the cell-targeting molecule of the present invention. Additionally, the present invention provides a method for delivering exogenous material to the inside of a cell(s) comprising contacting the cell(s), either in vitro or in vivo, with a cell-targeting molecule, pharmaceutical composition, and/or diagnostic composition of the present invention. The present invention further provides a method for delivering exogenous material to the inside of a cell(s) (e.g. a HER2-expressing cell) in a patient, the method comprising the step of administering to the patient a cell-targeting molecule of the present invention (with or without cytotoxic activity), wherein the target cell(s) is physically coupled with an extracellular target biomolecule of the cell-targeting molecule.

Among certain embodiments of the present invention is a method of delivering into a cell (e.g. a HER2-expressing cell), the method a T-cell epitope capable of being presented by a MHC class I molecule of the cell, the method comprising the step of contacting the cell with the cell-targeting molecule of the present invention which is associated with a heterologous, T-cell epitope and/or a composition thereof (e.g., a pharmaceutical or diagnostic composition of the present invention).

Among certain embodiments of the present invention is a method for "seeding" a tissue locus within a chordate, the method comprising the step of: administering to the chordate a cell-targeting molecule of the present invention, a pharmaceutical composition of the present invention, and/or a diagnostic composition of the present invention (see e.g. WO 2017/019623; WO 2018/140427). For certain further embodiments, the methods of the invention for "seeding" a tissue locus are for "seeding" a tissue locus which comprises a malignant, diseased, or inflamed tissue. The malignant, diseased, or inflamed tissue may be characterized by cells that are physically coupled with HER2/neu/ErbB2. The HER2/neu/ErbB2 target biomolecule can be physically coupled to the surface of the cells. For certain embodiments, the disease, disorder or condition may be characterized by cells that express the HER2/neu/ErbB2 target biomolecule (including cells that overexpress HER2). The HER2/neu/ErbB2 can be expressed (including overexpressed) at the surface of the cells. For certain further embodiments, the methods of the invention for "seeding" a tissue locus are for "seeding" a tissue locus which comprises the tissue selected from the group consisting of: diseased tissue, tumor mass, cancerous growth, tumor, infected tissue, or abnormal cellular mass. For certain further embodiments, the methods of the invention for "seeding" a tissue locus comprises administering to the chordate the cell-targeting molecule of the invention, the pharmaceutical composition of the invention, or the diagnostic composition of the invention comprising the heterologous, T-cell epitope selected from the group consisting of: peptides not natively presented by the target cells of the cell-targeting molecule in MHC class I complexes, peptides not natively present within any protein expressed by the target cell, peptides not natively present within the proteome of the target cell, peptides not natively present in the extracellular microenvironment of the site to be seeded, and peptides not natively present in the tumor mass or infected tissue site to be targeted. The diseased tissue, tumor mass, cancerous growth, tumor, infected tissue, or abnormal cellular mass may be characterized by cells that are physically coupled with HER2/neu/ErbB2. The HER2/neu/ErbB2 target biomolecule can be physically coupled to the surface of the cells. For certain embodiments, the disease, disorder or condition may be characterized by cells that express the HER2/neu/ErbB2 target biomolecule (including cells that overexpress HER2). The HER2/neu/ErbB2 can be expressed (including overexpressed) at the surface of the cells.

The use of any composition of matter of the present invention for the diagnosis, prognosis, and/or characterization of a disease, disorder, and/or condition is within the scope of the present invention. For example, the use of the cell-targeting molecule, pharmaceutical composition, diagnostic composition, polynucleotide, expression vector, and host cell of the present invention for the diagnosis, prognosis, and/or characterization of a disease, disorder, and/or condition is within the scope of the present invention. Among certain embodiments of the present invention is a method of using a cell-targeting molecule of the present invention comprising a detection promoting agent and/or composition of the present invention (e.g. a diagnostic composition) for the collection of information useful in the diagnosis, prognosis, or characterization of a disease, disorder, or condition. Among certain embodiments of the present invention is the method of detecting a cell (or subcellular compartment thereof) using a cell-targeting molecule and/or diagnostic composition of the present invention, the method comprising the steps of contacting a cell with the cell-targeting molecule and/or diagnostic composition and detecting the presence of said cell-targeting molecule and/or diagnostic composition. In certain embodiments, the step of contacting the cell(s) occurs in vitro. In certain embodiments, the step of contacting the cell(s) occurs in vivo. In certain embodiments, the step of detecting the cell(s) occurs in vitro. In certain embodiments, the step of detecting the cell(s) occurs in vivo. In certain further embodiments, the method involves the detection of the location of the cell-targeting molecule in an organism using one or more imaging procedures after the administration of the cell-targeting molecule to said organism. For example, cell-targeting molecules of the invention which incorporate detection promoting agents as described herein may be used to characterize diseases as potentially treatable by a related pharmaceutical composition of the present invention. For example, certain cell-targeting molecules of the present invention and compositions thereof (e.g. pharmaceutical compositions and diagnostic compositions of the present invention), and methods of the present invention may be used to determine if a patient belongs to a group that responds to a pharmaceutical composition of the present invention. For example, certain cell-targeting molecules of the present invention and compositions thereof may be used to identify cells which present a delivered heterologous epitope-peptide on a cellular surface and/or to identify subjects containing cells which present a heterologous epitope-peptide delivered by a cell-targeting molecule of the present invention. The "disease, disorder or condition" may be characterized by cells that are physically coupled with HER2/neu/ErbB2. The HER2/neu/ErbB2 target biomolecule can be physically coupled to the surface of the cells. In certain embodiments, the disease, disorder or condition may be characterized by cells that express the HER2/neu/ErbB2 target biomolecule (including cells that overexpress HER2). The HER2/neu/ErbB2 can be expressed (including overexpressed) at the surface of the cells.

Among certain embodiments of the present invention is a method of producing a molecule of the present invention, the method comprising the step of purifying the molecule of the present invention using a bacterial cell-wall protein domain interaction, such as, e.g., protein L from *P. magnus* or derivatives and binding domain fragments thereof or protein A from *S. aureus* or derivatives and binding domain fragments thereof. For certain further embodiments, the purifying step of the method involves the cell-targeting molecule comprising, consisting essentially of, or consisting of any one of the polypeptides shown in SEQ ID NOs: 22-36 or 97-108.

Among certain embodiments of the present invention are kits comprising a composition of matter of the present invention, and optionally, instructions for use, additional reagent(s), and/or pharmaceutical delivery device(s). For example, the present invention provides a kit comprising: (i) a cell-targeting molecule of the present invention, (ii) a pharmaceutical composition of the present invention, (iii) a diagnostic composition of the present invention, (iv) a polynucleotide of the present invention, (v) an expression vector of the present invention and/or (vi) a host cell of the present invention; and optionally, instructions for use, additional reagent(s), and/or pharmaceutical delivery device(s). The kit may further comprise reagents and other tools for detecting a cell type (e.g. a tumor cell) in a sample or in a subject.

These and other features, aspects and advantages of the present invention will become better understood with regard to the following description, appended claims, and accompanying figures. The aforementioned elements of the invention may be individually combined or removed freely in order to make other embodiments of the invention, without any statement to object to such synthesis or removal hereinafter.

BRIEF DESCRIPTION OF THE FIGURES

FIG. 17 also shows the cytotoxicity of treatment of the cells with 115111 (SEQ ID NO:29) alone. The cytotoxicity of 115111 (SEQ ID NO:29) alone appeared to be very similar to its cytotoxicity in the presence of excess trastuzumab, excess pertuzumab, or excess of both trastuzumab and pertuzumab.

DETAILED DESCRIPTION

Figure 1:
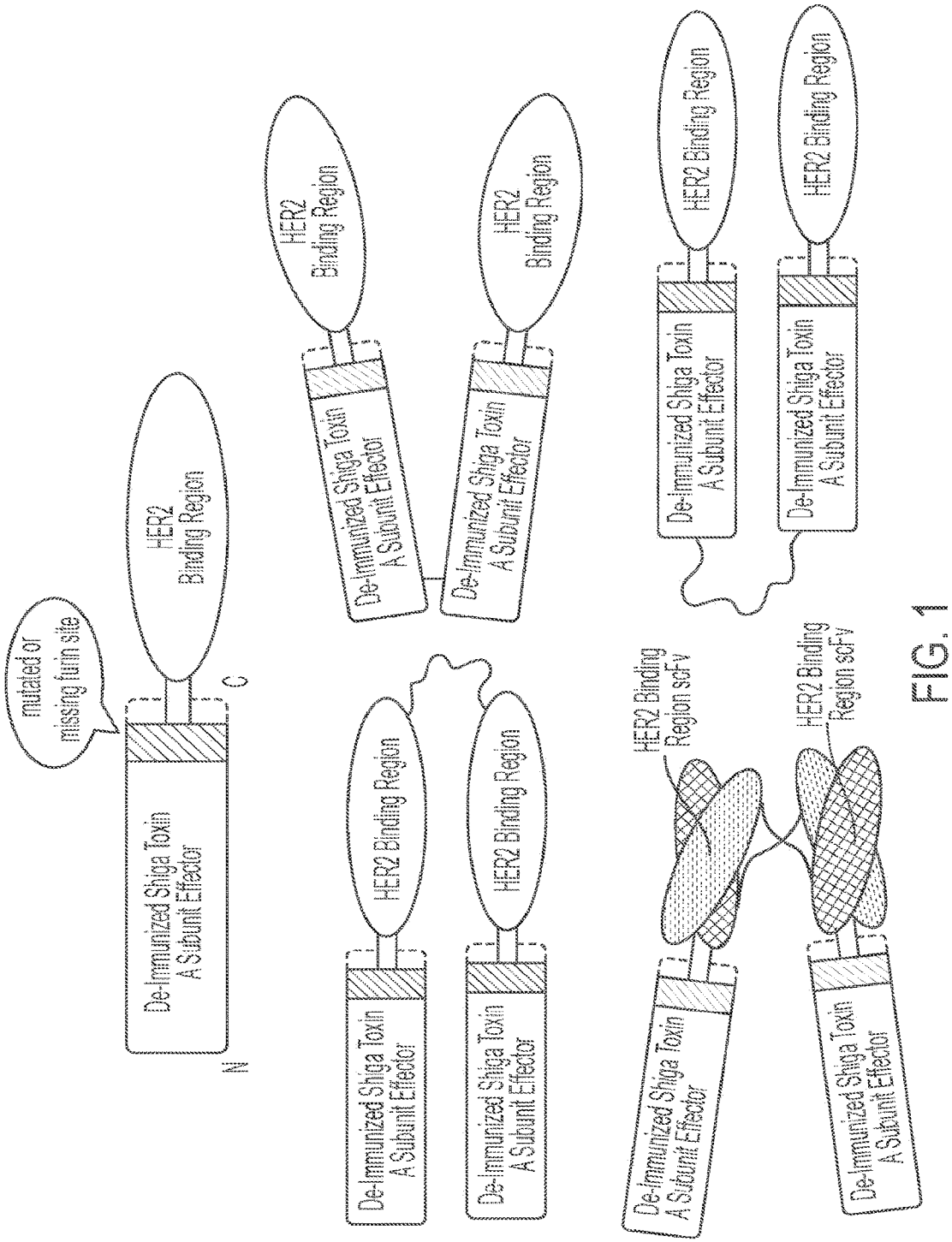
FIG. 1 depicts exemplary HER2-targeting molecules comprising one or more de-immunized Shiga toxin A Subunit effector polypeptides and one or more HER2 binding regions. These exemplary cell-targeting molecules each comprise a Shiga toxin effector polypeptide having de-immunizing mutations and a disrupted furin cleavage site near the carboxy terminus of the Shiga toxin effector polypeptide. A dashed For each sample molecule, the luminescent intensity of luciferase expressed during the assay in relative luminescent units (RLU times $e^3$) was plotted over the logarithm to base 10 of the concentration of the HER2-targeting molecule tested in picomolar (pM). These exemplary HER2-targeting molecules 115111 (SEQ ID NO:29), 115172 (SEQ ID NO:23), and 115411 (SEQ ID NO:30) exhibited ribosome inhibition activities comparable to a "control" molecule, a Shiga toxin effector polypeptide (SLTA-DI-2 (SEQ ID NO:20)) alone, not coupled with any targeting agent or binding region. Additionally, the protein synthesis in pertuzumab (100 μg/mL), or both (100 μg/mL of each antibody), pretreated for 1 hour prior to the addition of HER2-targeting molecules. The percent viability of HER2 positive cells was plotted over the logarithm to base 10 of the administered 115111 (SEQ ID NO:29) concentrations.

The present invention is described more fully hereinafter using illustrative, non-limiting embodiments, and references to the accompanying figures. This invention may, however, be embodied in many different forms and should not be construed as to be limited to the embodiments set forth below. Rather, these embodiments are provided so that this disclosure is thorough and conveys the scope of the invention to those skilled in the art.

In order that the present invention may be more readily understood, certain terms are defined below. Additional definitions may be found within the detailed description of the invention.

As used in the specification and the appended claims, the terms "a," "an" and "the" include both singular and the plural referents unless the context clearly dictates otherwise.

As used in the specification and the appended claims, the term "and/or" when referring to two species, A and B, means at least one of A and B. As used in the specification and the appended claims, the term "and/or" when referring to greater than two species, such as A, B, and C, means at least one of A, B, or C, or at least one of any combination of A, B, or C (with each species in singular or multiple possibility).

Throughout this specification, the word "comprise" or variations such as "comprises" or "comprising" will be understood to imply the inclusion of a stated integer (or components) or group of integers (or components), but not the exclusion of any other integer (or components) or group of integers (or components).

Throughout this specification, the term "including" is used to mean "including but not limited to". "Including" and "including but not limited to" are used interchangeably.

As used herein, the term "a plurality of" means more than one; such as at least 2, 3, 4, 5, 6, 7, 8, 9, 10, 11, 12, 13, 14, 15, 16, 17, 18, 19, 20, 21, 22, or 23.

The term "amino acid residue" or "amino acid" includes reference to an amino acid that is incorporated into a protein, polypeptide, or peptide. The term "polypeptide" includes any polymer of amino acids or amino acid residues. The term "polypeptide sequence" refers to a series of amino acids or amino acid residues which physically comprise a polypeptide. A "protein" is a macromolecule comprising one or more polypeptides or polypeptide "chains." A "peptide" is a small polypeptide of sizes less than about a total of 15 to 20 amino acid residues. The term "amino acid sequence" refers to a series of amino acids or amino acid residues which physically comprise a peptide or polypeptide depending on the length. Unless otherwise indicated, polypeptide and protein sequences disclosed herein are written from left to right representing their order from an amino-terminus to a carboxy-terminus.

The terms "amino acid," "amino acid residue," "amino acid sequence," or polypeptide sequence include naturally occurring amino acids (including L and D isosteriomers) and, unless otherwise limited, also include known analogs of natural amino acids that can function in a similar manner as naturally occurring amino acids, such as selenocysteine, pyrrolysine, N-formylmethionine, gamma-carboxyglutamate, hydroxyprolinehypusine, pyroglutamic acid, and selenomethionine. The amino acids referred to herein are described by shorthand designations as follows in Table A:

TABLE A

Amino Acid Nomenclature

| Name | 3-letter | 1-letter |
|---|---|---|
| Alanine | Ala | A |
| Arginine | Arg | R |
| Asparagine | Asn | N |
| Aspartic Acid or Aspartate | Asp | D |
| Cysteine | Cys | C |
| Glutamic Acid or Glutamate | Glu | E |
| Glutamine | Gln | Q |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

The phrase "conservative substitution" with regard to an amino acid residue of a peptide, peptide region, polypeptide region, protein, or molecule refers to a change in the amino acid composition of the peptide, peptide region, polypeptide region, protein, or molecule that does not substantially alter the function and structure of the overall peptide, peptide region, polypeptide region, protein, or molecule (see Creighton, *Proteins: Structures and Molecular Properties* (W. H. Freeman and Company, New York (2nd ed., 1992))).

As used herein, the term "HER2" is used interchangeably with the terms "neu" and "ErbB2".

For purposes of the present invention, the phrase "derived from" when referring to a polypeptide or polypeptide region means that the polypeptide or polypeptide region comprises amino acid sequences originally found in a "parental" protein and which may now comprise certain amino acid residue additions, deletions, truncations, rearrangements, or other alterations relative to the original polypeptide or polypeptide region as long as a certain function(s) and a structure(s) of the "parental" molecule are substantially conserved. The skilled worker will be able to identify a parental molecule from which a polypeptide or polypeptide region was derived using techniques known in the art, e.g., protein sequence alignment software.

For purposes of the claimed invention and with regard to a Shiga toxin polypeptide sequence or Shiga toxin derived polypeptide, the term "wild-type" generally refers to a naturally occurring, Shiga toxin protein sequence(s) found in a living species, such as, e.g., a pathogenic bacterium, wherein that Shiga toxin protein sequence(s) is one of the most frequently occurring variants. This is in contrast to infrequently occurring Shiga toxin protein sequences that, while still naturally occurring, are found in less than one percent of individual organisms of a given species when sampling a statistically powerful number of naturally occurring individual organisms of that species which comprise at least one Shiga toxin protein variant. A clonal expansion of a natural isolate outside its natural environment (regardless of whether the isolate is an organism or molecule comprising biological sequence information) does not alter the naturally occurring requirement as long as the clonal expansion does not introduce new sequence variety not present in naturally occurring populations of that species and/or does not change the relative proportions of sequence variants to each other.

The terms "associated," "associating," "linked," or "linking" with regard to the claimed invention refers to the state of two or more components of a molecule being joined, attached, connected, or otherwise coupled to form a single molecule or the act of making two molecules associated with each other to form a single molecule by creating an association, linkage, attachment, and/or any other connection between the two molecules. For example, the term "linked" may refer to two or more components associated by one or more atomic interactions such that a single molecule is formed and wherein the atomic interactions may be covalent and/or non-covalent. Non-limiting examples of covalent associations between two components include peptide bonds and cysteine-cysteine disulfide bonds. Non-limiting examples of non-covalent associations between two molecular components include ionic bonds.

For purposes of the present invention, the term "linked" refer to two or more molecular components associated by one or more atomic interactions such that a single molecule is formed and wherein the atomic interactions includes at least one covalent bond. For purposes of the present invention, the term "linking" refers to the act of creating a linked molecule as described above.

For purposes of the present invention, the term "fused" refers to two or more proteinaceous components associated by at least one covalent bond which is a peptide bond, regardless of whether the peptide bond involves the participation of a carbon atom of a carboxyl acid group or involves another carbon atom, such as, e.g., the α-carbon, β-carbon, γ-carbon, α-carbon, etc. Non-limiting examples of two proteinaceous components fused together include, e.g., an amino acid, peptide, or polypeptide fused to a polypeptide via a peptide bond such that the resulting molecule is a single, continuous polypeptide. For purposes of the present invention, the term "fusing" refers to the act of creating a fused molecule as described above, such as, e.g., a fusion protein generated from the recombinant fusion of genetic regions which when translated produces a single proteinaceous molecule.

The symbol "::" means the polypeptide regions before and after it are physically linked together to form a continuous polypeptide.

As used herein, the terms "expressed," "expressing," or "expresses," and grammatical variants thereof, refer to translation of a polynucleotide or nucleic acid into a protein. The expressed protein may remain intracellular, become a component of the cell surface membrane or be secreted into an extracellular space.

As used herein, cells which express a significant amount of an extracellular target biomolecule at least one cellular surface are "target positive cells" or "target+ cells" and are cells physically coupled to the specified, extracellular target biomolecule.

As used herein, the symbol "α" is shorthand for an immunoglobulin-type binding region capable of binding to the biomolecule following the symbol. The symbol "α" is used to refer to the functional characteristic of an immunoglobulin-type binding region based on its ability to bind to the biomolecule following the symbol with a binding affinity described by a dissociation constant ($K_D$) of $10^{-5}$ or less.

As used herein, the term "heavy chain variable ($V_H$) domain" or "light chain variable ($V_L$) domain" respectively refer to any antibody $V_H$ or $V_L$ domain (e.g. a human $V_H$ or $V_L$ domain) as well as any derivative thereof retaining at least qualitative antigen binding ability of the corresponding native antibody (e.g. a humanized $V_H$ or $V_L$ domain derived from a native murine $V_H$ or $V_L$ domain). A $V_H$ or $V_L$ domain consists of a "framework" region interrupted by the three CDRs or ABRs. The framework regions serve to align the CDRs or ABRs for specific binding to an epitope of an antigen. From amino-terminus to carboxy-terminus, both $V_H$ and $V_L$ domains comprise the following framework (FR) and CDR regions or ABR regions: FR1, CDR1, FR2, CDR2, FR3, CDR3, and FR4; or, similarly, FR1, ABR1, FR2, ABR2, FR3, ABR3, and FR4. As used herein, the terms "HCDR1," "HCDR2," or "HCDR3" are used to refer to CDRs 1, 2, or 3, respectively, in a $V_H$ domain, and the terms "LCDR1," "LCDR2," and "LCDR3" are used to refer to CDRs 1, 2, or 3, respectively, in a $V_L$ domain. As used herein, the terms "HABR1," "HABR2," or "HABR3" are used to refer to ABRs 1, 2, or 3, respectively, in a $V_H$ domain, and the terms "LABR1," "LABR2," or "LABR3" are used to refer to ABRs 1, 2, or 3, respectively, in a $V_L$ domain. For camelid $V_H$H fragments, IgNARs of cartilaginous fish, VNAR fragments, certain single domain antibodies, and derivatives thereof, there is a single, heavy chain variable domain comprising the same basic arrangement: FR1, CDR1, FR2, CDR2, FR3, CDR3, and FR4. As used herein, the terms "HCDR1," "HCDR2," or "HCDR3" may be used to refer to CDRs 1, 2, or 3, respectively, in a single heavy chain variable domain.

For purposes of the present invention, the term "effector" means providing a biological activity, such as cytotoxicity, biological signaling, enzymatic catalysis, subcellular routing, and/or intermolecular binding resulting in an allosteric effect(s) and/or the recruitment of one or more factors.

For purposes of the present invention, the phrases "Shiga toxin A Subunit effector polypeptide", "Shiga toxin effector polypeptide," "Shiga toxin effector polypeptide region," and "Shiga toxin effector region" refer to a polypeptide or polypeptide region derived from at least one Shiga toxin A Subunit of a member of the Shiga toxin family wherein the polypeptide or polypeptide region is capable of exhibiting at least one Shiga toxin function. For example, SEQ ID NOs: 19-21 are derived from StxA and SLT-1A.

For purposes of the present invention, a Shiga toxin effector function is a biological activity conferred by a polypeptide region derived from a Shiga toxin A Subunit or an original Shiga toxin A Subunit. Non-limiting examples of Shiga toxin effector functions include promoting cell entry; lipid membrane deformation; promoting cellular internalization; stimulating clathrin-mediated endocytosis; directing intracellular routing to various intracellular compartments such as, e.g., the Golgi, endoplasmic reticulum, and cytosol; directing intracellular routing with a cargo; inhibiting a ribosome function(s); catalytic activities, such as, e.g., N-glycosidase activity and catalytically inhibiting ribosomes; reducing protein synthesis, inducing caspase activity, activating effector caspases, effectuating cytostatic effects, and cytotoxicity. Shiga toxin catalytic activities include, for example, ribosome inactivation, protein synthesis inhibition, N-glycosidase activity, polynucleotide:adenosine glycosidase activity, RNase activity, and DNase activity. Shiga toxins are ribosome inactivating proteins (RIPs). RIPs can depurinate nucleic acids, polynucleosides, polynucleotides, rRNA, ssDNA, dsDNA, mRNA (and polyA), and viral nucleic acids (see e.g., Barbieri L et al., *Biochem J* 286: 1-4 (1992); Barbieri L et al., *Nature* 372: 624 (1994); Ling J et al., *FEBS Lett* 345: 143-6 (1994); Barbieri L et al., *Biochem J* 319: 507-13 (1996); Roncuzzi L, Gasperi-Campani A, *FEBS Lett* 392: 16-20 (1996); Stirpe F et al., *FEBS Lett* 382: 309-12 (1996); Barbieri L et al., *Nucleic Acids Res* 25: 518-22 (1997); Wang P, Tumer N, *Nucleic Acids Res* 27: 1900-5 (1999); Barbieri L et al., *Biochim Biophys Acta* 1480: 258-66 (2000); Barbieri L et al., *J Biochem* 128: 883-9 (2000); Brigotti M et al., *Toxicon* 39: 341-8 (2001); Brigotti M et al., *FASEB J* 16: 365-72 (2002); Bagga S et al., *J Biol Chem* 278: 4813-20 (2003); Picard D et al., *J Biol Chem* 280: 20069-75 (2005)). Some RIPs show antiviral activity and superoxide dismutase activity (Erice A et al., *Antimicrob Agents Chemother* 37: 835-8 (1993); Au T et al., *FEBS Lett* 471: 169-72 (2000); Parikh B, Tumer N, *Mini Rev Med Chem* 4: 523-43 (2004); Sharma N et al., *Plant Physiol* 134: 171-81 (2004)). Shiga toxin catalytic activities have been observed both in vitro and in vivo. Non-limiting examples of assays for Shiga toxin effector activity measure various activities, such as, e.g., protein synthesis inhibitory activity, depurination activity, inhibition of cell growth, cytotoxicity, supercoiled DNA relaxation activity, and nuclease activity.

As used herein, the retention of Shiga toxin effector function refers to being capable of exhibiting a level of Shiga toxin functional activity, as measured by an appropriate quantitative assay with reproducibility, comparable to a wild-type, Shiga toxin effector polypeptide control (e.g. a Shiga toxin A1 fragment) or cell-targeting molecule comprising a wild-type Shiga toxin effector polypeptide (e.g. a Shiga toxin A1 fragment) under the same conditions. For the Shiga toxin effector function of ribosome inactivation or ribosome inhibition, retained Shiga toxin effector function is exhibiting an $IC_{50}$ of 10,000 pM or less in an in vitro setting, such as, e.g., by using an assay known to the skilled worker and/or described herein. For the Shiga toxin effector function of cytotoxicity in a target positive cell-kill assay, retained Shiga toxin effector function is exhibiting a $CD_{50}$ of 1,000 nM or less, depending on the cell type and its expression of the appropriate extracellular target biomolecule, as shown, e.g., by using an assay known to the skilled worker and/or described herein.

For purposes of the claimed invention, the term "equivalent" with regard to ribosome inhibition means an empirically measured level of ribosome inhibitory activity, as measured by an appropriate quantitative assay with reproducibility, which is reproducibly within 10% or less of the activity of the reference molecule (e.g., the second cell-targeting molecule, third cell-targeting molecule, etc.) under the same conditions.

For purposes of the claimed invention, the term "equivalent" with regard to cytotoxicity means an empirically measured level of cytotoxicity, as measured by an appropriate quantitative assay with reproducibility, which is reproducibly within 10% or less of the activity of the reference molecule (e.g., the second cell-targeting molecule, third cell-targeting molecule, etc.) under the same conditions.

As used herein, the term "attenuated" with regard to cytotoxicity means a molecule exhibits or exhibited a $CD_{50}$ between 10-fold to 100-fold of a $CD_{50}$ exhibited by a reference molecule under the same conditions.

Inaccurate $IC_{50}$ and $CD_{50}$ values should not be considered when determining a level of Shiga toxin effector function activity. For some samples, accurate values for either $IC_{50}$ or $CD_{50}$ might be unobtainable due to the inability to collect the required data points for an accurate curve fit. For example, theoretically, neither an $IC_{50}$ nor $CD_{50}$ can be determined if greater than 50% ribosome inhibition or cell death, respectively, does not occur in a concentration series for a given sample. Data insufficient to accurately fit a curve as described in the analysis of the data from exemplary Shiga toxin effector function assays, such as, e.g., assays described in the Examples below, should not be considered as representative of actual Shiga toxin effector function.

A failure to detect activity in Shiga toxin effector function may be due to improper expression, polypeptide folding, and/or protein stability rather than a lack of cell entry, subcellular routing, and/or enzymatic activity. Assays for Shiga toxin effector functions may not require much polypeptide of the invention to measure significant amounts of Shiga toxin effector function activity. To the extent that an underlying cause of low or no effector function is determined empirically to relate to protein expression or stability, one of skill in the art may be able to compensate for such factors using protein chemistry and molecular engineering techniques known in the art, such that a Shiga toxin functional effector activity may be restored and measured. As examples, improper cell-based expression may be compensated for by using different expression control sequences; and improper polypeptide folding and/or stability may benefit from stabilizing terminal sequences, or compensatory mutations in non-effector regions which stabilize the three-dimensional structure of the molecule.

Certain Shiga toxin effector functions are not easily measurable, e.g. subcellular routing functions. For example, there is no routine, quantitative assay to distinguish whether the failure of a Shiga toxin effector polypeptide to be cytotoxic and/or deliver a heterologous epitope is due to improper subcellular routing, but at a time when tests are available, then Shiga toxin effector polypeptides may be analyzed for any significant level of subcellular routing as compared to the appropriate wild-type Shiga toxin effector polypeptide. However, if a Shiga toxin effector polypeptide component of a cell-targeting molecule of the present invention exhibits cytotoxicity comparable or equivalent to a wild-type Shiga toxin A Subunit construct, then the subcellular routing activity level is inferred to be comparable or equivalent, respectively, to the subcellular routing activity level of a wild-type Shiga toxin A Subunit construct at least under the conditions tested.

When new assays for individual Shiga toxin functions become available, Shiga toxin effector polypeptides and/or cell-targeting molecules comprising Shiga toxin effector polypeptides may be analyzed for any level of those Shiga toxin effector functions, such as a being within 1000-fold or 100-fold or less the activity of a wild-type Shiga toxin effector polypeptide or exhibiting 3-fold to 30-fold or greater activity as compared to a functional knockout, Shiga toxin effector polypeptide.

Sufficient subcellular routing may be merely deduced by observing a molecule's cytotoxic activity levels in cytotoxicity assays, such as, e.g., cytotoxicity assays based on T-cell epitope presentation or based on a toxin effector function involving a cytosolic and/or endoplasmic reticulum-localized, target substrate.

As used herein, the retention of "significant" Shiga toxin effector function refers to a level of Shiga toxin functional activity, as measured by an appropriate quantitative assay with reproducibility comparable to a wild-type Shiga toxin effector polypeptide control (e.g. a Shiga toxin A1 fragment). For in vitro ribosome inhibition, significant Shiga toxin effector function is exhibiting an $IC_{50}$ of 300 pM or less depending on the source of the ribosomes used in the assay (e.g. a bacterial, archaeal, or eukaryotic (algal, fungal, plant, or animal) source). This is significantly greater inhibition as compared to the approximate $IC_{50}$ of 100,000 pM for the catalytically disrupted SLT-1A 1-251 double mutant (Y77S/E167D). For cytotoxicity in a target-positive cell-kill assay in laboratory cell culture, significant Shiga toxin effector function is exhibiting a $CD_{50}$ of 100, 50, 30 nM, or less, depending on the target biomolecule(s) of the binding region and the cell type, particularly that cell type's expression and/or cell-surface representation of the appropriate extracellular target biomolecule(s) and/or the extracellular epitope(s) targeted by the molecule being evaluated. This is significantly greater cytotoxicity to the appropriate, target-positive cell population as compared to a Shiga toxin A Subunit alone (or a wild-type Shiga toxin A1 fragment), without a cell targeting binding region, which has a $CD_{50}$ of 100-10,000 nM, depending on the cell line.

For purposes of the present invention and with regard to the Shiga toxin effector function of a molecule of the present invention, the term "reasonable activity" refers to exhibiting at least a moderate level (e.g. within 11-fold to 1,000-fold) of Shiga toxin effector activity as defined herein in relation to a molecule comprising a naturally occurring (or wild-type) Shiga toxin, wherein the Shiga toxin effector activity is selected from the group consisting of: internalization efficiency, subcellular routing efficiency to the cytosol, delivered epitope presentation by a target cell(s), ribosome inhibition, and cytotoxicity. For cytotoxicity, a reasonable level of Shiga toxin effector activity includes being within 1,000-fold of a wild-type, Shiga toxin construct, such as, e.g., exhibiting a $CD_{50}$ of 500 nM or less when a wild-type Shiga toxin construct exhibits a $CD_{50}$ of 0.5 nM (e.g. a cell-targeting molecule comprising a wild-type Shiga toxin A1 fragment).

For purposes of the present invention and with regard to the cytotoxicity of a molecule of the present invention, the term "optimal" refers to a level of Shiga toxin catalytic domain mediated cytotoxicity that is within 2, 3, 4, 5, 6, 7, 8, 9, or 10-fold of the cytotoxicity of a molecule comprising wild-type Shiga toxin A1 fragment (e.g. a Shiga toxin A Subunit or certain truncated variants thereof) and/or a naturally occurring Shiga toxin.

It should be noted that even if the cytotoxicity of a Shiga toxin effector polypeptide is reduced relative to a wild-type Shiga toxin A Subunit or fragment thereof, in practice, applications using attenuated, Shiga toxin effector polypeptides may be equally or more effective than using wild-type Shiga toxin effector polypeptides because the highest potency variants might exhibit undesirable effects which are minimized or reduced in reduced cytotoxic-potency variants. Wild-type Shiga toxins are very potent, being able to kill an intoxicated cell after only one toxin molecule has reached the cytosol of the intoxicated cell or perhaps after only forty toxin molecules have been internalized into the intoxicated cell. Shiga toxin effector polypeptides with even considerably reduced Shiga toxin effector functions, such as, e.g., subcellular routing or cytotoxicity, as compared to wild-type Shiga toxin effector polypeptides may still be potent enough for practical applications, such as, e.g., applications involving targeted cell-killing, heterologous epitope delivery, and/or detection of specific cells and their subcellular compartments. In addition, certain reduced-activity Shiga toxin effector polypeptides may be particularly useful for delivering cargos (e.g. an additional exogenous material or T-cell epitope) to certain intracellular locations or subcellular compartments of target cells.

The term "selective cytotoxicity" with regard to the cytotoxic activity of a molecule refers to the relative level of cytotoxicity between a biomolecule target positive cell population (e.g. a targeted cell-type) and a non-targeted bystander cell population (e.g. a biomolecule target negative cell-type), which can be expressed as a ratio of the half-maximal cytotoxic concentration (CD50) for a targeted cell type over the $CD_{50}$ for an untargeted cell type to provide a metric of cytotoxic selectivity or indication of the preferentiality of killing of a targeted cell versus an untargeted cell.

The cell surface representation and/or density of a given extracellular target biomolecule (or extracellular epitope of a given target biomolecule) may influence the applications for which certain cell-targeting molecules of the present invention may be most suitably used. Differences in cell surface representation and/or density of a given target biomolecule between cells may alter, both quantitatively and qualitatively, the efficiency of cellular internalization and/or cytotoxicity potency of a given cell-targeting molecule of the present invention. The cell surface representation and/or density of a given target biomolecule can vary greatly among target biomolecule positive cells or even on the same cell at different points in the cell cycle or cell differentiation. The total cell surface representation of a given target biomolecule and/or of certain extracellular epitopes of a given target biomolecule on a particular cell or population of cells may be determined using methods known to the skilled worker, such as methods involving fluorescence-activated cell sorting (FACS) flow cytometry.

As used herein, the terms "disrupted," "disruption," or "disrupting," and grammatical variants thereof, with regard to a polypeptide region or feature within a polypeptide refers to an alteration of at least one amino acid within the region or composing the disrupted feature. Amino acid alterations include various mutations, such as, e.g., a deletion (such as a truncation), inversion, insertion, or substitution which alter the amino acid sequence of the polypeptide. Amino acid alterations also include chemical changes, such as, e.g., the alteration one or more atoms in an amino acid functional group or the addition of one or more atoms to an amino acid functional group.

As used herein, "de-immunized" means reduced antigenic and/or immunogenic potential after administration to a chordate as compared to a reference molecule, such as, e.g., a wild-type peptide region, polypeptide region, or polypeptide. This includes a reduction in overall antigenic and/or immunogenic potential despite the introduction of one or more, de novo, antigenic and/or immunogenic epitopes as compared to a reference molecule. For certain embodiments, "de-immunized" means a molecule exhibited reduced antigenicity and/or immunogenicity after administration to a mammal as compared to a "parental" molecule from which it was derived, such as, e.g., a wild-type Shiga toxin A1 fragment. In certain embodiments, the de-immunized, Shiga toxin effector polypeptide of the present invention is capable of exhibiting a relative antigenicity compared to a reference molecule which is reduced by 10%, 20%, 30%, 40%, 50%, 60%, 70%, 80%, 90%, or greater than the antigenicity of the reference molecule under the same conditions measured by the same assay, such as, e.g., an assay known to the skilled worker and/or described herein like a quantitative ELISA or Western blot analysis. In certain embodiments, the de-immunized, Shiga toxin effector polypeptide of the present invention is capable of exhibiting a relative immunogenicity compared to a reference molecule which is reduced by 10%, 20%, 30%, 40%, 50%, 60%, 70%, 80%, 90%, 95%, 97%, 99%, or greater than the immunogenicity of the reference molecule under the same conditions measured by the same assay, such as, e.g., an assay known to the skilled worker and/or described herein like a quantitative measurement of anti-molecule antibodies produced in a mammal(s) after receiving parenteral administration of the molecule at a given time-point.

The relative immunogenicities of exemplary cell-targeting molecules were determined using an assay for in vivo antibody responses to the cell-targeting molecules after repeat, parenteral administrations over periods of time.

For purposes of the present invention, the phrase "B-cell and/or CD4+ T-cell de-immunized" means that the molecule has a reduced antigenic and/or immunogenic potential after administration to a mammal regarding either B-cell antigenicity or immunogenicity and/or CD4+ T-cell antigenicity or immunogenicity. For certain embodiments, "B-cell de-immunized" means a molecule exhibited reduced B-cell antigenicity and/or immunogenicity after administration to a mammal as compared to a "parental" molecule from which it was derived, such as, e.g., a wild-type Shiga toxin A1 fragment. For certain embodiments, "CD4+ T-cell de-immunized" means a molecule exhibited reduced CD4 T-cell antigenicity and/or immunogenicity after administration to a mammal as compared to a "parental" molecule from which it was derived, such as, e.g., a wild-type Shiga toxin A 1 fragment.

The term "endogenous" with regard to a B-cell epitope, CD4+ T-cell epitope, B-cell epitope region, or CD4+ T-cell epitope region in a Shiga toxin effector polypeptide refers to an epitope present in a wild-type Shiga toxin A Subunit.

For purposes of the present invention, the phrase "CD8+ T-cell hyper-immunized" means that the molecule, when present inside a nucleated, chordate cell within a living chordate, has an increased antigenic and/or immunogenic potential regarding CD8+ T-cell antigenicity or immunogenicity. Commonly, CD8+ T-cell immunized molecules are capable of cellular internalization to an early endosomal compartment of a nucleated, chordate cell due either to an inherent feature(s) or as a component of a cell-targeting molecule.

For purposes of the present invention, the term "heterologous" means of a different source than an A Subunit of a naturally occurring Shiga toxin, e.g. a heterologous polypeptide is not naturally found as part of any A Subunit of a native Shiga toxin. The term "heterologous" with regard to T-cell epitope or T-cell epitope-peptide component of a polypeptide of the present invention refers to an epitope or peptide sequence which did not initially occur in the polypeptide to be modified, but which has been added to the polypeptide, whether added via the processes of embedding, fusion, insertion, and/or amino acid substitution as described herein, or by any other engineering means. The result is a modified polypeptide comprising a T-cell epitope foreign to the original, unmodified polypeptide, i.e. the T-cell epitope was not present in the original polypeptide.

The term "embedded" and grammatical variants thereof with regard to a T-cell epitope or T-cell epitope-peptide component of a polypeptide of the present invention refers to the internal replacement of one or more amino acids within a polypeptide region with different amino acids in order to generate a new polypeptide sequence sharing the same total number of amino acid residues with the starting polypeptide region. Thus, the term "embedded" does not include any external, terminal fusion of any additional amino acid, peptide, or polypeptide component to the starting polypeptide nor any additional internal insertion of any additional amino acid residues, but rather includes only substitutions for existing amino acids. The internal replacement may be accomplished merely by amino acid residue substitution or by a series of substitutions, deletions, insertions, and/or inversions. If an insertion of one or more amino acids is used, then the equivalent number of proximal amino acids must be deleted next to the insertion to result in an embedded T-cell epitope. This is in contrast to use of the term "inserted" with regard to a T-cell epitope contained within a polypeptide of the present invention to refer to the insertion of one or more amino acids internally within a polypeptide resulting in a new polypeptide having an increased number of amino acid residues compared to the starting polypeptide.

The term "inserted" and grammatical variants thereof with regard to a T-cell epitope contained within a polypeptide of the present invention refers to the insertion of one or more amino acids within a polypeptide resulting in a new polypeptide sequence having an increased number of amino acid residues compared to the starting polypeptide. The "pure" insertion of a T-cell epitope-peptide is when the resulting polypeptide increased in length by the number of amino acid residues equivalent to the number of amino acid residues in the entire, inserted T-cell epitope-peptide. The phrases "partially inserted," "embedded and inserted," and grammatical variants thereof with regard to a T-cell epitope contained within a polypeptide of the present invention, refers to when the resulting polypeptide increased in length, but by less than the number of amino acid residues equivalent to the length of the entire, inserted T-cell epitope-peptide. Insertions, whether "pure" or "partial," include any of the previously described insertions even if other regions of the polypeptide not proximal to the insertion site within the polypeptide are deleted thereby resulting in a decrease in the total length of the final polypeptide because the final polypeptide still comprises an internal insertion of one or more amino acids of a T-cell epitope-peptide within a polypeptide region.

As used herein, the term "T-cell epitope delivering" when describing a functional activity of a molecule means that a molecule provides the biological activity of localizing within a cell to a subcellular compartment that is competent to result in the proteasomal cleavage of a proteinaceous part of the molecule which comprises a T-cell epitope-peptide. The "T-cell epitope delivering" function of a molecule can be assayed by observing the MHC presentation of a T-cell epitope-peptide cargo of the molecule on a cell surface of a cell exogenously administered the molecule or in which the assay was begun with the cell containing the molecule in one or more of its endosomal compartments. Generally, the ability of a molecule to deliver a T-cell epitope to a proteasome can be determined where the initial location of the "T-cell epitope delivering" molecule is an early endosomal compartment of a cell, and then, the molecule is empirically shown to deliver the epitope-peptide to the proteasome of the cell. However, a "T-cell epitope delivering" ability may also be determined where the molecule starts at an extracellular location and is empirically shown, either directly or indirectly, to deliver the epitope into a cell and to proteasomes of the cell. For example, certain "T-cell epitope delivering" molecules pass through an endosomal compartment of the cell, such as, e.g. after endocytic entry into that cell. Alternatively, "T-cell epitope delivering" activity may be observed for a molecule starting at an extracellular location whereby the molecule does not enter any endosomal compartment of a cell—instead the "T-cell epitope delivering" molecule enters a cell and delivers a T-cell epitope-peptide to proteasomes of the cell, presumably because the "T-cell epitope delivering" molecule directed its own routing to a subcellular compartment competent to result in proteasomal cleavage of its T-cell epitope-peptide component.

For purposes of the present invention, the phrase "proximal to an amino-terminus" with reference to the position of a Shiga toxin effector polypeptide region of a cell-targeting molecule of the present invention refers to a distance wherein at least one amino acid residue of the Shiga toxin effector polypeptide region is within 1, 2, 3, 4, 5, 6, 7, 8, 9, 10, 11, 12 or more, e.g., up to 18-20 amino acid residues, of an amino-terminus of the cell-targeting molecule as long as the cell-targeting molecule is capable of exhibiting the appropriate level of Shiga toxin effector functional activity noted herein (e.g., a certain level of cytotoxic potency). Thus for certain embodiments of the present invention, any amino acid residue(s) fused amino-terminal to the Shiga toxin effector polypeptide should not reduce any Shiga toxin effector function (e.g., by sterically hindering a structure(s) near the amino-terminus of the Shiga toxin effector polypeptide region) such that a functional activity of the Shiga toxin effector polypeptide is reduced below the appropriate activity level required herein.

For purposes of the present invention, the phrase "more proximal to an amino-terminus" with reference to the position of a Shiga toxin effector polypeptide region within a cell-targeting molecule of the present invention as compared to another component (e.g., a cell-targeting, binding region, molecular moiety, and/or additional exogenous material) refers to a position wherein at least one amino acid residue of the amino-terminus of the Shiga toxin effector polypeptide is closer to the amino-terminus of a linear, polypeptide component of the cell-targeting molecule of the present invention as compared to the other referenced component.

For purposes of the present invention, the phrase "active enzymatic domain derived from one A Subunit of a member of the Shiga toxin family" refers to having the ability to inhibit protein synthesis via a catalytic ribosome inactivation mechanism. The enzymatic activities of naturally occurring (or wild-type) Shiga toxins may be defined by the ability to inhibit protein translation using assays known to the skilled worker, such as, e.g., in vitro assays involving RNA translation in the absence of living cells or in vivo assays involving RNA translation in a living cell. Using assays known to the skilled worker and/or described herein, the potency of a Shiga toxin enzymatic activity may be assessed directly by observing N-glycosidase activity toward ribosomal RNA (rRNA), such as, e.g., a ribosome nicking assay, and/or indirectly by observing inhibition of ribosome function and/or protein synthesis.

For purposes of the present invention, the term "Shiga toxin A1 fragment region" refers to a polypeptide region consisting essentially of a Shiga toxin A1 fragment and/or derived from a Shiga toxin A1 fragment of a Shiga toxin.

For purposes of the present invention, the terms "terminus," "amino-terminus," or "carboxy-terminus" with regard to a cell-targeting molecule refers generally to the last amino acid residue of a polypeptide chain of the cell-targeting molecule (e.g., a single, continuous polypeptide chain). A cell-targeting molecule may comprise more than one polypeptides or proteins, and, thus, a cell-targeting molecule of the present invention may comprise multiple amino-terminals and carboxy-terminals. For example, the "amino-terminus" of a cell-targeting molecule may be defined by the first amino acid residue of a polypeptide chain representing the amino-terminal end of the polypeptide, which is generally characterized by a starting, amino acid residue which does not have a peptide bond with any amino acid residue involving the primary amino group of the starting amino acid residue or involving the equivalent nitrogen for starting amino acid residues which are members of the class of N-alkylated alpha amino acid residues. Similarly, the "carboxy-terminus" of a cell-targeting molecule may be defined by the last amino acid residue of a polypeptide chain representing the carboxyl-terminal end of the polypeptide, which is generally characterized by a final, amino acid residue which does not have any amino acid residue linked by a peptide bond to the alpha-carbon of its primary carboxyl group.

For purposes of the present invention, the terms "terminus," "amino-terminus," or "carboxy-terminus" with regard to a polypeptide region refers to the regional boundaries of that region, regardless of whether additional amino acid residues are linked by peptide bonds outside of that region. In other words, the terminals of the polypeptide region regardless of whether that region is fused to other peptides or polypeptides. For example, a fusion protein comprising two proteinaceous regions, e.g., a binding region comprising a peptide or polypeptide and a Shiga toxin effector polypeptide, may have a Shiga toxin effector polypeptide region with a carboxy-terminus ending at amino acid residue 251 of the Shiga toxin effector polypeptide region despite a peptide bond involving residue 251 to an amino acid residue at position 252 representing the beginning of another proteinaceous region, e.g., the binding region. In this example, the carboxy-terminus of the Shiga toxin effector polypeptide region refers to residue 251, which is not a terminus of the fusion protein but rather represents an internal, regional boundary. Thus, for polypeptide regions, the terms "terminus," "amino-terminus," and "carboxy-terminus" are used to refer to the boundaries of polypeptide regions, whether the boundary is a physically terminus or an internal, position embedded within a larger polypeptide chain.

For purposes of the present invention, the phrase "carboxy-terminus region of a Shiga toxin A1 fragment" refers to a polypeptide region derived from a naturally occurring (or wild-type) Shiga toxin A1 fragment, the region beginning with a hydrophobic residue (e.g., V236 of StxA-A1 and SLT-1A1, and V235 of SLT-2A1) that is followed by a hydrophobic residue and the region ending with the furin-cleavage site conserved among Shiga toxin A1 fragment polypeptides and ending at the junction between the A1 fragment and the A2 fragment in native, Shiga toxin A Subunits. For purposes of the present invention, the carboxy-terminal region of a Shiga toxin A1 fragment includes a peptidic region derived from the carboxy-terminus of a Shiga toxin A1 fragment polypeptide, such as, e.g., a peptidic region comprising, consisting essentially of, or consisting of the carboxy-terminus of a Shiga toxin A1 fragment. Non-limiting examples of peptidic regions derived from the carboxy-terminus of a Shiga toxin A1 fragment include the amino acid residue sequences natively positioned from position 236 to position 239, 240, 241, 242, 243, 244, 245, 246, 247, 248, 249, 250, or 251 in Stx1A (SEQ ID NO:2) or SLT-1A (SEQ ID NO:1); and from position 235 to position 239, 240, 241, 242, 243, 244, 245, 246, 247, 248, 249, or 250 in SLT-2A (SEQ ID NO:3).

For purposes of the present invention, the phrase "proximal to the carboxy-terminus of an A1 fragment polypeptide" with regard to a linked molecular moiety and/or binding region refers to being within 1, 2, 3, 4, 5, 6, 7, 8, 9, 10, 11, or 12 amino acid residues from the amino acid residue defining the last residue of the Shiga toxin A1 fragment polypeptide.

For purposes of the present invention, the phrase "sterically covers the carboxy-terminus of the A1 fragment-derived region" includes any molecular moiety of a size of 4.5 kDa or greater (e.g., an immunoglobulin-type binding region) linked and/or fused to an amino acid residue in the carboxy-terminus of the A1 fragment-derived region, such as, e.g., the amino acid residue derived from the amino acid residue natively positioned at any one of positions 236 to 251 in Stx1A (SEQ ID NO:2) or SLT-1A (SEQ ID NO:1) or from 235 to 250 in SLT-2A (SEQ ID NO:3). For purposes of the present invention, the phrase "sterically covers the carboxy-terminus of the A1 fragment-derived region" also includes any molecular moiety of a size of 4.5 kDa or greater (e.g., an immunoglobulin-type binding region) linked and/or fused to an amino acid residue in the carboxy-terminus of the A1 fragment-derived region, such as, e.g., the amino acid residue carboxy-terminal to the last amino acid A1 fragment-derived region and/or the Shiga toxin effector polypeptide. For purposes of the present invention, the phrase "sterically covers the carboxy-terminus of the A1 fragment-derived region" also includes any molecular moiety of a size of 4.5 kDa or greater (e.g., an immunoglobulin-type binding region) physically preventing cellular recognition of the carboxy-terminus of the A1 fragment-derived region, such as, e.g. recognition by the ERAD machinery of a eukaryotic cell.

For purposes of the present invention, a binding region, such as, e.g., an immunoglobulin binding region or an immunoglobulin-type binding region, that comprises a polypeptide comprising at least forty amino acids and that is linked (e.g., fused) to the carboxy-terminus of the Shiga toxin effector polypeptide region comprising an A1 fragment-derived region is a molecular moiety which is "sterically covering the carboxy-terminus of the A1 fragment-derived region."

For purposes of the present invention, a binding region, such as, e.g., an immunoglobulin binding region or an immunoglobulin-type binding region, that comprises a polypeptide comprising at least forty amino acids and that is linked (e.g., fused) to the carboxy-terminus of the Shiga toxin effector polypeptide region comprising an A1 fragment-derived region is a molecular moiety "encumbering the carboxy-terminus of the A1 fragment-derived region."

For purposes of the present invention, the term "A1 fragment of a member of the Shiga toxin family" refers to the remaining amino-terminal fragment of a Shiga toxin A Subunit after proteolysis by furin at the furin-cleavage site conserved among Shiga toxin A Subunits and positioned between the A1 fragment and the A2 fragment in wild-type Shiga toxin A Subunits.

For purposes of the claimed invention, the phrase "furin-cleavage motif at the carboxy-terminus of the A1 fragment region" refers to a specific, furin-cleavage motif conserved among Shiga toxin A Subunits and bridging the junction between the A1 fragment and the A2 fragment in naturally occurring, Shiga toxin A Subunits.

For purposes of the present invention, the phrase "furin-cleavage site proximal to the carboxy-terminus of the A1 fragment region" refers to any identifiable, furin-cleavage site having an amino acid residue within a distance of less than 1, 2, 3, 4, 5, 6, 7 or more amino acid residues of the amino acid residue defining the last amino acid residue in the A1 fragment region or A1 fragment derived region, including a furin-cleavage motif located carboxy-terminal of an A1 fragment region or A1 fragment derived region, such as, e.g., at a position proximal to the linkage of the A1 fragment-derived region to another component of the molecule, such as, e.g., a molecular moiety of a cell-targeting molecule of the present invention.

For purposes of the present invention, the phrase "disrupted furin-cleavage motif" refers to (i) a specific furin-cleavage motif as described herein in Section I-B and (ii) which comprises a mutation and/or truncation that can confer a molecule with a reduction in furin-cleavage as compared to a reference molecule, such as, e.g., a reduction in furin-cleavage reproducibly observed to be 30%, 40%, 50%, 60%, 70%, 80%, 90%, 95%, 97%, 98%, 99%, or less (including 100% for no cleavage) than the furin-cleavage of a reference molecule observed in the same assay under the same conditions. The percentage of furin-cleavage as compared to a reference molecule can be expressed as a ratio of cleaved:uncleaved material of the molecule of interest divided by the cleaved:uncleaved material of the reference molecule (see e.g. WO 2015/191764; WO 2016/196344). Non-limiting examples of suitable reference molecules include certain molecules comprising a wild-type Shiga toxin furin-cleavage motif and/or furin-cleavage site as described herein and/or molecules used as reference molecules in the Examples below.

For purposes of the present invention, the phrase "furin-cleavage resistant" means a molecule or specific polypeptide region thereof exhibits reproducibly less furin cleavage than (i) the carboxy-terminus of a Shiga toxin A1 fragment in a wild-type Shiga toxin A Subunit or (ii) the carboxy-terminus of the Shiga toxin A1 fragment derived region of construct wherein the naturally occurring furin-cleavage site natively positioned at the junction between the A1 and A2 fragments is not disrupted; as assayed by any available means to the skilled worker, including by using a method described herein.

For purposes of the present invention, the phrase "active enzymatic domain derived form an A Subunit of a member of the Shiga toxin family" refers to a polypeptide structure having the ability to inhibit protein synthesis via catalytic inactivation of a ribosome based on a Shiga toxin enzymatic activity. The ability of a molecular structure to exhibit inhibitory activity of protein synthesis and/or catalytic inactivation of a ribosome may be observed using various assays known to the skilled worker, such as, e.g., in vitro assays involving RNA translation assays in the absence of living cells or in vivo assays involving the ribosomes of living cells. For example, using assays known to the skilled worker, the enzymatic activity of a molecule based on a Shiga toxin enzymatic activity may be assessed directly by observing N-glycosidase activity toward ribosomal RNA (rRNA), such as, e.g., a ribosome nicking assay, and/or indirectly by observing inhibition of ribosome function, RNA translation, and/or protein synthesis.

As used herein with respect to a Shiga toxin effector polypeptide, a "combination" describes a Shiga toxin effector polypeptide comprising two or more sub-regions wherein each sub-region comprises at least one of the following: (1) a disruption in an endogenous epitope or epitope region; (2) an embedded, heterologous, T-cell epitope-peptide; (3) an inserted, heterologous, T-cell epitope-peptide; and (4) a disrupted furin-cleavage motif at the carboxy-terminus of an A1 fragment region.

As used herein, the term "additional HER2-targeting therapeutic agent" means an additional therapeutic agent (e.g. a molecule) that targets HER2 to produce a therapeutic effect or benefit. This additional HER2-targeting therapeutic agent is complementary to the cell-targeting molecule of the present invention and does not compete directly with the cell-targeting molecule in its HER2-targeting activity. The additional HER2-targeting therapeutic agent may comprise, consist essentially of, or consist of an anti-HER2 antibody or small molecule inhibitor that interferes with HER2 signaling. For example, the additional HER2-targeting therapeutic agent may comprise, consist essentially of, or consists of a dual tyrosine kinase inhibitor, such as lapatinib and/or neratinib. The additional HER2-targeting therapeutic agent may comprise, consist essentially of, or consist of an anti-HER2 antibody therapy that binds to an antigenic determinant that does not overlap with the antigenic determinant bound by the cell-targeting molecule of the invention or that binds a HER2 molecule in such a manner that when bound the additional HER2-targeting therapeutic does not prevent the binding of that HER2 molecule by the cell-targeting molecule of the invention. For example, the additional HER2-targeting therapeutic agent may comprise, consist essentially of, or consist of anti-HER2 monoclonal antibody therapy and/or anti-HER2 antibody drug conjugate therapy, such as, e.g., T-DM1 (trastuzumab emtansine), trastuzumab, and/or pertuzumab. The additional HER2-targeting therapeutic agent may be selected from any one of or a combination of: lapatinib, neratinib, T-DM1 (trastuzumab emtansine), trastuzumab, and/or pertuzumab.

As used herein with respect to a molecule of the present invention, a "cell-targeting molecule" is used interchangeably with a "HER2-targeting molecule" or "HER2-binding molecule". All of the aforementioned molecule types include various "HER2-binding proteins".

INTRODUCTION

The present invention provides various cell-targeting molecules comprising one or more Shiga toxin effector polypeptides and at least one HER2-binding region. Certain embodiments of the cell-targeting molecules of the present invention comprise Shiga toxin effector polypeptides that combine structural elements resulting in two or more properties in a single molecule, such as, e.g., the ability to 1) exhibit reduced antigenicity and/or immunogenicity as compared to molecular variants lacking that particular combination of elements, 2) exhibit reduced protease-cleavage as compared to molecular variants lacking that particular combination of elements, 3) exhibit reduced non-specific toxicity to a multicellular organism at certain dosages as compared to molecular variants lacking that particular combination of elements, and/or 5) exhibit potent cytotoxicity. The cell-targeting molecules of the present invention may serve as scaffolds to create various cell-targeting molecules, such as, e.g., HER2-targeted, cytotoxic, therapeutic molecules; HER2-targeted, nontoxic, delivery vehicles; and HER2-targeted diagnostic molecules.

I. The General Structures of the Cell-Targeting Molecules of the Present Invention The present invention provides various cell-targeting molecules, each comprising (1) a cell-targeting, binding region and (2) a Shiga toxin effector polypeptide component. The Shiga toxin effector polypeptides of the present invention may be associated with and/or coupled to various, diverse, cell-targeting components (e.g. a molecular moiety and/or agent) to create cell-targeting molecules of the present invention. A cell-targeting molecule of the present invention comprises (1) a binding region capable of specifically binding an extracellular part of a target biomolecule and (2) a Shiga toxin effector polypeptide capable of exhibiting one or more Shiga toxin A Subunit effector functions. The association of a cell-targeting binding region(s) with a Shiga toxin effector polypeptide of the present invention enables the engineering of therapeutic and diagnostic molecules with desirable characteristics, such as, e.g., de-immunization, potent cytotoxicity, efficient intracellular routing, T-cell hyper-immunization, molecular stability, and in vivo tolerability at high dosages as compared to certain reference molecules.

The present invention provides various HER2-targeting molecules, each comprising (1) a cell-targeting, binding region capable of binding HER2 and (2) a Shiga toxin A Subunit effector polypeptide capable of exhibiting a Shiga toxin effector function. The Shiga toxin effector polypeptide may be associated with and/or coupled to various, diverse, HER2-targeting components (e.g. a molecular moiety and/or agent) to create cell-targeting molecules of the present invention. A cell-targeting molecule of the present invention comprises (1) a binding region capable of specifically binding an extracellular part of a HER2 target biomolecule and (2) a Shiga toxin effector polypeptide region comprising a Shiga toxin effector polypeptide capable of exhibiting one or more Shiga toxin A Subunit effector functions, such as, e.g., cytostasis, cytotoxicity, catalytic activity, promoting cellular internalization, directing intracellular routing to a certain subcellular compartment(s), and intracellular delivery of a material(s). For example, the cell-targeting molecules of the present invention may comprise a Shiga toxin A Subunit effector polypeptide component that comprises a Shiga toxin A1 fragment derived region, wherein the Shiga toxin A Subunit effector polypeptide comprises: (a) an embedded or inserted, heterologous, CD8+ T-cell epitope which disrupts an endogenous, B-cell and/or CD4+ T-cell epitope region; and (b) a disruption of at least three, endogenous, B-cell and/or CD4+ T-cell epitope regions which do not overlap with the embedded or inserted, heterologous, CD8+ T-cell epitope; wherein the Shiga toxin effector polypeptide comprises a disrupted furin-cleavage motif at the carboxy-terminus of the Shiga toxin A1 fragment region, wherein said furin-cleavage motif is disrupted by a carboxy-terminal truncation of the Shiga toxin A1 fragment region as compared to the carboxy-terminus of a wild-type Shiga toxin A Subunit; wherein the Shiga toxin A subunit effector polypeptide is capable of exhibiting a Shiga toxin effector function.

The Shiga toxin effector polypeptides of the present invention may be linked to one or more cell-targeting, binding regions that mediate cell-targeting via binding specificity to extracellular parts of target biomolecules, such as, e.g., a HER2 target biomolecule physically coupled to a cellular surface of a cell. One non-limiting example of a cell-targeting molecule of the present invention is a Shiga toxin effector polypeptide of the present invention fused to a proteinaceous, cell-targeting, binding region, such as, e.g., an immunoglobulin or immunoglobulin-type binding region. For example, the cell-targeting molecules of the present invention may comprise an immunoglobulin binding region capable of specifically binding an extracellular part of HER2/neu/ErbB2, and comprising a polypeptide comprising one or more of: an antibody variable fragment, a single-domain antibody fragment, a single-chain variable fragment, a Fd fragment, an antigen-binding fragment, an autonomous $V_H$ domain, a $V_HH$ fragment derived from a camelid antibody, a heavy-chain antibody domain derived from a cartilaginous fish antibody, a VNAR fragment, and an immunoglobulin new antigen receptor.

A. HER2/neu/ErbB2 Binding Regions

In certain embodiments, a binding region of a cell-targeting molecule of the present invention is a cell-targeting component, such as, e.g., a domain, molecular moiety, or agent, capable of binding specifically to an extracellular part of a HER2/neu/ErbB2 target biomolecule on a cell surface (i.e. an extracellular target biomolecule) with high affinity. There are numerous types of binding regions known to skilled worker or which may be discovered by the skilled worker using techniques known in the art. For example, any cell-targeting component that exhibits the requisite binding characteristics described herein may be used as the binding region in certain embodiments of the cell-targeting molecules of the present invention.

An extracellular part of a target biomolecule refers to a portion of its structure exposed to the extracellular environment when the molecule is physically coupled to a cell, such as, e.g., when the target biomolecule is expressed at a cellular surface by the cell. In this context, exposed to the extracellular environment means that part of the target biomolecule is accessible by, e.g., an antibody or at least a binding moiety smaller than an antibody such as a single-domain antibody domain, a Nanobody®, a heavy-chain antibody domain derived from camelids or cartilaginous fishes, a single-chain variable fragment, or any number of engineered alternative scaffolds to immunoglobulins (see below). The exposure to the extracellular environment of or accessibility to a part of target biomolecule physically coupled to a cell may be empirically determined by the skilled worker using methods well known in the art.

HER2, also recognized in the art as receptor tyrosine-protein kinase erbB-2, is a transmembrane protein which functions as a cell surface receptor for transducing signals across the cellular membrane to intracellular regulators of cell proliferation and apoptosis. HER2 is also recognized in the art as Neu, erbB-2, p185, CD340, NGL, and HER2/neu (Coussens L et al., *Science* 230: 1132-39 (1985); King C et al., *Science* 229: 974-6 (1985); Semba K et al., *Proc Natl Acad Sci USA* 82: 6497-501 (1985); Yamamoto T et al., *Nature* 319:230-234 (1986); Kokai Y et al., *Proc Natl Acad Sci USA* 85: 5389-93 (1988); Disis M et al., *Cancer Res* 54: 16-20 (1994); Yoshino I et al., *J Immunol* 152: 2393-400 (1994) see e.g., GenBank Acc. Nos. X03363; M17730; NM 004448; SEG HUMHER20). While the name HER2 might refer to multiple proteins with related structures and polypeptide sequences from various species, for the purposes of the structural examples of this section, the term "HER2" refers to the epidermal growth factor receptor proteins present in humans whose exact sequence might vary slightly based on the isoform and from individual to individual. For example, HER2 refers to the human protein represented by the exemplary polypeptide sequences UniProt P04626 and NCBI accessions NP_004439.2, NP_001005862.1, NP_001276865.1, NP_001276866.1, and NP_001276867.1; however, different isoforms and variants exist due to splicing, polymorphisms and/or mutations (see e.g. Siddig A et al., *Ann NY Acad Sci* 1138: 84-94 (2008); Poole E et al., *Int J Mol Epidemiol Genet* 2: 300-15 (2011); WO 2000/020579). A skilled worker will be able to identify other HER2 proteins in humans, even if they differ from the referenced sequences.

HER2 is overexpressed by many cancer cells, notably breast cancer cells, and its overexpression is strongly associated with increased metastasis, increased disease reoccurrence, and poor prognosis (see e.g. Slamon D et al., *Science* 235: 177-82 (1987)).

There are numerous HER2 binding regions known to the skilled worker which may be associated with a Shiga toxin effector polypeptide of the present invention to create a cell-targeting molecule of the present invention. For purposes of the present invention, the term "HER2 binding region" refers to a molecular moiety (e.g. a proteinaceous molecule) or agent capable of specifically binding an extracellular part of a HER2 molecule with high affinity, such as, e.g., having a dissociation constant with regard to HER2 of $10^{-5}$ to $10^{-12}$ moles per liter. As used herein, HER2 binding refers to the ability to bind to an extracellular part of an isoform or variant of human HER2 (also known as neu or ErbB2).

A binding region of a cell-targeting molecule of the present invention may be, e.g., a ligand, peptide, immunoglobulin-type binding region, monoclonal antibody, engineered antibody derivative, or engineered alternative to antibodies. For example, the binding region is an immunoglobulin binding region.

In certain embodiments, the binding region of a cell-targeting molecule of the present invention is a proteinaceous moiety capable of binding specifically to an extracellular part of target biomolecule with high affinity. A binding region of a cell-targeting molecule of the present invention may comprise one or more various peptidic or polypeptide moieties, such as randomly generated peptide sequences, naturally occurring ligands or derivatives thereof, immunoglobulin derived domains, synthetically engineered scaffolds as alternatives to immunoglobulin domains, and the like (see e.g., WO 2005/092917; WO 2007/033497; Cheung M et al., *Mol Cancer* 9: 28 (2010); US 2013/0196928; WO 2014/164693; WO 2015/113005; WO 2015/113007; WO 2015/138452; WO 2015/191764). In certain embodiments, a cell-targeting molecule of the present invention comprises a binding region comprising one or more polypeptides capable of selectively and specifically binding an extracellular target biomolecule.

There are numerous binding regions known in the art that are useful for targeting molecules to extracellular portions of HER2 via their binding characteristics, such as certain monoclonal antibodies, engineered antibody derivatives, and engineered alternatives to antibodies.

According to one specific, but non-limiting aspect, the binding region may comprise an immunoglobulin-type binding region. The term "immunoglobulin-type binding region" as used herein refers to a polypeptide region capable of binding one or more target biomolecules, such as an antigen or epitope. Binding regions may be functionally defined by their ability to bind to target molecules.

Immunoglobulin-type binding regions are commonly derived from antibody or antibody-like structures; however, alternative scaffolds from other sources are contemplated within the scope of the term. In certain embodiments, the binding region may comprise an immunoglobulin binding region derived from antibody or antibody-like structure.

Immunoglobulin (Ig) proteins have a structural domain known as an Ig domain. Ig domains range in length from about 70-110 amino acid residues and possess a characteristic Ig-fold, in which typically 7 to 9 antiparallel beta strands arrange into two beta sheets which form a sandwich-like structure. The Ig fold is stabilized by hydrophobic amino acid interactions on inner surfaces of the sandwich and highly conserved disulfide bonds between cysteine residues in the strands. Ig domains may be variable (IgV or V-set), constant (IgC or C-set) or intermediate (IgI or I-set). Some Ig domains may be associated with a complementarity determining region (CDR), also called a "complementary determining region," which is important for the specificity of antibodies binding to their epitopes. Ig-like domains are also found in non-immunoglobulin proteins and are classified on that basis as members of the Ig superfamily of proteins. The HUGO Gene Nomenclature Committee (HGNC) provides a list of members of the Ig-like domain containing family.

An immunoglobulin-type binding region may be a polypeptide sequence of an antibody or antigen-binding fragment thereof wherein the amino acid sequence has been varied from that of a native antibody or an Ig-like domain of a non-immunoglobulin protein, for example by molecular engineering or selection by library screening. Because of the relevance of recombinant DNA techniques and in vitro library screening in the generation of immunoglobulin-type binding regions, antibodies can be redesigned to obtain desired characteristics, such as smaller size, cell entry, or other improvements for in vivo and/or therapeutic applications. The possible variations are many and may range from the changing of just one amino acid to the complete redesign of, for example, a variable region. Typically, changes in the variable region will be made in order to improve the antigen-binding characteristics, improve variable region stability, or reduce the potential for immunogenic responses.

There are numerous immunoglobulin-type binding regions contemplated as components of the present invention. In certain embodiments, the immunoglobulin-type binding region is derived from an immunoglobulin binding region, such as an antibody paratope capable of binding an extracellular target biomolecule. In certain other embodiments, the immunoglobulin-type binding region comprises an engineered polypeptide not derived from any immunoglobulin domain but which functions like an immunoglobulin binding region by providing high-affinity binding to an extracellular target biomolecule. This engineered polypeptide may optionally include polypeptide scaffolds comprising, consisting of, or consisting essentially of complementary determining regions from immunoglobulins as described herein.

There are also numerous binding regions in the prior art that are useful for targeting polypeptides to specific cell-types via their high-affinity binding characteristics. In certain embodiments, the binding region of the cell-targeting molecule of the present invention is selected from the group which includes autonomous $V_H$ domains, single-domain antibody domains (sdAbs), heavy-chain antibody domains derived from camelids ($V_H$H fragments or $V_H$ domain fragments), heavy-chain antibody domains derived from camelid $V_H$H fragments or $V_H$ domain fragments, heavy-chain antibody domains derived from cartilaginous fishes, immunoglobulin new antigen receptors (IgNARs), $V_{NAR}$ fragments, single-chain variable (scFv) fragments, Nanobodies®, Fd fragments consisting of the heavy chain and $C_H$1 domains, single chain Fv-$C_H$3 minibodies, dimeric $C_H$2 domain fragments ($C_H$2 D), Fc antigen binding domains (Fcabs), isolated complementary determining region 3 (CDR3) fragments, constrained framework region 3, CDR3, framework region 4 (FR3-CDR3-FR4) polypeptides, small modular immunopharmaceutical (SMIP) domains, scFv-Fc fusions, multimerizing scFv fragments (diabodies, triabodies, tetrabodies), disulfide stabilized antibody variable (Fv) fragments, disulfide stabilized antigen-binding (Fab) fragments consisting of the $V_L$, $V_H$, CL and CH 1 domains, bivalent Nanobodies®, bivalent minibodies, bivalent F(ab')$_2$ fragments (Fab dimers), bispecific tandem $V_H$H fragments, bispecific tandem scFv fragments, bispecific Nanobodies®, bispecific minibodies, and any genetically manipulated counterparts of the foregoing that retain its paratope and binding function (see Ward E et al., Nature 341: 544-6 (1989); Davies J, Riechmann L, Biotechnology (NY) 13: 475-9 (1995); Reiter Y et al., Mol Biol 290: 685-98 (1999); Riechmann L, Muyldermans S, J Immunol Methods 231: 25-38 (1999); Tanha J et al., J Immunol Methods 263: 97-109 (2002); Vranken W et al., Biochemistry 41: 8570-9 (2002); Jespers L et al., J Mol Biol 337: 893-903 (2004); Jespers L et al., Nat Biotechnol 22: 1161-5 (2004); To R et al., J Biol Chem 280: 41395-403 (2005); Saerens D et al., Curr Opin Pharmacol 8: 600-8 (2008); Dimitrov D, MAbs 1: 26-8 (2009); Weiner L, Cell 148: 1081-4 (2012); Ahmad Z et al., Clin Dev Immunol 2012: 980250 (2012)). For example, the cell-targeting molecule of the present invention may comprise a binding region that comprises, consists essentially of, or consists of one or more of: an antibody variable fragment, a single-domain antibody fragment, a single-chain variable fragment, a Fd fragment, an antigen-binding fragment, an autonomous $V_H$ domain, a $V_H$H fragment derived from a camelid antibody, a heavy-chain antibody domain derived from a cartilaginous fish antibody, a VNAR fragment, and an immunoglobulin new antigen receptor. In certain further embodiments, the binding region comprises, consists essentially of, or consists of a single-chain variable fragment and/or a $V_H$H fragment derived from a camelid antibody. In certain further embodiments, the binding region comprises, consists essentially of, or consists of a single-chain variable fragment. In certain further embodiments, the binding region comprises, consists essentially of, or consists of a $V_H$H fragment derived from a camelid antibody.

There are a variety of binding regions comprising polypeptides derived from the constant regions of immunoglobulins, such as, e.g., engineered dimeric Fc domains, monomeric Fcs (mFcs), scFv-Fcs, $V_H$H-Fcs, $C_H$2 domains, monomeric $C_H$3s domains (m$C_H$3s), synthetically reprogrammed immunoglobulin domains, and/or hybrid fusions of immunoglobulin domains with ligands (Hofer T et al., Proc Natl Acad Sci U S. A. 105: 12451-6 (2008); Xiao J et al., *J Am Chem Soc* 131: 13616-13618 (2009); Xiao X et al., *Biochem Biophys Res Commun* 387: 387-92 (2009); Wozniak-Knopp G et al., *Protein Eng Des Sel* 23 289-97 (2010); Gong R et al., *PLoS ONE* 7: e42288 (2012); Wozniak-Knopp G et al., *PLoS ONE* 7: e30083 (2012); Ying T et al., *J Biol Chem* 287: 19399-408 (2012); Ying T et al., *J Biol Chem* 288: 25154-64 (2013); Chiang M et al., *J Am Chem Soc* 136: 3370-3 (2014); Rader C, Trends *Biotechnol* 32: 186-97 (2014); Ying T et al., *Biochimica Biophys Acta* 1844: 1977-82 (2014)). P911 In accordance with certain other embodiments, the binding region comprises an engineered, alternative scaffold to immunoglobulin domains. Engineered alternative scaffolds are known in the art which exhibit similar functional characteristics to immunoglobulin-derived structures, such as high-affinity and specific binding of target biomolecules, and may provide improved characteristics to certain immunoglobulin domains, such as, e.g., greater stability or reduced immunogenicity. Generally, alternative scaffolds to immunoglobulins are less than 20 kilodaltons, consist of a single polypeptide chain, lack cysteine residues, and exhibit relatively high thermodynamic stability.

In certain embodiments of the cell-targeting molecules of the present invention, the binding region comprises an alternative scaffold selected from the group which includes autonomous $V_H$ domains, single-domain antibody domains (sdAbs), heavy-chain antibody domains derived from camelids ($V_H$H fragments or $V_H$ domain fragments), heavy-chain antibody domains derived from camelid $V_H$H fragments or $V_H$ domain fragments, heavy-chain antibody domains derived from cartilaginous fishes, immunoglobulin new antigen receptors (IgNARs), VNAR fragments, single-chain variable (scFv) fragments, Nanobodies®, Fd fragments consisting of the heavy chain and CH 1 domains, permutated Fvs (pFv), single chain Fv-$C_H$3 minibodies, dimeric $C_H$2 domain fragments ($C_H$2D), Fc antigen binding domains (Fcabs), isolated complementary determining region 3 (CDR3) fragments, constrained framework region 3, CDR3, framework region 4 (FR3-CDR3-FR4) polypeptides, small modular immunopharmaceutical (SMIP) domains, scFv-Fc fusions, multimerizing scFv fragments (diabodies, triabodies, tetrabodies), disulfide stabilized antibody variable (Fv) fragments, disulfide stabilized antigen-binding (Fab) fragments consisting of the $V_L$, $V_H$, CL and $C_H$1 domains, bivalent Nanobodies®, bivalent minibodies, bivalent F(ab')$_2$ fragments (Fab dimers), bispecific tandem $V_H$H fragments, bispecific tandem scFv fragments, bispecific Nanobodies®, bispecific minibodies, and any genetically manipulated counterparts of the foregoing that retains its binding functionality (Wörn A, Plückthun A, *J Mol Biol* 305: 989-1010 (2001); Xu L et al., *Chem Biol* 9: 933-42 (2002); Wikman M et al., *Protein Eng Des Sel* 17: 455-62 (2004); Binz H et al., *Nat Biotechnol* 23: 1257-68 (2005); Hey T et al., *Trends Biotechnol* 23:514-522 (2005); Holliger P, Hudson P, *Nat Biotechnol* 23: 1126-36 (2005); Gill D, Damle N, *Curr Opin Biotech* 17: 653-8 (2006); Koide A, Koide S, *Methods Mol Biol* 352: 95-109 (2007); Byla P et al., *J Biol Chem* 285: 12096 (2010); Zoller F et al., *Molecules* 16: 2467-85 (2011); Alfarano P et al., *Protein Sci* 21: 1298-314 (2012); Madhurantakam C et al., *Protein Sci* 21: 1015-28 (2012); Varadamsetty G et al., *J Mol Biol* 424: 68-87 (2012); Reichen C et al., *J Struct Biol* 185: 147-62 (2014)).

For example, numerous alternative scaffolds have been identified which bind to an extracellular part of the human cell-surface receptor HER2 (see e.g. Wikman M et al., *Protein Eng Des Sel* 17: 455-62 (2004); Orlova A et al. *Cancer Res* 66: 4339-8 (2006); Ahlgren S et al., *Bioconjug Chem* 19: 235-43 (2008); Feldwisch J et al., *J Mol Biol* 398: 232-47 (2010); U.S. Pat. Nos. 5,578,482; 5,856,110; 5,869,445; 5,985,553; 6,333,169; 6,987,088; 7,019,017; 7,282,365; 7,306,801; 7,435,797; 7,446,185; 7,449,480; 7,560,111; 7,674,460; 7,815,906; 7,879,325; 7,884,194; 7,993,650; 8,241,630; 8,349,585; 8,389,227; 8,501,909; 8,512,967; 8,652,474; and U.S. patent application 2011/0059090). In addition to alternative antibody formats, antibody-like binding abilities may be conferred by non-proteinaceous compounds, such as, e.g., oligomers, RNA molecules, DNA molecules, carbohydrates, and glycocalyxcalixarenes (see e.g. Sansone F, Casnati A, *Chem Soc Rev* 42: 4623-39 (2013)) or partially proteinaceous compounds, such as, e.g., phenol-formaldehyde cyclic oligomers coupled with peptides and calixarene-peptide compositions (see e.g. U.S. Pat. No. 5,770,380).

In certain embodiments, the HER2 binding region is an immunoglobulin-type binding region. In certain embodiments, the immunoglobulin-type, HER2 binding region is derived from an immunoglobulin, HER2 binding region, such as an antibody paratope capable of binding an extracellular part of HER2. In certain other embodiments, the immunoglobulin-type, HER2 binding region comprises an engineered polypeptide not derived from any immunoglobulin domain but which functions like an immunoglobulin, HER2 binding region by providing high-affinity binding to an extracellular part of HER2. This engineered polypeptide may optionally include polypeptide scaffolds comprising, consisting of, or consisting essentially of complementary determining regions (such as, e.g., a heavy chain variable domain and/or light chain variable domain) and/or antigen binding regions from immunoglobulins as described herein.

There are numerous HER2 binding regions contemplated as components of the present invention. Non-limiting examples of immunoglobulin-type, HER2 binding regions include HER2-binding monoclonal antibodies and derivatives thereof, such as, e.g., anti-ErbB2, 4D5, 2C4, 7F3, 7C2, mumAb 4D5, chmAb 4D5, (rhu)mAb 4D5, huMAb4D5-1, huMAb4D5-2, huMAb4D5-3, huMAb4D5-4, huMAb4D5-5, huMAb4D5-6, huMAb4D5-7, huMAb4D5-8, trastuzumab, humanized 520C9, 4D5Fc8, hingeless rhu4D5, non-glycosylated rhu4D5 with mutated cysteine residues, pertuzumab, and humanized 2C4 (Hudziak R et al., *Mol Cell Biol* 9: 1165-72 (1989); McKenzie S et al., *Oncogene* 4:543-8 (1989); Bacus S et al., *Molecular Carcinogenesis* 3: 350-62 (1990); Hancock M et al., *Cancer Res* 51: 4575-80 (1991); Maier L et al., *Cancer Res* 51: 5361-5369 (1991); Stancovski I et al., *Proc Natl Acad Sci USA* 88: 8691-5 (1991); Tagliabue E et al., *Int J Cancer* 47: 933-937 (1991); Bacus S et al., *Cancer Res* 52: 2580-9 (1992); Carter P et al., *Proc Natl Acad Sci USA* 89: 4285-89 (1992); Harwerth I et al. *J Biol Chem* 267: 15160-7 (1992); Kasprzyk P et al., *Cancer Res* 52: 2771-6 (1992); Lewis G et al., *Cancer Immunol Immunother* 37: 255-63 (1993); Xu F et al., *Int J Cancer* 53: 401-8 (1993); Arteaga C et al., *Cancer Res* 54: 3758-65 (1994); Shawver L et al., *Cancer Res* 54: 1367-73 (1994); Klapper L et al. *Oncogene* 14: 2099-109 (1997); WO 1993/21319; WO 1994/00136; WO 1997/00271; WO 1998/77797; U.S. Pat. Nos. 5,772,997; 5,783,186; 5,821,337; 5,840,525; 6,949,245; and 7,625,859).

In certain embodiments, the cell-targeting molecule of the present invention comprises a binding region comprising an immunoglobulin-type polypeptide (e.g. an immunoglobulin polypeptide) selected for specific and high-affinity binding to human HER2 and/or the cellular surface of a HER2 positive cell. In certain embodiments of the cell-targeting molecule of the present invention, the binding region comprises at least one heavy chain variable (V$_H$) domain; and/or at least one light chain variable (V$_L$) domain. As described herein, the at least one heavy-chain variable domain polypeptide may be linked to the at least one light-chain variable domain polypeptide by a linker (such as a linker or inter-domain linker described herein). In certain embodiments of the cell-targeting molecule of the present invention, the binding region comprises a single-domain antibody fragment, such as, e.g., only a heavy chain variable (V$_H$H) domain (e.g. as derived from a camelid antibody).

The binding region of the cell-targeting molecule of the present invention may be defined by reference to its CDRs, such as those defined in SEQ ID NOs: 45-74. In certain embodiments of the cell-targeting molecule of the present invention, the binding region comprises a polypeptide(s) selected from the group consisting of: a) a heavy chain variable (V$_H$) domain comprising (i) a HCDR1 comprising or consisting essentially of one of the amino acid sequences as shown in SEQ ID NO:45, SEQ ID NO:51, SEQ ID NO:57 or SEQ ID NO:63; (ii) a HCDR2 comprising or consisting essentially of one of the amino acid sequence as shown in SEQ ID NO:46, SEQ ID NO:52, SEQ ID NO:58, or SEQ ID NO:64; and (iii) a HCDR3 comprising or consisting essentially of one of the amino acid sequence as shown in SEQ ID NO:47, SEQ ID NO:53, SEQ ID NO:59, or SEQ ID NO:65; and/or b) a light chain variable (V$_L$) domain comprising (i) a LCDR1 comprising or consisting essentially of one of the amino acid sequence as shown in SEQ ID NO:48, SEQ ID NO:54, SEQ ID NO:60, or SEQ ID NO:66; (ii) a LCDR2 comprising or consisting essentially of one of the amino acid sequence as shown in SEQ ID NO:49, SEQ ID NO:55, SEQ ID NO:61 or SEQ ID NO:67; and (iii) a LCDR3 comprising or consisting essentially of one of the amino acid sequence as shown in SEQ ID NO:50, SEQ ID NO:56, SEQ ID NO:62, or SEQ ID NO:68. In certain embodiments, the binding region comprises at least one heavy-chain variable domain polypeptide comprising (i) the HCDR1, HCDR2, and HCDR3 amino acid sequences shown in SEQ ID NOs: 51, SEQ ID NO:52, and SEQ ID NO:53, respectively; (ii) the HCDR1, HCDR2, and HCDR3 amino acid sequences shown in SEQ ID NO:57, SEQ ID NO:58, and SEQ ID NO:59, respectively; or (iii) the HCDR1, HCDR2, and HCDR3 amino acid sequences shown in SEQ ID NO:63, SEQ ID NO:64, and SEQ ID NO:65, respectively. In certain embodiments, the binding region comprises at least one light-chain variable domain polypeptide comprising (i) the LCDR1, LCDR2, and LCDR3 amino acid sequences shown in SEQ ID NO:54, SEQ ID NO:55, and SEQ ID NO:56, respectively; (ii) the LCDR1, LCDR2, and LCDR3 amino acid sequences shown in SEQ ID NO:60, SEQ ID NO:61, and SEQ ID NO:62, respectively; or (iii) the LCDR1, LCDR2, and LCDR3 amino acid sequences shown in SEQ ID NO:66, SEQ ID NO:67, and SEQ ID NO:68, respectively.

In certain embodiments, the binding region comprises at least one heavy-chain variable domain polypeptide comprising (i) the HCDR1, HCDR2, and HCDR3 amino acid sequences shown in SEQ ID NOs: 51, SEQ ID NO:52, and SEQ ID NO:53, respectively; (ii) the HCDR1, HCDR2, and HCDR3 amino acid sequences shown in SEQ ID NO:57, SEQ ID NO:58, and SEQ ID NO:59, respectively; or (iii) the HCDR1, HCDR2, and HCDR3 amino acid sequences shown in SEQ ID NO:63, SEQ ID NO:64, and SEQ ID NO:65, respectively; and at least one light-chain variable domain polypeptide comprising (i) the LCDR1, LCDR2, and LCDR3 amino acid sequences shown in SEQ ID NO:54, SEQ ID NO:55, and SEQ ID NO:56, respectively; (ii) the LCDR1, LCDR2, and LCDR3 amino acid sequences shown in SEQ ID NO:60, SEQ ID NO:61, and SEQ ID NO:62, respectively; or (iii) the LCDR1, LCDR2, and LCDR3 amino acid sequences shown in SEQ ID NO:66, SEQ ID NO:67, and SEQ ID NO:68, respectively. For example, the binding region may comprises at least one heavy-chain variable domain polypeptide comprising (i) the HCDR1, HCDR2, and HCDR3 amino acid sequences shown in SEQ ID NOs: 51, SEQ ID NO:52, and SEQ ID NO:53, respectively; and at least one light-chain variable domain polypeptide comprising: (i) the LCDR1, LCDR2, and LCDR3 amino acid sequences shown in SEQ ID NO:54, SEQ ID NO:55, and SEQ ID NO:56, respectively. For example, the binding region may comprises at least one heavy-chain variable domain polypeptide comprising (i) the HCDR1, HCDR2, and HCDR3 amino acid sequences shown in SEQ ID NOs: 57, SEQ ID NO:58, and SEQ ID NO:59, respectively; and at least one light-chain variable domain polypeptide comprising (i) the LCDR1, LCDR2, and LCDR3 amino acid sequences shown in SEQ ID NO:60, SEQ ID NO:61, and SEQ ID NO:62, respectively. For example, the binding region may comprises at least one heavy-chain variable domain polypeptide comprising (i) the HCDR1, HCDR2, and HCDR3 amino acid sequences shown in SEQ ID NOs: 63, SEQ ID NO:64, and SEQ ID NO:65, respectively; and at least one light-chain variable domain polypeptide comprising (i) the LCDR1, LCDR2, and LCDR3 amino acid sequences shown in SEQ ID NO:66, SEQ ID NO:67, and SEQ ID NO:68, respectively. The binding region having these CDRs may be an immunoglobulin binding region comprising a single-chain variable fragment.

In certain embodiments of the cell-targeting molecule of the present invention, the binding region comprises a polypeptide(s) selected from the group consisting of: a) a heavy chain only variable (V$_H$H) domain comprising (i) a HCDR1 comprising or consisting essentially of the amino acid sequences as shown in SEQ ID NO:69 or SEQ ID NO:72; (ii) a HCDR2 comprising or consisting essentially of the amino acid sequence as shown in SEQ ID NO:70 or SEQ ID NO:73; and/or (iii) a HCDR3 comprising or consisting essentially of the amino acid sequence as shown in SEQ ID NO:71 or SEQ ID NO:74. In certain further embodiments, the binding region comprises a polypeptide(s) selected from the group consisting of: a) a heavy chain only variable (V$_H$H) domain comprising (i) a HCDR1 comprising or consisting essentially of the amino acid sequences as shown in SEQ ID NO:69 or SEQ ID NO:72; (ii) a HCDR2 comprising or consisting essentially of the amino acid sequence as shown in SEQ ID NO:70 or SEQ ID NO:73; and (iii) a HCDR3 comprising or consisting essentially of the amino acid sequence as shown in SEQ ID NO:71 or SEQ ID NO:74. The binding region having these CDRs may be an immunoglobulin binding region comprising a heavy chain only variable (V$_H$H) domain derived from a camelid antibody (see e.g. Example 1, infra).

In certain embodiments of the cell-targeting molecule of the present invention, the binding region comprises, consists essentially of, or consists of an amino acid sequence that is at least 85% (such as at least 90%, 91%, 92%, 93%, 94%, 95%, 96%, 97%, 98%, 99% or more) identical to the amino acid sequence of: amino acids 269 to 501 of SEQ ID NO:24; amino acids 269 to 513 of SEQ ID NO:25; amino acids 269 to 499 of SEQ ID NO: 26 or SEQ ID NO:27; amino acids; amino acids 269-520 of SEQ ID NO:28; amino acids 269 to 519 of SEQ ID NO:29 or SEQ ID NO:30; amino acids 268 to 386 of SEQ ID NO:31; amino acids 269 to 499 of SEQ ID NO:32; amino acids 269 to 499 of SEQ ID NO:33; amino acids 253 to 370 of SEQ ID NO:34; amino acids 253 to 367 of SEQ ID NO:35; amino acids 269 to 514 of SEQ ID NO:36; amino acids 268 to 498 of SEQ ID NO:99; amino acids 268 to 499 of SEQ ID NO:100; amino acids 268 to 500 of SEQ ID NO:97; amino acids 268 to 512 of SEQ ID NO:98; amino acids 268 to 518 of SEQ ID NO:102 or SEQ ID NO:103; amino acids 268-519 of SEQ ID NO:101; amino acids 267 to 384 of SEQ ID NO:104; amino acids 268 to 498 of SEQ ID NO:105; amino acids 252 to 370 of SEQ ID NO:106; amino acids 252 to 366 of SEQ ID NO:107; and amino acids 268 to 513 of SEQ ID NO:108. In certain embodiments of the cell-targeting molecule of the present invention, the binding region comprises, consists essentially of, or consists of an amino acid sequence that is at least 85% (such as at least 90%, 91%, 92%, 93%, 94%, 95%, 96%, 97%, 98%, 99% or more) identical to the amino acid sequence of: amino acids 269 to 513 of SEQ ID NO:25; amino acids 269 to 499 of SEQ ID NO:26; amino acids 269 to 519 of SEQ ID NO:29 or SEQ ID NO:30; amino acids 268 to 386 of SEQ ID NO:31; amino acids 253 to 370 of SEQ ID NO:34; amino acids 253 to 367 of SEQ ID NO:35; or amino acids 269 to 514 of SEQ ID NO:36. In certain embodiments of the cell-targeting molecule of the present invention, the binding region comprises, consists essentially of, or consists of an amino acid sequence that is at least 85% (such as at least 90%, 91%, 92%, 93%, 94%, 95%, 96%, 97%, 98%, 99% or more) identical to amino acids 269 to 519 of SEQ ID NO:29 or SEQ ID NO:30.

In certain embodiments of the cell-targeting molecule of the present invention, the binding region comprises, consists essentially of, or consists of the polypeptide represented by any one of the following polypeptide sequences: amino acids 269 to 501 of SEQ ID NO:24; amino acids 269 to 513 of SEQ ID NO:25; amino acids 269 to 499 of SEQ ID NO: 26 or SEQ ID NO:27; amino acids; amino acids 269-520 of SEQ ID NO:28; amino acids 269 to 519 of SEQ ID NO:29 or SEQ ID NO:30; amino acids 268 to 386 of SEQ ID NO:31; amino acids 269 to 499 of SEQ ID NO:32; amino acids 269 to 499 of SEQ ID NO:33; amino acids 253 to 370 of SEQ ID NO:34; amino acids 253 to 367 of SEQ ID NO:35; amino acids 269 to 514 of SEQ ID NO:36 amino acids 268 to 498 of SEQ ID NO:99; amino acids 268 to 499 of SEQ ID NO:100; amino acids 268 to 500 of SEQ ID NO:97; amino acids 268 to 512 of SEQ ID NO:98; amino acids 268 to 518 of SEQ ID NO:102 or SEQ ID NO:103; amino acids 268-519 of SEQ ID NO:101; amino acids 267 to 384 of SEQ ID NO:104; amino acids 268 to 498 of SEQ ID NO:105; amino acids 252 to 370 of SEQ ID NO:106; amino acids 252 to 366 of SEQ ID NO:107; and amino acids 268 to 513 of SEQ ID NO:108. In certain embodiments of the cell-targeting molecule of the present invention, the binding region comprises, consists essentially of, or consists of the polypeptide represented by any one of the following polypeptide sequences: amino acids 269 to 513 of SEQ ID NO:25; amino acids 269 to 499 of SEQ ID NO:26; amino acids 269 to 519 of SEQ ID NO:29 or SEQ ID NO:30; amino acids 268 to 386 of SEQ ID NO:31; amino acids 253 to 370 of SEQ ID NO:34; amino acids 253 to 367 of SEQ ID NO:35; and amino acids 269 to 514 of SEQ ID NO:36. In certain embodiments of the cell-targeting molecule of the present invention, the binding region comprises, consists essentially of, or consists of the polypeptide represented by amino acids 269 to 519 of SEQ ID NO:29 or SEQ ID NO:30. In certain embodiments of the cell-targeting molecule of the present invention, the binding region comprises, consists essentially of, or consists of the polypeptide represented by amino acids 269 to 519 of SEQ ID NO:29, amino acids 268 to 386 of SEQ ID NO:31; amino acids 253 to 370 of SEQ ID NO:34; or amino acids 253 to 367 of SEQ ID NO:35. In certain embodiments, the binding region comprises, consists essentially of, or consists of the polypeptide represented by amino acids 269 to 519 of SEQ ID NO:29. In certain, embodiments, the binding region comprises, consists essentially of, or consists of the polypeptide represented by amino acids 268 to 386 of SEQ ID NO:31. In certain embodiments, the binding region comprises, consists essentially of, or consists of the polypeptide represented by amino acids 253 to 370 of SEQ ID NO:34. In certain embodiments, the binding region comprises, consists essentially of, or consists of the polypeptide represented by amino acids 253 to 367 of SEQ ID NO:35. In certain embodiments, the binding region comprises, consists essentially of, or consists of the polypeptide represented by amino acids 269 to 514 of SEQ ID NO:36.

In certain embodiments of the cell-targeting molecule of the present invention, the binding region comprises at least one heavy chain variable ($V_H$) domain comprising, consisting essentially of, or consisting of an amino acid sequence that is at least 85% (such as at least 90%, 91%, 92%, 93%, 94%, 95%, 96%, 97%, 98%, 99% or more) identical to the amino acid sequence shown in any one of: amino acids 253 to 367 of SEQ ID NO:35; amino acids 253 to 370 of SEQ ID NO:34; amino acids 268 to 386 of SEQ ID NO:31; amino acids 269 to 387 of SEQ ID NO: 26, 29, 30 or 36; amino acids 269 to 397 of SEQ ID NO:25; amino acids 381 to 500 of SEQ ID NO: 24 or 27; and amino acids 401 to 520 of SEQ ID NO:28. In certain further embodiments, the binding region comprises at least one heavy chain variable ($V_H$) domain comprising, consisting essentially of, or consisting of: amino acids 253 to 367 of SEQ ID NO:35; amino acids 253 to 370 of SEQ ID NO:34; amino acids 268 to 386 of SEQ ID NO:31; amino acids 269 to 387 of SEQ ID NO: 26, 29, 30 or 36; amino acids 269 to 397 of SEQ ID NO:25; amino acids 381 to 500 of SEQ ID NO: 24 or 27; and amino acids 401 to 520 of SEQ ID NO:28. In certain embodiments of the cell-targeting molecule of the present invention, the binding region comprises at least one heavy chain variable ($V_H$) domain comprising, consisting essentially of, or consisting of an amino acid sequence that is at least 85% (such as at least 90%, 91%, 92%, 93%, 94%, 95%, 96%, 97%, 98%, 99% or more) identical to the amino acid sequence shown in any one of: amino acids 269 to 387 of SEQ ID NO: 26, 29, 30 or 36; amino acids 269 to 397 of SEQ ID NO:25; amino acids 381 to 500 of SEQ ID NO: 24 or 27; and amino acids 401 to 520 of SEQ ID NO:28. In certain further embodiments of the cell-targeting molecule of the present invention, the binding region comprises at least one light chain variable ($V_L$) domain comprising, consisting essentially of, or consisting of an amino acid sequence that is at least 85% (such as at least 90%, 91%, 92%, 93%, 94%, 95%, 96%, 97%, 98%, 99% or more) identical to the amino acid sequence shown in any one of: amino acids 269 to 375 of SEQ ID NO: 24, 27, or 28; amino acids 393 to 499 of SEQ ID NO:26; amino acids 403 to 513 of SEQ ID NO:25; amino acids 408 to 514 of SEQ ID NO:36; and amino acids 413 to 519 of SEQ ID NO: 29 or 30. In certain further embodiments of the cell-targeting molecule of the present invention, the binding region comprises at least one light chain variable ($V_L$) domain comprising, consisting essentially of, or consisting of: amino acids 269 to 375 of SEQ ID NO: 24, 27, or 28; amino acids 393 to 499 of SEQ ID NO:26; amino acids 403 to 513 of SEQ ID NO:25; amino acids 408 to 514 of SEQ ID NO:36; and amino acids 413 to 519 of SEQ ID NO: 29 or 30. Any of heavy chain variable domain polypeptides described herein may be used in combination with any of the light chain variable domain polypeptides described herein.

In certain embodiments, the binding region may comprise: (a) at least one heavy chain variable ($V_H$) domain comprising, consisting essentially of, or consisting of: amino acids 269 to 387 of SEQ ID NOs: 26, 29, 30, or 36; amino acids 269 to 397 of SEQ ID NO:25; amino acids 381 to 500 of SEQ ID NO: 24 or 27; amino acids 401 to 522 of SEQ ID NO:36, or amino acids 401 to 520 of SEQ ID NO:28; and (b) at least one light chain variable ($V_L$) domain comprising, consisting essentially of, or consisting of: amino acids 269 to 375 of SEQ ID NO: 24, 27, or 28; amino acids 393 to 499 of SEQ ID NO:26; amino acids 403 to 513 of SEQ ID NO:25; amino acids 408 to 514 of SEQ ID NO:36; and amino acids 413 to 519 of SEQ ID NO: 29 or 30. For example, the binding region may comprise (a) at least one heavy chain variable ($V_H$) domain comprising, consisting essentially of, or consisting of amino acids 381 to 500 of SEQ ID NO:24; and (b) at least one light chain variable ($V_L$) domain comprising, consisting essentially of, or consisting of amino acids 269 to 375 of SEQ ID NO:24. For example, the binding region may comprise (a) at least one heavy chain variable ($V_H$) domain comprising, consisting essentially of, or consisting of amino acids 269 to 397 of SEQ ID NO:25; and (b) at least one light chain variable ($V_L$) domain comprising, consisting essentially of, or consisting of: amino acids 403 to 513 of SEQ ID NO:25. For example, the binding region may comprise (a) at least one heavy chain variable ($V_H$) domain comprising, consisting essentially of, or consisting of amino acids 269 to 387 of SEQ ID NO:26; and (b) at least one light chain variable ($V_L$) domain comprising, consisting essentially of, or consisting of amino acids 393 to 499 of SEQ ID NO:26. For example, the binding region may comprise (a) at least one heavy chain variable ($V_H$) domain comprising, consisting essentially of, or consisting of amino acids 381 to 500 of SEQ ID NO:27; and (b) at least one light chain variable ($V_L$) domain comprising, consisting essentially of, or consisting of amino acids 269 to 375 of SEQ ID NO:27. For example, the binding region may comprise (a) at least one heavy chain variable ($V_H$) domain comprising, consisting essentially of, or consisting of amino acids 401 to 520 of SEQ ID NO:28; and (b) at least one light chain variable ($V_L$) domain comprising, consisting essentially of, or consisting of amino acids 269 to 375 of SEQ ID NO:28. For example, the binding region may comprise (a) at least one heavy chain variable ($V_H$) domain comprising, consisting essentially of, or consisting of amino acids 269 to 387 of SEQ ID NO:29; and (b) at least one light chain variable ($V_L$) domain comprising, consisting essentially of, or consisting of amino acids 413 to 519 of SEQ ID NO:29. For example, the binding region may comprise (a) at least one heavy chain variable ($V_H$) domain comprising, consisting essentially of, or consisting of amino acids 269 to 387 of SEQ ID NO:30; and (b) at least one light chain variable ($V_L$) domain comprising, consisting essentially of, or consisting of amino acids 413 to 519 of SEQ ID NO:30. For example, the binding region may comprise (a) at least one heavy chain variable ($V_H$) domain comprising, consisting essentially of, or consisting of amino acids 269 to 387 of SEQ ID NO:36; and (b) at least one light chain variable ($V_L$) domain comprising, consisting essentially of, or consisting of amino acids 408 to 514 of SEQ ID NO:36.

In certain embodiments, the binding region comprises or consists essentially of amino acids 269-520 of SEQ ID NO:102.

In certain embodiments, the binding region comprises the heavy chain variable domain comprising or consisting essentially of amino acids 269 to 387 of SEQ ID NO:26, 29-30, or 36; 269 to 397 of SEQ ID NO:25; 381 to 500 of SEQ ID NO:27; or 401 to 522 of SEQ ID NO:36. In certain further embodiments, the binding region comprises the light chain variable domain comprising or consisting essentially of amino acids 269 to 375 of SEQ ID NO:27; 393 to 499 of SEQ ID NO:26; 403 to 513 of SEQ ID NO:25; 408 to 514 of SEQ ID NO:36; 413 to 519 of SEQ ID NO:29 or 30. In certain further embodiments, the binding region comprises or consists essentially of amino acids 269 to 513 of SEQ ID NO:25; 269 to 499 of SEQ ID NO:26; 269 to 519 of SEQ ID NO:29; 269 to 519 of SEQ ID NO:30; 268 to 386 of SEQ ID NO:31; 269 to 499 of SEQ ID NO:32; 269 to 499 of SEQ ID NO:33; 253 to 370 of SEQ ID NO:34; 253 to 367 of SEQ ID NO:35; or 269 to 514 of SEQ ID NO:36.

A natural ligand or derivative thereof may be utilized as the HER2 binding region for a cell-targeting molecule of the present invention. Native HER2 is known to heterodimerize with other members of the ErbB family upon binding ligands such as epidermal growth factors like epiregulin and heregulin (Moasser M, Oncogene 26: 6469-87 (2007); Riese D, Cullum R, Semin Cell Dev Biol 28: 49-56 (2014); Sollome J et al., Cell Signal 26: 70-82 (2014)). ErbB ligands which bind members of the ErbB family include EGF, TGF-α, amphiregulin, betacellulin, HB-EGF, epiregulin, HER2-68 and HER2-100, heregulins, herstatin, NRG-2, NRG-3, and NRG-4 (Justman Q et al., J Biol Chem 277: 20618-24 (2002); Jhabvala-Romero F., et al., Oncogene 22: 8178-86 (2003)). Examples of an ErbB ligand include the heregulins (HRG), such as the prototype heregulin disclosed in U.S. Pat. No. 5,641,869 and Marchionni M et al., Nature 362: 312-8 (1993). Examples of heregulins include heregulin-α, heregulin-β1, heregulin-β2 and heregulin-β3 (Holmes W et al., Science 256: 1205-10 (1992); U.S. Pat. No. 5,641,869); neu differentiation factor (NDF) (Peles et al., Cell 69: 205-16 (1992)); acetylcholine receptor-inducing activity (ARIA) (Falls D et al., Cell 72: 801-15 (1993)); glial growth factors (GGFs) (Marchionni M et al., Nature 362: 312-8 (1993)); sensory and motor neuron derived factor (SMDF) (Ho W et al., J Biol Chem 270: 14523-32 (1995)); γ-heregulin (Schaefer G et al., Oncogene 15: 1385-94 (1997)).

An ErbB ligand according to the present invention may also be a synthetic ErbB ligand. The synthetic ligand may be specific for a particular ErbB receptor or may recognize particular ErbB receptor complexes. An example of a synthetic ligand is the synthetic heregulin/EGF chimera biregulin (Jones J et al., FEBS Lett, 447: 227-31 (1999)) and the EGF-like domain fragment HRGβ1177-244. ErbB ligands or a part of an ErbB ligand that interacts with HER2 or a derivative thereof may be fused to Shiga toxin effector polypeptides of the invention to construct HER2-targeting, cell-targeting molecules of the invention that bind an extracellular part of HER2.

Synthetic peptides which bind an extracellular part of HER2 may be utilized as the binding region for targeting. Many peptides have been described which are capable of binding to HER2 (see e.g. U.S. Pat. Nos. 5,578,482; 5,856,110; 5,869,445; 5,985,553; 6,333,169; 6,987,088; 7,019,017; 7,282,365; 7,306,801; 7,435,797; 7,446,185; 7,449,480; 7,560,111; 7,674,460; 7,815,906, 7,879,325; 7,884, 194; 7,993,650; 8,241,630; 8,349,585; 8,389,227; 8,501, 909; 8,512,967; 8,652,474; and US 2011/0059090).

In certain embodiments, small molecules which bind an extracellular part of HER2 may be utilized as the binding region for targeting. Many small molecules have been described which are capable of binding to HER2 such as tyrosine kinase inhibitors, AZD8931, lapatinib, neratinib (HKI-272), dacomitinib (PF-00299804), afatinib (BIBW 2992) (Barlaam B et al., *ACS Med Chem Lett* 4: 742-6 (2013); Yu H, Riley G, *J Natl Compr Canc Netw* 11: 161-9 (2013); Roskoski R, *Pharmacol Res* 87C: 42-59 (2014)). Other small molecules which bind to an extracellular part of HER2 may be identified using methods well known to those of skill in the art, such as by derivatizing known EGFR binders like gefitinib, erlotinib, AEE788, AG1478, AG1571 (SU-5271), AP26113, CO-1686, XL647, vandetanib, and BMS-690514 (Kurokawa H, Arteaga C, *Clin Cancer Res* 7: 4436s-4442s (2001); Yigitbasi 0 et al., *Cancer Res* 64: 7977-84 (2004); Yu H, Riley G, *J Natl Compr Canc Netw* 11: 161-9 (2013); Roskoski R, *Pharmacol Res* 87C: 42-59 (2014)).

Any of the aforementioned HER2 binding molecules may be suitable for use as a HER2 binding region or modified to create one or more HER2 binding regions for use in a cell-targeting molecule of the present invention. Any of the above binding region structures may be used as a component of a molecule of the present invention as long as the binding region component has a dissociation constant of $10^{-5}$ to $10^{-12}$ moles per liter, preferably less than 200 nanomolar (nM), towards an extracellular part of a HER2 molecule.
HER2/neu/ErbB2 Target Biomolecules Bound by the Binding Regions In certain embodiments, the binding region of a cell-targeting molecules of the present invention comprises a proteinaceous region capable of binding specifically to an extracellular part of a HER2 biomolecule or an extracellular HER2 biomolecule, preferably which is physically coupled to the surface of a cell type of interest, such as, e.g., a cancer cell and/or tumor cell.

The term "target biomolecule" refers to a biological molecule, commonly a proteinaceous molecule or a protein modified by post-translational modifications, such as glycosylation, that is bound by a binding region of a cell-targeting molecule of the present invention resulting in the targeting of the cell-targeting molecule to a specific cell, cell-type, and/or location within a multicellular organism.

For purposes of the present invention, the term "extracellular" with regard to a target biomolecule refers to a biomolecule that has at least a portion of its structure exposed to the extracellular environment. The exposure to the extracellular environment of or accessibility to a part of target biomolecule coupled to a cell may be empirically determined by the skilled worker using methods well known in the art. Non-limiting examples of extracellular target biomolecules include cell membrane components, transmembrane spanning proteins, cell membrane-anchored biomolecules, cell-surface-bound biomolecules, and secreted biomolecules.

With regard to the present invention, the phrase "physically coupled" when used to describe a target biomolecule means covalent and/or non-covalent intermolecular interactions couple the target biomolecule, or a portion thereof, to the outside of a cell, such as a plurality of non-covalent interactions between the target biomolecule and the cell where the energy of each single interaction is on the order of at least about 1-5 kiloCalories (e.g., electrostatic bonds, hydrogen bonds, ionic bonds, Van der Walls interactions, hydrophobic forces, etc.). All integral membrane proteins can be found physically coupled to a cell membrane, as well as peripheral membrane proteins. For example, an extracellular target biomolecule might comprise a transmembrane spanning region, a lipid anchor, a glycolipid anchor, and/or be non-covalently associated (e.g. via non-specific hydrophobic interactions and/or lipid binding interactions) with a factor comprising any one of the foregoing.

Extracellular parts of target biomolecules may include various epitopes, including unmodified polypeptides, polypeptides modified by the addition of biochemical functional groups, and glycolipids (see e.g. U.S. Pat. No. 5,091,178; EP2431743).

The binding regions of the cell-targeting molecules of the present invention may be designed or selected based on numerous criteria, such as the cell-type specific expression of their HER2 target, the physical localization of their HER2 target biomolecules with regard to specific cell types, and/or the properties of their target HER2 biomolecules. For example, certain cell-targeting molecules of the present invention comprise binding regions capable of binding a cell-surface HER2 target biomolecule that is expressed at a cellular surface exclusively by only one cell-type of a species or only one cell-type within a multicellular organism. It is desirable, but not necessary, that an extracellular target HER2 biomolecule be intrinsically internalized or be readily forced to internalize upon interacting with a cell-targeting molecule of the present invention.

Among certain embodiments of the cell-targeting molecules of the present invention, the binding region is derived from an immunoglobulin-type polypeptide selected for specific and high-affinity binding to a HER2 antigen on the cell surface of a cancer or tumor cell, where the antigen is restricted in expression to cancer or tumor cells (see Glokler J et al., *Molecules* 15: 2478-90 (2010); Liu Y et al., *Lab Chip* 9: 1033-6 (2009). In accordance with other embodiments, the binding region is selected for specific and high-affinity binding to an extracellular part of HER2 on the cell surface of a cancer cell, where the HER2 is over-expressed or preferentially expressed by cancer cells as compared to non-cancer cells.

It will be appreciated by the skilled worker that any desired target HER2 biomolecule may be used to design or select a suitable binding region to be associated and/or coupled with a Shiga toxin effector polypeptide to produce a cell-targeting molecule of the present invention.

Any of the above binding regions described herein may be used alone or in combination with each individual embodiment of the present invention, including methods of the present invention.

The general structure of the cell-targeting molecules of the present invention is modular, in that various, diverse, HER2-targeting binding regions may be associated with various, Shiga toxin effector polypeptides of the present invention to create different, cell-targeting molecules of the present invention which exhibit differences in their cell-targeting activities due to differences in their binding regions. This enables a variety of cell-targeting activities to be exhibited by different embodiments of the cell-targeting molecules of the present invention such that different embodiments target different types of cells with Shiga toxin effector functions, such as, e.g., cytostasis, cytotoxicity, and intracellular delivery of exogenous materials. Furthermore, certain embodiments of the cell-targeting molecules of the present invention exhibit certain characteristics due to differences in their respective Shiga toxin effector polypeptide regions, such as, e.g., low antigenicity and/or immunogenicity when administered to a chordate, resistance to proteolytic cleavage by certain proteases, high stability when administered to a multicellular organism, in vivo tolerability at high dosages, ability to deliver a cargo to an intracellular location, and/or ability to deliver a T-cell epitope to a MHC class I molecule for presentation on a cellular surface.

For the purposes of the present invention, the specific order or orientation of the Shiga toxin effector polypeptide region and the cell-targeting, HER2-binding region is not fixed in relation to each other or within the cell-targeting molecule of the present invention unless expressly noted. For example, when the cell-targeting molecule of the present invention is a fusion protein with an amino-terminal(s) and carboxy-terminal(s), various arrangements of the components of the invention may be suitable (see e.g. FIG. 1). In certain embodiments of the cell-targeting molecules of the present invention, the arrangement of their components in relation to each other or within the cell-targeting molecule are limited as described herein. For example, certain endoplasmic reticulum retention/retrieval signal motifs (see e.g. WO 2015/138435) are commonly positioned on a carboxy-terminus of a cell-targeting molecule of the present invention and/or a carboxy-terminus of a protein component of a cell-targeting molecule of the present invention.

B. The General Structures of the Shiga Toxin A Subunit Effector Polypeptides

The cell-targeting molecules of the present invention comprise at least one, Shiga toxin effector polypeptide derived from wild-type Shiga toxin A Subunits that further comprise one or more structural modifications, such as, e.g., a mutation like a truncation and/or amino acid residue substitution(s). For certain embodiments, the present invention involves the engineering of improved, Shiga toxin A Subunit effector polypeptides comprising the combination of two or more of the following Shiga toxin effector polypeptide sub-regions: (1) a de-immunized sub-region, (2) a protease-cleavage resistant sub-region near the carboxy-terminus of a Shiga toxin A1 fragment region, and (3) a T-cell epitope-peptide embedded or inserted sub-region. For example, the Shiga toxin effector polypeptide of the present invention may comprise the combination of: (1) a de-immunized sub-region, (2) a protease-cleavage resistant sub-region near the carboxy-terminus of a Shiga toxin A1 fragment region, and (3) a T-cell epitope-peptide embedded or inserted sub-region that does not overlap with the de-immunized sub-region.

In certain embodiments, the cell-targeting molecule of the invention comprises a Shiga toxin effector polypeptide that comprises a Shiga toxin A 1 fragment region, wherein the Shiga toxin A subunit effector polypeptide comprises: (a) an embedded or inserted, heterologous, CD8+ T-cell epitope which disrupts an endogenous, B-cell and/or CD4+ T-cell epitope region (such as a region within the Shiga toxin A1 fragment region); (b) a disruption of at least three, endogenous, B-cell and/or CD4+ T-cell epitope regions (such as a three or more regions within the Shiga toxin A1 fragment region) which do not overlap with the embedded or inserted, heterologous, CD8+ T-cell epitope; and (c) a disrupted furin-cleavage motif at the carboxy-terminus of the Shiga toxin A1 fragment region; wherein the Shiga toxin A subunit effector polypeptide is capable of exhibiting a Shiga toxin effector function. In certain further embodiments, the Shiga toxin A subunit effector polypeptide is truncated at its carboxy-terminus, relative to a wild-type Shiga toxin A subunit, resulting in the elimination of one or more endogenous, B-cell and/or CD4+ T-cell epitope regions. In certain further embodiments, the furin-cleavage motif comprises a carboxy-terminal truncation as compared to the carboxy-terminus of a wild-type Shiga toxin A Subunit. In certain further embodiments, the furin-cleavage motif is disrupted by a carboxy-terminal truncation as compared to the carboxy-terminus of a wild-type Shiga toxin A Subunit. For certain embodiments, the cell-targeting molecule is capable of exhibiting less relative antigenicity and/or relative immunogenicity as compared to a reference molecule, such as, e.g., a wild-type Shiga toxin A effector polypeptide comprising a Shiga toxin A1 fragment region, a reference cell-targeting molecule comprising a wild-type Shiga toxin A effector polypeptide comprising a Shiga toxin A1 fragment region, or a reference cell-targeting molecule consisting of the cell-targeting molecule except for it lacks any combination of the following features present in the cell targeting molecule: (1) an embedded or inserted, CD8+ T-cell epitope, (2) a disruption of at least three, endogenous, B-cell and/or CD4+ T-cell epitope regions, and/or (3) a disrupted furin-cleavage motif at the carboxy-terminus of the Shiga toxin A1 fragment region.

For purposes of the present invention, a Shiga toxin effector polypeptide is a polypeptide derived from a Shiga toxin A Subunit member of the Shiga toxin family that is capable of exhibiting one or more Shiga toxin functions (see e.g., Cheung M et al., *Mol Cancer* 9: 28 (2010); WO 2014/164693; WO 2015/113005; WO 2015/113007; WO 2015/138452; WO 2015/191764) and comprises a Shiga toxin A1 fragment derived region having a carboxy-terminus. Shiga toxin functions include, e.g., increasing cellular internalization, directing subcellular routing from an endosomal compartment to the cytosol, avoiding intracellular degradation, catalytically inactivating ribosomes, and effectuating cytostatic and/or cytotoxic effects.

The Shiga toxin family of protein toxins is composed of various naturally occurring toxins which are structurally and functionally related, e.g., Shiga toxin, Shiga-like toxin 1, and Shiga-like toxin 2 (Johannes L, Römer W, *Nat Rev Microbiol* 8: 105-16 (2010)). Holotoxin members of the Shiga toxin family contain targeting domains that preferentially bind a specific glycosphingolipid present on the surface of some host cells and an enzymatic domain capable of permanently inactivating ribosomes once inside a cell (Johannes L, Römer W, *Nat Rev Microbiol* 8: 105-16 (2010)). Members of the Shiga toxin family share the same overall structure and mechanism of action (Engedal N et al., *Microbial Biotech* 4: 32-46 (2011)). For example, Stx, SLT-1 and SLT-2 display indistinguishable enzymatic activity in cell free systems (Head S et al., *J Biol Chem* 266: 3617-21 (1991); Tesh V et al., *Infect Immun* 61: 3392-402 (1993); Brigotti M et al., *Toxicon* 35:1431-1437 (1997)).

The Shiga toxin family encompasses true Shiga toxin (Stx) isolated from *S. dysenteriae* serotype 1, Shiga-like toxin 1 A Subunit variants (SLT1 or Stx1 or SLT-1 or Slt-I) isolated from serotypes of enterohemorrhagic *E. coli*, and Shiga-like toxin 2 variants (SLT2 or Stx2 or SLT-2) isolated from serotypes of enterohemorrhagic *E. coli*. SLT1 differs by only one amino acid residue from Stx, and both have been referred to as Verocytotoxins or Verotoxins (VTs) (O'Brien A, *Curr Top Microbiol Immunol* 180: 65-94 (1992)). Although SLT1 and SLT2 variants are only about 53-60% similar to each other at the primary amino acid sequence level, they share mechanisms of enzymatic activity and cytotoxicity common to the members of the Shiga toxin family (Johannes L, Romer W, *Nat Rev Microbiol* 8: 105-16 (2010)). Over 39 different Shiga toxins have been described, such as the defined subtypes Stx1a, Stx1c, Stx1d, and Stx2a-g (Scheutz F et al., *J Clin Microbiol* 50: 2951-63

(2012)). Members of the Shiga toxin family are not naturally restricted to any bacterial species because Shiga-toxin-encoding genes can spread among bacterial species via horizontal gene transfer (Strauch E et al., *Infect Immun* 69: 7588-95 (2001); Bielaszewska M et al., *Appl Environ Microbiol* 73: 3144-50 (2007); Zhaxybayeva O, Doolittle W, *Curr Biol* 21: R242-6 (2011)). As an example of interspecies transfer, a Shiga toxin was discovered in a strain of *A. haemolyticus* isolated from a patient (Grotiuz G et al., *J Clin Microbiol* 44: 3838-41 (2006)). Once a Shiga toxin encoding polynucleotide enters a new subspecies or species, the Shiga toxin amino acid sequence is presumed to be capable of developing slight sequence variations due to genetic drift and/or selective pressure while still maintaining a mechanism of cytotoxicity common to members of the Shiga toxin family (see Scheutz F et al., *J Clin Microbiol* 50: 2951-63 (2012)).

1. De-Immunized, Shiga Toxin A Subunit Effector Polypeptides

In certain embodiments, the Shiga toxin effector polypeptide of the present invention is de-immunized, such as, e.g., as compared to a wild-type Shiga toxin, wild-type Shiga toxin polypeptide, and/or Shiga toxin effector polypeptide comprising only wild-type polypeptide sequences. The de-immunized, Shiga toxin effector polypeptides of the present invention each comprise a disruption of at least one (such as, e.g., at least two, three, four, five, six, seven, eight, nine or more), putative, endogenous, epitope region in order to reduce the antigenic and/or immunogenic potential of the Shiga toxin effector polypeptide after administration of the polypeptide to a chordate. A Shiga toxin effector polypeptide and/or Shiga toxin A Subunit polypeptide, whether naturally occurring or not, can be de-immunized by a method described herein, described in WO 2015/113005 and/or WO 2015/113007, and/or known to the skilled worker, wherein the resulting molecule retains or exhibits one or more Shiga toxin A Subunit functions.

In certain embodiments, the Shiga toxin effector polypeptide of the present invention comprises a disruption of an endogenous epitope or epitope region, such as, e.g., a B-cell and/or CD4+ T-cell epitope. In certain embodiments, the Shiga toxin effector polypeptide of the present invention comprises a disruption of at least one (such as at least two, three, four, five, six, seven, eight or more) endogenous, B-cell and/or CD4+ T-cell epitope region. In certain embodiments, the Shiga toxin effector polypeptide of the present invention comprises a disruption of at least one (such as at least two, three, four, five, six, seven, eight or more), endogenous, epitope region described herein, wherein the disruption reduces the antigenic and/or immunogenic potential of the Shiga toxin effector polypeptide after administration of the polypeptide to a chordate, and wherein the Shiga toxin effector polypeptide is capable of exhibiting one or more Shiga toxin A Subunit functions, such as, e.g., a significant level of Shiga toxin cytotoxicity. For example, the Shiga toxin effector polypeptide of the present invention comprises a disruption of at least three, endogenous, B-cell and/or CD4+ T-cell epitope regions (such as, e.g., due to two or more mutations and one or more truncations relative to a wild-type Shiga toxin A Subunit).

The term "disrupted" or "disruption" as used herein with regard to an epitope region refers to the deletion of at least one (such as at least two, three, four, five, six, seven, eight or more) amino acid residue in an epitope region, inversion of two or more amino acid residues where at least one of the inverted amino acid residues is in an epitope region, insertion of at least one (such as at least two, three, four, five, six, seven, eight or more) amino acid into an epitope region, and a substitution of at least one amino acid residue in an epitope region. An epitope region disruption by mutation includes amino acid substitutions with non-standard amino acids and/or non-natural amino acids. Epitope regions may alternatively be disrupted by mutations comprising the modification of an amino acid by the addition of a covalently-linked chemical structure which masks at least one amino acid in an epitope region, see, e.g. PEGylation (see Zhang C et al., *BioDrugs* 26: 209-15 (2012), small molecule adjuvants (Flower D, *Expert Opin Drug Discov* 7: 807-17 (2012), and site-specific albumination (Lim S et al., *J Control Release* 207-93 (2015)).

Certain epitope regions and disruptions are indicated herein by reference to specific amino acid positions of native Shiga toxin A Subunits provided in the Sequence Listing, noting that naturally occurring Shiga toxin A Subunits may comprise precursor forms containing signal sequences of about 22 amino acids at their amino-terminals which are removed to produce mature Shiga toxin A Subunits and are recognizable to the skilled worker. Further, certain epitope region disruptions are indicated herein by reference to specific amino acids (e.g. S for a serine residue) natively present at specific positions within native Shiga toxin A Subunits (e.g. S33 for the serine residue at position 33 from the amino-terminus) followed by the amino acid with which that residue has been substituted in the particular mutation under discussion (e.g. S331 represents the amino acid substitution of isoleucine for serine at amino acid residue 33 from the amino-terminus).

In certain embodiments, the de-immunized, Shiga toxin effector polypeptide of the present invention comprises a disruption of at least one (such as at least two, three, four, five, six, seven, eight or more) epitope region provided herein. For example, the de-immunized, Shiga toxin effector polypeptide of the present invention may comprise a disruption of at least three epitope regions provided herein. In certain embodiments, the de-immunized, Shiga toxin effector polypeptide of the present invention comprises a disruption of at least four epitope regions provided herein. In certain embodiments, the de-immunized, Shiga toxin effector polypeptide of the present invention comprises a disruption of at least five epitope regions provided herein. In certain embodiments, the de-immunized, Shiga toxin effector polypeptide of the present invention comprises a disruption of at least one epitope region described in WO 2015/113005 or WO 2015/113007. As described herein, when the Shiga toxin effector polypeptide also comprises an embedded or inserted, heterologous, CD8+ T-cell epitope, at least some number of disrupted, endogenous, B-cell and/or CD4+ T-cell epitope region does not overlap with the embedded or inserted, heterologous, CD8+ T-cell epitope.

In certain embodiments, the de-immunized, Shiga toxin effector polypeptide of the present invention comprises, consists of, or consists essentially of a full-length Shiga toxin A Subunit (e.g. SLT-1A (SEQ ID NO:1), StxA (SEQ ID NO:2), or SLT-2A (SEQ ID NO:3)) comprising at least one disruption of the amino acid sequence selected from the group of natively positioned amino acids consisting of: 1-15 of SEQ ID NO:1 or SEQ ID NO:2; 3-14 of SEQ ID NO:3; 26-37 of SEQ ID NO:3; 27-37 of SEQ ID NO:1 or SEQ ID NO:2; 39-48 of SEQ ID NO:1 or SEQ ID NO:2; 42-48 of SEQ ID NO:3; 53-66 of SEQ ID NO:1, SEQ ID NO:2, or SEQ ID NO:3; 94-115 of SEQ ID NO:1, SEQ ID NO:2, or SEQ ID NO:3; 141-153 of SEQ ID NO:1 or SEQ ID NO:2; 140-156 of SEQ ID NO:3; 179-190 of SEQ ID NO:1 or SEQ ID NO:2; 179-191 of SEQ ID NO:3; 204 of SEQ ID NO:3;

205 of SEQ ID NO:1 or SEQ ID NO:2; 210-218 of SEQ ID NO:3; 240-258 of SEQ ID NO:3; 243-257 of SEQ ID NO:1 or SEQ ID NO:2; 254-268 of SEQ ID NO:1 or SEQ ID NO:2; 262-278 of SEQ ID NO:3; 281-297 of SEQ ID NO:3; and 285-293 of SEQ ID NO:1 or SEQ ID NO:2, or the equivalent position in a Shiga toxin A Subunit polypeptide, conserved Shiga toxin effector polypeptide sub-region, and/or non-native, Shiga toxin effector polypeptide sequence (such as the Shiga toxin effector polypeptides shown in SEQ ID NOs: 4-18).

In certain embodiments, the de-immunized Shiga toxin effector polypeptide of the present invention comprises, consists essentially of, or consists of a full-length or truncated Shiga toxin A Subunit (e.g. SLT-1A (SEQ ID NO:1), StxA (SEQ ID NO:2), SLT-2A (SEQ ID NO:3), or any one of SEQ ID NOs: 7-18 further comprising a disruption of at least one (such as at least two, three, four, five, six, seven, eight or more) endogenous, B-cell and/or CD4+ T-cell epitope region, wherein the B-cell region is selected from the group of natively positioned Shiga toxin A Subunit regions consisting of: 1-15 of SEQ ID NO:1 or SEQ ID NO:2; 3-14 of SEQ ID NO:3; 26-37 of SEQ ID NO:3; 27-37 of SEQ ID NO:1 or SEQ ID NO:2; 39-48 of SEQ ID NO:1 or SEQ ID NO:2; 42-48 of SEQ ID NO:3; 53-66 of SEQ ID NO:1, SEQ ID NO:2, or SEQ ID NO:3; 94-115 of SEQ ID NO:1, SEQ ID NO:2, or SEQ ID NO:3; 141-153 of SEQ ID NO:1 or SEQ ID NO:2; 140-156 of SEQ ID NO:3; 179-190 of SEQ ID NO:1 or SEQ ID NO:2; 179-191 of SEQ ID NO:3; 204 of SEQ ID NO:3; 205 of SEQ ID NO:1 or SEQ ID NO:2, and 210-218 of SEQ ID NO:3; 240-260 of SEQ ID NO:3; 243-257 of SEQ ID NO:1 or SEQ ID NO:2; 254-268 of SEQ ID NO:1 or SEQ ID NO:2; 262-278 of SEQ ID NO:3; 281-297 of SEQ ID NO:3; and 285-293 of SEQ ID NO:1 or SEQ ID NO:2; or the equivalent region in a Shiga toxin A Subunit or derivative thereof (such as the equivalent region in any one of the Shiga toxin 1 A Subunit variants shown in SEQ ID NOs: 4-6 and the Shiga-like toxin 2 A Subunit variants shown in SEQ ID NOs: 7-18); and the CD4+ T-cell epitope region is selected from the group of natively positioned Shiga toxin A Subunit regions consisting of: 4-33 of SEQ ID NO:1 or SEQ ID NO:2; 34-78 of SEQ ID NO:1 or SEQ ID NO:2; 77-103 of SEQ ID NO:1 or SEQ ID NO:2; 128-168 of SEQ ID NO:1 or SEQ ID NO:2; 160-183 of SEQ ID NO:1 or SEQ ID NO:2; 236-258 of SEQ ID NO:1 or SEQ ID NO:2; and 274-293 of SEQ ID NO:1 or SEQ ID NO:2; or the equivalent region in a Shiga toxin A Subunit or derivative thereof (such as the equivalent region in any one of the Shiga toxin 1 A Subunit variants shown in SEQ ID NOs: 4-6 and the Shiga-like toxin 2 A Subunit variants shown in SEQ ID NOs: 7-18). In certain embodiments, the B-cell epitope region is selected from the group of natively positioned Shiga toxin A Subunit regions consisting of: 1-15 of SEQ ID NO:1 or SEQ ID NO:2; 3-14 of SEQ ID NO:3; 26-37 of SEQ ID NO:3; 27-37 of SEQ ID NO:1 or SEQ ID NO:2; 39-48 of SEQ ID NO:1 or SEQ ID NO:2; 42-48 of SEQ ID NO:3; 53-66 of SEQ ID NO:1, SEQ ID NO:2, or SEQ ID NO:3; 94-115 of SEQ ID NO:1, SEQ ID NO:2, or SEQ ID NO:3; 141-153 of SEQ ID NO:1 or SEQ ID NO:2; 140-156 of SEQ ID NO:3; 179-190 of SEQ ID NO:1 or SEQ ID NO:2; 179-191 of SEQ ID NO:3; 204 of SEQ ID NO:3; 205 of SEQ ID NO:1 or SEQ ID NO:2; 210-218 of SEQ ID NO:3 and 243-257 of SEQ ID NO:1 or SEQ ID NO:2; or the equivalent region in a Shiga toxin A Subunit or derivative thereof (such as the equivalent region in any one of the Shiga toxin 1 A Subunit variants shown in SEQ ID NOs: 4-6 and the Shiga-like toxin 2 A Subunit variants shown in SEQ ID NOs: 7-18); and the CD4+ T-cell epitope region is selected from the group of natively positioned Shiga toxin A Subunit regions consisting of: 4-33 of SEQ ID NO:1 or SEQ ID NO:2; 34-78 of SEQ ID NO:1 or SEQ ID NO:2; 77-103 of SEQ ID NO:1 or SEQ ID NO:2; 128-168 of SEQ ID NO:1 or SEQ ID NO:2; 160-183 of SEQ ID NO:1 or SEQ ID NO:2; and 236-258 of SEQ ID NO:1 or SEQ ID NO:2; or the equivalent region in a Shiga toxin A Subunit or derivative thereof (such as the equivalent region in any one of the Shiga toxin 1 A Subunit variants shown in SEQ ID NOs: 4-6 and the Shiga-like toxin 2 A Subunit variants shown in SEQ ID NOs: 7-18).

In certain embodiments, the de-immunized Shiga toxin effector polypeptide of the present invention comprises, consists essentially of, or consists of a full-length or truncated Shiga toxin A Subunit (e.g. SLT-1A (SEQ ID NO:1), StxA (SEQ ID NO:2), Shiga toxin 1 A Subunit variant effector polypeptide (SEQ ID NOs: 4-6), SLT-2A (SEQ ID NO:3), or Shiga-like toxin 2 A Subunit variant effector polypeptide (SEQ ID NOs: 7-18)) comprising a disruption of at least three, endogenous, B-cell and/or CD4+ T-cell epitope regions, wherein the disruption comprises a mutation, relative to a wild-type Shiga toxin A Subunit, in the B-cell epitope region selected from the group of natively positioned Shiga toxin A Subunit regions consisting of: 1-15 of SEQ ID NO:1 or SEQ ID NO:2; 3-14 of SEQ ID NO:3; 26-37 of SEQ ID NO:3; 27-37 of SEQ ID NO:1 or SEQ ID NO:2; 39-48 of SEQ ID NO:1 or SEQ ID NO:2; 42-48 of SEQ ID NO:3; 53-66 of SEQ ID NO:1, SEQ ID NO:2, or SEQ ID NO:3; 94-115 of SEQ ID NO:1, SEQ ID NO:2, or SEQ ID NO:3; 141-153 of SEQ ID NO:1 or SEQ ID NO:2; 140-156 of SEQ ID NO:3; 179-190 of SEQ ID NO:1 or SEQ ID NO:2; 179-191 of SEQ ID NO:3; 204 of SEQ ID NO:3; 205 of SEQ ID NO:1 or SEQ ID NO:2; 210-218 of SEQ ID NO:3 and 243-257 of SEQ ID NO:1 or SEQ ID NO:2; or the equivalent region in a Shiga toxin A Subunit or derivative thereof (such as the equivalent region in any one of the Shiga toxin 1 A Subunit variants shown in SEQ ID NOs: 4-6 and Shiga-like toxin 2 A Subunit variants shown in SEQ ID NOs: 7-18); and/or the CD4+ T-cell epitope region selected from the group of natively positioned Shiga toxin A Subunit regions consisting of: 4-33 of SEQ ID NO:1 or SEQ ID NO:2; 34-78 of SEQ ID NO:1 or SEQ ID NO:2; 77-103 of SEQ ID NO:1 or SEQ ID NO:2; 128-168 of SEQ ID NO:1 or SEQ ID NO:2; 160-183 of SEQ ID NO:1 or SEQ ID NO:2; and 236-258 of SEQ ID NO:1 or SEQ ID NO:2; or the equivalent region in a Shiga toxin A Subunit or derivative thereof (such as the equivalent region in any one of the Shiga toxin 1 A Subunit variants shown in SEQ ID NOs: 4-6 and the Shiga-like toxin 2 A Subunit variants shown in SEQ ID NOs: 7-18). In certain embodiments, each of the at least three of the B-cell and/or CD4+ T-cell epitope regions comprises a disruption comprising an amino acid residue substitution relative to a wild-type Shiga toxin A Subunit sequence.

In certain embodiments, the Shiga toxin effector polypeptide of the present invention comprises, consists of, or consists essentially of a truncated Shiga toxin A Subunit. Truncations of Shiga toxin A Subunits might result in the deletion of an entire epitope region(s) without affecting Shiga toxin effector function(s). The smallest, Shiga toxin A Subunit fragment shown to exhibit significant enzymatic activity was a polypeptide composed of residues 75-247 of StxA (Al-Jaufy A et al., *Infect Immun* 62: 956-60 (1994)). Truncating the carboxy-terminus of SLT-1A, StxA, or SLT-2A to amino acids 1-251 removes two predicted B-cell epitope regions, two predicted CD4 positive (CD4+) T-cell epitopes, and a predicted, discontinuous, B-cell epitope.

Truncating the amino-terminus of SLT-1A, StxA, or SLT-2A to 75-293 removes at least three, predicted, B-cell epitope regions and three predicted CD4+ T-cell epitopes. Truncating both amino- and carboxy-terminals of SLT-1A, StxA, or SLT-2A to 75-251 deletes at least five, predicted, B-cell epitope regions; four, putative, CD4+ T-cell epitopes; and one, predicted, discontinuous, B-cell epitope.

In certain embodiments, a Shiga toxin effector polypeptide of the invention may comprise, consist of, or consist essentially of a full-length or truncated Shiga toxin A Subunit with at least one (such as at least two, three, four, five, six, seven, eight or more) mutation, e.g. deletion, insertion, inversion, or substitution, in a provided epitope region. In certain further embodiments, the polypeptides comprise a disruption which comprises a deletion of at least one amino acid within the epitope region. In certain further embodiments, the polypeptides comprise a disruption which comprises an insertion of at least one amino acid within the epitope region. In certain further embodiments, the polypeptides comprise a disruption which comprises an inversion of amino acids, wherein at least one inverted amino acid is within the epitope region. In certain further embodiments, the polypeptides comprise a disruption which comprises a substitution of at least one (such as at least two, three, four, five, six, seven, eight or more) amino acid within the epitope region. In certain further embodiments, the polypeptides comprise a disruption which comprises a mutation, such as an amino acid substitution to a non-standard amino acid or an amino acid with a chemically modified side chain. Numerous examples of single amino acid substitutions are provided in the Examples below.

In certain embodiments, the Shiga toxin effector polypeptides of the invention may comprise, consist of, or consist essentially of a full-length or truncated Shiga toxin A Subunit with one or more mutations as compared to the native sequence which comprises at least one amino acid substitution selected from the group consisting of: A, G, V, L, I, P, C, M, F, S, D, N, Q, H, and K. In certain further embodiments, the polypeptide may comprise, consist of, or consist essentially of a full-length or truncated Shiga toxin A Subunit with a single mutation as compared to the native sequence wherein the substitution is selected from the group consisting of: D to A, D to G, D to V, D to L, D to I, D to F, D to S, D to Q, E to A, E to G, E to V, E to L, E to I, E to F, E to S, E to Q, E to N, E to D, E to M, E to R, G to A, H to A, H to G, H to V, H to L, H to I, H to F, H to M, K to A, K to G, K to V, K to L, K to I, K to M, K to H, L to A, L to G, N to A, N to G, N to V, N to L, N to I, N to F, P to A, P to G, P to F, R to A, R to G, R to V, R to L, R to I, R to F, R to M, R to Q, R to S, R to K, R to H, S to A, S to G, S to V, S to L, S to I, S to F, S to M, T to A, T to G, T to V, T to L, T to I, T to F, T to M, T to S, Y to A, Y to G, Y to V, Y to L, Y to I, Y to F, and Y to M.

In certain embodiments, the Shiga toxin effector polypeptides of the invention comprise, consist of, or consist essentially of a full-length or truncated Shiga toxin A Subunit with one or more mutations as compared to the native amino acid residue sequence which comprises at least one amino acid substitution of an immunogenic residue and/or within an epitope region, wherein at least one substitution occurs at the natively positioned group of amino acids selected from the group consisting of: 1 of SEQ ID NO:1 or SEQ ID NO:2; 4 of SEQ ID NO:1, SEQ ID NO:2, or SEQ ID NO:3; 8 of SEQ ID NO:1, SEQ ID NO:2, or SEQ ID NO:3; 9 of SEQ ID NO:1, SEQ ID NO:2, or SEQ ID NO:3; 11 of SEQ ID NO:1, SEQ ID NO:2, or SEQ ID NO:3; 33 of SEQ ID NO:1 or SEQ ID NO:2; 43 of SEQ ID NO:1 or SEQ ID NO:2; 44 of SEQ ID NO:1 or SEQ ID NO:2; 45 of SEQ ID NO:1 or SEQ ID NO:2; 46 of SEQ ID NO:1 or SEQ ID NO:2; 47 of SEQ ID NO:1 or SEQ ID NO:2; 48 of SEQ ID NO:1, SEQ ID NO:2, or SEQ ID NO:3; 49 of SEQ ID NO:1 or SEQ ID NO:2; 50 of SEQ ID NO:1 or SEQ ID NO:2; 51 of SEQ ID NO:1 or SEQ ID NO:2; 53 of SEQ ID NO:1 or SEQ ID NO:2; 54 of SEQ ID NO:1 or SEQ ID NO:2; 55 of SEQ ID NO:1 or SEQ ID NO:2; 56 of SEQ ID NO:1 or SEQ ID NO:2; 57 of SEQ ID NO:1 or SEQ ID NO:2; 58 of SEQ ID NO:1, SEQ ID NO:2, or SEQ ID NO:3; 59 of SEQ ID NO:1, SEQ ID NO:2, or SEQ ID NO:3; 60 of SEQ ID NO:1 or SEQ ID NO:2; 61 of SEQ ID NO:1 or SEQ ID NO:2; 62 of SEQ ID NO:1 or SEQ ID NO:2; 84 of SEQ ID NO:1 or SEQ ID NO:2; 88 of SEQ ID NO:1 or SEQ ID NO:2; 94 of SEQ ID NO:1, SEQ ID NO:2, or SEQ ID NO:3; 96 of SEQ ID NO:1, SEQ ID NO:2, or SEQ ID NO:3; 104 of SEQ ID NO:1 or SEQ ID NO:2; 105 of SEQ ID NO:1 or SEQ ID NO:2; 107 of SEQ ID NO:1 or SEQ ID NO:2; 108 of SEQ ID NO:1 or SEQ ID NO:2; 109 of SEQ ID NO:1, SEQ ID NO:2, or SEQ ID NO:3; 110 of SEQ ID NO:1 or SEQ ID NO:2; 111 of SEQ ID NO:1 or SEQ ID NO:2; 112 of SEQ ID NO:1, SEQ ID NO:2, or SEQ ID NO:3; 141 of SEQ ID NO:1 or SEQ ID NO:2; 147 of SEQ ID NO:1, SEQ ID NO:2, or SEQ ID NO:3; 154 of SEQ ID NO:1 or SEQ ID NO:2; 179 of SEQ ID NO:1, SEQ ID NO:2, or SEQ ID NO:3; 180 of SEQ ID NO:1 or SEQ ID NO:2; 181 of SEQ ID NO:1 or SEQ ID NO:2; 183 of SEQ ID NO:1, SEQ ID NO:2, or SEQ ID NO:3; 184 of SEQ ID NO:1, SEQ ID NO:2, or SEQ ID NO:3; 185 of SEQ ID NO:1 or SEQ ID NO:2; 186 of SEQ ID NO:1, SEQ ID NO:2, or SEQ ID NO:3; 187 of SEQ ID NO:1 or SEQ ID NO:2; 188 of SEQ ID NO:1 or SEQ ID NO:2; 189 of SEQ ID NO:1 or SEQ ID NO:2; 198 of SEQ ID NO:1 or SEQ ID NO:2; 204 of SEQ ID NO:3; 205 of SEQ ID NO:1 or SEQ ID NO:2; 241 of SEQ ID NO:3; 242 of SEQ ID NO:1 or SEQ ID NO:2; 247 of SEQ ID NO:1 or SEQ ID NO:2; 247 of SEQ ID NO:3; 248 of SEQ ID NO:1 or SEQ ID NO:2; 250 of SEQ ID NO:3; 251 of SEQ ID NO:1 or SEQ ID NO:2; 264 of SEQ ID NO:1, SEQ ID NO:2, or SEQ ID NO:3; 265 of SEQ ID NO:1 or SEQ ID NO:2; and 286 of SEQ ID NO:1 or SEQ ID NO:2, or the equivalent position in a Shiga toxin A Subunit polypeptide, conserved Shiga toxin effector polypeptide sub-region, and/or non-native, Shiga toxin effector polypeptide sequence (such as the Shiga toxin 1 A Subunit variant effector polypeptides shown in SEQ ID NOs: 4-6 or the Shiga-like toxin 2 A Subunit variant effector polypeptides shown in SEQ ID NOs: 7-18).

In certain further embodiments, the Shiga toxin effector polypeptides of the invention comprise, consist of, or consist essentially of a full-length or truncated Shiga toxin A Subunit with at least one substitution of an immunogenic residue and/or within an epitope region, wherein at least one amino acid substitution is to a non-conservative amino acid (see, e.g., Table C, infra) relative to a natively occurring amino acid positioned at one of the following native positions: 1 of SEQ ID NO:1 or SEQ ID NO:2; 4 of SEQ ID NO:1, SEQ ID NO:2, or SEQ ID NO:3; 8 of SEQ ID NO:1, SEQ ID NO:2, or SEQ ID NO:3; 9 of SEQ ID NO:1, SEQ ID NO:2, or SEQ ID NO:3; 11 of SEQ ID NO:1, SEQ ID NO:2, or SEQ ID NO:3; 33 of SEQ ID NO:1 or SEQ ID NO:2; 43 of SEQ ID NO:1 or SEQ ID NO:2; 44 of SEQ ID NO:1 or SEQ ID NO:2; 45 of SEQ ID NO:1 or SEQ ID NO:2; 46 of SEQ ID NO:1 or SEQ ID NO:2; 47 of SEQ ID NO:1 or SEQ ID NO:2; 48 of SEQ ID NO:1, SEQ ID NO:2, or SEQ ID NO:3; 49 of SEQ ID NO:1 or SEQ ID NO:2; 50 of SEQ ID NO:1 or SEQ ID NO:2; 51 of SEQ ID NO:1 or SEQ ID NO:2; 53 of SEQ ID NO:1 or SEQ ID NO:2; 54 of SEQ ID NO:1 or SEQ ID NO:2; 55 of SEQ ID NO:1 or SEQ ID NO:2; 56 of SEQ ID NO:1 or SEQ ID NO:2; 57 of SEQ ID NO:1 or SEQ ID NO:2; 58 of SEQ ID NO:1, SEQ ID NO:2, or SEQ ID NO:3; 59 of SEQ ID NO:1, SEQ ID NO:2, or SEQ ID NO:3; 60 of SEQ ID NO:1 or SEQ ID NO:2; 61 of SEQ ID NO:1 or SEQ ID NO:2; 62 of SEQ ID NO:1 or SEQ ID NO:2; 84 of SEQ ID NO:1 or SEQ ID NO:2; 88 of SEQ ID NO:1 or SEQ ID NO:2; 94 of SEQ ID NO:1, SEQ ID NO:2, or SEQ ID NO:3; 96 of SEQ ID NO:1, SEQ ID NO:2, or SEQ ID NO:3; 104 of SEQ ID NO:1 or SEQ ID NO:2; 105 of SEQ ID NO:1 or SEQ ID NO:2; 107 of SEQ ID NO:1 or SEQ ID NO:2; 108 of SEQ ID NO:1 or SEQ ID NO:2; 109 of SEQ ID NO:1, SEQ ID NO:2, or SEQ ID NO:3; 110 of SEQ ID NO:1 or SEQ ID NO:2; 111 of SEQ ID NO:1 or SEQ ID NO:2; 112 of SEQ ID NO:1, SEQ ID NO:2, or SEQ ID NO:3; 141 of SEQ ID NO:1 or SEQ ID NO:2; 147 of SEQ ID NO:1, SEQ ID NO:2, or SEQ ID NO:3; 154 of SEQ ID NO:1 or SEQ ID NO:2; 179 of SEQ ID NO:1, SEQ ID NO:2, or SEQ ID NO:3; 180 of SEQ ID NO:1 or SEQ ID NO:2; 181 of SEQ ID NO:1 or SEQ ID NO:2; 183 of SEQ ID NO:1, SEQ ID NO:2, or SEQ ID NO:3; 184 of SEQ ID NO:1, SEQ ID NO:2, or SEQ ID NO:3; 185 of SEQ ID NO:1 or SEQ ID NO:2; 186 of SEQ ID NO:1, SEQ ID NO:2, or SEQ ID NO:3; 187 of SEQ ID NO:1 or SEQ ID NO:2; 188 of SEQ ID NO:1 or SEQ ID NO:2; 189 of SEQ ID NO:1 or SEQ ID NO:2; 198 of SEQ ID NO:1 or SEQ ID NO:2; 204 of SEQ ID NO:3; 205 of SEQ ID NO:1 or SEQ ID NO:2; 241 of SEQ ID NO:3; 242 of SEQ ID NO:1 or SEQ ID NO:2; 247 of SEQ ID NO:1 or SEQ ID NO:2; 247 of SEQ ID NO:3; 248 of SEQ ID NO:1 or SEQ ID NO:2; 250 of SEQ ID NO:3; 251 of SEQ ID NO:1 or SEQ ID NO:2; 264 of SEQ ID NO:1, SEQ ID NO:2, or SEQ ID NO:3; 265 of SEQ ID NO:1 or SEQ ID NO:2; and 286 of SEQ ID NO:1 or SEQ ID NO:2, or the equivalent position in a Shiga toxin A Subunit polypeptide, conserved Shiga toxin effector polypeptide sub-region, and/or non-native, Shiga toxin effector polypeptide sequence (such as the Shiga toxin effector polypeptide of any one of SEQ ID NOs: 4-18).

In certain embodiments, the Shiga toxin effector polypeptides of the invention comprise, consist essentially of, or consist of a full-length or truncated Shiga toxin A Subunit with one or more mutations as compared to the native amino acid residue sequence which comprises at least one amino acid substitution of an immunogenic residue and/or within an epitope region, wherein at least one substitution occurs at the natively positioned amino acid position selected from the group consisting of: 1 of SEQ ID NO:1 or SEQ ID NO:2; 11 of SEQ ID NO:1 or SEQ ID NO:2; 45 of SEQ ID NO:1 or SEQ ID NO:2; 54 of SEQ ID NO:1, SEQ ID NO:2; 55 of SEQ ID NO:1 or SEQ ID NO:2; 57 of SEQ ID NO:1, SEQ ID NO:2; 59 of SEQ ID NO:1, SEQ ID NO:2; 60 of SEQ ID NO:1 or SEQ ID NO:2; 61 of SEQ ID NO:1 or SEQ ID NO:2; 110 of SEQ ID NO:1 or SEQ ID NO:2; 141 of SEQ ID NO:1 or SEQ ID NO:2; 147 of SEQ ID NO:1 or SEQ ID NO:2; 188 of SEQ ID NO:1 or SEQ ID NO:2; 242 of SEQ ID NO:1 or SEQ ID NO:2; 248 of SEQ ID NO:1 or SEQ ID NO:2; and 251 of SEQ ID NO:1 or SEQ ID NO:2.

In certain further embodiments, the Shiga toxin effector polypeptides of the invention comprise or consist essentially of a full-length or truncated Shiga toxin A Subunit with at least one amino acid substitution selected from the group consisting of: K1 to A, G, V, L, I, F, M and H; T4 to A, G, V, L, I, F, M, and S; D6 to A, G, V, L, I, F, S, and Q; S8 to A, G, V, I, L, F, and M; T8 to A, G, V, I, L, F, M, and S; T9 to A, G, V, I, L, F, M, and S; S9 to A, G, V, L, I, F, and M; K 11 to A, G, V, L, I, F, M and H; T12 to A, G, V, I, L, F, M, and S; S33 to A, G, V, L, I, F, and M; S43 to A, G, V, L, I, F, and M; G44 to A and L; S45 to A, G, V, L, I, F, and M; T45 to A, G, V, L, I, F, and M; G46 to A and P; D47 to A, G, V, L, I, F, S, and Q; N48 to A, G, V, L, and M; L49 to A or G; F50; A51 to V; D53 to A, G, V, L, I, F, S, and Q; V54 to A, G, and L; R55 to A, G, V, L, I, F, M, Q, S, K, and H; G56 to A and P; I57 to A, G, M, and F; L57 to A, G, M, and F; D58 to A, G, V, L, I, F, S, and Q; P59 to A, G, and F; E60 to A, G, V, L, I, F, S, Q, N, D, M, and R; E61 to A, G, V, L, I, F, S, Q, N, D, M, and R; G62 to A; D94 to A, G, V, L, I, F, S, and Q; R84 to A, G, V, L, I, F, M, Q, S, K, and H; V88 to A and G; I88 to A, G, and V; D94; S96 to A, G, V, I, L, F, and M; T104 to A, G, V, I, L, F, M, and S; A105 to L; T107 to A, G, V, I, L, F, M, and S; S107 to A, G, V, L, I, F, and M; L108 to A, G, and M; S109 to A, G, V, I, L, F, and M; T109 to A, G, V, I, L, F, M, and S; G110 to A; D111 to A, G, V, L, I, F, S, and Q; S112 to A, G, V, L, I, F, and M; D141 to A, G, V, L, I, F, S, and Q; G147 to A; V154 to A and G; R179 to A, G, V, L, I, F, M, Q, S, K, and H; T180 to A, G, V, L, I, F, M, and S; T181 to A, G, V, L, I, F, M, and S; D183 to A, G, V, L, I, F, S, and Q; D184 to A, G, V, L, I, F, S, and Q; L185 to A, G, and V; S186 to A, G, V, I, L, F, and M; G187 to A; R188 to A, G, V, L, I, F, M, Q, S, K, and H; S189 to A, G, V, I, L, F, and M; D197 to A, G, V, L, I, F, S, and Q; D198 to A, G, V, L, I, F, S, and Q; R204 to A, G, V, L, I, F, M, Q, S, K, and H; R205 to A, G, V, L, I, F, M, Q, S, K and H; C242 to A, G, V, and S; S247 to A, G, V, I, L, F, and M; Y247 to A, G, V, L, I, F, and M; R247 to A, G, V, L, I, F, M, Q, S, K, and H; R248 to A, G, V, L, I, F, M, Q, S, K, and H; R250 to A, G, V, L, I, F, M, Q, S, K, and H; R251 to A, G, V, L, I, F, M, Q, S, K, and H; C262 to A, G, V, and S; D264 to A, G, V, L, I, F, S, and Q; G264 to A; and T286 to A, G, V, L, I, F, M, and S.

In certain further embodiments, the Shiga toxin effector polypeptides of the invention comprise, consist of, or consist essentially of a full-length or truncated Shiga toxin A Subunit with at least one (such as at least two, three, four, five, six, seven, eight, nine, ten, eleven, twelve, thirteen or more) of the following amino acid substitutions: K1A, K1M, T4I, D6R, S8I, TBV, T9I, S9I, K11A, K11H, T12K, S33I, S33C, S43N, G44L, S45V, S45I, T45V, T45I, G46P, D47M, D47G, N48V, N48F, L49A, F50T, A51V, D53A, D53N, D53G, V54L, V54I, R55A, R55V, R55L, G56P, I57F, I57M, D58A, D58V, D58F, P59A, P59F, E60I, E60T, E60R, E61A, E61V, E61L, G62A, R84A, V88A, D94A, S96I, T104N, A105L, T107P, L108M, S109V, T109V, G110A, D111T, S112V, D141A, G147A, V154A, R179A, T180G, T181I, D183A, D183G, D184A, D184A, D184F, L185V, L185D, S186A, S186F, G187A, G187T, R188A, R188L, S189A, D198A, R204A, R205A, C242S, S247I, Y247A, R247A, R248A, R250A, R251A, or D264A, G264A, T286A, and/or T286I. In certain further embodiments, the Shiga toxin effector polypeptides of the invention comprise, consist essentially of, or consist of a full-length or truncated Shiga toxin A Subunit with at least one (such as at least two, three, four, five, six, seven, eight, nine, ten, eleven, twelve, thirteen or more) of the following amino acid substitutions: K1A, S45I, V54I, R55L, I57F, P59F, E60T, E61L, G110A, D141A, G147A, R188A, C242S, R248A, and R251A. These epitope disrupting substitutions may be combined to form a de-immunized, Shiga toxin effector polypeptide with multiple substitutions per epitope region and/or multiple epitope regions disrupted while still retaining Shiga toxin effector function. For example, substitutions at the natively positioned K1A, K1M, T4I, D6R, S8I, TBV, T9I, S9I, K11A, K11H, T12K, S33I, S33C, S43N, G44L, S45V, S45I, T45V, T45I, G46P, D47M, D47G, N48V, N48F, L49A, F50T, A51V, D53A, D53N, D53G, V54L, V54I, R55A, R55V, R55L, G56P, I57F, I57M, D58A, D58V, D58F, P59A, P59F, E60I, E60T, E60R, E61A, E61V, E61L, G62A, R84A, V88A, D94A, S96I, T104N, A105L, T107P, L108M, S109V, T109V, G110A, D111T, S112V, D141A, G147A, V154A, R179A, T180G, T181I, D183A, D183G, D184A, D184A, D184F, L185V, L185D, S186A, S186F, G187A, G187T, R188A, R188L, S189A, D198A, R204A, R205A, C242S, S247I, Y247A, R247A, R248A, R250A, R251A, or D264A, G264A, T286A, and/or T286I may be combined, where possible, with substitutions at the natively positioned residues K1A, K1M, T4I, D6R, S8I, T8V, T9I, S9I, K11A, K11H, T12K, S33I, S33C, S43N, G44L, S45V, S45I, T45V, T45I, G46P, D47M, D47G, N48V, N48F, L49A, F50T, A51V, D53A, D53N, D53G, V54L, V54I, R55A, R55V, R55L, G56P, I57F, I57M, D58A, D58V, D58F, P59A, P59F, E60I, E60T, E60R, E61A, E61V, E61L, G62A, R84A, V88A, D94A, S96I, T104N, A105L, T107P, L108M, S109V, T109V, G110A, D111T, S112V, D141A, G147A, V154A, R179A, T180G, T181I, D183A, D183G, D184A, D184A, D184F, L185V, L185D, S186A, S186F, G187A, G187T, R188A, R188L, S189A, D198A, R204A, R205A, C242S, S247I, Y247A, R247A, R248A, R250A, R251A, or D264A, G264A, T286A, and/or T286I to create de-immunized, Shiga toxin effector polypeptides of the invention. For example, the Shiga toxin effector polypeptides of the invention may comprise, consist essentially of, or consist of a full-length or truncated Shiga toxin A Subunit comprising the following substitutions at native positions in a Shiga toxin A Subunit: K1A, S45I, V54I, R55L, I57F, P59F, E60T, E61L, G110A, G147A, C242S, R248A, and R251A. These substitutions correspond to those present in the Shiga toxin effector polypeptide of the exemplary cell-targeting molecule shown in any one of SEQ ID NOs: 24-27 and 97-100. For example, the Shiga toxin effector polypeptides of the invention may comprise, consist essentially of, or consist of a full-length or truncated Shiga toxin A Subunit comprising the following substitutions at native positions in a Shiga toxin A Subunit: S45I, V54I, R55L, I57F, P59F, E60T, E61L, G110A, R188A, C242S, R248A, and R251A. These substitutions correspond to those present in the Shiga toxin effector polypeptide of the exemplary cell-targeting molecule shown in any one of SEQ ID NOs: 28-29, 31-32, 34, 36, 101-102, 104-105, 106, and 108. For example, the Shiga toxin effector polypeptides of the invention may comprise, consist essentially of, or consist of a full-length or truncated Shiga toxin A Subunit comprising the following substitutions at native positions in a Shiga toxin A Subunit: S45I, V54I, R55L, I57F, P59F, E60T, E61L, G110A, D141A, R188A, C242S, R248A, and R251A. These substitutions correspond to those present in the Shiga toxin effector polypeptide of the exemplary cell-targeting molecule shown in any one of SEQ ID NOs: 30 or 103.

Any of the de-immunized, Shiga toxin effector polypeptide sub-regions and/or epitope disrupting mutations described herein may be used alone or in combination with each individual embodiment of the present invention, including methods of the present invention.

2. Protease-Cleavage Resistant, Shiga Toxin A Subunit Effector Polypeptides

In certain embodiments, the Shiga toxin effector polypeptide of the present invention comprises (1) a Shiga toxin A1 fragment derived region having a carboxy-terminus and (2) a disrupted furin-cleavage motif at the carboxy-terminus of the Shiga toxin A1 fragment region. Improving the stability of connections between the Shiga toxin component and other components of cell-targeting molecules, e.g., cell-targeting binding regions, can improve their toxicity profiles after administration to organisms by reducing non-specific toxicities caused by the breakdown of the connection and loss of cell-targeting, such as, e.g., as a result of proteolysis. In certain embodiments, the protease-cleavage resistant Shiga toxin effector polypeptide of the present invention has a carboxy-terminal truncation as compared to the carboxy-terminus of a wild-type Shiga toxin A Subunit.

Shiga toxin A Subunits of members of the Shiga toxin family comprise a conserved, furin-cleavage site at the carboxy-terminal of their A1 fragment regions important for Shiga toxin function. Furin-cleavage site motifs and furin-cleavage sites can be identified by the skilled worker using standard techniques and/or by using the information herein.

The model of Shiga toxin cytotoxicity is that intracellular proteolytic processing of Shiga toxin A Subunits by furin in intoxicated cells is essential for 1) liberation of the A1 fragment from the rest of the Shiga holotoxin, 2) escape of the A1 fragment from the endoplasmic reticulum by exposing a hydrophobic domain in the carboxy-terminus of the A1 fragment, and 3) enzymatic activation of the A1 fragment (see Johannes L, Romer W, *Nat Rev Microbiol* 8: 105-16 (2010)). The efficient liberation of the Shiga toxin A1 fragment from the A2 fragment and the rest of the components of the Shiga holotoxin in the endoplasmic reticulum of intoxicated cells is essential for efficient intracellular routing to the cytosol, maximal enzymatic activity, efficient ribosome inactivation, and achieving optimal cytotoxicity, i.e. comparable to a wild-type Shiga toxin (see e.g. WO 2015/191764 and references therein).

During Shiga toxin intoxication, the A Subunit is proteolytically cleaved by furin at the carboxy bond of a conserved arginine residue (e.g. the arginine residue at position 251 in StxA and SLT-1A and the arginine residue at position 250 in Stx2A and SLT-2A). Furin cleavage of Shiga toxin A Subunits occurs in endosomal and/or Golgi compartments. Furin is a specialized serine endoprotease which is expressed by a wide variety of cell types, in all human tissues examined, and by most animal cells. Furin cleaves polypeptides comprising accessible motifs often centered on the minimal, dibasic, consensus motif R-x-(R/K/x)-R. The A Subunits of members of the Shiga toxin family comprise a conserved, surface-exposed, extended loop structure (e.g. 242-261 in StxA and SLT-1A, and 241-260 in SLT-2) with a conserved S-R/Y-x-x-R motif which is cleaved by furin. The surface exposed, extended loop structure positioned at amino acid residues 242-261 in StxA is required for furin-induced cleavage of StxA, including features flanking the minimal, furin-cleavage motif R-x-x-R.

Furin-cleavage motifs and furin-cleavage sites in Shiga toxin A Subunits and Shiga toxin effector polypeptides can be identified by the skilled worker using standard methods and/or by using the information herein. Furin cleaves the minimal, consensus motif R-x-x-R (Schalken J et al., *J Clin Invest* 80: 1545-9 (1987); Bresnahan P et al., *J Cell Biol* 111: 2851-9 (1990); Hatsuzawa K et al., *J Biol Chem* 265: 22075-8 (1990); Wise R et al., *Proc Natl Acad Sci USA* 87: 9378-82 (1990); Molloy S et al., *J Biol Chem* 267: 16396-402 (1992)). Consistent with this, many furin inhibitors comprise peptides comprising the motif R-x-x-R. An example of a synthetic inhibitor of furin is a molecule comprising the peptide R-V-K-R (SEQ ID NO:157) (Henrich S et al., *Nat Struct Biol* 10: 520-6 (2003)). In general, a peptide or protein comprising a surface accessible, dibasic amino acid motif with two positively charged, amino acids separated by two amino acid residues may be predicted to be sensitive to furin-cleavage with cleavage occurring at the carboxy bond of the last basic amino acid in the motif.

Consensus motifs in substrates cleaved by furin have been identified with some degree of specificity. A furin-cleavage site motif has been described that comprises a region of twenty, continuous, amino acid residues, which can be labeled P14 through P6' (Tian S et al., *Int J Mol Sci* 12: 1060-5 (2011)) using the nomenclature described in Schechter I, Berger, A, *Biochem Biophys Res Commun* 32: 898-902 (1968). According to this nomenclature, the furin-cleavage site is at the carboxy bond of the amino acid residue designated P1, and the amino acid residues of the furin-cleavage motif are numbered P2, P3, P4, etc., in the direction going toward the amino-terminus from this reference P1 residue. The amino acid residues of the motif going toward the carboxy-terminus from the P1 reference residue are numbered with the prime notation P2', P3', P4', etc. Using this nomenclature, the P6 to P2' region delineates the core substrate of the furin cleavage motif which is bound by the enzymatic domain of furin. The two flanking regions P14 to P7 and P3' to P6' are often rich in polar, amino acid residues to increase the accessibility to the core furin cleavage site located between them.

A general, furin-cleavage site is often described by the consensus motif R-x-x-R which corresponds to P4-P3-P2-P1; where "R" represents an arginine residue (see Table A, supra), a dash "-" represents a peptide bond, and a lowercase "x" represents any amino acid residue. However, other residues and positions may help to further define furin-cleavage motifs. A slightly more refined furin-cleavage site, consensus motif is often reported as the consensus motif R-x-[K/R]-R (where a forward slash "/" means "or" and divides alternative amino acid residues at the same position), which corresponds to P4-P3-P2-P1, because it was observed that furin has a strong preference for cleaving substrates containing this motif.

In addition to the minimal, furin-cleavage site R-x-x-R, a larger, furin-cleavage motif has been described with certain amino acid residue preferences at certain positions. By comparing various known furin substrates, certain physico-chemical properties have been characterized for the amino acid residues in a 20 amino acid residue long, furin-cleavage site motif. The P6 to P2' region of the furin-cleavage motif delineates the core furin-cleavage site which physically interacts with the enzymatic domain of furin. The two flanking regions P14 to P7 and P3' to P6' are often hydrophilic being rich in polar, amino acid residues to increase the surface accessibility of the core furin-cleavage site located between them.

In general, the furin-cleavage motif region from position P5 to P1 tends to comprise amino acid residues with a positive charge and/or high isoelectric points. In particular, the P1 position, which marks the position of furin proteolysis, is generally occupied by an arginine but other positively charged, amino acid residues may occur in this position. Positions P2 and P3 tend to be occupied by flexible, amino acid residues, and in particular P2 tends to be occupied by arginine, lysine, or sometimes by very small and flexible amino acid residues like glycine. The P4 position tends to be occupied by positively charged, amino acid residues in furin substrates. However, if the P4 position is occupied by an aliphatic, amino acid residue, then the lack of a positively charged, functional group can be compensated for by a positively charged residue located at position(s) P5 and/or P6. Positions P1' and P2' are commonly occupied by aliphatic and/or hydrophobic amino acid residues, with the P1' position most commonly being occupied by a serine.

The two, hydrophilic, flanking regions tend to be occupied by amino acid residues which are polar, hydrophilic, and have smaller amino acid functional groups; however, in certain verified furin substrates, the flanking regions do not contain any hydrophilic, amino acid residues (see Tian S, *Biochem Insights* 2: 9-20 (2009)).

The twenty amino acid residue, furin-cleavage motif and furin-cleavage site found in native, Shiga toxin A Subunits at the junction between the Shiga toxin A1 fragment and A2 fragment is well characterized in certain Shiga toxins. For example in StxA (SEQ ID NO:2) and SLT-1A (SEQ ID NO:1) or another Shiga toxin 1 A Subunit effector polypeptide (e.g. SEQ ID NOs: 4-6), this furin-cleavage motif is natively positioned from L238 to F257, and in SLT-2A (SEQ ID NO:3 or Shiga toxin effector polypeptides based on Shiga-like toxin 2 A Subunit variants (e.g. SEQ ID NOs: 7-18), this furin-cleavage motif is natively positioned from V237 to Q256. Based on amino acid homology, experiment, and/or furin-cleavage assays described herein, the skilled worker can identify furin-cleavage motifs in other native, Shiga toxin A Subunits or Shiga toxin effector polypeptides, where the motifs are actual furin-cleavage motifs or are predicted to result in the production of A1 and A2 fragments after furin cleavage of those molecules within a eukaryotic cell.

In certain embodiments, the Shiga toxin effector polypeptide of the present invention comprises (1) a Shiga toxin A1 fragment derived polypeptide having a carboxy-terminus and (2) a disrupted furin-cleavage motif at the carboxy-terminus of the Shiga toxin A1 fragment derived polypeptide. The carboxy-terminus of a Shiga toxin A1 fragment derived polypeptide may be identified by the skilled worker by using techniques known in the art, such as, e.g., by using protein sequence alignment software to identify (i) a furin-cleavage motif conserved with a naturally occurring Shiga toxin, (ii) a surface exposed, extended loop conserved with a naturally occurring Shiga toxin, and/or (iii) a stretch of amino acid residues which are predominantly hydrophobic (i.e. a hydrophobic "patch") that may be recognized by the ERAD system.

A protease-cleavage resistant, Shiga toxin effector polypeptide of the present invention (1) may be completely lacking any furin-cleavage motif at a carboxy-terminus of its Shiga toxin A1 fragment region and/or (2) comprise a disrupted furin-cleavage motif at the carboxy-terminus of its Shiga toxin A1 fragment region and/or region derived from the carboxy-terminus of a Shiga toxin A1 fragment. A disruption of a furin-cleavage motif include various alterations to an amino acid residue in the furin-cleavage motif, such as, e.g., a post-translation modification(s), an alteration of one or more atoms in an amino acid functional group, the addition of one or more atoms to an amino acid functional group, the association to a non-proteinaceous moiety(ies), and/or the linkage to an amino acid residue, peptide, polypeptide such as resulting in a branched proteinaceous structure.

Protease-cleavage resistant, Shiga toxin effector polypeptides may be created from a Shiga toxin effector polypeptide and/or Shiga toxin A Subunit polypeptide, whether naturally occurring or not, using a method described herein, described in WO 2015/191764, and/or known to the skilled worker, wherein the resulting molecule still retains one or more Shiga toxin A Subunit functions.

For purposes of the present invention with regard to a furin-cleavage site or furin-cleavage motif, the term "disruption" or "disrupted" refers to an alteration from the naturally occurring furin-cleavage site and/or furin-cleavage motif, such as, e.g., a mutation, that results in a reduction in furin-cleavage proximal to the carboxy-terminus of a Shiga toxin A1 fragment region, or identifiable region derived thereof, as compared to the furin-cleavage of a wild-type Shiga toxin A Subunit or a polypeptide derived from a wild-type Shiga toxin A Subunit comprising only wild-type polypeptide sequences. An alteration to an amino acid residue in the furin-cleavage motif includes a mutation in the furin-cleavage motif, such as, e.g., a deletion, insertion, inversion, substitution, and/or carboxy-terminal truncation of the furin-cleavage motif, as well as a post-translation modification, such as, e.g., as a result of glycosylation, albumination, and the like which involve conjugating or linking a molecule to the functional group of an amino acid residue. Because the furin-cleavage motif is comprised of about twenty, amino acid residues, in theory, alterations, modifications, mutations, deletions, insertions, and/or truncations involving one or more amino acid residues of any one of these twenty positions might result in a reduction of furin-cleavage sensitivity (Tian S et al., Sci Rep 2: 261 (2012)). The disruption of a furin-cleavage site and/or furin-cleavage motif may or may not increase resistance to cleavage by other proteases, such as, e.g., trypsin and extracellular proteases common in the vascular system of mammals. The effects of a given disruption to cleavage sensitivity of a given protease may be tested by the skilled worker using techniques known in the art.

For purposes of the present invention, a "disrupted furin-cleavage motif" is furin-cleavage motif comprising an alteration to one or more amino acid residues derived from the 20 amino acid residue region representing a conserved, furin-cleavage motif found in native, Shiga toxin A Subunits at the junction between the Shiga toxin A1 fragment and A2 fragment regions and positioned such that furin cleavage of a Shiga toxin A Subunit results in the production of the A1 and A2 fragments; wherein the disrupted furin-cleavage motif exhibits reduced furin cleavage in an experimentally reproducible way as compared to a reference molecule comprising a wild-type, Shiga toxin A1 fragment region fused to a carboxy-terminal polypeptide of a size large enough to monitor furin cleavage using the appropriate assay known to the skilled worker and/or described herein.

Examples of types of mutations which can disrupt a furin-cleavage site and furin-cleavage motif are amino acid residue deletions, insertions, truncations, inversions, and/or substitutions, including substitutions with non-standard amino acids and/or non-natural amino acids. In addition, furin-cleavage sites and furin-cleavage motifs can be disrupted by mutations comprising the modification of an amino acid by the addition of a covalently-linked structure which masks at least one amino acid in the site or motif, such as, e.g., as a result of PEGylation, the coupling of small molecule adjuvants, and/or site-specific albumination.

If a furin-cleavage motif has been disrupted by mutation and/or the presence of non-natural amino acid residues, certain disrupted furin-cleavage motifs may not be easily recognizable as being related to any furin-cleavage motif; however, the carboxy-terminus of the Shiga toxin A1 fragment derived region will be recognizable and will define where the furin-cleavage motif would be located were it not disrupted. For example, a disrupted furin-cleavage motif may comprise less than the twenty, amino acid residues of the furin-cleavage motif due to a carboxy-terminal truncation as compared to a Shiga toxin A Subunit and/or Shiga toxin A1 fragment.

In certain embodiments, the Shiga toxin effector polypeptide of the present invention comprises (1) a Shiga toxin A1 fragment derived polypeptide having a carboxy-terminus and (2) a disrupted furin-cleavage motif at the carboxy-terminus of the Shiga toxin A1 fragment polypeptide region; wherein the Shiga toxin effector polypeptide (and any cell-targeting molecule comprising it) is more furin-cleavage resistant as compared to a reference molecule, such as, e.g., a wild-type Shiga toxin polypeptide comprising the carboxy-terminus of an A1 fragment and/or the conserved, furin-cleavage motif between A1 and A2 fragments. For example, a reduction in furin cleavage of one molecule compared to a reference molecule may be determined using an in vitro, furin-cleavage assay described in the Examples below, conducted using the same conditions, and then performing a quantitation of the band density of any fragments resulting from cleavage to quantitatively measure in change in furin cleavage.

In certain embodiments, the Shiga toxin effector polypeptide is more resistant to furin-cleavage in vitro and/or in vivo as compared to a wild-type, Shiga toxin A Subunit.

In general, the protease-cleavage sensitivity of a cell-targeting molecule of the present invention is tested by comparing it to the same molecule having its furin-cleavage resistant, Shiga toxin effector polypeptide replaced with a wild-type, Shiga toxin effector polypeptide comprising a Shiga toxin A1 fragment. In certain embodiments, the molecules of the present invention comprising a disrupted furin-cleavage motif exhibits a reduction in in vitro furin cleavage of 30%, 40%, 50%, 60%, 70%, 80%, 90%, 95%, 97%, 98% or greater compared to a reference molecule comprising a wild-type, Shiga toxin A1 fragment fused at its carboxy-terminus to a peptide or polypeptide, such as, e.g., the reference molecule SLT-1A-WT::scFv-1 described in Example 2, below.

Several furin-cleavage motif disruptions have been described. For example, mutating the two conserved arginines to alanines in the minimal R-x-x-R motif completely blocked processing by furin and/or furin-like proteases (see e.g Duda A et al., J Virology 78: 13865-70 (2004)). Because the furin-cleavage site motif is comprised of about twenty amino acid residues, in theory, certain mutations involving one or more of any one of these twenty, amino acid residue positions might abolish furin cleavage or reduce furin cleavage efficiency (see e.g. Tian S et al., Sci Rep 2: 261 (2012)).

In certain embodiments, the molecules of the present invention comprise a Shiga toxin effector polypeptide derived from at least one A Subunit of a member of the Shiga toxin family wherein the Shiga toxin effector polypeptide comprises a disruption in one or more amino acids derived from the conserved, highly accessible, protease-cleavage sensitive loop of Shiga toxin A Subunits. For example, in StxA and SLT-1A, this highly accessible, protease-sensitive loop is natively positioned from amino acid residues 242 to 261, and in SLT-2A, this conserved loop is natively positioned from amino acid residues 241 to 260. Based on polypeptide sequence homology, the skilled worker can identify this conserved, highly accessible loop structure in other Shiga toxin A Subunits. Certain mutations to the amino acid residues in this loop can reduce the accessibility of certain amino acid residues within the loop to proteolytic cleavage and this might reduce furin-cleavage sensitivity.

In certain embodiments, a molecule of the present invention comprises a Shiga toxin effector polypeptide comprising a disrupted furin-cleavage motif comprising a mutation in the surface-exposed, protease sensitive loop conserved among Shiga toxin A Subunits. In certain further embodiments, a molecule of the present invention comprises a Shiga toxin effector polypeptide comprising a disrupted furin-cleavage motif comprising a mutation in this protease-sensitive loop of Shiga toxin A Subunits, the mutation which reduce the surface accessibility of certain amino acid residues within the loop such that furin-cleavage sensitivity is reduced.

In certain embodiments, the disrupted furin-cleavage motif of a Shiga toxin effector polypeptide of the present invention comprises a disruption in terms of existence, position, or functional group of one or both of the consensus amino acid residues P1 and P4, such as, e.g., the amino acid residues in positions 1 and 4 of the minimal furin-cleavage motif R/Y-x-x-R. For example, mutating one or both of the two arginine residues in the minimal, furin consensus site R-x-x-R to alanine will disrupt a furin-cleavage motif and prevent furin-cleavage at that site. Similarly, amino acid residue substitutions of one or both of the arginine residues in the minimal furin-cleavage motif R-x-x-R to any non-conservative amino acid residue known to the skilled worker will reduced the furin-cleavage sensitivity of the motif. In particular, amino acid residue substitutions of arginine to any non-basic amino acid residue which lacks a positive charge, such as, e.g., A, G, P, S, T, D, E, Q, N, C, I, L, M, V, F, W, and Y, will result in a disrupted furin-cleavage motif.

In certain embodiments, the disrupted furin-cleavage motif of a Shiga toxin effector polypeptide of the present invention comprises a disruption in the spacing between the consensus amino acid residues P4 and P1 in terms of the number of intervening amino acid residues being other than two, and, thus, changing either P4 and/or P1 into a different position and eliminating the P4 and/or P1 designations. For example, deletions within the furin-cleavage motif of the minimal furin-cleavage site or the core, furin-cleavage motif will reduce the furin-cleavage sensitivity of the furin-cleavage motif.

In certain embodiments, the disrupted furin-cleavage motif comprises one or more amino acid residue substitutions, as compared to a wild-type, Shiga toxin A Subunit. In certain further embodiments, the disrupted furin-cleavage motif comprises one or more amino acid residue substitutions within the minimal furin-cleavage site R/Y-x-x-R, such as, e.g., for StxA and SLT-1A (and other Shiga toxin 1 A Subunit variants) derived Shiga toxin effector polypeptides, the natively positioned amino acid residue R248 substituted with any non-positively charged, amino acid residue and/or R251 substituted with any non-positively charged, amino acid residue; and for SLT-2A (and other Shiga-like toxin 2 A Subunit variants) derived Shiga toxin effector polypeptides, the natively positioned amino acid residue R/Y247 substituted with any non-positively charged, amino acid residue and/or R250 substituted with any non-positively charged, amino acid residue. In certain further embodiments, the disrupted furin-cleavage motif comprises one or more amino acid residue substitutions within the minimal furin-cleavage site R/Y-x-x-R, such as, e.g., for StxA and SLT-1A derived Shiga toxin effector polypeptides (and other Shiga toxin 1 A Subunit variants), the natively positioned amino acid residues R248 and R251 are substituted with an alanine residue; and for SLT-2A derived Shiga toxin effector polypeptides (and other Shiga-like toxin 2 A Subunit variants), the natively positioned amino acid residues R/Y247 and R250 substituted with an alanine residue.

In certain embodiments, the disrupted furin-cleavage motif comprises an un-disrupted, minimal furin-cleavage site R/Y-x-x-R but instead comprises a disrupted flanking region, such as, e.g., amino acid residue substitutions in one or more amino acid residues in the furin-cleavage motif flanking regions natively position at, e.g., 241-247 and/or 252-259. In certain further embodiments, the disrupted furin cleavage motif comprises a substitution of one or more of the amino acid residues located in the P1-P6 region of the furin-cleavage motif; mutating P1' to a bulky amino acid, such as, e.g., R, W, Y, F, and H; and mutating P2' to a polar and hydrophilic amino acid residue; and substituting one or more of the amino acid residues located in the P1'-P6' region of the furin-cleavage motif with one or more bulky and hydrophobic amino acid residues In certain embodiments, the disruption of the furin-cleavage motif comprises a deletion, insertion, inversion, and/or mutation of at least one amino acid residue within the furin-cleavage motif. In certain embodiments, a protease-cleavage resistant, Shiga toxin effector polypeptide of the present invention may comprise a disruption of the amino acid sequence natively positioned at 248-251 of the A Subunit of Shiga-like toxin 1 (SEQ ID NO:1), Shiga toxin (SEQ ID NO:2), or another Shiga toxin 1 A Subunit variant (e.g. SEQ ID NOs: 4-6) or at 247-250 of the A Subunit of Shiga-like toxin 2 (SEQ ID NO:3) or a Shiga-like toxin 2 variant (e.g. SEQ ID NOs: 7-18) or the equivalent position in a conserved Shiga toxin effector polypeptide and/or non-native Shiga toxin effector polypeptide sequence. In certain further embodiments, protease-cleavage resistant, Shiga toxin effector polypeptides comprise a disruption which comprises a deletion of at least one amino acid within the furin-cleavage motif. In certain further embodiments, protease-cleavage resistant, Shiga toxin effector polypeptides comprise a disruption which comprises an insertion of at least one amino acid within the protease-cleavage motif region. In certain further embodiments, the protease-cleavage resistant, Shiga toxin effector polypeptides comprise a disruption which comprises an inversion of amino acids, wherein at least one inverted amino acid is within the protease motif region. In certain further embodiments, the protease-cleavage resistant, Shiga toxin effector polypeptides comprise a disruption which comprises a mutation, such as an amino acid substitution to a non-standard amino acid or an amino acid with a chemically modified side chain. Examples of single amino acid substitutions are provided in the Examples below.

In certain embodiments of the molecules of the present invention, the disrupted furin-cleavage motif comprises the deletion of nine, ten, eleven or more of the carboxy-terminal amino acid residues within the furin-cleavage motif. In these embodiments, the disrupted furin-cleavage motif will not comprise a furin-cleavage site or a minimal furin-cleavage motif. In other words, certain embodiments lack a furin-cleavage site at the carboxy-terminus of the A 1 fragment region.

In certain embodiments, the disrupted furin-cleavage motif comprises both an amino acid residue deletion and an amino acid residue substitution as compared to a wild-type, Shiga toxin A Subunit. In certain further embodiments, the disrupted furin-cleavage motif comprises one or more amino acid residue deletions and substitutions within the minimal furin-cleavage site R/Y-x-x-R, such as, e.g., for StxA and SLT-1A (and other Shiga toxin 1 A Subunit variants) derived Shiga toxin effector polypeptides, the natively positioned amino acid residue R248 substituted with any non-positively charged, amino acid residue and/or R251 substituted with any non-positively charged, amino acid residue; and for SLT-2A (and other Shiga-like toxin A Subunit 2 variants) derived Shiga toxin effector polypeptides, the natively positioned amino acid residue R/Y247 substituted with any non-positively charged, amino acid residue and/or R250 substituted with any non-positively charged, amino acid residue.

In certain embodiments, the disrupted furin-cleavage motif comprises an amino acid residue deletion and an amino acid residue substitution as well as a carboxy-terminal truncation as compared to a wild-type, Shiga toxin A Subunit. In certain further embodiments, the disrupted furin-cleavage motif comprises one or more amino acid residue deletions and substitutions within the minimal furin-cleavage site R/Y-x-x-R, such as, e.g., for StxA and SLT-1A (and other Shiga toxin 1 A Subunit variants) derived Shiga toxin effector polypeptides, the natively positioned amino acid residue R248 substituted with any non-positively charged, amino acid residue and/or R251 substituted with any non-positively charged, amino acid residue; and for SLT-2A (and other Shiga-like toxin A Subunit 2 variants) derived Shiga toxin effector polypeptides, the natively positioned amino acid residue R/Y247 substituted with any non-positively charged, amino acid residue and/or R250 substituted with any non-positively charged, amino acid residue.

In certain further embodiments, the disrupted furin-cleavage motif comprises both an amino acid substitution within the minimal furin-cleavage site R/Y-x-x-R and a carboxy-terminal truncation as compared to a wild-type, Shiga toxin A Subunit, such as, e.g., for StxA and SLT-1A (and other Shiga toxin 1 A Subunit variants) derived Shiga toxin effector polypeptides, truncations ending at the natively amino acid position 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, or greater and comprising the natively positioned amino acid residue R248 and/or R251 substituted with any non-positively charged, amino acid residue where appropriate; and for SLT-2A (and other Shiga-like toxin A Subunit 2 variants) derived Shiga toxin effector polypeptides, truncations ending at the natively amino acid position 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, or greater and comprising the natively positioned amino acid residue R/Y247 and/or R250 substituted with any non-positively charged, amino acid residue where appropriate. In certain further embodiments, the furin-cleavage motif is disrupted by a carboxy-terminal truncation of the Shiga toxin A1 fragment region as compared to the carboxy-terminus of a wild-type Shiga toxin A Subunit; wherein the carboxy-terminal truncation ends at the natively amino acid position 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, or greater; and wherein the disrupted furin-cleavage motif comprises the natively positioned amino acid residue R248 and/or R251 of the A Subunit of Shiga-like toxin 1 (SEQ ID NO:1), Shiga toxin (SEQ ID NO:2) or another Shiga toxin 1 A Subunit variant (see e.g. SEQ ID NOs: 4-6), or the natively positioned amino acid residue R/Y247 and/or R250 of the A Subunit of Shiga-like toxin 2 (SEQ ID NO:3) or a Shiga-like toxin 2 A Subunit effector polypeptide variant (e.g. SEQ ID NOs: 7-18) substituted with an alanine residue. In certain further embodiments, the furin-cleavage motif is disrupted by a carboxy-terminal truncation of the Shiga toxin A1 fragment region as compared to the carboxy-terminus of a wild-type Shiga toxin A Subunit; wherein the carboxy-terminal truncation ends at the natively amino acid position 250, 249, 248, 247, or less. In certain embodiments, the carboxy-terminal truncation ends at the natively amino acid position 247, 248, 249, 250, 251, 252, 253, 254, 255, 256, 257, 258, 259, 260, or 261. In certain embodiments, the carboxy-terminal truncation ends at the natively amino acid position 250. In certain embodiments, the carboxy-terminal truncation ends at the natively amino acid position 251. In certain embodiments, the carboxy-terminal truncation ends at the natively amino acid position 252. In certain embodiments, the carboxy-terminal truncation ends at the natively amino acid position 253. In certain embodiments, the carboxy-terminal truncation ends at the natively amino acid position 254. In certain embodiments, the carboxy-terminal truncation ends at the natively amino acid position 255. In certain embodiments, the carboxy-terminal truncation ends at the natively amino acid position 256. In certain embodiments, the carboxy-terminal truncation ends at the natively amino acid position 257. In certain embodiments, the carboxy-terminal truncation ends at the natively amino acid position 258. In certain embodiments, the carboxy-terminal truncation ends at the natively amino acid position 259. In certain embodiments, the carboxy-terminal truncation ends at the natively amino acid position 260. In certain embodiments, the carboxy-terminal truncation ends at the natively amino acid position 261.

In certain embodiments, the disrupted furin-cleavage motif comprises an insertion of one or more amino acid residues as compared to a wild-type, Shiga toxin A Subunit as long as the inserted amino residue(s) does not create a de novo furin-cleavage site. In certain embodiments, the insertion of one or more amino acid residues disrupts the natural spacing between the arginine residues in the minimal, furin-cleavage site R/Y-x-x-R, such as, e.g., StxA and SLT-1A (and other Shiga toxin 1 A Subunit variants) derived polypeptides comprising an insertion of one or more amino acid residues at 249 or 250 and thus between R248 and R251; or SLT-2A derived polypeptides (and other Shiga-like toxin 2 A Subunit variants) comprising an insertion of one or more amino acid residues at 248 or 249 and thus between R/Y247 and R250.

In certain embodiments, the disrupted furin-cleavage motif comprises both an amino acid residue insertion and a carboxy-terminal truncation as compared to a wild-type, Shiga toxin A Subunit. In certain embodiments, the disrupted furin-cleavage motif comprises both an amino acid residue insertion and an amino acid residue substitution as compared to a wild-type, Shiga toxin A Subunit. In certain embodiments, the disrupted furin-cleavage motif comprises both an amino acid residue insertion and an amino acid residue deletion as compared to a wild-type, Shiga toxin A Subunit.

In certain embodiments, the disrupted furin-cleavage motif comprises an amino acid residue deletion, an amino acid residue insertion, and an amino acid residue substitution as compared to a wild-type, Shiga toxin A Subunit.

In certain embodiments, the disrupted furin-cleavage motif comprises an amino acid residue deletion, insertion, substitution, and carboxy-terminal truncation as compared to a wild-type, Shiga toxin A Subunit.

In certain embodiments, the Shiga toxin effector polypeptide comprising a disrupted furin-cleavage motif is directly fused by a peptide bond to a molecular moiety comprising an amino acid, peptide, and/or polypeptide wherein the fused structure involves a single, continuous polypeptide. In these fusion embodiments, the amino acid sequence following the disrupted furin-cleavage motif should not create a de novo, furin-cleavage site at the fusion junction.

Any of the above protease-cleavage resistant, Shiga toxin effector polypeptide sub-regions and/or disrupted furin-cleavage motifs may be used alone or in combination with each individual embodiment of the present invention, including methods of the present invention.

3. T-Cell Hyper-Immunized, Shiga Toxin A Subunit Effector Polypeptides

In certain embodiments, the Shiga toxin effector polypeptide of the present invention comprises an embedded or inserted epitope-peptide and a Shiga toxin A1 fragment derived region. In certain further embodiments, the epitope-peptide is a heterologous, T-cell epitope-peptide, such as, e.g., an epitope considered heterologous to Shiga toxin A Subunits. In certain further embodiments, the Shiga toxin effector polypeptide of the present invention comprises an embedded or inserted epitope-peptide within the Shiga toxin A1 fragment region. In certain further embodiments, the epitope-peptide is a CD8+ T-cell epitope. In certain further embodiments, the CD8+ T-cell epitope-peptide has a binding affinity to a MHC class I molecule characterized by a dissociation constant ($K_D$) of $10^{-4}$ molar or less and/or the resulting MHC class I-epitope-peptide complex has a binding affinity to a T-cell receptor (TCR) characterized by a dissociation constant ($K_D$) of $10^{-4}$ molar or less.

In certain embodiments, the Shiga toxin effector polypeptide of the present invention comprises an embedded or inserted, heterologous, T-cell epitope, such as, e.g., a human CD8+ T-cell epitope. In certain further embodiments, the heterologous, T-cell epitope is embedded or inserted so as to disrupt an endogenous epitope or epitope region (e.g. a B-cell epitope and/or CD4+ T-cell epitope) identifiable in a naturally occurring Shiga toxin polypeptide or parental Shiga toxin effector polypeptide from which the Shiga toxin effector polypeptide of the present invention is derived. For example, the Shiga toxin effector polypeptide of the present invention may comprise an embedded or inserted, heterologous, CD8+ T-cell epitope which disrupts an endogenous, B-cell and/or CD4+ T-cell epitope region within the Shiga toxin A1 fragment derived region.

For certain embodiments of the present invention, the Shiga toxin effector polypeptide (and any cell-targeting molecule comprising it) is CD8+ T-cell hyper-immunized, such as, e.g., as compared to a wild-type Shiga toxin polypeptide. The CD8+ T-cell hyper-immunized, Shiga toxin effector polypeptides of the present invention each comprise an embedded or inserted T-cell epitope-peptide. Hyper-immunized, Shiga toxin effector polypeptides can be created from Shiga toxin effector polypeptides and/or Shiga toxin A Subunit polypeptides, whether naturally occurring or not, using a method described herein, described in WO 2015/113005, and/or known to the skilled worker, wherein the resulting molecule still retains one or more Shiga toxin A Subunit functions.

For purposes of the claimed invention, a T-cell epitope is a molecular structure which is comprised by an antigenic peptide and can be represented by a linear, amino acid sequence. Commonly, T-cell epitopes are peptides of sizes of eight to eleven amino acid residues (Townsend A, Bodmer H, *Annu Rev Immunol* 7: 601-24 (1989)); however, certain T-cell epitope-peptides have lengths that are smaller than eight or larger than eleven amino acids long (see e.g. Livingstone A, Fathman C, *Annu Rev Immunol* 5: 477-501 (1987); Green K et al., *Eur J Immunol* 34: 2510-9 (2004)). In certain embodiments, the embedded or inserted epitope is at least seven amino acid residues in length. In certain embodiments, the embedded or inserted epitope is bound by a TCR with a binding affinity characterized by a $K_D$ less than 10 mM (e.g. 1-100 µM) as calculated using the formula in Stone J et al., *Immunology* 126: 165-76 (2009). However, it should be noted that the binding affinity within a given range between the MHC-epitope and TCR may not correlate with antigenicity and/or immunogenicity (see e.g. Al-Ramadi B et al., *J Immunol* 155: 662-73 (1995)), such as due to factors like MHC-peptide-TCR complex stability, MHC-peptide density and MHC-independent functions of TCR cofactors such as CD8 (Baker B et al., *Immunity* 13: 475-84 (2000); Hornell T et al., *J Immunol* 170: 4506-14 (2003); Woolridge L et al., *J Immunol* 171: 6650-60 (2003)).

A heterologous, T-cell epitope is an epitope not already present in a wild-type Shiga toxin A Subunit; a naturally occurring Shiga toxin A Subunit; and/or a parental, Shiga toxin effector polypeptide used as a source polypeptide for modification by a method described herein, described in WO 2015/113005, and/or known to the skilled worker.

A heterologous, T-cell epitope-peptide may be incorporated into a source polypeptide via numerous methods known to the skilled worker, including, e.g., the processes of creating one or more amino acid substitutions within the source polypeptide, fusing one or more amino acids to the source polypeptide, inserting one or more amino acids into the source polypeptide, linking a peptide to the source polypeptide, and/or a combination of the aforementioned processes. The result of such a method is the creation of a modified variant of the source polypeptide which comprises one or more embedded or inserted, heterologous, T-cell epitope-peptides.

T-cell epitopes may be chosen or derived from a number of source molecules for use in the present invention. T-cell epitopes may be created or derived from various naturally occurring proteins. T-cell epitopes may be created or derived from various naturally occurring proteins foreign to mammals, such as, e.g., proteins of microorganisms. T-cell epitopes may be created or derived from mutated human proteins and/or human proteins aberrantly expressed by malignant human cells. T-cell epitopes may be synthetically created or derived from synthetic molecules (see e.g., Carbone F et al., *J Exp Med* 167: 1767-9 (1988); Del Val M et al., *J Virol* 65: 3641-6 (1991); Appella E et al., *Biomed Pept Proteins Nucleic Acids* 1: 177-84 (1995); Perez S et al., *Cancer* 116: 2071-80 (2010)).

Although any T-cell epitope-peptide is contemplated as being used as a heterologous, T-cell epitope of the present invention, certain epitopes may be selected based on desirable properties. One objective of the present invention is to create CD8+ T-cell hyper-immunized, Shiga toxin effector polypeptides for administration to vertebrates, meaning that the heterologous, T-cell epitope is highly immunogenic and can elicit robust immune responses in vivo when displayed complexed with a MHC class I molecule on the surface of a cell. In certain embodiments, the Shiga toxin effector polypeptide of the present invention comprises one or more, embedded or inserted, heterologous, T-cell epitopes which are CD8+ T-cell epitopes. A Shiga toxin effector polypeptide of the present invention that comprises a heterologous, CD8+ T-cell epitope is considered a CD8+ T-cell hyper-immunized, Shiga toxin effector polypeptide.

T-cell epitope components of the present invention may be chosen or derived from a number of source molecules already known to be capable of eliciting a vertebrate immune response. T-cell epitopes may be derived from various naturally occurring proteins foreign to vertebrates, such as, e.g., proteins of pathogenic microorganisms and non-self, cancer antigens. In particular, infectious microorganisms may contain numerous proteins with known antigenic and/or immunogenic properties. Further, infectious microorganisms may contain numerous proteins with known antigenic and/or immunogenic sub-regions or epitopes.

For example, the proteins of intracellular pathogens with mammalian hosts are sources for T-cell epitopes. There are numerous intracellular pathogens, such as viruses, bacteria, fungi, and single-cell eukaryotes, with well-studied antigenic proteins or peptides. T-cell epitopes can be selected or identified from human viruses or other intracellular pathogens, such as, e.g., bacteria like *mycobacterium*, fungi like toxoplasmae, and protists like trypanosomes.

For example, there are many immunogenic, viral peptide components of viral proteins from viruses that are infectious to humans. Numerous, human T-cell epitopes have been mapped to peptides within proteins from influenza A viruses, such as peptides in the proteins HA glycoproteins FE17, S139/1, $C_H65$, C05, hemagglutinin 1 (HA1), hemagglutinin 2 (HA2), nonstructural protein 1 and 2 (NS1 and NS 2), matrix protein 1 and 2 (M1 and M2), nucleoprotein (NP), neuraminidase (NA)), and many of these peptides have been shown to elicit human immune responses, such as by using ex vivo assay. Similarly, numerous, human T-cell epitopes have been mapped to peptide components of proteins from human cytomegaloviruses (HCMV), such as peptides in the proteins pp65 (UL83), UL128-131, immediate-early 1 (IE-1; UL123), glycoprotein B, tegument proteins, and many of these peptides have been shown to elicit human immune responses, such as by using ex vivo assays.

Another example is there are many immunogenic, cancer antigens in humans. The CD8+ T-cell epitopes of cancer and/or tumor cell antigens can be identified by the skilled worker using techniques known in the art, such as, e.g., differential genomics, differential proteomics, immunoproteomics, prediction then validation, and genetic approaches like reverse-genetic transfection (see e.g., Admon A et al., *Mol Cell Proteomics* 2: 388-98 (2003); Purcell A, Gorman J, *Mol Cell Proteomics* 3: 193-208 (2004); Comber J, Philip R, *Ther Adv Vaccines* 2: 77-89 (2014)). There are many antigenic and/or immunogenic T-cell epitopes already identified or predicted to occur in human cancer and/or tumor cells. For example, T-cell epitopes have been predicted in human proteins commonly mutated or overexpressed in neoplastic cells, such as, e.g., ALK, CEA, N-acetylglucosaminyl-transferase V (GnT-V), HCA587, HER2/neu, MAGE, Melan-A/MART-1, MUC-1, p53, and TRAG-3 (see e.g., van der Bruggen P et al., *Science* 254: 1643-7 (1991); Kawakami Y et al., *J Exp Med* 180: 347-52 (1994); Fisk B et al., *J Exp Med* 181: 2109-17 (1995); Guilloux Y et al., *J Exp Med* 183: 1173 (1996); Skipper J et al., *J Exp Med* 183: 527 (1996); Brossart P et al., 93: 4309-17 (1999); Kawashima I et al., *Cancer Res* 59: 431-5 (1999); Papadopoulos K et al., *Clin Cancer Res* 5: 2089-93 (1999); Zhu B et al., *Clin Cancer Res* 9: 1850-7 (2003); Li B et al., *Clin Exp Immunol* 140: 310-9 (2005); Ait-Tahar K et al., *Int J Cancer* 118: 688-95 (2006); Akiyama Y et al., *Cancer Immunol Immunother* 61: 2311-9 (2012)). In addition, synthetic variants of T-cell epitopes from human cancer cells have been created (see e.g., Lazoura E, Apostolopoulos V, *Curr Med Chem* 12: 629-39 (2005); Douat-Casassus C et al., *J Med Chem* 50: 1598-609 (2007)).

While any T-cell epitope may be used in the polypeptides and molecules of the present invention, certain T-cell epitopes may be preferred based on their known and/or empirically determined characteristics. For example, in many species, the MHC alleles in its genome encode multiple MHC-I molecular variants. Because MHC class I protein polymorphisms can affect antigen-MHC class I complex recognition by CD8+ T-cells, T-cell epitopes may be chosen for use in the present invention based on knowledge about certain MHC class I polymorphisms and/or the ability of certain antigen-MHC class I complexes to be recognized by T-cells having different genotypes.

There are well-defined peptide-epitopes that are known to be immunogenic, MHC class I restricted, and/or matched with a specific human leukocyte antigen (HLA) variant(s). For applications in humans or involving human target cells, HLA-class I-restricted epitopes can be selected or identified by the skilled worker using standard techniques known in the art. The ability of peptides to bind to human MHC class I molecules can be used to predict the immunogenic potential of putative T-cell epitopes. The ability of peptides to bind to human MHC class I molecules can be scored using software tools. T-cell epitopes may be chosen for use as a heterologous, T-cell epitope component of the present invention based on the peptide selectivity of the HLA variants encoded by the alleles more prevalent in certain human populations. For example, the human population is polymorphic for the alpha chain of MHC class I molecules due to the varied alleles of the HLA genes from individual to individual. In certain T-cell epitopes may be more efficiently presented by a specific HLA molecule, such as, e.g., the commonly occurring HLA variants encoded by the HLA-A allele groups HLA-A2 and HLA-A3.

When choosing T-cell epitopes for use as a heterologous, T-cell epitope component of the present invention, multiple factors may be considered that can influence epitope generation and transport to receptive MHC class I molecules, such as, e.g., the presence and epitope specificity of the following factors in the target cell: proteasome, ERAAP/ERAP1, tapasin, and TAPs.

When choosing T-cell epitopes for use as a heterologous, T-cell epitope component of the present invention, epitope may be selected which best match the MHC class I molecules present in the cell-type or cell populations to be targeted. Different MHC class I molecules exhibit preferential binding to particular peptide sequences, and particular peptide-MHC class I variant complexes are specifically recognized by the t-cell receptors (TCRs) of effector T-cells. The skilled worker can use knowledge about MHC class I molecule specificities and TCR specificities to optimize the selection of heterologous, T-cell epitopes used in the present invention.

In addition, multiple, immunogenic, T-cell epitopes for MHC class I presentation may be embedded in the same Shiga toxin effector polypeptide of the present invention, such as, e.g., for use in the targeted delivery of a plurality of T-cell epitopes simultaneously.

Any of the protease-cleavage resistant, Shiga toxin effector polypeptide sub-regions and/or disrupted furin-cleavage motifs described herein may be used alone or in combination with each individual embodiment of the present invention, including methods of the present invention.

C. Additional Exogenous Materials

In certain embodiments, the cell-targeting molecules of the present invention comprises an additional exogenous material. An "additional exogenous material" as used herein refers to one or more atoms or molecules, often not generally present in both Shiga toxins and native target cells, where the cell-targeting molecule of the present invention can be used to specifically transport such material to the interior of a cell. In one sense, the entire cell-targeting molecule of the invention is an exogenous material which will enter the cell; thus, the "additional" exogenous materials are heterologous materials linked to but other than the core cell-targeting molecule itself. Non-limiting examples of additional exogenous materials are radionuclides, peptides, detection promoting agents, proteins, small molecule chemotherapeutic agents, and polynucleotides.

In certain embodiments of the cell-targeting molecules of the present invention, the additional exogenous material is one or more radionuclides, such as, e.g., $^{211}$At, $^{131}$I, $^{125}$I, $^{90}$Y, $^{111}$In, $^{186}$Re, $^{188}$Re, $^{153}$Sm, $^{212}$Bi, $^{32}$P, $^{60}$C, and/or radioactive isotopes of lutetium.

In certain embodiments, the additional exogenous material comprises a proapoptotic peptide, polypeptide, or protein, such as, e.g., BCL-2, caspases (e.g. fragments of caspase-3 or caspase-6), cytochromes, granzyme B, apoptosis-inducing factor (AIF), BAX, tBid (truncated Bid), and proapoptotic fragments or derivatives thereof (see e.g., Ellerby H et al., *Nat Med* 5: 1032-8 (1999); Mai J et al., *Cancer Res* 61: 7709-12 (2001); Jia L et al., *Cancer Res* 63: 3257-62 (2003); Liu Y et al., *Mol Cancer Ther* 2: 1341-50 (2003); Perea S et al., *Cancer Res* 64: 7127-9 (2004); Xu Y et al., *J Immunol* 173: 61-7 (2004); Dälken B et al., *Cell Death Differ* 13: 576-85 (2006); Wang T et al., *Cancer Res* 67: 11830-9 (2007); Kwon M et al., *Mol Cancer Ther* 7: 1514-22 (2008); Qiu X et al., *Mol Cancer Ther* 7: 1890-9 (2008); Shan L et al., *Cancer Biol Ther* 11: 1717-22 (2008); Wang F et al., *Clin Cancer Res* 16: 2284-94 (2010); Kim J et al., *J Virol* 85: 1507-16 (2011)).

In certain embodiments, the additional exogenous material comprises a protein or polypeptide comprising an enzyme. In certain other embodiments, the additional exogenous material is a nucleic acid, such as, e.g. a ribonucleic acid that functions as a small inhibiting RNA (siRNA) or microRNA (miRNA). In certain embodiments, the additional exogenous material is an antigen, such as antigens derived from pathogens, bacterial proteins, viral proteins, proteins mutated in cancer, proteins aberrantly expressed in cancer, or T-cell complementary determining regions. For example, exogenous materials include antigens, such as those characteristic of antigen-presenting cells infected by bacteria, and T-cell complementary determining regions capable of functioning as exogenous antigens. Exogenous materials comprising polypeptides or proteins may optionally comprise one or more antigens whether known or unknown to the skilled worker.

In certain embodiments of the cell-targeting molecules of the present invention, all heterologous antigens and/or epitopes associated with the Shiga toxin effector polypeptide are arranged in the cell-targeting molecule amino-terminal to the carboxy-terminus of the Shiga toxin A1 fragment region of the Shiga toxin effector polypeptide. In certain further embodiments, all heterologous antigens and/or epitopes associated with the Shiga toxin effector polypeptide are associated, either directly or indirectly, with the Shiga toxin effector polypeptide at a position amino-terminal to the carboxy-terminus of the Shiga toxin A1 fragment region of the Shiga toxin effector polypeptide. In certain further embodiments, all additional exogenous material(s) that is an antigen is arranged amino-terminal to the Shiga toxin effector polypeptide, such as, e.g., fused directly or indirectly to the amino terminus of the Shiga toxin effector polypeptide.

In certain embodiments of the cell-targeting molecules of the present invention, the additional exogenous material is a cytotoxic agent, such as, e.g., a small molecule chemotherapeutic agent, anti-neoplastic agent, cytotoxic antibiotic, alkylating agent, antimetabolite, topoisomerase inhibitor, and/or tubulin inhibitor. Non-limiting examples of cytotoxic agents suitable for use with the present invention include aziridines, cisplatins, tetrazines, procarbazine, hexamethylmelamine, vinca alkaloids, taxanes, camptothecins, etoposide, doxorubicin, mitoxantrone, teniposide, novobiocin, aclarubicin, anthracyclines, actinomycin, amanitin, amatoxins, bleomycin, centanamycin (indolecarboxamide), plicamycin, mitomycin, daunorubicin, epirubicin, idarubicins, dolastatins, maytansines, maytansionoids, duromycin, docetaxel, duocarmycins, adriamycin, calicheamicin, auristatins, pyrrolobenzodiazepines, pyrrolobenzodiazepine dimers (PBDs), carboplatin, 5-fluorouracil (5-FU), capecitabine, mitomycin C, paclitaxel, 1,3-Bis(2-chloroethyl)-1-nitrosourea (BCNU), rifampicin, cisplatin, methotrexate, gemcitabine, aceglatone, acetogenins (e.g. bullatacin and bullatacinone), aclacinomysins, AG1478, AG1571, aldophosphamide glycoside, alkyl sulfonates (e.g., busulfan, improsulfan, and piposulfan), alkylating agents (e.g. thiotepa and cyclosphosphamide), aminolevulinic acid, aminopterin, amsacrine, ancitabine, anthramycin, arabinoside, azacitidine, azaserine, aziridines (e.g., benzodopa, carboquone, meturedopa, and uredopa), azauridine, bestrabucil, bisantrene, bisphosphonates (e.g. clodronate), bleomycins, bortezomib, bryostatin, cactinomycin, callystatin, carabicin, carminomycin, carmofur, carmustine, carzinophilin, CC-1065, chlorambucil, chloranbucil, chlornaphazine, chlorozotocin, chromomycinis, chromoprotein enediyne antibiotic chromophores, CPT-11, cryptophycins (e.g. cryptophycin 1 and cryptophycin 8), cyclophosphamide, cytarabine, dacarbazine, dactinomycin, daunomycin, defofamine, demecolcine, detorubicin, diaziquone, 6-diazo-5-oxo-L-norleucine, dideoxyuridine, difluoromethylornithine (DMFO), doxifluridine, doxorubicins (e.g., morpholinodoxorubicin, cyanomorpholino-doxorubicin, 2-pyrrolinodoxorubicin, and deoxydoxorubicin), dynemicins, edatraxate, edatrexate, eleutherobins, elformithine, elliptinium acetate, enediyne antibiotics (e.g. calicheamicins), eniluracil, enocitabine, epirubicins, epothilone, esorubicins, esperamicins, estramustine, ethylenimines, 2-ethylhydrazide, etoglucid, fludarabine, folic acid analogues (e.g., denopterin, methotrexate, pteropterin, and trimetrexate), folic acid replenishers (e.g. frolinic acid), fotemustine, fulvestrant, gacytosine, gallium nitrate, gefitinib, gemcitabine, hydroxyurea, ibandronate, ifosfamide, imatinib mesylate, erlotinib, fulvestrant, letrozole, PTK787/ZK 222584 (Novartis, Basel, CH), oxaliplatin, leucovorin, rapamycin, lapatinib, lonafarnib, sorafenib, methylamelamines (e.g., altretamine, triethy lenemelamine, triethy lenephosphoramide, triethylenethiophosphoramide and trimethylomelamine), pancratistatins, sarcodictyins, spongistatins, nitrogen mustards (e.g., chlorambucil, chlornaphazine, cyclophosphamide, mechlorethamine, mechlorethamine oxide hydrochloride, melphalan, novembichin, phenesterine, prednimustine, trofosfamide, and uracil mustard), nitrosureas (e.g., carmustine, fotemustine, lomustine, nimustine, and ranimnustine), dynemicins, neocarzinostatin chromophores, anthramycin, detorubicin, epirubicins, marcellomycins, mitomycins (e.g. mitomycin C), mycophenolic acid, nogalamycins, olivomycins, peplomycins, potfiromycins, puromycins, quelamycins, rodorubicins, ubenimex, zinostatins, zorubicins, purine analogs (e.g., fludarabine, 6-mercaptopurine, thiamiprine, and thioguanine), pyrimidine analogs (e.g., ancitabine, azacitidine, 6-azauridine, dideoxyuridine, doxifluridine, enocitabine, and floxuridine), aceglatone, lentinan, lonidainine, maytansinoids (e.g. maytansins and ansamitocins), mitoguazone, mitoxantrone, mopidanmol, nitraerine, pentostatin, phenamet, pirarubicin, podophyllinic acid, 2-ethylhydrazide, rhizoxin, sizofuran, spirogermanium, tenuazonic acid, triaziquone, 2,2',2"trichlorotriethylamine, trichothecenes (e.g., T-2 toxin, verracurin A, roridin A, and anguidine), urethan, vindesine, mannomustine, mitobronitol, mitolactol, pipobroman, arabinoside, cyclophosphamide, toxoids (e.g. paclitaxel and doxetaxel), 6-thioguanine, mercaptopurine, platinum, platinum analogs (e.g. cisplatin and carboplatin), etoposide (VP-16), mitoxantrone, vinorelbine, novantrone, daunomycin, xeloda, topoisomerase inhibitor RFS 2000, retinoids (e.g. retinoic acid), capecitabine, lomustine, losoxantrone, mercaptopurines, nimustine, nitraerine, rapamycin, razoxane, roridin A, spongistatins, streptonigrins, streptozocins, sutent, T-2 toxin, thiamiprine, thiotepa, toxoids (e.g. paclitaxel and doxetaxel), tubercidins, verracurin A, vinblastine, vincristine, and structural analogs of any of the aforementioned (e.g. synthetic analogs), and/or derivatives of any of the aforementioned (see e.g., Lindell T et al., *Science* 170: 447-9 (1970); Remillard S et al., *Science* 189: 1002-5 (1975); Ravry M et al., *Am J Clin Oncol* 8: 148-50 (1985); Ravry M et al., *Cancer Treat Rep* 69: 1457-8 (1985); Sternberg C et al., *Cancer* 64: 2448-58 (1989); Bai R et al., *Biochem Pharmacol* 39: 1941-9 (1990); Boger D, Johnson D, *Proc Natl Acad Sci USA* 92: 3642-9 (1995); Beck J et al., *Leuk Lymphoma* 41: 117-24 (2001); Cassady J et al., *Chem Pharm Bull* (Tokyo) 52: 1-26 (2004); Sapra P et al., *Clin Cancer Res* 11: 5257-64 (2005); Okeley N et al., *Clinc Cancer Res* 16: 888-97 (2010); Oroudjev E et al., *Mol Cancer Ther* 9: 2700-13 (2010); Ellestad G, *Chirality* 23: 660-71 (2011); Kantarjian H et al., *Lancet Oncol* 13: 403-11 (2012); Moldenhauer G et al., *J Natl Cancer Inst* 104: 622-34 (2012); Meulendijks D et al., *Invest New Drugs* 34: 119-28 (2016)).

D. Structure-Function Relationships of Cell-Targeting Molecules of the Invention For certain embodiments of the cell-targeting molecules of the present invention, there specific structure-function relationships that have been observed, such as, e.g., component relative orientation effects on cytotoxic potency; furin-cleavage sensitivity effects on in vivo tolerability at certain dosages; furin-cleavage sensitivity effects on in vitro stability; furin-cleavage sensitivity effects on in vivo half-life; and furin-cleavage sensitivity effects on in vivo, non-specific toxicity in multicellular organisms.

In certain embodiments of the cell-targeting molecules of the present invention, the specific order or orientation of the Shiga toxin effector polypeptide region and binding region is fixed such that the binding region is located within the cell-targeting molecules more proximal to the carboxy-terminus of the Shiga toxin effector polypeptide region than to the amino-terminus of the Shiga toxin effector polypeptide region. In certain embodiments of the cell-targeting molecules of the present invention, the arrangement of the Shiga toxin effector polypeptide region within the cell-targeting molecule is limited to being at and/or proximal to the amino-terminus of a polypeptide component of the cell-targeting molecule (see FIG. 1). For example, certain embodiments of the cell-targeting molecule of the present invention comprise 1) a binding region oriented within the cell-targeting molecule at a position carboxy-terminal to the Shiga toxin effector polypeptide region, 2) a binding region associated with the Shiga toxin effector polypeptide region at a position distal from the amino-terminus of the Shiga toxin effector polypeptide region (e.g. distances of 50, 100, 200, or 250 amino acid residues or greater), 3) a binding region not sterically covering the amino-terminus of the Shiga toxin effector polypeptide region, and/or 4) a binding region not sterically hindering a structure(s) near the amino-terminus of the Shiga toxin effector polypeptide region (see e.g. FIG. 1; WO 2015/138452). In certain further embodiments, the cell-targeting molecules of the present invention are capable of exhibiting more optimal cytotoxic potency, such as, e.g., exhibiting a $CD_{50}$ value which is 3-fold, 4-fold, 5-fold, 6-fold, 7-fold, 8-fold, 9-fold, 10-fold, or higher than a related cell-targeting reference molecule comprising the same Shiga toxin A Subunit effector polypeptide region(s) and binding region(s), wherein the binding region is 1) amino-terminal to the Shiga toxin A Subunit effector polypeptide region, 2) associated with the Shiga toxin effector polypeptide region at a position proximal to the amino-terminus of the Shiga toxin effector polypeptide region (e.g. distances of less than 50, 40, 30, 20, or 10 amino acid residues or less), 3) not sterically covering the amino-terminus of the Shiga toxin effector polypeptide region, and/or 4) not sterically hindering a structure(s) near the amino-terminus of the Shiga toxin effector polypeptide region (see e.g. FIG. 1; WO 2015/138452).

In certain embodiments, the Shiga toxin A Subunit effector polypeptide of the present invention comprises a Shiga toxin A1 fragment derived region comprising a disrupted furin-cleavage motif at the carboxy-terminus of the Shiga toxin A1 fragment derived region (such as a disrupted furin-cleavage site located at the carboxy-terminus of a Shiga toxin A1 fragment region) (see e.g. FIG. 1; WO 2015/191764). In certain further embodiments, the Shiga toxin effector polypeptide is more furin-cleavage resistant as compared to a related reference molecule, such as, e.g., a molecule comprising a wild-type, Shiga toxin A Subunit or Shiga toxin A1 fragment (see e.g. WO 2015/191764). In certain further embodiments, the Shiga toxin effector polypeptide of the present invention exhibits a reduction in furin-cleavage reproducibly observed to be 30%, 40%, 50%, 60%, 70%, 80%, 90%, 95%, 97%, 98%, 99%, or less (including 100% for no cleavage) than the furin-cleavage of a reference molecule observed in the same assay under the same conditions. In certain further embodiments, the Shiga toxin effector polypeptide is more cleavage resistant to a protease other than furin as compared to a related reference molecule, such as, e.g., a molecule comprising a wild-type, Shiga toxin A Subunit or Shiga toxin A1 fragment.

Certain cell-targeting molecules of the present invention exhibit cytotoxic potencies within 100-fold, 20-fold, 10-fold, 5-fold, or less than a reference molecule comprising a wild-type Shiga toxin effector polypeptide region despite the lack of any compensatory structural feature for the disrupted furin-cleavage motif in the Shiga toxin effector polypeptide. For cell-targeting molecules comprising Shiga toxin A Subunit derived regions which do not maintain the furin cleavage event, i.e. molecules comprising Shiga toxin A Subunit derived components which are not cleaved by furin inside target cells, one alternative for preserving maximal cytotoxicity is compensation. Compensation for the lack of furin cleavage of a Shiga toxin A Subunit region in cytotoxic molecule might be accomplished by presenting the Shiga toxin A Subunit region in a "pre-processed" form. For example, a cell-targeting molecule comprising a Shiga toxin A Subunit region may be constructed such that the carboxy-terminus of the Shiga toxin A Subunit derived polypeptide is 1) proximal to a carboxy-terminus of the molecule and 2) matches or resembles a native Shiga toxin A1 fragment after cleavage by furin (see WO 2015/191764). Such compensation is not required in certain cell-targeting molecules of the present invention, rather it is intentionally avoided in order to provide one or more function(s), such as, e.g., improved in vivo tolerability at certain dosages; increased in vitro stability; increased in vivo half-life; and/or reduced in vivo, non-specific toxicity in multicellular organisms. For certain embodiments, these beneficial function(s) are present without any significant reduction in cytotoxic potency of the cell-targeting molecule of the present invention as compared to a reference molecule comprising a wild-type Shiga toxin effector polypeptide.

In certain embodiments, the cell-targeting molecule of the present invention comprises a Shiga toxin A Subunit effector polypeptide comprising a Shiga toxin A1 fragment derived region comprising a disrupted furin-cleavage motif at the carboxy-terminus of the Shiga toxin A1 fragment derived region (such as a disrupted furin-cleavage site located at the carboxy-terminus of a Shiga toxin A1 fragment region) (see e.g. FIG. 1; WO 2015/191764) but do not comprise any compensatory protease cleavage site proximal to the carboxy-terminus of the Shiga toxin A1 fragment derived region and/or oriented between the Shiga toxin effector polypeptide and a relatively large, molecule moiety (e.g. a binding region of a size greater than 4.5 kDa, 6, kDa, 9 kDa, 12 kDa, 15 kDa, 20 kDa, 25 kDa, 28 kDa, 30 kDa, 41 kDa, or 50 kDa). In certain further embodiments, the cell-targeting molecule of the present invention comprises a Shiga toxin effector polypeptide which is more furin-cleavage resistant as compared to a related reference molecule, such as, e.g., a molecule comprising a wild-type, Shiga toxin A Subunit or Shiga toxin A1 fragment (see e.g. WO 2015/191764). In certain further embodiments, the cell-targeting molecule of the present invention exhibits a reduction in furin-cleavage of 30%, 40%, 50%, 60%, 70%, 80%, 90%, 95%, 97%, 98%, 99%, or 100% less than the furin-cleavage of a reference molecule observed in the same assay under the same conditions while the cell-targeting molecule exhibits a cytotoxic potency within 100-fold, 20-fold, 10-fold, 5-fold, or less than a reference molecule comprising a wild-type Shiga toxin effector polypeptide region. In certain further embodiments, the cell-targeting molecule of the present invention exhibits an improvement in in vivo tolerability as compared to a related reference molecule comprising a Shiga toxin effector polypeptide having a wild-type furin cleavage motif and/or wild-type furin cleavage site at the carboxy-terminus of its Shiga toxin A1 fragment region (see e.g. WO 2015/191764). For example, an increase in in vivo tolerability may be determined by comparing measurements of mortality, signs of morbidity, and/or certain clinical signs in groups of laboratory animals administered different molecules at the same dosages (see e.g. Examples, infra; WO 2015/191764; WO 2016/196344).

In certain embodiments, the cell-targeting molecule of the present invention comprises a Shiga toxin A Subunit effector polypeptide comprising a Shiga toxin A1 fragment derived region comprising a disrupted furin-cleavage motif at the carboxy-terminus of the Shiga toxin A1 fragment derived region (such as a disrupted furin-cleavage site located at the carboxy-terminus of a Shiga toxin A1 fragment derived region) (see e.g. FIG. 1; WO 2015/191764). For certain further embodiments, the cell-targeting molecule of the present invention that comprise a cytotoxic component, the cell-targeting molecule exhibits reduced non-specific toxicity as compared to more protease-cleavage sensitive variants, which have greater propensity to break apart and thereby release the cytotoxic component from the binding region, especially when administered to living materials, such as, e.g., a population of cells, a tissue, and/or an organism. Furthermore, certain protease-cleavage resistant, cell-targeting molecules of the present invention may exhibit increased, in vivo, half-lives after administration to living materials (e.g., certain chordates) as compared to more protease-cleavage sensitive variants based on the protease-cleavage resistance conferred to the cell-targeting molecule by the disrupted furin-cleavage motif at the carboxy-terminus of the Shiga toxin A1 fragment derived region.

III. Linkages Connecting Components of the Invention and/or Their Subcomponents

Individual cell-targeting binding regions, Shiga toxin effector polypeptides, and/or components of the cell-targeting molecules present invention may be suitably linked to each other via one or more linkers well known in the art and/or described herein. Individual polypeptide subcomponents of the binding regions, e.g. heavy chain variable regions (VH), light chain variable regions ($V_L$), CDR, and/or ABR regions, may be suitably linked to each other via one or more linkers well known in the art and/or described herein. Proteinaceous components of the invention, e.g., multi-chain binding regions, may be suitably linked to each other or other polypeptide components of the invention via one or more linkers well known in the art. Peptide components of the invention, e.g., KDEL family endoplasmic reticulum retention/retrieval signal motifs, may be suitably linked to another component of the invention via one or more linkers, such as a proteinaceous linker, which are well known in the art.

Suitable linkers are generally those which allow each polypeptide component of the present invention to fold with a three-dimensional structure very similar to the polypeptide components produced individually without any linker or other component. Suitable linkers include single amino acids, peptides, polypeptides, and linkers lacking any of the aforementioned, such as various non-proteinaceous carbon chains, whether branched or cyclic.

Suitable linkers may be proteinaceous and comprise one or more amino acids, peptides, and/or polypeptides. Proteinaceous linkers are suitable for both recombinant fusion proteins and chemically linked conjugates. A proteinaceous linker typically has from about 2 to about 50 amino acid residues, such as, e.g., from about 5 to about 30 or from about 6 to about 25 amino acid residues. The length of the linker selected will depend upon a variety of factors, such as, e.g., the desired property or properties for which the linker is being selected. In certain embodiments, the linker is proteinaceous and is linked near the terminus of a protein component of the present invention, typically within about 20 amino acids of the terminus.

Suitable linkers may be non-proteinaceous, such as, e.g. chemical linkers. Various non-proteinaceous linkers known in the art may be used to link cell-targeting binding regions to the Shiga toxin effector polypeptide components of the cell-targeting molecules of the present invention, such as linkers commonly used to conjugate immunoglobulin polypeptides to heterologous polypeptides. For example, polypeptide regions may be linked using the functional side chains of their amino acid residues and carbohydrate moieties such as, e.g., a carboxy, amine, sulfhydryl, carboxylic acid, carbonyl, hydroxyl, and/or cyclic ring group. For example, disulfide bonds and thioether bonds may be used to link two or more polypeptides. In addition, non-natural amino acid residues may be used with other functional side chains, such as ketone groups. Examples of non-proteinaceous chemical linkers include but are not limited to N-succinimidyl (4-iodoacetyl)-aminobenzoate, S-(N-succinimidyl) thioacetate (SATA), N-succinimidyl-oxycarbonyl-cumethyl-a-(2-pyridyldithio) toluene (SMPT), N-succinimidyl 4-(2-pyridyldithio)-pentanoate (SPP), succinimidyl 4-(N-maleimidomethyl) cyclohexane carboxylate (SMCC or MCC), sulfosuccinimidyl (4-iodoacetyl)-aminobenzoate, 4-succinimidyl-oxycarbonyl-α-(2-pyridyldithio) toluene, sulfosuccinimidyl-6-(α-methyl-α-(pyridyldithiol)-toluamido) hexanoate, N-succinimidyl-3-(-2-pyridyldithio)-propionate (SPDP), succinimidyl 6(3(-(-2-pyridyldithio)-propionamido) hexanoate, sulfosuccinimidyl 6(3(-(-2-pyridyldithio)-propionamido) hexanoate, maleimidocaproyl (MC), maleimidocaproyl-valine-citrulline-p-aminobenzyloxycarbonyl (MC-vc-PAB), 3-maleimidobenzoic acid N-hydroxysuccinimide ester (MBS), alpha-alkyl derivatives, sulfoNHS-ATMBA (sulfosuccinimidyl N-[3-(acetylthio)-3-methylbutyryl-beta-alanine]), sulfodichlorophenol, 2-iminothiolane, 3-(2-pyridyldithio)-propionyl hydrazide, Ellman's reagent, dichlorotriazinic acid, and S-(2-thiopyridyl)-L-cysteine.

Suitable linkers, whether proteinaceous or non-proteinaceous, may include, e.g., protease sensitive, environmental redox potential sensitive, pH sensitive, acid cleavable, photocleavable, and/or heat sensitive linkers.

Proteinaceous linkers may be chosen for incorporation into recombinant fusion cell-targeting molecules of the present invention. For recombinant fusion cell-targeting proteins of the invention, linkers typically comprise about 2 to 50 amino acid residues, preferably about 5 to 30 amino acid residues. Commonly, proteinaceous linkers comprise a majority of amino acid residues with polar, uncharged, and/or charged residues, such as, e.g., threonine, proline, glutamine, glycine, and alanine. Non-limiting examples of proteinaceous linkers include alanine-serine-glycine-glycine-proline-glutamate (ASGGPE (SEQ ID NO:158)), valine-methionine (VM), alanine-methionine (AM), AM($G_2$ to $4S$)$_x$AM where G is glycine, S is serine, and x is an integer from 1 to 10 (SEQ ID NO:159).

Proteinaceous linkers may be selected based upon the properties desired. Proteinaceous linkers may be chosen by the skilled worker with specific features in mind, such as to optimize one or more of the fusion molecule's folding, stability, expression, solubility, pharmacokinetic properties, pharmacodynamic properties, and/or the activity of the fused domains in the context of a fusion construct as compared to the activity of the same domain by itself. For example, proteinaceous linkers may be selected based on flexibility, rigidity, and/or cleavability. The skilled worker may use databases and linker design software tools when choosing linkers. In certain linkers may be chosen to optimize expression. In certain linkers may be chosen to promote intermolecular interactions between identical polypeptides or proteins to form homomultimers or different polypeptides or proteins to form heteromultimers. For example, proteinaceous linkers may be selected which allow for desired non-covalent interactions between polypeptide components of the cell-targeting molecules of the invention, such as, e.g., interactions related to the formation dimers and other higher order multimers.

Flexible proteinaceous linkers are often greater than 12 amino acid residues long and rich in small, non-polar amino acid residues, polar amino acid residues, and/or hydrophilic amino acid residues, such as, e.g., glycines, serines, and threonines. Flexible proteinaceous linkers may be chosen to increase the spatial separation between components and/or to allow for intramolecular interactions between components. For example, various "GS" linkers are known to the skilled worker and are composed of multiple glycines and/or one or more serines, sometimes in repeating units, such as, e.g., $G_xS)_n$ (SEQ ID NO:160), $(S_xG)_n$ (SEQ ID NO:161), $(GGGGS)_n$ (SEQ ID NO:162), and $(G)_n$, in which x is 1 to 6 and n is 1 to 30 (SEQ ID NO:163). Non-limiting examples of flexible proteinaceous linkers include GKSSGSGSESKS (SEQ ID NO:164), EGKSSGSGSESKEF (SEQ ID NO:165), GSTSGSGKSSEGKG (SEQ ID NO:166), GST-SGSGKSSEGSGSTKG (SEQ ID NO:167), GST-SGSGKPGSGEGSTKG (SEQ ID NO:96), SRSSG (SEQ ID NO:168), and SGSSC (SEQ ID NO:169).

Rigid proteinaceous linkers are often stiff alpha-helical structures and rich in proline residues and/or one or more strategically placed prolines. Rigid linkers may be chosen to prevent intramolecular interactions between linked components.

Suitable linkers may be chosen to allow for in vivo separation of components, such as, e.g., due to cleavage and/or environment-specific instability. In vivo cleavable proteinaceous linkers are capable of unlinking by proteolytic processing and/or reducing environments often at a specific site within an organism or inside a certain cell type. In vivo cleavable proteinaceous linkers often comprise protease sensitive motifs and/or disulfide bonds formed by one or more cysteine pairs. In vivo cleavable proteinaceous linkers may be designed to be sensitive to proteases that exist only at certain locations in an organism, compartments within a cell, and/or become active only under certain physiological or pathological conditions (such as, e.g., involving proteases with abnormally high levels, proteases overexpressed at certain disease sites, and proteases specifically expressed by a pathogenic microorganism). For example, there are proteinaceous linkers known in the art which are cleaved by proteases present only intracellularly, proteases present only within specific cell types, and proteases present only under pathological conditions like cancer or inflammation, such as, e.g., R-x-x-R motif and AMGRSGGGCAGNRVGSSLSCG-GLNLQAM (SEQ ID NO:170).

In certain embodiments of the cell-targeting molecules of the present invention, a linker may be used which comprises one or more protease sensitive sites to provide for cleavage by a protease present within a target cell. In certain embodiments of the cell-targeting molecules of the invention, a linker may be used which is not cleavable to reduce unwanted toxicity after administration to a vertebrate organism.

Suitable linkers may include, e.g., protease sensitive, environmental redox potential sensitive, pH sensitive, acid cleavable, photocleavable, and/or heat sensitive linkers, whether proteinaceous or non-proteinaceous (see e.g., Doronina S et al., *Bioconjug Chem* 17: 114-24 (2003); Saito G et al., *Adv Drug Deliv Rev* 55: 199-215 (2003); Jeffrey S et al., *J Med Chem* 48: 1344-58 (2005); Sanderson R et al., *Clin Cancer Res* 11: 843-52 (2005); Erickson H et al., *Cancer Res* 66: 4426-33 (2006); Chen X et al., *Adv Drug Deliv Rev* 65: 1357-69 (2013)). Suitable cleavable linkers may include linkers comprising cleavable groups which are known in the art.

Suitable linkers may include pH sensitive linkers. For example, certain suitable linkers may be chosen for their instability in lower pH environments to provide for dissociation inside a subcellular compartment of a target cell (see e.g., van Der Velden V et al., *Blood* 97: 3197-204 (2001); Ulbrich K, Subr V, *Adv Drug Deliv Rev* 56: 1023-50 (2004)). For example, linkers that comprise one or more trityl groups, derivatized trityl groups, bismaleimideothoxy propane groups, adipic acid dihydrazide groups, and/or acid labile transferrin groups, may provide for release of components of the cell-targeting molecules of the invention, e.g. a polypeptide component, in environments with specific pH ranges. In certain linkers may be chosen which are cleaved in pH ranges corresponding to physiological pH differences between tissues, such as, e.g., the pH of tumor tissue is lower than in healthy tissues.

Photocleavable linkers are linkers that are cleaved upon exposure to electromagnetic radiation of certain wavelength ranges, such as light in the visible range. Photocleavable linkers may be used to release a component of a cell-targeting molecule of the invention, e.g. a polypeptide component, upon exposure to light of certain wavelengths. Non-limiting examples of photocleavable linkers include a nitrobenzyl group as a photocleavable protective group for cysteine, nitrobenzyloxycarbonyl chloride cross-linkers, hydroxypropylmethacrylamide copolymer, glycine copolymer, fluorescein copolymer, and methylrhodamine copolymer. Photocleavable linkers may have particular uses in linking components to form cell-targeting molecules of the invention designed for treating diseases, disorders, and conditions that can be exposed to light using fiber optics.

In certain embodiments of the cell-targeting molecules of the present invention, a cell-targeting binding region is linked to a Shiga toxin effector polypeptide of the present invention using any number of means known to the skilled worker, including both covalent and noncovalent linkages.

In certain embodiments of the cell-targeting molecules of the present invention, the molecule comprises a binding region which is a scFv with a linker connecting a heavy chain variable ($V_H$) domain and a light chain variable ($V_L$) domain. There are numerous linkers known in the art suitable for this purpose, such as, e.g., the 15-residue (Gly$_4$Ser)$_3$ peptide (SEQ ID NO:171). Suitable scFv linkers which may be used in forming non-covalent multivalent structures include GGS, (SEQ ID NO:172), GGGGS (SEQ ID NO:94), GGGGSGGG (SEQ ID NO:173), GGSGGGG (SEQ ID NO:174), GSTSGGGSGGGSGGGSS (SEQ ID NO:175), and GSTSGSGKPGSSEGSTKG (SEQ ID NO:176).

Suitable methods for linkage of the components of the cell-targeting molecules of the present invention may be by any method presently known in the art for accomplishing such, so long as the attachment does not substantially impede the binding capability of the cell-targeting binding region, the cellular internalization of the Shiga toxin effector polypeptide component, and/or when appropriate the desired Shiga toxin effector function(s) as measured by an appropriate assay, including assays described herein.

The components of the cell-targeting molecule, e.g. a Shiga toxin A Subunit effector polypeptide and/or immunoglobulin-type HER2-binding region, may be engineered to provide a suitable attachment moiety for the linkage of additional components, e.g. an additional exogenous material (see e.g. WO2018/106895).

For the purposes of the cell-targeting molecules of the present invention, the specific order or orientation is not fixed for the components: the Shiga toxin effector polypeptide(s), the binding region(s), and any optional linker(s), in relation to each other or the entire cell-targeting molecule unless specifically noted. The components of the cell-targeting molecules of the present invention may be arranged in any order provided that the desired activity(ies) of the binding region and Shiga toxin effector polypeptide are not eliminated.

IV. Examples of Structural Variations of the Shiga Toxin Effector Polypeptides and Cell-Targeting Molecules of the Invention In certain embodiments, a Shiga toxin effector polypeptide of the present invention may comprise, consist of, or consist essentially of a truncated Shiga toxin A Subunit. Truncations of Shiga toxin A Subunits might result in the deletion of an entire epitope(s) and/or epitope region(s), B-cell epitopes, CD4+ T-cell epitopes, and/or furin-cleavage sites without affecting Shiga toxin effector functions, such as, e.g., catalytic activity and cytotoxicity. The smallest Shiga toxin A Subunit fragment shown to exhibit full enzymatic activity was a polypeptide composed of residues 1-239 of Slt1A (LaPointe P et al., *J Biol Chem* 280: 23310-18 (2005)). The smallest Shiga toxin A Subunit fragment shown to exhibit significant enzymatic activity was a polypeptide composed of residues 75-247 of StxA (Al-Jaufy A et al., *Infect Immun* 62: 956-60 (1994)).

Although Shiga toxin effector polypeptides of the present invention may commonly be smaller than the full-length Shiga toxin A Subunit, it is preferred that the Shiga toxin effector polypeptide region of a cell-targeting molecule of the present invention maintain the polypeptide region from amino acid position 77 to 239 (SLT-1A (SEQ ID NO:1), StxA (SEQ ID NO:2), or Shiga toxin 1 A Subunit variants, e.g. SEQ ID NOs: 4-6) or the equivalent in other A Subunits of members of the Shiga toxin family (e.g. 77 to 238 of SEQ ID NOs: 3 and 7-18)). For example, in certain embodiments of the molecules of the present invention, the Shiga toxin effector polypeptides of the present invention derived from SLT-1A may comprise, consist of, or consist essentially of amino acids 75 to 251 of SEQ ID NO:1, 1 to 241 of SEQ ID NO:1, 1 to 251 of SEQ ID NO:1, or amino acids 1 to 261 of SEQ ID NO:1, further comprising relative to a wild-type Shiga toxin A Subunit at least one amino acid residue which is mutated or has been deleted in an endogenous epitope and/or epitope region, and/or wherein there is a disrupted, furin-cleavage motif region at the carboxy-terminus of a Shiga toxin A1 fragment derived region. Similarly, Shiga toxin effector polypeptide regions derived from Shiga toxin 1 A Subunit variants (such as Stx1cA, Stx1dA, and Stx1eA) may comprise, consist essentially of, or consist of amino acids 75 to 251 of SEQ ID NOs: 4-6, 1 to 241 of SEQ ID NOs: 4-6, or 1 to 251 of SEQ ID NOs: 4-6, further comprising relative to a wild-type Shiga toxin A Subunit at least one amino acid residue which is mutated or has been deleted in an endogenous epitope and/or epitope region, and/or wherein there is a disrupted, furin-cleavage motif region at the carboxy-terminus of a Shiga toxin A1 fragment derived region. Additionally, Shiga toxin effector polypeptide regions derived from SLT-2 may comprise, consist of, or consist essentially of amino acids 75 to 251 of SEQ ID NO:3, 1 to 241 of SEQ ID NO:3, 1 to 251 of SEQ ID NO:3, or amino acids 1 to 261 of SEQ ID NO:3, further comprising relative to a wild-type Shiga toxin A Subunit at least one amino acid residue which is mutated or has been deleted in an endogenous epitope and/or epitope region, and/or wherein there is a disrupted, furin-cleavage motif region at the carboxy-terminus of a Shiga toxin A1 fragment derived region. Likewise, Shiga toxin effector polypeptide regions derived from Shiga-like toxin 2 A Subunit variants (such as Stx2cA variant 1, Stx2cA variant 2, Stx2cA variant 3, Stx2cA variant 4, Stx2cA variant 5, Stx2cA variant 6, Stx2dA variant 1, Stx2dA variant 2, Stx2dA variant 3, Stx2eA variant 1, Stx2eA variant 2, and Stx2fA) may comprise, consist essentially of, or consist of amino acids 1 to 241 of SEQ ID NOs: 7-18, further comprising relative to a wild-type Shiga toxin A Subunit at least one amino acid residue which is mutated or has been deleted in an endogenous epitope and/or epitope region, and/or wherein there is a disrupted, furin-cleavage motif region at the carboxy-terminus of a Shiga toxin A1 fragment derived region.

In certain embodiments, the Shiga toxin effector polypeptide comprises, consists essentially of, or consists of: (i) amino acids 75 to 251 of any one of SEQ ID NOs: 1-6; (ii) amino acids 1 to 241 of any one of SEQ ID NOs: 1-18; (iii)

amino acids 1 to 251 of any one of SEQ ID NOs: 1-6; and/or (iv) amino acids 1 to 261 of any one of SEQ ID NOs: 1-3. In certain embodiments, the Shiga toxin effector polypeptide comprises, consists essentially of, or consists of: (i) amino acids 75 to 251 of any one of SEQ ID NOs: 1-6; (ii) amino acids 1 to 241 of any one of SEQ ID NOs: 1-18; (iii) amino acids 1 to 251 of any one of SEQ ID NOs: 1-6; and/or (iv) amino acids 1 to 261 of any one of SEQ ID NOs: 1-3, wherein relative to a wild-type Shiga toxin A Subunit at least one amino acid residue is mutated or has been deleted in an endogenous epitope and/or epitope region, and/or wherein there is a disrupted, furin-cleavage motif region at the carboxy-terminus of a Shiga toxin A1 fragment derived region.

The invention further provides variants of Shiga toxin effector polypeptides and cell-targeting molecules of the present invention, wherein the Shiga toxin effector polypeptide differs from a naturally occurring Shiga toxin A Subunit by only or up to 1, 2, 3, 4, 5, 6, 7, 8, 9, 10, 15, 20, 25, 30, 35, 40 or more amino acid residues (but by no more than that which retains at least 85%, 90%, 95%, 99% or more amino acid sequence identity). Thus, a molecule of the present invention derived from an A Subunit of a member of the Shiga toxin family may comprise additions, deletions, truncations, or other alterations from the original sequence as long as at least 85%, 90%, 91%, 92%, 93%, 94%, 95%, 96%, 97%, 98%, 99% or more amino acid sequence identity is maintained to a naturally occurring Shiga toxin A Subunit and wherein relative to a wild-type Shiga toxin A Subunit at least one amino acid residue is mutated or has been deleted in an endogenous epitope and/or epitope region, and/or wherein there is a disrupted, furin-cleavage motif region at the carboxy-terminus of a Shiga toxin A1 fragment derived region.

Accordingly, in certain embodiments, the Shiga toxin effector polypeptide of a molecule of the present invention comprises, consists of, or consists essentially of amino acid sequences having at least 55%, 60%, 65%, 70%, 75%, 80%, 85%, 90%, 95%, 97%, 98%, 99%, 99.5% or 99.7% overall sequence identity to a naturally occurring Shiga toxin A Subunit (or a fragment thereof), such as SLT-1A (SEQ ID NO:1), StxA (SEQ ID NO:2), Shiga toxin 1 A Subunit variants (e.g. SEQ ID NOs: 4-6), SLT-2A (SEQ ID NO:3), and/or Shiga-like toxin 2 A Subunit variants (e.g. SEQ ID NOs: 7-18), wherein relative to a wild-type Shiga toxin A Subunit at least one amino acid residue is mutated or has been deleted in an endogenous epitope and/or epitope region, and/or wherein there is a disrupted, furin-cleavage motif region at the carboxy-terminus of a Shiga toxin A1 fragment derived region. In certain embodiments, the Shiga toxin effector polypeptide comprises, consists essentially of, or consists of an amino acid sequence that is at least 85% identical (such as at least 90%, 91%, 92%, 93%, 94%, 95%, 96%, 97%, 98%, 99%, 99.5% or 99.7% identical) to a wild-type Shiga toxin A Subunit amino acid sequence selected from: (i) amino acids 75 to 251 of any one of SEQ ID NOs: 1-6; (ii) amino acids 1 to 241 of any one of SEQ ID NOs: 1-18; (iii) amino acids 1 to 251 of any one of SEQ ID NOs: 1-6; and (iv) amino acids 1 to 261 of any one of SEQ ID NOs: 1-3. In certain embodiments, the Shiga toxin effector polypeptide comprises, consists essentially of, or consists of an amino acid sequence that is at least 85% identical (such as at least 90%, 91%, 92%, 93%, 94%, 95%, 96%, 97%, 98%, 99%, 99.5% or 99.7% identical) to a wild-type Shiga toxin A Subunit amino acid sequence selected from: (i) amino acids 75 to 251 of any one of SEQ ID NOs: 1-3; (ii) amino acids 1 to 241 of any one of SEQ ID NOs: 1-3; (iii) amino acids 1 to 251 of any one of SEQ ID NOs: 1-3; or (iv) amino acids 1 to 261 of any one of SEQ ID NOs: 1-3. In certain embodiments, the Shiga toxin effector polypeptide comprises, consists essentially of, or consists of an amino acid sequence that is at least 85% identical (such as at least 90%, 91%, 92%, 93%, 94%, 95%, 96%, 97%, 98%, 99%, 99.5% or 99.7% identical) to a wild-type Shiga toxin A Subunit amino acid sequence selected from: (i) amino acids 75 to 251 of SEQ ID NO:1; (ii) amino acids 1 to 241 of SEQ ID NO:1; (iii) amino acids 1 to 251 of SEQ ID NO:1; or (iv) amino acids 1 to 261 of any one of SEQ ID NO:1. In certain embodiments, the Shiga toxin effector polypeptide comprises, consists essentially of, or consists of an amino acid sequence that is at least 85% identical (such as at least 90%, 91%, 92%, 93%, 94%, 95%, 96%, 97%, 98%, 99%, 99.5% or 99.7% identical) to a wild-type Shiga toxin A Subunit amino acid sequence selected from: (i) amino acids 75 to 251 of SEQ ID NO:2; (ii) amino acids 1 to 241 of SEQ ID NO:2; (iii) amino acids 1 to 251 of SEQ ID NO:2; or (iv) amino acids 1 to 261 of SEQ ID NO:2. In certain embodiments, the Shiga toxin effector polypeptide comprises, consists essentially of, or consists of an amino acid sequence that is at least 85% identical (such as at least 90%, 91%, 92%, 93%, 94%, 95%, 96%, 97%, 98%, 99%, 99.5% or 99.7% identical) to a wild-type Shiga toxin A Subunit amino acid sequence selected from: (i) amino acids 75 to 251 of any one of SEQ ID NO:3; (ii) amino acids 1 to 241 of SEQ ID NO:3; (iii) amino acids 1 to 251 of SEQ ID NO:3; or (iv) amino acids 1 to 261 of SEQ ID NO:3.

Optionally, either a full-length or a truncated version of the Shiga toxin A Subunit may comprise the Shiga toxin effector polypeptide region of a molecule of the present invention, wherein the Shiga toxin derived polypeptide comprises one or more mutations (e.g. substitutions, deletions, insertions, or inversions) as compared to a naturally occurring Shiga toxin. It is preferred in certain embodiments of the invention that the Shiga toxin effector polypeptides have sufficient sequence identity to a naturally occurring (or wild-type) Shiga toxin A Subunit to retain cytotoxicity after entry into a cell, either by well-known methods of host cell transformation, transfection, infection or induction, or by internalization mediated by a cell-targeting binding region linked with the Shiga toxin effector polypeptide. The most critical residues for enzymatic activity and/or cytotoxicity in the Shiga toxin A Subunits have been mapped to the following residue-positions: asparagine-75, tyrosine-77, glutamate-167, arginine-170, and arginine-176 among others (Di R et al., Toxicon 57: 525-39 (2011)). In any one of the embodiments of the invention, the Shiga toxin effector polypeptides may preferably but not necessarily maintain one or more conserved amino acids at positions, such as those found at positions 77, 167, 170, and 176 in StxA, SLT-1A, or the equivalent conserved position in other members of the Shiga toxin family which are typically required for cytotoxic activity. The capacity of a cytotoxic molecule of the invention to cause cell death, e.g. its cytotoxicity, may be measured using any one or more of a number of assays well known in the art.

A. Examples of De-Immunized, Shiga Toxin Effector Polypeptides

In certain embodiments, the de-immunized, Shiga toxin effector polypeptide of the present invention may consist essentially of a truncated Shiga toxin A Subunit having two or more mutations. Truncations of Shiga toxin A Subunits might result in the deletion of an entire epitope(s) and/or epitope region(s), B-cell epitopes, CD4+ T-cell epitopes, and/or furin-cleavage sites without affecting Shiga toxin effector functions, such as, e.g., catalytic activity and cytotoxicity. Truncating the carboxy-terminus of SLT-1A, StxA, or SLT-2A to amino acids 1-251 removes two predicted B-cell epitope regions, two predicted CD4 positive (CD4+) T-cell epitopes, and a predicted discontinuous B-cell epitope. These epitopes are also absent from the Shiga toxin effector polypeptides shown in SEQ ID NOs: 4-18. The Shiga toxin 1 A Subunit effector polypeptides shown in SEQ ID NOs: 4-6 relate to fragments of wild-type Shiga toxin A Subunit variants which have been truncated at position 251, and the Shiga-like toxin 2 A Subunit effector polypeptides shown in SEQ ID NOs: 7-18 relate to fragments of the Shiga-like toxin 2 A Subunit variants which have been truncated at position 250. Truncating the amino-terminus of SLT-1A, StxA, or SLT-2A to 75-293 removes at least three predicted B-cell epitope regions and three predicted CD4+ T-cell epitopes. Truncating both amino- and carboxy-terminals of SLT-1A, StxA, or SLT-2A to 75-251 deletes at least five predicted B-cell epitope regions, four putative CD4+ T-cell epitopes and one predicted discontinuous B-cell epitope.

In certain embodiments, a de-immunized, Shiga toxin effector polypeptide of the present invention may comprise, consist of, or consist essentially of a full-length or truncated Shiga toxin A Subunit with at least one mutation (relative to a wild-type Shiga toxin polypeptide), e.g. deletion, insertion, inversion, or substitution, in a provided, endogenous, B-cell and/or CD4+ T-cell epitope region. In certain embodiments, the Shiga toxin effector polypeptide of the present invention comprises a disruption which comprises a mutation (relative to a wild-type Shiga toxin polypeptide) which includes a deletion of at least one amino acid residue within the endogenous, B-cell and/or CD4+ T-cell epitope region. In certain embodiments, the Shiga toxin effector polypeptide of the present invention comprises a disruption which comprises an insertion of at least one amino acid residue within the endogenous, B-cell and/or CD4+ T-cell epitope region. In certain embodiments, the Shiga toxin effector polypeptide of the present invention comprises a disruption which comprises an inversion of amino acid residues, wherein at least one inverted amino acid residue is within the endogenous, B-cell and/or CD4+ T-cell epitope region. In certain embodiments, the Shiga toxin effector polypeptide of the present invention comprises a disruption which comprises a mutation (relative to a wild-type Shiga toxin polypeptide), such as, e.g., an amino acid substitution, an amino acid substitution to a non-standard amino acid, and/or an amino acid residue with a chemically modified side chain. Non-limiting examples of de-immunized, Shiga toxin effector sub-regions suitable for use in the present invention are described in WO 2015/113005, WO 2015/113007 and WO 2015/191764. Numerous, non-limiting examples of Shiga toxin effector polypeptides of the present invention which comprise amino acid substitutions are provided in the Examples.

In other embodiments, the de-immunized, Shiga toxin effector polypeptide of the present invention comprises a truncated Shiga toxin A Subunit which is shorter than a full-length Shiga toxin A Subunit wherein at least one amino acid residue is disrupted in a natively positioned, B-cell and/or CD4+ T-cell epitope region.

To create a de-immunized, Shiga toxin effector polypeptide, in principle modifying any amino acid residue in a provided epitope region by various means can result in a disruption of an epitope, such as, e.g., a modification which represents a deletion, insertion, inversion, rearrangement, substitution, and chemical modification of a side chain relative to a wild-type Shiga toxin polypeptide. However, modifying certain amino acid residues and using certain amino acid modifications are more likely to successfully reduce antigenicity and/or immunogenicity while maintaining a certain level of a Shiga toxin effector function(s). For example, terminal truncations and internal amino acid substitutions are preferred because these types of modifications maintain the overall spacing of the amino acid residues in a Shiga toxin effector polypeptide and thus are more likely to maintain Shiga toxin effector polypeptide structure and function.

Among certain embodiments of the present invention, the de-immunized, Shiga toxin effector polypeptide comprising, consisting of, or consisting essentially of amino acids 75 to 251 of SLT-1A (SEQ ID NO:1), StxA (SEQ ID NO:2), and/or SLT-2A (SEQ ID NO:3) wherein at least one amino acid residue is disrupted in a natively positioned, epitope region. Among certain other embodiments are de-immunized, Shiga toxin effector polypeptides which comprise or consist essentially of amino acids 1 to 241 of SLT-1A (SEQ ID NO:1), StxA (SEQ ID NO:2), and/or SLT-2A (SEQ ID NO:3) wherein at least one amino acid residue is disrupted in a natively positioned, epitope region. Further embodiments are de-immunized, Shiga toxin effector polypeptides which comprise, consist of, or consist essentially of amino acids 1 to 251 of SLT-1A (SEQ ID NO:1), StxA (SEQ ID NO:2), and/or SLT-2A (SEQ ID NO:3) wherein at least one amino acid residue is disrupted in a natively positioned, epitope region provided. Further embodiments are Shiga toxin effector polypeptides comprising amino acids 1 to 261 of SLT-1A (SEQ ID NO:1), StxA (SEQ ID NO:2), and/or SLT-2A (SEQ ID NO:3) wherein at least one amino acid residue is disrupted in a natively positioned, epitope region. Among certain embodiments of the present invention, the de-immunized, Shiga toxin effector polypeptide comprises, consists essentially of, or consists of amino acids 75 to 251 of any one of SEQ ID NOs: 1-6, wherein at least one amino acid residue is disrupted in a natively positioned, epitope region. Among certain other embodiments are de-immunized, Shiga toxin effector polypeptides which comprise, consist essentially of, or consist of amino acids 1 to 241 of SEQ ID NOs: 1-18, wherein at least one amino acid residue is disrupted in a natively positioned, epitope region. Further embodiments are de-immunized, Shiga toxin effector polypeptides which comprise, consist essentially of, or consist of amino acids 1 to 251 of SEQ ID NOs: 1-6, wherein at least one amino acid residue is disrupted in a natively positioned, epitope region provided. Further embodiments are Shiga toxin effector polypeptides comprising amino acids 1 to 261 of SEQ ID NOs: 1-3, wherein at least one amino acid residue is disrupted in a natively positioned, epitope region. In certain embodiments, the de-immunized, Shiga toxin effector polypeptide comprises, consists essentially of, or consists of amino acids 75 to 251 of any one of SEQ ID NOs: 1-6, wherein at least one amino acid residue is disrupted in a natively positioned, epitope region. Among certain further embodiments are de-immunized, Shiga toxin effector polypeptides which comprise, consist essentially of, or consist of amino acids 1 to 241 of SEQ ID NOs: 1-6, wherein at least one amino acid residue is disrupted in a natively positioned, epitope region. Further embodiments are de-immunized, Shiga toxin effector polypeptides which comprise, consist essentially of, or consist of amino acids 1 to 251 of SEQ ID NOs: 1-6, wherein at least one amino acid residue is disrupted in a natively positioned, epitope region provided. Further embodiments are Shiga toxin effector polypeptides comprising amino acids 1 to 261 of SEQ ID NOs: 1-3, wherein at least one amino acid residue is disrupted in a natively positioned, epitope region.

There are numerous, diverse, internal amino acid substitutions that can be used to create de-immunized, Shiga toxin effector polypeptides of the invention. Of the possible substitute amino acids to use within an epitope region, the following substitute amino acid residues are predicted to be the most likely to reduce the antigenicity and/or immunogenicity of an epitope—G, D, E, S, T, R, K, and H. Except for glycine, these amino acid residues may all be classified as polar and/or charged residues. Of the possible amino acids to substitute with, the following amino acids A, G, V, L, I, P, C, M, F, S, D, N, Q, H, and K are predicted to be the most likely to reduce antigenicity and/or immunogenicity while providing the retention of a significant level of a Shiga toxin effector function(s), depending on the amino acid substituted for. Generally, the substitution should change a polar and/or charged amino acid residue to a non-polar and uncharged residue (see e.g. WO 2015/113007). In addition, it may be beneficial to epitope disruption to reduce the overall size and/or length of the amino acid residue's R-group functional side chain (see e.g. WO 2015/113007). However despite these generalities of substitutions most likely to confer epitope disruption, because the aim is to preserve significant Shiga toxin effector function(s), the substitute amino acid might be more likely to preserve Shiga toxin effector function(s) if it resembles the amino acid substituted for, such as, e.g., a nonpolar and/or uncharged residue of similar size substituted for a polar and/or charged residue.

In the Examples below and in WO 2015/113007, many mutations have been empirically tested for effect(s) on the Shiga toxin effector function of various Shiga toxin effector polypeptides and cell-targeting molecules. Table B summarizes the results described in WO 2015/113007 and WO 2016/196344 where an amino acid substitution, alone or in combination with one or more other substitutions, did not prevent the exhibition of a potent level of a Shiga toxin effector function(s). Table B uses the epitope region numbering scheme described in WO 2016/196344.

TABLE B

Amino Acid Substitutions in Shiga Toxin Effector Polypeptides

| Epitope Region Disrupted | Substitution | natively positioned amino acid positions B-Cell Epitope Region | T-Cell Epitope |
|---|---|---|---|
| 1 | K1A | 1-15 | |
| 1 | K1M | 1-15 | |
| 1 | T4I | 1-15 | 4-33 |
| 1 | D6R | 1-15 | 4-33 |
| 1 | S8I | 1-15 | 4-33 |
| 1 | T9V | 1-15 | 4-33 |
| 1 | T9I | 1-15 | 4-33 |
| 1 | K11A | 1-15 | 4-33 |
| 1 | K11H | 1-15 | 4-33 |
| 1 | T12K | 1-15 | 4-33 |
| 2 | S33I | 27-37 | 4-33 |
| 2 | S33C | 27-37 | 4-33 |
| 3 | S43N | 39-48 | 34-78 |
| 3 | G44L | 39-48 | 34-78 |
| 3 | T45V | 39-48 | 34-78 |
| 3 | T45I | 39-48 | 34-78 |
| 3 | S45V | 39-48 | 34-78 |
| 3 | S45I | 39-48 | 34-78 |
| 3 | G46P | 39-48 | 34-78 |
| 3 | D47G | 39-48 | 34-78 |
| 3 | D47M | 39-48 | 34-78 |
| 3 | N48V | 39-48 | 34-78 |
| 3 | N48F | 39-48 | 34-78 |

TABLE B-continued

Amino Acid Substitutions in Shiga Toxin Effector Polypeptides

| Epitope Region Disrupted | Substitution | natively positioned amino acid positions B-Cell Epitope Region | T-Cell Epitope |
|---|---|---|---|
| — | L49A | immunogenic residue | 34-78 |
| — | F50T | | 34-78 |
| — | A51V | | 34-78 |
| 4 | D53A | 53-66 | 34-78 |
| 4 | D53G | 53-66 | 34-78 |
| 4 | D53N | 53-66 | 34-78 |
| 4 | V54L | 53-66 | 34-78 |
| 4 | V54I | 53-66 | 34-78 |
| 4 | R55A | 53-66 | 34-78 |
| 4 | R55V | 53-66 | 34-78 |
| 4 | R55L | 53-66 | 34-78 |
| 4 | G56P | 53-66 | 34-78 |
| 4 | I57M | 53-66 | 34-78 |
| 4 | I57F | 53-66 | 34-78 |
| 4 | D58A | 53-66 | 34-78 |
| 4 | D58V | 53-66 | 34-78 |
| 4 | D58F | 53-66 | 34-78 |
| 4 | P59A | 53-66 | 34-78 |
| 4 | P59F | 53-66 | 34-78 |
| 4 | E60I | 53-66 | 34-78 |
| 4 | E60T | 53-66 | 34-78 |
| 4 | E60R | 53-66 | 34-78 |
| 4 | E61A | 53-66 | 34-78 |
| 4 | E61V | 53-66 | 34-78 |
| 4 | E61L | 53-66 | 34-78 |
| 4 | G62A | 53-66 | 34-78 |
| — | R84A | | 77-103 |
| — | V88A | | 77-103 |
| 5 | D94A | 94-115 | 77-103 |
| 5 | S96I | 94-115 | 77-103 |
| 5 | T104N | 94-115 | |
| 5 | A105L | 94-115 | |
| 5 | T107P | 94-115 | |
| 5 | L108M | 94-115 | |
| 5 | S109V | 94-115 | |
| 5 | G110A | 94-115 | |
| 5 | D111T | 94-115 | |
| 5 | S112V | 94-115 | |
| 6 | D141A | 141-153 | 128-168 |
| 6 | G147A | 141-153 | 128-168 |
| — | V154A | | 128-168 |
| 7 | R179A | 179-190 | 160-183 |
| 7 | T180G | 179-190 | 160-183 |
| 7 | T181I | 179-190 | 160-183 |
| 7 | D183A | 179-190 | 160-183 |
| 7 | D183G | 179-190 | 160-183 |
| 7 | D184A | 179-190 | |
| 7 | D184F | 179-190 | |
| 7 | L185V | 179-190 | |
| 7 | S186A | 179-190 | |
| 7 | S186F | 179-190 | |
| 7 | G187A | 179-190 | |
| 7 | G187T | 179-190 | |
| 7 | R188A | 179-190 | |
| 7 | R188L | 179-190 | |
| 7 | S189A | 179-190 | |
| — | D198A | immunogenic residue | |
| — | R205A | immunogenic residue | |
| — | C242S | | 236-258 |
| 8 | R248A | 243-257 | 236-258 |
| 8 | R251A | 243-257 | 236-258 |

Based on the empirical evidence in WO 2015/113007 and WO 2016/196344, certain amino acid positions in the A Subunits of Shiga toxins are predicted to tolerate epitope disruptions while still retaining significant Shiga toxin effector functions. For example, the following natively occurring positions tolerate amino acid substitutions, either alone or in combination, while retaining a Shiga toxin effector function(s) such as cytotoxicity-1 of SEQ ID NO:1 or SEQ ID NO:2; 4 of SEQ ID NO:1, SEQ ID NO:2, or SEQ ID NO:3; 8 of SEQ ID NO:1, SEQ ID NO:2, or SEQ ID NO:3;

9 of SEQ ID NO:1, SEQ ID NO:2, or SEQ ID NO:3; 11 of SEQ ID NO:1, SEQ ID NO:2, or SEQ ID NO:3; 33 of SEQ ID NO:1 or SEQ ID NO:2; 43 of SEQ ID NO:1 or SEQ ID NO:2; 44 of SEQ ID NO:1 or SEQ ID NO:2; 45 of SEQ ID NO:1 or SEQ ID NO:2; 46 of SEQ ID NO:1 or SEQ ID NO:2; 47 of SEQ ID NO:1 or SEQ ID NO:2; 48 of SEQ ID NO:1, SEQ ID NO:2, or SEQ ID NO:3; 49 of SEQ ID NO:1 or SEQ ID NO:2; 50 of SEQ ID NO:1 or SEQ ID NO:2; 51 of SEQ ID NO:1 or SEQ ID NO:2; 53 of SEQ ID NO:1 or SEQ ID NO:2; 54 of SEQ ID NO:1 or SEQ ID NO:2; 55 of SEQ ID NO:1 or SEQ ID NO:2; 56 of SEQ ID NO:1 or SEQ ID NO:2; 57 of SEQ ID NO:1 or SEQ ID NO:2; 58 of SEQ ID NO:1, SEQ ID NO:2, or SEQ ID NO:3; 59 of SEQ ID NO:1, SEQ ID NO:2, or SEQ ID NO:3; 60 of SEQ ID NO:1 or SEQ ID NO:2; 61 of SEQ ID NO:1 or SEQ ID NO:2; 62 of SEQ ID NO:1 or SEQ ID NO:2; 84 of SEQ ID NO:1 or SEQ ID NO:2; 88 of SEQ ID NO:1 or SEQ ID NO:2; 94 of SEQ ID NO:1, SEQ ID NO:2, or SEQ ID NO:3; 96 of SEQ ID NO:1, SEQ ID NO:2, or SEQ ID NO:3; 104 of SEQ ID NO:1 or SEQ ID NO:2; 105 of SEQ ID NO:1 or SEQ ID NO:2; 107 of SEQ ID NO:1 or SEQ ID NO:2; 108 of SEQ ID NO:1 or SEQ ID NO:2; 109 of SEQ ID NO:1, SEQ ID NO:2, or SEQ ID NO:3; 110 of SEQ ID NO:1 or SEQ ID NO:2; 111 of SEQ ID NO:1 or SEQ ID NO:2; 112 of SEQ ID NO:1, SEQ ID NO:2, or SEQ ID NO:3; 141 of SEQ ID NO:1 or SEQ ID NO:2; 147 of SEQ ID NO:1, SEQ ID NO:2, or SEQ ID NO:3; 154 of SEQ ID NO:1 or SEQ ID NO:2; 179 of SEQ ID NO:1, SEQ ID NO:2, or SEQ ID NO:3; 180 of SEQ ID NO:1 or SEQ ID NO:2; 181 of SEQ ID NO:1 or SEQ ID NO:2; 183 of SEQ ID NO:1, SEQ ID NO:2, or SEQ ID NO:3; 184 of SEQ ID NO:1, SEQ ID NO:2, or SEQ ID NO:3; 185 of SEQ ID NO:1 or SEQ ID NO:2; 186 of SEQ ID NO:1, SEQ ID NO:2, or SEQ ID NO:3; 187 of SEQ ID NO:1 or SEQ ID NO:2; 188 of SEQ ID NO:1 or SEQ ID NO:2; 189 of SEQ ID NO:1 or SEQ ID NO:2; 198 of SEQ ID NO:1 or SEQ ID NO:2; 204 of SEQ ID NO:3; 205 of SEQ ID NO:1 or SEQ ID NO:2; 241 of SEQ ID NO:3; 242 of SEQ ID NO:1 or SEQ ID NO:2; 247 of SEQ ID NO:1 or SEQ ID NO:2; 247 of SEQ ID NO:3; 248 of SEQ ID NO:1 or SEQ ID NO:2; 250 of SEQ ID NO:3; 251 of SEQ ID NO:1 or SEQ ID NO:2; 264 of SEQ ID NO:1, SEQ ID NO:2, or SEQ ID NO:3; 265 of SEQ ID NO:1 or SEQ ID NO:2; and 286 of SEQ ID NO:1 or SEQ ID NO:2.

The empirical data in WO 2015/113007 and WO 2016/196344 point towards other epitope disrupting substitutions and combinations of epitope disrupting substitutions that can reduce antigenicity and/or immunogenicity of a Shiga toxin effector polypeptide while retaining the ability of the Shiga toxin effector polypeptide to exhibit a significant Shiga toxin effector function such as, e.g., new combinations of the aforementioned truncations and positions tolerating substitutions as well as new substitutions at identical positions or conserved positions in related Shiga toxin A Subunits.

It is predictable that other amino acid substitutions to amino acid residues of a conservative functional group of a substitution tested herein may reduce antigenicity and/or immunogenicity while preserving a significant Shiga toxin effector function. For example, other substitutions known to the skilled worker to be similar to any of K1A, K1M, T4I, D6R, S8I, T8V, T9I, S9I, K11A, K11H, T12K, S33I, S33C, S43N, G44L, S45V, S45I, T45V, T45I, G46P, D47M, D47G, N48V, N48F, L49A, F50T, A51V, D53A, D53N, D53G, V54L, V54I, R55A, R55V, R55L, G56P, I57F, I57M, D58A, D58V, D58F, P59A, P59F, E60I, E60T, E60R, E61A, E61V, E61L, G62A, R84A, V88A, D94A, S96I, T104N, A105L, T107P, L108M, S109V, T109V, G110A, D111T, S112V, D141A, G147A, V154A, R179A, T180G, T181I, D183A, D183G, D184A, D184A, D184F, L185V, L185D, S186A, S186F, G187A, G187T, R188A, R188L, S189A, D198A, R204A, R205A, C242S, R247A, S247I, Y247A, R248A, R250A, R251A, or D264A, G264A, T286A, and/or T286I may disrupt an endogenous epitope while maintaining at least one Shiga toxin effector function. In particular, amino acid substitutions to conservative amino acid residues similar to K1A, K1M, T4I, S8I, T8V, T9I, S9I, K11A, K11H, S33I, S33C, S43N, G44L, S45V, S45I, T45V, T45I, G46P, D47M, N48V, N48F, L49A, A51V, D53A, D53N, V54L, V54I, R55A, R55V, R55L, G56P, I57F, I57M, D58A, D58V, D58F, P59A, E60I, E60T, E61A, E61V, E61L, G62A, R84A, V88A, D94A, S96I, T104N, T107P, L108M, S109V, T109V, G110A, D111T, S112V, D141A, G147A, V154A, R179A, T180G, T181I, D183A, D183G, D184A, D184F, L185V, S186A, S186F, G187A, R188A, R188L, S189A, D198A, R204A, R205A, C242S, S247I, Y247A, R247A, R248A, R250A, R251A, D264A, G264A, T286A, and T286I may have the same or similar effects. In certain embodiments, a Shiga toxin effector polypeptide of the invention may comprise similar conservative amino acid substitutions to empirically tested ones, such as, e.g., K1 to G, V, L, I, F, and H; T4 to A, G, V, L, F, M, and S; S8 to A, G, V, L, F, and M; T8 to A, G, V, I, L, F, and M; T9 to A, G, L, F, M, and S; S9 to A, G, L, I, F, and M; K11 to G, V, L, I, F, and M; S33 to A, G, V, L, F, and M; S43 to A, G, V, L, I, F, and M; S45 to A, G, L, F, and M; T45 to A, G, L, F, and M; D47 to A, V, L, I, F, S, and Q; N48 to A, G, L, and M; L49 to G; Y49 to A; D53 to V, L, I, F, S, and Q; R55 to G, I, F, M, Q, S, K, and H; D58 to G, L, I, S, and Q; P59 to G; E60 to A, G, V, L, F, S, Q, N, D, and M; E61 to G, I, F, S, Q, N, D, M, and R; R84 to G, V, L, I, F, M, Q, S, K, and H; V88 to G; I88 to G; D94 to G, V, L, I, F, S, and Q; S96 to A, G, V, L, F, and M; T107 to A, G, V, L, I, F, M, and S; S107 to A, G, V, L, I, F, and M; S109 to A, G, I, L, F, and M; T109 to A, G, I, L, F, M, and S; S112 to A, G, L, I, F, and M; D141 to V, L, I, F, S, and Q; V154 to G; R179 to G, V, L, I, F, M, Q, S, K, and H; T180 to A, V, L, I, F, M, and S; T181 to A, G, V, L, F, M, and S; D183 to V, L, I, F, S, and Q; D184 to G, V, L, I, S, and Q; S186 to G, V, I, L, and M; R188 to G, V, I, F, M, Q, S, K, and H; S189 to G, V, I, L, F, and M; D197 to V, L, I, F, S, and Q; D198 to A, V, L, I, F, S, and Q; R204 to G, V, L, I, F, M, Q, S, K, and H; R205 to G, V, L, I, F, M, Q, S, K and H; S247 to A, G, V, I, L, F, and M; Y247 to A, G, V, L, I, F, and M; R247 to A, G, V, L, I, F, M, Q, S, K, and H; R248 to G, V, L, I, F, M, Q, S, K, and H; R250 to G, V, L, I, F, M, Q, S, K, and H; R251 to G, V, L, I, F, M, Q, S, K, and H; D264 to A, G, V, L, I, F, S, and Q; and T286 to A, G, V, L, I, F, M, and S.

Similarly, amino acid substitutions which remove charge, polarity, and/or reduce side chain length can disrupt an epitope while maintaining at least one Shiga toxin effector function. In certain embodiments, a Shiga toxin effector polypeptide of the invention may comprise one or more epitopes disrupted by substitutions such that side chain charge is removed, polarity is removed, and/or side chain length is reduced such as, e.g., substituting the appropriate amino acid selected from the following group A, G, V, L, I, P, C, M, F, S, D, N, Q, H, or K for the amino acid residue at position 1 of SEQ ID NO:1 or SEQ ID NO:2; 4 of SEQ ID NO:1, SEQ ID NO:2, or SEQ ID NO:3; 6 of SEQ ID NO:1 or SEQ ID NO:2; 8 of SEQ ID NO:1, SEQ ID NO:2, or SEQ ID NO:3; 9 of SEQ ID NO:1, SEQ ID NO:2, or SEQ ID NO:3; 11 of SEQ ID NO:1, SEQ ID NO:2, or SEQ ID NO:3; 12 of SEQ ID NO:1, SEQ ID NO:2, or SEQ ID NO:3;

33 of SEQ ID NO:1 or SEQ ID NO:2; 43 of SEQ ID NO:1 or SEQ ID NO:2; 44 of SEQ ID NO:1 or SEQ ID NO:2; 45 of SEQ ID NO:1 or SEQ ID NO:2; 46 of SEQ ID NO:1 or SEQ ID NO:2; 47 of SEQ ID NO:1 or SEQ ID NO:2; 48 of SEQ ID NO:1, SEQ ID NO:2, or SEQ ID NO:3; 49 of SEQ ID NO:1 or SEQ ID NO:2; 50 of SEQ ID NO:1 or SEQ ID NO:2; 51 of SEQ ID NO:1 or SEQ ID NO:2; 53 of SEQ ID NO:1 or SEQ ID NO:2; 54 of SEQ ID NO:1 or SEQ ID NO:2; 55 of SEQ ID NO:1 or SEQ ID NO:2; 56 of SEQ ID NO:1 or SEQ ID NO:2; 57 of SEQ ID NO:1, SEQ ID NO:2, or SEQ ID NO:3; 58 of SEQ ID NO:1, SEQ ID NO:2, or SEQ ID NO:3; 59 of SEQ ID NO:1, SEQ ID NO:2, or SEQ ID NO:3; 60 of SEQ ID NO:1 or SEQ ID NO:2; 61 of SEQ ID NO:1 or SEQ ID NO:2; 62 of SEQ ID NO:1 or SEQ ID NO:2; 84 of SEQ ID NO:1 or SEQ ID NO:2; 88 of SEQ ID NO:1, SEQ ID NO:2, or SEQ ID NO:3; 94 of SEQ ID NO:1, SEQ ID NO:2, or SEQ ID NO:3; 96 of SEQ ID NO:1, SEQ ID NO:2, or SEQ ID NO:3; 104 of SEQ ID NO:1 or SEQ ID NO:2; 105 of SEQ ID NO:1 or SEQ ID NO:2; 107 of SEQ ID NO:1, SEQ ID NO:2, or SEQ ID NO:3; 108 of SEQ ID NO:1 or SEQ ID NO:2; 109 of SEQ ID NO:1, SEQ ID NO:2, or SEQ ID NO:3; 110 of SEQ ID NO:1 or SEQ ID NO:2; 111 of SEQ ID NO:1 or SEQ ID NO:2; 112 of SEQ ID NO:1, SEQ ID NO:2, or SEQ ID NO:3; 141 of SEQ ID NO:1 or SEQ ID NO:2; 147 of SEQ ID NO:1, SEQ ID NO:2, or SEQ ID NO:3; 154 of SEQ ID NO:1 or SEQ ID NO:2; 179 of SEQ ID NO:1, SEQ ID NO:2, or SEQ ID NO:3; 180 of SEQ ID NO:1 or SEQ ID NO:2; 181 of SEQ ID NO:1 or SEQ ID NO:2; 183 of SEQ ID NO:1, SEQ ID NO:2, or SEQ ID NO:3; 184 of SEQ ID NO:1, SEQ ID NO:2, or SEQ ID NO:3; 185 of SEQ ID NO:1 or SEQ ID NO:2; 186 of SEQ ID NO:1, SEQ ID NO:2, or SEQ ID NO:3; 187 of SEQ ID NO:1 or SEQ ID NO:2; 188 of SEQ ID NO:1 or SEQ ID NO:2; 189 of SEQ ID NO:1 or SEQ ID NO:2; 197 of SEQ ID NO:3; 198 of SEQ ID NO:1 or SEQ ID NO:2; 204 of SEQ ID NO:3; 205 of SEQ ID NO:1 or SEQ ID NO:2; 241 of SEQ ID NO:3; 242 of SEQ ID NO:1 or SEQ ID NO:2; 247 of SEQ ID NO:1 or SEQ ID NO:2; 247 of SEQ ID NO:3; 248 of SEQ ID NO:1 or SEQ ID NO:2; 250 of SEQ ID NO:3; 251 of SEQ ID NO:1 or SEQ ID NO:2; 264 of SEQ ID NO:1, SEQ ID NO:2, or SEQ ID NO:3; 265 of SEQ ID NO:1 or SEQ ID NO:2; and 286 of SEQ ID NO:1 or SEQ ID NO:2. In certain embodiments, a Shiga toxin effector polypeptide of the present invention may comprise one or more of the following amino acid substitutions: K1 to A, G, V, L, I, F, M and H; T4 to A, G, V, L, I, F, M, and S; D6 to A, G, V, L, I, F, S, and Q; S8 to A, G, V, I, L, F, and M; T8 to A, G, V, I, L, F, M, and S; T9 to A, G, V, I, L, F, M, and S; S9 to A, G, V, L, I, F, and M; K11 to A, G, V, L, I, F, M and H; T12 to A, G, V, I, L, F, M, and S; S33 to A, G, V, L, I, F, and M; S43 to A, G, V, L, I, F, and M; G44 to A and L; S45 to A, G, V, L, I, F, and M; T45 to A, G, V, L, I, F, and M; G46 to A and P; D47 to A, G, V, L, I, F, S, and Q; N48 to A, G, V, L, and M; L49 to A or G; F50; A51 to V; D53 to A, G, V, L, I, F, S, and Q; V54 to A, G, and L; R55 to A, G, V, L, I, F, M, Q, S, K, and H; G56 to A and P; I57 to A, G, M, and F; L57 to A, G, M, and F; D58 to A, G, V, L, I, F, S, and Q; P59 to A, G, and F; E60 to A, G, V, L, I, F, S, Q, N, D, M, and R; E61 to A, G, V, L, I, F, S, Q, N, D, M, and R; G62 to A; D94 to A, G, V, L, I, F, S, and Q; R84 to A, G, V, L, I, F, M, Q, S, K, and H; V88 to A and G; 188 to A, G, and V; D94; S96 to A, G, V, I, L, F, and M; T104 to A, G, V, I, L, F, M, and S; A105 to L; T107 to A, G, V, I, L, F, M, and S; S107 to A, G, V, L, I, F, and M; L108 to A, G, and M; S109 to A, G, V, I, L, F, and M; T109 to A, G, V, I, L, F, M, and S; G110 to A; D111 to A, G, V, L, I, F, S, and Q; S112 to A, G, V, L, I, F, and M; D141 to A, G, V, L, I, F, S, and Q; G147 to A; V154 to A and G; R179 to A, G, V, L, I, F, M, Q, S, K, and H; T180 to A, G, V, L, I, F, M, and S; T181 to A, G, V, L, I, F, M, and S; D183 to A, G, V, L, I, F, S, and Q; D184 to A, G, V, L, I, F, S, and Q; L185 to A, G, and V; S186 to A, G, V, I, L, F, and M; G187 to A; R188 to A, G, V, L, I, F, M, Q, S, K, and H; S189 to A, G, V, I, L, F, and M; D197 to A, G, V, L, I, F, S, and Q; D198 to A, G, V, L, I, F, S, and Q; R204 to A, G, V, L, I, F, M, Q, S, K, and H; R205 to A, G, V, L, I, F, M, Q, S, K and H; C242 to A, G, V, and S; S247 to A, G, V, I, L, F, and M; Y247 to A, G, V, L, I, F, and M; R247 to A, G, V, L, I, F, M, Q, S, K, and H; R248 to A, G, V, L, I, F, M, Q, S, K, and H; R250 to A, G, V, L, I, F, M, Q, S, K, and H; R251 to A, G, V, L, I, F, M, Q, S, K, and H; C262 to A, G, V, and S; D264 to A, G, V, L, I, F, S, and Q; G264 to A; and T286 to A, G, V, L, I, F, M, and S.

In addition, any amino acid substitution in one epitope region of a Shiga toxin effector polypeptide which disrupts an epitope while retaining significant Shiga toxin effector function is combinable with any other amino acid substitution in the same or a different epitope region which disrupts an epitope while retaining significant Shiga toxin effector function to form a de-immunized, Shiga toxin effector polypeptide with multiple epitope regions disrupted while still retaining a significant level of Shiga toxin effector function. In certain embodiments, a Shiga toxin effector polypeptide of the invention may comprise combinations of two or more of the aforementioned substitutions and/or the combinations of substitutions described in WO 2015/113007 and/or WO 2016/196344.

Based on the empirical evidence in the Examples and in WO 2015/113007 and WO 2016/196344, certain amino acid regions in the A Subunits of Shiga toxins are predicted to tolerate epitope disruptions while still retaining significant Shiga toxin effector functions. For example, the epitope regions natively positioned at 1-15, 39-48, 53-66, 55-66, 94-115, 180-190, 179-190, and 243-257 tolerated multiple amino acid substitution combinations simultaneously without compromising Shiga toxin enzymatic activity and cytotoxicity.

In certain embodiments, the de-immunized, Shiga toxin effector polypeptide of the present invention comprises, consists essentially of, or consists of an amino acid sequence that is at least 85% (such as at least 90%, 91%, 92%, 93%, 94%, 95%, 96%, 97%, 98%, 99% or more) identical to an amino acid sequence selected from any one of SEQ ID NOs: 19-21 and 75-89. For example, the de-immunized Shiga toxin effector polypeptide of the present invention comprises any of the following sets of substitutions: (i) K1A, S45I, V54I, R55L, I57F, P59F, E60T, E61L, G110A, G147A, C242S, R248A, and R251A; (ii) S45I, V54I, R55L, I57F, P59F, E60T, E61L, G110A, R188A, C242S, R248A, and R251A; or (iii) S45I, V54I, R55L, I57F, P59F, E60T, E61L, G110A, D141A, R188A, C242S, R248A, and R251A.

B. Examples of Furin-Cleavage Resistant, Shiga Toxin Effector Polypeptides

In certain embodiments, the Shiga toxin effector polypeptide of the present invention may comprise a disrupted, furin cleavage motif and/or furin cleavage site at the carboxy-terminus of a Shiga toxin A1 fragment derived region. In certain further embodiments, the Shiga toxin effector polypeptide does not comprise any known compensatory structure which may provide furin cleavage proximal to the carboxy-terminus of the Shiga toxin A1 fragment derived region. Non-limiting examples of disrupted furin cleavage motifs and furin cleave sites suitable for use in the present invention are described in WO 2015/191764.

Certain furin-cleavage motif disruptions are indicated herein by reference to specific amino acid positions of native Shiga toxin A Subunits provided in the Sequence Listing, noting that naturally occurring Shiga toxin A Subunits includes precursor forms containing signal sequences of about 22 amino acids at their amino-terminals which are removed to produce mature Shiga toxin A Subunits and are recognizable to the skilled worker. Further, certain furin-cleavage motif disruptions comprising mutations are indicated herein by reference to specific amino acids (e.g. R for an arginine residue) natively present at specific positions within native Shiga toxin A Subunits (e.g. R251 for the arginine residue at position 251 from the amino-terminus) followed by the amino acid with which that residue has been substituted in the particular mutation under discussion (e.g. R251A represents the amino acid substitution of alanine for arginine at amino acid residue 251 from the amino-terminus).

In certain embodiments, the Shiga toxin effector polypeptide of the present invention comprises a Shiga toxin A1 fragment derived region, wherein the Shiga toxin A1 fragment derived region comprises a disrupted furin-cleavage motif at the carboxy-terminus of a Shiga toxin A1 fragment derived region, and such embodiments are referred to herein as "furin-cleavage resistant" or "protease-cleavage resistant," Shiga toxin effector polypeptides to describe their property(ies) relative to wild-type, Shiga toxin A Subunits and/or wild-type, Shiga toxin A1 fragment fusion proteins.

In certain embodiments, the protease-cleavage resistant, Shiga toxin effector polypeptide of the present invention consists essentially of a truncated Shiga toxin A Subunit having two or more mutations.

In certain embodiments, the protease-cleavage resistant, Shiga toxin effector polypeptide of the present invention comprises the disrupted furin-cleavage motif comprising the amino acid residue substitution (relative to a wild-type Shiga toxin polypeptide) of one or both of the arginine residues in the minimal, furin-cleavage site consensus motif with A, G, or H. In certain embodiments, the protease-cleavage resistant, Shiga toxin effector polypeptide of the present invention comprises a disruption which comprises an amino acid substitution within a furin-cleavage motif region, wherein the substitution occurs at the natively positioned amino acid selected from the group consisting of: 247 of SEQ ID NO:3, 248 of SEQ ID NO:1 or SEQ ID NO:2, 250 of SEQ ID NO:3, 251 of SEQ ID NO:1 or SEQ ID NO:2, or the equivalent position in a conserved Shiga toxin effector polypeptide and/or non-native Shiga toxin effector polypeptide sequence, such as, e.g., position 247 of SEQ ID NOs: 7-18, 248 of SEQ ID NOs: 4-6, 250 of SEQ ID NOs: 7-18, or 251 of SEQ ID NOs: 4-6. In certain further embodiments, the substitution is to any non-conservative amino acid and the substitution occurs at the natively positioned amino acid residue position. In certain further embodiments, the mutation comprises an amino acid substitution selected from the group consisting of: R247A, R248A, R250A R251A, or the equivalent position in a conserved Shiga toxin effector polypeptide and/or non-native Shiga toxin effector polypeptide sequence.

In certain embodiments, the protease-cleavage resistant, Shiga toxin effector polypeptide of the present invention comprises the disrupted furin-cleavage motif comprising the mutation which is a deletion. In certain further embodiments, the disrupted furin-cleavage motif comprises a mutation which is a deletion of the region natively positioned at 247-252 in StxA (SEQ ID NO:2), SLT-1A (SEQ ID NO:1), and other Shiga toxin 1 A Subunit variants (e.g. SEQ ID NOs: 4-6), or the region natively positioned at 246-251 in SLT-2A (SEQ ID NO:3) and Shiga-like toxin 2 A Subunit variants (e.g. SEQ ID NOs: 7-18); a deletion of the region natively positioned at 244-246 in StxA (SEQ ID NO:2), SLT-1A (SEQ ID NO:1), and other Shiga toxin 1 A Subunit variants (e.g. SEQ ID NOs: 4-6), or the region natively positioned at 243-245 in SLT-2A (SEQ ID NO:3) and Shiga-like toxin 2 A Subunit variants (e.g. SEQ ID NOs: 7-18); or a deletion of the region natively positioned at 253-259 in StxA (SEQ ID NO:2) and SLT-1A (SEQ ID NO:3), or the region natively positioned at 252-258 in SLT-2A (SEQ ID NO:3).

In certain embodiments of the protease-cleavage resistant, Shiga toxin effector polypeptide of the present invention comprises a Shiga toxin A1 fragment region comprising a disrupted furin-cleavage motif at the carboxy-terminus of the Shiga toxin A1 fragment region that is disrupted by a carboxy-terminal truncation as compared to the carboxy-terminus of a wild-type Shiga toxin A Subunit, and wherein the truncation results in the deletion of one or more amino acid residues within the furin-cleavage motif as compared to the wild-type Shiga toxin A Subunit. In certain further embodiments, the disrupted furin-cleavage motif comprises the carboxy-terminal truncation which deletes one or more amino acid residues within the minimal cleavage site Y/R-x-x-R, such as, e.g., for StxA and SLT-1A derived Shiga toxin effector polypeptides, truncations ending at the natively amino acid residue position 250, 249, 248, 247, 246, 245, 244, 243, 242, 241, 240, or less; and for SLT-2A derived Shiga toxin effector polypeptides, truncations ending at the natively amino acid residue position 249, 248, 247, 246, 245, 244, 243, 242, 241, or less. Certain further embodiments comprise the disrupted furin-cleavage motif comprising a combination of any of the aforementioned mutations, where possible.

In certain embodiments, the disrupted furin-cleavage motif comprises the mutation(s) that is a partial, carboxy-terminal truncation of the furin-cleavage motif however, certain molecules of the present invention do not comprise the disrupted furin-cleavage motif which is a complete, carboxy-terminal truncation of the entire 20 amino acid residue, furin-cleavage motif. For example, certain, Shiga toxin effector polypeptides of the present invention comprise the disrupted furin-cleavage motif comprising a partial, carboxy-terminal truncation of the Shiga toxin A1 fragment region up to native position 240 in StxA (SEQ ID NO:2), SLT-1A (SEQ ID NO:1), or another Shiga toxin 1 A Subunit variant (e.g. SEQ ID NOs: 4-6) but not a carboxy-terminal truncation at position 239 or less. Similarly, certain, certain, Shiga toxin effector polypeptides of the present invention comprise the disrupted furin-cleavage motif comprising a partial, carboxy-terminal truncation of the Shiga toxin A1 fragment region up to native position 239 in SLT-2A (SEQ ID NO:3) or a Shiga-like toxin 2 A Subunit variant (e.g. SEQ ID NOs: 7-18) but not a carboxy-terminal truncation at position 238 or less. In the largest carboxy-terminal truncation of the furin-cleavage resistant, Shiga toxin effector polypeptide of the present invention, mutations comprising the disrupted furin-cleavage motif, positions P14 and P13 of the furin-cleavage motif are still present.

In certain embodiments, the disrupted furin-cleavage motif comprises both an amino acid residue substitution within the furin-cleavage motif and a carboxy-terminal truncation as compared to a wild-type, Shiga toxin A Subunit. In certain further embodiments, the disrupted furin-cleavage motif comprises both an amino acid residue substitution within the minimal furin-cleavage site R/Y-x-x-R and a carboxy-terminal truncation as compared to a wild-type, Shiga toxin A Subunit, such as, e.g., for StxA and SLT-1A derived Shiga toxin effector polypeptides (and Shiga toxin 1 A Subunit variants), truncations ending at the natively amino acid residue position 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, or greater and comprising the natively positioned amino acid residue R248 and/or R251 substituted with any non-positively charged, amino acid residue where appropriate; and for SLT-2A derived Shiga toxin effector polypeptides (and Shiga-like toxin 2 A Subunit variants), truncations ending at the natively amino acid residue position 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, or greater and comprising the natively positioned amino acid residue R/Y247 and/or R250 substituted with any non-positively charged, amino acid residue where appropriate. In certain embodiments, the truncated Shiga toxin effector polypeptide comprising a disrupted furin-cleavage motif also comprises the furin-cleavage motif, amino acid residues at positions P9, P8, and/or P7 in order to maintain optimal cytotoxicity.

In certain embodiments, the disrupted furin-cleavage motif comprises a mutation(s) which is one or more internal, amino acid residue deletions, as compared to a wild-type, Shiga toxin A Subunit. In certain further embodiments, the disrupted furin-cleavage motif comprises a mutation(s) which has one or more amino acid residue deletions within the minimal furin-cleavage site R/Y-x-x-R. For example, StxA and SLT-1A derived Shiga toxin effector polypeptides (and other Shiga toxin 1 A Subunit variants) comprising internal deletions of the natively positioned amino acid residues R248 and/or R251, which may be combined with deletions of surrounding residues such as, e.g., 249, 250, 247, 252, etc.; and SLT-2A derived Shiga toxin effector polypeptides (and Shiga-like toxin 2 A Subunit variants) comprising internal deletions of the natively positioned amino acid residues R/Y247 and/or R250, which may be combined with deletions of surrounding residues such as, e.g., 248, 249, 246, 251, etc. In certain further embodiments, the disrupted furin-cleavage motif comprises a mutation which is a deletion of four, consecutive, amino acid residues which deletes the minimal furin-cleavage site R/Y-x-x-R, such as, e.g., StxA and SLT-1A derived Shiga toxin effector polypeptides (and other Shiga toxin 1 A Subunit variants) lacking R248-R251 and SLT-2A derived Shiga toxin effector polypeptides (and Shiga-like toxin 2 A Subunit variants) lacking R/Y247-R250. In certain further embodiments, the disrupted furin-cleavage motif comprises a mutation(s) having one or more amino acid residue deletions in the amino acid residues flanking the core furin-cleavage motif, such as, e.g., a deletion of 244-247 and/or 252-255 in SLT-1A, StxA, or another Shiga toxin 1 A Subunit variant. In certain further embodiments, the disrupted furin-cleavage motif comprises a mutation which is an internal deletion of the entire surface-exposed, protease-cleavage sensitive loop as compared to a wild-type, Shiga toxin A Subunit, such as, e.g., for StxA and SLT-1A derived Shiga toxin effector polypeptides (and other Shiga toxin 1 A Subunit variants), a deletion of natively positioned amino acid residues 241-262; and for SLT-2A derived Shiga toxin effector polypeptides, a deletion of natively positioned amino acid residues 240-261.

In certain embodiments, the disrupted furin-cleavage motif comprises both a mutation which is an internal, amino acid residue deletion within the furin-cleavage motif and a mutation which is carboxy-terminal truncation as compared to a wild-type, Shiga toxin A Subunit. In certain further embodiments, the disrupted furin-cleavage motif comprises both a mutation which is an amino acid residue deletion within the minimal furin-cleavage site R/Y-x-x-R and a mutation which is a carboxy-terminal truncation as compared to a wild-type, Shiga toxin A Subunit. For example, protease-cleavage resistant, Shiga toxin effector polypeptides may comprise a disrupted furin-cleavage motif comprising mutation(s) which are deletions of the natively positioned amino acid residues 248-249 and/or 250-251 in a truncated StxA or SLT-1A polypeptide (or another Shiga toxin 1 A Subunit variant) which still has amino acid residue 247 and/or 252, or the amino acid residues 247-248 and/or 249-250 in a truncated SLT-2A (or a Shiga-like toxin 2 A Subunit variant) which still has amino acid residue 246 and/or 251. In certain further embodiments, the disrupted furin-cleavage motif comprises a mutation having a deletion of four, consecutive, amino acid residues which deletes the minimal furin-cleavage site R/Y-x-x-R and a carboxy-terminal truncation as compared to a wild-type, Shiga toxin A Subunit, such as, e.g., for StxA and SLT-1A (and other Shiga toxin 1 A Subunit variants) derived Shiga toxin effector polypeptides, truncations ending at the natively amino acid residue position 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, or greater and lacking R248-R251; and for SLT-2A derived Shiga toxin effector polypeptides (and Shiga toxin 2 A Subunit variants), truncations ending at the natively amino acid residue position 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, or greater and lacking R/Y247-R250.

C. Examples of Shiga Toxin Effector Polypeptides Having an Embedded Epitope

In certain embodiments, the Shiga toxin effector polypeptide of the present invention may comprise one or more embedded or inserted, heterologous, T-cell epitopes for purposes of de-immunization and/or delivery to a MHC class I presentation pathway of a target cell. For certain embodiments and/or certain Shiga toxin effector polypeptide sub-regions, embedding or partial embedding a T-cell epitope may be preferred over inserting a T-cell epitope because, e.g., embedding-type modifications are more likely to be successful in diverse sub-regions of a Shiga toxin effector polypeptide whereas successful insertions may be more limited to a smaller subset of Shiga toxin effector polypeptide sub-regions. The term "successful" is used here to mean the modification to the Shiga toxin effector polypeptide (e.g. introduction of a heterologous, T-cell epitope) results in a modified Shiga toxin effector polypeptide which retains one or more Shiga toxin effector functions at the requisite level of activity either alone or as a component of a cell-targeting molecule.

Any of the Shiga toxin effector polypeptide sub-regions described in WO 2015/113007 may be suitable for certain embodiments of the present invention, and any of the Shiga toxin effector polypeptides described in WO 2015/113007 may be modified into a Shiga toxin effector polypeptide of the present invention, e.g., by the addition of one or more new epitope region disruptions for de-immunization (such one as described herein) and/or a furin-cleavage motif disruption (such as one described herein).

In certain embodiments, the Shiga toxin effector polypeptide of the present invention consists essentially of a truncated Shiga toxin A Subunit comprising an embedded or inserted, heterologous, T-cell epitope and one or more other mutations. In certain embodiments, the Shiga toxin effector polypeptide of the present invention comprises an embedded or inserted, heterologous, T-cell epitope and is smaller than a full-length, Shiga toxin A Subunit, such as, e.g., derived from the polypeptide represented by amino acids 77 to 239 of SLT-1A (SEQ ID NO:1) or StxA (SEQ ID NO:2) or the equivalent in other A Subunits of members of the Shiga toxin family (e.g. amino acids 77 to 238 of SLT-2A (SEQ ID NO:3)). For example, the Shiga toxin effector polypeptide of the present invention comprising an embedded or inserted, heterologous, T-cell epitope may comprise, consist essentially of, or consist of an amino acid sequence that is at least 85% (such as at least 90%, 91%, 92%, 93%, 94%, 95%, 96%, 97%, 98%, 99% or more) identical to an amino acid sequence selected from any one of SEQ ID NOs: 19-21 and 75-89. For example, the Shiga toxin effector polypeptide of the present invention comprising an embedded, heterologous epitope comprises: V54I, R55L, I57F, P59F, E60T, and E61L.

D. Examples of Combination Shiga Toxin Effector Polypeptides

A combination Shiga toxin effector polypeptide of the present invention comprises two or more sub-regions (i.e. non-overlapping sub-regions) wherein each sub-region comprises at least one of the following: (1) a disruption in an endogenous epitope or epitope region; (2) an embedded, heterologous, T-cell epitope-peptide; (3) an inserted, heterologous, T-cell epitope-peptide; and (4) a disrupted furin-cleavage motif at the carboxy-terminus of a Shiga toxin A1 fragment derived region. In certain further embodiments, the combination Shiga toxin effector polypeptide comprises a carboxy-terminal truncation relative to a wild-type Shiga toxin A Subunit. In certain further embodiments, the carboxy-terminal truncation results in the removal of one or more endogenous, B-cell and/or CD4+ T-cell epitope regions present in an untruncated, wild-type Shiga toxin A Subunit.

Certain embodiments of the combination Shiga toxin effector polypeptides of the present invention comprise both (1) a disruption in an endogenous epitope or epitope region and (2) a disrupted furin-cleavage motif at the carboxy-terminus of an A1 fragment derived region. It is predicted that any of the individual, de-immunized, Shiga toxin effector sub-regions described in WO 2015/113007 and WO 2016/196344 (see e.g. Table B, supra) may generally be combined with any Shiga toxin effector sub-region comprising a disrupted furin-cleavage motif described herein, described in WO 2015/191764, and/or known in the art in order to create a Shiga toxin effector polypeptide of the present invention.

In certain embodiments of the present invention, the Shiga toxin effector polypeptide consists essentially of the polypeptide shown in SEQ ID NO:37 which further comprises a disruption of at least one, endogenous, B-cell and/or T-cell epitope region which does not overlap with an embedded or inserted, heterologous, CD8+ T-cell epitope; wherein the disruption comprises one or more amino acid residue substitutions relative to a wild-type Shiga toxin. In certain further embodiments the substitution is selected from the group consisting of: K1 to A, G, V, L, I, F, M and H; T4 to A, G, V, L, I, F, M, and S; D6 to A, G, V, L, I, F, S, Q and R; S8 to A, G, V, I, L, F, and M; T8 to A, G, V, I, L, F, and M; T9 to A, G, V, I, L, F, M, and S; S9 to A, G, V, L, I, F, and M; K11 to A, G, V, L, I, F, M and H; T12 to A, G, V, I, L, F, M, S, and K; S12 to A, G, V, I, L, F, and M; S33 to A, G, V, L, I, F, M, and C; S43 to A, G, V, L, I, F, and M; G44 to A or L; S45 to A, G, V, L, I, F, and M; T45 to A, G, V, L, I, F, and M; G46 to A and P; D47 to A, G, V, L, I, F, S, M, and Q; N48 to A, G, V, L, M and F; L49 to A, V, C, and G; Y49 to A, G, V, L, I, F, M, and T; F50 to A, G, V, L, I, and T; D53 to A, G, V, L, I, F, S, and Q; V54 to A, G, I, and L; R55 to A, G, V, L, I, F, M, Q, S, K, and H; G56 to A and P; I57 to A, G, V, and M; L57 to A, V, C, G, M, and F; D58 to A, G, V, L, I, F, S, and Q; P59 to A, G, and F; E60 to A, G, V, L, I, F, S, Q, N, D, M, T, and R; E61 to A, G, V, L, I, F, S, Q, N, D, M, and R; G62 to A; R84 to A, G, V, L, I, F, M, Q, S, K, and H; V88 to A and G; I88 to A, V, C, and G; D94 to A, G, V, L, I, F, S, and Q; S96 to A, G, V, I, L, F, and M; T104 to A, G, V, L, I, F, M; and N; A105 to L; T107 to A, G, V, L, I, F, M, and P; S107 to A, G, V, L, I, F, M, and P; L108 to A, V, C, and G; S109 to A, G, V, I, L, F, and M; T109 to A, G, V, I, L, F, M, and 5; G110 to A; S112 to A, G, V, L, I, F, and M; D111 to A, G, V, L, I, F, 5, Q, and T; S112 to A, G, V, L, I, F, and M; D141 to A, G, V, L, I, F, S, and Q; G147 to A; V154 to A and G. R179 to A, G, V, L, I, F, M, Q, S, K, and H; T180 to A, G, V, L, I, F, M, and S; T181 to A, G, V, L, I, F, M, and S; D183 to A, G, V, L, I, F, S, and Q; D184 to A, G, V, L, I, F, S, and Q; L185 to A, G, V and C; S186 to A, G, V, I, L, F, and M; G187 to A; R188 to A, G, V, L, I, F, M, Q, S, K, and H; S189 to A, G, V, I, L, F, and M; D198 to A, G, V, L, I, F, S, and Q; R204 to A, G, V, L, I, F, M, Q, S, K, and H; R205 to A, G, V, L, I, F, M, Q, S, K and H; S247 to A, G, V, I, L, F, and M; Y247 to A, G, V, L, I, F, and M; R247 to A, G, V, L, I, F, M, Q, S, K, and H; R248 to A, G, V, L, I, F, M, Q, S, K, and H; R250 to A, G, V, L, I, F, M, Q, S, K, and H; R251 to A, G, V, L, I, F, M, Q, S, K, and H; D264 to A, G, V, L, I, F, S, and Q; G264 to A; and T286 to A, G, V, L, I, F, M, and S. In certain further embodiments, there are multiple disruptions of multiple, endogenous B-cell and/or CD8+ T-cell epitope regions wherein each disruption involves at least one amino acid residue substitution selected from the group consisting of: K1 to A, G, V, L, I, F, M and H; T4 to A, G, V, L, I, F, M, and S; D6 to A, G, V, L, I, F, S, Q and R; S8 to A, G, V, I, L, F, and M; T9 to A, G, V, I, L, F, M, and S; S9 to A, G, V, L, I, F, and M; K11 to A, G, V, L, I, F, M and H; T12 to A, G, V, I, L, F, M, S, and K; 512 to A, G, V, I, L, F, and M; S33 to A, G, V, L, I, F, M, and C; S43 to A, G, V, L, I, F, and M; G44 to A or L; S45 to A, G, V, L, I, F, and M; T45 to A, G, V, L, I, F, and M; G46 to A and P; D47 to A, G, V, L, I, F, S, M, and Q; N48 to A, G, V, L, M and F; L49 to A, V, C, and G; Y49 to A, G, V, L, I, F, M, and T; F50 to A, G, V, L, I, and T; A51 to V; D53 to A, G, V, L, I, F, S, and Q; V54 to A, G, I, and L; R55 to A, G, V, L, I, F, M, Q, S, K, and H; G56 to A and P; I57 to A, G, V, and M; L57 to A, V, C, G, M, and F; D58 to A, G, V, L, I, F, S, and Q; P59 to A, G, and F; E60 to A, G, V, L, I, F, S, Q, N, D, M, T, and R; E61 to A, G, V, L, I, F, S, Q, N, D, M, and R; G62 to A; R84 to A, G, V, L, I, F, M, Q, S, K, and H; V88 to A and G; I88 to A, V, C, and G; D94 to A, G, V, L, I, F, S, and Q; S96 to A, G, V, I, L, F, and M; T104 to A, G, V, L, I, F, M; and N; A105 to L; T107 to A, G, V, L, I, F, M, and P; S107 to A, G, V, L, I, F, M, and P; L108 to A, V, C, and G; S109 to A, G, V, I, L, F, and M; T109 to A, G, V, I, L, F, M, and S; G110 to A; S112 to A, G, V, L, I, F, and M; D111 to A, G, V, L, I, F, S, Q, and T; S112 to A, G, V, L, I, F, and M; D141 to A, G, V, L, I, F, S, and Q; G147 to A; V154 to A and G. R179 to A, G, V, L, I, F, M, Q, S, K, and H; T180 to A, G, V, L, I, F, M, and S; T181 to A, G, V, L, I, F, M, and S; D183 to A, G, V, L, I, F, S, and Q; D184 to A, G, V, L, I, F, S, and Q; L185 to A, G, V and C; S186 to A, G, V, I, L, F, and M; G187 to A; R188 to A, G, V, L, I, F, M, Q, S, K, and H; S189 to A, G, V, I, L, F, and M; D198 to A, G, V, L, I, F, S, and Q; R204 to A, G, V, L, I, F, M, Q, S, K, and H; R205 to A, G, V, L, I, F, M, Q, S, K and H; S247 to A, G, V, I, L, F, and M; Y247 to A, G, V, L, I, F, and M; R247 to A, G, V, L, I, F, M, Q, S, K, and H; R248 to A, G, V, L, I, F, M, Q, S, K, and H; R250 to A, G, V, L, I, F, M, Q, S, K, and H; R251 to A, G, V, L, I, F, M, Q, S, K, and H; D264 to A, G, V, L, I, F, S, and Q; G264 to A; and T286 to A, G, V, L, I, F, M, and S.

Certain embodiments of the Shiga toxin effector polypeptides of the present invention comprise both (1) an embedded or inserted, heterologous, T-cell epitope-peptide and (2) a disrupted furin-cleavage motif at the carboxy-terminus of an A1 fragment derived region. Any of the Shiga toxin effector polypeptide sub-regions comprising an embedded or inserted, heterologous, T-cell epitope described in the Examples below or in WO 2015/113007 may generally be combined with any protease-cleavage resistant, Shiga toxin effector polypeptide sub-region (e.g., modified, Shiga toxin A Subunit sub-regions described herein, described in WO 2015/191764, and/or known in the art) in order to create a combination, Shiga toxin effector polypeptide which, as a component of a cell-targeting molecule, is both protease-cleavage resistant and capable of delivering a heterologous, T-cell epitope to the MHC class I presentation pathway of a target cell. Non-limiting examples of this type of combination Shiga toxin effector polypeptide are shown in SEQ ID NOs: 19-21 and 75-89.

In certain embodiments of the present invention, the Shiga toxin effector polypeptide comprises an embedded or inserted, heterologous, T-cell epitope and a disrupted furin-cleavage motif at the carboxy-terminus of a Shiga toxin A1 fragment derived region. For example in certain embodiments, the Shiga toxin effector polypeptide of the present invention is derived from amino acids 75 to 251 of SEQ ID NO:1, 1 to 241 of SEQ ID NO:1, 1 to 251 of SEQ ID NO:1, or amino acids 1 to 261 of SEQ ID NO:1, wherein the Shiga toxin effector polypeptide comprises at least one embedded or inserted, heterologous T-cell epitope and a disrupted furin-cleavage motif at the carboxy-terminus of a Shiga toxin A1 fragment derived region. Similarly in other embodiments, the Shiga toxin effector polypeptide of the present invention is derived from amino acids 75 to 251 of SEQ ID NO:2, 1 to 241 of SEQ ID NO:2, 1 to 251 of SEQ ID NO:2, or amino acids 1 to 261 of SEQ ID NO:2, wherein the Shiga toxin effector polypeptide comprises at least one embedded or inserted, heterologous T-cell epitope and a disrupted furin-cleavage motif at the carboxy-terminus of a Shiga toxin A1 fragment derived region. Additionally, the Shiga toxin effector polypeptide may be derived from amino acids 75 to 251 of SEQ ID NO:3, 1 to 241 of SEQ ID NO:3, 1 to 251 of SEQ ID NO:3, or amino acids 1 to 261 of SEQ ID NO:3, wherein the Shiga toxin effector polypeptide comprises at least one embedded or inserted, heterologous T-cell epitope and a disrupted furin-cleavage motif at the carboxy-terminus of a Shiga toxin A1 fragment derived region. In certain embodiments, the Shiga toxin effector polypeptide comprises, consists essentially of, or consists of (i) amino acids 75 to 251 of any one of SEQ ID NOs: 1-18; (ii) amino acids 1 to 241 of any one of SEQ ID NOs: 1-18; (iii) amino acids 1 to 251 of any one of SEQ ID NOs: 1-18; and (iv) amino acids 1 to 261 of any one of SEQ ID NOs: 1-18, wherein the Shiga toxin effector polypeptide comprises at least one embedded or inserted, heterologous T-cell epitope and a disrupted furin-cleavage motif at the carboxy-terminus of a Shiga toxin A1 fragment derived region. In certain embodiments, the Shiga toxin effector polypeptide comprises, consists essentially of, or consists of: (i) amino acids 75 to 251 of SEQ ID NOs: 1-6, (ii) 1 to 241 of SEQ ID NOs: 1-18, (iii) 1 to 251 of SEQ ID NOs:1-6, or (iv) amino acids 1 to 261 of SEQ ID NOs: 1-3, wherein the Shiga toxin effector polypeptide comprises at least one embedded or inserted, heterologous, CD8+ T-cell epitope and a disrupted furin-cleavage motif at the carboxy-terminus of a Shiga toxin A1 fragment derived region. In certain embodiments, the Shiga toxin effector polypeptide comprises, consists essentially of, or consists of: (i) amino acids 75 to 251 of any one of SEQ ID NOs: 1-6; (ii) amino acids 1 to 241 of any one of SEQ ID NOs: 1-18 and 75-89; (iii) amino acids 1 to 251 of any one of SEQ ID NOs: 1-6 and 75-89; or (iv) amino acids 1 to 261 of any one of SEQ ID NOs: 1-3; wherein the Shiga toxin effector polypeptide comprises at least one embedded or inserted, heterologous T-cell epitope and a disrupted furin-cleavage motif at the carboxy-terminus of a Shiga toxin A1 fragment derived region. In certain embodiments, the Shiga toxin effector polypeptide comprises, consists essentially of, or consists of: (i) amino acids 75 to 251 of any one of SEQ ID NOs: 1-6; (ii) amino acids 1 to 241 of any one of SEQ ID NOs: 1-18 and 75-89; (iii) amino acids 1 to 251 of any one of SEQ ID NOs: 1-6 and 75-89; or (iv) amino acids 1 to 261 of any one of SEQ ID NOs: 1-3; wherein the Shiga toxin effector polypeptide comprises at least one embedded or inserted, heterologous T-cell epitope and a disrupted furin-cleavage motif at the carboxy-terminus of a Shiga toxin A1 fragment derived region.

Certain embodiments of the combination Shiga toxin effector polypeptides of the present invention comprise both (1) a disruption in an endogenous epitope or epitope region and (2) an embedded, heterologous, T-cell epitope-peptide. However, the Shiga toxin effector sub-regions comprising inserted or embedded, heterologous, T-cell epitopes described herein or in WO 2015/191764 are generally not combinable with every de-immunized, Shiga toxin effector sub-regions described herein, except where empirically shown to be successfully combined such that the resulting combination molecule retained a sufficient level of a Shiga toxin effector function(s). The disclosure herein shows how such embodiments may be made and tested to empirically demonstrate success.

The term "successful" is used here to mean two or more amino acid residue substitutions in a Shiga toxin effector polypeptide results in a functional feature, such as, e.g., de-immunization, reduced furin-cleavage, and/or ability to deliver an embedded or inserted epitope, while the modified Shiga toxin effector polypeptide retains one or more Shiga toxin effector functions. The approaches and assays described herein show how to design, make and empirically test embodiments of the present invention, which represent combination, Shiga toxin effector polypeptides and cell-targeting molecules comprising the same.

For example, in certain embodiments of the present invention, the Shiga toxin effector polypeptides is derived from amino acids 75 to 251 of SEQ ID NO:1, 1 to 241 of SEQ ID NO:1, 1 to 251 of SEQ ID NO:1, or amino acids 1 to 261 of SEQ ID NO:1, wherein the Shiga toxin effector polypeptide comprises at least one embedded or inserted, heterologous T-cell epitope and at least one amino acid is disrupted in an endogenous, B-cell and/or CD4+ T-cell epitope region and wherein the disrupted amino acid does not overlap with the embedded or inserted epitope. Similarly in other embodiments, the Shiga toxin effector polypeptide of the present invention is derived from amino acids 75 to 251 of SEQ ID NO:2, 1 to 241 of SEQ ID NO:2, 1 to 251 of SEQ ID NO:2, or amino acids 1 to 261 of SEQ ID NO:2, wherein the Shiga toxin effector polypeptide comprises at least one embedded or inserted, heterologous T-cell epitope and at least one amino acid is disrupted in an endogenous, B-cell and/or CD4+ T-cell epitope region and wherein the disrupted amino acid does not overlap with the embedded or inserted epitope. Additionally, the Shiga toxin effector polypeptide may be derived from amino acids 75 to 251 of SEQ ID NO:3, 1 to 241 of SEQ ID NO:3, 1 to 251 of SEQ ID NO:3, or amino acids 1 to 261 of SEQ ID NO:3, wherein the Shiga toxin effector polypeptide comprises at least one embedded or inserted, heterologous T-cell epitope and at least one amino acid is disrupted in an endogenous, B-cell and/or CD4+ T-cell epitope region and wherein the disrupted amino acid does not overlap with the embedded or inserted epitope. In certain embodiments, the Shiga toxin effector polypeptide is derived from the polypeptide that comprises, consists essentially of, or consists of (i) amino acids 75 to 251 of any one of SEQ ID NOs: 1-6; (ii) amino acids 1 to 241 of any one of SEQ ID NOs: 1-18; (iii) amino acids 1 to 251 of any one of SEQ ID NOs: 1-6; and (iv) amino acids 1 to 261 of any one of SEQ ID NOs: 1-3, wherein the Shiga toxin effector polypeptide comprises at least one embedded or inserted, heterologous T-cell epitope and at least one amino acid is disrupted in an endogenous, B-cell and/or CD4+ T-cell epitope region and wherein the disrupted amino acid does not overlap with the embedded or inserted epitope. In certain embodiments, the Shiga toxin effector polypeptide is derived from the polypeptide that comprises, consists essentially of, or consists of: (i) amino acids 75 to 251 of SEQ ID NOs: 1-6, (ii) 1 to 241 of SEQ ID NOs: 1-18, (iii) 1 to 251 of SEQ ID NOs: 1-6, or (iv) amino acids 1 to 261 of SEQ ID NOs: 1-3, wherein the Shiga toxin effector polypeptide comprises at least one embedded or inserted, heterologous T-cell epitope and at least one amino acid is disrupted in an endogenous, B-cell and/or CD4+ T-cell epitope region and wherein the disrupted amino acid does not overlap with the embedded or inserted epitope and wherein the embedded or inserted, heterologous T-cell epitope disrupts an additional endogenous, B-cell and/or CD4+ T-cell epitope region.

The combination, Shiga toxin effector polypeptides of the present invention combine the features of their respective sub-regions, such as, e.g., a furin-cleavage motif disruption, individual epitope disruptions, and/or a heterologous T-cell epitope cargo, and these combinations sometimes result in Shiga toxin effector polypeptides with synergistic reductions in immunogenicity as compared to the sum of their partially de-immunized sub-regions. In particular, the exemplary, Shiga toxin effector polypeptides shown in SEQ ID NOs: 19-21 and 75-89 are synergistically de-immunized due to the combination of two or more sub-regions, one of which comprises an embedded, heterologous, T-cell epitope and another of which comprises an endogenous epitope disrupted by one or more amino acid residue substitutions.

In certain embodiments, the combination, de-immunized, protease-cleavage resistant, Shiga toxin effector polypeptides comprising embedded, T-cell epitopes of the present invention comprises one or more substitutions selected from the group of substitutions at native positions in a Shiga toxin A Subunit consisting of K1R and K11R.

In certain embodiments, the combination, de-immunized, protease-cleavage resistant, Shiga toxin effector polypeptides comprising embedded, T-cell epitopes of the present invention comprise, consist of, or consist essentially of one of the polypeptides represented by the polypeptide sequence shown in any one of SEQ ID NOs: 19-21 and 75-89, represented by amino acids 2 to 252 of SEQ ID NO:35, or represented by amino acids 1 to 251 of SEQ ID NO:107.

De-immunized, Shiga toxin effector polypeptides of the present invention which exhibit no cytotoxicity or reduced cytotoxicity at certain concentrations, e.g. Shiga toxin effector polypeptides comprising R179A, may still be useful as de-immunized, Shiga toxin effector polypeptides for delivering exogenous materials into cells. Similarly, CD8+ T-cell hyper-immunized, Shiga toxin effector polypeptides of the present invention which exhibit no cytotoxicity or reduced cytotoxicity at certain concentrations, e.g. a Shiga toxin effector polypeptide comprising an epitope embedded into its catalytic domain (see e.g. WO 2015/113005, Example 1-F), may still be useful for delivering a T-cell epitope(s) to a desired subcellular compartment of a cell in which the Shiga toxin effector polypeptide is present or as a component of a cell-targeting molecule for delivery of a T-cell epitope (s) into a target cell.

E. Examples of Cell-Targeting Molecules of the Present Invention

The Shiga toxin effector polypeptides described herein may be used as components of cell-targeting molecules that target various HER2 target biomolecules and epitopes with the aforementioned. The following examples describe in more detail certain structures of exemplary cell-target molecules of the present invention which target cells physically coupled to HER2 at a cellular surface, e.g. cells which express HER2. The cell-targeting molecule of the present invention may be a HER2-targeting molecule comprising (i) an immunoglobulin binding region capable of specifically binding an extracellular part of HER2/neu/ErbB2, and comprising one or more of: an antibody variable fragment, a single-domain antibody fragment, a single-chain variable fragment, a Fd fragment, an antigen-binding fragment, an autonomous $V_H$ domain, a $V_H$H fragment derived from a camelid antibody, a heavy-chain antibody domain derived from a cartilaginous fish antibody, a VNAR fragment, and an immunoglobulin new antigen receptor; and (ii) a Shiga toxin A Subunit effector polypeptide comprising a Shiga toxin A1 fragment region, wherein the Shiga toxin A subunit effector polypeptide comprises: (a) an embedded or inserted, heterologous, CD8+ T-cell epitope which disrupts an endogenous, B-cell and/or CD4+ T-cell epitope region within the Shiga toxin A1 fragment region; and (b) a disruption of a plurality of endogenous, B-cell and/or CD4+ T-cell epitope regions within the Shiga toxin A1 fragment region which do not overlap with the embedded or inserted, heterologous, CD8+ T-cell epitope; wherein the Shiga toxin A1 fragment region comprises a disrupted furin-cleavage motif at the carboxy-terminus of the Shiga toxin A1 fragment region; wherein the Shiga toxin A subunit effector polypeptide comprises a carboxy-terminal truncation as compared to the carboxy-terminus of a wild-type Shiga toxin A Subunit; wherein the carboxy-terminal truncation results in the removal of one or more endogenous, B-cell and/or CD4+ T-cell epitope regions described herein; wherein the Shiga toxin A subunit effector polypeptide is capable of exhibiting a Shiga toxin effector function (e.g. catalytic activity); wherein the HER2-targeting molecule has reduced B-cell antigenicity or immunogenicity and/or reduced CD4+ T-cell antigenicity or immunogenicity; and wherein the binding region and the Shiga toxin effector polypeptide are fused forming a continuous polypeptide such that the binding region is associated with the carboxy-terminus of the Shiga toxin A subunit effector polypeptide.

Other Structural Variations It is within the scope of the present invention to use fragments, variants, and/or derivatives of the cell-targeting molecules of the present invention which contain a functional binding site to any extracellular part of a target biomolecule, and even more preferably capable of binding a target biomolecule with high affinity (e.g. as shown by $K_D$). For example, any binding region which binds an extracellular part of a target biomolecule with a dissociation constant ($K_D$) of $10^{-5}$ to $10^{-12}$ moles/liter, preferably less than 200 nM, may be substituted for use in making cell-targeting molecules of the invention and methods of the invention.

The skilled worker will recognize that variations may be made to the Shiga toxin effector polypeptides and cell-targeting molecules of the present invention, and polynucleotides encoding any of the former, without diminishing their biological activities, e.g., by maintaining the overall structure and function of the Shiga toxin effector polypeptide, such as in conjunction with one or more 1) endogenous epitope disruptions which reduce antigenic and/or immunogenic potential, 2) furin-cleavage motif disruptions which reduce proteolytic cleavage, and/or 3) embedded or inserted epitopes which reduce antigenic and/or immunogenic potential or are capable of being delivered to a MHC I molecule for presentation on a cell surface. For example, some modifications may facilitate expression, facilitate purification, improve pharmacokinetic properties, and/or improve immunogenicity. Such modifications are well known to the skilled worker and include, for example, a methionine added at the amino-terminus to provide an initiation site, additional amino acids placed on either terminus to create conveniently located restriction sites or termination codons, and biochemical affinity tags fused to either terminus to provide for convenient detection and/or purification. A common modification to improve the immunogenicity of a polypeptide produced using a non-chordate system (e.g. a prokaryotic cell) is to remove, after the production of the polypeptide, the starting methionine residue, which may be formylated during production, such as, e.g., in a bacterial host system, because, e.g., the presence of N-formylmethionine (fMet) might induce undesirable immune responses in chordates.

Also contemplated herein is the inclusion of additional amino acid residues at the amino and/or carboxy termini of a Shiga toxin effector polypeptide of the present invention, a cell-targeting molecule of the present invention, or a proteinaceous component of a cell-targeting molecules of the present invention, such as sequences for epitope tags or other moieties. The additional amino acid residues may be used for various purposes including, e.g., facilitating cloning, facilitating expression, post-translational modification, facilitating synthesis, purification, facilitating detection, and administration. Non-limiting examples of epitope tags and moieties are chitin binding protein domains, enteropeptidase cleavage sites, Factor Xa cleavage sites, FlAsH tags, FLAG tags, green fluorescent proteins (GFP), glutathione-S-transferase moieties, HA tags, maltose binding protein domains, myc tags, polyhistidine tags, ReAsH tags, strep-tags, strep-tag II, TEV protease sites, thioredoxin domains, thrombin cleavage site, and V5 epitope tags.

In certain of the above embodiments, the polypeptide sequence of the Shiga toxin effector polypeptides and/or cell-targeting molecules of the present invention are varied by one or more conservative amino acid substitutions introduced into the polypeptide region(s) as long as all required structural features are still present and the Shiga toxin effector polypeptide is capable of exhibiting any required function(s), either alone or as a component of a cell-targeting molecule. As used herein, the term "conservative substitution" denotes that one or more amino acids are replaced by another, biologically similar amino acid residue. Examples include substitution of amino acid residues with similar characteristics, e.g. small amino acids, acidic amino acids, polar amino acids, basic amino acids, hydrophobic amino acids and aromatic amino acids (see, for example, Table C). An example of a conservative substitution with a residue normally not found in endogenous, mammalian peptides and proteins is the conservative substitution of an arginine or lysine residue with, for example, ornithine, canavanine, aminoethylcysteine, or another basic amino acid. For further information concerning phenotypically silent substitutions in peptides and proteins see, e.g., Bowie J et al., *Science* 247: 1306-10 (1990).

TABLE C

Examples of Conservative Amino Acid Substitutions

| I | II | III | IV | V | VI | VII | VIII | IX | X | XI | XII | XIII | XIV |
|---|----|-----|----|----|----|-----|------|----|----|----|-----|------|-----|
| A | D | H | C | F | N | A | C | F | A | C | A | A | D |
| G | E | K | I | W | Q | G | M | H | C | D | C | C | E |
| P | Q | R | L | Y | S | I | P | W | F | E | D | D | G |
| S | N |   | M | T | L |   |   | Y | G | H | G | E | K |
| T |   |   | V |   | V |   |   |   | H | K | N | G | P |
|   |   |   |   |   |   |   |   |   | I | N | P | H | Q |
|   |   |   |   |   |   |   |   |   | L | Q | S | K | R |
|   |   |   |   |   |   |   |   |   | M | R | T | N | S |
|   |   |   |   |   |   |   |   |   | R | S | V | Q | T |
|   |   |   |   |   |   |   |   |   | T | T |   | R |   |
|   |   |   |   |   |   |   |   |   | V |   |   | S |   |
|   |   |   |   |   |   |   |   |   | W |   |   | P |   |
|   |   |   |   |   |   |   |   |   | Y |   |   | T |   |

In the conservative substitution scheme in Table C, exemplary conservative substitutions of amino acids are grouped by physicochemical properties—I: neutral, hydrophilic; II: acids and amides; III: basic; IV: hydrophobic; V: aromatic, bulky amino acids, VI hydrophilic uncharged, VII aliphatic uncharged, VIII non-polar uncharged, IX cycloalkenyl-associated, X hydrophobic, XI polar, XII small, XIII turn-permitting, and XIV flexible. For example, conservative amino acid substitutions include the following: 1) S may be substituted for C; 2) M or L may be substituted for F; 3) Y may be substituted for M; 4) Q or E may be substituted for K; 5) N or Q may be substituted for H; and 6) H may be substituted for N.

Additional conservative amino acid substitutions include the following: 1) S may be substituted for C; 2) M or L may be substituted for F; 3) Y may be substituted for M; 4) Q or E may be substituted for K; 5) N or Q may be substituted for H; and 6) H may be substituted for N.

In certain embodiments, the Shiga toxin effector polypeptides and cell-targeting molecules of the present invention may comprise functional fragments or variants of a polypeptide region of the present invention described herein that have, at most, 20, 15, 10, 9, 8, 7, 6, 5, 4, 3, 2, or 1 amino acid substitutions compared to a polypeptide sequence recited herein (and which retain at least 85%, 90%, 95%, 96%, 97%, 98%, 99% or more amino acid sequence identity to the polypeptide sequences recited herein), as long as it (1) comprises at least one embedded or inserted, heterologous T-cell epitope and at least one amino acid is disrupted in an endogenous, B-cell and/or CD4+ T-cell epitope region, wherein the disrupted amino acid does not overlap with the embedded or inserted epitope; (2) comprises at least one embedded or inserted, heterologous T-cell epitope and a disrupted furin-cleavage motif at the carboxy-terminus of a Shiga toxin A1 fragment derived region; (3) comprises a disrupted furin-cleavage motif at the carboxy-terminus of a Shiga toxin A1 fragment derived region and comprises at least one amino acid is disrupted in an endogenous, B-cell and/or CD4+ T-cell epitope region, wherein the disrupted amino acid does not overlap with the disrupted furin-cleavage motif; or (4) comprises at least one embedded or inserted, heterologous T-cell epitope, at least one amino acid is disrupted in an endogenous, B-cell and/or CD4+ T-cell epitope region, wherein the disrupted amino acid does not overlap with the embedded or inserted epitope, and a disrupted furin-cleavage motif at the carboxy-terminus of a Shiga toxin A1 fragment derived region. Variants of the Shiga toxin effector polypeptides and cell-targeting molecules of the invention are within the scope of the present invention as a result of changing a polypeptide described herein by altering one or more amino acid residues or deleting or inserting one or more amino acid residues, such as within the binding region or Shiga toxin effector polypeptide region, in order to achieve desired properties, such as changed cytotoxicity, changed cytostatic effects, changed immunogenicity, and/or changed serum half-life. The Shiga toxin effector polypeptides and cell-targeting molecules of the present invention may further be with or without a signal sequence.

Accordingly, in certain embodiments, the cell-targeting molecule of the present invention comprises, consists essentially of, or consists of an amino acid sequence that is at least 85% (such as at least 90%, 91%, 92%, 93%, 94%, 95%, 96%, 97%, 98%, or 99%) identical to the amino acid sequence shown in any one of SEQ ID NOs: 22-36 and 97-108. In certain embodiments, the cell-targeting molecule of the present invention comprises, consists essentially of, or consists of an amino acid sequence that is at least 85% (such as at least 90%, 91%, 92%, 93%, 94%, 95%, 96%, 97%, 98%, 99% or more) identical to the amino acid sequence shown in any one of SEQ ID NOs: 25-31, 34-36, 97-104, and 106-108. In certain embodiments, the cell-targeting molecule of the present invention comprises, consists essentially of, or consists of an amino acid sequence that is at least 85% (such as at least 90%, 91%, 92%, 93%, 94%, 95%, 96%, 97%, 98%, 99% or more) identical to the amino acid sequence shown in any one of SEQ ID NOs: 29, 31, 34, 35, 36, 102, 104, and 106-108. In certain embodiments, the cell-targeting molecule of the present invention comprises, consists essentially of, or consists of an amino acid sequence that is at least 85% (such as at least 90%, 91%, 92%, 93%, 94%, 95%, 96%, 97%, 98%, 99% or more) identical to the amino acid sequence shown in any one of SEQ ID NOs: 29 or 102. In certain embodiments, the cell-targeting molecule of the present invention comprises, consists essentially of, or consists of an amino acid sequence that is at least 85% (such as at least 90%, 91%, 92%, 93%, 94%, 95%, 96%, 97%, 98%, 99% or more) identical to the amino acid sequence shown in any one of SEQ ID NOs: 31 or 104. In certain embodiments, the cell-targeting molecule of the present invention comprises, consists essentially of, or consists of an amino acid sequence that is at least 85% (such as at least 90%, 91%, 92%, 93%, 94%, 95%, 96%, 97%, 98%, 99% or more) identical to the amino acid sequence shown in any one of SEQ ID NOs: 34 or 106. In certain embodiments, the cell-targeting molecule of the present invention comprises, consists essentially of, or consists of an amino acid sequence that is at least 85% (such as at least 90%, 91%, 92%, 93%, 94%, 95%, 96%, 97%, 98%, 99% or more) identical to the amino acid sequence shown in any one of SEQ ID NOs: 35 or 107. In certain embodiments, the cell-targeting molecule of the present invention comprises, consists essentially of, or consists of an amino acid sequence that is at least 85% (such as at least 90%, 91%, 92%, 93%, 94%, 95%, 96%, 97%, 98%, 99% or more) identical to the amino acid sequence shown in any one of SEQ ID NOs: 36 or 108.

Accordingly, in certain embodiments, the Shiga toxin effector polypeptides of the present invention comprise, consists essentially of, or consists of amino acid sequences having at least 55%, 60%, 65%, 70%, 75%, 80%, 85%, 90%, 95%, 97%, 98%, or 99%, overall sequence identity to a naturally occurring (e.g. a wild-type) Shiga toxin A Subunit or fragment thereof, such as, e.g., Shiga toxin A Subunit, such as SLT-1A (SEQ ID NO:1), StxA (SEQ ID NO:2), SLT-2A (SEQ ID NO:3), Stx1cA (SEQ ID NO:4), Stx1dA (SEQ ID NO:5), Stx1eA (SEQ ID NO:6), Stx2cA variant 1 (SEQ ID NO:7), Stx2cA variant 2 (SEQ ID NO:8), Stx2cA variant 3 (SEQ ID NO:9), Stx2cA variant 4 (SEQ ID NO:10), Stx2cA variant 5 (SEQ ID NO:11), Stx2cA variant 6 (SEQ ID NO:12), Stx2dA variant 1 (SEQ ID NO:13), Stx2dA variant 2 (SEQ ID NO:14), Stx2dA variant 3 (SEQ ID NO:15), Stx2eA variant 1 (SEQ ID NO:16), Stx2eA variant 2 (SEQ ID NO:17), and/or Stx2fA (SEQ NO:18), wherein the Shiga toxin effector polypeptide (1) comprises at least one embedded or inserted, heterologous T-cell epitope and at least one amino acid is disrupted in an endogenous, B-cell and/or CD4+ T-cell epitope region, and wherein the disrupted amino acid does not overlap with the embedded or inserted epitope; (2) comprises at least one embedded or inserted, heterologous T-cell epitope and a disrupted furin-cleavage motif at the carboxy-terminus of a Shiga toxin A1 fragment derived region; or (3) comprises a disrupted furin-cleavage motif at the carboxy-terminus of a Shiga toxin A1 fragment derived region and comprises at least one amino acid is disrupted in an endogenous, B-cell and/or CD4+ T-cell epitope region, and wherein the disrupted amino acid does not overlap with the disrupted furin-cleavage motif; or (4) comprises (i) at least one embedded or inserted, heterologous T-cell epitope, (ii) at least one amino acid is disrupted in an endogenous, B-cell and/or CD4+ T-cell epitope region, wherein the disrupted amino acid does not overlap with the embedded or inserted epitope, and (iii) a disrupted furin-cleavage motif at the carboxy-terminus of a Shiga toxin A1 fragment derived region. As described herein, fragments of the Shiga toxin A Subunit may comprise, consist essentially of, or consists of: (i) amino acids 75 to 251 of any one of SEQ ID NOs: 1-6, 37, and 75-89; (ii) amino acids 1 to 241 of any one of SEQ ID NOs: 1-18, 37, and 75-89; (iii) amino acids 1 to 251 of any one of SEQ ID NOs: 1-6, 37 and 75-89; or (iv) amino acids 1 to 261 of any one of SEQ ID NOs: 1-3. For example, the fragments of the Shiga toxin A Subunit may comprise, consist essentially of, or consists of amino acids: (i) 75 to 251 of any one SEQ ID NOs: 75-89, (ii) 1 to 241 of any one of SEQ ID NOs: 75-89, (iii) 1 to 251 of any one of SEQ ID NOs: 75-89, or (iv) 1 to 261 of any one of SEQ ID NOs: 1-3.

In certain embodiments of the Shiga toxin effector polypeptides of the present invention, one or more amino acid residues may be mutated, inserted, or deleted in order to increase the enzymatic activity of the Shiga toxin effector polypeptide. In certain embodiments of the Shiga toxin effector polypeptides of the present invention, one or more amino acid residues may be mutated or deleted in order to reduce or eliminate catalytic and/or cytotoxic activity of the Shiga toxin effector polypeptide. For example, the catalytic and/or cytotoxic activity of the A Subunits of members of the Shiga toxin family may be diminished or eliminated by mutation or truncation.

The cytotoxicity of the A Subunits of members of the Shiga toxin family may be altered, reduced, or eliminated by mutation and/or truncation. The positions labeled tyrosine-77, glutamate-167, arginine-170, tyrosine-114, and tryptophan-203 have been shown to be important for the catalytic activity of Stx, Stx1, and Stx2 (Hovde C et al., *Proc Natl Acad Sci USA* 85: 2568-72 (1988); Deresiewicz R et al., *Biochemistry* 31: 3272-80 (1992); Deresiewicz R et al., *Mol Gen Genet* 241: 467-73 (1993); Ohmura M et al., *Microb Pathog* 15: 169-76 (1993); Cao C et al., *Microbiol Immunol* 38: 441-7 (1994); Suhan M, Hovde C, *Infect Immun* 66: 5252-9 (1998)). Mutating both glutamate-167 and arginine-170 eliminated the enzymatic activity of Slt-I A1 in a cell-free ribosome inactivation assay (LaPointe P et al., *J Biol Chem* 280: 23310-18 (2005)). In another approach using de novo expression of Slt-I A1 in the endoplasmic reticulum, mutating both glutamate-167 and arginine-170 eliminated Slt-I A1 fragment cytotoxicity at that expression level (LaPointe P et al., *J Biol Chem* 280: 23310-18 (2005)). A truncation analysis demonstrated that a fragment of StxA from residues 75 to 268 still retains significant enzymatic activity in vitro (Haddad J et al., *J Bacteriol* 175: 4970-8 (1993)). A truncated fragment of Slt-I A1 containing residues 1-239 displayed significant enzymatic activity in vitro and cytotoxicity by de novo expression in the cytosol (LaPointe P et al., *J Biol Chem* 280: 23310-18 (2005)). Expression of a Slt-I A1 fragment truncated to residues 1-239 in the endoplasmic reticulum was not cytotoxic because it could not retrotranslocate to the cytosol (LaPointe Petal., *J Biol Chem* 280: 23310-18 (2005)).

The most critical residues for enzymatic activity and/or cytotoxicity in the Shiga toxin A Subunits were mapped to the following residue-positions: asparagine-75, tyrosine-77, tyrosine-114, glutamate-167, arginine-170, arginine-176, and tryptophan-203 among others (Di R et al., *Toxicon* 57: 525-39 (2011)). In particular, a double-mutant construct of Stx2A containing glutamate-E167-to-lysine and arginine-176-to-lysine mutations was completely inactivated; whereas, many single mutations in Stx1 and Stx2 showed a 10-fold reduction in cytotoxicity. Further, truncation of Stx1A to 1-239 or 1-240 reduced its cytotoxicity, and similarly, truncation of Stx2A to a conserved hydrophobic residue reduced its cytotoxicity. The most critical residues for binding eukaryotic ribosomes and/or eukaryotic ribosome inhibition in the Shiga toxin A Subunit have been mapped to the following residue-positions arginine-172, arginine-176, arginine-179, arginine-188, tyrosine-189, valine-191, and leucine-233 among others (McCluskey A et al., *PLoS One* 7: e31191 (2012). However, certain modification may increase a Shiga toxin functional activity exhibited by a Shiga toxin effector polypeptide of the present invention. For example, mutating residue-position alanine-231 in Stx1A to glutamate increased Stx1A's enzymatic activity in vitro (Suhan M, Hovde C, *Infect Immun* 66: 5252-9 (1998)).

In certain embodiments of Shiga toxin effector polypeptides of the present invention derived from SLT-1A (SEQ ID NO:1) or StxA (SEQ ID NO:2), the one or more amino acid residues mutated include substitution of the asparagine at position 75, tyrosine at position 77, tyrosine at position 114, glutamate at position 167, arginine at position 170, arginine at position 176, and/or substitution of the tryptophan at position 203. Examples of such substitutions will be known to the skilled worker based on the prior art, such as asparagine at position 75 to alanine, tyrosine at position 77 to serine, substitution of the tyrosine at position 114 to serine, substitution of the glutamate position 167 to glutamate, substitution of the arginine at position 170 to alanine, substitution of the arginine at position 176 to lysine, substitution of the tryptophan at position 203 to alanine, and/or substitution of the alanine at 231 with glutamate. Other mutations which either enhance or reduce Shiga toxin enzymatic activity and/or cytotoxicity are within the scope of the invention and may be determined using well known techniques and assays disclosed herein.

In certain embodiments, the cell-targeting molecule of the present invention may be monovalent and/or monomeric. In certain embodiments, the cell-targeting molecule of the present invention may not be multivalent and/or multimeric. As demonstrated by the Examples of the application, monovalent and/or monomeric forms of certain cell-targeting molecules may exhibit low levels of toxicity when used in vivo while still exhibiting potent cytotoxic to HER2-expressing cells.

The Shiga toxin effector polypeptides and cell-targeting molecules of the present invention may optionally be conjugated to one or more additional agents, which may include therapeutic agents, diagnostic agents, and/or other additional exogenous materials known in the art, including such agents as described herein. In certain embodiments, the Shiga toxin effector polypeptide or cell-targeting molecule of the present invention is PEGylated or albuminated, such as, e.g., to provide de-immunization, disrupt furin-cleavage by masking the extended loop and/or the furin-cleavage motif at the carboxy-terminus of a Shiga toxin A1 fragment derived region, improve pharmacokinetic properties, and/or improve immunogenicity (see e.g., Wang Q et al., *Cancer Res* 53: 4588-94 (1993); Tsutsumi Y et al., *Proc Natl Acad Sci USA* 97: 8548-53 (2000); Buse J, El-Aneed A, *Nanomed* 5: 1237-60 (2010); Lim S et al., *J Control Release* 207-93 (2015)).

V. General Functions of the Cell-Targeting Molecules of the Present Invention

The functional association of Shiga toxin effector polypeptides of the present invention with cell-targeting binding regions enables the creation of cell-targeting molecules which selectively kill, inhibit the growth of, deliver exogenous material to, and/or detect specific cell types. The properties of the Shiga toxin effector polypeptide of the present invention enable the creation of cell-targeting molecules with improved therapeutic windows in chordates as compared to prior Shiga toxin effector polypeptides.

For certain embodiments, the cell-targeting molecule of the present invention provides, after administration to a chordate, one or more of the following: 1) potent and selective killing of targeted cells, e.g., infected or malignant cells, at low administration doses, 2) linkage stability between the cell-targeting binding region and the Shiga toxin effector polypeptide region while the cell-targeting molecule is present in extracellular spaces, 3) low levels of off-target cell deaths and/or unwanted tissue damage, and 4) cell-targeted delivery of heterologous, CD8+ T-cell epitopes for presentation by target cells in order to initiate desirable, T-cell mediated, immune responses, such as, e.g., the recruitment of CD8+ T-cells and the localized release of cytokines at a tissue locus.

The Shiga toxin effector polypeptides and cell-targeting molecules of the present invention are useful in diverse applications involving, e.g., cell-killing; cell growth inhibition; intracellular, cargo delivery; biological information gathering; immune response stimulation; and/or remediation of a health condition. The Shiga toxin effector polypeptides of the present invention are useful as components of various therapeutic and/or diagnostic molecules, such as, e.g. ligand-toxin fusions, immunotoxins, and/or immuno-conjugates. The cell-targeting molecules of the present invention are useful as therapeutic and/or diagnostic molecules, such as, e.g., as cell-targeting, cytotoxic, therapeutic molecules; cell-targeting, nontoxic, delivery vehicles; and/or cell-targeting, diagnostic molecules; for examples in applications involving the in vivo targeting of specific cell types for the diagnosis or treatment of a variety of diseases, including cancers, immune disorders, and microbial infections.

Depending on the embodiment, a Shiga toxin effector polypeptide or cell-targeting molecule of the present invention may have or provide one or more of the following characteristics or functionalities: (1) de-immunization, (2) protease-cleavage resistance, (3) potent cytotoxicity at certain concentrations, (4) intracellular delivery of a cargo consisting of an additional material (e.g. a heterologous, T-cell epitope), (4) selective cytotoxicity, (6) low off-target toxicity in multicellular organisms at certain doses or dosages, (7) delivery of a heterologous, T-cell epitope to the MHC class I presentation pathway of a target cell, and/or (8) stimulation of CD8+ T-cell immune response(s). Certain embodiments of the Shiga toxin effector polypeptides and cell-targeting molecules of the present invention are multifunctional because the molecules have two or more of the characteristics or functionalities described herein. Certain further embodiments of the cell-targeting molecules of the present invention provide all of the aforementioned characteristics and functionalities in a single molecule.

The associating, coupling, and/or linking of a cell-targeting binding region(s) with a Shiga toxin effector polypeptide(s) of the present invention enables the engineering of cell-targeting molecules with Shiga toxin function(s) that can produce less adverse effects after administration at certain doses or dosages to a multicellular organism such as a mammal. Non-limiting examples of adverse effects include off-target toxicities, untargeted cytotoxicities, and/or unwanted immune responses. Certain embodiments of the Shiga toxin effector polypeptides and cell-targeting molecules of the present invention are particularly useful in applications involving administration of a Shiga toxin effector polypeptide and/or cell-targeting molecule to a chordate because of functional properties, such as, e.g., de-immunization, reduced off-target toxicities, and/or targeted stimulation of desirable immune responses such as via cell-surface presentation of a cell-targeting molecule delivered, CD8+ T-cell epitope.

In certain embodiments, the cell-targeting molecules of the present invention are capable of binding extracellular target biomolecules associated with the cell surface of particular cell types and entering those cells. Once internalized within a targeted cell type, certain embodiments of the cell-targeting molecules of the invention are capable of routing an enzymatically active, cytotoxic, Shiga toxin effector polypeptide fragment into the cytosol of the target cell and eventually killing the cell. Alternatively, nontoxic or reduced-toxicity variants of the cell-targeting molecules of the present invention may be used to deliver additional exogenous materials into target cells, such as epitopes, peptides, proteins, polynucleotides, and detection promoting agents. This system is modular, in that any number of diverse binding regions can be used to target a Shiga toxin effector polypeptide of the present invention to various, diverse cell types.

A. De-Immunization for Applications Involving Administration to a Chordate

The de-immunization of the Shiga toxin effector polypeptides of the present invention is accomplished by engineering disruptions of one or more, endogenous, B-cell and/or CD4+ T-cell epitopes regions of a Shiga toxin A Subunit or Shiga toxin effector polypeptide, including via mutation and/or truncation or via the conjugation of a covalently-linked chemical structure. Because B-cell epitopes often coincide or overlap with epitopes of mature CD4+ T-cells, the disruption of an endogenous, B-cell epitope region often simultaneously disrupts an endogenous, CD4+ T-cell epitope or vice versa.

Certain embodiments of the Shiga toxin effector polypeptides and cell-targeting molecules of the present invention are de-immunized with respect to one or more B-cell and/or CD4+ T-cell epitopes meaning that these molecules exhibit reduced antigenic and/or immunogenic potential as compared to prior, Shiga toxin effector polypeptides and cell-targeting molecules lacking identical disruptions to the same B-cell and/or CD4+ T-cell epitope or epitope regions and/or lacking any disruption to the same B-cell and/or CD4+ T-cell epitope(s) or epitope region(s). Certain further embodiments exhibit potent if not wild-type levels of Shiga toxin A Subunit catalytic domain dependent cytotoxicity despite the presence of multiple mutations providing the de-immunized property. The de-immunized, Shiga toxin effector polypeptides and cell-targeting molecules of the present invention are useful for applications involving the parenteral administration of a Shiga toxin effector polypeptide and/or cell-targeting molecule to a chordate such as, e.g., a mammal, amphibian, bird, fish, reptiles, or shark, because of the reduced likelihood of producing undesirable immune responses invoked by the administrated molecule.

The various de-immunized, Shiga toxin effector polypeptides of the present invention might differ in their antigenicity profiles when administered to various chordate species, but all the de-immunized polypeptides of the invention exhibit reduced antigenicity and/or immunogenicity in at least one organism as measured by at least one quantitative assay. In particular, certain embodiments of the cell-targeting molecules of the present invention are de-immunized with respect to a mammalian recipient, such as, e.g., the molecule invokes lower quantities and/or frequencies of "anti-cell-targeting molecule" antibodies when administered to that mammal as compared to a reference molecule (e.g. a related cell-targeting molecule comprising a wild-type Shiga toxin A1 fragment). In addition, Shiga toxin effector polypeptides of the present invention having disruptions of multiple, endogenous, epitope regions are expected to more greatly reduced the probability of the occurrence of undesirable immune responses in a chordate recipient of such a polypeptide.

For certain embodiments of the Shiga toxin effector polypeptides and cell-targeting molecules of the present invention, the de-immunization property(ies) is a result of the structural change(s) which include the disrupted furin-cleavage motif at the carboxy-terminus of a Shiga toxin A1 fragment derived region.

For certain embodiments of the Shiga toxin effector polypeptides and cell-targeting molecules of the present invention, the de-immunization property(ies) is a result of the structural change(s) which include the embedding and/or inserting of a T-cell epitope which disrupts an endogenous, B-cell and/or CD4+ T-cell epitope region.

For certain embodiments, the desired biological function(s) of the parental, Shiga toxin polypeptide from which the de-immunized, Shiga toxin effector polypeptide was derived are preserved, such as, e.g., the Shiga toxin A Subunit functions of promoting cellular internalization, directing intracellular routing, and potent cytotoxicity. Preservation refers to the retention of a minimal level of activity as described herein.

B. Reduced Protease-Cleavage Sensitivity

Certain embodiments of the Shiga toxin effector polypeptides and cell-targeting molecules of the present invention exhibit reduced protease-cleavage sensitivity as compared to related molecules comprising wild-type, Shiga toxin A1 fragment regions. Certain further embodiments exhibit potent if not optimal, Shiga toxin A Subunit catalytic domain dependent cytotoxicity despite this reduced protease-cleavage sensitivity and lack of a canonical furin-cleavage event within an intoxicated cell.

Certain embodiments of the protease-cleavage resistant, cell-targeting molecules of the present invention (i.e. a cell-targeting molecule comprising a Shiga toxin effector polypeptide comprising a disrupted furin-cleavage motif at the carboxy-terminus of its Shiga toxin A1 fragment region) exhibit improved in vivo tolerability as compared to related molecules comprising a wild-type, Shiga toxin A 1 fragment region. Certain further embodiments exhibit potent if not optimal, Shiga toxin A Subunit catalytic domain dependent cytotoxicity despite this reduced protease-cleavage sensitivity and lack of a canonical furin-cleavage event within an intoxicated cell.

Previously, it was believed that cytotoxic, Shiga toxin A Subunit constructs comprising Shiga toxin A1 fragment catalytic regions must maintain or somehow compensate for the naturally occurring proteolytic processing by furin within intoxicated cells in order to preserve the Shiga toxin's natural adaptations for efficient and potent cytotoxicity. It was unexpectedly discovered that the furin cleavage event was not required for potent cytotoxicity because potent Shiga toxin cytotoxicity at the level of a wild-type Shiga toxin control construct was achieved in the absence of any furin cleavage event at the carboxy-terminus of the Shiga toxin A1 fragment despite the presence of a carboxy-terminal moiety (see e.g. WO 2015/191764; WO 2016/196344). The lack of a furin-cleavage event within the intoxicated cell may prevent the efficient liberation of a Shiga toxin A1 fragment-like region and, thus, result in the continued linkage of a relatively large moiety (e.g. greater than 28 kDa in size) to the Shiga toxin A1 fragment region. However despite this possibility, potent, Shiga toxin cytotoxicity was achieved with furin-cleavage deficient constructs comprising a Shiga toxin effector polypeptide region and lacking any known compensatory feature(s), such as, e.g., providing intracellular cleavage proximal to the carboxy-terminus of a Shiga toxin A1 fragment derived region (see e.g. WO 2015/191764; WO 2016/196344).

This suggests that the persistence and/or inefficient release of a relatively large, molecular moiety linked to the A1 fragment region did not necessarily reduce the potency of Shiga toxin cytotoxicity. This was surprising because the optimal Shiga toxin intoxication process was thought to require liberation of the Shiga toxin A1 fragments from all other large molecular moieties to efficiently retrotranslocate liberated A1 fragments from the endoplasmic reticulum to the cytosol where the A1 fragments can form an enzymatically active structure that catalytically inactivates the intoxicated cell's ribosomes. In particular, the persistence and/or inefficient release of a relatively large molecular moiety covering the carboxy-terminus of the Shiga toxin A1 fragment was expected to interfere with the Shiga toxin A1 fragment's natural mechanism of efficiently gaining access to the cytosol, which involves the exposure of the A1 fragment's, hydrophobic, carboxy-terminal domain and recognition of this domain by the ERAD system (see Di R et al., Toxicon 57: 525-39 (2011); Li S et al., *PLoS One* 7: e41119 (2012)).

The lack of an intoxicated-cell-mediated, furin-cleavage event for a molecule comprising a Shiga toxin A Subunit derivative may be hypothetically compensated for. Non-limiting examples of potential, compensatory approaches include 1) terminating one carboxy-terminus of the construct with the carboxy-terminus of a Shiga toxin A1 fragment-like polypeptide region, 2) producing the Shiga toxin derived construct such that the Shiga toxin A Subunit polypeptide is already nicked near the carboxy-terminus of its Shiga toxin A 1 fragment-like polypeptide, 3) engineering a heterologous and/or ectopic protease site that can functionally substitute for the lack of the native, Shiga toxin, furin-cleavage event, and 4) a combination of approach 3 and 4.

In the first approach, the carboxy-terminus of the Shiga toxin A1 fragment-like polypeptide is not covered by any carboxy-terminal moiety, and, thus, the carboxy-terminus of the Shiga toxin A1 fragment-like polypeptide is permanently exposed for recognition by the ERAD machinery in the endoplasmic reticulum. In the last three approaches, the Shiga toxin A1 fragment-like polypeptide can be designed to intracellularly dissociate from one or more other components of the construct by the time the molecule reaches the endoplasmic reticulum of an intoxicated cell such that in the endoplasmic reticulum the carboxy-terminus of the Shiga toxin A 1 fragment-like polypeptide becomes exposed for recognition by the ERAD machinery. For example, a cytotoxic molecule comprising a Shiga toxin A Subunit effector polypeptide could be pretreated with a protease to nick the polypeptide region near the carboxy terminus of the A1 fragment-like region prior to contacting a target cell. Alternatively, the cytotoxic molecule could be engineered to comprise a protease site which is cleaved by an intracellular protease of the target cell.

These hypothetical approaches for designing Shiga toxin A Subunit effector polypeptides which compensate for the lack of an intoxicated-cell-mediated, furin-cleavage event may significantly alter the efficiency and potency of cytotoxicity as compared to a wild-type Shiga holotoxin or Shiga toxin A Subunit construct comprising only wild-type sequences which include the optimal, naturally occurring, furin-cleavage site. For example, currently no compensatory approach relying on a target cell endoprotease other than furin is known which can provide fully compensatory cytotoxicity equivalent to furin cleavage and alternative cellular proteases to furin like calpains have been shown to be less efficient in facilitating Shiga toxin cytotoxicity (Garred O et al., *Exp Cell Res* 218: 39-49 (1995); Garred O et al., *J Biol Chem* 270: 10817-21 (1995); Kurmanova A et al., *Biochem Biophys Res Commun* 357: 144-9 (2007)).

The present invention provides furin-cleavage resistant Shiga toxin A Subunit effector polypeptides which are potently cytotoxic, whether due to compensation for a lack of a furin cleavage event within the intoxicated cell or due to some unexplained reason. Certain cell-targeting molecules of the present invention are at least as efficiently and potently cytotoxic as cell-targeting molecules comprising protease-cleavage sensitive, wild-type Shiga toxin effector polypeptide regions (see e.g. WO 2016/196344).

C. Improved Stability and In Vivo Tolerability

In certain embodiments, the molecules of the present invention (e.g. cell-targeting molecules of the invention) exhibit increased stability and/or improved in vivo tolerability as compared to more furin-cleavage sensitive analogs and/or less de-immunized analogs (an analog being a closely related molecule lacking one or more structural features of the present invention).

The increased stability of a cell-targeting molecule compared to a reference molecule can be exhibited in vitro and/or in vivo. The stability of a therapeutic or diagnostic molecule over time is an important feature and can affect for which applications the molecule may be practically employed. Molecular stability includes in vitro and in vivo, such as, e.g., stability within an organism after administration and during storage over a range of temperatures and concentrations. For certain immunotoxins or ligand-toxin fusions, the stability of the linkage between the toxin and other components can affect the amount of non-specific toxicity caused by the presence and/or quantity of untargeted toxin over time within the organism.

Certain cell-targeting molecules of the present invention exhibit reduced non-specific toxicity in vivo, manifested as increased in vivo tolerability as compared to more protease-cleavage sensitive variants. In vivo tolerability can be determined by the skilled worker using techniques known in the art and/or described herein. In addition to assessing in vivo tolerability using mortality, signs of morbidity may be used for assessing in vivo tolerability, such as, e.g., aspects of body weight, physical appearance, measureable clinical signs, unprovoked behavior, and responses to external stimuli (see e.g. Morton D, Griffiths P, *Vet Rec* 116: 431-43 (1985); *Montgomery C, Cancer Bull* 42: 230-7 (1990); Ullman-Culleré M, Foltz C, *Lab Anim Sci* 49: 319-23 (1999); Clingerman K, Summers L, *J Am Assoc Lab Anim Sci* 51: 31-6 (2012)). Euthanasia may be used in response to signs of morbidity and/or morbundity and, thus, create a mortality time-point. For example, a decrease in body weight of 15-20% in 2-3 days can be used as a sign of morbidity in rodents and as a justification for euthanization (see e.g. Institute of Laboratory Animal Research 2011. *Guide for the care and use of laboratory animals*, 8th ed., Washington, D.C., U.S.: National Academies Press).

The improved in vivo tolerability observed for exemplary, cell-targeting molecules of the present invention as compared to more furin-cleavage sensitive analogs suggests that much higher doses of these cell-targeting molecules of the invention may be safely administered to mammals as compared to the doses of related molecules comprising a furin-cleavage sensitive, Shiga toxin effector polypeptide region. Certain cell-targeting molecules of the invention might exhibit reduced non-specific toxicity as compared to more protease sensitive variants because the protease resistance serves to protect and preserve the linkage between the Shiga toxin effector component and the cell-targeting moiety component.

In addition, in vivo tolerability for cell-targeting molecules of the present invention may be related to the de-immunization properties of a given cell-targeting molecule. Thus, higher doses of such de-immunized, cell-targeting molecules of the invention may be safely administered to mammals as compared to the doses of related molecules comprising an "un-de-immunized" or less de-immunized, Shiga toxin effector polypeptide (e.g. a wild-type Shiga toxin A1 fragment).

In addition, certain molecules of the invention exhibit increased half-lives, both in vitro and/or in vivo, as compared to more protease-cleavage sensitive variants. Molecular stability can be assayed by determining the half-life of a molecule of interest with regard to the association of its components. Certain embodiments of the molecules of the invention will have longer half-lives as compared to furin-cleavage sensitive variants, especially with regard to the continued association of the Shiga toxin effector polypeptide component and one or more other components. For example, certain embodiments of the molecules of the invention will have longer half-lives with regard to the continued association of the Shiga toxin effector polypeptide component and another component, e.g. a cell-targeting binding region, as compared to a furin-cleavage sensitive variant wherein the furin-cleavage sensitive site(s) lies between those two components.

D. Cell-Kill via Shiga Toxin A Subunit Cytotoxicity

Certain embodiments of the Shiga toxin effector polypeptides and cell-targeting molecules of the present invention are cytotoxic. Certain further embodiments of the cell-targeting molecules of the present invention are cytotoxic only due to the presence of one or more Shiga toxin effector polypeptide components. The A Subunits of members of the Shiga toxin family each comprise an enzymatically active polypeptide region capable of killing a eukaryotic cell once in the cell's cytosol. Because members of the Shiga toxin family are adapted to killing eukaryotic cells, molecules derived from Shiga toxins, such as, e.g., molecules comprising certain embodiments of the Shiga toxin effector polypeptides of the present invention can exhibit potent cell-kill activities.

For certain embodiments of the cell-targeting molecules of the present invention, upon contacting a cell physically coupled with an extracellular target biomolecule of the binding region of the cell-targeting molecule (e.g. a target positive cell), the cell-targeting molecule is capable of causing death of the cell. For certain further embodiments, the CD50 value of the cell-targeting molecule is less than 5, 2.5, 1, 0.5, or 0.25 nM, which is vastly more potent than an untargeted, wild-type, Shiga toxin effector polypeptide (e.g. SEQ ID NOs: 1-18).

Cell-kill may be accomplished using a molecule of the present invention under varied conditions of target cells, such as, e.g., an ex vivo manipulated target cell, a target cell cultured in vitro, a target cell within a tissue sample cultured in vitro, or a target cell in an in vivo setting like within a multicellular organism.

In certain embodiments, the Shiga toxin effector polypeptides and cell-targeting molecules of the present invention comprise (1) a de-immunized, Shiga toxin effector sub-region, (2) a protease-cleavage resistant region near the carboxy-terminus of a Shiga toxin A1 fragment derived region, (3) a carboxy-terminal, endoplasmic reticulum retention/retrieval signal motif; and/or (4) a heterologous, T-cell epitope embedded or inserted region; however, for certain further embodiments, these structural modifications do not significantly alter the potency of Shiga toxin cytotoxicity as compared to a reference molecules comprising a wild-type Shiga toxin A Subunit polypeptide, such as, e.g., a wild-type Shiga toxin A1 fragment. Thus, Shiga toxin effector polypeptides and cell-targeting molecules of the present invention which are de-immunized, protease cleavage resistant, and/or carrying embedded or inserted, heterologous, epitopes can maintain potent cytotoxicity while providing one or more various other functionalities or properties.

Already cytotoxic cell-targeting molecules comprising Shiga toxin effector polypeptides may be engineered by the skilled worker using the information and methods provided herein to be more cytotoxic and/or to have redundant, backup cytotoxicities operating via completely different mechanisms. These multiple cytotoxic mechanisms may complement each other by their diversity of functions (such as by providing potent killing via two mechanisms of cell-killing, direct and indirect, as well as mechanisms of immuno-stimulation to the local area), redundantly backup each other (such as by providing one cell-killing mechanism in the absence of the other mechanisms—like if a target cell is resistant to or acquires some immunity to a subset of previously active mechanisms), and/or protect against developed resistance (by limiting resistance to the less probable situation of the malignant or infected cell blocking multiple, different cell-killing mechanisms simultaneously).

E. Delivery of a T-Cell Epitope for MHC Class I Presentation on a Cell Surface

In certain embodiments, the Shiga toxin effector polypeptides and cell-targeting molecules of the present invention comprise a T-cell epitope, which enables the engineering of "T-cell epitope delivering" molecules with virtually unlimited choices of epitope-peptide cargos for delivery and cell-surface presentation by a nucleated, chordate cell. For certain embodiments, the Shiga toxin effector polypeptides and cell-targeting molecules of the present invention are each capable of delivering one or more T-cell epitopes, associated with the Shiga toxin effector polypeptides and/or cell-targeting molecules, to the proteasome of a cell. The delivered T-cell epitope are then proteolytic processed and presented by the MHC class I pathway on the surface of the cell. By engineering MHC class I epitopes into cell-targeting molecules, the targeted delivery and presentation of immuno-stimulatory antigens may be accomplished in order to harness and direct a beneficial function(s) of a chordate immune system.

For certain embodiments, the cell-targeting molecule of the present invention is capable of delivering a T-cell epitope to a MHC class I molecule of a cell for cell-surface presentation. In certain embodiments, the Shiga toxin effector polypeptide or cell-targeting molecule of the present invention comprises a heterologous, T-cell epitope, whether as an additional exogenous material or embedded or inserted within a Shiga toxin effector polypeptide. For certain further embodiments, the Shiga toxin effector polypeptide or cell-targeting molecule of the present invention is capable of delivering an embedded or inserted T-cell epitope to a MHC class I molecule for cell-surface presentation.

For certain embodiments, the Shiga toxin effector polypeptide of the present invention is capable of delivering a T-cell epitope, which is embedded or inserted in the Shiga toxin effector polypeptide, to a MHC class I molecule of a cell in which the Shiga toxin effector polypeptide is present for presentation of the T-cell epitope by the MHC class I molecule on a surface of the cell. For certain further embodiments, the T-cell epitope is a heterologous, T-cell epitope. For certain further embodiments, the T-cell epitope functions as CD8+ T-cell epitope, whether already known or identified in the future using methods which are currently routine to the skilled worker.

For certain embodiments, the cell-targeting molecule of the present invention is capable of delivering a T-cell epitope, which is associated with the cell-targeting molecule, to a MHC class I molecule of a cell for presentation of the T-cell epitope by the MHC class I molecule on a surface of the cell. For certain further embodiments, the T-cell epitope is a heterologous, T-cell epitope which is embedded or inserted in the Shiga toxin effector polypeptide. For certain further embodiments, the T-cell epitope functions as CD8+ T-cell epitope, whether already known or identified in the future using methods which are currently routine to the skilled worker.

For certain embodiments, upon contacting a cell with the cell-targeting molecule of the present invention, the cell-targeting molecule is capable of delivering a T-cell epitope-peptide, which is associated with the cell-targeting molecule, to a MHC class I molecule of the cell for presentation of the T-cell epitope-peptide by the MHC class I molecule on a surface of the cell. For certain further embodiments, the T-cell epitope-peptide is a heterologous epitope which is embedded or inserted in a Shiga toxin effector polypeptide. For certain further embodiments, the T-cell epitope-peptide functions as CD8+ T-cell epitope, whether already known or identified in the future using methods which are currently routine to the skilled worker.

The addition of a heterologous epitope into or presence of a heterologous epitope in a cell-targeting molecule of the present invention, whether as an additional exogenous material or embedded or inserted within a Shiga toxin effector polypeptide, enables methods of using such cell-targeting molecules for the cell-targeted delivery of a chosen epitope for cell-surface presentation by a nucleated, target cell within a chordate.

One function of certain, CD8+ T-cell hyper-immunized, Shiga toxin effector polypeptides and cell-targeting molecules of the present invention is the delivery of one or more T-cell epitope-peptides to a MHC class I molecule for MHC class I presentation by a cell. Delivery of exogenous, T-cell epitope-peptides to the MHC class I system of a target cell can be used to induce the target cell to present the T-cell epitope-peptide in association with MHC class I molecules on the cell surface, which subsequently leads to the activation of CD8+ effector T-cells to attack the target cell.

The skilled worker, using techniques known in the art, can associate, couple, and/or link certain, Shiga toxin effector polypeptides of the present invention to various other cell-targeting binding region to create cell-targeting molecules of the present invention which target specific, extracellular, target biomolecules physically coupled to cells and promote target-cell internalization of these cell-targeting molecules. All nucleated vertebrate cells are believed to be capable of presenting intracellular epitopes using the MHC class I system. Thus, extracellular target biomolecules of the cell-targeting molecules of the invention may in principle target any nucleated vertebrate cell for T-cell epitope delivery to a MHC class I presentation pathway of such a cell.

The epitope-delivering functions of the Shiga toxin effector polypeptides and cell-targeting molecules of the present invention can be detected and monitored by a variety of standard methods known in the art to the skilled worker and/or described herein. For example, the ability of cell-targeting molecules of the present invention to deliver a T-cell epitope-peptide and drive presentation of the epitope-peptide by the MHC class I system of target cells may be investigated using various in vitro and in vivo assays, including, e.g., the direct detection/visualization of MHC class I/peptide complexes, measurement of binding affinities for the heterologous, T-cell epitope-peptide to MHC class I molecules, and/or measurement of functional consequences of MHC class I-peptide complex presentation on target cells by monitoring cytotoxic T-lymphocyte (CTL) responses (see e.g. Examples, infra).

Certain assays to monitor this function of the polypeptides and molecules of the present invention involve the direct detection of a specific MHC class I/peptide antigen complex in vitro or ex vivo. Common methods for direct visualization and quantitation of peptide-MHC class I complexes involve various immuno-detection reagents known to the skilled worker. For example, specific monoclonal antibodies can be developed to recognize a particular MHC/class I/peptide antigen complex. Similarly, soluble, multimeric T cell receptors, such as the TCR-STAR reagents (Altor Bioscience Corp., Mirmar, Fla., U.S.) can be used to directly visualize or quantitate specific MHC I/antigen complexes (Zhu X et al., *J Immunol* 176: 3223-32 (2006)). These specific mAbs or soluble, multimeric T-cell receptors may be used with various detection methods, including, e.g. immunohistochemistry, flow cytometry, and enzyme-linked immuno assay (ELISA).

An alternative method for direct identification and quantification of MHC I/peptide complexes involves mass spectrometry analyses, such as, e.g., the ProPresent Antigen Presentation Assay (ProImmune, Inc., Sarasota, Fla., U.S.) in which peptide-MCH class I complexes are extracted from the surfaces of cells, then the peptides are purified and identified by sequencing mass spectrometry (Falk K et al., *Nature* 351: 290-6 (1991)).

In certain assays to monitor the T-cell epitope delivery and MHC class I presentation function of the polypeptides and molecules of the present invention involve computational and/or experimental methods to monitor MHC class I and peptide binding and stability. Several software programs are available for use by the skilled worker for predicting the binding responses of peptides to MHC class I alleles, such as, e.g., The Immune Epitope Database and Analysis Resource (IEDB) Analysis Resource MHC-I binding prediction Consensus tool (Kim Y et al., *Nucleic Acid Res* 40: W525-30 (2012). Several experimental assays have been routinely applied, such as, e.g., cell surface binding assays and/or surface plasmon resonance assays to quantify and/or compare binding kinetics (Miles K et al., *Mol Immunol* 48: 728-32 (2011)). Additionally, other MHC-peptide binding assays based on a measure of the ability of a peptide to stabilize the ternary MHC-peptide complex for a given MHC class I allele, as a comparison to known controls, have been developed (e.g., MHC-peptide binding assay from ProImmmune, Inc.).

Alternatively, measurements of the consequence of MHC class I/peptide antigen complex presentation on the cell surface can be performed by monitoring the cytotoxic T-cell (CTL) response to the specific complex. These measurements by include direct labeling of the CTLs with MHC class I tetramer or pentamer reagents. Tetramers or pentamers bind directly to T cell receptors of a particular specificity, determined by the Major Histocompatibility Complex (MHC) allele and peptide complex. Additionally, the quantification of released cytokines, such as interferon gamma or interleukins by ELISA or enzyme-linked immunospot (ELIspot) is commonly assayed to identify specific CTL responses. The cytotoxic capacity of CTL can be measured using a number of assays, including the classical 51 Chromium (Cr) release assay or alternative non-radioactive cytotoxicity assays (e.g., CytoTox96® non-radioactive kits and CellTox™ CellTiter-GLO® kits available from Promega Corp., Madison, Wis., U.S.), Granzyme B ELISpot, Caspase Activity Assays or LAMP-1 translocation flow cytometric assays. To specifically monitor the killing of target cells, carboxyfluorescein diacetate succinimidyl ester (CFSE) can be used to easily and quickly label a cell population of interest for in vitro or in vivo investigation to monitor killing of epitope specific CSFE labeled target cells (Durward M et al., *J Vis Exp* 45 pii 2250 (2010)).

In vivo responses to MHC class I presentation can be followed by administering a MHC class I/antigen promoting agent (e.g., a peptide, protein or inactivated/attenuated virus vaccine) followed by challenge with an active agent (e.g. a virus) and monitoring responses to that agent, typically in comparison with unvaccinated controls. Ex vivo samples can be monitored for CTL activity with methods similar to those described previously (e.g. CU cytotoxicity assays and quantification of cytokine release).

HLA-A, HLA-B, and/or HLA-C molecules are isolated from the intoxicated cells after lysis using immune affinity (e.g., an anti-MHC antibody "pulldown" purification) and the associated peptides (i.e., the peptides presented by the isolated MHC molecules) are recovered from the purified complexes. The recovered peptides are analyzed by sequencing mass spectrometry. The mass spectrometry data is compared against a protein database library consisting of the sequence of the exogenous (non-self) peptide (T-cell epitope X) and the international protein index for humans (representing "self" or non-immunogenic peptides). The peptides are ranked by significance according to a probability database. All detected antigenic (non-self) peptide sequences are listed. The data is verified by searching against a scrambled decoy database to reduce false hits (see e.g. Ma B, Johnson R, *Mol Cell* Proteomics 11: 0111.014902 (2012)). The results will demonstrate that peptides from the T-cell epitope X are presented in MHC complexes on the surface of intoxicated target cells.

The set of presented peptide-antigen-MHC complexes can vary between cells due to the antigen-specific HLA molecules expressed. T-cells can then recognize specific peptide-antigen-MHC complexes displayed on a cell surface using different TCR molecules with different antigen-specificities.

Because multiple T-cell epitopes may be delivered by a cell-targeting molecule of the invention, such as, e.g., by embedding two or more different T-cell epitopes in a single proteasome delivering effector polypeptide, a single cell-targeting molecule of the invention may be effective chordates of the same species with different MHC class variants, such as, e.g., in humans with different HLA alleles. This may allow for the combining within a single molecule of different T-cell epitopes with different effectiveness in different subpopulations of subjects based on MHC complex protein diversity and polymorphisms. For example, human MHC complex proteins, HLA proteins, vary among humans based on genetic ancestry, e.g. African (sub-Saharan), Amerindian, Caucasoid, Mongoloid, New Guinean and Australian, or Pacific islander.

The applications involving the T-cell epitope delivering polypeptides and molecules of the present invention are vast. Every nucleated cell in a mammalian organism may be capable of MHC class I pathway presentation of immunogenic, T-cell epitope-peptides on their cell outer surfaces complexed to MHC class I molecules. In addition, the sensitivity of T-cell epitope recognition is so exquisite that only a few MHC-I peptide complexes are required to be presented to result in an immune response, e.g., even presentation of a single complex can be sufficient for recognition by an effector T-cell (Sykulev Y et al., *Immunity* 4: 565-71 (1996)).

The activation of T-cell responses are desired characteristics of certain anti-cancer, anti-neoplastic, anti-tumor, and/or anti-microbial biologic drugs to stimulate the patient's own immune system toward targeted cells. Activation of a robust and strong T-cell response is also a desired characteristic of many vaccines. The presentation of a T-cell epitope by a target cell within an organism can lead to the activation of robust immune responses to a target cell and/or its general locale within an organism. Thus, the targeted delivery of a T-cell epitope for presentation may be utilized for as a mechanism for activating T-cell responses during a therapeutic regime.

The presentation of a T-cell immunogenic epitope-peptide by the MHC class I system targets the presenting cell for killing by CTL-mediated lysis and also triggers immune stimulation in the local microenvironment. By engineering immunogenic epitope sequences within Shiga toxin effector polypeptide components of target-cell-internalizing therapeutic molecules, the targeted delivery and presentation of immuno-stimulatory antigens may be accomplished. The presentation of immuno-stimulatory non-self antigens, such as e.g. known viral antigens with high immunogenicity, by target cells signals to other immune cells to destroy the target cells as well as to recruit more immune cells to the area.

The presentation of an immunogenic, T-cell epitope-peptide by the MHC class I complex targets the presenting cell for killing by CTL-mediated cytolysis. The presentation by targeted cells of immuno-stimulatory non-self antigens, such as, e.g., known viral epitope-peptides with high immunogenicity, can signal to other immune cells to destroy the target cells and recruit more immune cells to the target cell site within a chordate.

Thus, already cytotoxic molecules, such as e.g. therapeutic or potentially therapeutic molecules comprising Shiga toxin effector polypeptides, may be engineered using methods of the present invention into more cytotoxic molecules and/or to have an additional cytotoxic mechanism operating via delivery of a T-cell epitope, presentation, and stimulation of effector T-cells. These multiple cytotoxic mechanisms may complement each other (such as by providing both direct target-cell-killing and indirect (CTL-mediated) cell-killing, redundantly backup each other (such as by providing one mechanism of cell-killing in the absence of the other), and/or protect against the development of therapeutic resistance (by limiting resistance to the less probable situation of the malignant or infected cell evolving to block two different cell-killing mechanisms simultaneously).

In addition, a cytotoxic molecule comprising a Shiga toxin effector polypeptide region that exhibits catalytic-based cytotoxicity may be engineered by the skilled worker using routine methods into enzymatically inactive variants. For example, the cytotoxic Shiga toxin effector polypeptide component of a cytotoxic molecule may be conferred with reduced activity and/or rendered inactive by the introduction of one or mutations and/or truncations such that the resulting molecule can still be cytotoxic via its ability to deliver a T-cell epitope to the MHC class I system of a target cell and subsequent presentation to the surface of the target cell. In another example, a T-cell epitope may be inserted or embedded into a Shiga toxin effector polypeptide such that the Shiga toxin effector polypeptide is inactivated by the added epitope (see e.g. WO 2015/113005). This approach removes one cytotoxic mechanism while retaining or adding another and may also provide a molecule capable of exhibiting immuno-stimulation to the local area of a target cell(s) within an organism via delivered T-cell epitope presentation or "antigen seeding." Furthermore, non-cytotoxic variants of the cell-targeting molecules of the present invention which comprise embedded or inserted, heterologous, T-cell epitopes may be useful in applications involving immune-stimulation within a chordate and/or labeling of target cells within a chordate with MHC class I molecule displayed epitopes.

The ability to deliver a T-cell epitope of certain Shiga toxin effector polypeptides and cell-targeting molecules of the present invention may be accomplished under varied conditions and in the presence of non-targeted bystander cells, such as, e.g., an ex vivo manipulated target cell, a target cell cultured in vitro, a target cell within a tissue sample cultured in vitro, or a target cell in an in vivo setting like within a multicellular organism.

F. Cell-Kill via Targeted Cytotoxicity and/or Engagement of Cytotoxic T-Cells

For certain embodiments, the cell-targeting molecule of the present invention can provide 1) delivery of a T-cell epitope for MHC class I presentation by a target cell and/or 2) potent cytotoxicity. For certain embodiments of the cell-targeting molecules of the present invention, upon contacting a cell physically coupled with an extracellular target biomolecule of the cell-targeting binding region, the cell-targeting molecule of the invention is capable of causing death of the cell. The mechanism of cell-kill may be direct, e.g. via the enzymatic activity of a toxin effector polypeptide region, or indirect via CTL-mediated cytolysis.

1. Indirect Cell-Kill via T-Cell Epitope Delivery and MHC Class I Presentation

Certain embodiments of the cell-targeting molecules of the present invention are cytotoxic because they comprise a CD8+ T-cell epitope capable of being delivered to the MHC class I presentation pathway of a target cell and presented on a cellular surface of the target cell. For example, T-cell epitope delivering, CD8+ T-cell hyper-immunized, Shiga toxin effector polypeptides of the present invention, with or without endogenous epitope de-immunization, may be used as components of cell-targeting molecules for applications involving indirect cell-killing.

In certain embodiments of the cell-targeting molecules of the present invention, upon contacting a cell physically coupled with an extracellular target biomolecule of the cell-targeting binding region, the cell-targeting molecule of the invention is capable of indirectly causing the death of the cell, such as, e.g., via the presentation of one or more T-cell epitopes by the target cell and the subsequent recruitment of CTLs which kill the target cell.

The presentation of an antigenic peptide complexed with a MHC class I molecule by a cell sensitizes the presenting cell to targeted killing by cytotoxic T-cells (CTLs) via the induction of apoptosis, lysis, and/or necrosis. In addition, the CTLs which recognize the target cell may release immuno-stimulatory cytokines, such as, e.g., interferon gamma (IFN-gamma), tumor necrosis factor alpha (TNF), macrophage inflammatory protein-1 beta (MIP-1beta), and interleukins such as IL-17, IL-4, and IL-22. Furthermore, CTLs activated by recognition of a presented epitope may indiscriminately kill other cells proximal to the presenting cell regardless of the peptide-MHC class I complex repertoire presented by those proximal cells (Wiedemann A et al., *Proc Natl Acad Sci USA* 103: 10985-90 (2006)).

Because of MHC allele diversity within different species, a cell-targeting molecule of the present invention comprising only a single epitope may exhibit varied effectiveness to different patients or subjects of the same species. However, certain embodiments of the cell-targeting molecules of the present invention may each comprise multiple, T-cell epitopes that are capable of being delivered to the MHC class I system of a target cell simultaneously. Thus, for certain embodiments of the cell-targeting molecules of the present invention, a cell-targeting molecule is used to treat different subjects with considerable differences in their MHC molecules' epitope-peptide binding affinities (i.e. considerable differences in their MHC alleles and/or MHC genotypes). In addition, certain embodiments of the cell-targeting molecules of the present invention reduce or prevent target cell adaptations to escape killing (e.g. a target cancer cell mutating to escape therapeutic effectiveness or "mutant escape") by using multiple cell-killing mechanisms simultaneously (e.g. direct killing and indirect killing via multiple different T-cell epitopes simultaneously).

2. Direct Cell-Kill via Cell-Targeted, Shiga Toxin Cytotoxicity

Certain embodiments of the cell-targeting molecules of the present invention are cytotoxic because they comprise a catalytically active, Shiga toxin effector polypeptide and regardless of the presence of an immunogenic, CD8+ T-cell epitope in the molecule. For example, CD8+ T-cell hyper-immunized, Shiga toxin effector polypeptides of the present invention, with or without endogenous epitope de-immunization, may be used as components of cell-targeting molecules for applications involving direct cell-killing, such as, e.g., via the ribotoxic, enzymatic activity of a Shiga toxin effector polypeptide or ribosome binding and interference with ribosome function due to a non-catalytic mechanism(s).

For certain embodiments of the CD8+ T-cell hyper-immunized, cell-targeting molecules of the present invention, upon contacting a cell physically coupled with an extracellular target biomolecule of the cell-targeting binding region, the cell-targeting molecule of the invention is capable of directly causing the death of the cell, such as, e.g., without the involvement of an untargeted, cytotoxic T-cell (see Section V-D, supra).

G. Selective Cytotoxicity Among Cell Types

Certain cell-targeting molecules of the present invention have uses in the selective killing of specific target cells in the presence of untargeted, bystander cells. By targeting the delivery of Shiga toxin effector polypeptides of the present invention to specific cells via a cell-targeting binding region (s), the cell-targeting molecules of the present invention can exhibit cell-type specific, restricted cell-kill activities resulting in the exclusive or preferential killing selected cell types in the presence of untargeted cells. Similarly, by targeting the delivery of immunogenic T-cell epitopes to the MHC class I pathway of target cells, the subsequent presentation of T-cell epitopes and CTL-mediated cytolysis of target cells induced by the cell-targeting molecules of the invention can be restricted to exclusively or preferentially killing selected cell types in the presence of untargeted cells. In addition, both the cell-targeted delivery of a cytotoxic, Shiga toxin effector polypeptide region and an immunogenic, T-cell epitope can be accomplished by a single cell-targeting molecule of the present invention such that deliver of both potentially cytotoxic components is restricted exclusively or preferentially to target cells in the presence of untargeted cells.

For certain embodiments, the cell-targeting molecule of the present invention is cytotoxic at certain concentrations. In certain embodiments, upon administration of the cell-targeting molecule of the present invention to a mixture of cell types, the cytotoxic cell-targeting molecule is capable of selectively killing those cells which are physically coupled with an extracellular target biomolecule compared to cell types not physically coupled with an extracellular target biomolecule. For certain embodiments, the cytotoxic cell-targeting molecule of the present invention is capable of selectively or preferentially causing the death of a specific cell type within a mixture of two or more different cell types. This enables targeting cytotoxic activity to specific cell types with a high preferentiality, such as a 3-fold cytotoxic effect, over "bystander" cell types that do not express the target biomolecule. Alternatively, the expression of the target biomolecule of the binding region may be non-exclusive to one cell type if the target biomolecule is expressed in low enough amounts and/or physically coupled in low amounts with cell types that are not to be targeted. This enables the targeted cell-killing of specific cell types with a high preferentiality, such as a 3-fold cytotoxic effect, over "bystander" cell types that do not express significant amounts of the target biomolecule or are not physically coupled to significant amounts of the target biomolecule.

For certain further embodiments, upon administration of the cytotoxic cell-targeting molecule to two different populations of cell types, the cytotoxic cell-targeting molecule is capable of causing cell death as defined by the half-maximal cytotoxic concentration ($CD_{50}$) on a population of target cells, whose members express an extracellular target biomolecule of the binding region of the cytotoxic cell-targeting molecule, at a dose at least three-times lower than the CD50 dose of the same cytotoxic cell-targeting molecule to a population of cells whose members do not express an extracellular target biomolecule of the binding region of the cytotoxic cell-targeting molecule.

For certain embodiments, the cytotoxic activity of a cell-targeting molecule of the present invention toward populations of cell types physically coupled with an extracellular target biomolecule is at least 3-fold higher than the cytotoxic activity toward populations of cell types not physically coupled with any extracellular target biomolecule of the binding region. According to the present invention, selective cytotoxicity may be quantified in terms of the ratio (a/b) of (a) cytotoxicity towards a population of cells of a specific cell type physically coupled with a target biomolecule of the binding region to (b) cytotoxicity towards a population of cells of a cell type not physically coupled with a target biomolecule of the binding region. In certain embodiments, the cytotoxicity ratio is indicative of selective cytotoxicity which is at least 3-fold, 5-fold, 10-fold, 15-fold, 20-fold, 25-fold, 30-fold, 40-fold, 50-fold, 75-fold, 100-fold, 250-fold, 500-fold, 750-fold, or 1000-fold higher for populations of cells or cell types physically coupled with a target biomolecule of the binding region compared to populations of cells or cell types not physically coupled with a target biomolecule of the binding region.

For certain embodiments, the preferential cell-killing function or selective cytotoxicity of a cell-targeting molecule of the present invention is due to an additional exogenous material (e.g. a cytotoxic material) and/or heterologous, T-cell epitope present in a Shiga toxin effector polypeptide of the present invention and not necessarily a result of the catalytic activity of a Shiga toxin effector polypeptide region.

This preferential cell-killing function allows a targeted cell to be killed by certain cytotoxic, cell-targeting molecules of the present invention under varied conditions and in the presence of non-targeted bystander cells, such as ex vivo manipulated mixtures of cell types, in vitro cultured tissues with mixtures of cell types, or in vivo in the presence of multiple cell types (e.g. in situ or in a native location within a multicellular organism).

H. Delivery of Additional Exogenous Material into the Interior of Targeted Cells In addition to cytotoxic, cytostatic, and immune stimulation applications, cell-targeting molecules of the present invention optionally may be used for targeted intracellular delivery functions, such as, e.g., in applications involving information gathering and diagnostic functions.

Because the cell-targeting molecules of the invention, including reduced cytotoxicity and/or nontoxic forms thereof, are capable of entering cells physically coupled with an extracellular target biomolecule recognized by the cell-targeting molecule's binding region, certain embodiments of the cell-targeting molecules of the invention may be used to deliver additional exogenous materials into the interior of targeted cell types. For example, non-toxic variants of the cytotoxic, cell-targeting molecules of the invention, or optionally cytotoxic variants, may be used to deliver additional exogenous materials to and/or label the interiors of cells physically coupled with an extracellular target biomolecule of the binding region of the cell-targeting molecule. Various types of cells and/or cell populations which express target biomolecules to at least one cellular surface may be targeted by the cell-targeting molecules of the invention for receiving exogenous materials. The functional components of the present invention are modular, in that various Shiga toxin effector polypeptides, additional exogenous materials, and binding regions may be associated with each other to provide cell-targeting molecules suitable for diverse applications involving cargo delivery, such as, e.g., non-invasive, in vivo imaging of tumor cells.

This delivery of exogenous material function of certain cell-targeting molecules of the present invention may be accomplished under varied conditions and in the presence of non-targeted bystander cells, such as, e.g., an ex vivo manipulated target cell, a target cell cultured in vitro, a target cell within a tissue sample cultured in vitro, or a target cell in an in vivo setting like within a multicellular organism. Furthermore, the selective delivery of exogenous material to certain cells by certain cell-targeting molecules of the present invention may be accomplished under varied conditions and in the presence of non-targeted bystander cells, such as ex vivo manipulated mixtures of cell types, in vitro cultured tissues with mixtures of cell types, or in vivo in the presence of multiple cell types (e.g. in situ or in a native location within a multicellular organism).

Shiga toxin effector polypeptides and cell-targeting molecules which are not capable, such as a certain concentration ranges, of killing a target cell and/or delivering an embedded or inserted epitope for cell-surface presentation by a MHC molecule of a target cell may still be useful for delivering exogenous materials into cells, such as, e.g., detection promoting agents.

For certain embodiments, the Shiga toxin effector polypeptides of the present invention exhibits low to zero cytotoxicity and thus are referred to herein as "non-cytotoxic and/or reduced cytotoxic." For certain embodiments, the cell-targeting molecule of the present invention exhibits low to zero cytotoxicity and may be referred to as "non-cytotoxic" and/or "reduced cytotoxic variants." For example, certain embodiments of the molecules of the present invention do not exhibit a significant level of Shiga toxin based cytotoxicity wherein at doses of less than 1000 nM, 500 nM, 100 nM, 75 nM, 50 nM, there is no significant amount of cell death as compared to the appropriate reference molecule, such as, e.g., as measured by an assay known to the skilled worker and/or described herein. For certain further embodiments, the molecules of the present invention do not exhibit any toxicity at dosages of 1-100 μg per kg of a mammalian recipient. Reduced-cytotoxic variants may still be cytotoxic at certain concentrations or dosages but exhibit reduced cytotoxicity, such as, e.g., are not capable of exhibiting a significant level of Shiga toxin cytotoxicity in certain situations.

Shiga toxin effector polypeptides of the present invention, and certain cell-targeting molecules comprising the same, can be rendered non-cytotoxic, such as, e.g., via the addition of one or more amino acid substitutions known to the skilled worker to inactive a Shiga toxin A Subunit and/or Shiga toxin effector polypeptide, including exemplary substitutions described herein. The non-cytotoxic and reduced cytotoxic variants of the cell-targeting molecules of the present invention may be in certain situations more suitable for delivery of additional exogenous materials than more cytotoxic variants.

Information Gathering for Diagnostic Functions

In certain cell-targeting molecules of the present invention have uses in the in vitro and/or in vivo detection of specific cells, cell types, and/or cell populations, as well as specific subcellular compartments of any of the aforementioned. Reduced-cytotoxicity and/or nontoxic forms of the cytotoxic, cell-targeting molecules of the invention that are conjugated to detection promoting agents optionally may be used for diagnostic functions, such as for companion diagnostics used in conjunction with a therapeutic regimen comprising the same or a related binding region, such as, e.g., a binding region with high-affinity binding to the same target biomolecule, an overlapping epitope, and/or the same epitope.

In certain embodiments, the cell-targeting molecules described herein are used for both diagnosis and treatment, or for diagnosis alone. When the same cytotoxic cell-targeting molecule is used for both diagnosis and treatment, for certain embodiments of the present invention the cell-targeting molecule variant which incorporates a detection promoting agent for diagnosis may have its cytotoxicity reduced or may be rendered nontoxic by catalytic inactivation of its Shiga toxin effector polypeptide region(s) via one or more amino acid substitutions, including exemplary substitutions described herein. For example, certain nontoxic variants of the cell-targeting molecules of the present invention exhibit less than 5%, 4%, 3%, 2%, or 1% death of target cells after administration of a dose less than 1 mg/kg. Reduced-cytotoxicity variants may still be cytotoxic at certain concentrations or dosages but exhibit reduced cytotoxicity, such as, e.g., are not capable of exhibiting a significant level of Shiga toxin cytotoxicity as described herein.

The ability to conjugate detection promoting agents known in the art to various cell-targeting molecules of the present invention provides useful compositions for the detection of certain cells, such as, e.g., cancer, tumor, immune, and/or infected cells. These diagnostic embodiments of the cell-targeting molecules of the invention may be used for information gathering via various imaging techniques and assays known in the art. For example, diagnostic embodiments of the cell-targeting molecules of the invention may be used for information gathering via imaging of intracellular organelles (e.g. endocytic, Golgi, endoplasmic reticulum, and cytosolic compartments) of individual cancer cells, immune cells, and/or infected cells in a patient or biopsy sample.

Various types of information may be gathered using the diagnostic embodiments of the cell-targeting molecules of the invention whether for diagnostic uses or other uses. This information may be useful, for example, in diagnosing neoplastic cell types, determining therapeutic susceptibilities of a patient's disease, assaying the progression of anti-neoplastic therapies over time, assaying the progression of immunomodulatory therapies over time, assaying the progression of antimicrobial therapies over time, evaluating the presence of infected cells in transplantation materials, evaluating the presence of unwanted cell types in transplantation materials, and/or evaluating the presence of residual tumor cells after surgical excision of a tumor mass.

For example, subpopulations of patients might be ascertained using information gathered using the diagnostic variants of the cell-targeting molecules of the invention, and then individual patients could be further categorized into subpopulations based on their unique characteristic(s) revealed using those diagnostic embodiments. For example, the effectiveness of specific pharmaceuticals or therapies might be a criterion used to define a patient subpopulation. For example, a nontoxic diagnostic variant of a particular cytotoxic, cell-targeting molecule of the invention may be used to differentiate which patients are in a class or subpopulation of patients predicted to respond positively to a cytotoxic variant of that cell-targeting molecule of the invention. Accordingly, associated methods for patient identification, patient stratification, and diagnosis using cell-targeting molecules of the present invention, including non-toxic variants of cytotoxic, cell-targeting molecules of the present invention, are considered to be within the scope of the present invention.

The expression of the target biomolecule by a cell need not be native in order for cell-targeting by a cell-targeting molecule of the present invention, such as, e.g., for direct cell-kill, indirect cell-kill, delivery of exogenous materials like T-cell epitopes, and/or information gathering. Cell surface expression of the target biomolecule could be the result of an infection, the presence of a pathogen, and/or the presence of an intracellular microbial pathogen. Expression of a target biomolecule could be artificial such as, for example, by forced or induced expression after infection with a viral expression vector, see e.g. adenoviral, adeno-associated viral, and retroviral systems. Expression of HER2 can be induced by exposing a cell to ionizing radiation (Wattenberg M et al., *Br J Cancer* 110: 1472-80 (2014)).

VI. Production, Manufacture, and Purification of Shiga Toxin Effector Polypeptides of the Invention and Cell-Targeting Molecules Comprising the Same The Shiga toxin effector polypeptides and certain cell-targeting molecules of the present invention may be produced using techniques well known to those of skill in the art. For example, Shiga toxin effector polypeptides and cell-targeting molecules of the invention may be manufactured by standard synthetic methods, by use of recombinant expression systems, or by any other suitable method. Thus, Shiga toxin effector polypeptides and cell-targeting molecules of the invention may be synthesized in a number of ways, including, e.g. methods comprising: (1) synthesizing a polypeptide or polypeptide component of a cell-targeting molecule using standard solid-phase or liquid-phase methodology, either stepwise or by fragment assembly, and isolating and purifying the final polypeptide compound product; (2) expressing a polynucleotide that encodes a protein or protein component of a cell-targeting molecule of the invention in a host cell and recovering the expression product from the host cell or host cell culture; or (3) cell-free, in vitro expression of a polynucleotide encoding a polypeptide or polypeptide component of a cell-targeting molecule of the invention, and recovering the expression product; or by any combination of the methods of (1), (2) or (3) to obtain fragments of the protein component, subsequently joining (e.g. ligating) the peptide or polypeptide fragments to obtain a polypeptide component, and recovering the polypeptide component.

It may be preferable to synthesize a Shiga toxin effector polypeptide of the present invention, cell-targeting molecule of the present invention, or a protein component of a cell-targeting molecule of the invention by means of solid-phase or liquid-phase peptide synthesis. Polypeptides and cell-targeting molecules of the present invention may suitably be manufactured by standard synthetic methods. Thus, peptides may be synthesized by, e.g. methods comprising synthesizing the peptide by standard solid-phase or liquid-phase methodology, either stepwise or by fragment assembly, and isolating and purifying the final peptide product. In this context, reference may be made to WO 1998/011125 or, inter alia, Fields G et al., *Principles and Practice of Solid-Phase Peptide Synthesis* (Synthetic Peptides, Grant G, ed., Oxford University Press, U.K., 2nd ed., 2002) and the synthesis examples therein.

Shiga toxin effector polypeptides and cell-targeting molecules of the present invention may be prepared (produced and purified) using recombinant techniques well known in the art. In general, methods for preparing proteins by culturing host cells transformed or transfected with a vector comprising the encoding polynucleotide and purifying or recovering the protein from cell culture are described in, e.g., Sambrook J et al., *Molecular Cloning: A Laboratory Manual* (Cold Spring Harbor Laboratory Press, NY, U.S., 1989); Dieffenbach C et al., *PCR Primer: A Laboratory Manual* (Cold Spring Harbor Laboratory Press, N.Y., U.S., 1995). Any suitable host cell may be used to produce a polypeptide and/or cell-targeting protein of the invention. Host cells may be cells stably or transiently transfected, transformed, transduced or infected with one or more expression vectors which drive expression of a polypeptide of the invention. In addition, a Shiga toxin effector polypeptide and/or cell-targeting molecule of the invention may be produced by modifying the polynucleotide encoding a polypeptide or cell-targeting protein of the invention that result in altering one or more amino acids or deleting or inserting one or more amino acids in order to achieve desired properties, such as changed cytotoxicity, changed cytostatic effects, and/or changed serum half-life.

There are a wide variety of expression systems which may be chosen to produce a polypeptide or cell-targeting protein of the present invention. For example, host organisms for expression of cell-targeting proteins of the invention include prokaryotes, such as *E. coli* and *B. subtilis*, eukaryotic cells, such as yeast and filamentous fungi (like *S. cerevisiae, P. pastoris, A. awamori*, and *K lactis*), algae (like *C. reinhardtii*), insect cell lines, mammalian cells (like CHO cells), plant cell lines, and eukaryotic organisms such as transgenic plants (like *A. thaliana* and *N benthamiana*).

Accordingly, the present invention also provides methods for producing a Shiga toxin effector polypeptide and/or cell-targeting molecule of the present invention according to above recited methods and using a polynucleotide encoding part or all of a polypeptide of the invention or a protein component of a cell-targeting protein of the invention, an expression vector comprising at least one polynucleotide of the invention capable of encoding part or all of a polypeptide or cell-targeting protein of the invention when introduced into a host cell, and/or a host cell comprising a polynucleotide or expression vector of the invention.

When a protein is expressed using recombinant techniques in a host cell or cell-free system, it is advantageous to separate (or purify) the desired protein away from other components, such as host cell factors, in order to obtain preparations that are of high purity or are substantially homogeneous. Purification can be accomplished by methods well known in the art, such as centrifugation techniques, extraction techniques, chromatographic and fractionation techniques (e.g. size separation by gel filtration, charge separation by ion-exchange column, hydrophobic interaction chromatography, reverse phase chromatography, chromatography on silica or cation-exchange resins such as DEAE and the like, chromatofocusing, and Protein A Sepharose chromatography to remove contaminants), and precipitation techniques (e.g. ethanol precipitation or ammonium sulfate precipitation). Any number of biochemical purification techniques may be used to increase the purity of a polypeptide and/or cell-targeting molecule of the present invention. In certain embodiments, the polypeptides and cell-targeting molecules of the invention may optionally be purified in homo-multimeric forms (e.g. a molecular complex comprising two or more polypeptides or cell-targeting molecules of the invention).

In the Examples below are descriptions of non-limiting examples of methods for producing exemplary, Shiga toxin effector polypeptides and cell-targeting molecules of the present invention, as well as specific but non-limiting aspects of production methods.

VII. Pharmaceutical and Diagnostic Compositions Comprising Cell-Targeting Molecules of the Present Invention The present invention provides Shiga toxin effector polypeptides and cell-targeting molecules for use, alone or in combination with one or more additional therapeutic agents, in a pharmaceutical composition, for treatment or prophylaxis of conditions, diseases, disorders, or symptoms described in further detail below (e.g. cancers, malignant tumors, non-malignant tumors, growth abnormalities, immune disorders, and microbial infections). For certain embodiments, the one or more additional therapeutic agents comprises one or more additional HER2-targeting therapeutic agent, as described herein. The additional HER2-targeting therapeutic agent may comprise, consist essentially of, or consist of an anti-HER2 antibody therapy or small molecule inhibitor that interferes with HER2 signaling. The additional HER2-targeting therapeutic agent may comprise, consist essentially of, or consist of a small molecule inhibitor that interferes with HER2 signaling. For example, the additional HER2-targeting therapeutic agent may comprise, consist essentially of, or consists of a dual tyrosine kinase inhibitor, such as lapatinib and/or neratinib. For example, the additional HER2-targeting therapeutic agent may comprise, consist essentially of, or consist of lapatinib. For example, the additional HER2-targeting therapeutic agent may comprise, consist essentially of, or consist of neratinib. The additional HER2-targeting therapeutic agent may comprise, consist essentially of, or consist of an anti-HER2 antibody therapy that binds to an antigenic determinant that does not overlap with the antigenic determinant bound by the cell-targeting molecule of the invention or that binds a HER2 molecule in such a manner that when bound the additional HER2-targeting therapeutic does not prevent the binding of that HER2 molecule by the cell-targeting molecule of the invention. For example, the additional HER2-targeting therapeutic agent may comprise, consist essentially of, or consist of anti-HER2 monoclonal antibody therapy and/or anti-HER2 antibody drug conjugate therapy. For example, the additional HER2-targeting therapeutic agent may comprise, consist essentially of, or consist of: T-DM1, trastuzumab, and/or pertuzumab. For example, the additional HER2-targeting therapeutic agent may comprise, consist essentially of, or consist of: T-DM1. For example, the additional HER2-targeting therapeutic agent may comprise, consist essentially of, or consist of: trastuzumab, and/or pertuzumab. For example, the additional HER2-targeting therapeutic agent may comprise, consist essentially of, or consist of trastuzumab. For example, the additional HER2-targeting therapeutic agent may comprise, consist essentially of, or consist of pertuzumab.

In certain embodiments, the pharmaceutical composition further comprises at least one pharmaceutically acceptable carrier, excipient, or vehicle, as described herein. The present invention further provides pharmaceutical compositions comprising a Shiga toxin polypeptide or cell-targeting molecule of the present invention, or a pharmaceutically acceptable salt or solvate thereof, according to the invention, together with at least one pharmaceutically acceptable carrier, excipient, or vehicle. In certain embodiments, the pharmaceutically acceptable excipient includes a solvent, a dispersion medium, a coating, an antimicrobial agent, an isotonic agent, or an absorption delaying agent; and/or wherein the pharmaceutical composition further comprises an aqueous or non-aqueous carrier; a surfactant; a stabilizer, a preservative, a buffer, an antioxidant, a wetting agent, an emulsifying agent, a dispersing agent; an isotonic agent; and/or an antibacterial or antifungal agent.

In certain embodiments, the pharmaceutical composition of the present invention may comprise homo-multimeric and/or hetero-multimeric forms of a Shiga toxin effector polypeptides or cell-targeting molecule of the present invention. In certain embodiments, the pharmaceutical composition of the present invention may comprise monomeric and/or monovalent forms of the cell-targeting molecule of the present invention. In certain embodiments, the pharmaceutical composition of the present invention may be enriched for monomeric and/or monovalent forms of a cell-targeting molecule of the present invention. As demonstrated by the Examples of the application, compositions comprising predominantly monovalent and/or monomeric forms of certain cell-targeting molecules may exhibit low levels of toxicity when used in vivo while still exhibiting potent cytotoxic to HER2-expressing cells. The pharmaceutical compositions of the invention are useful in methods of treating, ameliorating, or preventing a disease, condition, disorder, or symptom described in further detail below. The disease, disorder, or condition may be characterized by cells that are physically coupled with HER2. The HER2 target biomolecule can be physically coupled to the surface of the cells. In certain embodiments, the disease, disorder or condition may be characterized by cells that express the HER2 target biomolecule (including cells that overexpress HER2). The HER2 can be expressed (including overexpressed) at the surface of the cells. Each such disease, condition, disorder, or symptom is envisioned to be a separate embodiment with respect to uses of a pharmaceutical composition according to the invention. The invention further provides pharmaceutical compositions for use in at least one method of treatment according to the invention, as described in more detail below.

As used herein, the terms "patient" and "subject" are used interchangeably to refer to any organism, commonly vertebrates such as humans and animals, which presents symptoms, signs, and/or indications of at least one disease, disorder, or condition. These terms include mammals such as the non-limiting examples of primates, livestock animals (e.g. cattle, horses, pigs, sheep, goats, etc.), companion animals (e.g. cats, dogs, etc.) and laboratory animals (e.g. mice, rabbits, rats, etc.).

As used herein, "treat," "treating," or "treatment" and grammatical variants thereof refer to an approach for obtaining beneficial or desired clinical results. The terms may refer to slowing the onset or rate of development of a condition, disorder or disease, reducing or alleviating symptoms associated with it, generating a complete or partial regression of the condition, or some combination of any of the above. For the purposes of this invention, beneficial or desired clinical results include, but are not limited to, reduction or alleviation of symptoms, diminishment of extent of disease, stabilization (e.g. not worsening) of state of disease, delay or slowing of disease progression, amelioration or palliation of the disease state, and remission (whether partial or total), whether detectable or undetectable. "Treat," "treating," or "treatment" can also mean prolonging survival relative to expected survival time if not receiving treatment. A subject (e.g. a human) in need of treatment may thus be a subject already afflicted with the disease or disorder in question. The terms "treat," "treating," or "treatment" includes inhibition or reduction of an increase in severity of a pathological state or symptoms relative to the absence of treatment, and is not necessarily meant to imply complete cessation of the relevant disease, disorder, or condition. With regard to tumors and/or cancers, treatment includes reduction in overall tumor burden and/or individual tumor size.

As used herein, the terms "prevent," "preventing," "prevention" and grammatical variants thereof refer to an approach for preventing the development of, or altering the pathology of, a condition, disease, or disorder. Accordingly, "prevention" may refer to prophylactic or preventive measures. For the purposes of this invention, beneficial or desired clinical results include, but are not limited to, prevention or slowing of symptoms, progression or development of a disease, whether detectable or undetectable. A subject (e.g. a human) in need of prevention may thus be a subject not yet afflicted with the disease or disorder in question. The term "prevention" includes slowing the onset of disease relative to the absence of treatment, and is not necessarily meant to imply permanent prevention of the relevant disease, disorder or condition. Thus "preventing" or "prevention" of a condition may in certain contexts refer to reducing the risk of developing the condition, or preventing or delaying the development of symptoms associated with the condition.

As used herein, an "effective amount" or "therapeutically effective amount" is an amount or dose of a composition (e.g. a therapeutic composition, compound, or agent) that produces at least one desired therapeutic effect in a subject, such as preventing or treating a target condition or beneficially alleviating a symptom associated with the condition. The most desirable therapeutically effective amount is an amount that will produce a desired efficacy of a particular treatment selected by one of skill in the art for a given subject in need thereof. This amount will vary depending upon a variety of factors understood by the skilled worker, including but not limited to the characteristics of the therapeutic composition (including activity, pharmacokinetics, pharmacodynamics, and bioavailability), the physiological condition of the subject (including age, sex, disease type, disease stage, general physical condition, responsiveness to a given dosage, and type of medication), the nature of the pharmaceutically acceptable carrier or carriers in the formulation, and the route of administration. One skilled in the clinical and pharmacological arts will be able to determine a therapeutically effective amount through routine experimentation, namely by monitoring a subject's response to administration of a composition and adjusting the dosage accordingly (see e.g. *Remington: The Science and Practice of Pharmacy* (Gennaro A, ed., Mack Publishing Co., Easton, Pa., U.S., 19th ed., 1995)).

Diagnostic compositions of the present invention comprise a cell-targeting molecule of the present invention and one or more detection promoting agents. When producing or manufacturing a diagnostic composition of the present invention, a cell-targeting molecule of the present invention may be directly or indirectly linked to one or more detection promoting agents. There are numerous standard techniques known to the skilled worker for incorporating, affixing, and/or conjugating various detection promoting agents to proteins or proteinaceous components of molecules, especially to immunoglobulins and immunoglobulin-derived domains.

There are numerous detection promoting agents known to the skilled worker, such as isotopes, dyes, colorimetric agents, contrast enhancing agents, fluorescent agents, bioluminescent agents, and magnetic agents, which can be operably linked to the polypeptides or cell-targeting molecules of the invention for information gathering methods, such as for diagnostic and/or prognostic applications to diseases, disorders, or conditions of an organism (see e.g. Cai W et al., *J Nucl Med* 48: 304-10 (2007); Nayak T, Brechbiel M, *Bioconjug Chem* 20: 825-41 (2009); Paudyal P et al., *Oncol Rep* 22: 115-9 (2009); Qiao J et al., *PLoS ONE* 6: e18103 (2011); Sano K et al., *Breast Cancer Res* 14: R61 (2012)). These agents may be associated with, linked to, and/or incorporated within the polypeptide or cell-targeting molecule of the invention at any suitable position. For example, the linkage or incorporation of the detection promoting agent may be via an amino acid residue(s) of a molecule of the present invention or via some type of linkage known in the art, including via linkers and/or chelators. The incorporation of the agent is in such a way to enable the detection of the presence of the diagnostic composition in a screen, assay, diagnostic procedure, and/or imaging technique.

Similarly, there are numerous imaging approaches known to the skilled worker, such as non-invasive in vivo imaging techniques commonly used in the medical arena, for example: computed tomography imaging (CT scanning), optical imaging (including direct, fluorescent, and bioluminescent imaging), magnetic resonance imaging (MRI), positron emission tomography (PET), single-photon emission computed tomography (SPECT), ultrasound, and x-ray computed tomography imaging.

VIII. Production or Manufacture of Pharmaceutical and/or Diagnostic Compositions Comprising Cell-Targeting Molecules of the Present Invention Pharmaceutically acceptable salts or solvates of any of the Shiga toxin effector polypeptides and cell-targeting molecules of the present invention are within the scope of the present invention.

The term "solvate" in the context of the present invention refers to a complex of defined stoichiometry formed between a solute (in casu, a proteinaceous compound or pharmaceutically acceptable salt thereof according to the invention) and a solvent. The solvent in this connection may, for example, be water, ethanol or another pharmaceutically acceptable, typically small-molecular organic species, such as, but not limited to, acetic acid or lactic acid. When the solvent in question is water, such a solvate is normally referred to as a hydrate.

Polypeptides and proteins of the present invention, or salts thereof, may be formulated as pharmaceutical compositions prepared for storage or administration, which typically comprise a therapeutically effective amount of a molecule of the present invention, or a salt thereof, in a pharmaceutically acceptable carrier. The term "pharmaceutically acceptable carrier" includes any of the standard pharmaceutical carriers. Pharmaceutically acceptable carriers for therapeutic molecule use are well known in the pharmaceutical art, and are described, for example, in *Remington's Pharmaceutical Sciences* (Mack Publishing Co. (A. Gennaro, ed., 1985). As used herein, "pharmaceutically acceptable carrier" includes any and all physiologically acceptable, i.e. compatible, solvents, dispersion media, coatings, antimicrobial agents, isotonic, and absorption delaying agents, and the like. Pharmaceutically acceptable carriers or diluents include those used in formulations suitable for oral, rectal, nasal or parenteral (including subcutaneous, intramuscular, intravenous, intradermal, and transdermal) administration. Exemplary pharmaceutically acceptable carriers include sterile aqueous solutions or dispersions and sterile powders for the extemporaneous preparation of sterile injectable solutions or dispersions. Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyloleate. Proper fluidity can be maintained, for example, by the use of coating materials, such as lecithin, by the maintenance of the required particle size in the case of dispersions, and by the use of surfactants. In certain embodiments, the carrier is suitable for intravenous, intramuscular, subcutaneous, parenteral, spinal or epidermal administration (e.g. by injection or infusion). Depending on selected route of administration, the protein or other pharmaceutical component may be coated in a material intended to protect the compound from the action of low pH and other natural inactivating conditions to which the active protein may encounter when administered to a patient by a particular route of administration.

The formulations of the pharmaceutical compositions of the invention may conveniently be presented in unit dosage form and may be prepared by any of the methods well known in the art of pharmacy. In such form, the composition is divided into unit doses containing appropriate quantities of the active component. The unit dosage form can be a packaged preparation, the package containing discrete quantities of the preparations, for example, packeted tablets, capsules, and powders in vials or ampoules. The unit dosage form can also be a capsule, cachet, or tablet itself, or it can be the appropriate number of any of these packaged forms. It may be provided in single dose injectable form, for example in the form of a pen. Compositions may be formulated for any suitable route and means of administration. Subcutaneous or transdermal modes of administration may be particularly suitable for therapeutic proteins described herein.

The pharmaceutical compositions of the present invention may also contain adjuvants such as preservatives, wetting agents, emulsifying agents and dispersing agents. Preventing the presence of microorganisms may be ensured both by sterilization procedures, and by the inclusion of various antibacterial and antifungal agents, for example, paraben, chlorobutanol, phenol sorbic acid, and the like. Isotonic agents, such as sugars, sodium chloride, and the like into the compositions, may also be desirable. In addition, prolonged absorption of the injectable pharmaceutical form may be brought about by the inclusion of agents which delay absorption such as, aluminum monostearate and gelatin.

A pharmaceutical composition of the present invention also optionally includes a pharmaceutically acceptable antioxidant. Exemplary pharmaceutically acceptable antioxidants are water soluble antioxidants such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propylgallate, alpha-tocopherol, and the like; and metal chelating agents, such as citric acid, ethylenediamine tetraacetic acid (EDTA), sorbitol, tartaric acid, phosphoric acid, and the like.

In another aspect, the present invention provides pharmaceutical compositions comprising one or a combination of different polypeptides and/or cell-targeting molecules of the invention, or an ester, salt or amide of any of the foregoing, and at least one pharmaceutically acceptable carrier.

Therapeutic compositions are typically sterile and stable under the conditions of manufacture and storage. The composition may be formulated as a solution, microemulsion, liposome, or other ordered structure suitable to high drug concentration. The carrier may be a solvent or dispersion medium containing, for example, water, alcohol such as ethanol, polyol (e.g., glycerol, propylene glycol, and liquid polyethylene glycol), or any suitable mixtures. The proper fluidity may be maintained, for example, by the use of a coating such as lecithin, by the maintenance of the required particle size in the case of dispersion and by use of surfactants according to formulation chemistry well known in the art. In certain embodiments, isotonic agents, e.g., sugars and polyalcohols such as mannitol, sorbitol, or sodium chloride, may be desirable in the composition. Prolonged absorption of injectable compositions may be brought about by including in the composition an agent that delays absorption for example, monostearate salts and gelatin.

Solutions or suspensions used for intradermal or subcutaneous application typically include one or more of: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfate; chelating agents such as ethylenediaminetetraacetic acid; buffers such as acetates, citrates or phosphates; and tonicity adjusting agents such as, e.g., sodium chloride or dextrose. The pH can be adjusted with acids or bases, such as hydrochloric acid or sodium hydroxide, or buffers with citrate, phosphate, acetate and the like. Such preparations may be enclosed in ampoules, disposable syringes or multiple dose vials made of glass or plastic.

Sterile injectable solutions may be prepared by incorporating a polypeptide or cell-targeting molecule of the invention in the required amount in an appropriate solvent with one or a combination of ingredients described above, as required, followed by sterilization microfiltration. Dispersions may be prepared by incorporating the active compound into a sterile vehicle that contains a dispersion medium and other ingredients, such as those described above. In the case of sterile powders for the preparation of sterile injectable solutions, the methods of preparation are vacuum drying and freeze-drying (lyophilization) that yield a powder of the active ingredient in addition to any additional desired ingredient from a sterile-filtered solution thereof.

When a therapeutically effective amount of a polypeptide and/or cell-targeting molecule of the invention is designed to be administered by, e.g. intravenous, cutaneous or subcutaneous injection, the binding agent will be in the form of a pyrogen-free, parenterally acceptable aqueous solution. Methods for preparing parenterally acceptable protein solutions, taking into consideration appropriate pH, isotonicity, stability, and the like, are within the skill in the art. A preferred pharmaceutical composition for intravenous, cutaneous, or subcutaneous injection will contain, in addition to binding agents, an isotonic vehicle such as sodium chloride injection, Ringer's injection, dextrose injection, dextrose and sodium chloride injection, lactated Ringer's injection, or other vehicle as known in the art. A pharmaceutical composition of the present invention may also contain stabilizers, preservatives, buffers, antioxidants, or other additives well known to those of skill in the art.

As described elsewhere herein, a polypeptide and/or cell-targeting molecule of the present invention may be prepared with carriers that will protect the active therapeutic agent against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art (see e.g. Sustained and Controlled Release Drug Delivery Systems (Robinson J, ed., Marcel Dekker, Inc., NY, U.S., 1978)).

In certain embodiments, the pharmaceutical composition of the present invention comprises a buffer, such as e.g., citrate, citric acid, histidine, phosphate, succinate, and/or succinic acid. In certain embodiments, the pharmaceutical composition of the present invention comprises a preservative, antibacterial, or antifungal agent, such as e.g., mannitol or sorbitol. In certain embodiments, the pharmaceutical composition of the present invention comprises a detergent such as, e.g., polysorbate 20 or polysorbate 80. In certain embodiments, the pharmaceutical composition of the present invention comprises a cryoprotectant such as, e.g., polysorbate 20 or polysorbate 80. In certain embodiments, the pharmaceutical composition of the present invention comprises an excipient, such as, e.g., arginine, arginine sulfate, glycerol, mannitol, methionine, polysorbate 20, polysorbate 80, sorbitol, sucrose, and/or trehalose. In certain further embodiments, the pharmaceutical composition of the present invention comprises one or more of (including all of): citrate, polysorbate 20, sodium, sorbitol, and chloride. In certain further embodiments, the pharmaceutical composition comprises a 20 millimolar concentration of citrate, 200 millimolar concentration of sorbitol, and 0.2% polysorbate 20. In certain further embodiments, at room temperature (e.g. about 25° C.) the pharmaceutical composition has a pH of about 5.3 to 5.7, a pH between 5.4 and 5.6, and/or a pH of 5.5.

In certain embodiments, the composition of the present invention (e.g. a pharmaceutical and/or diagnostic composition) may be formulated to ensure a desired in vivo distribution of a cell-targeting molecule of the present invention. For example, the blood-brain barrier excludes many large and/or hydrophilic compounds. To target a therapeutic molecule or composition of the present invention to a particular in vivo location, they can be formulated, for example, in liposomes which may comprise one or more moieties that are selectively transported into specific cells or organs, thus enhancing targeted drug delivery. Exemplary targeting moieties include folate or biotin; mannosides; antibodies; surfactant protein A receptor; p120 catenin and the like.

Pharmaceutical compositions include parenteral formulations designed to be used as implants or particulate systems. Examples of implants are depot formulations composed of polymeric or hydrophobic components such as emulsions, ion exchange resins, and soluble salt solutions. Examples of particulate systems are microspheres, microparticles, nanocapsules, nanospheres, and nanoparticles (see e.g. Honda M et al., *Int J Nanomedicine* 8: 495-503 (2013); Sharma A et al., *Biomed Res Int* 2013: 960821 (2013); Ramishetti S, Huang L, *Ther Deliv* 3: 1429-45 (2012)). Controlled release formulations may be prepared using polymers sensitive to ions, such as, e.g. liposomes, polaxamer 407, and hydroxyapatite.

The pharmaceutically acceptable carrier in the pharmaceutical compositions of the present invention may comprise: a physiologically acceptable solvent, dispersion medium, coating, antimicrobial agent, isotonic agent, absorption delaying agent, sterile aqueous solution or dispersion, or sterile powder; an aqueous or non-aqueous carrier, such as water, alcohol (e.g. ethanol), polyol (e.g. glycerol, propylene glycol, or polyethylene glycol), and mixtures thereof; vegetable oil; or an injectable organic ester, such as ethyloleate. The pharmaceutical composition of the invention may further comprises an adjuvant, such as a preservative, wetting agent, emulsifying agent, or dispersing agent; an antibacterial or antifungal agent, such as a paraben, chlorobutanol, phenol, or sorbic acid; an isotonic agent, such as a sugar, a polyalcohol such as mannitol or sorbitol, or sodium chloride; an absorption-delaying agent, such as aluminum monostearate or gelatin; a coating, such as lecithin; a pharmaceutically acceptable antioxidant; a surfactant; a buffer; and/or a stabilizer. In certain embodiments, the pharmaceutically acceptable antioxidant is a water soluble antioxidant, such as ascorbic acid, cysteine hydrochloride, sodium bisulfate, sodium metabisulfite, or sodium sulfite; an oil-soluble antioxidant, such as ascorbyl palmitate, butylated hydroxyanisole (BHA), butylated hydroxytoluene (BHT), lecithin, propylgallate, or alpha-tocopherol; or a metal chelating agent, such as citric acid, ethylenediamine tetraacetic acid (EDTA), sorbitol, tartaric acid, or phosphoric acid.

IX. Polynucleotides, Expression Vectors, and Host Cells of the Present Invention Beyond the polypeptides and cell-targeting molecules of the present invention, the polynucleotides that encode the polypeptides and cell-targeting molecules of the invention, or functional portions thereof, are also encompassed within the scope of the present invention. The term "polynucleotide" is equivalent to the term "nucleic acid," each of which includes one or more of: polymers of deoxyribonucleic acids (DNAs), polymers of ribonucleic acids (RNAs), analogs of these DNAs or RNAs generated using nucleotide analogs, and derivatives, fragments and homologs thereof. The polynucleotide of the present invention may be single-, double-, or triple-stranded. Such polynucleotides are specifically disclosed to include all polynucleotides capable of encoding an exemplary protein, for example, taking into account the wobble known to be tolerated in the third position of RNA codons, yet encoding for the same amino acid as a different RNA codon (see Stothard P, *Biotechniques* 28: 1102-4 (2000)).

In one aspect, the present invention provides polynucleotides which encode a Shiga toxin effector polypeptide and/or cell-targeting molecule of the present invention, or a fragment or derivative thereof. The polynucleotides may include, e.g., a nucleic acid sequence encoding a polypeptide at least 50%, 55%, 60%, 65%, 70%, 75%, 80%, 85%, 90%, 95%, 99% or more, identical to a polypeptide comprising one of the amino acid sequences of a polypeptide or cell-targeting molecule of the present invention. The invention also includes polynucleotides comprising nucleotide sequences that hybridize under stringent conditions to a polynucleotide which encodes Shiga toxin effector polypeptide and/or cell-targeting molecule of the invention, or a fragment or derivative thereof, or the antisense or complement of any such sequence.

Derivatives or analogs of the molecules of the present invention (e.g., Shiga toxin effector polypeptides of the present invention and cell-targeting molecules comprising the same) include, inter alia, polynucleotide (or polypeptide) molecules having regions that are substantially homologous to the polynucleotides (or Shiga toxin effector polypeptides and cell-targeting molecules of the present invention), e.g. by at least about 45%, 50%, 70%, 80%, 85%, 90%, 95%, 98%, or even 99% identity (with a preferred identity of 80-99%) over a polynucleotide (or polypeptide) sequence of the same size or when compared to an aligned sequence in which the alignment is done by a computer homology program known in the art. An exemplary program is the GAP program (Wisconsin Sequence Analysis Package, Version 8 for UNIX, Genetics Computer Group, University Research Park, Madison, Wis., U.S.) using the default settings, which uses the algorithm of Smith T, Waterman M, *Adv Appl Math* 2: 482-9 (1981). Also included are polynucleotides capable of hybridizing to the complement of a sequence encoding the cell-targeting proteins of the invention under stringent conditions (see e.g. Ausubel F et al., *Current Protocols in Molecular Biology* (John Wiley & Sons, New York, N.Y., U.S., 1993)), and below. Stringent conditions are known to those skilled in the art and may be found, e.g., in *Current Protocols in Molecular Biology* (John Wiley & Sons, NY, U.S., Ch. Sec. 6.3.1-6.3.6 (1989)).

The present invention further provides expression vectors that comprise the polynucleotides within the scope of the present invention. The polynucleotides capable of encoding the Shiga toxin effector polypeptides and/or cell-targeting molecules of the invention may be inserted into known vectors, including bacterial plasmids, viral vectors and phage vectors, using material and methods well known in the art to produce expression vectors. Such expression vectors will include the polynucleotides necessary to support production of contemplated Shiga toxin effector polypeptides and/or cell-targeting molecules of the invention within any host cell of choice or cell-free expression systems (e.g. pTxb1 and pIVEX2.3). The specific polynucleotides comprising expression vectors for use with specific types of host cells or cell-free expression systems are well known to one of ordinary skill in the art, can be determined using routine experimentation, and/or may be purchased.

The term "expression vector," as used herein, refers to a polynucleotide, linear or circular, comprising one or more expression units. The term "expression unit" denotes a polynucleotide segment encoding a polypeptide of interest and capable of providing expression of the nucleic acid segment in a host cell. An expression unit typically comprises a transcription promoter, an open reading frame encoding the polypeptide of interest, and a transcription terminator, all in operable configuration. An expression vector contains one or more expression units. Thus, in the context of the present invention, an expression vector encoding a Shiga toxin effector polypeptide and/or cell-targeting molecule of the invention comprising a single polypeptide chain includes at least an expression unit for the single polypeptide chain, whereas a protein comprising, e.g. two or more polypeptide chains (e.g. one chain comprising a $V_L$ domain and a second chain comprising a $V_H$ domain linked to a toxin effector polypeptide) includes at least two expression units, one for each of the two polypeptide chains of the protein. For expression of multi-chain cell-targeting proteins of the invention, an expression unit for each polypeptide chain may also be separately contained on different expression vectors (e.g. expression may be achieved with a single host cell into which expression vectors for each polypeptide chain has been introduced).

Expression vectors capable of directing transient or stable expression of polypeptides and proteins are well known in the art. The expression vectors generally include, but are not limited to, one or more of the following: a heterologous signal sequence or peptide, an origin of replication, one or more marker genes, an enhancer element, a promoter, and a transcription termination sequence, each of which is well known in the art. Optional regulatory control sequences, integration sequences, and useful markers that can be employed are known in the art.

The term "host cell" refers to a cell which can support the replication or expression of the expression vector. Host cells may be prokaryotic cells, such as *E. coli* or eukaryotic cells (e.g. yeast, insect, amphibian, bird, or mammalian cells). Creation and isolation of host cell lines comprising a polynucleotide of the invention or capable of producing a polypeptide and/or cell-targeting molecule of the present invention can be accomplished using standard techniques known in the art.

Shiga toxin effector polypeptides and/or proteins within the scope of the present invention may be variants or derivatives of the polypeptides and molecules described herein that are produced by modifying the polynucleotide encoding a polypeptide and/or proteinaceous component of a cell-targeting molecule by altering one or more amino acids or deleting or inserting one or more amino acids that may render it more suitable to achieve desired properties, such as more optimal expression by a host cell.

X. Molecules of the Present Invention Immobilized on Solid Substrates

Certain embodiments of the present invention include a molecule of the present invention (e.g. a Shiga toxin effector polypeptide, a cell-targeting molecule, fusion protein, or polynucleotide of the present invention), or any effector fragment thereof, immobilized on a solid substrate. Solid substrates contemplated herein include, but are not limited to, microbeads, nanoparticles, polymers, matrix materials, microarrays, microtiter plates, or any solid surface known in the art (see e.g. U.S. Pat. No. 7,771,955). In accordance with these embodiments, a molecule of the present invention may be covalently or non-covalently linked to a solid substrate, such as, e.g., a bead, particle, or plate, using techniques known to the skilled worker (see e.g. Jung Y et al., *Analyst* 133: 697-701 (2008)). Immobilized molecules of the present invention (e.g. a HER2-targeting molecule which comprises, consists of, or consists essentially of any one of SEQ ID NOs: 29, 36, 102, and 108) may be used for screening applications using techniques known in the art (see e.g. Bradbury A et al., *Nat Biotechnol* 29: 245-54 (2011); Sutton C, *Br J Pharmacol* 166: 457-75 (2012); Diamante L et al., *Protein Eng Des Sel* 26: 713-24 (2013); Houlihan G et al., *J Immunol Methods* 405: 47-56 (2014)).

Non-limiting examples of solid substrates to which a molecule of the invention may be immobilized on include:

microbeads, nanoparticles, polymers, nanopolymers, nanotubes, magnetic beads, paramagnetic beads, superparamagnetic beads, streptavidin coated beads, reverse-phase magnetic beads, carboxy terminated beads, hydrazine terminated beads, silica (sodium silica) beads and iminodiacetic acid (IDA)-modified beads, aldehyde-modified beads, epoxy-activated beads, diaminodipropylamine (DADPA)-modified beads (beads with primary amine surface group), biodegradable polymeric beads, polystyrene substrates, amino-polystyrene particles, carboxyl-polystyrene particles, epoxy-polystyrene particles, dimethylamino-polystyrene particles, hydroxy-polystyrene particles, colored particles, flow cytometry particles, sulfonate-polystyrene particles, nitrocellulose surfaces, reinforced nitrocellulose membranes, nylon membranes, glass surfaces, activated glass surfaces, activated quartz surfaces, polyvinylidene difluoride (PVDF) membranes, polyacrylamide-based substrates, poly-vinyl chloride substrates, poly-methyl methacrylate substrates, poly(dimethyl siloxane) substrates, and photopolymers which contain photoreactive species (such as nitrenes, carbenes, and ketyl radicals) capable of forming covalent linkages. Other examples of solid substrates to which a molecule of the invention may be immobilized on are commonly used in molecular display systems, such as, e.g., cellular surfaces, phages, and virus particles.

XI. Delivery Devices and Kits

In certain embodiments, the invention relates to a device comprising one or more compositions of matter of the present invention, such as a pharmaceutical composition or diagnostic composition, for delivery to a subject in need thereof. Thus, a delivery device comprising one or more compositions of the present invention can be used to administer to a patient a composition of matter of the present invention by various delivery methods, including: intravenous, subcutaneous, intramuscular or intraperitoneal injection; oral administration; transdermal administration; pulmonary or transmucosal administration; administration by implant, osmotic pump, cartridge or micro pump; or by other means recognized by a person of skill in the art.

Also within the scope of the present invention are kits comprising at least one composition of matter of the invention, and optionally, packaging and instructions for use. For example, the present invention provides a kit comprising: (i) a HER2-targeting molecule of the present invention, (ii) a pharmaceutical composition of the present invention, (iii) a diagnostic composition of the present invention, (iv) a polynucleotide of the present invention, (v) an expression vector of the present invention and/or (vi) a host cell of the present invention; and optionally, packaging and instructions for use. Kits may be useful for drug administration and/or diagnostic information gathering. A kit of the invention may optionally comprise at least one additional reagent (e.g., standards, markers and the like). Kits typically include a label indicating the intended use of the contents of the kit. The kit may further comprise reagents and other tools for detecting a cell type (e.g. a tumor cell) in a sample or in a subject, or for diagnosing whether a patient belongs to a group that responds to a therapeutic strategy which makes use of a compound, composition, or related method of the present invention, e.g., such as a method described herein.

XII. Methods for Using Cell-Targeting Molecules of the Present Invention and/or Pharmaceutical and/or Diagnostic Compositions Thereof Generally, it is an object of the present invention to provide pharmacologically active agents, as well as compositions comprising the same, that can be used in the prevention and/or treatment of diseases, disorders, and conditions, such as certain cancers, tumors, growth abnormalities, immune disorders, or further pathological conditions mentioned herein. Accordingly, the present invention provides methods of using the polypeptides, cell-targeting molecules, and pharmaceutical compositions of the invention for the targeted killing of cells, for delivering additional exogenous materials into targeted cells, for labeling of the interiors of targeted cells, for collecting diagnostic information, for the delivering of T-cell epitopes to the MHC class I presentation pathway of target cells, and for treating diseases, disorders, and conditions as described herein. For example, the methods of the present invention may be used to prevent or treat cancers, cancer initiation, tumor initiation, metastasis, and/or disease reoccurrence.

In particular, it is an object of the invention to provide such pharmacologically active agents, compositions, and/or methods that have certain advantages compared to the agents, compositions, and/or methods that are currently known in the art. Accordingly, the present invention provides methods of using Shiga toxin effector polypeptides and cell-targeting molecules with specified protein sequences and pharmaceutical compositions thereof. For example, any of the amino acid sequences described herein may be specifically utilized as a component of the cell-targeting molecule used in the following methods or any method for using a cell-targeting molecule known to the skilled worker, such as, e.g., various methods described in WO 2014/164680, WO 2014/164693, WO 2015/138435, WO 2015/138452, WO 2015/113005, WO 2015/113007, WO 2015/191764, US20150259428, WO 2016/196344, WO 2017/019623, and WO 2018/140427.

The present invention provides methods of killing a cell comprising the step of contacting the cell, either in vitro or in vivo, with a Shiga toxin effector polypeptide, cell-targeting molecule, or pharmaceutical composition of the present invention. The Shiga toxin effector polypeptides, cell-targeting molecules, and pharmaceutical compositions of the present invention can be used to kill a specific cell type upon contacting a cell or cells with one of the claimed compositions of matter. For certain embodiments, the cell(s) is physically coupled with HER2. For certain embodiments, the cell(s) expresses (including over-expresses) HER2. The HER2 may be expressed (including overexpressed) at the surface of the cells. For certain embodiments, a cell-targeting molecule or pharmaceutical composition of the present invention can be used to kill specific cell types in a mixture of different cell types, such as mixtures comprising cancer cells, infected cells, and/or hematological cells. For certain embodiments, a cell-targeting molecule, or pharmaceutical composition of the present invention can be used to kill cancer cells in a mixture of different cell types. For certain embodiments, a cytotoxic Shiga cell-targeting molecule, or pharmaceutical composition of the present invention can be used to kill specific cell types in a mixture of different cell types, such as pre-transplantation tissues. For certain embodiments, a Shiga toxin effector polypeptide, cell-targeting molecule, or pharmaceutical composition of the present invention can be used to kill specific cell types in a mixture of cell types, such as pre-administration tissue material for therapeutic purposes. For certain embodiments, a cell-targeting molecule or pharmaceutical composition of the present invention can be used to selectively kill cells infected by viruses or microorganisms, or otherwise selectively kill cells expressing a particular extracellular target biomolecule, such as a cell surface localized HER2 variant. The Shiga toxin effector polypeptides, cell-targeting molecules, and pharmaceutical compositions of the present invention have varied applications, including, e.g., uses in depleting unwanted cell types from tissues either in vitro or in vivo, uses as antiviral agents, and uses in purging transplantation tissues of unwanted cell types. For certain embodiments, the cell expresses muc-4 and/or CD44. For certain embodiments, the cell is resistant to cytotoxicity caused by T-DM1 (trastuzumab emtansine) and/or trastuzumab. For certain further embodiments the cell(s) are in the presence of pertuzumab, T-DM1 (trastuzumab emtansine), lapatinib, and/or neratinib; and/or had previously been contacted with pertuzumab, T-DM1 (trastuzumab emtansine), lapatinib, and/or neratinib. Among certain embodiments of the present invention is a method of killing a cell (e.g. a HER2-expressing cell) comprising the step of contacting the cell with the cell-targeting molecule of the present invention or the pharmaceutical composition of the present invention wherein the cell is in the presence of pertuzumab, T-DM1 (trastuzumab emtansine), lapatinib, and/or neratinib; and/or had previously been contacted with pertuzumab, T-DM1 (trastuzumab emtansine), lapatinib and/or neratinib. For certain further embodiments the cell(s) are in the presence of T-DM1 (trastuzumab emtansine). For certain further embodiments the cell(s) are in the presence of pertuzumab. For certain further embodiments the cell(s) are in the presence of lapatinib. For certain further embodiments the cell(s) are in the presence of neratinib. For certain further embodiments the cell(s) had previously been contacted with pertuzumab. For certain further embodiments the cell(s) had previously been contacted with T-DM1 (trastuzumab emtansine). For certain further embodiments the cell(s) had previously been contacted with lapatinib. For certain further embodiments the cell(s) had previously been contacted with neratinib.

For certain embodiments, certain Shiga toxin effector polypeptides, cell-targeting molecules, and pharmaceutical compositions of the present invention, alone or in combination with other compounds or pharmaceutical compositions, can show potent cell-kill activity when administered to a population of cells, in vitro or in vivo in a subject such as in a patient in need of treatment. By targeting the delivery of enzymatically active Shiga toxin A Subunit effector polypeptides and/or T-cell epitopes using high-affinity binding regions to specific cell types, cell-kill activities can be restricted to specifically and selectively killing certain cell types within an organism, such as certain cancer cells, neoplastic cells, malignant cells, non-malignant tumor cells, and/or infected cells.

The present invention provides a method of killing a cell in a patient in need thereof, the method comprising the step of administering to the patient at least one cell-targeting molecule of the present invention or a pharmaceutical composition thereof.

For certain embodiments, the cell-targeting molecule of the present invention or pharmaceutical compositions thereof can be used to kill a cancer cell in a patient by targeting an extracellular biomolecule found physically coupled with a cancer or tumor cell. The terms "cancer cell" or "cancerous cell" refers to various neoplastic cells which grow and divide in an abnormally accelerated and/or unregulated fashion and will be clear to the skilled person. The term "tumor cell" includes both malignant and non-malignant cells. Generally, cancers and/or tumors can be defined as diseases, disorders, or conditions that are amenable to treatment and/or prevention. The cancers and tumors (either malignant or non-malignant) which are comprised of cancer cells and/or tumor cells which may benefit from methods and compositions of the invention will be clear to the skilled person. Neoplastic cells are often associated with one or more of the following: unregulated growth, lack of differentiation, local tissue invasion, angiogenesis, and metastasis. The diseases, disorders, and conditions resulting from cancers and/or tumors (either malignant or non-malignant) which may benefit from the methods and compositions of the present invention targeting certain cancer cells and/or tumor cells will be clear to the skilled person. For example, disease, disorder, or condition may be characterized by cells that are physically coupled with HER2. The HER2 target biomolecule may be physically coupled to the surface of the cells. For certain embodiments, the disease, disorder or condition may be characterized by cells that express the HER2 target biomolecule (including cells that overexpress HER2). The HER2 may be expressed (including overexpressed) at the surface of the cells.

Certain embodiments of the cell-targeting molecules and compositions of the present invention may be used to treat diseases, disorders or conditions (such as, e.g., HER2 positive cancers and/or tumors) in a patient after the patient has already received a HER2-targeted therapeutic agent. In many situations, cell-surface HER2 expression persists during disease progression after a therapeutic treatment such as, e.g., a HER2-targeted therapy using an anti-HER2 monoclonal antibody therapy or anti-HER2 antibody drug conjugate therapy, or a chemotherapeutic agent therapy using a tyrosine kinase inhibitor. Thus, HER2 is still present as a target on the surfaces of malignant/target cells and available for targeting by a cell-targeting molecule of the present invention for cell-surface docking and cellular internalization. Furthermore, as demonstrated by the Examples, the cell-targeting molecules of the present invention (and compositions comprising the cell-targeting molecules) can be used in combination with other HER2-targeted therapeutic agents, such as the anti-HER2 antibody therapies that bind to non-overlapping antigenic determinants of HER2; or the tyrosine kinase inhibitors that have a different HER2-targeting activity to the cell-targeting molecules of the invention. Accordingly, the "patient in need thereof" that is administered with at least one cell-targeting molecule or a pharmaceutical composition thereof in the methods of the present invention, includes a patient(s) that has been previously treated with an additional HER2-targeting therapeutic agent; and/or is undergoing treatment with an additional HER2-targeting therapeutic agent. For certain embodiments, the patient(s) has been previously treated with an additional HER2-targeting therapeutic agent as described herein. For certain embodiments, the patient(s) is undergoing treatment with an additional HER2-targeting therapeutic agent as described herein. For certain embodiments, the "patient in need thereof" does not respond to, or does not benefit from, treatment with one or more additional HER2-targeting therapeutic agent. For example, this can be due to, inter alia, acquired and/or intrinsic resistance. For certain embodiments, the additional HER2-targeting therapeutic agent comprises a tyrosine kinase inhibitor, an anti-HER2 monoclonal antibody therapy or an anti-HER2 antibody drug conjugate therapy. For certain embodiments, the additional HER2-targeting therapeutic agent comprises one or more of: pertuzumab, trastuzumab, T-DM1 (trastuzumab emtansine), lapatinib and/or neratinib. For certain embodiments, the additional HER2-targeting therapeutic agent is pertuzumab. For certain embodiments, the additional HER2-targeting therapeutic agent is trastuzumab. For certain embodiments, additional HER2-targeting therapeutic agent is T-DM1 (trastuzumab emtansine). For certain embodiments, the additional HER2-targeting therapeutic agent is lapatinib. For certain embodiments, the additional HER2-targeting therapeutic agent is neratinib.

As used herein, the reference to "a patient in need thereof" that "has been previously treated with an additional HER2-targeting therapeutic agent" includes patients that were last administered treatment with an additional HER2-targeting therapeutic agent at least 6 months (such as at least 5 months, 4 months, 3 months, 2 months or 1 month), at least 6 weeks (such as at least 5 weeks, 4 weeks, 3 weeks, 2 weeks or 1 week) or at least 144 hours (such as at least 120 hours, 96 hours, 72 hours, 48 hours, 24 hours, 12 hours, or 6 hours) prior to treatment with the cell-targeting molecule or pharmaceutical composition of the present invention.

As used herein, the reference to "a patient in need thereof" that "is undergoing treatment with an additional HER2-targeting therapeutic agent" includes patients that are simultaneously or sequentially administered with the cell-targeting molecule or pharmaceutical composition of the present invention and an additional HER2-targeting therapeutic agent. The patient may be administered with the additional HER2-targeting therapeutic agent at least 1 hour (such as at least 6 hours, 12 hours, 24 hours, 48 hours, 72 hours, 96 hours, 120 hours, or 144 hours), 1 week (such as at least 2 weeks, 3 weeks, 4 weeks, 5 weeks or 6 weeks) or 1 month (such as at least 2 months, 3 months, 4 months, 5 months or 6 months) prior to, or subsequent to, treatment with the cell-targeting molecule or pharmaceutical composition of the present invention.

As used herein, the reference to a "patient in need thereof" that does not respond to, or does not benefit from, treatment with one or more additional HER2-targeting therapeutic agent includes patients that are resistant to or have developed resistance to the one or more additional HER2-targeting therapeutic agent. For examples, drug resistance may arise from the expression of drug efflux pumps or cytochrome P450 enzymes (e.g. CYP3A4) as well as obstacles preventing HER2 epitope binding, e.g. HER2 epitope masking of the epitope bound by the HER2-targeting therapeutic. For example, drug resistance may arise from the existence of activated survival/proliferation pathways redundant to HER2 signaling or downstream of HER2 activity thereby bypassing HER2. For example, drug resistance may arise from the existence of mutations in HER2 that alter the drug's effectiveness, such as, e.g., mutations in the ATP-binding pocket bound by a HER2 inhibitor. Resistance mechanisms tied to the additional HER2-targeting therapeutic agent mechanism of action can be avoided by HER2-targeting molecules of the present invention that effectuating a different mechanism of action.

Certain embodiments of the cell-targeting molecules and compositions of the present invention may be used to treat cancers and/or tumors in a subject after the subject has already received a HER2-targeted therapy. In many situations HER2 persists during disease progression after a therapeutic treatment such as, e.g., a HER2-targeted therapy using an anti-HER2 monoclonal antibody therapy or anti-HER2 antibody drug conjugate therapy, or a chemotherapeutic agent therapy using a tyrosine kinase inhibitor. Thus, HER2 is still present as a target on the surfaces of malignant/target cells and available for targeting by a cell-targeting molecule of the present invention.

Certain embodiments of the cell-targeting molecules and compositions of the present invention may be used to kill cancer stem cells, tumor stem cells, pre-malignant cancer-initiating cells, and tumor-initiating cells, which commonly are slow dividing and resistant to cancer therapies like chemotherapy and radiation.

Because of the Shiga toxin A Subunit based mechanism of action, compositions of matter of the present invention may be more effectively used in methods involving their combination with, or in complementary fashion with other therapies, such as, e.g., chemotherapies, immunotherapies, radiation, stem cell transplantation, and immune checkpoint inhibitors, and/or effective against chemoresistant/radiation-resistant and/or resting tumor cells/tumor initiating cells/stem cells. Similarly, compositions of matter of the present invention may be more effectively used in methods involving in combination with other cell-targeted therapies targeting other than the same epitope on, non-overlapping, or different targets for the same disease disorder or condition. These other therapies or other cell-targeted therapies include the additional HER2-targeting therapeutic agent(s) described herein.

Certain embodiments of the cell-targeting molecules of the present invention, or pharmaceutical compositions thereof, can be used to kill an immune cell (whether healthy or malignant) in a patient by targeting an extracellular biomolecule found physically coupled with an immune cell.

For certain embodiments of the cell-targeting molecule of the present invention, or pharmaceutical compositions thereof, can be used to kill an infected cell in a patient by targeting an extracellular biomolecule found physically coupled with an infected cell.

For certain embodiments of the cell-targeting molecules of the present invention, or pharmaceutical compositions thereof, can be used to "seed" a locus within a chordate with non-self, T-cell epitope-peptide presenting cells in order to activate the immune system to enhance policing of the locus. For certain further embodiments of this "seeding" method of the present invention, the locus is a tumor mass or infected tissue site. In preferred embodiments of this "seeding" method of the present invention, the non-self, T-cell epitope-peptide is selected from the group consisting of: peptides not already presented by the target cells of the cell-targeting molecule, peptides not present within any protein expressed by the target cell, peptides not present within the proteome or transcriptome of the target cell, peptides not present in the extracellular microenvironment of the site to be seeded, and peptides not present in the tumor mass or infect tissue site to be targeting.

This "seeding" method functions to label one or more target cells within a chordate with one or more MHC class I presented T-cell epitopes for recognition by effector T-cells and activation of downstream immune responses. By exploiting the cell internalizing, intracellularly routing, and T-cell epitope delivering functions of the cell-targeting molecules of the present invention, the target cells which display the delivered T-cell epitope are harnessed to induce recognition of the presenting target cell by host T-cells and induction of further immune responses including target-cell-killing by CTLs. This "seeding" method of using a cell-targeting molecule of the present invention can provide a temporary vaccination-effect by inducing adaptive immune responses to attack the cells within the seeded microenvironment, such as, e.g. a tumor mass or infected tissue site, whether presenting a cell-targeting molecule-delivered T-cell epitope(s) or not. This "seeding" method may also induce the breaking of immuno-tolerance to a target cell population, a tumor mass, and/or infected tissue site within a chordate.

Certain methods of the present invention involving the seeding of a locus within a chordate with one or more antigenic and/or immunogenic epitopes may be combined with the administration of immunologic adjuvants, whether administered locally or systemically, to stimulate the immune response to certain antigens, such as, e.g., the co-administration of a composition of the present invention with one or more immunologic adjuvants like a cytokine, bacterial product, or plant saponin. Other examples of immunologic adjuvants which may be suitable for use in the methods of the present invention include aluminum salts and oils, such as, e.g., alums, aluminum hydroxide, mineral oils, squalene, paraffin oils, peanut oils, and thimerosal.

Additionally, the present invention provides a method of treating a disease, disorder, or condition in a patient, the method comprising the step of administering to a patient in need thereof a therapeutically effective amount of at least one of the cell-targeting molecules of the present invention, or a pharmaceutical composition thereof. The disease, disorder or condition may be characterized by cells that are physically coupled with HER2/neu/ErbB2. The HER2/neu/ErbB2 may be physically coupled to the surface of the cells. For certain embodiments, the disease, disorder or condition may be characterized by cells that express (including overexpress) HER2/neu/ErbB2. The HER2/neu/ErbB2 may be expressed (including overexpressed) at the surface of the cells. Contemplated diseases, disorders, and conditions that can be treated using this method include cancers, malignant tumors, non-malignant tumors, growth abnormalities, immune disorders, and microbial infections. The cancer, tumor, growth abnormality, immune disorder, or microbial infection may be characterized by cells that are physically coupled with HER2/neu/ErbB2. The HER2/neu/ErbB2 may be physically coupled to the surface of the cells. For certain embodiments, the cancer, tumor, growth abnormality, immune disorder, or microbial infection may be characterized by cells that express (including overexpress) HER2/neu/ErbB2. The HER2/neu/ErbB2 may be expressed (including overexpressed) at the surface of the cells. Administration of a "therapeutically effective dosage" of a composition of the present invention can result in a decrease in severity of disease symptoms, an increase in frequency and duration of disease symptom-free periods, or a prevention of impairment or disability due to the disease affliction. The "patient in thereof" is as described herein. For certain embodiments, the "patient in need thereof" has been previously treated with one or more additional HER2-targeting therapeutic agent; and/or is undergoing treatment with one or more additional HER2-targeting therapeutic agent. For certain embodiments, the "patient in need thereof" has been previously treated with one or more additional HER2-targeting therapeutic agent is as described herein. For certain embodiments, the "patient in need thereof" is undergoing treatment with one or more additional HER2-targeting therapeutic agent is as described herein. For certain embodiments, the "patient in need thereof" does not respond to, or does not benefit from, treatment with one or more additional HER2-targeting therapeutic agent is as described herein. The one or more additional HER2-targeting therapeutic agent is as described herein. For example, the additional HER2-targeting therapeutic agent may comprise a dual tyrosine kinase inhibitor; such as e.g. lapatinib and/or neratinib. For example, the additional HER2-targeting therapeutic agent may comprise an anti-HER2 antibody that binds an antigenic determinant in HER2 that does not overlap with the antigenic determinant in HER2 bound by the HER2-targeting molecule; such as e.g. T-DM1, trastuzumab, and/or pertuzumab. For example, the additional HER2-targeting therapeutic agent may comprise anti-HER2 antibody drug conjugate therapy; such as T-DM1. For certain embodiments, the one or more additional HER2-targeting therapeutic agent is selected from: lapatinib, neratinib, T-DM1, trastuzumab, and pertuzumab.

The therapeutically effective amount of a composition of the present invention will depend on the route of administration, the type of organism being treated, and the physical characteristics of the specific patient under consideration. These factors and their relationship to determining this amount are well known to skilled practitioners in the medical arts. This amount and the method of administration can be tailored to achieve optimal efficacy, and may depend on such factors as weight, diet, concurrent medication and other factors, well known to those skilled in the medical arts. The dosage sizes and dosing regimen most appropriate for human use may be guided by the results obtained by the present invention, and may be confirmed in properly designed clinical trials. An effective dosage and treatment protocol may be determined by conventional means, starting with a low dose in laboratory animals and then increasing the dosage while monitoring the effects, and systematically varying the dosage regimen as well. Numerous factors may be taken into consideration by a clinician when determining an optimal dosage for a given subject. Such considerations are known to the skilled person.

An acceptable route of administration may refer to any administration pathway known in the art, including but not limited to aerosol, enteral, nasal, ophthalmic, oral, parenteral, rectal, vaginal, or transdermal (e.g. topical administration of a cream, gel or ointment, or by means of a transdermal patch). "Parenteral administration" is typically associated with injection at or in communication with the intended site of action, including infraorbital, infusion, intraarterial, intracapsular, intracardiac, intradermal, intramuscular, intraperitoneal, intrapulmonary, intraspinal, intrasternal, intrathecal, intrauterine, intravenous, subarachnoid, subcapsular, subcutaneous, transmucosal, or transtracheal administration.

For administration of a pharmaceutical composition of the present invention, the dosage range will generally be from about 0.001 to 10 milligrams per kilogram (mg/kg), and more, usually 0.001 to 0.5 mg/kg, of the subject's body weight. Exemplary dosages may be 0.001 mg/kg body weight, 0.005 mg/kg body weight, 0.0075 mg/kg body weight, 0.015 mg/kg body weight, 0.020 mg/kg body weight, or 0.025 mg/kg body weight or within the range of 0.001 to 0.030 mg/kg. Exemplary dosages may be 0.01 mg/kg body weight, 0.03 mg/kg body weight, 0.05 mg/kg body weight, 0.075 mg/kg body weight, or 0.1 mg/kg body weight or within the range of 0.01 to 0.1 mg/kg. An exemplary treatment regime is a once or twice daily administration, or a once or twice weekly administration, once every two weeks, once every three weeks, once every four weeks, once a month, once every two or three months or once every three to 6 months. Dosages may be selected and readjusted by the skilled health care professional as required to maximize therapeutic benefit for a particular patient.

Pharmaceutical compositions of the present invention will typically be administered to the same patient on multiple occasions. Intervals between single dosages can be, for example, two to five days, weekly, monthly, every two or three months, every six months, or yearly. Intervals between administrations can also be irregular, based on regulating blood levels or other markers in the subject or patient. Dosage regimens for a composition of the present invention include intravenous administration to a subject of 1 to 50 μg of HER2-targeting molecule per kilogram (kg) body weight with the composition administered once or twice a week for three or more consecutive weeks, such as for four or five weeks. Exemplary dosage regimens for a composition of the present invention include intravenous administration to a subject of 1 to 25 μg of HER2-targeting molecule per kg body weight with the composition administered once or twice a week for three or more consecutive weeks, such as for four or five weeks. Dosage regimens for a composition of the present invention include intravenous administration to a subject of 10 to 50 μg of HER2-targeting molecule per kg body weight with the composition administered once or twice a week for three or more consecutive weeks, such as for four or five weeks. Dosage regimens for a composition of the present invention include intravenous administration of 0.01 to 1 mg/kg body weight or 0.03 to 3 mg/kg body weight with the composition administered every two to four weeks for six dosages, then every three months at 0.01 to 3 mg/kg body weight or 0.01 to 0.03 mg/kg body weight.

A pharmaceutical composition of the present invention may be administered via one or more routes of administration, using one or more of a variety of methods known in the art. As will be appreciated by the skilled worker, the route and/or mode of administration will vary depending upon the desired results. Routes of administration for cell-targeting molecules and pharmaceutical compositions of the present invention include, e.g. intravenous, intramuscular, intradermal, intraperitoneal, subcutaneous, spinal, or other parenteral routes of administration, for example by injection or infusion. For other embodiments, a cell-targeting molecule or pharmaceutical composition of the invention may be administered by a non-parenteral route, such as a topical, epidermal or mucosal route of administration, for example, intranasally, orally, vaginally, rectally, sublingually, or topically.

Therapeutic cell-targeting molecules or pharmaceutical compositions of the present invention may be administered with one or more of a variety of medical devices known in the art. For example, in one embodiment, a pharmaceutical composition of the invention may be administered with a needleless hypodermic injection device. Examples of well-known implants and modules useful in the present invention are in the art, including e.g., implantable micro-infusion pumps for controlled rate delivery; devices for administering through the skin; infusion pumps for delivery at a precise infusion rate; variable flow implantable infusion devices for continuous drug delivery; and osmotic drug delivery systems. These and other such implants, delivery systems, and modules are known to those skilled in the art.

The cell-targeting molecule or pharmaceutical composition of the present invention may be administered alone or in combination with one or more other therapeutic or diagnostic agents. A combination therapy may include a cell-targeting molecule of the present invention, or pharmaceutical composition thereof, combined with at least one other therapeutic agent selected based on the particular patient, disease or condition to be treated. Examples of other such agents include, inter alia, a cytotoxic, anti-cancer or chemotherapeutic agent, an anti-inflammatory or anti-proliferative agent, an antimicrobial or antiviral agent, growth factors, cytokines, an analgesic, a therapeutically active small molecule or polypeptide, a single chain antibody, a classical antibody or fragment thereof, or a nucleic acid molecule which modulates one or more signaling pathways, and similar modulating therapeutic molecules which may complement or otherwise be beneficial in a therapeutic or prophylactic treatment regimen.

The cell-targeting molecule or pharmaceutical composition of the present invention may be administered alone or in combination with one or more other HER2-targeting therapeutic agents. The cell-targeting molecule or pharmaceutical composition of the present invention may be administered alone or in combination with one or more additional HER2-targeting therapeutic agents, such as, e.g., T-DM1 (trastuzumab emtansine), trastuzumab, pertuzumab, and/or lapatinib. A combination therapy may include a cell-targeting molecule of the present invention, or pharmaceutical composition thereof, combined with at least one other therapeutic agent selected based on the particular patient, disease or condition to be treated. Examples of other such agents include, inter alia, a cytotoxic, anti-cancer or chemotherapeutic agent, an anti-inflammatory or anti-proliferative agent, an antimicrobial or antiviral agent, growth factors, cytokines, an analgesic, a therapeutically active small molecule or polypeptide, a single chain antibody, a classical antibody or fragment thereof, or a nucleic acid molecule which modulates one or more signaling pathways, and similar modulating therapeutic molecules which may complement or otherwise be beneficial in a therapeutic or prophylactic treatment regimen. For certain embodiments, the methods of the invention for treating a disease, disorder, or condition in a patient in need thereof may further comprise administering to the patient a therapeutically effective amount of one or more additional HER2-targeting therapeutic agent. The additional HER2-targeting therapeutic agent is as described herein. For example, the additional HER2-targeting therapeutic agent may comprise a dual tyrosine kinase inhibitor; such as lapatinib and/or neratinib. For example, the additional HER2-targeting therapeutic agent may comprise an anti-HER2 antibody that binds an antigenic determinant in HER2 that does not overlap with the antigenic determinant in HER2 bound by the HER2-targeting molecule; such as T-DM1, trastuzumab, and/or pertuzumab for the HER2-targeting molecule which comprises, consists of, or consists essentially of any one of SEQ ID NOs: 29, 36, 102, and 108. For example, the additional HER2-targeting therapeutic agent may comprise anti-HER2 antibody drug conjugate therapy; such as T-DM1.

Treatment of a patient with cell-targeting molecule or pharmaceutical composition of the present invention preferably leads to cell death of targeted cells and/or the inhibition of growth of targeted cells. As such, cytotoxic, cell-targeting molecules of the present invention, and pharmaceutical compositions comprising them, will be useful in methods for treating a variety of pathological disorders in which killing or depleting target cells may be beneficial, such as, inter alia, cancer, tumors, other growth abnormalities, immune disorders, and infected cells. The present invention provides methods for suppressing cell proliferation, and treating cell disorders involving HER2-expressing cells, including neoplasia.

In certain embodiments, the cell-targeting molecules and pharmaceutical compositions of the present invention are for use in the treatment or prevention of a disease, disorder, or condition in a patient in need thereof. The disease, disorder or condition may be characterized by cells that are physically coupled with HER2 (e.g. the cells express HER2 such that HER2 is expressed on the surfaces of the cells). In certain embodiments, the cell-targeting molecules and pharmaceutical compositions of the present invention are for use in the treatment or prevention of a cancer, tumor (malignant and non-malignant), growth abnormality, immune disorder, and/or microbial infection in a patient in need thereof. In certain embodiments, the cell-targeting molecules and pharmaceutical compositions of the present invention are for use in the treatment or prevention of a cancer, tumor (malignant and non-malignant), and/or growth abnormality in a patient in need thereof. In certain embodiments, the cell-targeting molecules and pharmaceutical compositions of the present invention are for use in the treatment or prevention of a cancer and/or tumor (malignant and non-malignant) in a patient in need thereof. The cancer, tumor, growth abnormality, immune disorder, and/or microbial infection may be characterized by cells that are physically coupled with HER2 (e.g. the cells express HER2 such that HER2 is expressed on the surfaces of the cells). The "patient in thereof" is as described herein. In certain embodiments, the "patient in need thereof" has been previously treated with one or more additional HER2-targeting therapeutic agent; and/or is undergoing treatment with one or more additional HER2-targeting therapeutic agent. For certain embodiments, the "patient in need thereof" has been previously treated with one or more additional HER2-targeting therapeutic agent is as described herein. For certain embodiments, the "patient in need thereof" is undergoing treatment with one or more additional HER2-targeting therapeutic agent is as described herein. For certain embodiments, the "patient in need thereof" does not respond to, or does not benefit from, treatment with one or more additional HER2-targeting therapeutic agent is as described herein. For certain embodiments, the treatment or prevention of a disease, disorder, or condition in a patient in need thereof may further comprise a step of administering to the patient a therapeutically effective amount of one or more additional HER2-targeting therapeutic agent. The additional HER2-targeting therapeutic agent is as described herein.

In certain embodiments, the present invention provides methods for treating malignancies or neoplasms and other blood cell associated cancers in a mammalian subject, such as a human, the method comprising the step of administering to a subject in need thereof a therapeutically effective amount of a cytotoxic cell-targeting molecule or pharmaceutical composition of the present invention.

The cell-targeting molecules and pharmaceutical compositions of the present invention have varied applications. The cell-targeting molecules and pharmaceutical compositions of the present invention are commonly anti-neoplastic agents—meaning they are capable of treating and/or preventing the development, maturation, or spread of neoplastic or malignant cells by inhibiting the growth and/or causing the death of cancer or tumor cells. However, certain embodiments of the cell-targeting molecule or pharmaceutical composition of the present invention is used to treat an immune disorder, such as, e.g., a T-cell-, B-cell-, plasma cell- or antibody-mediated disease or disorder.

Certain embodiments of the cell-targeting molecules and pharmaceutical compositions of the present invention can be utilized in a method of treating cancer comprising administering to a patient, in need thereof, a therapeutically effective amount of a cell-targeting molecule and/or pharmaceutical composition of the present invention. For certain embodiments of the methods of the present invention, the cancer being treated is selected from the group consisting of: bone cancer (such as multiple myeloma or Ewing's sarcoma), breast cancer, central/peripheral nervous system cancer (such as brain cancer, neurofibromatosis, or glioblastoma), gastrointestinal cancer (such as stomach cancer or colorectal cancer), germ cell cancer (such as ovarian cancers and testicular cancers, glandular cancer (such as pancreatic cancer, parathyroid cancer, pheochromocytoma, salivary gland cancer, or thyroid cancer), head-neck cancer (such as nasopharyngeal cancer, oral cancer, or pharyngeal cancer), hematological cancers (such as leukemia, lymphoma, or myeloma), kidney-urinary tract cancer (such as renal cancer and bladder cancer), liver cancer, lung/pleura cancer (such as mesothelioma, small cell lung carcinoma, or non-small cell lung carcinoma), prostate cancer, sarcoma (such as angiosarcoma, fibrosarcoma, Kaposi's sarcoma, or synovial sarcoma), skin cancer (such as basal cell carcinoma, squamous cell carcinoma, or melanoma), and uterine cancer. For certain embodiments, the cancer to be treated is selected from the group consisting of: breast cancer, gastric cancer, urothelial cancer, bladder cancer, urothelial bladder cancer, serous uterine cancer, extrahepatic biliary tract cancer, and biliary carcinoma. For certain embodiments, the cancer being treated is breast cancer and/or gastrointestinal cancer.

Among certain embodiments of the present invention is using the Shiga toxin effector polypeptide or cell-targeting molecule of the present invention as a component of a pharmaceutical composition or medicament for the treatment or prevention of a cancer, tumor, other growth abnormality, immune disorder, and/or microbial infection. For example, skin tumors may be treated with such a medicament in efforts to reduce tumor size or eliminate the tumor completely.

Among certain embodiment of the present invention is a method of using a Shiga toxin effector polypeptide, cell-targeting molecule, pharmaceutical composition, and/or diagnostic composition of the present invention to label or detect the interiors of neoplastic cells. This method may be based on the ability of certain cell-targeting molecules of the present invention to enter specific cell types and route within cells via retrograde intracellular transport, to the interior compartments of specific cell types are labeled for detection. This can be performed on cells in situ within a patient or on cells and tissues removed from an organism, e.g. biopsy material.

Among certain embodiment of the present invention is a method of using a Shiga toxin effector polypeptide, cell-targeting molecule, pharmaceutical composition, and/or diagnostic composition of the present invention to detect the presence of a cell type for the purpose of information gathering regarding diseases, conditions and/or disorders. The disease, disorder, or condition may be characterized by cells that are physically coupled with HER2. The HER2 target biomolecule may be physically coupled to the surface of the cells. For certain embodiments, the disease, disorder or condition may be characterized by cells that express the HER2 target biomolecule (including cells that overexpress HER2). The HER2 may be expressed (including overexpressed) at the surface of the cells. The method comprises contacting a cell with a diagnostically sufficient amount of a cell-targeting molecule of the present invention in order to detect the molecule by an assay or diagnostic technique. The phrase "diagnostically sufficient amount" refers to an amount that provides adequate detection and accurate measurement for information gathering purposes by the particular assay or diagnostic technique utilized. Generally, the diagnostically sufficient amount for whole organism in vivo diagnostic use will be a non-cumulative dose of between 0.001 to 10 milligrams of the detection promoting agent linked cell-targeting molecule of the invention per kg of subject per subject. Typically, the amount of cell-targeting molecule of the invention used in these information gathering methods will be as low as possible provided that it is still a diagnostically sufficient amount. For example, for in vivo detection in an organism, the amount of Shiga toxin effector polypeptide, cell-targeting molecule, or pharmaceutical composition of the invention administered to a subject will be as low as feasibly possible.

The cell-type specific targeting of cell-targeting molecules of the present invention combined with detection promoting agents provides a way to detect and image cells physically coupled with an extracellular target biomolecule of a binding region of the molecule of the invention. Imaging of cells using the cell-targeting molecules of the present invention may be performed in vitro or in vivo by any suitable technique known in the art. Diagnostic information may be collected using various methods known in the art, including whole body imaging of an organism or using ex vivo samples taken from an organism. The term "sample" used herein refers to any number of things, but not limited to, fluids such as blood, urine, serum, lymph, saliva, anal secretions, vaginal secretions, and semen, and tissues obtained by biopsy procedures. For example, various detection promoting agents may be utilized for non-invasive in vivo tumor imaging by techniques such as magnetic resonance imaging (MRI), optical methods (such as direct, fluorescent, and bioluminescent imaging), positron emission tomography (PET), single-photon emission computed tomography (SPECT), ultrasound, x-ray computed tomography, and combinations of the aforementioned (see, Kaur S et al., *Cancer Lett* 315: 97-111 (2012), for review).

Among certain embodiment of the present invention is a method of using a Shiga toxin effector polypeptide, cell-targeting molecule, or pharmaceutical composition of the present invention in a diagnostic composition to label or detect the interiors of a hematologic cell, cancer cell, tumor cell, infected cell, and/or immune cell (see e.g., Koyama Y et al., *Clin Cancer Res* 13: 2936-45 (2007); Ogawa M et al., *Cancer Res* 69: 1268-72 (2009); Yang L et al., *Small* 5: 235-43 (2009)). Based on the ability of certain cell-targeting molecules of the invention to enter specific cell types and route within cells via retrograde intracellular transport, the interior compartments of specific cell types are labeled for detection. This can be performed on cells in situ within a patient or on cells and tissues removed from an organism, e.g. biopsy material.

Diagnostic compositions of the present invention may be used to characterize a disease, disorder, or condition as potentially treatable by a related pharmaceutical composition of the present invention. Certain compositions of matter of the present invention may be used to determine whether a patient belongs to a group that responds to a therapeutic strategy which makes use of a compound, composition or related method of the present invention as described herein or is well suited for using a delivery device of the invention.

Diagnostic compositions of the present invention may be used after a disease, e.g. a cancer, is detected in order to better characterize it, such as to monitor distant metastases, heterogeneity, and stage of cancer progression. The phenotypic assessment of disease disorder or infection can help prognostic and prediction during therapeutic decision making. In disease reoccurrence, certain methods of the invention may be used to determine if local or systemic problem.

Diagnostic compositions of the present invention may be used to assess responses to therapies regardless of the type of the type of therapy, e.g. small molecule drug, biological drug, or cell-based therapy. For example, certain embodiments of the diagnostics of the invention may be used to measure changes in tumor size, changes in antigen positive cell populations including number and distribution, or monitoring a different marker than the antigen targeted by a therapy already being administered to a patient (see Smith-Jones P et al., *Nat. Biotechnol* 22: 701-6 (2004); Evans M et al., *Proc. Natl. Acad. Sci. USA* 108: 9578-82 (2011)).

For certain embodiments of the method used to detect the presence of a cell type may be used to gather information regarding diseases, disorders, and conditions, such as, for example bone cancer (such as multiple myeloma or Ewing's sarcoma), breast cancer, central/peripheral nervous system cancer (such as brain cancer, neurofibromatosis, or glioblastoma), gastrointestinal cancer (such as stomach cancer or colorectal cancer), germ cell cancer (such as ovarian cancers and testicular cancers, glandular cancer (such as pancreatic cancer, parathyroid cancer, pheochromocytoma, salivary gland cancer, or thyroid cancer), head-neck cancer (such as nasopharyngeal cancer, oral cancer, or pharyngeal cancer), hematological cancers (such as leukemia, lymphoma, or myeloma), kidney-urinary tract cancer (such as renal cancer and bladder cancer), liver cancer, lung/pleura cancer (such as mesothelioma, small cell lung carcinoma, or non-small cell lung carcinoma), prostate cancer, sarcoma (such as angiosarcoma, fibrosarcoma, Kaposi's sarcoma, or synovial sarcoma), skin cancer (such as basal cell carcinoma, squamous cell carcinoma, or melanoma), uterine cancer, acute lymphoblastic leukemia (ALL), T acute lymphocytic leukemia/lymphoma (ALL), acute myelogenous leukemia, acute myeloid leukemia (AML), B-cell chronic lymphocytic leukemia (B-CLL), B-cell prolymphocytic lymphoma, Burkitt's lymphoma (BL), chronic lymphocytic leukemia (CLL), chronic myelogenous leukemia (CML-BP), chronic myeloid leukemia (CML), diffuse large B-cell lymphoma, follicular lymphoma, hairy cell leukemia (HCL), Hodgkin's Lymphoma (HL), intravascular large B-cell lymphoma, lymphomatoid granulomatosis, lymphoplasmacytic lymphoma, MALT lymphoma, mantle cell lymphoma, multiple myeloma (MM), natural killer cell leukemia, nodal marginal B-cell lymphoma, Non-Hodgkin's lymphoma (NHL), plasma cell leukemia, plasmacytoma, primary effusion lymphoma, pro-lymphocytic leukemia, promyelocytic leukemia, small lymphocytic lymphoma, splenic marginal zone lymphoma, T-cell lymphoma (TCL), heavy chain disease, monoclonal gammopathy, monoclonal immunoglobulin deposition disease, myelodysplastic syndromes (MDS), smoldering multiple myeloma, and Waldenstrom macroglobulinemia.

In certain embodiments, the Shiga toxin effector polypeptides and cell-targeting molecules of the present invention, or pharmaceutical compositions thereof, are used for both diagnosis and treatment, or for diagnosis alone. In some situations, it would be desirable to determine or verify the HLA variant(s) and/or HLA alleles expressed in the subject and/or diseased tissue from the subject, such as, e.g., a patient in need of treatment, before selecting a cell-targeting molecule of the invention for use in treatment(s).

Any embodiment of the Shiga toxin effector polypeptide of the present invention and cell-targeting molecule of the present invention (e.g. embodiments of embodiment Sets #1-3 in the Summary) may be used with each individual embodiment of the methods of the present invention.

The present invention is further illustrated by the following non-limiting examples of 1) Shiga toxin effector polypeptides of the present invention, 2) cell-targeting molecules of the present invention, and 3) cytotoxic, cell-targeting molecules of the present invention comprising the aforementioned polypeptides and capable of specifically targeting certain cell types.

EXAMPLES

The following examples demonstrate certain embodiments of the present invention. However, it is to be understood that these examples are for illustration purposes only and do not intend, nor should any be construed, to be wholly definitive as to conditions and scope of this invention. The experiments in the following examples were carried out using standard techniques, which are well known and routine to those of skill in the art, except where otherwise described.

The following examples describe several, exemplary, cytotoxic, Shiga toxin A Subunit derived polypeptide scaffolds comprising Shiga toxin effector polypeptides of the present invention. The Shiga toxin effector polypeptides in the Examples are de-immunized while retaining potent cytotoxic activities.

The following examples also describe several, cytotoxic, cell-targeting molecules, each molecule comprising a Shiga toxin effector polypeptide linked, either directly or indirectly, to a cell-targeting binding region capable of specifically binding an extracellular part of a HER2 target biomolecule physically associated with a cellular surface of a cell. Exemplary, cytotoxic, cell-targeting molecules described below bound to cell-surface, target biomolecules expressed by targeted, tumor cell-types and entered those targeted cells. The internalized, cell-targeting molecules effectively routed their Shiga toxin effector polypeptides to the cytosols of target cells where the Shiga toxin effector polypeptides inactivated ribosomes and subsequently caused the apoptotic death of the targeted cells.

Additionally, some of the exemplary cell-targeting molecules comprise protease-cleavage resistant, de-immunized, Shiga toxin effector polypeptides that exhibit improved in vivo immunogenicity profiles (reductions in antibody responses) as compared to parental cytotoxic molecules comprising a furin-cleavage resistant, Shiga toxin effector polypeptide that has not been further de-immunized by the disruption of additional, endogenous epitope regions. Furthermore, these exemplary, protease-cleavage resistant, de-immunized cell-targeting molecules exhibit improved in vivo tolerability as compared to related cell-targeting molecules comprising more protease-cleavage sensitive Shiga toxin effector polypeptide regions.

The Examples below describe certain, cell-targeting molecules of the present invention and their properties. Certain Examples describe cell-targeting molecules of the present invention wherein a Shiga toxin effector polypeptide component (1) is de-immunized; (2) is on or proximal to an amino-terminus of a polypeptide component of the cell-targeting molecule; (3) is furin-cleavage resistant; and/or (4) comprises an embedded or inserted T-cell epitope.

Example 1. HER2-Targeting Molecules Comprising Furin-Cleavage Resistant, Shiga Toxin A Subunit Derived Polypeptides Various HER2-targeting molecules, each comprising (1) at least one immunoglobulin-type binding region targeting HER2 and (2) at least one Shiga toxin A Subunit effector polypeptide were constructed and tested for use in killing HER2-positive cancer cells.

A. Construction and Production of HER2-Targeting Molecules

Cytotoxic, cell-targeting molecules were designed to target HER2 using various Shiga toxin A Subunit effector polypeptides (each capable of providing one or more Shiga toxin A Subunit functions) and various immunoglobulin-type binding regions, each capable of binding an extracellular part of human HER2, as cell-targeting binding regions. The immunoglobulin-type binding region of these HER2-targeting molecules was either a single-chain antibody variable fragment or a camelid $V_HH$ that binds with high-affinity, specificity, and selectivity to a cell-surface HER2 target biomolecule physically coupled to the surface of human cancer cells. Polynucleotides were constructed which encode fusion proteins comprising the aforementioned components: (1) at least one anti-HER2 antibody variable fragment and (2) at least one Shiga toxin A Subunit effector polypeptide. These polynucleotides were used to produce cytotoxic, cell-targeting molecules of the present invention, including 114773 (SEQ ID NO:22), 115172 (SEQ ID NO:23), 114778 (SEQ ID NO:24), 114795 (SEQ ID NO:25), 114791 (SEQ ID NO:26), 114912 (SEQ ID NO:28), 115111 (SEQ ID NO:29), 115411 (SEQ ID NO:30), 114898 (SEQ ID N031), 115195 (SEQ ID NO:32), 115194 (SEQ ID NO:33), 115645 (SEQ ID NO:34), and 115845 (SEQ ID NO:35). All of the cell-targeting molecules tested in the experiments of this Example, including reference cell-targeting molecules, were produced in a bacterial system and purified by column chromatography using techniques well-known to the skilled worker. The purification of certain exemplary HER2-targeting molecules of the present invention was facilitated by the use of a fused affinity tag, such as, e.g., a chitin-binding domain (SEQ ID NO:43) or a 6×His polyhistidine tag (SEQ ID NO:44).

1. Chitin Affinity Based Purification

For certain exemplary HER2-binding proteins of this Example, cloning and purification were done essentially as described in the manufacturer's manual for the IMPACT™ (Intein Mediated Purification with an Affinity Chitin-binding Tag) system (New England Biolabs, Ipswich, Mass., U.S.A.). An affinity tag used to purify some of the HER2-targeting molecules of this Example was the intein chitin binding domain (CBD) sequence (SEQ ID NO:43), which was fused to the carboxy-terminals of some of the fusion proteins of this Example using the E. coli expression vector pTxb1 (New England Biolabs, Ipswich, Mass., U.S.A.). These CBD fusion proteins were expressed in bacteria, extracted from the soluble fraction, and then allowed to bind to a chitin column. The intein was then cleaved away from the fusion protein by incubation with dithiolthreitol (DTT), and the HER2-binding proteins of interest were eluted away from the chitin column after removal of the CBD affinity tag (SEQ ID NO:43).

Figure 2:
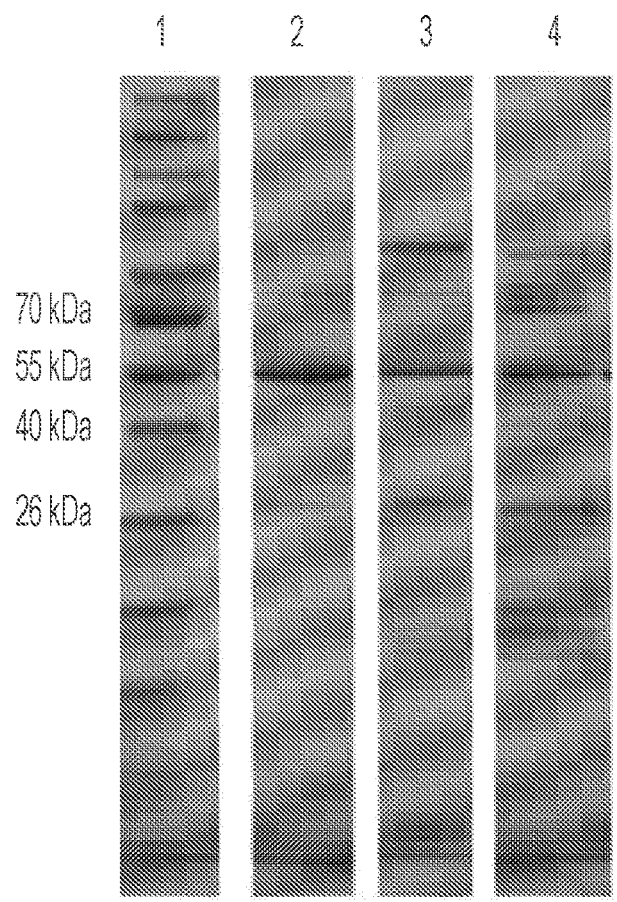

Exemplary HER2-targeting fusion proteins of the present invention 114778 (SEQ ID NO:24), 114795 (SEQ ID NO:25), and 114791 (SEQ ID NO:26) were expressed and samples were analyzed by SDS-PAGE (FIG. 2). All three of these protein samples were predominantly comprised by a protein species of about 55 kDa as measured by SDS-PAGE in reducing conditions (FIG. 2).

These exemplary HER2-targeting molecules were then tested for cytotoxic activity using the following cytotoxicity assay. Certain human tumor cell-line cells were plated in 20 µL cell culture medium in 384-well plates (typically at 1-2×10³ cells per well for adherent cells, plated the day prior or day of addition of HER2-targeting molecule). A series of dilutions (typically 10-fold) of the molecules to be tested was prepared in an appropriate buffer, and 5 µL of the dilutions or buffer-only control were added to the plated cells. Control wells containing only cell culture medium were used for baseline correction. The cell samples were incubated with the HER2-targeting molecule or just buffer for 3 or 5 days at 37° C. and in an atmosphere of 5% carbon dioxide (CO2). The total cell survival or percent viability was determined using a luminescent readout using the CellTiter-Glo® Luminescent Cell Viability Assay (Promega Corp., Madison, Wis., U.S.A.) according to the manufacturer's instructions. The human cells tested included cells from the HCC1954 and NCI/ADR-RES cell lines, where certain samples of NCI/ADR-RES cells were transfected with a HER2 expression vector to make them express HER2 to a cell-surface in sufficient quantities to make them HER2 positive (referred to herein as "NCI/ADR-RES-HER2+").

The Percent Viability of cells in experimental wells was calculated using the following equation: (Test RLU−Average Media RLU)±(Average Cells RLU−Average Media RLU)×100. The logarithm of the cell-targeting molecule protein concentration versus Percent Viability was plotted in Prism (GraphPad Prism, San Diego, Calif., U.S.A.) and log (inhibitor) versus response (3 parameter) analysis or and log (inhibitor) versus normalized response analysis were used to determine the half-maximal cytotoxic concentration (CD50) value for the tested molecule. The CD50 value(s) for each molecule tested were calculated, when possible. When $CD_{50}$ values could not be calculated based on the shape of the curve over the concentrations tested, then a $CD_{50}$ value was noted as being beyond the maximum tested concentration. All graphs and non-linear regressions were done with GraphPad Prism and flow cytometry data was analyzed with FloJo software.

Figure 3:
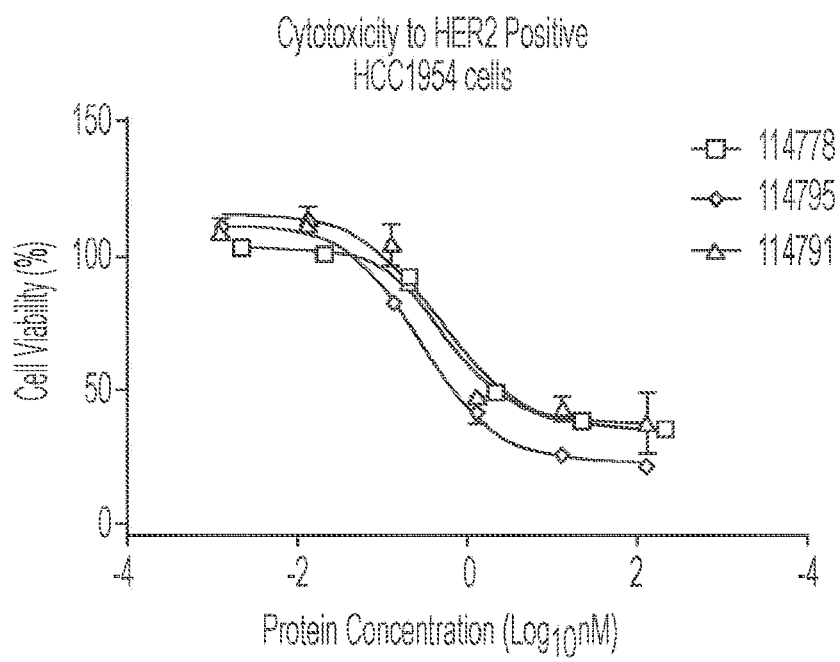
Figure 3:
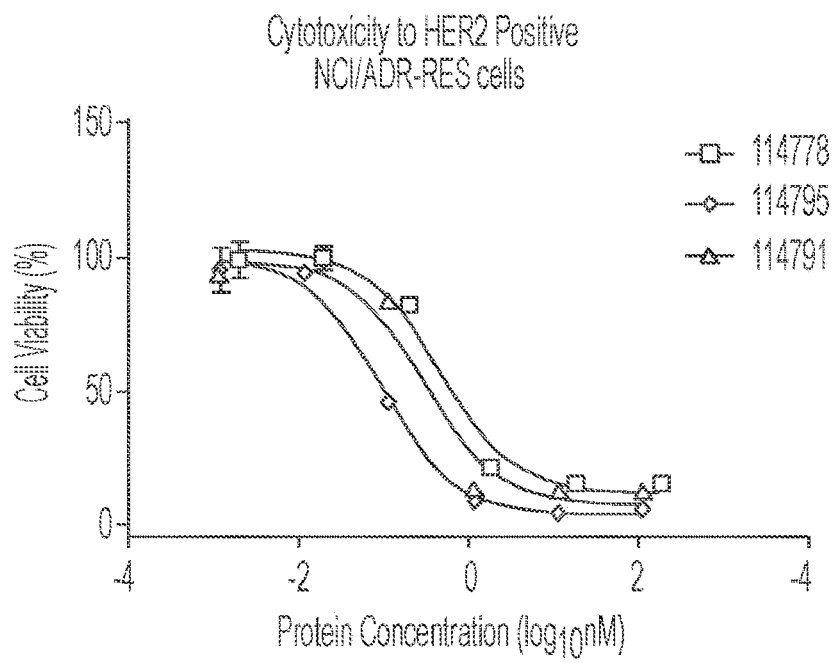

Results of the cytotoxicity assay are reported below (see Table 1 and FIG. 3). The exemplary HER2-targeting molecules 114778 (SEQ ID NO:24), 114795 (SEQ ID NO:25), and 114791 (SEQ ID NO:26) were cytotoxic to HER2 positive cells (Table 1; FIG. 3). In some experiments, HER2 negative cells were also treated with the maximum concentration of the HER2-targeting molecule in the dilution series, and, under these conditions, the HER2 negative cells did not show any change in viability as compared to a buffer only control.

TABLE 1

Cytotoxicities of Exemplary HER2-Targeting Molecules of the Present Invention Purified Using a Chitin-Binding Affinity Tag and Intein-Mediated Cleavage Away from the Tag
Purification Method: Chitin binding via intein tag and tag cleavage with DTT

| HER2-Targeting Molecule | $CD_{50}$ (ng/mL) HER2 positive HCC1954 cells | $CD_{50}$ (ng/mL) HER2 positive NCI/ADR-RES cells |
| --- | --- | --- |
| 114778 | 36.9 | 26.4 |
| 114791 | 20.9 | 17.1 |
| 114795 | 14.9 | 5.5 |

This data demonstrated similar cytotoxic potencies among 114795 (SEQ ID NO:25), 114778 (SEQ ID NO:24), and 114791 (SEQ ID NO:26), all of which were fusion proteins purified using the IMPACT™ CBD intein affinity tag, chitin-binding purification system.

2. Protein L Affinity Based Purification

Figure 4:
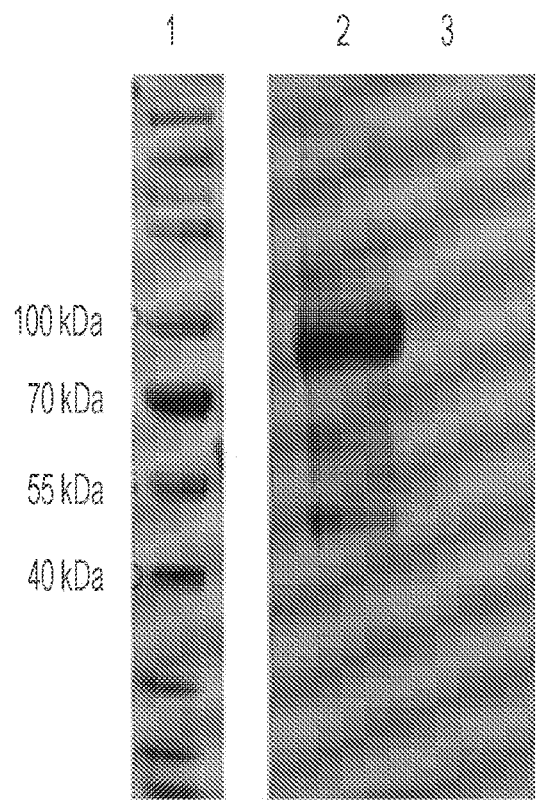
Figure 5:
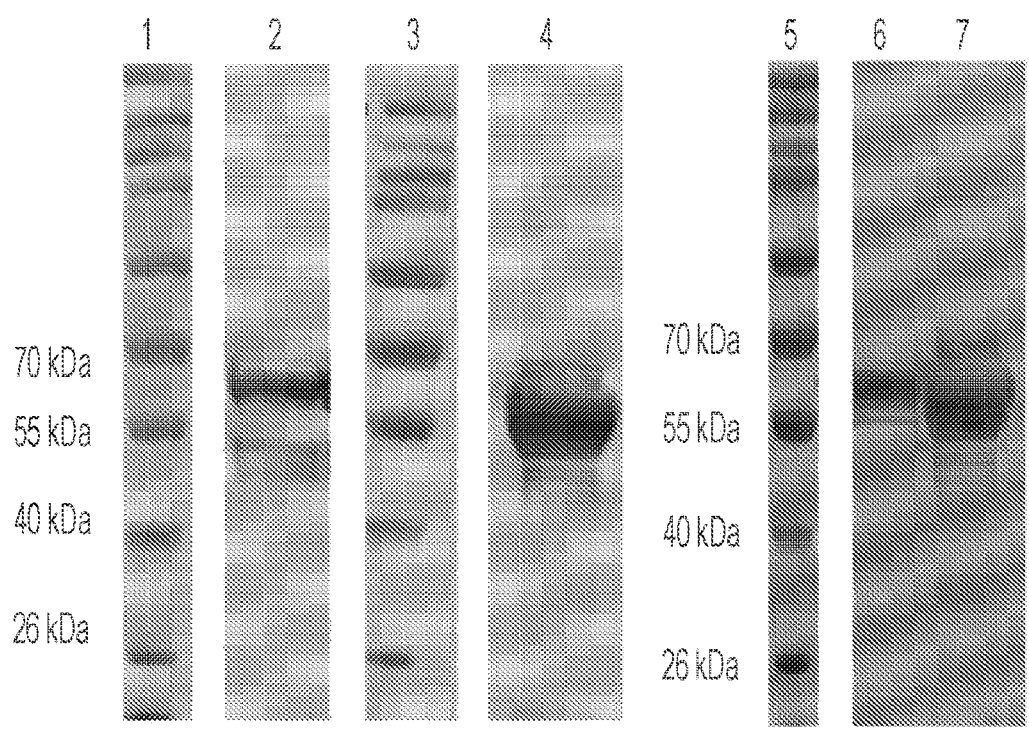

An alternative method of protein purification based on Protein L binding affinity was used and compared to the intein-CBD affinity tag method used above involving the IMPACT™ system. The binding affinity between bacterial Protein L and certain scFv's was used to purify exemplary HER2-targeting molecules of the present invention: 114773 (SEQ ID NO:22) comprising a carboxy-terminal intein-CBD tag (SEQ ID NO:43), 114912 (SEQ ID NO:28), 115111 (SEQ ID NO:29), and 115411 (SEQ ID NO:30). FIGS. 4-5 show SDS-PAGE analyses of samples of 114773 (SEQ ID NO:22), 114791 (SEQ ID NO:26), 114912 (SEQ ID NO:28), 115111 (SEQ ID NO:29), and 115411 (SEQ ID NO:30) after purification using a Protein L binding affinity method.

FIG. 4 shows an SDS-PAGE analysis of 114773 (SEQ ID NO:22) (with a carboxy-terminal intein-CBD tag (SEQ ID NO:43)) and 114791 (SEQ ID NO:26) (with a carboxy-terminal intein-CBD tag (SEQ ID NO:43)) samples after purification using a Protein L binding affinity method. FIG. 5 shows SDS-PAGE analysis of 114912 (SEQ ID NO:28) (without any intein-CBD tag), 115111 (SEQ ID NO:29) (without any intein-CBD tag), and 115411 (SEQ ID NO:30) (without any intein-CBD tag).

Exemplary HER2-targeting molecules 114912 (SEQ ID NO:28) and 115111 (SEQ ID NO:29) purified using Protein L binding were tested for cytotoxic activity using the assay as described above for the samples purified using the CBD intein system. The results of the cytotoxicity assay are reported below (see Table 2 and FIG. 6).

TABLE 2

Cytotoxicities of Exemplary HER2-Targeting Molecules of the Present Invention Purified Using Protein L Binding Affinity Purification Method: Protein L binding via scFv

| | $CD_{50}$ (ng/mL) | | | | | |
| --- | --- | --- | --- | --- | --- | --- |
| HER2-targeting molecule | HER2 positive HCC1954 cells | HER2 positive NCI/ADR-RES cells | HER2 positive JIMT-1 cells | HER2 positive SK-OV-3 cells | HER2 positive HCC1419 cells | HER2 negative JIMT-1 cells |
| 114912 | 9.0 | 14.0 | 78.9 | 43.2 | 33.3 | >2,000 |
| 115111 | 1.6 | 2.8 | 5.9 | 6.4 | 11.8 | >2,000 |

Figure 6:
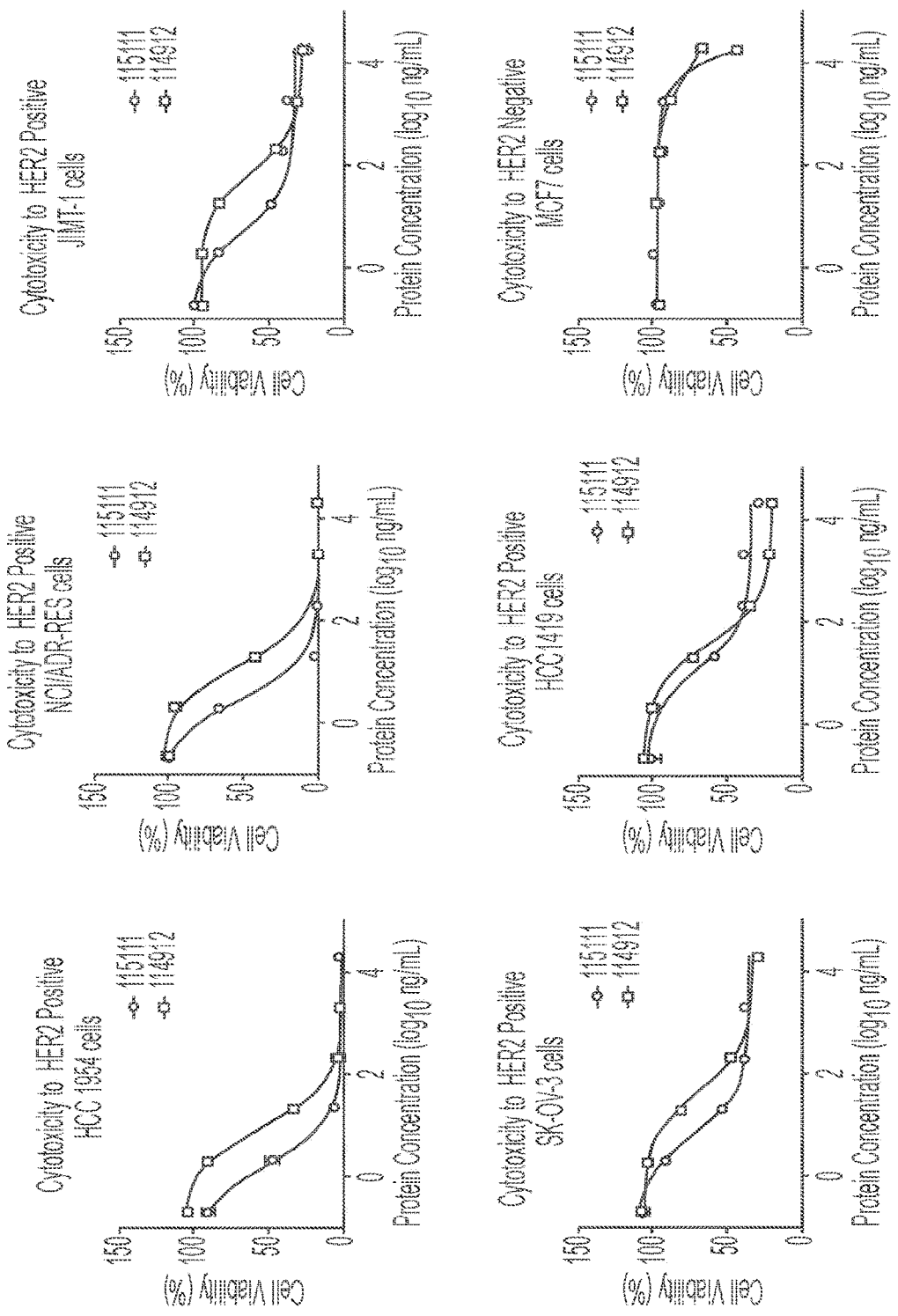

The exemplary HER2-targeting fusion proteins 114912 (SEQ ID NO:28) and 115111 (SEQ ID NO:29) were cytotoxic to HER2 positive cells (Table 2; FIG. 6). This data demonstrated the greater cytotoxic potency of 115111 (SEQ ID NO:29) as compared to 114912 (SEQ ID NO:28), both of which were purified using Protein L affinity. No cytotoxicity toward MCF-7 cells, which express very low levels of HER2, was observed for most of the HER2-targeting molecule concentrations tested (FIG. 6).

Additional exemplary HER2-targeting molecules of the present invention that are related to 115111 (SEQ ID NO:29) were tested for cytotoxic activities toward HER2 positive cell lines using the cytotoxicity assay described above. The proteins 115172 (SEQ ID NO:23), 115195 (SEQ ID NO:32), and 115194 (SEQ ID NO:33) are related to 115111 (SEQ ID NO:29) because they each comprise identical heavy and light variable domains.

The skilled worker will appreciate that the length of the linker between variable domains (or "interdomain linker") in a scFv can affect the spontaneous assembly of non-covalent, multimeric, multivalent molecules. Generally, linkers that are between three amino acid residues and twelve amino acid residues in length (e.g. the pentamer G4S (SEQ ID NO:94)) promote diabody formation via intermolecular variable domain swapping; whereas longer linkers (e.g. $(G_4S)_5$ (SEQ ID NO:92)) allow for intramolecular heavy and light chain pairing, resulting in predominantly monomeric molecules (see e.g. WO 2018/140427). 115111 (SEQ ID NO:29) comprises a 25-mer interdomain linker and was verified to predominantly form monovalent monomers. 115195 (SEQ ID NO:32) comprises a pentamer interdomain linker and was verified to predominantly form divalent dimers. 115194 (SEQ ID NO:33) comprises an identical scFv to 115195 (SEQ ID NO:32) having the same pentamer interdomain linker and is predicted to form divalent dimers like 115195 (SEQ ID NO:32). 115172 (SEQ ID NO:23) and 115194 (SEQ ID NO:33) differ from 115111 (SEQ ID NO:29) and 115195 (SEQ ID NO:32) in that its Shiga toxin A Subunit effector polypeptide SLTA-FR (SEQ ID NO:37) comprises mostly wild-type sequences, having mutations only in the minimal furin-cleavage site at the carboxy-terminus of the A1 fragment and disrupting Epitope Region #8 (Table B, supra). Cytotoxicity data for these molecules are reported below (see Table 3 and FIG. 7.

TABLE 3

Cytotoxicity of 115111 and Related HER2-Targeting Molecules

| Cell Line | Cancer Type | HER2 Expression | $CD_{50}$ (ng/mL) | | | |
|---|---|---|---|---|---|---|
| | | | 115111 | 115195 | 115172 | 115194 |
| HCC1954 | breast | high | 4.6 | 5.6 | 1.5 | 3.1 |
| NCI/ADR-RES-HER2+ | ovarian, transfected with HER2 | high | 5.1 | 3.6 | 1.8 | 1.8 |
| HCC1569 | breast | high | 21.1 (45%) | 17.2 (55%) | 9.1 (25%) | 9.9 (35%) |
| JIMT-1 | breast | medium | 5.9 (35%) | 6.7 (37%) | 3.3 (21%) | 6.8 (22%) |
| ST486 | lymphoma | negative | ~5,000 | ~5,000 | ~5,000 | ~5,000 |

Figure 7:
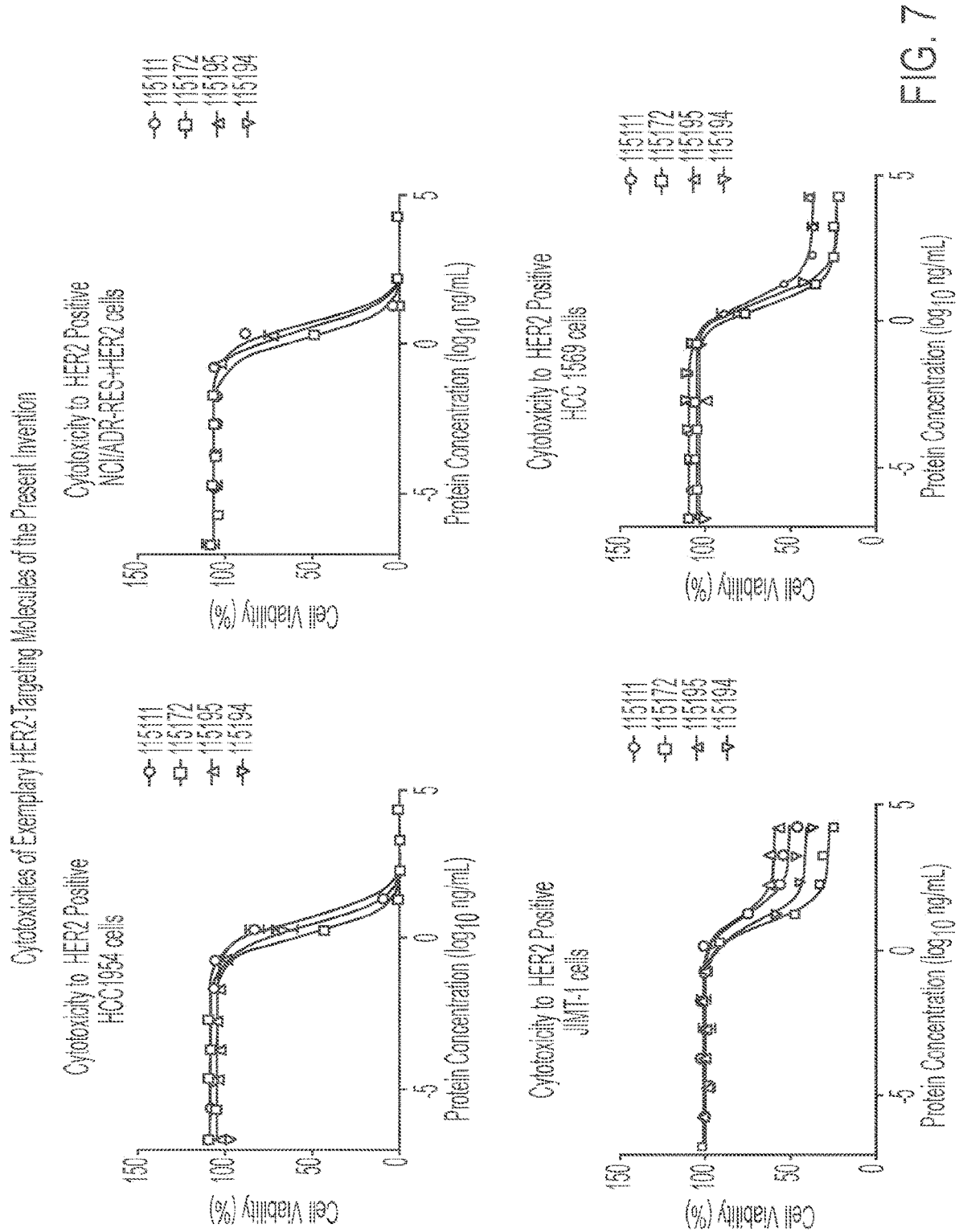
Figure 8:
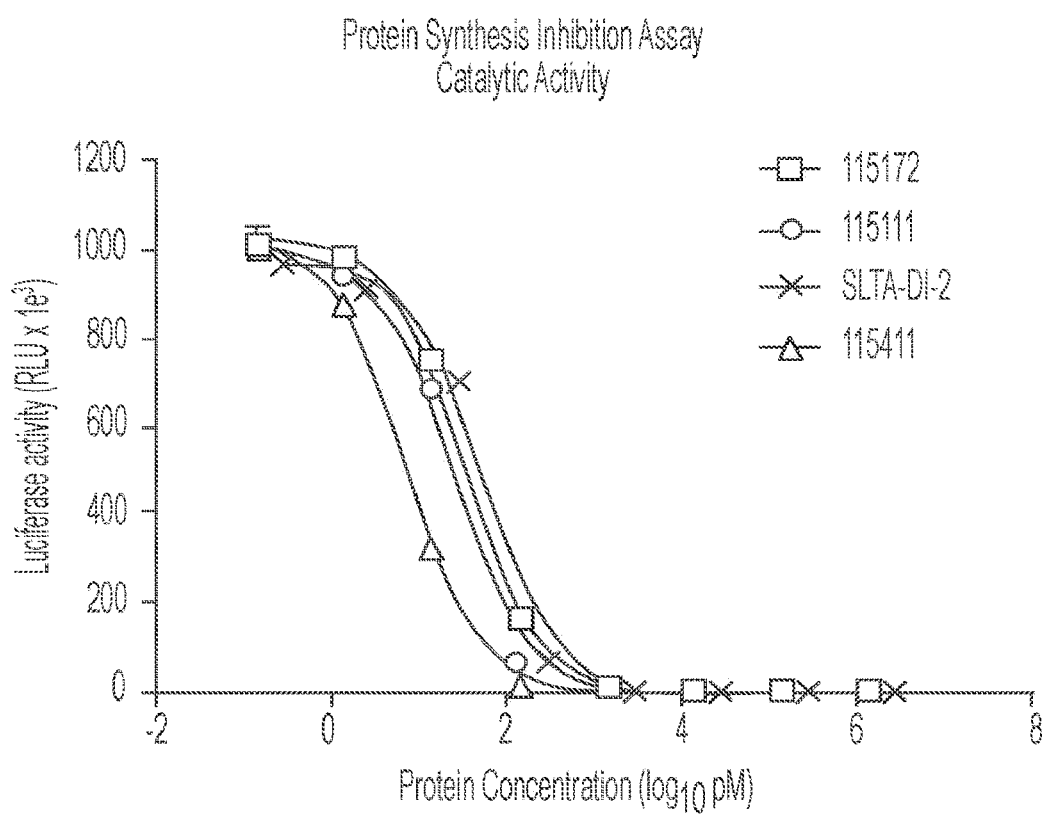
Figure 9:
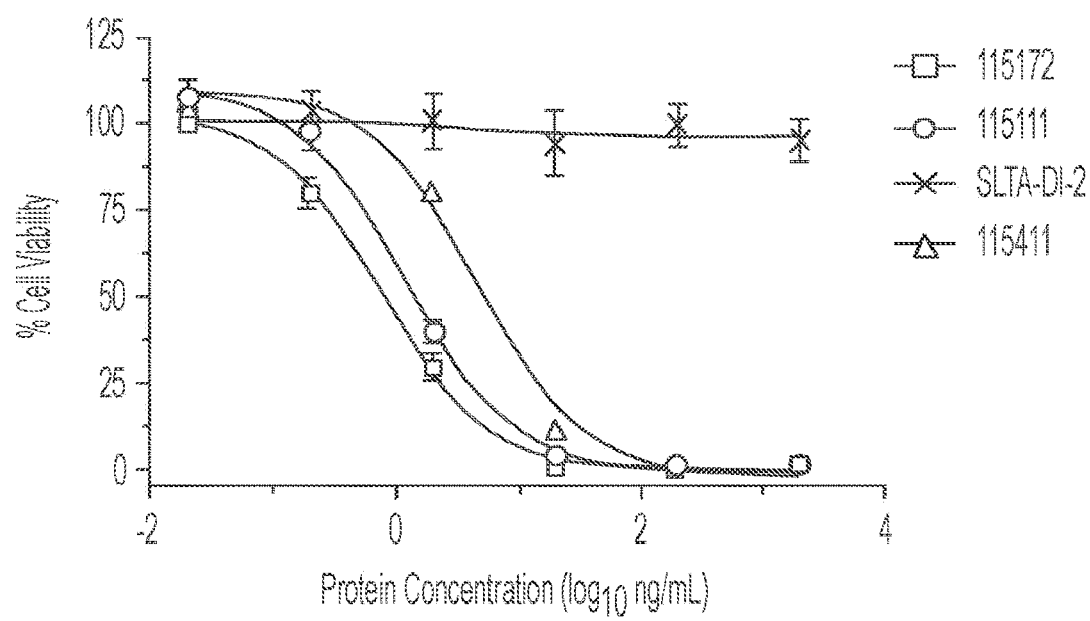

The data from this cytotoxicity experiment indicated that the monomer 115111 (SEQ ID NO:29), the dimer 115195 (SEQ ID NO:32), the predicted monomer 115172 (SEQ ID NO:23), and the predicted dimer 115194 (SEQ ID NO:33) all exhibited similar cytotoxic activities in vitro (see e.g. Table 3 and FIG. 7). No cytotoxicity toward HER2 negative cells was observed for most of the HER2-targeting molecule concentrations tested (e.g. at concentrations below 100 ng/mL).

B. Testing In Vitro Activities of Exemplary HER2-Targeting Molecules of the Present Invention 1. Ribosome Inhibition Activities Exemplary HER2-targeting molecules of the present invention 115111 (SEQ ID NO:29) and 115411 (SEQ ID NO:30) were tested for enzymatic activity after purification using Protein L binding as described above. Their catalytic activities regarding ribosome inactivation were compared with the de-immunized SLT-1A1 fragment alone (DI-2 (SEQ ID NO:20)) and the HER2-targeting molecule 115172 (SEQ ID NO:23) comprising a mostly wild-type SLT-1A sequence having alterations only to mutate the furin cleave motif (SLTA-FR) and disrupt Epitope Region #8 (Table B, supra) (SEQ ID NO:37).

Figure 12:
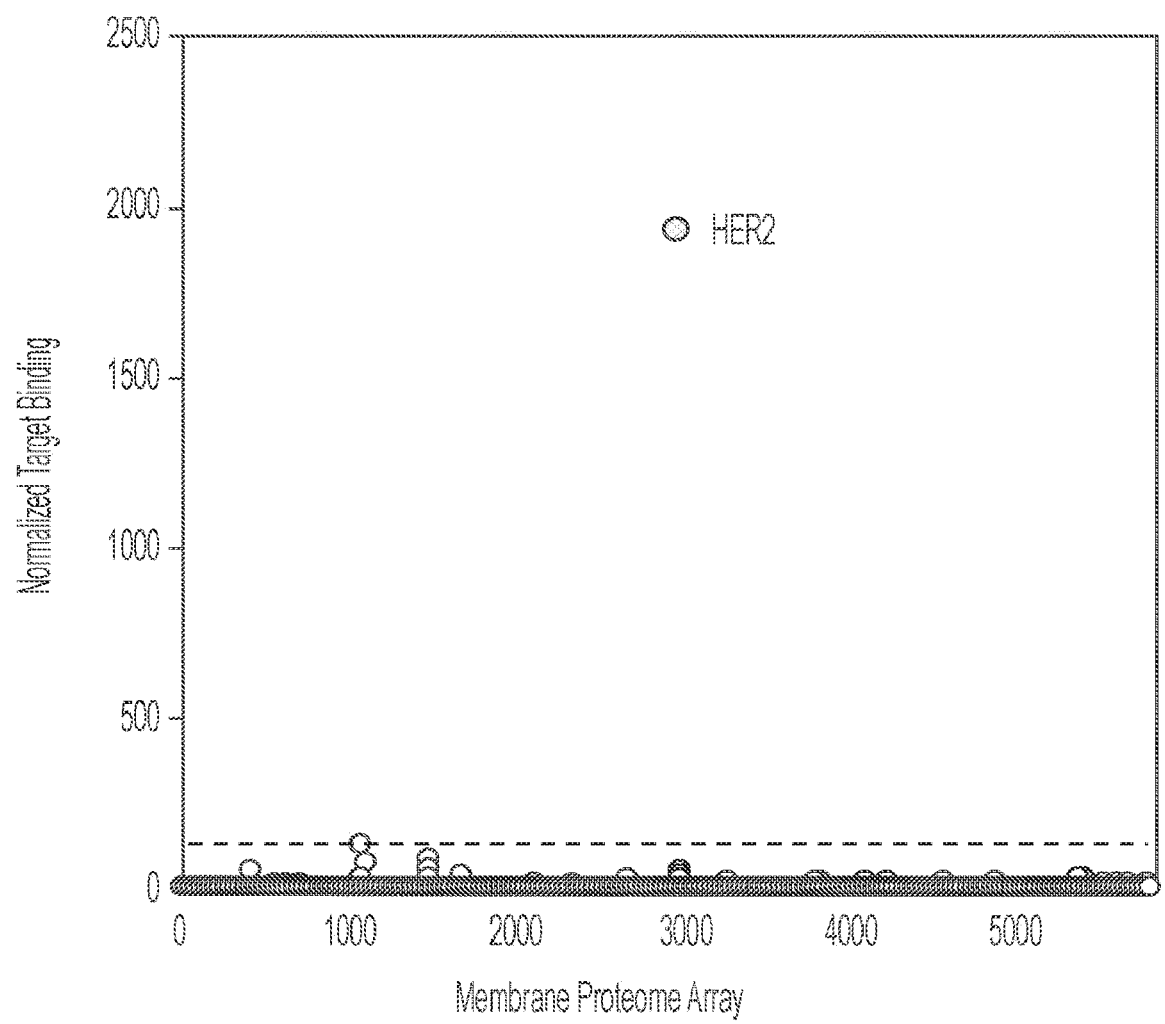

The ribosome inhibition assay used a cell-free, in vitro protein translation assay using the TNT® Quick Coupled Transcription/Translation kit (L1170 Promega Madison, Wis., U.S.A.). The kit includes Luciferase T7 Control DNA (L4821 Promega Madison, Wis., U.S.A.) and TNT® Quick Master Mix. The ribosome activity reaction was prepared according to manufacturer instructions. A series (typically 10-fold) of dilutions were prepared in appropriate buffer and a series of identical TNT reaction mixture components were created for each dilution. The protein samples were combined with each of the TNT reaction mixtures along with the Luciferase T7 Control DNA. The test samples were incubated for 1.5 hours at 30° C. After the incubation, Luciferase Assay Reagent (E1483 Promega, Madison, Wis., U.S.A.) was added to all test samples and the amount of luciferase protein translation was measured by luminescence according to the manufacturer instructions. The level of translational inhibition was determined by non-linear regression analysis of log-transformed concentrations of total protein versus relative luminescence units. Using statistical software (GraphPad Prism, San Diego, Calif., U.S.A.), the half maximal inhibitory concentration ($IC_{50}$) value was calculated for each sample using the Prism software function of log (inhibitor) vs. response (three parameters) [$Y=Bottom+((Top-Bottom)/(1+10^{(X-Log\ IC_{50})}))$] under the heading dose-response-inhibition. The results of the ribosome inhibition assay are reported below (see Table 4 and FIG. 8).

TABLE 4

Ribosome Inhibition Activities and Cytotoxicities of Exemplary HER2-Targeting Molecules Purified Using Protein L Binding Affinity

| HER2-Targeting Molecule | Ribosome Inhibition $IC_{50}$ (pM) | Cytotoxicity $CD_{50}$ HER2 positive NCI/ADR-RES cells |
|---|---|---|
| 115172 | 32.01 | 0.77 ng/mL |
| 115111 | 24.20 | 1.15 ng/mL |
| 115411 | 6.60 | 4.59 ng/mL |
| SLTA-DI-2 | 20.27 | >2,000 ng/mL |

The exemplary HER2-targeting fusion proteins of the present invention 115172 (SEQ ID NO:23), 115111 (SEQ ID NO:29), and 115411 (SEQ ID NO:30) inhibited ribosomes with high potency, e.g. in the low picomolar (pM) range (see Table 4; FIG. 8). The $IC_{50}$ value for ribosome inhibition measured for 115111 (SEQ ID NO:29) was 24.2 pM (Table 4). The similar levels of protein ribosome inhibition exhibited by the Shiga toxin effector polypeptide SLTA-DI-2 (SEQ ID NO:20) and the exemplary HER2-targeting molecules 115172 (SEQ ID NO:23), 115111 (SEQ ID NO:29) and 115411 (SEQ ID NO:30) demonstrated these molecules retained the expected mechanism of action (catalytic inhibition of protein synthesis) as fusion proteins wherein the Shiga toxin A Subunit effector polypeptide component of either 115111 (SEQ ID NO:29) or 115411 (SEQ ID NO:30) or 115172 (SEQ ID NO:23), was fused to an immunoglobulin-type HER2-targeting binding region.

The exemplary HER2-targeting molecules 115172 (SEQ ID NO:23), 115111 (SEQ ID NO:29), and 115411 (SEQ ID NO:30) were also tested for cytotoxic activity toward HER2 positive NCI/ADR-RES cells transfected with HER2 as described above and the results are reported here, in Table 4 above, and in FIG. 9. The cytotoxic activities of these exemplary HER2-targeting fusion proteins were compared with the de-immunized SLT-1A1 fragment alone (SLTA-DI-2 (SEQ ID NO:20)) and the HER2-targeting molecule 115172 (SEQ ID NO:23) comprising a Shiga-like toxin A1 fragment SLTA-FR (SEQ ID NO:37) having alterations to mutate the furin cleavage motif and disrupt Epitope Region #8 (Table B, supra). The cytotoxicity data from this experiment demonstrated that the HER2-targeting moiety was necessary to kill target cells, as there was no cytotoxic effect at concentrations up to 2,000 μg/mL with the untargeted SLTA-DI-2 construct (SEQ ID NO:20) (see FIG. 9). The cytotoxicity $CD_{50}$ value measured for 115111 (SEQ ID NO:29) was 1.2 ng/mL to NCI/ADR-RES-HER2+ cells.

2. HER2 Binding Activities

To investigate the cell-binding properties of exemplary HER2-targeting molecules of the present invention, the binding activities of HER2-targeting molecules to human HER2 positive HCC1954 cells were measured using a flow cytometry-based method. A dilution series of each HER2-targeting molecule being tested was added to cells, the cells were washed, and cell-bound HER2-targeting protein was detected using an anti-SLTA-DI-2 monoclonal antibody (mAb) conjugated to FITC, which recognizes de-immunized Shiga toxin effector polypeptides (e.g. SEQ ID NO:20). The FITC signal was measured using flow cytometry to generate mean fluorescent intensity (MFI) values for each sample. The MFI values were plotted as a function of log transformed HER2-targeting molecule concentration to determine the Bmax and $K_D$ using a non-linear curve regression analysis (Prism (GraphPad Prism, San Diego, Calif., U.S.A., Prism software function sigmoidal 4PL). Results of this study are reported below (see Table 5 and FIG. 10).

TABLE 5

Binding of HER2-Targeting Molecules to HER2 Positive HCC1954 Cells

| HER2-Targeting Molecule | $K_D$ (μg/mL) | Bmax (MFI) |
|---|---|---|
| 114912 | 1.28 | 2119 |
| 115111 | 0.42 | 2747 |
| 115845 | 0.32 | 2707 |
| 115195 | 0.30 | 2447 |
| 115645 | 0.25 | 1327 |

The exemplary HER2-targeting fusion proteins of the present invention 115111 (SEQ ID NO:29), 115845 (SEQ ID NO:35), and 115195 (SEQ ID NO:32) exhibited similar binding in vitro to HCC1954 cells. 115111 (SEQ ID NO:29) bound HER2 positive HCC1954 cells with a $K_D$ of 0.42 μg/mL, and 115845 bound HER2 positive HCC1954 cells with a $K_D$ of 0.32 μg/mL. In this binding assay, 114912 (SEQ ID NO:28) exhibited slightly less binding affinity to HCC1954 cells compared to the other HER2-targeting molecules tested. In this assay, 115645 (SEQ ID NO:34) exhibited a similar $K_D$ but had a reduced Bmax compared to the other HER2-targeting molecules tested.

a. HER2 Epitope Mapping of Binding by Exemplary HER2-Targeting Molecule 115111

The extracellular epitope of human HER2 bound by 115111 (SEQ ID NO:29) was mapped to identify contact residues using a shotgun mutagenesis method by Integral Molecular (Philadelphia, Pa., U.S.A.). To determine the optimal concentration of 115111 (SEQ ID NO:29) for screening HER2 epitope binding, HEK-293T cells were transfected with a vector designed to express a wild-type (WT) construct of a target human HER2 protein (UniProt ID: P04626 (SEQ ID NO:38)) or with vector alone in a 384-well format. Serial dilutions of 115111 (SEQ ID NO:29) were tested via high-throughput flow cytometry for immunoreactivity against cells expressing the WT HER2 target protein (SEQ ID NO:38) or vector alone. The optimal screening concentration for 115111 (SEQ ID NO:29) for this binding assay was determined based on the raw signal values and signal-to-background calculations. The same process was conducted to determine the optimal screening concentration for trastuzumab, a control HER2-binding antibody.

An alanine scanning mutagenesis library based on the human HER2 protein (SEQ ID NO:38) mentioned above was created and screened for 115111 (SEQ ID NO:29) binding in duplicate by high-throughput flow cytometry. For each test point, background fluorescence was subtracted from the raw data, which were then normalized to 115111 (SEQ ID NO:29) binding with WT HER2 protein (SEQ ID NO:38). Critical mutagenesis clones were identified related to the binding of 115111 (SEQ ID NO:29) to WT HER2 (SEQ ID NO:38). The primary critical residues for 115111 (SEQ ID NO:29) binding to HER2 (SEQ ID NO:38) were residues whose mutations were reduced for 115111 (SEQ ID NO:29) binding when tested with 115111 (SEQ ID NO:29) but were similar to WT HER2 target protein control when tested for trastuzumab binding (a HER2-binding, positive control mAb). The resulting mean binding reactivity values for selected critical residue positions in WT human HER2 (SEQ ID NO:38) expressed as a percentage of WT HER2 binding with 115111 (SEQ ID NO:29) measured using this epitope mapping assay are listed in Table 6.

TABLE 6

Certain Critical and Secondary Residues in HER2 Involved in Binding 115111

| HER2 mutation | Binding Reactivity (% WT) 115111 | trastuzumab |
|---|---|---|
| Y112A | 9.2 | 87.7 |
| Q178A | 34.9 | 119.5 |
| L181A | 20.1 | 95.8 |
| G152A | 39.2 | 89.7 |

Using the approach above, the HER2 epitope bound by 115111 (SEQ ID NO:29) appeared to comprise Y112, Q178, and L181, which all map to domain I of the HER2 extracellular domain (ECD) (NCBI accessions NP_004439.2, amino acid residues 23 to 653) (SEQ ID NO:39). One residue, G152, was identified in the epitope mapping assay as a secondary residue in that it did not meet the threshold guidelines for being 'critical', but the G152A mutation did result in a large decrease of 115111 (SEQ ID NO:29) binding compared to the WT HER2 (SEQ ID NO:38). Binding to the G152A expressing clone showed a level of binding that was 39% of WT binding as opposed to the 35% threshold level required to categorize G152 a primary critical residue. The G152 position in HER2 is in close proximity to the primary critical residues mapped using the assay, which suggested that it may also be part of the epitope in human HER2 (SEQ ID NO:38) bound by 115111 (SEQ ID NO:29).

FIG. 11 shows a diagram of human HER2 with markings to highlight the critical and secondary residues for binding by 115111 (SEQ ID NO:29) as measured by the approach described above. In FIG. 11 on the left, primary residues critical for 115111 (SEQ ID NO:29) binding to HER2 (SEQ ID NO:38) are visualized as red spheres based on a crystal structure of the HER2 (PDB 1S78, Franklin M et al., *Cancer Cell* 5: 317-28 (2004)) along with a secondary residue visualized as a blue sphere. In FIG. 11 on the right, the critical HER2 binding residues for 115111 (SEQ ID NO:29) binding are shown as blue spheres, for pertuzumab binding are shown as magenta spheres, and for trastuzumab binding are shown as purple spheres based on the data above and information in Cho H et al., *Nature* 421: 756-60 (2003); Franklin M et al., *Cancer Cell* 5: 317-28 (2004). The HER2 epitope bound by 115111 (SEQ ID NO:29) was mapped within the HER2 extracellular domain (ECD) (SEQ ID NO:39) to domain I; in contrast, pertuzumab binds to an epitope mapped to domain II of the ECD of HER2 and trastuzumab binds to an epitope mapped to domain IV of the ECD of HER2 (SEQ ID NO:39) (see FIG. 11). Thus, 115111 (SEQ ID NO:29) binds an epitope in HER2 that is different from the epitopes bound by trastuzumab and pertuzumab.

b. HER2 Binding Specificity of Exemplary HER2-Targeting Molecule 115111

The binding specificity, affinity, and selectivity of the exemplary HER2-targeting fusion protein of the present invention 115111 (SEQ ID NO:29) were tested by analyzing binding of this purified fusion protein to a membrane proteome array, which comprised 5,300 different proteins transfected to be expressed on the cell surface of HEK-293T cells (Integral Molecular, Inc., Philadelphia, Pa., U.S.A.). The results shown in FIG. 12 show that only HER2 was identified and validated among the 5,300 proteins as a selective binding target of 115111 (SEQ ID NO:29).

3. Cytotoxic Activities

1. Cytotoxic Activities In Vitro Compared to Other Drugs

The cytotoxicity of 115111 (SEQ ID NO:29) to HER2 positive cells was evaluated in comparison to and in combination with reference HER2-targeted therapeutics, including T-DM1 (trastuzumab emtansine), trastuzumab, and pertuzumab. As all of these therapeutic molecules specifically bind to an extracellular part of human HER2, these molecules might compete for HER2 binding with each other or otherwise interact so as to alter their functional activities when combined. For example, when different, cytotoxic, HER2-targeted molecules are administered in combination, either a reduction or increase in cytotoxic activities toward HER2 positive cells might be observed. In a further example, when different, cytotoxic, HER2-targeted molecules are administered in combination, an increase in the death of HER2-expressing cells might be observed as result of additive or synergistic effects on cytotoxicity.

To investigate the number of possible HER2 receptors on the cell surfaces of cells of different cell types, an experiment was performed to quantify the number of HER2-targeted antibody molecules bound per cell. This experiment involved the incubation of cells with an anti-HER2 antibody conjugated to phycoerythrin (PE) (anti-HER2-PE, clone 24D2, Biolegend, San Diego, Calif., U.S.A.). Then the samples were analyzed using flow cytometry to quantify binding. Standard curves generated with BD Quantibrite™ PE beads having known PE loads were used to convert MFI signal values to the number of antibodies bound per cell for each sample. These HER2 positive cells were then used in cytotoxicity assays performed essentially as described above to compare the cytotoxic activities of 115111 (SEQ ID NO:29) to T-DM1 and lapatinib. Results from these cytotoxicity assays are reported below and in Table 7, and a representative data set for T-DM1 is shown in FIG. 13.

115111 (SEQ ID NO:29) exhibited potent cytotoxicity to all HER2+ cells tested in this experiment: HCC1954, NCI-N87, HCC1569, HCC1419, AU565, and JIMT-1 cells (Table 7; see also Tables 2-3, 8-10; FIGS. 6-7, and 13-19).

Figure 13:
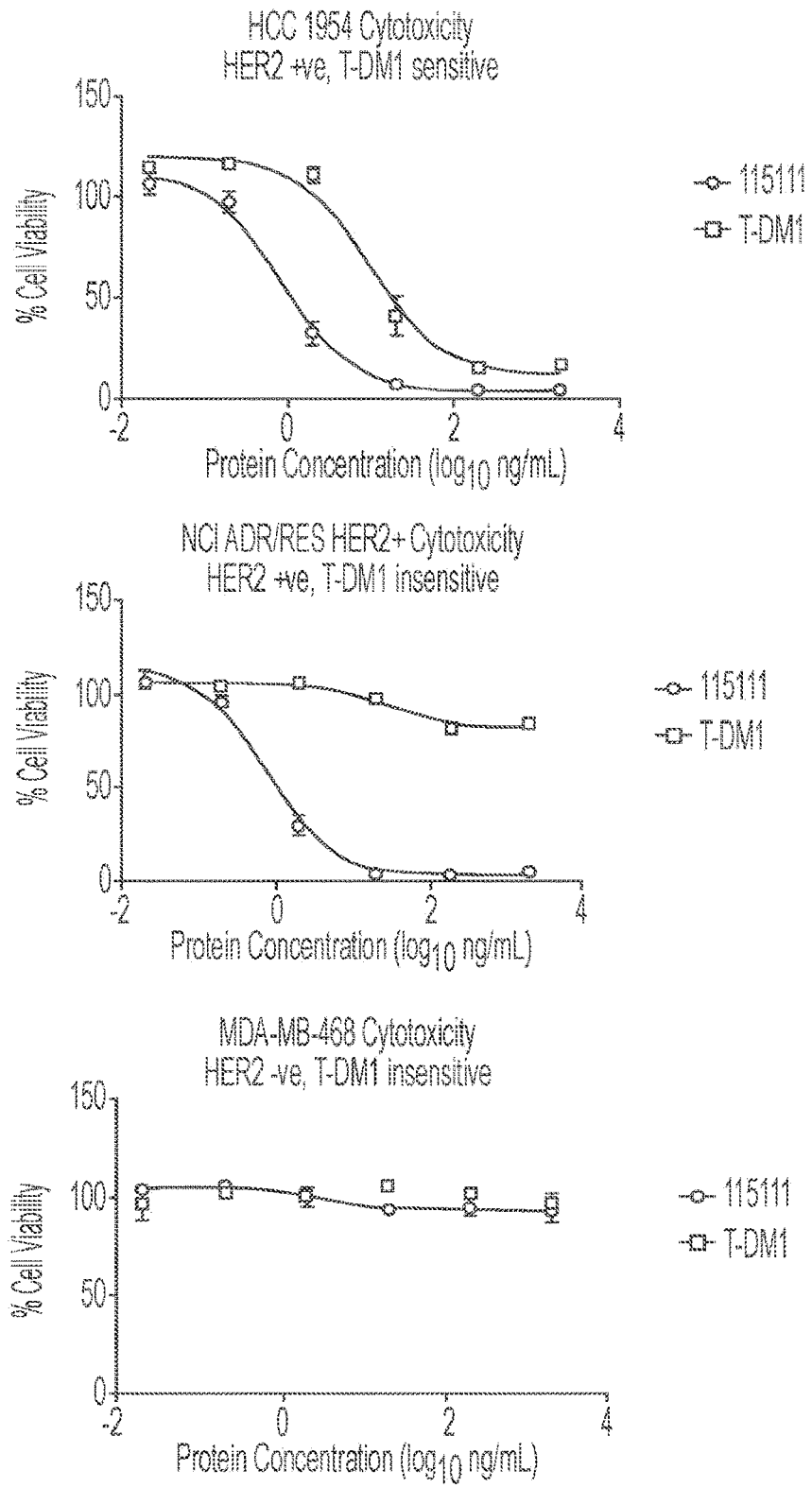

Both 115111 (SEQ ID NO:29) and T-DM1 were potently cytotoxic to HCCC1954, NCI-N87, HCC1569, HCC1419, and AU565 cells (Table 7), with 115111 exhibiting higher cytotoxic potency than T-DM1 to HCCC1954, NCI-N87, HCC1569, and HCC1419 cells (Table 7; see e.g. FIG. 13). 115111 (SEQ ID NO:29) exhibited more potent cytotoxicity than T-DM1 toward NCI/ADR-RES-HER2+ and JIMT-1 cells (Table 7; see FIG. 13).

NCI/ADR-RES cells are considered resistant to T-DM1 due to MDR1 expression. Because 115111 (SEQ ID NO:29) killed HER2 positive NCI/ADR-RES cells (Tables 2-3 and 7; FIGS. 6-7, 9, and 13), 115111 (SEQ ID NO:29) is likely to be cytotoxic to other HER2 positive cells expressing p-glycoprotein 1 (Pgp) type multidrug resistance efflux pumps.

JIMT-1 cells are considered resistant to trastuzumab due to epitope masking via MUC-4 and/or CD44 expression (see e.g. Wilken J, Maihle N, *Ann N Y Acad Sci* 1210: 53-65 (2010)). Because 115111 (SEQ ID NO:29) killed JIMT-1 cells (Tables 1-2 and 7; FIGS. 6-7), the presence of MUC-4 and/or CD44 does not prevent 115111 (SEQ ID NO:29) cytotoxicity, such as, e.g., via epitope masking (see e.g. FIGS. 6-7 and Table 7).

As 115111 (SEQ ID NO:29) binds to an extracellular part of HER2 and internalizes into target cells to seeking out their ribosomes for inactivation, the cytotoxicity activity of 115111 (SEQ ID NO:29) is not dependent on the binding to or inactivation of a kinase domain of HER2. In contrast, lapatinib is a dual tyrosine kinase inhibitor which targets HER2 and EGFR by binding to their kinase domains and inhibiting kinase activity. Cancer therapies relying on drugs like lapatinib may be rendered less effective due to the development of resistance mechanisms, such as protective mutations in the kinase catalytic domain of HER2 or de novo aberrations resulting in constitutive/unregulated HER2-signaling-pathway activation or overactivation of the HER2 signaling pathway at a point downstream of HER2 thereby bypassing the receptor, such as in the absence of HER2 kinase activity or even HER2 expression. Thus, certain HER2-targeting molecules of the present invention (e.g. 115111 (SEQ ID NO:29)) may be effective in refractory or

TABLE 7

HER2 Positive Cell Binding Sites per Cell and In Vitro Cytotoxic Activities of 115111 as Compared to T-DM1 and Lapatinib

| Cell Line | cancer type | HER2 Positive Cell Binding antibodies bound per cell | In Vitro Cytotoxicity $CD_{50}$ 115111 | T-DM1 | lapatinib |
|---|---|---|---|---|---|
| HCC1954 | breast | 2,250,000 | 1.39 ng/mL | 8.98 ng/mL | 786 nM |
| NCI-N87 | gastric | 2,270,000 | 3.76 ng/mL | 18.48 ng/mL | 112 nM |
| NCI/ADR-RES-HER2+ | ovarian, transfected with HER2 | 1,340,000 | 1.17 ng/mL | no viability change | 2,704 nM |
| HCC1569 | breast | DNT | 2.17 ng/mL | 13.66 ng/mL | 885 nM |
| HCC1419 | breast | 3,070,000 | 6.58* ng/mL | 74.56* ng/mL | DNT |
| AU565 | breast | DNT | 7.04 ng/mL | 0.63 ng/mL | DNT |
| JIMT-1 | breast | 307,000 | 6.55* ng/mL | 248.7* ng/mL | 5,650 nM |

*Indicates that cell viability plateaus above 20% in this assay;
DNT = did not test non-responding treatment resistance settings, e.g., tumors resistant to therapies involving tyrosine kinase inhibitors, such as, e.g., lapatinib, and/or neratinib.

2. Cytotoxic Activities in the Presence of Other Drugs a. Lapatinib and T-DM1

Figure 14:
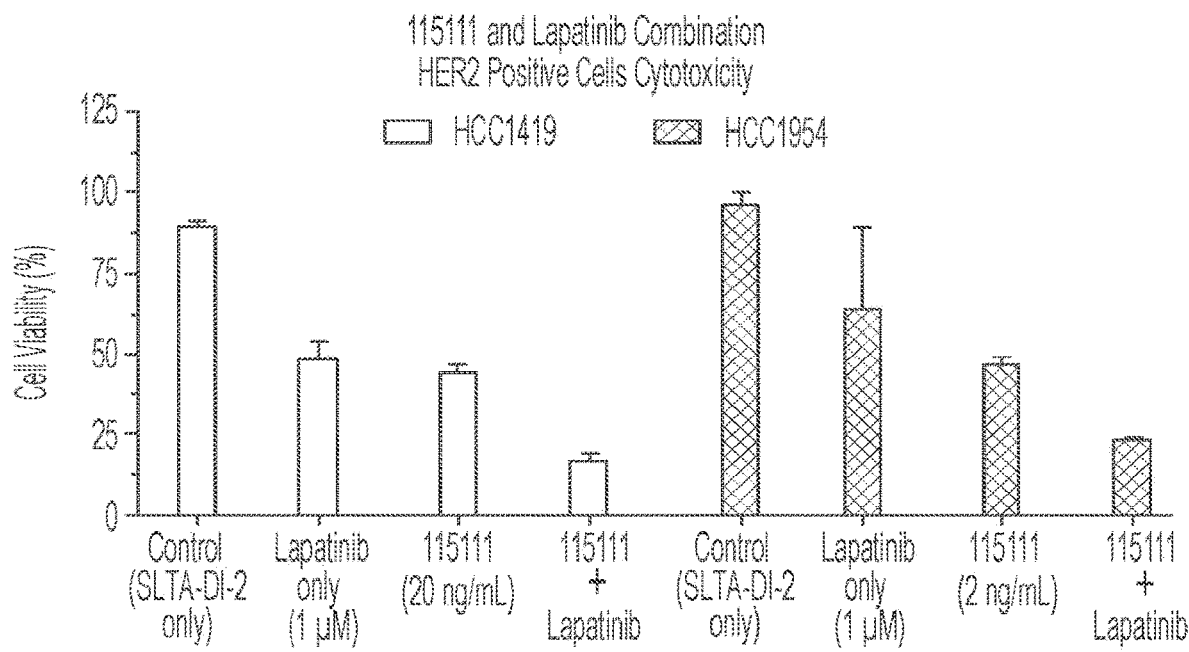
Figure 15:
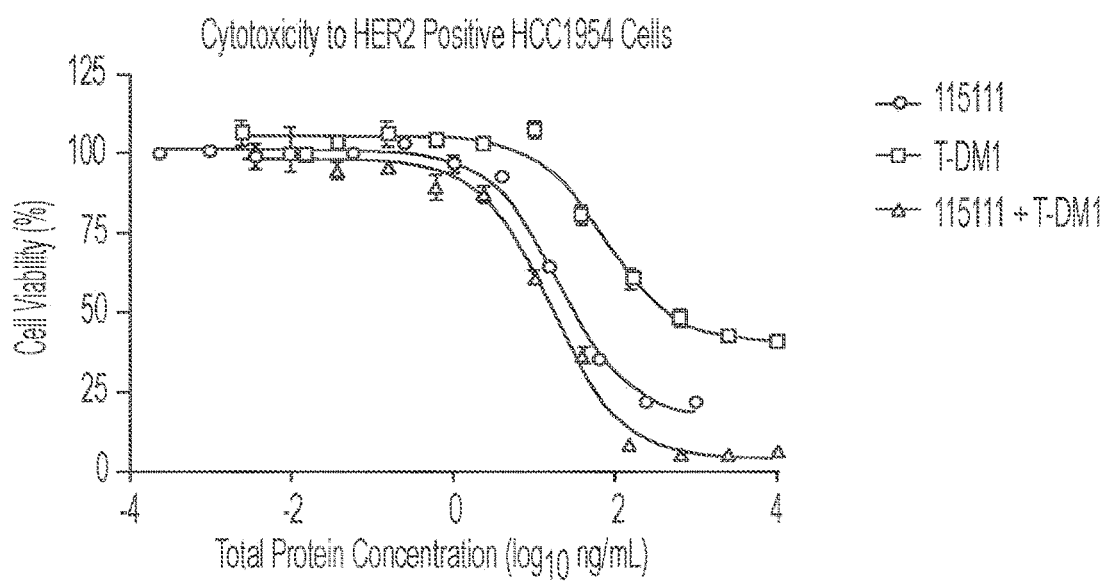

The cytotoxicity of 115111 (SEQ ID NO:29) to HER2 positive cells was evaluated in combination with lapatinib or T-DM1 using a cytotoxicity assay performed essential as described above. The cytotoxicities of 115111 (SEQ ID NO:29) over range of concentrations combined with either 1 µM lapatinib or a range of T-DM1 concentrations are shown in FIGS. 14 and 15. Neither combination appeared deleterious to the cytotoxicity caused by 115111 (SEQ ID NO:29) to HER2 positive cells observed in this in vitro cell-kill assay. Furthermore, the results of these experiments show the potential of combinations of 115111 (SEQ ID NO:29) with other agents to achieve even more potent cytotoxicity to HER2-expressing cells.

FIG. 14 shows the results of cytotoxicity assays using HER2 positive HCC1419 or HCC1954 cells where 115111 (SEQ ID NO:29), lapatinib, or a combination of both were administered to the cells. Concentrations for 115111 (SEQ ID NO:29) and lapatinib were selected such that the single agent resulted in about 50% viability for each cell line. The results of this experiment showed that 115111 (SEQ ID NO:29) may be administered with lapatinib to achieve more cytotoxicity than either administrated individually. The data in FIG. 14 showed that a higher percentage of cells were killed by the combination 115111 (SEQ ID NO:29) and lapatinib than by treatment with either lapatinib or 115111 (SEQ ID NO:29) alone. These results showed that 115111 (SEQ ID NO:29) may be combined with laptinib and/or may be administered in the presence of laptinib without significant loss in 115111 (SEQ ID NO:29) cell-kill activity to HER2 positive cells. Furthermore, these results suggested that the administration of the combination of 115111 (SEQ ID NO:29) (or a similar HER2-targeting molecule of the present invention) and lapatinib may kill more HER2 positive cells than using either one alone at the same respective dose.

FIG. 15 shows the results of a cytotoxicity assay using HER2 positive HCC1954 cells where 115111 (SEQ ID NO:29), T-DM1, or a combination of both were administered to the cells. The data in FIG. 15 showed that a higher percentage of cells were killed by the combination 115111 (SEQ ID NO:29) and T-DM1 than by treatment with either T-DM1 or 115111 (SEQ ID NO:29) alone. These results showed that 115111 (SEQ ID NO:29) may be combined with T-DM1 and/or may be administered in the presence of T-DM1 without significant loss in 115111 (SEQ ID NO:29) cell-kill activity to HER2 positive cells. Furthermore, these results suggested that the administration of the combination of 115111 (SEQ ID NO:29) (or a similar HER2-targeting molecule of the present invention) and T-DM1 may kill more HER2 positive cells than using either one alone at the same respective dose.

b. T-DM1 and Trastuzumab

Figure 16:
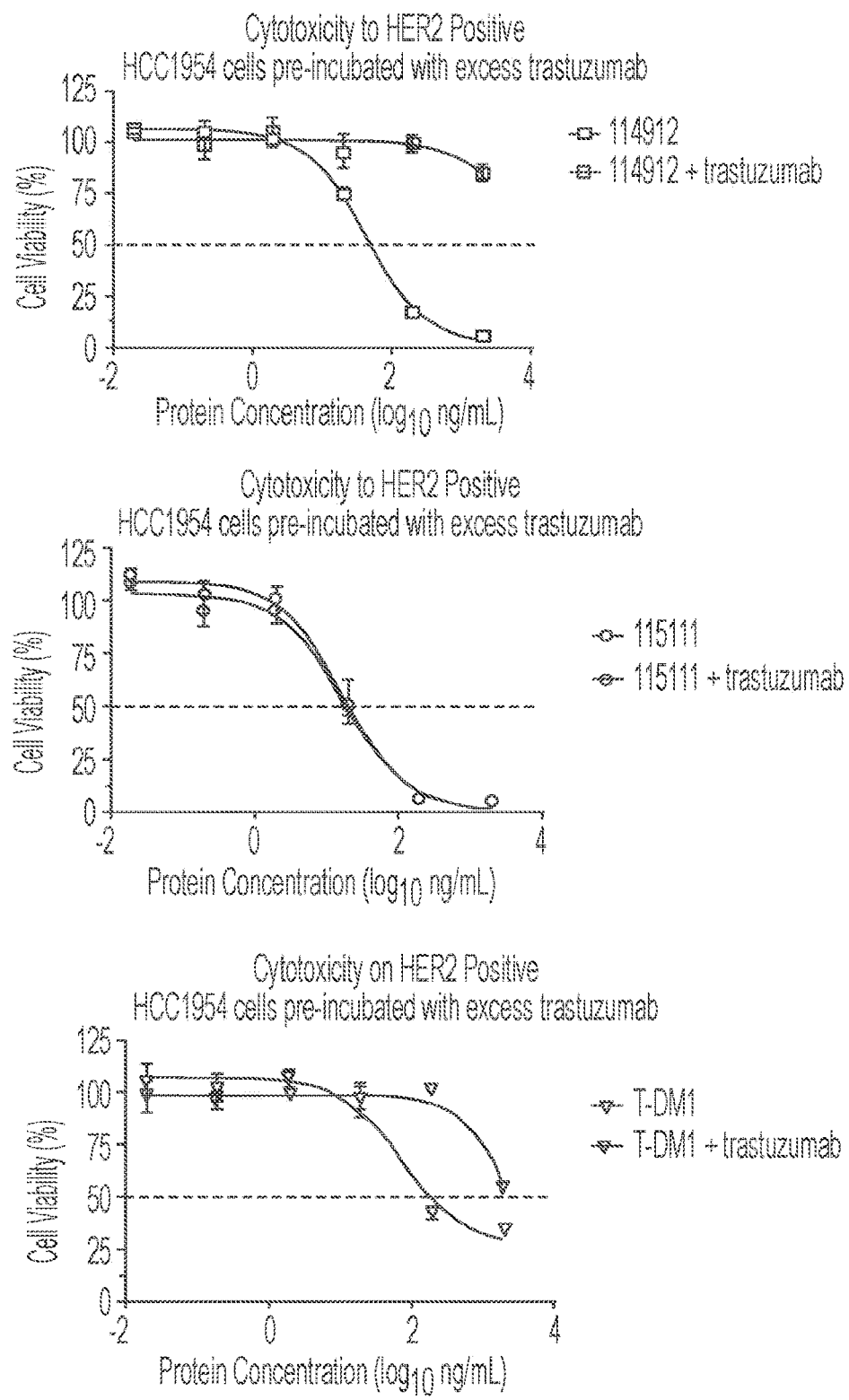

The cytotoxic activities of 114912 (SEQ ID NO:28) and 115111 (SEQ ID NO:29) to HER2 positive HCC1954 cells were evaluated in the presence of excess trastuzumab using a cytotoxicity assay performed essentially as described above, except that the cells were pre-treated with trastuzumab (20 µg/mL) for one hour prior to addition of the other HER2-targeting molecules. FIG. 16 shows the results of cytotoxicity assays using HER2 positive HCC1954 cells where 114912 (SEQ ID NO:28) and 115111 (SEQ ID NO:29) cytotoxic activities were evaluated in comparison to T-DM1, both in the absence of trastuzumab and in the presence of excess trastuzumab. The pretreatment of HER2 positive cancer cells with excess trastuzumab did not alter the cytotoxic activity of 115111 (SEQ ID NO:29) (see FIG. 16, middle). This was in contrast to the combination of excess trastuzumab with T-DM1 or the exemplary HER2-targeting molecule 114912 (SEQ ID NO:28), both of which comprise the heavy and light variable domains of the trastuzumab antigen binding regions. These data suggest that HER2-targeting molecules of the present invention may kill cells in the presence of other HER2-binding therapeutics which bind non-overlapping epitopes and do not compete or interfere with the HER2-targeting molecule's mechanism of action (see FIG. 11, trastuzumab binds to an epitope mapped to domain IV of the ECD whereas 115111 (SEQ ID NO:29) interacts with domain I of the ECD). The monoclonal antibody trastuzumab exhibited no cytotoxicity in this in vitro cytotoxic assay (involving just HER2 positive cancer cells and culture medium).

c. Trastuzumab and Pertuzumab

Figure 17:
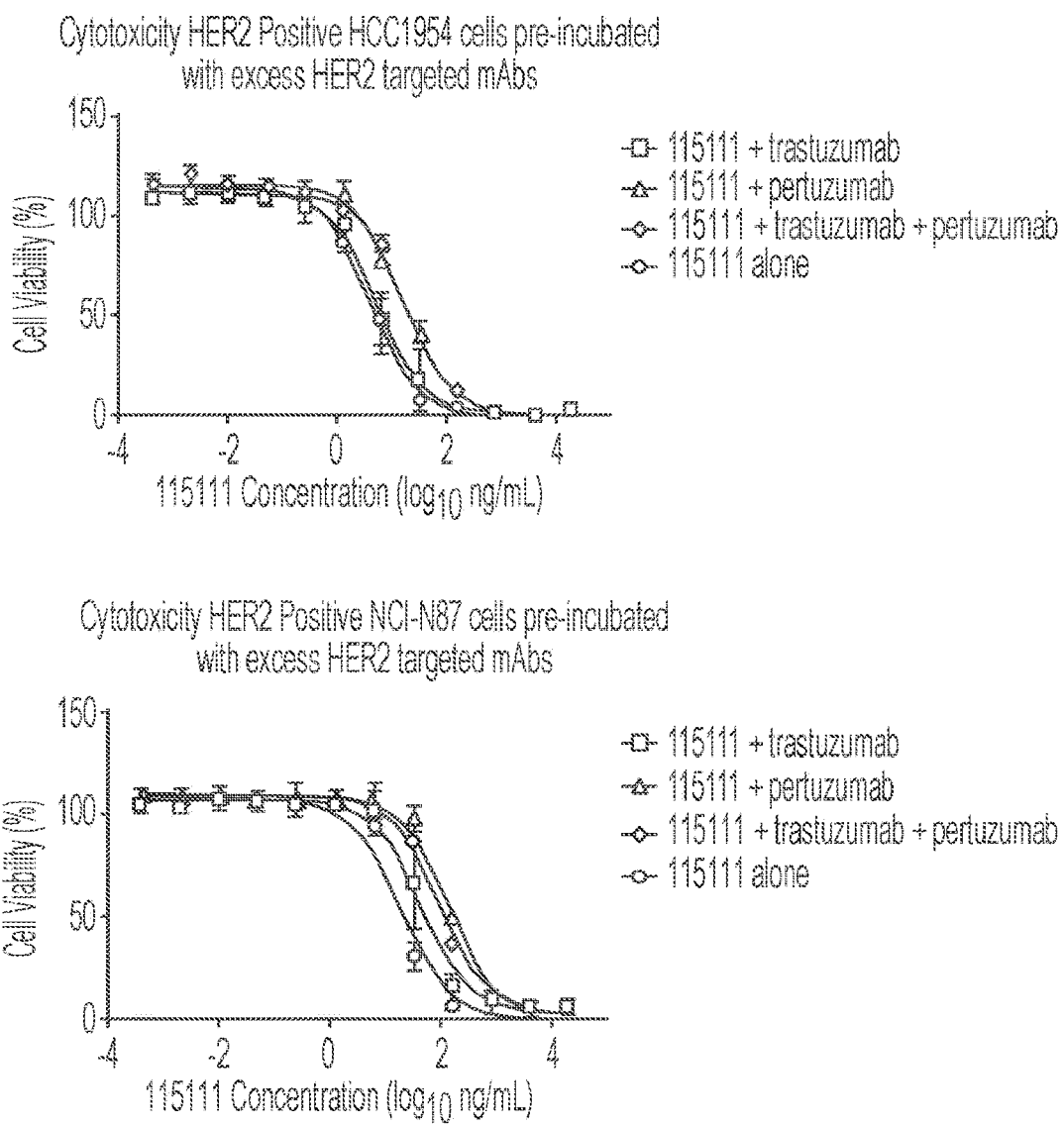
FIG. 17 shows the exemplary HER2-targeting molecule 115111 (SEQ ID NO:29) is cytotoxic to cells in the presence of excess trastuzumab, pertuzumab, or both trastuzumab and pertuzumab. The top graph of FIG. 17 shows that the exemplary HER2-targeting molecule 115111 (SEQ ID NO:29) was cytotoxic to HCC1954 cells pre-incubated with excess trastuzumab, pertuzumab, or both. The bottom graph shows that the exemplary HER2-targeting molecule 115111 (SEQ ID NO:29) was cytotoxic to NCI-N87 cells pre-incubated with excess trastuzumab, pertuzumab, or both.

The cytotoxic activities of 115111 (SEQ ID NO:29) to HER2 positive cells over a range of concentrations were evaluated in the presence of excess trastuzumab, excess pertuzumab, or an excess of both trastuzumab and pertuzumab using a cytotoxicity assay performed essentially as described above, except that the cells were pre-treated with trastuzumab (100 µg/mL), pertuzumab (100 µg/mL) or both trastuzumab (100 µg/ml) and pertuzumab (100 µg/mL) (for a total of 200 µg/mL antibody) for one hour prior to addition of the other HER2-targeting molecules. FIG. 17 and Table 8 show the results of the cytotoxicity assay using HER2 positive HCC1954 or NCI-N87 cells where 115111 (SEQ ID NO:29) activity was evaluated in the presence of excess trastuzumab, pertuzumab, or both. The HER2-targeting fusion protein 115111 (SEQ ID NO:29) killed HCC1954 cells in the presence of excess trastuzumab (FIGS. 16-17). 115111 (SEQ ID NO:29) killed HCC1954 cells and NCI-N87 cells in the presence of both excess trastuzumab and excess pertuzumab or in the excess of both (FIG. 17). The monoclonal antibodies trastuzumab or pertuzumab exhibited no cell-killing activity in this in vitro cytotoxic assay (involving just the cancer cells and culture medium).

TABLE 8

Cytotoxic Activities of 115111 in the Presence of Excess Trastuzumab, Pertuzumab, or both Trastuzumab and Pertuzumab

| Test Condition | $CD_{50}$ (ng/mL) | |
| --- | --- | --- |
|  | HCC-1954 | NCI-N87 |
| 115111 alone | 3.9 | 19.2 |
| 115111 + trastuzumab | 5.4 | 44.0 |
| 115111 + pertuzumab | 18.0 | 140.0 |
| 115111 + trastuzumab and pertuzumab | 16.4 | 89.7 |

Figure 11:
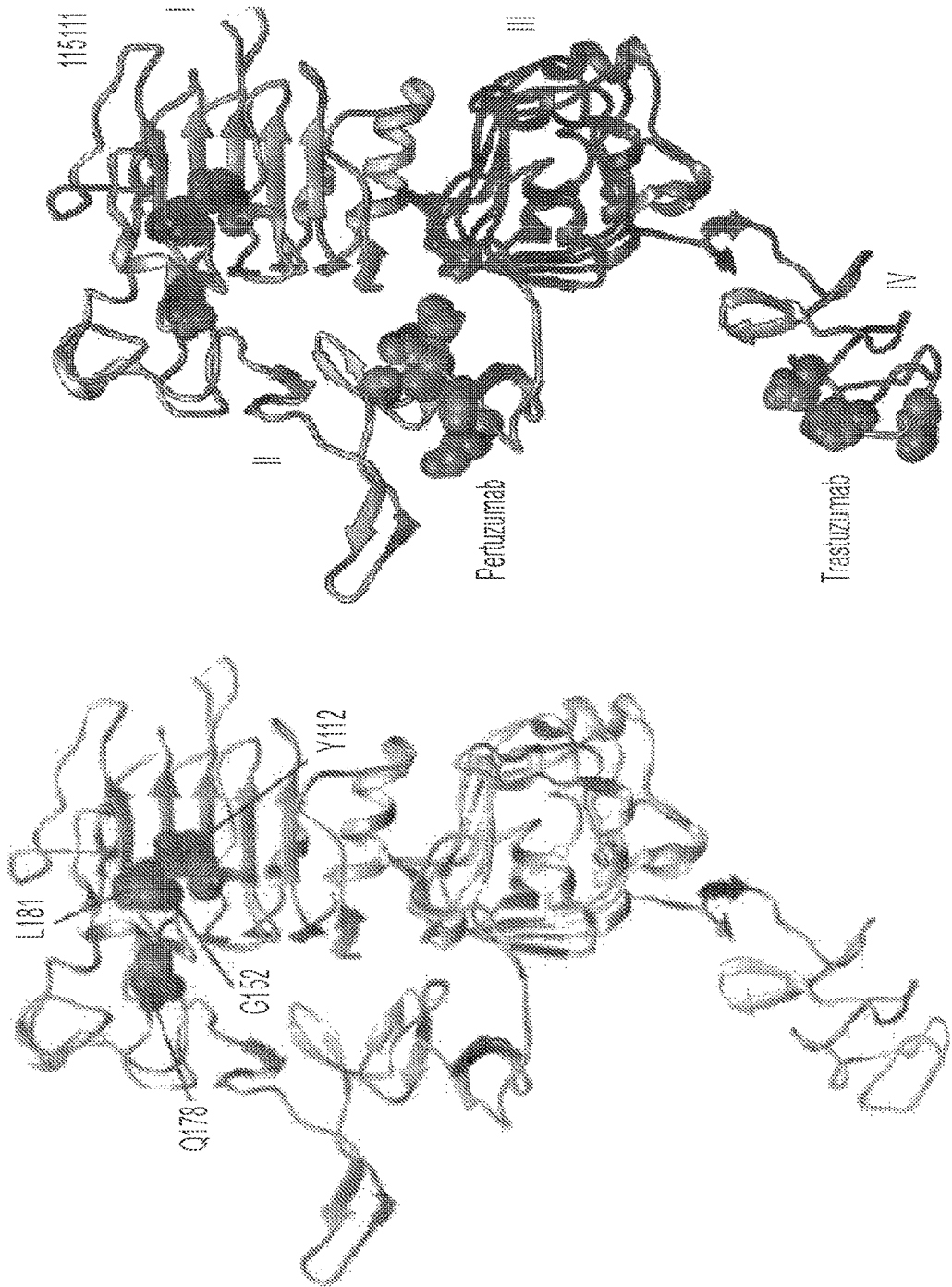

The data in FIG. 17 and Table 8 showed that the HER2-targeting molecule 115111 (SEQ ID NO:29), tested at concentrations up to 20 µg/mL, was cytotoxic to HER2-expressing cells in the presence of excess trastuzumab or pertuzumab (either 100 µg/mL individually or 100 µg/mL of each, for a total of 200 µg/mL concurrent exposure) thereby suggesting a potential combination therapy involving administering 115111 (SEQ ID NO:29) and another HER-targeting therapeutic, such as a monoclonal antibody like trastuzumab or pertuzumab having a non-overlapping HER2 binding epitope (see e.g. FIG. 11). Thus, the exemplary HER2-targeting molecule 115111 (SEQ ID NO:29) has the potential to be effective in killing HER2 expressing cancer cells in combination with other HER2-targeted therapies as long as their HER2 binding epitopes are different.

The mechanism of action of the HER2-targeting molecules of the present invention—internalization and targeted ribosome inactivation—is different than that of monoclonal antibodies targeting HER2 (trastuzumab binding HER2 induces ADCC and inhibits HER2 signaling) (pertuzumab binding HER2 inhibits dimerization) and is different than antibody drug conjugates like T-DM1 (targeted microtubule inhibition). Cancer therapies relying on drugs using mechanisms of action other than the one(s) used by HER2-targeting molecules may be rendered less effective due to the development of resistance mechanisms specific to one or more of these other mechanisms of action. For example, tumors may become resistant to therapies involving monoclonal antibodies which bind specific HER2 epitopes, such as, e.g., T-DM1, trastuzumab, and/or pertuzumab, and/or involving tyrosine kinase inhibitors, such as, e.g., lapatinib and/or neratinib. Certain HER2-targeting molecules of the present invention (e.g. 115111 (SEQ ID NO:29)) may be effective in refractory or non-responding treatment resistance settings, e.g., tumors resistant to therapies involving T-DM1, trastuzumab, pertuzumab, lapatinib, and/or neratinib. Furthermore, the unique mechanism of action of HER2-targeting molecules of the present invention may offer new opportunities for monotherapies for benefit-treatment resistant/non-responder patients as well as for combination therapies combining different and/or complementary mechanisms of action, such as combinations with T-DM1, trastuzumab, pertuzumab, lapatinib, and/or neratinib.

3. Cytotoxicities of Exemplary HER2-Targeting Molecules Based on Exposure Duration To study the cytotoxic effects of exemplary HER2-targeting molecules of the present invention, kinetic cell-kill experiments were performed. The cell-kill assay described above was used here but with different durations of exposure of the HER2-expressing cells to HER2-targeting molecules. In this study, HER2 positive SKBR3 or HCC1954 were exposed to a HER2-targeting molecule for a specific and short duration of time (e.g. 1 or 4 hours), then the cells were washed and the media replaced ("washout"). Control samples were incubated with the HER2-targeting molecule continuously throughout the experiment (with "no washing"). All data was normalized by comparing results to samples treated with vehicle alone under the same conditions. Results from this study are shown in Tables 9-10 and FIGS. 18-19.

TABLE 9

Cytotoxicity of Exemplary HER2-Targeting Molecules to HER2 Positive SKBR3 Cells after Different Durations of Exposure

| | SKBR3 | |
| --- | --- | --- |
| Test Condition | $CD_{50}$ (ng/mL) | Fold change from continuous |
| 114912 continuous | 44.6 | N/A |
| 114912 4-hour exposure | 430.1 | 9.6 |
| 114912 1-hour exposure | 3736.0 | 83.7 |
| 115111 continuous | 11.1 | N/A |
| 115111 4-hour exposure | 25.0 | 2.2 |
| 115111 1-hour exposure | 118.3 | 10.6 |

* 'N/A' denotes not applicable

TABLE 10

Cytotoxicity of HER2 Positive HCC1954 Cells Under Different Duration of Exposure

| | HCC-1954 | | |
| --- | --- | --- | --- |
| Test Condition | $CD_{50}$ (ng/mL) | Fold change from continuous | Cell viability at 2 µg/mL (%) |
| Experiment 1 | | | |
| 115111 continuous | 37.3 | | 4.5% |
| 115111 4-hour exposure | 137.3 | 3.7 | 10.0% |
| 114898 continuous | 110.1 | | 9.6% |
| 114898 4-hour exposure | 487.4 | 4.4 | 44.9% |
| Experiment 2 | | | |
| 115111 continuous | 5.6 | | 2.6% |
| 115111 4-hour exposure | 14.9 | 2.7 | 3.1% |
| 115195 continuous | 3.9 | | 3.5% |
| 115195 4-hour exposure | 14.3 | 3.7 | 3.5% |
| 115645 continuous | 41.5 | | 16.4% |
| 115645 4-hour exposure | 422.3 | 10.2 | 55% |
| 115845 continuous | 25.3 | | 16.2% |
| 115845 4-hour exposure | 179.4 | 7.1 | 45.2% |

Under continuous exposure, 115111 (SEQ ID NO:29) exhibited a $CD_{50}$ value of 5.6 ng/mL toward HER2 positive HCC1954 cells, which is similar to the $CD_{50}$ value of 3.9 ng/mL measured for 115195 (SEQ ID NO:32). Under continuous exposure, 115111 (SEQ ID NO:29) exhibited $CD_{50}$ values of 5.6 and 37.3 ng/mL toward HCC1954 cells, which is similar to the $CD_{50}$ value 25.3 ng/mL measured for 115845 (SEQ ID NO:35) and 41.5 ng/mL measured for 115645 (SEQ ID NO:34). However, the shorter exposure condition revealed some surprising differences between 115111 (SEQ ID NO:29) and 115195 (SEQ ID NO:32) and the other HER2-targeting molecules tested.

Figure 18:
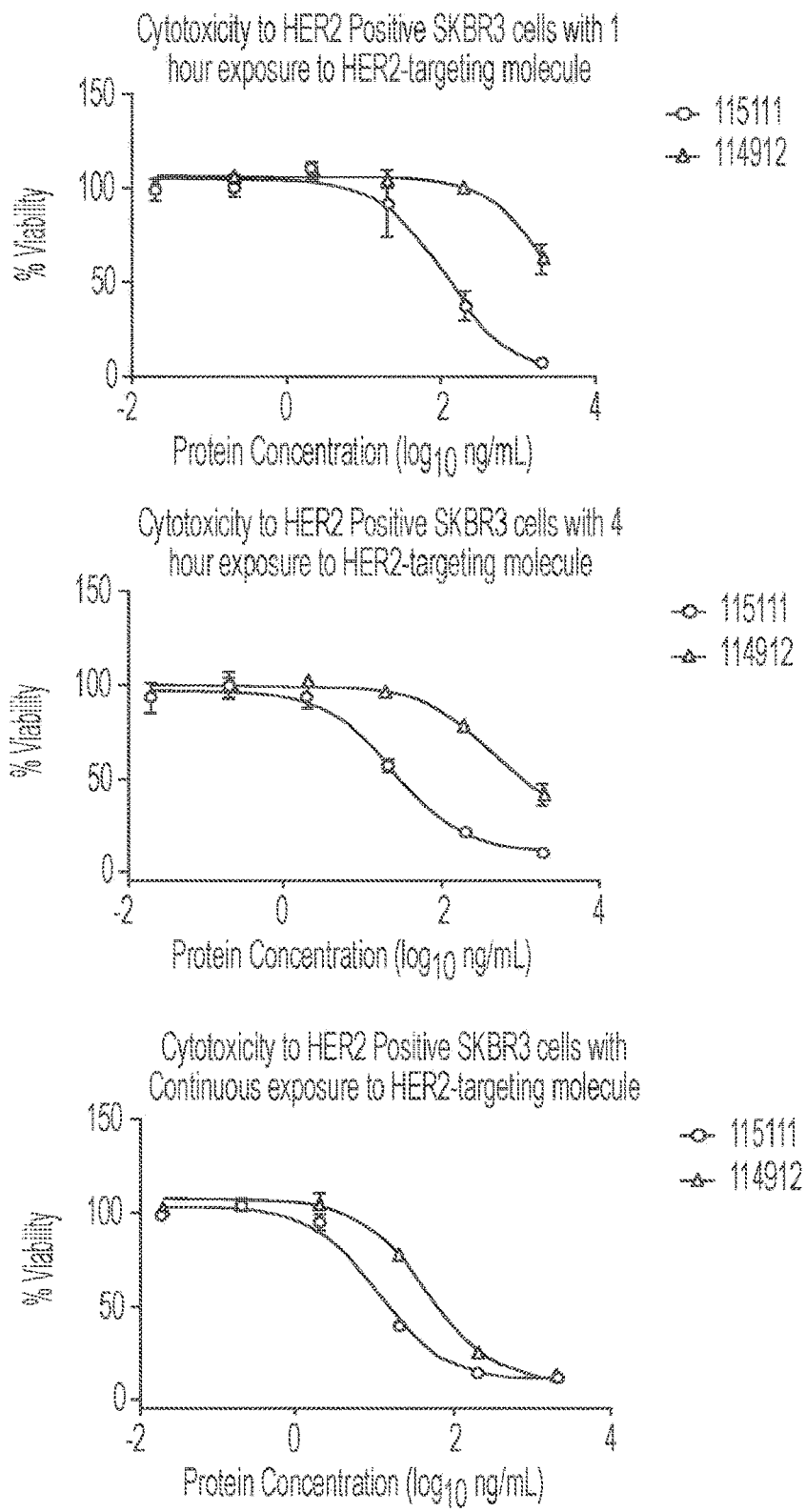
FIG. 18 graphically shows that the exemplary HER2-targeting molecule 115111 (SEQ ID NO:29) is more potently cytotoxic than exemplary HER2-targeting molecule 114912 (SEQ ID NO:28) to HER2 expressing cells for shorter exposure durations. The percent viability of HER2 positive SKBR3 cells was plotted over the logarithm to base 10 of the administered HER2-targeting molecule concentrations. The top graph of FIG. 18 shows that the exemplary HER2-targeting molecule 115111 (SEQ ID NO:29) was more cytotoxic to SKBR3 cells than 114912 (SEQ ID NO:28) at higher concentrations under the conditions of 1-hour exposures. The middle graph of FIG. 18 shows that the exemplary HER2-targeting molecule 115111 (SEQ ID NO:29) was more cytotoxic to SKBR3 cells than 114912 (SEQ ID NO:28) at higher concentrations under the conditions of 4-hour exposures. The bottom graph shows that the exemplary HER2-targeting molecules 115111 (SEQ ID NO:29) and 114912 (SEQ ID NO:28) exhibited similar cytotoxicities under the conditions of continuous exposure.
Figure 19:
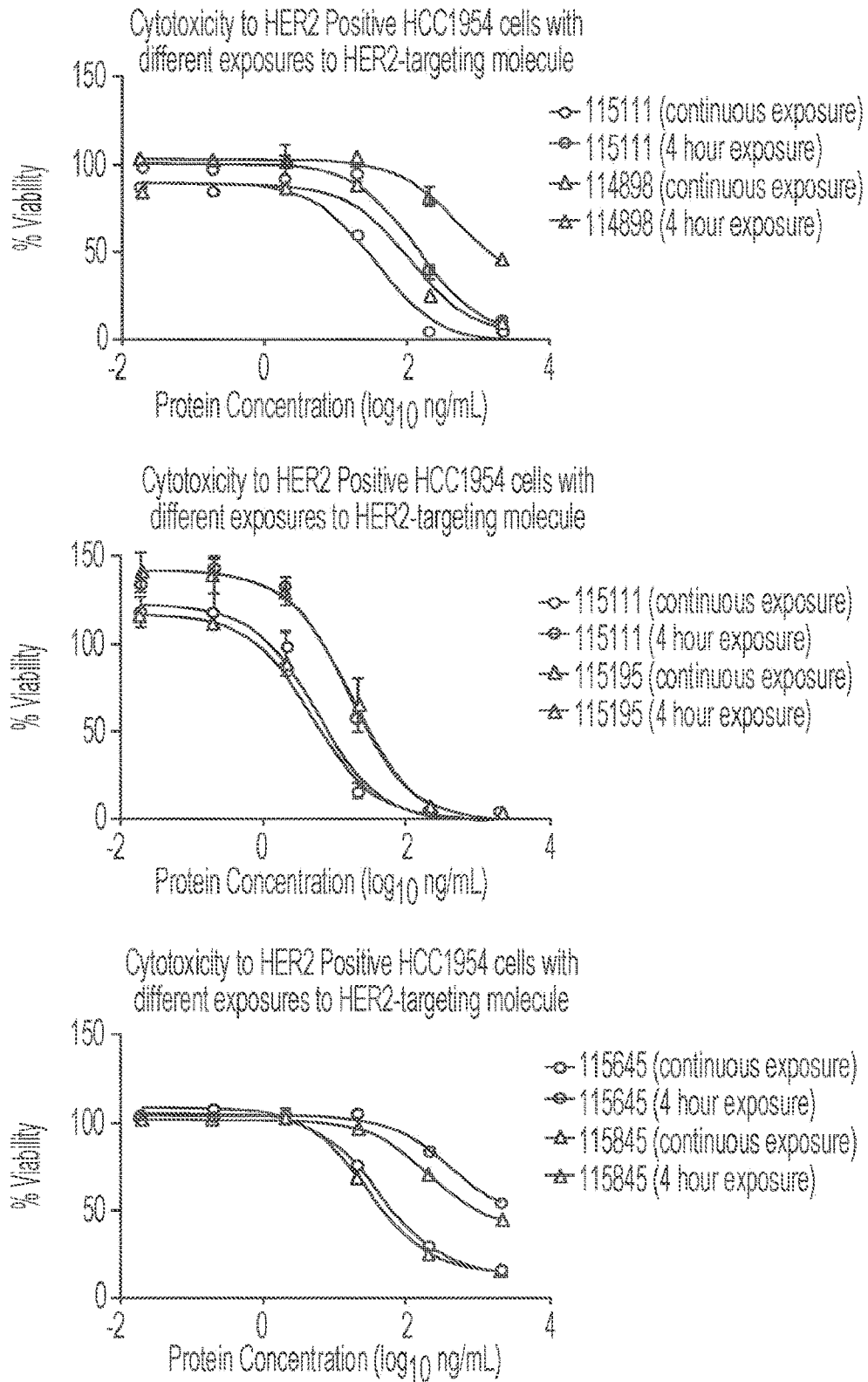
FIG. 19 graphically shows that the exemplary HER2-targeting molecule 115111 (SEQ ID NO:29) is more potently cytotoxic than other exemplary HER2-targeting molecules for shorter exposure durations. The percent viability of HER2 positive HCC1954 cells was plotted over the logarithm to base 10 of the administered HER2-targeting molecule concentrations. The top graph of FIG. 19 shows that the exemplary HER2-targeting molecule 115111 (SEQ ID NO:29) was more cytotoxic to HCC1954 cells than 114898 (SEQ ID NO:31) under the conditions with 4-hour exposures. The middle graph of FIG. 19 shows that the exemplary HER2-targeting molecules 115111 (SEQ ID NO:29) and 115195 (SEQ ID NO:32) exhibited similar cytotoxicities to each other under the conditions of both 4-hour exposures and continuous exposure and that these molecules exhibited the least difference in cytotoxic potency when comparing the 4 hour (short) incubation results with the continuous exposure results. The bottom graph of FIG. 19 shows that the exemplary HER2-targeting molecule 115645 (SEQ ID NO:34) and 115845 (SEQ ID NO:35) exhibited similar cytotoxicities to each other under the conditions of both 4-hour exposures and continuous exposure and that the activity of both of these HER2-targeting molecules was reduced in cytotoxic potency under the shorter four hour incubation with the HER2-targeting molecule as compared to continuous exposure for days.

The data from these experiments demonstrated that 115111 (SEQ ID NO:29) has potent cytotoxic activity when exposed to HER2-expressing cells for just a short duration (1 to 4 hours) (see Tables 9-10 and FIGS. 18-19). The dimeric/divalent 115195 (SEQ ID NO:32) is related to monomeric/monovalent 115111 (SEQ ID NO:29), differing only in a linker (which affects multimerization), exhibited similar activity to 115111 (SEQ ID NO:29) under both continuous and washout conditions (Table 10, FIG. 19). In contrast, other HER2-targeting molecules like 114912 (SEQ ID NO:28), 114898 (SEQ ID NO:31), 115645 (SEQ ID NO:34), and 115845 (SEQ ID NO:35) exhibited greater reductions in cytotoxic activity at shorter exposure durations as compared to continuous exposure (see e.g. Tables 9-10 and FIGS. 18-19).

The HER2 binding and catalytic activity data shown above did not provide a clear indication that the cytotoxic potency under relatively short durations of exposure would be highest for 115111 (SEQ ID NO:29) and 115195 (SEQ ID NO:32) as opposed to other HER2-targeting molecules tested, such as the trastuzumab based 114912 (SEQ ID NO:28). Furthermore, the cytotoxicity assay data above gathered under conditions of continuous exposure (e.g. 3 to 5 days) did not provide any indication as to which HER2-targeting molecules would be more potent under conditions of shorter exposure durations (e.g. 4 hours or less).

Comparing different HER2-targeting molecules, it is apparent that the binding affinity does not always correlate with the cytotoxic activity. For example, 115645 (SEQ ID NO:34) and 115845 (SEQ ID NO:35) have similar cytotoxic activities toward HER2 positive HCC 1954 (Table 10; FIG.

Figure 10:
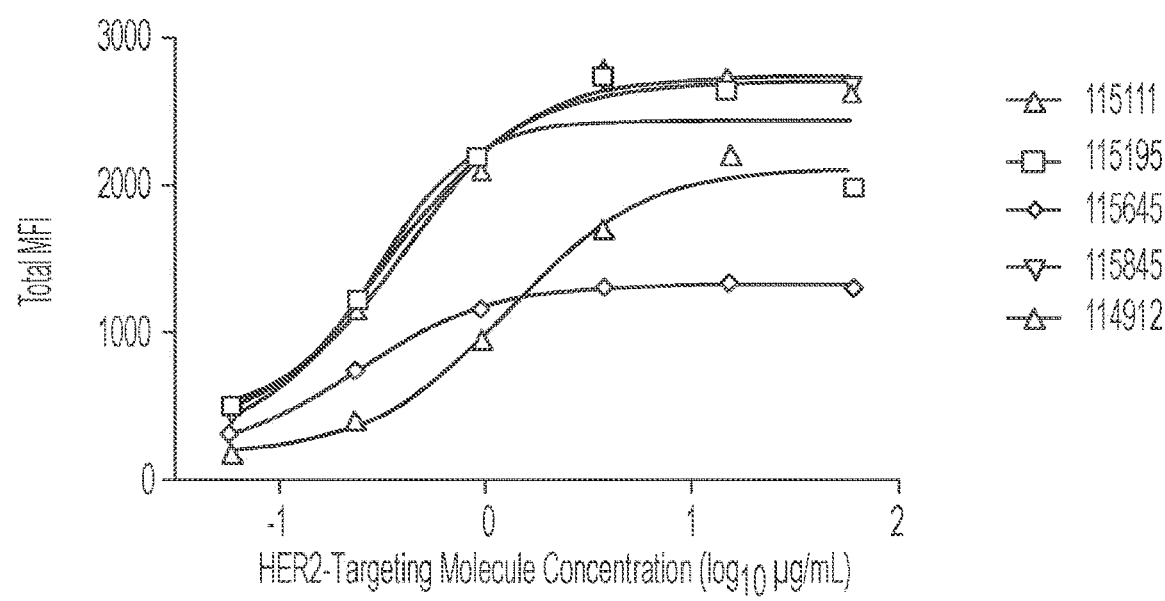

19) but differ in HER2 binding as measured by Bmax (Table 5 and FIG. 10). Conversely, 115111 (SEQ ID NO:29) is more potently cytotoxic to HCC1954 cells than 115845 (SEQ ID NO:35) (see Tables 7-9; FIGS. 6-7 and 18-19), but these two HER2-targeting molecules demonstrated similar Bmax and $K_D$ binding characteristics to those cells (see Tables 5 and 10; FIG. 10). The shorter duration exposures reveal quite large differences between molecules, and this finding could not be predicted by the HER2 binding data, catalytic data, and the continuous exposure data.

4. Species Cross-Reactivity of HER2 Binding

In preparation for animal studies, in vitro binding assays were used to investigate the binding of 115111 (SEQ ID NO:29) to recombinant HER2 proteins from different species. The wells of enzyme-linked immunosorbent assay (ELISA) plates were coated with recombinant HER2 extracellular domain (ECD) proteins derived from human (SEQ ID NO:38), cynomolgus monkey species (GenBank EHH58073.1 and NCBI reference XP 001090430.1 (SEQ ID NOs: 40-41)), and mouse (UniProt P70424 (SEQ ID NO:42)) sources. The wells were blocked, washed, and then incubated with one of the exemplary HER2-targeting molecules: 115111 (SEQ ID NO:29), 115195 (SEQ ID NO:32), or 114912 (SEQ ID NO:28). Unbound protein was removed by washing, and HER2 bound HER2-targeting molecules were detected using a horse radish peroxidase (HRP)-conjugated mAb anti-SLTA-DI-2 that recognizes the Shiga toxin effector polypeptide component in these molecules. The results of these binding assays are reported below (see Table 11 and FIG. 20).

TABLE 11

Binding to Recombinant HER2 Proteins from Different Species

| HER2 ECD recombinant protein | 115111 binding | | 115195 binding | | 114912 binding | |
|---|---|---|---|---|---|---|
| | $K_D$ (ng/mL) | Bmax (Abs 450 nM) | $K_D$ (ng/mL) | Bmax (Abs 450 nM) | $K_D$ (ng/mL) | Bmax (Abs 450 nM) |
| human | 19.11 | 4.00 | 12.30 | 3.96 | 44.80 | 3.57 |
| cynomolgus monkey | 19.34 | 3.99 | 12.70 | 3.99 | 61.86 | 3.92 |

Figure 20:
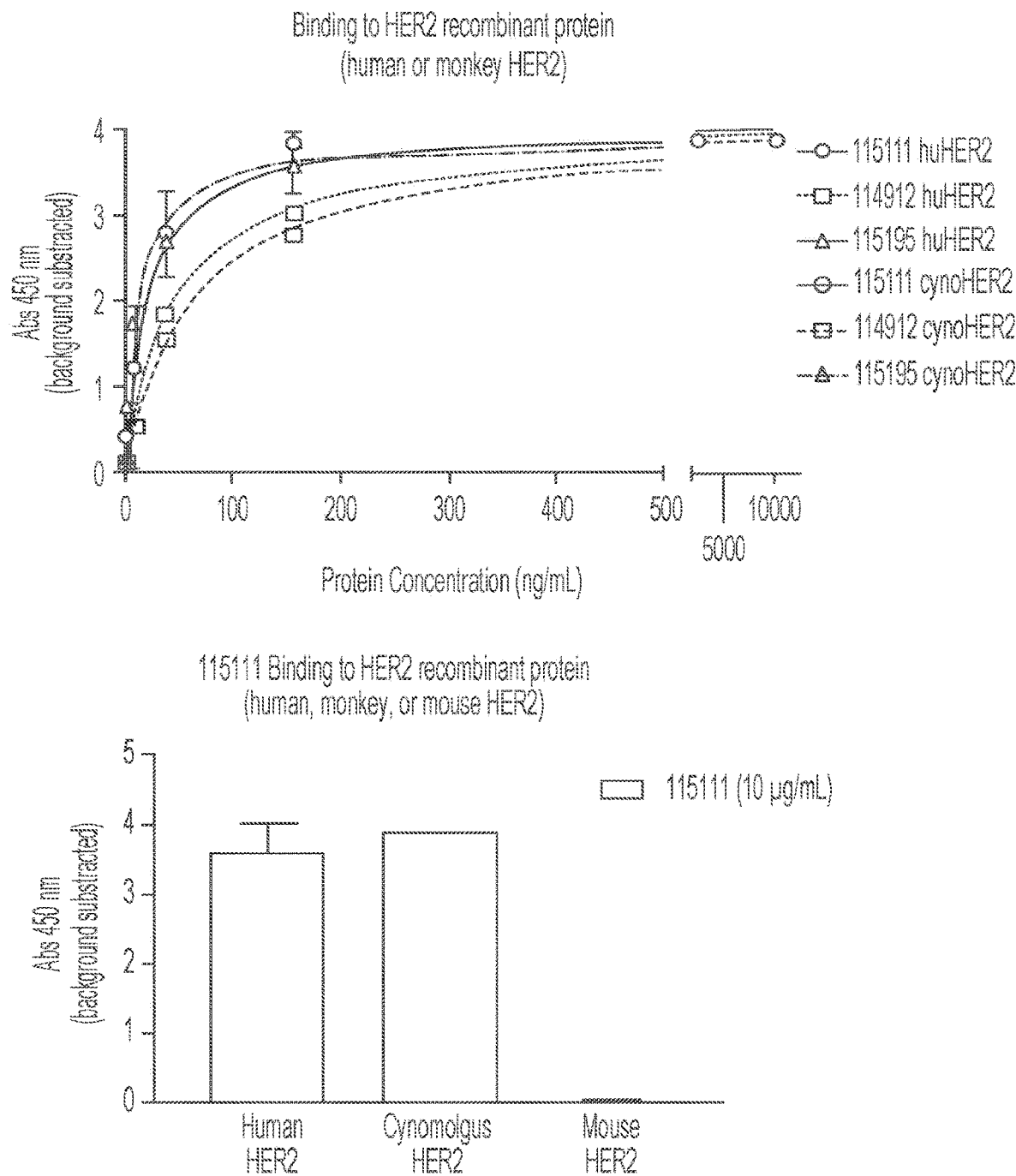
FIG. 20 graphically shows the in vitro HER2 binding characteristics of exemplary HER2-targeting molecules of the present invention using recombinant HER2 proteins of human (SEQ ID NO:39), mouse (SEQ ID NO:42), or cynomolgus monkey (SEQ ID NO:40) origin. The top section of FIG. 20 graphs the ELISA signal for 114912 (SEQ ID NO:28), 115111 (SEQ ID NO:29), and 115195 (SEQ ID NO:32) tested over a series of HER2-targeting molecule concentrations. The background subtracted ELISA signal measured in absorbance at 450 nanometers (nm) is graphed on the Y-axis versus the HER2-targeting molecule concentration in ng/mL on the x-axis. The 115111 (SEQ ID NO:29) and 115195 (SEQ ID NO:32) bound both human HER2 ECD protein ("huHER2") and cynomolgus monkey HER2 ECD protein ("cynoHER2") with similar binding characteristics, which appeared to be at slightly higher affinities at most concentrations in this assay than the HER2 binding exhibited by 114912 (SEQ ID NO:28), a trastuzumab binding domain-derived molecule. The bottom section of FIG. 20 shows the background subtracted ELISA signal measured in absorbance at 450 nm for the binding of 115111 (SEQ ID NO:29) to human HER2, cynomolgus monkey HER2, or mouse HER2 tested at 10 μg/mL of HER2-targeting molecule. The exemplary HER2-targeting molecule 115111 (SEQ ID NO:29) bound both recombinant human HER2 protein and recombinant cynomolgus monkey HER protein but did not exhibit appreciable binding to recombinant mouse HER2 protein in this assay.

The data in Table 11 and FIG. 20 show that 115111 (SEQ ID NO:29), the related molecule 115195 (SEQ ID NO:32) (which is a divalent dimer variant of the monovalent 115111 (SEQ ID NO:29) differing only in a linker), and the trastuzumab binding domain-derived molecule 114912 (SEQ ID NO:28) all bound to both human and cynomolgus monkey recombinant HER2 ECD proteins (Sino Biological Inc., Beijing, CN, catalog nos. 10004-H02H and 90295-C02H, respectively). In this assay, 114912 (SEQ ID NO:28) did not bind the mouse HER2 ECD protein (Sino Biological Inc., Beijing, CN, catalog no. 50714-M02H). 115111 (SEQ ID NO:29) did not bind to the mouse HER2 ECD protein in this assay (FIG. 20). As shown in Table 11 and FIG. 20, the monomeric/monovalent 115111 (SEQ ID NO:29) and the related dimeric/divalent 115195 (SEQ ID NO:32) exhibited similar binding to human and cynomolgus monkey recombinant HER2 ECD proteins. Although 114912 (SEQ ID NO:28) bound with a similar affinity to human and cynomolgus monkey HER2 ECD proteins as 115111 (SEQ ID NO:29) and 115195 (SEQ ID NO:32) regarding Bmax (see Table 11; FIG. 20), the trastuzumab based 114912 (SEQ ID NO:28) exhibited a slightly higher $K_D$ (2 to 5-fold) as compared to both 115111 (SEQ ID NO:29) and 115195 (SEQ ID NO:32) (see Table 11).

Summary of In Vitro Data:

Based on the in vitro data above, the most promising HER2-targeting molecules tested were 114912 (SEQ ID NO:28), 115111 (SEQ ID NO:29), 115195 (SEQ ID NO:32), 115172 (SEQ ID NO:23), 115194 (SEQ ID NO:33), 115411 (SEQ ID NO:30), 115645 (SEQ ID NO:34), and 115845 (SEQ ID NO:35) (see Tables 1-3 and 9-10; FIGS. 3,6-7, and 18-19). These HER2-targeting molecules exhibited potent cytotoxic activities in vitro under conditions of continuous exposure. In the in vitro ribosome inhibition assay, no significant differences were observed between the HER2-targeting molecules tested. In the in vitro cell-binding assay, some differences were observed between the HER2-targeting molecules tested; however, binding characteristics do not necessarily correlate with cytotoxic potency (see above discussion regarding 115645 (SEQ ID NO:34) and 115845 (SEQ ID NO:35)). The in vitro cytotoxicity data above gave no indication of which molecule(s) from among 115111 (SEQ ID NO:29), 115195 (SEQ ID NO:32), 115172 (SEQ ID NO:23), 115194 (SEQ ID NO:33), and 115411 (SEQ ID NO:30) would be the most effective and safe in vivo. However, the Shiga toxin A Subunit effector polypeptide components in 115172 (SEQ ID NO:23) and 115194 (SEQ ID NO:33) were less de-immunized than the Shiga toxin A Subunit effector polypeptide components of the other promising HER2-targeting molecules 115111 (SEQ ID NO:29), 115411 (SEQ ID NO:30), and 115195 (SEQ ID NO:32). Thus, administration of 115111 (SEQ ID NO:29), 115411 (SEQ ID NO:30), or 115195 (SEQ ID NO:32) to animals was expected to be better tolerated than administration of either 115172 (SEQ ID NO:23) or 115194 (SEQ ID NO:33). Animal studies involving the administration of different exemplary HER2-targeting molecules at different dosages were undertaken, particularly to discern any differences in their safety profiles and/or efficacy for treating cancer and to pick the most promising candidate to take into human clinical trials. Neither the in vitro data above nor the fact that 115111 (SEQ ID NO:29) was monovalent whereas 115195 (SEQ ID NO:32) forms a dimeric divalent molecule suggested which one of these two exemplary HER2-targeting molecules might perform better in vivo.

C. In Vivo Studies of Exemplary HER-Targeting Molecules of the Present Invention Animal models were used to investigate the in vivo effects of exemplary HER-targeting molecules of the present invention. Different mouse strains were used to test the effect(s) of 115111 (SEQ ID NO:29) after administration on both healthy, immunocompetent mice and on xenograft tumors in immunocompromised mice resulting from the injection into those mice of human neoplastic cells which express HER2 on their cell surfaces. Non-human primates were used to investigate the effect(s) of 115111 (SEQ ID NO:29) after intravenous administration to healthy non-human primates. The exemplary HER2-targeting molecule 115111 (SEQ ID NO:29) was observed to be better tolerated than other HER2-targeting molecules tested in animals. Surprisingly, 115111 (SEQ ID NO:29) administration was observed to be better tolerated than administration of the closely related candidate HER2-targeting molecule 115195 (SEQ ID NO:32).

1. Serum Exposure

Immunocompetent C57BL/6 mice were used to investigate the serum exposure (pharmacokinetics) of 115111 (SEQ ID NO:29) and 115195 (SEQ ID NO:32) after intravenous (IV) administration of a single dose at 1 milligram per kilogram (mg/kg) of body weight. The HER2-targeting molecules 115111 (SEQ ID NO:29) and 115195 (SEQ ID NO:32) were each diluted in phosphate buffered saline (PBS) and administered by IV to mice, with three mice were per treatment group. At each timepoint, blood sera were collected from each mouse, and the concentration of HER2-targeting molecule was measured by means of a mesoscale discovery assay (Cambridge Biomedical Inc., Boston, Mass., U.S.A.) using recombinant, human HER2 protein to capture any HER2-binding molecules and using the anti-SLTA-DI-2 mAb for quantitation of HER2-targeting molecule present, both quantified using standard curves. Results from this study are shown in Table 12.

TABLE 12

Serum Exposure to Exemplary HER2-Targeting Molecules in C57BL/6 Mice after Repeat Dosing

| | Serum HER2-Targeting Molecule (ng/mL) | |
|---|---|---|
| Time (hr) | 115111 | 115195 |
| 0.083 | 22,344 | 30,280 |
| 0.5 | 3,603 | 29,899 |
| 1 | 1,354 | 23,334 |
| 2 | 355 | 13,518 |
| 4 | 182 | 6,742 |
| 8 | 84 | 3,428 |
| 12 | 21 | 602 |
| 24 | — | 111 |

Data in Table 12 indicate that the serum exposure of 115195 (SEQ ID NO:32) was significantly longer than that of 115111 (SEQ ID NO:29) in mice.

2. Tolerability a. Tolerability in Immunocompetent Mice

Immunocompetent BALB/c mice were used to investigate the toxicity and immunogenicity of exemplary HER2-targeting molecules 115111 (SEQ ID NO:29), 115172 (SEQ ID NO:23), 115195 (SEQ ID NO:32), and 115194 (SEQ ID NO:33) after repeated administrations over time to the same mice (6 doses total per mouse). 115111 (SEQ ID NO:29), 115172 (SEQ ID NO:23), 115195 (SEQ ID NO:32), and 115194 (SEQ ID NO:33) were diluted in PBS and administered to mice (n=6 per group at intravenous (IV) at doses 1 mg/kg of body weight with dosing on days 1, 3, 5, 8, 10, and 12). As a control, vehicle-only samples were administered to a negative control treatment group. The body weights and health of the mice were monitored during the study. Treatment tolerability results from this study are shown in Table 13 and FIG. 21, with changes in body weight and deaths as indicators of tolerability. The percentage change in the mean body weight of the treatment group compared to Day 0 is shown along with the number of animal deaths per total animals in the treatment group.

TABLE 13

Effects of Exemplary HER2-Targeting Molecules in BALB/c Mice after Repeat Dosing

| Sample | Days dosed | Amount per Dose | Percentage Body Weight Nadir (Day) | Deaths/ Number of Mice in Group |
|---|---|---|---|---|
| Vehicle Control | 1, 3, 5, 8, 10, 12 | N/A | −2% (14) | 0/6 |
| 115111 | 1, 3, 5, 8, 10, 12 | 1 | −1% (12) | 0/6 |
| 115195 | 1,3, 5, 8, 10, 12 | 1 | −24% (14) | 5/6 |
| 115172 | 1,3, 5, 8, 10, 12 | 1 | −9.5% (12) | 0/6 |

TABLE 13-continued

Effects of Exemplary HER2-Targeting Molecules in BALB/c Mice after Repeat Dosing

| Sample | Days dosed | Amount per Dose | Percentage Body Weight Nadir (Day) | Deaths/ Number of Mice in Group |
|---|---|---|---|---|
| 115194 | 1, 3, 5, 8 (dosing halted) | 1 | −28% (11) | 6/6 |

* 'N/A' denotes not applicable

Figure 21:
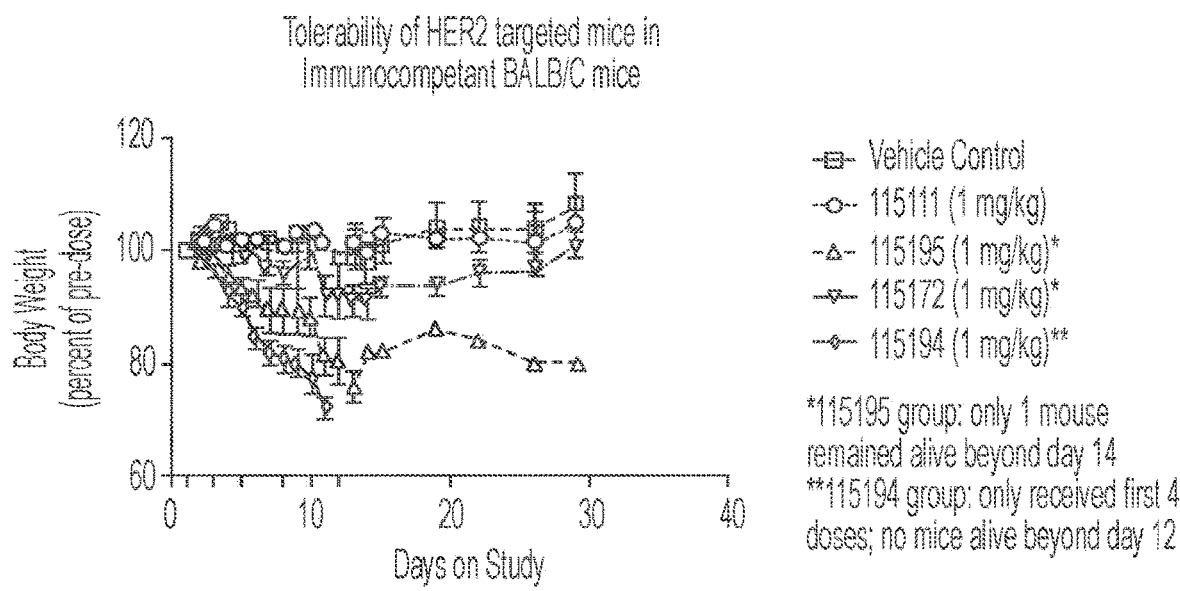
FIG. 21 graphically shows the body weight of immunocompetent mice administered repeat doses of exemplary HER2-targeting molecules of the present invention. The mean body weight change per treatment group calculated using the pre-dose weights of the mice in each group are graphed on the Y-axis versus the day of the study. Groups of BALB/c mice were intravenously administered a vehicle-only control or 1 milligram per kilogram (mg/kg) of body weight of one of these exemplary HER2-targeting molecules: 115111 (SEQ ID NO:29), 115172 (SEQ ID NO:23), 115195 (SEQ ID NO:32), or 115194 (SEQ ID NO:33). In the 11594 (SEQ ID NO:33) treatment group, all mice had died by study Day 12. In the 115195 (SEQ ID NO:32) treatment group, all but one of the mice died by study Day 14. By contrast, the 115111 (SEQ ID NO:29) treatment group showed minimal weight changes similar to the vehicle only control group.

The data from this study demonstrated that 115111 (SEQ ID NO:29) was the most well-tolerated molecule among the exemplary HER-targeting molecules tested (see Table 13 and FIG. 21). The group of mice that received 115111 (SEQ ID NO:29) exhibit no loss in body weight compared to the control group and an absence of animal deaths. By contrast, the group of mice administered 115195 (SEQ ID NO:32) lost an average of over 20% body weight per mouse and 5 of 6 mice (83%) died during the first two weeks of the study. This indicates that the monomeric/monovalent 115111 (SEQ ID NO:29) was better tolerated than the related dimeric/divalent molecule 115195 (SEQ ID NO:32). In addition, the 115111 (SEQ ID NO:29) molecule, comprising SLTA-DI-2 (SEQ ID NO:20), was better tolerated as compared to 115172 (SEQ ID NO:23), which comprises the SLTA-FR (SEQ ID NO:37) component. This might be expected as 115111 (SEQ ID NO:29) comprises a more de-immunized Shiga toxin effector polypeptide component compared to 115172 (SEQ ID NO:23). The group of mice that received 115172 (SEQ ID NO:23) had an average of 9.5% body weight loss and no animal deaths with all the mice recovering body weight after dosing was complete. The least tolerated molecule in this study was 115194 (SEQ ID NO:33), which was dimeric/divalent and comprised the SLTA-FR Shiga toxin effector polypeptide component (SEQ ID NO:37). The group of mice that received 115194 (SEQ ID NO:33) had the most body weight loss, resulting in a cessation of dosing after the $4^{th}$ dose; however, all the mice (6 of 6 (100%)) in this dosing group died by Day 12 of the study.

Together, these data indicated that 115111 (SEQ ID NO:29) was the most well-tolerated HER2-targeting molecule in the study. Based on the serum exposure data for 115111 (SEQ ID NO:29) and 115195 (SEQ ID NO:32), one might expect administration of 115195 (SEQ ID NO:32) to result in less free Shiga toxin in the serum and thus better tolerability. However, 115195 (SEQ ID NO:32) resulted in more toxicity for reasons not yet fully elucidated.

Immunocompetent C57BL/6 mice were used to investigate the tolerability of 115111 (SEQ ID NO:29) after repeated administrations over time to the same mice (2 cycles, 12 doses total per mouse). A 115111 (SEQ ID NO:29) sample was diluted in PBS and administered intravenously (IV) to mice (n=6-10 mice per group) at doses of 0.1 mg/kg of body weight. As a control, the in vivo effects of the less de-immunized 115172 (SEQ ID NO:23) (see e.g. WO 2016/196344) and 115411 (SEQ ID NO:30) were studied in parallel in the same study. As a control, vehicle-only samples were administered to a negative control treatment group. The body weights and health of the mice were monitored during the study and the results for mice dosed at 1 mg/kg per dose are shown in Table 14 and FIG. 22.

TABLE 14

Effects of Exemplary HER2-Targeting Molecules in C57BL/6 Mice after Repeat Dosing

| Sample | Days dosed | Amount per Dose | Body Weight Nadir % (Day) | Deaths/ Number of Mice in Group |
|---|---|---|---|---|
| Vehicle Control | 1, 3, 5, 8, 10, 12; 22, 24, 26, 29, 31, 33 | N/A | — | 0/6 |
| 115111 | 1, 3, 5, 8, 10, 12; 22, 24, 26, 29, 31, 33 | 1 | −6.2% (11) | 0/6 |
| 115172 | 1, 3, 5, 8, 10, 12, 22 (dosing halted) | 1 | −14.5% (11) | 6/6 |
| 115411 | 1, 3, 5, 8, 10, 12; 22, 24, 26, 29, 31, 33 | 1 | −10.2% (13) | 0/6 |

* 'N/A' denotes not applicable

Figure 22:
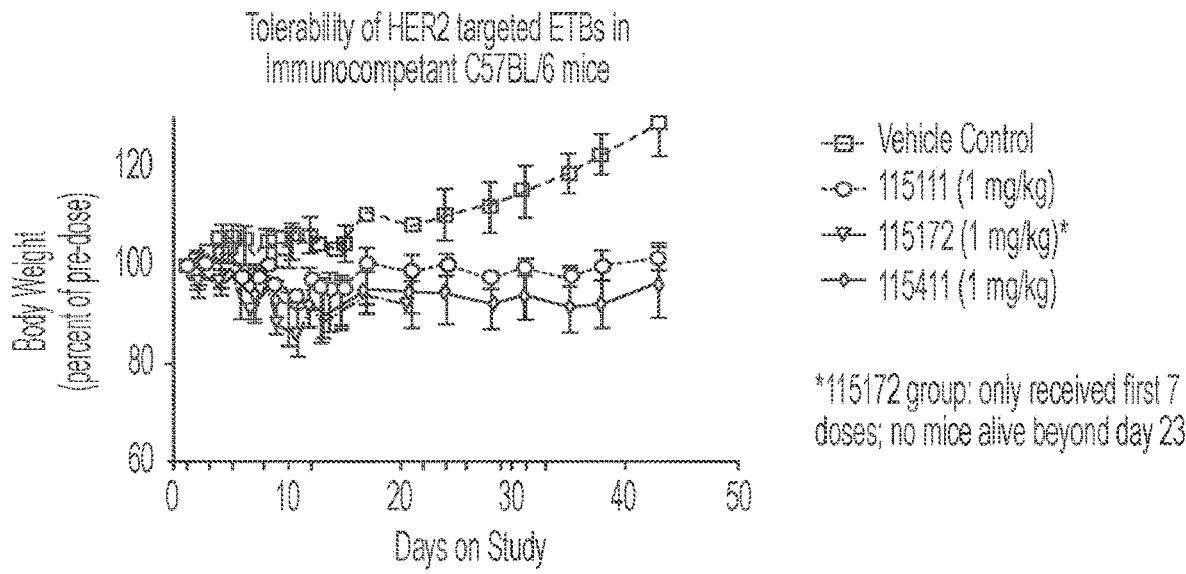
FIG. 22 graphically shows the body weight of immunocompetent mice administered repeat doses of exemplary HER2-targeting molecules of the present invention. The mean body weight change per treatment group calculated using the pre-dose weights of the mice in each group are graphed on the Y-axis versus the day of the study. Groups of C57BL/6 mice were intravenously administered a vehicle-only control or 1 mg/kg of body weight of one of these exemplary HER2-targeting molecules: 115111 (SEQ ID NO:29), 115172 (SEQ ID NO:23), or 115411 (SEQ ID NO:30). In the 115172 (SEQ ID NO:23) treatment group, all mice had died by study Day 23. By contrast, the mice in the 115111 (SEQ ID NO:29) treatment group tolerated 115111 (SEQ ID NO:29) dosing through study Day 45 (end of the study).
Figure 23:
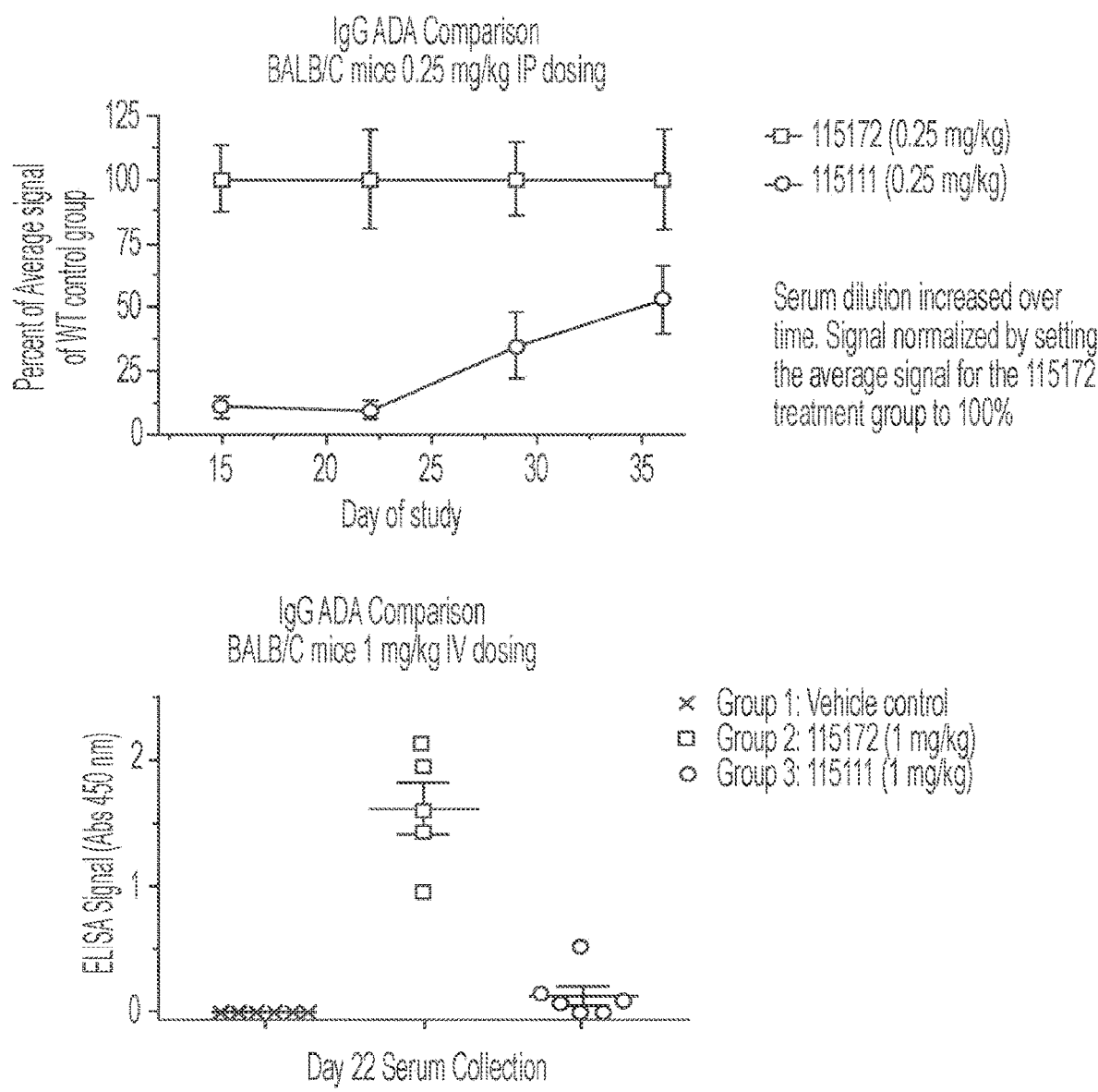
FIG. 23 shows that administration of the exemplary HER2-targeting molecule 115111 (SEQ ID NO:29) comprising a de-immunized Shiga toxin effector polypeptide resulted in reduced, in vivo, antibody response(s) by a mammalian immune system compared to 115172 (S 115111 (SEQ ID NO:29) or 115172 (SEQ ID NO:23) at doses between 0.25 to 1 mg/kg body weight. The top graph of FIG. 23 shows the amount of anti-drug antibodies measured in the blood sera of the 115111 (SEQ ID NO:29) treatment group as a percentage of the 115172 (SEQ ID NO:23) treatment group measured during different days of a study using BALB/c mice administered 0.25 mg/kg body weight of 115111 (SEQ ID NO:29) or 115172 (SEQ ID NO:23) by intraperitoneal injection (IP). The bottom graph of FIG. 23 shows the ELISA signal measured as absorbance at 450 nm shows the amount of anti-drug antibodies measured in blood sera collected on study Day 22 of a study using groups of BALB/c mice intravenously (IV) administered 1 mg/kg body weight of 115111 (SEQ ID NO:29), 115172 (SEQ ID NO:23), or a vehicle-only control. The sera from the 115111 (SEQ ID NO:29) treatment group exhibited much less anti-drug antibodies than the sera from 115172 (SEQ ID NO:23) treatment group collected on Day 22.
Figure 24:
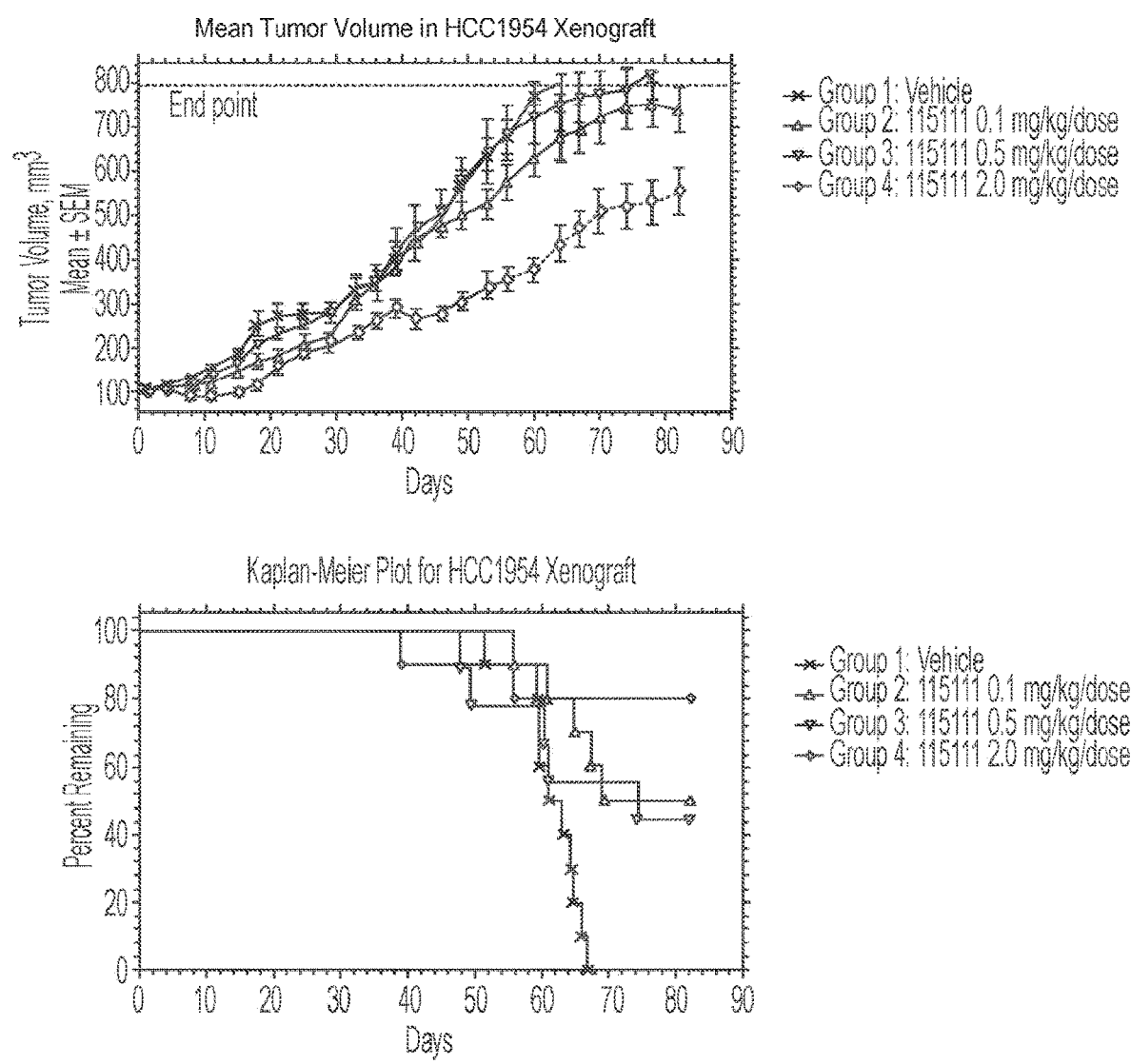
FIG. 24 graphically shows the results from a subcutaneous HCC1954 xenograft murine model study of human breast cancer. The top section of FIG. 24 graphs the change in human tumor burdens over time for groups of SCID Beige mice after receiving either the exemplary HER2-targeting molecule 115111 (SEQ ID NO:29) of the present invention or a vehicle-only control sample. The mean tumor volume measured in cubic millimeters for each group of mice was graphed versus time (days post-tumor implant). Administration of the exemplary HER2-targeting molecule 115111 (SEQ ID NO:29) delayed and reduced the increase in tumor burden observed for the vehicle only control group at all dosages displayed, 0.1 mg to 2 mg per kilogram body weight per dose in cycles over 31 to 33 days. The bottom section of FIG. 24 graphs the survival of groups of mice in the same study as above until Day 84 using a Kaplan Meier estimator plot. On the y-axis is the percent survival of mice within a dosage group, and the x-axis is in days of the study. The repeated administration of 115111 (SEQ ID NO:29) at 0.1 to 2 mg/kg body weight provided survival benefits compared to the vehicle-only control sample.

The body weight and animal death results in Table 14 showed that 115111 (SEQ ID NO:29) and 115411 (SEQ ID NO:30) were better tolerated than 115172 (SEQ ID NO:23). None of the mice in the 115111 (SEQ ID NO:29) or 115411 (SEQ ID NO:30) treatment groups died, whereas 6 of 6 mice (100%) died in the 115172 (SEQ ID NO:23) treatment group during the first twenty-two days of the study. The body weight data in FIG. 22 showed that 115111 (SEQ ID NO:29) was better tolerated than 115172 (SEQ ID NO:23). These results indicate the 115111 (SEQ ID NO:29) and 115411 (SEQ ID NO:30) molecules, comprising SLTA-DI-2 (SEQ ID NO:20), were better tolerated as compared to 115172 (SEQ ID NO:23), which comprised the less de-immunized SLTA-FR Shiga toxin effector polypeptide component (SEQ ID NO:37).

b. Immunogenicity

Immunocompetent BALB/c mice were used to investigate the immunogenicities of 115111 (SEQ ID NO:29), 115172 (SEQ ID NO:23), 115195 (SEQ ID NO:32), and 115194 (SEQ ID NO:33) after repeated administrations over time to the same mice (6 doses total per mouse). In one study, 115111 (SEQ ID NO:29), 115172 (SEQ ID NO:23), 115195 (SEQ ID NO:32), and 115194 (SEQ ID NO:33) were diluted in PBS and administered to mice (n=6 per group) at intravenous (IV) doses of 1 mg/kg of body weight. Immune response results measured in this study are reported below and in FIG. 23. In another study, 115111 (SEQ ID NO:29), 115172 (SEQ ID NO:23), or a vehicle-only control sample were administered to mice (n=6 per group) via intraperitoneal (IP) injection at doses of 0.25 mg/kg of body weight.

The quantities of anti-drug antibodies (ADA) to HER2-targeting molecule in the mice were monitored during these studies. The anti-drug antibody levels were monitored by taking serum samples from the mice, diluting the samples, and incubating the diluted samples with the HER2-targeting molecule being tested (115111 (SEQ ID NO:29) or 115172 (SEQ ID NO:23)) overnight to form immune complexes. Then, molecules comprising a human HER2 binding domain (e.g. a HER2-targeting molecule of the present invention) were captured using an ELISA method involving a plate coated with recombinant human HER2 protein. The quantity of immune complexes present in each sample was then estimated using an anti-mouse immunoglobulin G conjugated to horseradish peroxidase (IgG-HRP) to quantify the number of anti-mouse IgG's captured by the human HER2 ELISA method. Results from this anti-drug antibody (ADA) assay are shown in FIG. 23.

The top of FIG. 23 showed the more de-immunized 115111 (SEQ ID NO:29) resulted in a lower IgG anti-drug antibody (ADA) ELISA signal than 115172 (SEQ ID NO:23) during the first 36 days of a study involving intraperitoneal (IP) dosing at 0.25 mg/kg body weight. The bottom of FIG. 23 showed administration of the more de-immunized 115111 (SEQ ID NO:29) resulted in a lower IgG ADA ELISA signal than administration of 115172 (SEQ ID NO:23) at Day 22 of the study involving IV dosing at 1 mg/kg body weight. These results are not unexpected as 115111 (SEQ ID NO:29) comprised a more de-immunized Shiga toxin effector polypeptide component compared to 115172 (SEQ ID NO:23).

c. Non-Human Primates

Two toxicology studies were performed in cynomolgus monkeys involving the administration of 115111 (SEQ ID NO:29) in six intravenous (IV) bolus doses, three times per week for 2 weeks, to evaluate the potential reversibility, progression or delayed progression of any findings following a 3-week (or 18 days for the low dose study) post-dose observation period.

A "high dose" good laboratory practice (GLP) study tested doses of 50, 150, and 300 μg/kg of body weight. These "high" doses were not well tolerated.

A "low dose" GLP study tested doses of 1, 5, and 25 μg/kg of body weight. These "low" doses showed effects that were not considered to have adversely impacted the health of the animals and so the No-Observed-Adverse-Effect Level (NOAEL) and Highest Non-Severely Toxic Dose (HNSTD) for these two studies was 25 μg/kg body weight (i.e. the highest dose tested in the "low-dose" study).

3. HER2 Expressing Tumor Xenograft Efficacy

A mouse model of human breast cancer was used to test the effect(s) of 115111 (SEQ ID NO:29) after intraperitoneal (IP) administration. First, human neoplastic cells which express HER2 on their cell surfaces were injected into the mice and then the mice were treated with 115111 (SEQ ID NO:29).

The activity of 115111 (SEQ ID NO:29) was studied in a subcutaneous tumor model using SCID Beige mice bearing subcutaneous, human HER2 positive tumors. HCC1954 cells from a human breast cancer derived cell line were implanted subcutaneously, then treatment was initiated when tumors reached an average of 100-150 $mm^3$, thereby defining study Day 0. The mice were intravenously administered two cycles of 115111 (SEQ ID NO:29) at doses of 0.1, 0.5 or 2 mg/kg body weight on study days 1, 3, 5, 8, 10, 12, 22, 24, 26, 29, 31 (and 33 for the groups administered doses of 0.1 or 0.5 mg/kg). Tumor volume was monitored during the treatment period and results are shown from Day 0 to Day 60 (latest point where greater than fifty percent of the animals in all groups survived) are shown in FIG. 24. In addition, survival results from the study are shown from Day 0 to Day 84 (end of study) in FIG. 24.

This study showed that repeat administration of 115111 (SEQ ID NO:29) at 0.1, 0.5, and 2 mg/kg body weight resulted in delays in tumor growth and provided survival benefits through study Day 84 (see e.g. FIG. 24). Weight losses observed in the 115111 (SEQ ID NO:29) treatment group that was administered doses of 2 mg/kg of body weight resulted in the last scheduled dose (Day 33) to be withheld, and two mice in the 2 mg/kg 115111 (SEQ ID NO:29) treatment group died during the study.

SUMMARY

Surprisingly, the exemplary HER2-targeting molecule 115111 (SEQ ID NO:29) was much safer to administer to animals at doses ranging between 1 to 2 mg/kg body weight than any other exemplary HER2-targeting molecules tested in this Example. This safety result could not be predicted from the in vitro data above. It was particularly surprising that the monomer 115111 (SEQ ID NO:29) was better tolerated than the dimer 115195 (SEQ ID NO:32) because these two molecules share identical components: the Shiga toxin effector polypeptide, heavy variable chain, light variable chain, and linker between the Shiga toxin effector polypeptide and the HER2-binding region are the same in these molecules. Furthermore, the in vitro data revealed no significant difference between these molecules except that 115195 (SEQ ID NO:32) was dimeric and divalent whereas 115111 (SEQ ID NO:29) was monomeric and monovalent. For example, both 115195 (SEQ ID NO:32) and 115111 (SEQ ID NO:29) exhibited similar cytotoxicity in vitro (see Tables 3 and 10; FIG. 19) and similar binding characteristics to HER2 positive cells (see Tables 5 and 11; FIG. 10). Both 115111 (SEQ ID NO:29) and 115195 (SEQ ID NO:32) maintained cytotoxic potency at shorter durations of exposure compared to continuous exposure (see Tables 9-10 and FIGS. 18-19). 115111 (SEQ ID NO:29) exhibited more cytotoxic potency than 114912 (SEQ ID NO:28) (see Tables 2 and 9; and FIGS. 6 and 18), under conditions involving continuous or shorter exposures. The HER2-targeting molecules 114912 (SEQ ID NO:28) and 114778 (SEQ ID NO:24), both of which are partly based on the widely used medicine trastuzumab (Herceptin®), were not among the most potent HER2-targeting molecules tested herein.

Example 2. Subject Response Prediction and Appropriate Subject Identification for a Therapeutic Use of a HER2-Targeting Molecule of the Present Invention Exemplary HER2-targeting molecules, such as one described above in Example 1, are administered to patient derived cell-lines in vitro in order to identify the most sensitive or resistant histologies and/or histological subtypes for different diseases, disorders, and/or conditions. Then, patients are categorized into different subpopulations using methods known to the skilled worker. For example, panels of breast cancer derived cell-lines (or alternatively gastric, ovary, lung, colorectal, melanoma, or pancreas) are tested in vitro using the cytotoxicity assay described in Example 1 or other methods known to the skilled worker. In addition, these cytotoxicity assays are performed in combination with an additional HER2-targeted therapeutic, such as, e.g., including T-DM1 (trastuzumab emtansine), trastuzumab, and pertuzumab, and/or an additional drug which impinges on HER2 function, such as, e.g., lapatinib and/or neratinib. The cytotoxicity results reveal certain associations useful to identify or predict which indications, cell-types, histologies, histological subtypes, and/or subjects may respond or be resistant to a particular HER2-targeting molecule of the present invention and/or a particular combination of a HER2-targeting molecule of the present invention and an additional therapeutic, such as another HER2-targeted therapeutic described herein, based on information regarding each cell line, such as, e.g., molecular markers (including biomarker expression, gene copy numbers, mutations and polymorphisms, pro-proliferation pathway activation or growth-inhibitor pathway inhibition, metabolic activities, genotyping); responses to standard chemotherapeutic/cytotoxic agents, hormonal agents (e.g. estrogen, estradiol, etc.), and biologic agents (e.g. immune checkpoint inhibitor); and abilities to grow on plastic and in soft agar, as well as to grow in vivo subcutaneously and orthotopically. Further, malignant tissue specimens of cancers from individual patients or circulating tumor cells are tested for the presence of biomarkers of sensitivity/resistance using routine methods known to the skilled worker. Based on this biomarker associations, histologic associations, and cell characteristics in vitro, patients are selected or categorized as appropriate candidates (or inappropriate) to receive HER2-targeting molecule therapies (including combination therapies) as part of the treatment regimen for their malignancy.

While some embodiments of the invention have been described by way of illustration, it will be apparent that the invention may be put into practice with many modifications, variations and adaptations, and with the use of numerous equivalents or alternative solutions that are within the scope of persons skilled in the art, without departing from the spirit of the invention or exceeding the scope of the claims.

All publications, patents, and patent applications are herein incorporated by reference in their entirety to the same extent as if each individual publication, patent or patent application was specifically and individually indicated to be incorporated by reference in its entirety. The international patent application publications WO 2014/164680, WO 2014/164693, WO 2015/138435, WO 2015/138452, WO 2015/113005, WO 2015/113007, WO 2015/191764, WO 2016/196344, WO 2017/019623, and WO 2018/140427 are each incorporated herein by reference in its entirety. The disclosures of U.S. patent applications US2015/259428, US2016/17784, US2017/143814, and U.S. 62/659,116 are each incorporated herein by reference in its entirety. The complete disclosures of all electronically available biological sequence information from GenBank (National Center for Biotechnology Information, U.S.) for amino acid and nucleotide sequences cited herein are each incorporated herein by reference in their entirety.

Sequence Listing

| ID Number | Text Description | Biological Sequence |
|---|---|---|
| SEQ ID NO: 1 | Shiga-like toxin 1 Subunit A (SLT-1A) | KEFTLDFSTAKTYVDSLNVIRSAIGTPLQTISSGGTSLLMIDS<br>GSGDNLFAVDVRGIDPEEGRFNNLRLIVERNNLYVTGFVNR<br>TNNVFYRFADFSHVTFPGTTAVTLSGDSSYTTLQRVAGISR<br>TGMQINRHSLTTSYLDLMSHSGTSLTQSVARAMLRFVTVT<br>AEALRFRQIQRGFRTTLDDLSGRSYVMTAEDVDLTLNWGR<br>LSSVLPDYHGQDSVRVGRISFGSINAILGSVALILNCHHHAS<br>RVARMASDEFPSMCPADGRVRGITHNKILWDSSTLGAILM<br>RRTISS |
| SEQ ID NO: 2 | Shiga toxin Subunit A (StxA) | KEFTLDFSTAKTYVDSLNVIRSAIGTPLQTISSGGTSLLMIDS<br>GTGDNLFAVDVRGIDPEEGRFNNLRLIVERNNLYVTGFVN<br>RTNNVFYRFADFSHVTFPGTTAVTLSGDSSYTTLQRVAGIS<br>RTGMQINRHSLTTSYLDLMSHSGTSLTQSVARAMLRFVTV<br>TAEALRFRQIQRGFRTTLDDLSGRSYVMTAEDVDLTLNWG |

-continued

Sequence Listing

| ID Number | Text Description | Biological Sequence |
|---|---|---|
| | | RLSSVLPDYHGQDSVRVGRISFGSINAILGSVALILNCHHHA SRVARMASDEFPSMCPADGRVRGITHNKILWDSSTLGAIL MRRTISS |
| SEQ ID NO: 3 | Shiga-like toxin 2 Subunit A (SLT-2A) | DEFTVDFSSQKSYVDSLNSIRSAISTPLGNISQGGVSVSVINH VLGGNYISLNVRGLDPYSERFNHLRLIMERNNLYVAGFINT ETNIFYRFSDFSHISVPDVITVSMTTDSSYSSLQRIADLERTG MQIGRHSLVGSYLDLMEFRGRSMTRASSRAMLRFVTVIAE ALRFRQIQRGFRPALSEASPLYTMTAQDVDLTLNWGRISNV LPEYRGEEGVRIGRISFNSLSAILGSVAVILNCHSTGSYSVRS VSQKQKTECQIVGDRAAIKVNNVLWEANTIAALLNRKPQD LTEPNQ |
| SEQ ID NO: 4 | Shiga toxin subtype c Subunit A (Stx1cA) | KEFTLDFSTAKTYVDSLNVIRSAIGTPLQTISSGGTSLLMIDS GTGDNLFAVDVRGIDPEEGRFNNLRLIVERNNLYVTGFVN RTNNVFYRFADFSHVTFPGTTAVTLSGDSSYTTLQRVAGIS RTGMQINRHSLTTSYLDLMSHSGTSLTQSVARAMLRFVTV TAEALRFRQIQRGFRTTLDDLSGRSYVMTAEDVDLTLNWG RLSSVLPDYHGQDSVRVGRISFGSVNAILGSVALILNCHHH ASRVAR |
| SEQ ID NO: 5 | Shiga toxin subtype d Subunit A (Stx1dA) | KEFTLDFSTAKKYVDSLNVIRSAIGTPLQTISSGGTSLLMIDS GTGDNLFAVDIMGLEPEEERFNNLRLIVERNNLYVTGFVNR TNNVFYRFADFSHVTFPGTRAVTLSGDSSYTTLQRVAGISR TGMQINRHSLTTSYLDLMSYSGTSLTQSVARAMLRFVTVT AEALRFRQIQRGFRTTLDDLSGRSYVMTAEDVDLTLNWGR LSSILPDYHGQDSVRVGRISFGSINAILGSVALILNCHHHASR VAR |
| SEQ ID NO: 6 | Shiga toxin subtype e Subunit A (Stx1eA) | QDFTVDFSTAKKYVDSLNAIRSAIGTPLHSISSGGTSLLMID NGTGDNLFAVDIRGLDPEEERFDNLRLIIERNNLYVTGFVN RTSNIFYRFADFSHVTFPGTRAVTLSGDSSYTTLQRVAGIGR TGMQINRHSLTTSYLDLMSYSGSSLTQPVARAMLRFVTVT AEALRFRQIQRGFRTTLDDVSGHSYTMTVEDVDLTLNWGR LSSVLPDYHGQDSVRVGRISFGGVNAILGSVALILNCHHHT SRVSR |
| SEQ ID NO: 7 | Shiga toxin subtype 2c Subunit A (Stx2cA) variant 1 | REFTIDFSTQQSYVSSLNSIRTEISTPLE- HISQGTTSVSVINHT PPGSYFAVDIRGLDVYQARFDHLRLIIEQNNLYVAGFVNTA TNTFYRFSDFTHISVPGVTTVSMTTDSSYTTLQRVAALERS GMQISRHSLVSSYLALMEFSGNTMTRDASRAVLRFVTVTA EALRFRQIQREFRQALSETAPVYTMTPGDVDLTLNWGRISN VLPEYRGEDGVRVGRISFNNISAILGTVAVILNCHHQGARS VR |
| SEQ ID NO: 8 | Shiga toxin subtype 2c Subunit A (Stx2cA) variant 2 | REFTIDFSTQQSYVSSLNSIRTEISTPLE- HISQGTTSVSVINHT PPGSYFAVDIRGLDVYQARFDHLRLIIEQNNLYVAGFVNTA TNTFYRFSDFAHISVPGVTTVSMTTDSSYTTLQRVAALERS GMQISRHSLVSSYLALMEFSGNTMTRDASRAVLRFVTVTA EALRFRQIQREFRQALSETAPVYTMTPGDVDLTLNWGRISN VLPEYRGEDGVRVGRISFNNISAILGTVAVILNCHHQGARS VR |
| SEQ ID NO: 9 | Shiga toxin subtype 2c Subunit A (Stx2cA) variant 3 | REFTIDFSTQQSYVSSLNSIRTEISTPLE- HISQGTTSVSVINHT PPGSYFAVDIRGLDIYQARFDHLRLIIEQNNLYVAGFVNTAT NTFYRFSDFTHISVPGVTTVSMTTDSSYTTLQRVAALERSG MQISRHSLVSSYLALMEFSGNTMTRDASRAVLRFVTVTAE ALRFRQIQREFRQALSETAPVYTMTPGDVDLTLNWGRISNV LPEYRGEDGVRVGRISFNNISAILGTVAVILNCHHQGARSVR |
| SEQ ID NO: 10 | Shiga toxin subtype 2c Subunit A (Stx2cA) variant 4 | REFTIDFSTQQSYVSSLNSIRTEISTPLE- HISQGTTSVSVINHT PPGSYFAVDIRGLDVYQARFDHLRLIIEQNNLYVAGFVNTA TNTFYRFSDFTHISVPSVTTVSMTTDSSYTTLQRVAALERSG MQISRHSLVSSYLALMEFSGNTMTRDASRAVLRFVTVTAE ALRFRQIQREFRQALSETAPVYTMTPGDVDLTLNWGRISNV LPEYRGEDGVRVGRISFNNISAILGTVAVILNCHHQGARSVR |
| SEQ ID NO: 11 | Shiga toxin subtype 2c Subunit A (Stx2cA) | REFTIDFSTQQSYVSSLNSIRTEISTPLE- HISQGTTSVSVINHT PPGSYFAVDIRGLDVYQARFDHLRLIIEQNNLYMAGFVNTA TNTFYRFSDFTHISVPSVTTVSMTTDSSYTTLQRVAALERSG MQISRHSLVSSYLALMEFSGNTMTRDASRAVLRFVTVTAE |

Sequence Listing

| ID Number | Text Description | Biological Sequence |
|---|---|---|
| | variant 5 | ALRFRQIQREFRQALSETAPVYTMTPGDVDLTLNWGRISNV<br>LPEYRGEDGVRVGRISFNNISAILGTVAVILNCHHQGARSVR |
| SEQ ID NO: 12 | Shiga toxin subtype 2c Subunit A (Stx2cA) variant 6 | REFTIDFSTQQSYVSSLNSIRTEISTPLE-<br>HISQGTTSVSVINHT<br>PPGSYFAVDIRGLDVYQARFDHLRLIIEQNNLYVAGFVNTA<br>TNTFYRFSDFTHISVPGVTTVSMTTDSSYTTLQRVAALERS<br>GMQISRHSLVSSYLALMEFSGNTMTRDASRAVLRFVTVTA<br>EALRFRQIQREFRQVLSETAPVYTMTPGDVDLTLNWGRISN<br>VLPEYRGEDGVRVGRISFNNISAILSTVAVILNCHHQGARSVR |
| SEQ ID NO: 13 | Shiga toxin subtype 2d Subunit A (Stx2dA) variant 1 | REFTIDFSTQQSYVSSLNSIRTEISTPLE-<br>HISQGTTSVSVINHT<br>PPGSYFAVDIRGLDVYQARFDHLRLIIEQNNLYVAGFVNTA<br>TNTFYRFSDFAHISVPGVTTVSMTTDSSYTTLQRVAALERS<br>GMQISRHSLVSSYLALMEFSGNTMTRDASRAVLRFVTVTA<br>EALRFRQIQREFRQALSETAPVYTMTPGDVDLTLNWGRISN<br>VIPEYRGEDGVRVGRISFNNISAILGTVAVILNCHHQGARSVR |
| SEQ ID NO: 14 | Shiga toxin subtype 2d Subunit A (Stx2dA) variant 2 | REFMIDFSTQQSYVSSLNSIRTEISTPLE-<br>HISQGTTSVSVINHT<br>PPGSYFAVDIRGLDVYQARFDHLRLIIEQNNLYVAGFVNTA<br>TNTFYRFSDFTHISVPGVTTVSMTTDSSYTTLQRVAALERS<br>GMQISRHSLVSSYLALMEFSGNTMTRDASRAVLRFVTVTA<br>EALRFRQIQREFRQALSETAPVYTMTPEEVDLTLNWGRISN<br>VLPEFRGEGGVRVGRISFNNISAILGTVAVILNCHHQGARSVR |
| SEQ ID NO: 15 | Shiga toxin subtype 2d Subunit A (Stx2dA) variant 3 | REFTIDFSTQQSYVSSLNSIRTEISTPLE-<br>HISQGTTSVSVINHT<br>PPGSYFAVDIRGLDVYQARFDHLRLIIEQNNLYVAGFVNTA<br>TNTFYRFSDFTHISVPGVTTVSMTTDSSYTTLQRVAALERS<br>GMQISRHSLVSSYLALMEFSGNTMTRDASRAVLRFVTVTA<br>EALRFRQIQREFRQALSETAPVYTMTPGDVDLTLNWGRISN<br>VIPEYRGEDGVRVGRISFNNISAILSTVAVILNCHHQGARSVR |
| SEQ ID NO: 16 | Shiga toxin subtype 2e Subunit A (Stx2eA) variant 1 | QEFTIDFSTQQSYVSSLNSIRTAISTPLEHISQ-<br>GATSVSVINHT<br>PPGSYISVGIRGLDVYQERFDHLRLIIERNNLYVAGFVNTTT<br>NTFYRFSDFAHISLPGVTTISMTTDSSYTTLQRVAALERSG<br>MQISRHSLVSSYLALMEFSGNTMTRDASRAVLRFVTVTAE<br>ALRFRQIQREFRLALSETAPVYTMTPEDVDLTLNWGRISNV<br>LPEYRGEAGVRVGRISFNNISAILGTVAVILNCHHQGARSVR |
| SEQ ID NO: 17 | Shiga toxin subtype 2e Subunit A (Stx2eA) variant 2 | QEFTIDFSTQQSYVSSLNSIRTAISTPLEHISQ-<br>GATSVSVINHT<br>PPGSYISVGIRGLDVYQAHFDHLRLIIEQNNLYVAGFVNTA<br>TNTFYRFSDFAHISLPGVTTISMTTDSSYTTLQRVAALERSG<br>MQISRHSLVSSYLALMEFSGNTMTREASRAVLRFVTVTAE<br>ALRFRQIQREFRQALSETAPVYTMTPEDVDLTLNWGRISNV<br>LPEYRGEDGVRVGRISFNNISAILGTVAVILNCHHQGARSVR |
| SEQ ID NO: 18 | Shiga toxin subtype 2f Subunit A (Stx2fA) | DEFTVDFSSQKSYVDSLNSIRSAISTPLGNISQGGVSVSINH<br>VPGGNYISLNVRGLDPYSERFNHLRLIMERNNLYVAGFINT<br>ETNTFYRFSDFSHISVPDVITVSMTTDSSYSSLQRIADLERTG<br>MQIGRHSLVGSYLDLMEFRGRSMTRASSRAMLRFVTVIAE<br>ALRFRQIQRGFRPALSEASPLYTMTAQDVDLTLNWGRISNV<br>LPEYRGEEGVRIGRISFNSLSAILGSVAVILNCHSTGSYSVR |
| SEQ ID NO: 19 | SLTA-DI-1 | AEFTLDFSTAKTYVDSLNVIRSAIGTPLQTISSGGTSLLMIDS<br>GIGDNLFAVDILGFDFTLGRFNNLRLIVERNNLYVAGISR<br>TNNVFYRFADFSHVTFPGTTAVTLSADSSYTTLQRVAGISR<br>TGMQINRHSLTTSYLDLMSHSATSLTQSVARAMLRFVTVT<br>AEALRFRQIQRGFRTTLDDLSGRSYVMTAEDVDLTLNWGR<br>LSSVLPDYHGQDSVRVGRISFGSINAILGSVALILNSHHHAS<br>AVAA |
| SEQ ID NO: 20 | SLTA-DI-2 | KEFTLDFSTAKTYVDSLNVIRSAIGTPLQTISSGGTSLLMIDS<br>GIGDNLFAVDILGFDFTLGRFNNLRLIVERNNLYVTGFVNR<br>TNNVFYRFADFSHVTFPGTTAVTLSADSSYTTLQRVAGISR<br>TGMQINRHSLTTSYLDLMSHSGTSLTQSVARAMLRFVTVT<br>AEALRFRQIQRGFRTTLDDLSGASYVMTAEDVDLTLNWGR<br>LSSVLPDYHGQDSVRVGRISFGSINAILGSVALILNSHHHAS<br>AVAA |
| SEQ ID NO: 21 | SLTA-DI-3 | REFTLDFSTARTYVDSLNVIRSAIGTPLQTISSGGTSLLMIDS<br>GIGDNLFAVDILGFDFTLGRFNNLRLIVERNNLYVTGFVNR |

| | | Sequence Listing |
|---|---|---|
| ID Number | Text Description | Biological Sequence |
| | | TNNVFYRFADFSHVTFPGTTAVTLSADSSYTTLQRVAGISR TGMQINRHSLTTSYLALMSHSGTSLTQSVARAMLRFVTVT AEALRFRQIQRGFRTTLDDLSGASYVMTAEDVDLTLNWGR LSSVLPDYHGQDSVRVGRISFGSINAILGSVALILNSHHHAS AVAA |
| SEQ ID NO: 22 | 114773 (SLTA-FR::scFv1) | MKEFTLDFSTAKTYVDSLNVIRSAIGTPLQTISSGGTSLLMI DSGSGDNLFAVDVRGIDPEEGRFNNLRLIVERNNLYVTGFV NRTNNVFYRFADFSHVTFPGTTAVTLSGDSSYTTLQRVAGI SRTGMQINRHSLTTSYLDLMSHSGTSLTQSVARAMLRFVT VTAEALRFRQIQRGFRTTLDDLSGRSYVMTAEDVDLTLNW GRLSSVLPDYHGQDSVRVGRISFGSINAILGSVALILNCHHH ASAVAAEFPKPSTPPGSSGGAPDIQMTQSPSSLSASVGDRV TITCRASQDVNTAVAWYQQKPGKAPKLLIYSASFLYSGVPS RFSGSRSGTDFTLTISSLQPEDFATYYCQQHYTTPPTFGQGT KVEIKGGGGSEVQLVESGGGLVQPGGSLRLSCAASGFNIKD TYIHWVRQAPGKGLEWVARIYPTNGYTRYADSVKGRFTIS ADTSKNTAYLQMNSLRAEDTAVYYCSRWGGDGFYAMDY WGQGTLVTVSSA |
| SEQ ID NO: 23 | 115172 (S LTA-FR::scFv-6) | MKEFTLDFSTAKTYVDSLNVIRSAIGTPLQTISSGGTSLLMI DSGSGDNLFAVDVRGIDPEEGRFNNLRLIVERNNLYVTGFV NRTNNVFYRFADFSHVTFPGTTAVTLSGDSSYTTLQRVAGI SRTGMQINRHSLTTSYLDLMSHSGTSLTQSVARAMLRFVT VTAEALRFRQIQRGFRTTLDDLSGRSYVMTAEDVDLTLNW GRLSSVLPDYHGQDSVRVGRISFGSINAILGSVALILNCHHH ASAVAAEFPKPSTPPGSSGGAPQVQLQQSGPELKKPGETVK ISCKASGYPFTNYGMNWVKQAPGQGLKWMGWINTSTGES TFADDFKGRFDFSLETSANTAYLQINNLKSEDSATYFCARW EVYHGYVPYWGQGTTVTVSSGGGGSGGGGSGGGGSGGG GSGGGGSDIQMTQSPSSLSASVGDRVTITCKASQDVYNAV AWYQQKPGQSPKLLIYSASSRYTGVPSRFTGSGSGPDFTFTI SSVQAEDLAVYFCQQHFRTPFTFGSGTKLEIK |
| SEQ ID NO: 24 | 114778 (SLTA-DI-1::scFv-1) | MAEFTLDFSTAKTYVDSLNVIRSAIGTPLQTISSGGTSLLMI DSGIGDNLFAVDILGFDFTLGRFNNLRLIVERNNLYVTGFV NRTNNVFYRFADFSHVTFPGTTAVTLSADSSYTTLQRVAGI SRTGMQINRHSLTTSYLDLMSHSATSLTQSVARAMLRFVT VTAEALRFRQIQRGFRTTLDDLSGRSYVMTAEDVDLTLNW GRLSSVLPDYHGQDSVRVGRISFGSINAILGSVALILNSHHH ASAVAAEFPKPSTPPGSSGGAPDIQMTQSPSSLSASVGDRV TITCRASQDVNTAVAWYQQKPGKAPKLLIYSASFLYSGVPS RFSGSRSGTDFTLTISSLQPEDFATYYCQQHYTTPPTFGQGT KVEIKGGGGSEVQLVESGGGLVQPGGSLRLSCAASGFNIKD TYIHWVRQAPGKGLEWVARIYPTNGYTRYADSVKGRFTIS ADTSKNTAYLQMNSLRAEDTAVYYCSRWGGDGFYAMDY WGQGTLVTVSSA |
| SEQ ID NO: 25 | 114795 (SLTA-DI-1::scFv2) | MAEFTLDFSTAKTYVDSLNVIRSAIGTPLQTISSGGTSLLMI DSGIGDNLFAVDILGFDFTLGRFNNLRLIVERNNLYVTGFV NRTNNVFYRFADFSHVTFPGTTAVTLSADSSYTTLQRVAGI SRTGMQINRHSLTTSYLDLMSHSATSLTQSVARAMLRFVT VTAEALRFRQIQRGFRTTLDDLSGRSYVMTAEDVDLTLNW GRLSSVLPDYHGQDSVRVGRISFGSINAILGSVALILNSHHH ASAVAAEFPKPSTPPGSSGGAPQVQLLQSGAELKKPGESLK ISCKGSGYSFTSYWIAWVRQMPGKGLEYMGLIYPGDSDTK YSPSFQGQVTISVDKSVSTAYLQWSSLKPSDSAVYFCARHD VGYCSSSNCAKWPEYFQHWGQGTLVTVSSGGGGSQSVLT QPPSVSAAPGQKVTISCSGSSSNIGNNYVSWYQQLPGTAPK LLIYGHTNRPAGVPDRFSGSKSGTSASLAISGFRSEDEADYY CAAWDDSLSGWVFGGGTKLTVLA |
| SEQ ID NO: 26 | 114791 (SLTA-DI-1::scFv3) | MAEFTLDFSTAKTYVDSLNVIRSAIGTPLQTISSGGTSLLMI DSGIGDNLFAVDILGFDFTLGRFNNLRLIVERNNLYVTGFV NRTNNVFYRFADFSHVTFPGTTAVTLSADSSYTTLQRVAGI SRTGMQINRHSLTTSYLDLMSHSATSLTQSVARAMLRFVT VTAEALRFRQIQRGFRTTLDDLSGRSYVMTAEDVDLTLNW GRLSSVLPDYHGQDSVRVGRISFGSINAILGSVALILNSHHH ASAVAAEFPKPSTPPGSSGGAPQVQLQQSGPELKKPGETVK ISCKASGYPFTNYGMNWVKQAPGQGLKWMGWINTSTGES TFADDFKGRFDFSLETSANTAYLQINNLKSEDSATYFCARW EVYHGYVPYWGQGTTVTVSSGGGGSDIQLTQSHKFLSTSV GDRVSITCKASQDVYNAVAWYQQKPGQSPKLLIYSASSRY TGVPSRFTGSGSGPDFTFTISSVQAEDLAVYFCQQHFRTPFT FGSGTKLEIK |

Sequence Listing

| ID Number | Text Description | Biological Sequence |
|---|---|---|
| SEQ ID NO: 27 | SLTA-DI-1::scFv4 | MAEFTLDFSTAKTYVDSLNVIRSAIGTPLQTISSGGTSLLMI
DSGIGDNLFAVDILGFDFTLGRFNNLRLIVERNNLYVTGFV
NRTNNVFYRFADFSHVTFPGTTAVTLSADSSYTTLQRVAGI
SRTGMQINRHSLTTSYLDLMSHSATSLTQSVARAMLRFVT
VTAEALRFRQIQRGFRTTLDDLSGRSYVMTAEDVDLTLNW
GRLSSVLPDYHGQDSVRVGRISFGSINAILGSVALILNSHHH
ASAVAAEFPKPSTPPGSSGGAPDIQMTQSPSSLSASVGDRV
TITCKASQDVSIGVAWYQQKPGKAPKLLIYSASYRYTGVPS
RFSGSGSGTDFTLTISSLQPEDFATYYCQQYYIYPYTFGQGT
KVEIKGGGGSEVQLVESGGGLVQPGGSLRLSCAASGFTFTD
YTMDWVRQAPGKGLEWVADVNPNSGGSIYNQRFKGRFTL
SVDRSKNTLYLQMNSLRAEDTAVYYCARNLGPSFYFDYW
GQGTLVTVSSA |
| SEQ ID NO: 28 | 114912 (SLTA-DI-2::scFv-5) | MKEFTLDFSTAKTYVDSLNVIRSAIGTPLQTISSGGTSLLMI
DSGIGDNLFAVDILGFDFTLGRFNNLRLIVERNNLYVTGFV
NRTNNVFYRFADFSHVTFPGTTAVTLSADSSYTTLQRVAGI
SRTGMQINRHSLTTSYLDLMSHSGTSLTQSVARAMLRFVT
VTAEALRFRQIQRGFRTTLDDLSGASYVMTAEDVDLTLNW
GRLSSVLPDYHGQDSVRVGRISFGSINAILGSVALILNSHHH
ASAVAAEFPKPSTPPGSSGGAPDIQMTQSPSSLSASVGDRV
TITCRASQDVNTAVAWYQQKPGKAPKLLIYSASFLYSGVPS
RFSGSRSGTDFTLTISSLQPEDFATYYCQQHYTTPPTFGQGT
KVEIKGGGGSGGGGSGGGGSGGGGSGGGGSEVQLVESGG
GLVQPGGSLRLSCAASGFNIKDTYIHWVRQAPGKGLEWVA
RIYPTNGYTRYADSVKGRFTISADTSKNTAYLQMNSLRAE
DTAVYYCSRWGGDGFYAMDYWGQGTLVTVSS |
| SEQ ID NO: 29 | 115111 (SLTA-DI-2::scFv-6) | MKEFTLDFSTAKTYVDSLNVIRSAIGTPLQTISSGGTSLLMI
DSGIGDNLFAVDILGFDFTLGRFNNLRLIVERNNLYVTGFV
NRTNNVFYRFADFSHVTFPGTTAVTLSADSSYTTLQRVAGI
SRTGMQINRHSLTTSYLDLMSHSGTSLTQSVARAMLRFVT
VTAEALRFRQIQRGFRTTLDDLSGASYVMTAEDVDLTLNW
GRLSSVLPDYHGQDSVRVGRISFGSINAILGSVALILNSHHH
ASAVAAEFPKPSTPPGSSGGAPQVQLQQSGPELKKPGETVK
ISCKASGYPFTNYGMNWVKQAPGQGLKWMGWINTSTGES
TFADDFKGRFDFSLETSANTAYLQINNLKSEDSATYFCARW
EVYHGYVPYWGQGTTVTVSSGGGGSGGGGSGGGGSGGG
GSGGGGSDIQMTQSPSSLSASVGDRVTITCKASQDVYNAV
AWYQQKPGQSPKLLIYSASSRYTGVPSRFTGSGSGPDFTFTI
SSVQAEDLAVYFCQQHFRTPFTFGSGTKLEIK |
| SEQ ID NO: 30 | 115411 (SLTA-DI-3::scFv-7) | MREFTLDFSTARTYVDSLNVIRSAIGTPLQTISSGGTSLLMID
SGIGDNLFAVDILGFDFTLGRFNNLRLIVERNNLYVTGFVN
RTNNVFYRFADFSHVTFPGTTAVTLSADSSYTTLQRVAGIS
RTGMQINRHSLTTSYLALMSHSGTSLTQSVARAMLRFVTV
TAEALRFRQIQRGFRTTLDDLSGASYVMTAEDVDLTLNWG
RLSSVLPDYHGQDSVRVGRISFGSINAILGSVALILNSHHHA
SAVAASPSTPPTPSPSTPPASQVQLVQSGPEVKKPGASVKVS
CKASGYPFTNYGMNWVRQAPGQGLEWMGWINTSTGESTF
ADDFKGRVTMTTDTSTSTTYMELRSLRPDDTAVYFCARWE
VYHGYVPYWGQGTLVTVSSGGGGSGGGGSGGGGSGGGG
SGGGGGSDIQMTQSPSSLSASIGDRVTITCKASQDVYNAVAW
YQQKPGEAPKLLVYSASSRYTGVPSRFSGSGSGTDFTFTISS
LQPEDIATYFCQQHFRTPFTFAPGTKLEIK |
| SEQ ID NO: 31 | 114898 | MKEFTLDFSTAKTYVDSLNVIRSAIGTPLQTISSGGTSLLMI
DSGIGDNLFAVDILGFDFTLGRFNNLRLIVERNNLYVTGFV
NRTNNVFYRFADFSHVTFPGTTAVTLSADSSYTTLQRVAGI
SRTGMQINRHSLTTSYLDLMSHSGTSLTQSVARAMLRFVT
VTAEALRFRQIQRGFRTTLDDLSGASYVMTAEDVDLTLNW
GRLSSVLPDYHGQDSVRVGRISFGSINAILGSVALILNSHHH
ASAVAAHHSEDPSSKAPKAPEVQLVESGGGLVQAGGSLR
LSCAASGITFSINTMGWYRQAPGKQRELVALISSIGDTYYA
DSVKGRFTISRDNAKNTVYLQMNSLKPEDTAVYYCKRFRT
AAQGTDYWGQGTQVTVSSA |
| SEQ ID NO: 32 | 115195 | MKEFTLDFSTAKTYVDSLNVIRSAIGTPLQTISSGGTSLLMI
DSGIGDNLFAVDILGFDFTLGRFNNLRLIVERNNLYVTGFV
NRTNNVFYRFADFSHVTFPGTTAVTLSADSSYTTLQRVAGI
SRTGMQINRHSLTTSYLDLMSHSGTSLTQSVARAMLRFVT
VTAEALRFRQIQRGFRTTLDDLSGASYVMTAEDVDLTLNW
GRLSSVLPDYHGQDSVRVGRISFGSINAILGSVALILNSHHH
ASAVAAEFPKPSTPPGSSGGAPQVQLQQSGPELKKPGETVK |

Sequence Listing

| ID Number | Text Description | Biological Sequence |
|---|---|---|
| | | ISCKASGYPFTNYGMNWVKQAPGQGLKWMGWINTSTGES TFADDFKGRFDFSLETSANTAYLQINNLKSEDSATYFCARW EVYHGYVPYWGQGTTVTVSSGGGGSDIQMTQSPSSLSASV GDRVTITCKASQDVYNAVAWYQQKPGQSPKLLIYSASSRY TGVPSRFTGSGSGPDFTFTISSVQAEDLAVYFCQQHFRTPFT FGSGTKLEIK |
| SEQ ID NO: 33 | 115194 | MKEFTLDFSTAKTYVDSLNVIRSAIGTPLQTISSGGTSLLMI DSGSGDNLFAVDVRGIDPEEGRFNNLRLIVERNNLYVTGFV NRTNNVFYRFADFSHVTFPGTTAVTLSGDSSYTTLQRVAGI SRTGMQINRHSLTTSYLDLMSHSGTSLTQSVARAMLRFVT VTAEALRFRQIQRGFRTTLDDLSGRSYVMTAEDVDLTLNW GRLSSVLPDYHGQDSVRVGRISFGSINAILGSVALILNCHHH ASAVAAEFPKPSTPPGSSGGAPQVQLQQSGPELKKPGETVK ISCKASGYPFTNYGMNWVKQAPGQGLKWMGWINTSTGES TFADDFKGRFDFSLETSANTAYLQINNLKSEDSATYFCARW EVYHGYVPYWGQGTTVTVSSGGGGSDIQMTQSPSSLSASV GDRVTITCKASQDVYNAVAWYQQKPGQSPKLLIYSASSRY TGVPSRFTGSGSGPDFTFTISSVQAEDLAVYFCQQHFRTPFT FGSGTKLEIK |
| SEQ ID NO: 34 | 115645 | MKEFTLDFSTAKTYVDSLNVIRSAIGTPLQTISSGGTSLLMI DSGIGDNLFAVDILGFDFTLGRFNNLRLIVERNNLYVTGFV NRTNNVFYRFADFSHVTFPGTTAVTLSADSSYTTLQRVAGI SRTGMQINRHSLTTSYLDLMSHSGTSLTQSVARAMLRFVT VTAEALRFRQIQRGFRTTLDDLSGASYVMTAEDVDLTLNW GRLSSVLPDYHGQDSVRVGRISFGSINAILGSVALILNSHHH ASAVAAEVQLVESGGGLVQAGGSLRLSCAASGITFSINTMG WYRQAPGKQRELVALISSIGDTYYADSVKGRFTISRDNAK NTVYLQMNSLKPEDTAVYYCKRFRTAAQGTDYWGQGTQ VTVSSA |
| SEQ ID NO: 35 | 115845 | MKEFTLDFSTAKTYVDSLNVIRSAIGTPLQTISSGGTSLLMI DSGIGDNLFAVDILGFDFTLGRFNNLRLIVERNNLYVTGFV NRTNNVFYRFADFSHVTFPGTTAVTLSADSSYTTLQRVAGI SRTGMQINRHSLTTSYLALMSHSGTSLTQSVARAMLRFVT VTAEALRFRQIQRGFRTTLDDLSGASYVMTAEDVDLTLNW GRLSSVLPDYHGQDSVRVGRISFGSINAILGSVALILNSHHH ASAVAAQVQLQESGGGSVQAGGSLKLTCAASGYIFNSCGM GWYRQSPGREREVLSRISGDGDTWHKESVKGRFTISQDNV KKTLYLQMNSLKPEDTAVYFCAVCYNLETYWGQGTQVTV SSHHHHHH |
| SEQ ID NO: 36 | SLTA-DI-2::scFv-8 | MKEFTLDFSTAKTYVDSLNVIRSAIGTPLQTISSGGTSLLMI DSGIGDNLFAVDILGFDFTLGRFNNLRLIVERNNLYVTGFV NRTNNVFYRFADFSHVTFPGTTAVTLSADSSYTTLQRVAGI SRTGMQINRHSLTTSYLDLMSHSGTSLTQSVARAMLRFVT VTAEALRFRQIQRGFRTTLDDLSGASYVMTAEDVDLTLNW GRLSSVLPDYHGQDSVRVGRISFGSINAILGSVALILNSHHH ASAVAAEFPKPSTPPGSSGGAPQVQLQQSGPELKKPGETVK ISCKASGYPFTNYGMNWVKQAPGQGLKWMGWINTSTGES TFADDFKGRFDFSLETSANTAYLQINNLKSEDSATYFCARW EVYHGYVPYWGQGTTVTVSSGGGGSGGGGSGGGGSGGG GSDIQMTQSPSSLSASVGDRVTITCKASQDVYNAVAWYQQ KPGQSPKLLIYSASSRYTGVPSRFTGSGSGPDFTFTISSVQAE DLAVYFCQQHFRTPFTFGSGTKLEIK |
| SEQ ID NO: 37 | SLTA-FR | KEFTLDFSTAKTYVDSLNVIRSAIGTPLQTISSGGTSLLMIDS GSGDNLFAVDVRGIDPEEGRFNNLRLIVERNNLYVTGFVN TNNVFYRFADFSHVTFPGTTAVTLSGDSSYTTLQRVAGISR TGMQINRHSLTTSYLDLMSHSGTSLTQSVARAMLRFVTVT AEALRFRQIQRGFRTTLDDLSGRSYVMTAEDVDLTLNWGR LSSVLPDYHGQDSVRVGRISFGSINAILGSVALILNCHHHAS AVAA |
| SEQ ID NO: 38 | HER2 from *Homo sapiens* | MELAALCRWGLLLALLPPGAASTQVCTGTDMKLRLPASPE THLDMLRHLYQGCQVVQGNLELTYLPTNASLSFLQDIQEV QGYVLIAHNQVRQVPLQRLRIVRGTQLFEDNYALAVLDNG DPLNNTTPVTGASPGGLRELQLRSLTEILKGGVLIQRNPQLC YQDTILWKDIFHKNNQLALTLIDTNRSRACHPCSPMCKGSR CWGESSEDCQSLTRTVCAGGCARCKGPLPTDCCHEQCAAG CTGPKHSDCLACLHFNHSGICELHCPALVTYNTDTFESMPN PEGRYTFGASCVTACPYNYLSTDVGSCTLVCPLHNQEVTA EDGTQRCEKCSKPCARVCYGLGMEHLREVRAVTSANIQEF AGCKKIFGSLAFLPESFDGDPASNTAPLQPEQLQVFETLEEI |

| | | |
|---|---|---|
| | | TGYLYISAWPDSLPDLSVFQNLQVIRGRILHNGAYSLTLQG<br>LGISWLGRSLRELGSGLALIHHNTHLCFVHTVPWDQLFRN<br>PHQALLHTANRPEDECVGEGLACHQLCARGHCWGPGPTQ<br>CVNCSQFLRGQECVEECRVLQGLPREYVNARHCLPCHPEC<br>QPQNGSVTCFGPEADQCVACAHYKDPPFCVARCPSGVKPD<br>LSYMPIWKFPDEEGACQPCPINCTHSCVDLDDKGCPAEQR<br>ASPLTSIISAVVGILLVVVLGVVFGILIKRRQKIRKYTMRR<br>LLQETELVEPLTPSGAMPNQAQMRILKETELRKVKVLGSG<br>AFGTVYKGIWIPDGENVKIPVAIKVLRENTSPKANKEILDEA<br>YVMAGVGSPYVSRLLGICLTSTVQLVTQLMPYGCLLDHVR<br>ENRGRLGSQDLLNWCMQIAKGMSYLEDVRLVHRDLAARN<br>VLVKSPNHVKITDFGLARLLDIDETEYHADGGKVPIKWMA<br>LESILRRRFTHQSDVWSYGVTVWELMTFGAKPYDGIPAREI<br>PDLLEKGERLPQPPICTIDVYMIMVKCWMIDSECRPRFREL<br>VSEFSRMARDPQRFVVIQNEDLGPASPLDSTFYRSLLEDDD<br>MGDLVDAEEYLVPQQGFFCPDPAPGAGGMVHHRHRSSST<br>RSGGGDLTLGLEPSEEEAPRSPLAPSEGAGSDVFDGDLGMG<br>AAKGLQSLPTHDPSPLQRYSEDPTVPLPSETDGYVAPLTCS<br>PQPEYVNQPDVRPQPPSPREGPLPAARPAGATLERPKTLSP<br>GKNGVVKDVFAFGGAVENPEYLTPQGGAAPQPHPPPAFSP<br>AFDNLYYWDQDPPERGAPPSTFKGTPTAENPEYLGLDVPV |
| SEQ ID<br>NO: 39 | predicted<br>extracellular<br>domain of HER2<br>from Homo<br>sapiens | TQVCTGTDMKLRLPASPETHLDMLRHLYQGCQVVQGNLE<br>LTYLPTNASLSFLQDIQEVQGYVLIAHNQVRQVPLQRLRIV<br>RGTQLFEDNYALAVLDNGDPLNNTTPVTGASPGGLRELQL<br>RSLTEILKGGVLIQRNPQLCYQDTILWKDIFHKNNQLALTLI<br>DTNRSRACHPCSPMCKGSRCWGESSEDCQSLTRTVCAGGC<br>ARCKGPLPTDCCHEQCAAGCTGPKHSDCLACLHFNHSGIC<br>ELHCPALVTYNTDTFESMPNPEGRYTFGASCVTACPYNYL<br>STDVGSCTLVCPLHNQEVTAEDGTQRCEKCSKPCARVCYG<br>LGMEHLREVRAVTSANIQEFAGCKKIFGSLAFLPESFDGDP<br>ASNTAPLQPEQLQVFETLEEITGYLYISAWPDSLPDLSVFQN<br>LQVIRGRILHNGAYSLTLQGLGISWLGRSLRELGSGLALIH<br>HNTHLCFVHTVPWDQLFRNPHQALLHTANRPEDECVGEGL<br>ACHQLCARGHCWGPGPTQCVNCSQFLRGQECVEECRVLQ<br>GLPREYVNARHCLPCHPECQPQNGSVTCFGPEADQCVACA<br>HYKDPPFCVARCPSGVKPDLSYMPIWKFPDEEGACQPCPIN<br>CTHSCVDLDDKGCPAEQRASPLT |
| SEQ ID<br>NO: 40 | HER2 from<br>Macaca<br>fascicularis | MELAAWYRWGLLLALLPPGAAGTQVCTGTDMKLRLPASP<br>ETHLDMLRHLYQGCQVVQGNLELTYLPTNASLSFLQDIQE<br>VQGYVLIAHNQVRQVPLQRLRIVRGTQLFEDNYALAVLDN<br>GNPLNNTTPVTGASPGGLRELQLRSLTEILKGGVLIQRNPQL<br>CYQDTILWKDIFHKNNQLALTLIDTNRSRACHPCSPVCKGS<br>RCWGESSEDCQSLTRTVCAGGCARCKGPLPTDCCHEQCAA<br>GCTGPKHSDCLACLHFNHSGICELHCPALVTYNTDTFESMP<br>NPEGRYTFGASCVTACPYNYLSTDVGSCTLVCPLHNQEVT<br>AEDGTQRCEKCSKPCARVCYGLGMEHLREVRAVTSANIQE<br>FAGCKKIFGSLAFLPESFDGDPASNTAPLQPEQLRVFETLEE<br>ITGYLYISAWPDSLPDLSVLQNLQVIRGRILHNGAYSLTLQG<br>LGISWLGRSLRELGSGLALIHHNTRLCFVHTVPWDQLFRN<br>PHQALLHTANRPEDECVGEGLACHQLCARGHCWGPGPTQ<br>CVNCSQFLRGQECVEECRVLQGLPREYVNARHCLPCHPEC<br>QPQNGSVTCFGPEADQCVACAHYKDPPFCVARCPSGVKPD<br>LSYMPIWKFPDEEGTCQSCPINCTHSCVDLDDKGCPAEQRA<br>SPLTSIISAVVGILLVVVLGVVFGILIKRRQKIRKYTMRRLL<br>QETELVEPLTPSGAMPNQAQMRILKETELRKVKVLGSGAF<br>GTVYKGIWIPDGENVKIPVAIKVLRENTSPKANKEILDEAY<br>VMAGVGSPYVSRLLGICLTSTVQLVTQLMPYGCLLDHVRE<br>NRGRLGSQDLLNWCMQIAKGMSYLEDVRLVHRDLAARN<br>VLVKSPNHVKITDFGLARLLDIDETEYHADGGKVPIKWMA<br>LESILRRRFTHQSDVWSYGVTVWELMTFGAKPYDGIPAREI<br>PDLLEKGERLPQPPICTIDVYMIMVKCWMIDSECRPRFREL<br>VSEFSRMARDPQRFVVIQNEDLGPASPLDSTFYRSLLEDDD<br>MGDLVDAEEYLVPQQGFFCPDPAPGTGGMVHHRHRSSST<br>RSGGGDLTLGLEPSEEEAPRSPRAPSEGTGSDVFDGDLGMG<br>AAKGLQSLPAHDPSPLQRYSEDPTVPLPSETDGYVAPLTCS<br>PQPEYVNQPDVRPQPPLPQEGPLSPARPTGATLERPKTLSPG<br>KNGVVKDVFAFGGAVENPEYLAPRGGAAPQPHLPPAFSPA<br>FDNLYYWDQDPSERGAPPSTFKGTPTAENPEYLGLDVPV |
| SEQ ID<br>NO: 41 | HER2 from<br>Macaca mulatta | MELAAWYRWGLLLALLPPGAAGTQVCTGTDMKLRLPASP<br>ETHLDMLRHLYQGCQVVQGNLELTYLPTNASLSFLQDIQE<br>VQGYVLIAHNQVRQVPLQRLRIVRGTQLFEDNYALAVLDN<br>GDLLNNTTPVTGASPGGLRELQLRSLTEILKGGVLIQRNPQ |

| | | |
|---|---|---|
| | | Sequence Listing |
| ID Number | Text Description | Biological Sequence |
| | | LCYQDTILWKDIFHKNNQLALTLIDTNRSRACHPCSPVCKG SRCWGESSEDCQSLTRTVCAGGCARCKGPLPTDCCHEQCA AGCTGPKHSDCLACLHFNHSGICELHCPALVTYNTDTFESM PNPEGRYTFGASCVTACPYNYLSTDVGSCTLVCPLHNQEV TAEDGTQRCEKCSKPCARVCYGLGMEHLREVRAVTSANIQ EFAGCKKIFGSLAFLPESFDGDPASNTAPLQPEQLRVFETLE EITGYLYISAWPDSLPDLSVLQNLQVIRGRILHNGAYSLTLQ GLGISWLGLRSLRELGSGLALIHHNTRLCFVHTVPWDQLFR NPHQALLHTANRPEDECVGEGLACHQLCARGHCWGPGPT QCVNCSQFLRGQECVEECRVLQGLPREYVNARHCLPCHPE CQPQNGSVTCFGPEADQCVACAHYKDPPFCVARCPSGVKP DLSYMPIWKFPDEEGTCQSCPINCTHSCVDLDDKGCPAEQR ASPLTSIISAVVGILLVVVLGVVFGILIKRRQQKIRKYTMRR LLQETELVEPLTPSGAMPNQAQMRILKETELRKVKVLGSG AFGTVYKGIWIPDGENVKIPVAIKVLRENTSPKANKEILDEA YVMAGVGSPYVSRLLGICLTSTVQLVTQLMPYGCLLDHVR ENRGRLGSQDLLNWCMQIAKGMSYLEDVRLVHRDLAARN VLVKSPNHVKITDFGLARLLDIDETEYHADGGKVPIKWMA LESILRRRFTHQSDVWSYGVTVWELMTFGAKPYDGIPAREI PDLLEKGERLPQPPICTIDVYMIMVKCWMIDSECRPRFREL VSEFSRMARDPQRFVVIQNEDLGPASPLDSTFYRSLLEDDD MGDLVDAEEYLVPQQGFFCPDPAPGTGGMVHHRHRSSST RSGGGDLTLGLEPSEEEAPRSPRAPSEGTGSDVFDGDLGMG AAKGLQSLPAHDPSPLQRYSEDPTVPLPSETDGYVAPLTCS PQPEYVNQPDVRPQPPSPQEGPLSPARPTGATLERPKTLSPG KNGVVKDVFAFGGAVENPEYLAPRGGAAPQPHLPPAFSPA FDNLYYWDQDPSERGAPPSTFKGTPTAENPEYLGLDVPV |
| SEQ ID NO: 42 | HER2 from *Mus musculus* | MELAAWCRWGFLLALLSPGAAGTQVCTGTDMKLRLPASP ETHLDMLRHLYQGCQVVQGNLELTYLPANASLSFLQDIQE VQGYMLIAHNRVKHVPLQRLRIVRGTQLFEDKYALAVLDN RDPLDNVTTAAPGRTPEGLRELQLRSLTEILKGGVLIRGNP QLCYQDMVLWKDVLRKNNQLAPVDMDTNRSRACPPCAP TCKDNHCWGESPEDCQILTGTICTSGCARCKGRLPTDCCHE QCAAGCTGPKHSDCLACLHFNHSGICELHCPALITYNTDTF ESMLNPEGRYTFGASCVTTCPYNYLSTEVGSCTLVCPPNNQ EVTAEDGTQRCEKCSKPCAGVCYGLGMEHLRGARAITSDN IQEFAGCKKIFGSLAFLPESFDGNPSSGVAPLKPEHLQVFET LEEITGYLYISAWPESFQDLSVFQNLRVIRGRILHDGAYSLT LQGLGIHSLGLRSLRELGSGLALIHRNTHLCFVNTVPWDQL FRNPHQALLHSGNRPEEACGLEGLVCNSLCARGHCWGPGP TQCVNCSQFLRGQECVEECRVWKGLPREYVRGKHCLPCHP ECQPQNSSETCYGSEADQCEACAHYKDSSSCVARCPSGVK PDLSYMPIWKYPDEEGICQPCPINCTHSCVDLDERGCPAEQ RASPVTFIIATVVGVLLFLIIVVVIGILIKRRRQKIRKYTMRR LLQETELVEPLTPSGAVPNQAQMRILKETELRKLKVLGSGA FGTVYKGIWIPDGENVKIPVAIKVLRENTSPKANKEILDEAY VMAGVGSPYVSRLLGICLTSTVQLVTQLMPYGCLLDHVRE HRGRLGSQDLLNWCVQIAKGMSYLEEVRLVHRDLAARNV LVKSPNHVKITDFGLARLLDIDETEYHADGGKVPIKWMAL ESILRRRFTHQSDVWSYGVTVWELMTFGAKPYDGIPAREIP DLLEKGERLPQPPICTIDVYMIMVKCWMIDSECRPRFRELV SEFSRMARDPQRFVVIQNEDLGPSSPMDSTFYRSLLEDDDM GELVDAEEYLVPQQGFFSPDPALGTGSTAHRRHRSSSARSG GGELTLGLEPSEEEPPRSPLAPSEGAGSDVFDGDLAVGVTK GLQSLSPHDLSPLQRYSEDPTLPLPPETDGYVAPLACSPQPE YVNQPEVRPQSPLTPEGPPPPIRPAGATLERPKTLSPGKNGV VKDVFAFGGAVENPEYLAPRAGTASQPHPSPAFSPAFDNL YYWDQNSSEQGPPPSTFEGTPTAENPEYLGLDVPV |
| SEQ ID NO: 43 | intein and chitin binding domain | CITGDALVALPEGESVRIADIVPGARPNSDNAIDLKVLDRH GNPVLADRLFHSGEHPVYTVRTVEGLRVTGTANHPLLCLV DVAGVPTLLWKLIDEIKPGDYAVIQRSAFSVDCAGFARGKP EFAPTTYTVGVPGLVRFLEAHHRDPDAQAIADELTDGRFY YAKVASVTDAGVQPVYSLRVDTADHAFITNGFVSHATGLT GLNSGLTTNPGVSAWQVNTAYTAGQLVTYNGKTYKCLQP HTSLAGWEPSNVPALWQLQ |
| SEQ ID NO: 44 | polyhistidine tag (6 × His) | HHHHHH |
| SEQ ID NO: 45 | vhCDR1 | DTYIH |

-continued

| Sequence Listing | | |
|---|---|---|
| ID Number | Text Description | Biological Sequence |
| SEQ ID NO: 46 | vhCDR2 | RIYPTNGYTRYADSVKG |
| SEQ ID NO: 47 | vhCDR3 | WGGDGFYAMDY |
| SEQ ID NO: 48 | vlCDR1 | RASQDVNTAVA |
| SEQ ID NO: 49 | vlCDR2 | SASFLYS |
| SEQ ID NO: 50 | vlCDR3 | QQHYTTPPT |
| SEQ ID NO: 51 | vhCDR1 | SYWIA |
| SEQ ID NO: 52 | vhCDR2 | LIYPGDSDTKYSPSFQG |
| SEQ ID NO: 53 | vhCDR3 | HDVGYCSSSNCAKWPEYFQH |
| SEQ ID NO: 54 | vlCDR1 | SGSSSNIGNNYVS |
| SEQ ID NO: 55 | vlCDR2 | SASYRYT |
| SEQ ID NO:56 | vlCDR3 | QQYYIYPYT |
| SEQ ID NO: 57 | vhCDR1 | NYGMN |
| SEQ ID NO: 58 | vhCDR2 | WINTSTGESTFADDFKG |
| SEQ ID NO: 59 | vhCDR3 | WEVYHGYVPY |
| SEQ ID NO: 60 | vlCDR1 | KASQDVYNAVA |
| SEQ ID NO: 61 | vlCDR2 | SASSRYT |
| SEQ ID NO: 62 | vlCDR3 | QQHFRTPFT |
| SEQ ID NO: 63 | vhCDR1 | DYTMD |
| SEQ ID NO: 64 | vhCDR2 | DVNPNSGGSIYNQRFKG |
| SEQ ID NO: 65 | vhCDR3 | NLGPSFYFDY |
| SEQ ID NO: 66 | vlCDR1 | KASQDVSIGVA |
| SEQ ID NO: 67 | vlCDR2 | SASYRYT |
| SEQ ID NO: 68 | vlCDR3 | QQYYIYPYT |
| SEQ ID NO: 69 | vhhCDR1 | INTMG |
| SEQ ID NO: 70 | vhhCDR2 | LISSIGDTYYADSVKG |

| | | |
|---|---|---|
| SEQ ID NO: 71 | vhhCDR3 | FRTAAQGTDY |
| SEQ ID NO: 72 | vhhCDR1 | SCGMG |
| SEQ ID NO: 73 | vhhCDR2 | RISGDGDTWHKESVKG |
| SEQ ID NO: 74 | vhhCDR3 | CYNLETY |
| SEQ ID NO: 75 | SLT-1A-combo variant 1 | KEFILRFSVAHKYVDSLNVIRSAIGTPLQTISSGGTSLLMIDS GSGDNLFAVDVRGIDPEEGRFNNLRLIVERNNLYVTGFVNR TNNVFYRFADFSHVTFPGTTAVTLSGDSSYTTLQRVAGISR TGMQINRHSLTTSYLDLMSHSGTSLTQSVARAMLRFVTVT AEALRFRQIQRGFRTTLDDLSGRSYVMTAEDVDLTLNWG LSSVLPDYHGQDSVRVGRISFGSINAILGSVALILNCHHHAS AVAA |
| SEQ ID NO: 76 | SLT-1A-combo variant 2 | KEFTLDFSTAKTYVDSLNVIRSAIGTPLQTISSGGTSLLMIDN LVPMVATVVDVRGIDPEEGRFNNLRLIVERNNLYVTGFVN RTNNVFYRFADFSHVTFPGTTAVTLSGDSSYTTLQRVAGIS RTGMQINRHSLTTSYLDLMSHSGTSLTQSVARAMLRFVTV TAEALRFRQIQRGFRTTLDDLSGRSYVMTAEDVDLTLNWG RLSSVLPDYHGQDSVRVGRISFGSINAILGSVALILNCHHHA SAVAA |
| SEQ ID NO: 77 | SLT-1A-combo variant 3 | KEFTLDFSTAKTYVDSLNVIRSAIGTPLQTISSGGTSLLMIDS NLVPMVATVVDVRGIDPEEGRFNNLRLIVERNNLYVTGFVN RTNNVFYRFADFSHVTFPGTTAVTLSGDSSYTTLQRVAGIS RTGMQINRHSLTTSYLDLMSHSGTSLTQSVARAMLRFVTV TAEALRFRQIQRGFRTTLDDLSGRSYVMTAEDVDLTLNWG RLSSVLPDYHGQDSVRVGRISFGSINAILGSVALILNCHHHA SAVAA |
| SEQ ID NO: 78 | SLT-1A-combo variant 4 | KEFTLDFSTAKTYVDSLNVIRSAIGTPLQTISSGGTSLLMIDS GILGFVFTLDVRGIDPEEGRFNNLRLIVERNNLYVTGFVNRT NNVFYRFADFSHVTFPGTTAVTLSGDSSYTTLQRVAGISRT GMQINRHSLTTSYLDLMSHSGTSLTQSVARAMLRFVTVTA EALRFRQIQRGFRTTLDDLSGRSYVMTAEDVDLTLNWGRL SSVLPDYHGQDSVRVGRISFGSINAILGSVALILNCHHHASA VAA |
| SEQ ID NO: 79 | SLT-1A-combo variant 5 | KEFTLDFSTAKTYVDSLNVIRSAIGTPLQTISSGGTSLLMIDS GSGDNLFAVGILGFDFTLGRFNNLRLIVERNNLYVTGFVNR TNNVFYRFADFSHVTFPGTTAVTLSGDSSYTTLQRVAGISR TGMQINRHSLTTSYLDLMSHSGTSLTQSVARAMLRFVTVT AEALRFRQIQRGFRTTLDDLSGRSYVMTAEDVDLTLNWGR LSSVLPDYHGQDSVRVGRISFGSINAILGSVALILNCHHHAS AVAA |
| SEQ ID NO: 80 | SLT-1A-combo variant 6 | KEFTLDFSTAKTYVDSLNVIRSAIGTPLQTISSGGTSLLMIDS GSGDNLFAVDILGFVFTLGRFNNLRLIVERNNLYVTGFVNR TNNVFYRFADFSHVTFPGTTAVTLSGDSSYTTLQRVAGISR TGMQINRHSLTTSYLDLMSHSGTSLTQSVARAMLRFVTVT AEALRFRQIQRGFRTTLDDLSGRSYVMTAEDVDLTLNWGR LSSVLPDYHGQDSVRVGRISFGSINAILGSVALILNCHHHAS AVAA |
| SEQ ID NO: 81 | SLT-1A-combo variant 7 | KEFTLDFSTAKTYVDSLNVIRSAIGTPLQTISSGGTSLLMIDS GSGDNLFAVDILGFDFTLGRFNNLRLIVERNNLYVTGFVNR TNNVFYRFADFSHVTFPGTTAVTLSGDSSYTTLQRVAGISR TGMQINRHSLTTSYLDLMSHSGTSLTQSVARAMLRFVTVT AEALRFRQIQRGFRTTLDDLSGRSYVMTAEDVDLTLNWGR LSSVLPDYHGQDSVRVGRISFGSINAILGSVALILNCHHHAS AVAA |
| SEQ ID NO: 82 | SLT-1A-combo variant 8 | KEFTLDFSTAKTYVDSLNVIRSAIGTPLQTISSGGTSLLMIDS GSGDNLFAVGILGFVFTLGRFNNLRLIVERNNLYVTGFVNR TNNVFYRFADFSHVTFPGTTAVTLSGDSSYTTLQRVAGISR TGMQINRHSLTTSYLDLMSHSGTSLTQSVARAMLRFVTVT AEALRFRQIQRGFRTTLDDLSGRSYVMTAEDVDLTLNWGR |

-continued

| Sequence Listing | | |
|---|---|---|
| ID Number | Text Description | Biological Sequence |
| | | LSSVLPDYHGQDSVRVGRISFGSINAILGSVALILNCHHHAS<br>AVAA |
| SEQ ID NO: 83 | SLT-1A-combo variant 9 | KEFILDFSTAKTYVDSLNVIRSAIGTPLQTISSGGTSLLMIDS<br>GIGDNLFAVDVRGIAPIEARFNNLRLIVERNNLYVTGFVNR<br>TNNVFYRFADFSHVTFPGTTAVTLSADSSYTTLQRVAGISR<br>TGMQINRHSLTTSYLDLMSHSATSLTQSVARAMLRFVTVT<br>AEALRFRQIQRGFRTTLAALSGASYVMTAEDVDLTLNWGR<br>LSSVLPDYHGQDSVRVGRISFGSINAILGSVALILNSHHHAS<br>AVAA |
| SEQ ID NO: 84 | SLT-1A-combo variant 10 | KEFTLDFSTAKTYVDSLNVIRSAIGTPLQTISSGGTSLLMIDS<br>GSGDNLFAVGILGFVFTLEGRFNNLRLIVERNNLYVTGFVN<br>RTNNVFYRFADFSHVTFPGTTAVTLSGDSSYTTLQRVAGIS<br>RTGMQINRHSLTTSYLDLMSHSGTSLTQSVARAMLRFVTV<br>TAEALRFRQIQRGFRTTLDDLSGRSYVMTAEDVDLTLNWG<br>RLSSVLPDYHGQDSVRVGRISFGSINAILGSVALILNCHHHA<br>SAVAA |
| SEQ ID NO: 85 | SLT-1A-combo variant 11 | KEFTLDFSTAKTYVDSLNVIRSAIGTPLQTISSGGTSLLMIDS<br>GSGDNLFAVNLVPMVATVGRFNNLRLIVERNNLYVTGFVN<br>RTNNVFYRFADFSHVTFPGTTAVTLSGDSSYTTLQRVAGIS<br>RTGMQINRHSLTTSYLDLMSHSGTSLTQSVARAMLRFVTV<br>TAEALRFRQIQRGFRTTLDDLSGRSYVMTAEDVDLTLNWG<br>RLSSVLPDYHGQDSVRVGRISFGSINAILGSVALILNCHHHA<br>SAVAA |
| SEQ ID NO: 86 | SLT-1A-combo variant 12 | KEFTLDFSTAKTYVDSLNVIRSAIGTPLQTISSGGTSLLMIDS<br>GSGDNLFAVDVRGIDPEEGRFNNLRLIVERNNLYVTGFVNR<br>TNNVFYRFADFSHVTFPGTNLVPMVATVSYTTLQRVAGIS<br>RTGMQINRHSLTTSYLDLMSHSGTSLTQSVARAMLRFVTV<br>TAEALRFRQIQRGFRTTLDDLSGRSYVMTAEDVDLTLNWG<br>RLSSVLPDYHGQDSVRVGRISFGSINAILGSVALILNCHHHA<br>SAVAA |
| SEQ ID NO: 87 | SLT-1A-combo variant 13 | KEFTLDFSTAKTYVDSLNVIRSAIGTPLQTISSGGTSLLMIDS<br>GSGDNLFAVDVRGIDPEEGRFNNLRLIVERNNLYVTGFVNR<br>TNNVFYRFADFSHVTFPGTTAVTLSGDSSYTTLQRVAGISR<br>TGMQINRHSLTTSYLDLMSHSGTSLTQSVARAMLRFVTVT<br>AEALRFRQIQRGFRGILGDVFTLSYVMTAEDVDLTLNWGR<br>LSSVLPDYHGQDSVRVGRISFGSINAILGSVALILNSHHHAS<br>AVAA |
| SEQ ID NO: 88 | SLT-1A-combo variant 14 | KEFTLDFSTAKTYVDSLNVIRSAIGTPLQTISSGGTSLLMIDS<br>GSGDNLFAVDVRGIDPEEGRFNNLRLIVERNNLYVTGFVNR<br>TNNVFYRFADFSHVTFPGTTAVTLSGDSSYTTLQRVAGISR<br>TGMQINRHSLTTSYLDLMSHSGTSLTQSVARAMLRFVTVT<br>AEALRFRQIQRGFRTTLDDLSGRSYVMTAEDVDLTLNWGR<br>LSSVLPDYHGQDSVRVGRISFGSINAILGSVALILNCHHHIL<br>RFSVAHKASAVAA |
| SEQ ID NO: 89 | SLT-1A-combo variant 15 | KEFTLDFSTAKTYVDSLNVIRSAIGTPLQTISSGGTSLLMIDS<br>GSGDNLFAVDILGFDFTLGRFNNLRLIVERNNLYVTGFVNR<br>TNNVFYRFADFSHVTFPGTTAVTLSGDSSYTTLQRVAGISR<br>TGMQINRHSLTTSYLDLMSHSGTSLTQSVARAMLRFVTVT<br>AEALRFRQIQRGFRTTLDDLSGRSYVMTAEDVDLTLNWGR<br>LSSVLPDYHGQDSVRVGRISFGSINAILGSVALILNCHHHAR<br>NLVPMVATVASAVAA |
| SEQ ID NO: 90 | linker 1 | EFPKPSTPPGSSGGAP |
| SEQ ID NO: 91 | linker 2 | GGGGSGG |
| SEQ ID NO: 92 | linker 3 | GGGGSGGGGSGGGGSGGGGSGGGGS |
| SEQ ID NO: 93 | linker 4 | GSTSGSGKPGSGEGS |
| SEQ ID NO: 94 | linker 5 | GGGGS |

Sequence Listing

| ID Number | Text Description | Biological Sequence |
|---|---|---|
| SEQ ID NO: 95 | linker 6 | AHHSEDPSSKAPKAP |
| SEQ ID NO: 96 | linker 7 | GSTSGSGKPGSGEGSTKG |
| SEQ ID NO: 97 | exemplary HER2-targeting molecule #1 | AEFTLDFSTAKTYVDSLNVIRSAIGTPLQTISSGGTSLLMIDS GIGDNLFAVDILGFDFTLGRFNNLRLIVERNNLYVTGFVNR TNNVFYRFADFSHVTFPGTTAVTLSADSSYTTLQRVAGISR TGMQINRHSLTTSYLDLMSHSATSLTQSVARAMLRFVTVT AEALRFRQIQRGFRTTLDDLSGRSYVMTAEDVDLTLNWGR LSSVLPDYHGQDSVRVGRISFGSINAILGSVALILNSHHHAS AVAAEFPKPSTPPGSSGGAPDIQMTQSPSSLSASVGDRVTIT CRASQDVNTAVAWYQQKPGKAPKLLIYSASFLYSGVPSRF SGSRSGTDFTLTISSLQPEDFATYYCQQHYTTPPTFGQGTKV EIKGGGGSEVQLVESGGGLVQPGGSLRLSCAASGFNIKDTY IHWVRQAPGKGLEWVARIYPTNGYTRYADSVKGRFTISAD TSKNTAYLQMNSLRAEDTAVYYCSRWGGDGFYAMDYWG QGTLVTVSSA |
| SEQ ID NO: 98 | exemplary HER2-targeting molecule #2 | AEFTLDFSTAKTYVDSLNVIRSAIGTPLQTISSGGTSLLMIDS GIGDNLFAVDILGFDFTLGRFNNLRLIVERNNLYVTGFVNR TNNVFYRFADFSHVTFPGTTAVTLSADSSYTTLQRVAGISR TGMQINRHSLTTSYLDLMSHSATSLTQSVARAMLRFVTVT AEALRFRQIQRGFRTTLDDLSGRSYVMTAEDVDLTLNWGR LSSVLPDYHGQDSVRVGRISFGSINAILGSVALILNSHHHAS AVAAEFPKPSTPPGSSGGAPQVQLLQSGAELKKPGESLKIS CKGSGYSFTSYWIAWVRQMPGKGLEYMGLIYPGDSDTKY SPSFQGQVTISVDKSVSTAYLQWSSLKPSDSAVYFCARHDV GYCSSSNCAKWPEYFQHWGQGTLVTVSSGGGGSQSVLTQ PPSVSAAPGQKVTISCSGSSSNIGNNYVSWYQQLPGTAPKL LIYGHTNRPAGVPDRFSGSKSGTSASLAISGFRSEDEADYY CAAWDDSLSGWVFGGGTKLTVLA |
| SEQ ID NO: 99 | exemplary HER2-targeting molecule #3 | AEFTLDFSTAKTYVDSLNVIRSAIGTPLQTISSGGTSLLMIDS GIGDNLFAVDILGFDFTLGRFNNLRLIVERNNLYVTGFVNR TNNVFYRFADFSHVTFPGTTAVTLSADSSYTTLQRVAGISR TGMQINRHSLTTSYLDLMSHSATSLTQSVARAMLRFVTVT AEALRFRQIQRGFRTTLDDLSGRSYVMTAEDVDLTLNWGR LSSVLPDYHGQDSVRVGRISFGSINAILGSVALILNSHHHAS AVAAEFPKPSTPPGSSGGAPQVQLQQSGPELKKPGETVKIS CKASGYPFTNYGMNWVKQAPGQGLKWMGWINTSTGEST FADDFKGRFDFSLETSANTAYLQINNLKSEDSATYFCARWE VYHGYVPYWGQGTTVTVSSGGGGSDIQLTQSHKFLSTSVG DRVSITCKASQDVYNAVAWYQQKPGQSPKLLIYSASSRYT GVPSRFTGSGSGPDFTFTISSVQAEDLAVYFCQQHFRTPFTF GSGTKLEIK |
| SEQ ID NO: 100 | exemplary HER2-targeting molecule #4 | AEFTLDFSTAKTYVDSLNVIRSAIGTPLQTISSGGTSLLMIDS GIGDNLFAVDILGFDFTLGRFNNLRLIVERNNLYVTGFVNR TNNVFYRFADFSHVTFPGTTAVTLSADSSYTTLQRVAGISR TGMQINRHSLTTSYLDLMSHSATSLTQSVARAMLRFVTVT AEALRFRQIQRGFRTTLDDLSGRSYVMTAEDVDLTLNWGR LSSVLPDYHGQDSVRVGRISFGSINAILGSVALILNSHHHAS AVAAEFPKPSTPPGSSGGAPDIQMTQSPSSLSASVGDRVTIT CKASQDVSIGVAWYQQKPGKAPKLLIYSASYRYTGVPSRF SGSGSGTDFTLTISSLQPEDFATYYCQQYYIYPYTFGQGTKV EIKGGGGSEVQLVESGGGLVQPGGSLRLSCAASGFTFTDYT MDWVRQAPGKGLEWVADVNPNSGGSIYNQRFKGRFTLSV DRSKNTLYLQMNSLRAEDTAVYYCARNLGPSFYFDYWGQ GTLVTVSSA |
| SEQ ID NO: 101 | exemplary HER2-targeting molecule #5 | KEFTLDFSTAKTYVDSLNVIRSAIGTPLQTISSGGTSLLMIDS GIGDNLFAVDILGFDFTLGRFNNLRLIVERNNLYVTGFVNR TNNVFYRFADFSHVTFPGTTAVTLSADSSYTTLQRVAGISR TGMQINRHSLTTSYLDLMSHSGTSLTQSVARAMLRFVTVT AEALRFRQIQRGFRTTLDDLSGASYVMTAEDVDLTLNWGR LSSVLPDYHGQDSVRVGRISFGSINAILGSVALILNSHHHAS AVAAEFPKPSTPPGSSGGAPDIQMTQSPSSLSASVGDRVTIT CRASQDVNTAVAWYQQKPGKAPKLLIYSASFLYSGVPSRF SGSRSGTDFTLTISSLQPEDFATYYCQQHYTTPPTFGQGTKV EIKGGGGSGGGGSGGGGSGGGGSGGGGSEVQLVESGGGL VQPGGSLRLSCAASGFNIKDTYIHWVRQAPGKGLEWVARI |

| Sequence Listing | | |
|---|---|---|
| ID Number | Text Description | Biological Sequence |
| | | YPTNGYTRYADSVKGRFTISADTSKNTAYLQMNSLRAEDT AVYYCSRWGGDGFYAMDYWGQGTLVTVSS |
| SEQ ID NO: 102 | exemplary HER2-targeting molecule #6 | KEFTLDFSTAKTYVDSLNVIRSAIGTPLQTISSGGTSLLMIDS GIGDNLFAVDILGFDFTLGRFNNLRLIVERNNLYVTGFVNR TNNVFYRFADFSHVTFPGTTAVTLSADSSYTTLQRVAGISR TGMQINRHSLTTSYLDLMSHSGTSLTQSVARAMLRFVTVT AEALRFRQIQRGFRTTLDDLSGASYVMTAEDVDLTLNWGR LSSVLPDYHGQDSVRVGRISFGSINAILGSVALILNSHHHAS AVAAEFPKPSTPPGSSGGAPQVQLQQSGPELKKPGETVKIS CKASGYPFTNYGMNWVKQAPGQGLKWMGWINTSTGEST FADDFKGRFDFSLETSANTAYLQINNLKSEDSATYFCARWE VYHGYVPYWGQGTTVTVSSGGGGSGGGGSGGGGSGGGG SGGGGSDIQMTQSPSSLSASVGDRVTITCKASQDVYNAVA WYQQKPGQSPKLLIYSASSRYTGVPSRFTGSGSGPDFTFTIS SVQAEDLAVYFCQQHFRTPFTFGSGTKLEIK |
| SEQ ID NO: 103 | exemplary HER2-targeting molecule #7 | REFTLDFSTARTYVDSLNVIRSAIGTPLQTISSGGTSLLMIDS GIGDNLFAVDILGFDFTLGRFNNLRLIVERNNLYVTGFVNR TNNVFYRFADFSHVTFPGTTAVTLSADSSYTTLQRVAGISR TGMQINRHSLTTSYLALMSHSGTSLTQSVARAMLRFVTVT AEALRFRQIQRGFRTTLDDLSGASYVMTAEDVDLTLNWGR LSSVLPDYHGQDSVRVGRISFGSINAILGSVALILNSHHHAS AVAASPSTPPTPSPSTPPASQVQLVQSGPEVKKPGASVKVS CKASGYPFTNYGMNWVRQAPGQGLEWMGWINTSTGESTF ADDFKGRVTMTTDTSTSTTYMELRSLRPDDTAVYFCARWE VYHGYVPYWGQGTLVTVSSGGGGSGGGGSGGGGSGGGG SGGGGSDIQMTQSPSSLSASIGDRVTITCKASQDVYNAVAW YQQKPGEAPKLLVYSASSRYTGVPSRFSGSGSGTDFTFTISS LQPEDIATYFCQQHFRTPFTFAPGTKLEIK |
| SEQ ID NO: 104 | exemplary HER2-targeting molecule #8 | KEFTLDFSTAKTYVDSLNVIRSAIGTPLQTISSGGTSLLMIDS GIGDNLFAVDILGFDFTLGRFNNLRLIVERNNLYVTGFVNR TNNVFYRFADFSHVTFPGTTAVTLSADSSYTTLQRVAGISR TGMQINRHSLTTSYLDLMSHSGTSLTQSVARAMLRFVTVT AEALRFRQIQRGFRTTLDDLSGASYVMTAEDVDLTLNWGR LSSVLPDYHGQDSVRVGRISFGSINAILGSVALILNSHHHAS AVAAAHHSEDPSSKAPKAPEVQLVESGGGLVQAGGSLRLS CAASGITFSINTMGWYRQAPGKQRELVALISSIGDTYYADS VKGRFTISRDNAKNTVYLQMNSLKPEDTAVYYCKRFRTAA QGTDYWGQGTQVTVSSA |
| SEQ ID NO: 105 | exemplary HER2-targeting molecule #9 | KEFTLDFSTAKTYVDSLNVIRSAIGTPLQTISSGGTSLLMIDS GIGDNLFAVDILGFDFTLGRFNNLRLIVERNNLYVTGFVNR TNNVFYRFADFSHVTFPGTTAVTLSADSSYTTLQRVAGISR TGMQINRHSLTTSYLDLMSHSGTSLTQSVARAMLRFVTVT AEALRFRQIQRGFRTTLDDLSGASYVMTAEDVDLTLNWGR LSSVLPDYHGQDSVRVGRISFGSINAILGSVALILNSHHHAS AVAAEFPKPSTPPGSSGGAPQVQLQQSGPELKKPGETVKIS CKASGYPFTNYGMNWVKQAPGQGLKWMGWINTSTGEST FADDFKGRFDFSLETSANTAYLQINNLKSEDSATYFCARWE VYHGYVPYWGQGTTVTVSSGGGGSDIQMTQSPSSLSASVG DRVTITCKASQDVYNAVAWYQQKPGQSPKLLIYSASSRYT GVPSRFTGSGSGPDFTFTISSVQAEDLAVYFCQQHFRTPFTF GSGTKLEIK |
| SEQ ID NO: 106 | exemplary HER2-targeting molecule #10 | KEFTLDFSTAKTYVDSLNVIRSAIGTPLQTISSGGTSLLMIDS GIGDNLFAVDILGFDFTLGRFNNLRLIVERNNLYVTGFVNR TNNVFYRFADFSHVTFPGTTAVTLSADSSYTTLQRVAGISR TGMQINRHSLTTSYLDLMSHSGTSLTQSVARAMLRFVTVT AEALRFRQIQRGFRTTLDDLSGASYVMTAEDVDLTLNWGR LSSVLPDYHGQDSVRVGRISFGSINAILGSVALILNSHHHAS AVAAEVQLVESGGGLVQAGGSLRLSCAASGITFSINTMGW YRQAPGKQRELVALISSIGDTYYADSVKGRFTISRDNAKNT VYLQMNSLKPEDTAVYYCKRFRTAAQGTDYWGQGTQVT VSSA |
| SEQ ID NO: 107 | exemplary HER2-targeting molecule #11 | KEFTLDFSTAKTYVDSLNVIRSAIGTPLQTISSGGTSLLMIDS GIGDNLFAVDILGFDFTLGRFNNLRLIVERNNLYVTGFVNR TNNVFYRFADFSHVTFPGTTAVTLSADSSYTTLQRVAGISR TGMQINRHSLTTSYLALMSHSGTSLTQSVARAMLRFVTVT AEALRFRQIQRGFRTTLDDLSGASYVMTAEDVDLTLNWGR LSSVLPDYHGQDSVRVGRISFGSINAILGSVALILNSHHHAS AVAAQVQLQESGGGSVQAGGSLKLTCAASGYIFNSCGMG |

| ID Number | Text Description | Biological Sequence |
|---|---|---|
| | | WYRQSPGRERELVSRISGDGDTWHKESVKGRFTISQDNVK KTLYLQMNSLKPEDTAVYFCAVCYNLETYWGQGTQVTVSS |
| SEQ ID NO: 108 | exemplary HER2-targeting molecule #12 | KEFTLDFSTAKTYVDSLNVIRSAIGTPLQTISSGGTSLLMIDS GIGDNLFAVDILGFDFTLGRFNNLRLIVERNNLYVTGFVNR TNNVFYRFADFSHVTFPGTTAVTLSADSSYTTLQRVAGISR TGMQINRHSLTTSYLDLMSHSGTSLTQSVARAMLRFVTVT AEALRFRQIQRGFRTTLDDLSGASYVMTAEDVDLTLNWGR LSSVLPDYHGQDSVRVGRISFGSINAILGSVALILNSHHHAS AVAAEFPKPSTPPGSSGGAPQVQLQQSGPELKKPGETVKIS CKASGYPFTNYGMNWVKQAPGQGLKWMGWINTSTGEST FADDFKGRFDFSLETSANTAYLQINNLKSEDSATYFCARWE VYHGYVPYWGQGTTVTVSSGGGGSGGGGSGGGGSGGGG SDIQMTQSPSSLSASVGDRVTITCKASQDVYNAVAWYQQK PGQSPKLLIYSASSRYTGVPSRFTGSGSGPDFTFTISSVQAED LAVYFCQQHFRTPFTFGSGTKLEIK |
| SEQ ID NO: 179 | (G4S)7 | GGGGSGGGGSGGGGSGGGGSGGGGSGGGGSGGGGS |
| SEQ ID NO: 180 | (G4S)3 | GGGGSGGGGSGGGGS |
| SEQ ID NO: 181 | linker 8 | SPSTPPTPSPSTPPA |

The invention claimed is:

1. A method of treating a disease, disorder, or condition involving HER2-expressing cells in a patient, the method comprising administering to a patient in need thereof a therapeutically effective amount of a HER2-targeting molecule comprising a polypeptide sequence of SEQ ID NO: 29 or SEQ ID NO: 102, and at least one pharmaceutically acceptable excipient or carrier, wherein the patient is refractory to treatment with at least one dual tyrosine kinase inhibitor or anti-HER2 monoclonal antibody prior to administration of the HER2-targeting molecule.

2. The method of claim 1, wherein the method further comprises administering to the patient in need thereof a therapeutically effective amount of at least one additional dual tyrosine kinase inhibitor or anti-HER2 monoclonal antibody, wherein the at least one additional dual tyrosine kinase inhibitor or anti-HER2 monoclonal antibody is administered simultaneously or sequentially with the HER2-targeting molecule.

3. The method of claim 2, wherein the at least one anti-HER2 monoclonal antibody binds an antigenic determinant in HER2 that does not overlap with the antigenic determinant in HER2 bound by the HER2-targeting molecule.

4. The method of claim 1, wherein the at least one pharmaceutically acceptable excipient or carrier is selected from citrate, sorbitol, polysorbate 20, chloride, and sodium.

5. The method of claim 1, wherein the at least one dual tyrosine kinase inhibitor or anti-HER2 monoclonal antibody is selected from lapatinib, neratinib, trastuzumab, and pertuzumab.

6. The method of claim 2, wherein the at least one dual tyrosine kinase inhibitor or anti-HER2 monoclonal antibody is selected from lapatinib, neratinib, trastuzumab, and pertuzumab.

* * * * *